(12) United States Patent
Amann et al.

(10) Patent No.: US 10,464,981 B2
(45) Date of Patent: *Nov. 5, 2019

(54) TUMOR NECROSIS FACTOR (TNF) FAMILY LIGAND TRIMER-CONTAINING ANTIGEN BINDING MOLECULES

(71) Applicant: Hoffmann-La Roche Inc., Little Falls, NJ (US)

(72) Inventors: Maria Amann, Duebendorf (CH); Peter Bruenker, Hittnau (CH); Christina Claus, Ennetbaden (CH); Claudia Ferrara Koller, Zug (CH); Sandra Grau-Richards, Birmsdorf (CH); Christian Klein, Bonstetten (CH); Viktor Levitski, Schlieren (CH); Ekkehard Moessner, Kreuzlingen (CH); Pablo Umana, Wollerau (CH)

(73) Assignee: HOFFMANN-LA ROCHE, INC., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/087,405

(22) Filed: Mar. 31, 2016

(65) Prior Publication Data

US 2016/0340399 A1 Nov. 24, 2016

(30) Foreign Application Priority Data

Mar. 31, 2015 (EP) .................................... 15161880

(51) Int. Cl.
| | | |
|---|---|---|
| *C07K 16/28* | (2006.01) | |
| *C07K 16/30* | (2006.01) | |
| *C07K 16/40* | (2006.01) | |
| *C07K 14/525* | (2006.01) | |
| *C07K 14/705* | (2006.01) | |
| *A61K 39/395* | (2006.01) | |
| *A61K 38/00* | (2006.01) | |

(52) U.S. Cl.
CPC .......... *C07K 14/525* (2013.01); *A61K 39/395* (2013.01); *C07K 14/705* (2013.01); *C07K 14/70596* (2013.01); *C07K 16/2803* (2013.01); *C07K 16/2863* (2013.01); *C07K 16/2887* (2013.01); *C07K 16/3007* (2013.01); *C07K 16/3053* (2013.01); *C07K 16/40* (2013.01); *A61K 38/00* (2013.01); *C07K 2317/31* (2013.01); *C07K 2317/526* (2013.01); *C07K 2317/55* (2013.01); *C07K 2317/60* (2013.01); *C07K 2317/622* (2013.01); *C07K 2319/035* (2013.01); *C07K 2319/30* (2013.01)

(58) Field of Classification Search
CPC ................ C07K 14/525; C07K 14/705; C07K 14/70596; C07K 16/2803; C07K 16/2863; C07K 16/2887; C07K 16/3007; C07K 16/3053; C07K 16/40; C07K 2317/31; C07K 2317/526; C07K 2317/55; C07K 2317/60; C07K 2317/622; C07K 2319/035; C07K 2319/30; A61K 39/395; A61K 38/00

See application file for complete search history.

(56) References Cited

U.S. PATENT DOCUMENTS

| | | | |
|---|---|---|---|
| 5,731,168 | A | 3/1998 | Carter et al. |
| 5,821,333 | A | 10/1998 | Carter et al. |
| 6,737,056 | B1 | 5/2004 | Presta |
| 8,552,024 | B2 | 10/2013 | Ackermann et al. |
| 8,945,571 | B2 | 2/2015 | Hosse et al. |
| 8,969,526 | B2 | 3/2015 | Baehner et al. |
| 9,011,847 | B2 | 4/2015 | Bacac et al. |
| 9,266,938 | B2 | 2/2016 | Ast et al. |
| 9,346,872 | B2 | 5/2016 | Duerner et al. |
| 9,481,730 | B2 | 11/2016 | Bruenker et al. |
| 2013/0287802 | A1 | 10/2013 | Govindappa et al. |
| 2014/0044674 | A1 | 2/2014 | Duerner et al. |
| 2014/0370019 | A1 | 12/2014 | Bruenker et al. |
| 2015/0315296 | A1 | 5/2015 | Schaefer et al. |
| 2015/0218244 | A1 | 6/2015 | Emrich et al. |
| 2016/0060356 | A1 | 3/2016 | Bacac et al. |
| 2016/0060357 | A1 | 3/2016 | Bacac et al. |
| 2016/0200833 | A1 | 7/2016 | Amann et al. |
| 2016/0159917 | A1 | 9/2016 | Bruenker et al. |
| 2016/0340399 | A1 | 11/2016 | Amann et al. |
| 2016/0340413 | A1 | 11/2016 | Duerner et al. |
| 2017/0114141 | A1 | 4/2017 | Amann et al. |

(Continued)

FOREIGN PATENT DOCUMENTS

| | | |
|---|---|---|
| AU | 2011265482 | 1/2012 |
| AU | 2011 265 482 B2 | 8/2013 |
| AU | 2013/263717 B2 | 11/2013 |

(Continued)

OTHER PUBLICATIONS

D. Müller et al., Journal of Immunotherapy 31(8):714-722 (Oct. 1, 2008).

(Continued)

*Primary Examiner* — Robert S Landsman
(74) *Attorney, Agent, or Firm* — Samuel Kais

(57) ABSTRACT

The invention relates to novel TNF family ligand trimer-containing antigen binding molecules comprising (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, and to methods of producing these molecules and to methods of using the same.

22 Claims, 38 Drawing Sheets

Specification includes a Sequence Listing.

(56) References Cited

U.S. PATENT DOCUMENTS

2017/0247467 A1 8/2017 Amann et al.
2017/0129962 A1 11/2017 Regula et al.

FOREIGN PATENT DOCUMENTS

| EP | 1736482 | 12/2006 |
|---|---|---|
| WO | 2004/039841 | 5/2004 |
| WO | 2004/69876 A2 | 8/2004 |
| WO | 2007/014744 | 2/2007 |
| WO | 2008/022152 A2 | 2/2008 |
| WO | 2009/00538 A1 | 12/2008 |
| WO | 2009/040550 A1 | 4/2009 |
| WO | 2010/010051 A1 | 1/2010 |
| WO | 2011/020783 A2 | 2/2011 |
| WO | 2011/109789 | 9/2011 |
| WO | 2011/020783 A2 | 2/2012 |
| WO | 2012/020006 | 2/2012 |
| WO | 2012/130471 A1 | 10/2012 |
| WO | 2014/161845 A1 | 10/2014 |
| WO | 2014/180754 | 11/2014 |
| WO | 2015/184203 A1 | 12/2015 |
| WO | 2015183902 A1 | 12/2015 |
| WO | 2016/075278 A1 | 5/2016 |
| WO | 2016156291 | 10/2016 |

OTHER PUBLICATIONS

E. Bremer, ISRN Onconlogy 176(2):1-26 (Jan. 1, 2013).
Kermer et al., Mol Cancer Ther 13(0:112-121 ( 2014).
N. Hornig et al., Journal of Immunotherapy 35(5):418-429 (Jun. 1, 2012).
N. Zhang et al., Clinical Cancer Research 13(9):2758-2767 (Jan. 28, 2010).
Written Opinion of the International Searching Authority for PCT/EP2016/056765 (dated Jun. 2016).
Aggarwal et al., "Signalling pathways of the TNF superfamily: a double-edged sword" Nat Rev Immunol 3(9):745-756 (Sep. 2003).
Ascierto P. et al., "Clinical Experiences With Anti-CD137 and Anti-PD1 Therapeutic Antibodies" Seminars in Oncology 27(5):508-516 (Oct. 2010).
Banner et al., "Crystal Structure of the Soluble Human 55 kd TNF Receptor-Human TNFβ Complex: Implications for TNF Receptor Activation" Cell 73:431-445 ( 1993).
Bauer et al., "Targeted Bioactivity of Membrane-Anchored TNF by an Antibody-Derived TNF Fusion Protein" J Immunol 172(6):3930-3939 ( 2004).
Bodmer et al. et al., "The molecular architecture of the TNF superfamily" Trends Biochem Sci 27:19-26 ( 2002).
Broll et al., "CD137 Expression in Tumor Vessel Walls High Correlation With Malignant Tumors" Am. J. Chin. Pathol 115:543-549 ( 2001).
Buechele et al., "4-1BB ligand modulates direct and Rituximab-induced NK-cell reactivity in chronic lymphocytic leukemia" J Immunol 42:737-748 ( 2012).
Choi et al., "4-1BB Functions As a Survival Factor in Dendritic Cells" J Immunol 182:4107-4115 ( 2009).
Cuadros C. et al., "Vaccination with dendritic cells pulsed with apoptotic tumors in combination with anti-OX40 and anti-4-1BB monoclonal antibodies induces T cell-mediated protective. immunity in Her-2/neu transgenic mice." Int J Cancer 116:934-943 ( 2005).
Curran M. A. et al., "Combination CTLA-4 blockade and 4-1BB activation enhances tumor rejection by increasing T-cell infiltration, proliferation, and cytokine production." PLoS One 6:e19499. ( 2011).
Diehl et al., "In Vivo Triggering Through 4-1BB Enables Th-Independent Priming of CTL in the Presence of an Intact CD28 Costimulatory Pathway" J Immunol 168:3755-3762 ( 2002).

Dubrot et al., "Treatment with anti-CD137 mAbs causes intense accumulations of liver T cells without selective antitumor immunotherapeutic effects in this organ" Cancer Immunol Immunother 59:1223-1233 ( 2010).
Futagawa et al., "Expression and function of 4-1 BB and 4-1BB ligand on murine dendritic cells" International Immonology 14:275-286 ( 2002).
Gaugitsch et al., "A novel transiently expressed, integral membrane protein linked to cell activation. Molecular cloning via the rapid degradation signal AUUUA" J Biol Chem. 267(16):11267-11273 (Jun. 5, 1992).
Guo Z. et al., "Combined TIM-3 blockade and CD137 activation affords the long-term protection in a murine model of ovarian cancer." J Transl Med 11:215 ( 2013).
Heinisch et al., "CD137 activation abrogates granulocytemacrophage colony-stimulating factor-mediated anti-apoptosis in neutrophils" Eur. J. Immunol. 30:3441-3346 ( 2000).
Ju S.A. et al., "Eradication of established renal cell carcinoma by a combination of 5-fluorouracil and anti-4-1BB monoclonal antibody in mice." Int J Cancer 122:2784-2790. ( 2008).
Kienzle et al., "CD137 (ILA/4-1BB), expressed by primary human monocytes, induces monocyte activation and apoptosis of B lymphocytes" International Immunology 12:73-82 ( 2000).
Kim et al., "4-1BB Engagement Costimulates NKT Cell Activation and Exacerbates NKT Cell Ligand-Induced Airway Hyperresponsiveness and Inflammation" J Immunol 180:2062-2068 ( 2008).
Kim, Y. H. et al., "Mechanism involved in synergistic anticancer effects of anti-4-1BB and cyclophosphamide therapy." Mol Cancer Ther 8:469-478 ( 2009).
Kwon et al., "cDNA sequences of two inducible T-cell genes" P Natl Acad Sci USA 86:1963-1967 ( 1989).
Lee et al., "Combinatorial therapy for liver metastatic colon cancer: dendritic cell vaccine and low-dose agonistic anti-4-1BB antibody costimulatory signal" J Surg Res 169:e43-50 ( 2011).
Levitsky V. et al., "The clonal composition of a peptide-specific oligoclonal CTL repertoire selected in response to persistent EBV infection is stable over time." J Immunol 161:594-601 ( 1998).
Li et al., "Inhibitory Fcγ Receptor Engagement Drives Adjuvant and Anti-Tumor Activities of Agonistic CD40 Antibodies" Science 333:1030-1034 ( 2011).
Lin et al., "Fe-dependent expression of CD137 on human NK cells: insights into agonistic effects of anti-CD137 monoclonal antibodies" Blood 112:699-707 ( 2008).
Melero et al., "Monoclonal Antibodies Against the 4-1BB T-cell Activation Molecule Eradicate Established Tumors" Nature Medicine 3(6):682-685 ( 1997).
Melero et al., "NK1.1 Cells Express 4-1BB (CDw137) Costimulatory Molecule and Are Required for Tumor Immunity Elicited by Anti-4-1BB Monoclonal Antibodies" Cellular Immunology 190:167-172 ( 1998).
Merchant et al., "An efficient route to human bispecific IgG" Nat Biotechnol 16(7):677-681 ( 1998).
Morales-Kastresana, A. et al., "Combined immunostimulatory monoclonal antibodies extend survival in an aggressive transgenic hepatocellular carcinoma mouse model." Clin Cancer Res 19:6151-6162 ( 2013).
Mueller et al., "A Novel Antibody-4-1BBL Fusion Protein for Targeted Costimulation in Cancer Immunotherapy" J Immunother (XP009183889), 31(8):714-722 ( 2008).
Mueller et al., "Activity of soluble OX40 ligand is enhanced by oligomerization and cell surface immobilization" FEBS J. 275:2296-2304 ( 2008).
Murillo et al., "In vivo depletion of DC impairs the anti-tumor effect of agonistic anti-CD137 mAB" Eur. J. Immunol. 39:2424-2436 ( 2009).
Narazaki et al., "CD137 agonist antibody prevents cnacer recurrence: contribution of CD137 on both hematopoietic and nonhematopoietic cells" Blood 115:1941-1948 ( 2010).
Nishimoto, et al., "Costimulation of mast cells by 4-1BB, a member of the tumor necrosis factor receptor superfamily, with the high-affinity IgE receptor" Blood 106:4241-4248 ( 2005).

(56) References Cited

OTHER PUBLICATIONS

Olofsson, et al., "CD137 Is Expressed in Human Atherosclerosis and Promotes Development of Plaque Inflammation in Hypercholesterolemic Mice" Circulation 117:1292-1301 (2011).

Palazon et al., "Agonist Anti-CD137 mAb Act on Tumor Endothelial Cells to Enhance Recruitment of Activated T Lymphocytes" Cancer Research 71:801-811 (2011).

Schwarz et al., "ILA, the Human 4-1BB Homologue, Is Inducible in Lymphoid and Other Cell Lineages" Blood 85:1043-1052 (1995).

Shao, Z. et al., "CD137 ligand, a member of the tumor necrosis factor family, regulates immune.responses via reverse signal transduction." J Leukoc Biol 89:21-29 (2011).

Shi, W. et al., "Augmented antitumor effects of radiation therapy by 4-1BB antibody (BMS-469492) treatment." Anticancer Res 26:3445-3453 (2006).

Simeone et al., "Immunomodulating antibodies in the treatment of metastatic melanoma: The experience with anti-CTLA-4, anti-CD137, and anti-PD1" Journal of Immunotoxicology 9:241-247 (2012).

Snell et al., "T-cell intrinsic effects of GITR and 4-1BB during viral infection and cancer immunotherapy" Immunological Reviews 244:197-217 (2011).

Stagg et al., "Anti-ErbB-2 mAb therapy requires type I and II interferons and synergizes with anti-PD-1 or anti-CD137 mAb therapy" Proc. Nall. Acad. Sci. USA 108:7142-7147 (2011).

Teng et al., "CD1d-Based Combination Therapy Eradicates Established Tumors in Mice" J Immunol 183:1911-1920 (2009).

von Kempis et al., "Differentiation-dependent and stimulus-specific expression of ILA, the human 4-1BB-homologue, in cells of mesenchymal origin" Osteoarthritis and Cartilage 5:394-406 (1997).

Wei, H. et al., "Combinatorial PD-1 blockade and CD137 activation has therapeutic efficacy in murine cancer models and synergizes with cisplatin." PLoS One 8:e84927 (2013).

Wilcox et al., "Cutting Edge: Expression of Functional CD137 Receptor by Dendritic Cells" J Immunol 168:4262-4267 (2002).

Wilcox et al., "Ligation of CD137 receptor prevents and reverses established anergy of CD8 cytolytic T lymphocytes in vivo" Blood 103:177-184 (2004).

Written Opinion for PCT/2016/056765 (dated Jun. 2, 2016).

Zhang et al., "CD137 Promoted Proliferation and Survival of Human B Cells" J Immunol 184:787-795 (2010).

Zhang, N. et al., "Targeted and untargeted CD137L fusion proteins for the immunotherapy of experimental solid tumors." Clin. Cancer Res. 13:2758-2767 (2007).

Baumann et al., "Functional expression of CD134 by neutrophils" Eur. J. Immunol. 34:2268-2275 (2004).

Bremer et al., "Targeting of the Tumor Necrosis Factor Receptor Superfamily for Cancer Immunotherapy" ISRN Oncology 2013:1-25 (2013).

Carter, "Bispecific human IgC by design" J Immunol Methods 248(1-2):7-15 (Feb. 1, 2001).

Croft et al., "The significance of OX40 and OX40L to T-cell biology and immune disease" Immunological Reviews 229:173-191 (2009).

Graff et al., "Directed evolution of an anti-carcinoembryonic antigen scFv with a 4-day monovalent dissociation half-time at 37 degrees C" Protein Eng. Des. Sel. 17(4):293-304 (Jun. 2004).

Hornig et al., "Evaluating combinations of costimulatory antibody-ligand fusion proteins for targeted cancer immunotherapy" Can Immunol Immunotherapy:1369-1380 (May 17, 2013).

Written Opinion of the International Searching Authority PCT/EP2015/076528 (dated Mar. 2016).

Wyzgol et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand1" The Journal of Immunology 183:1851-1861 (2009).

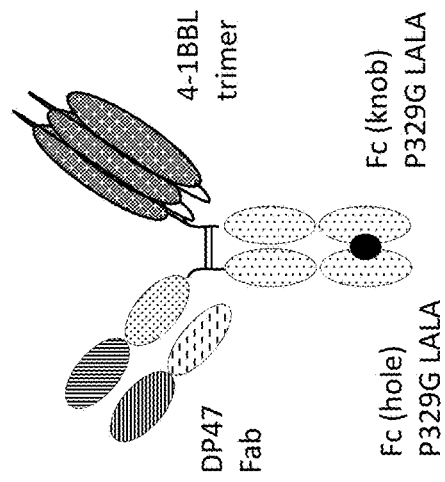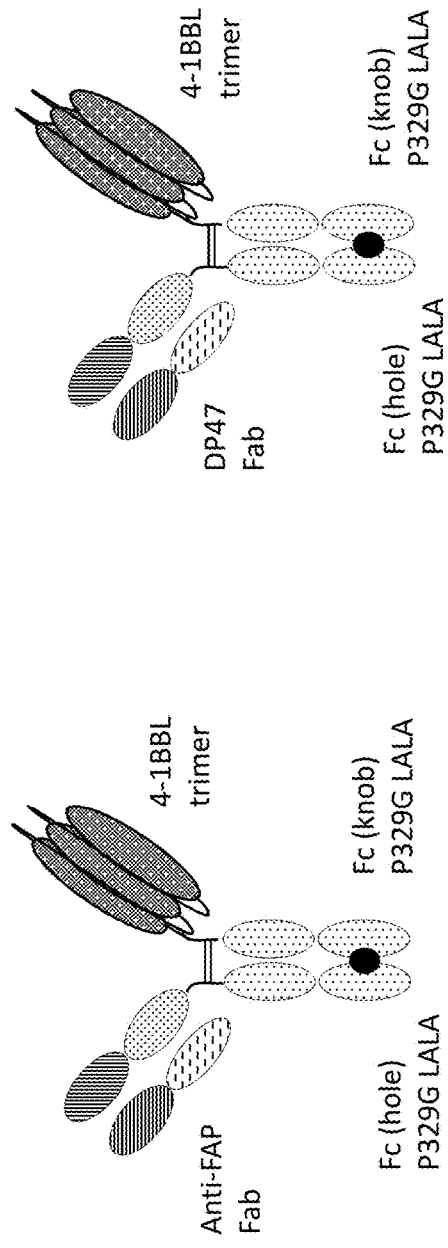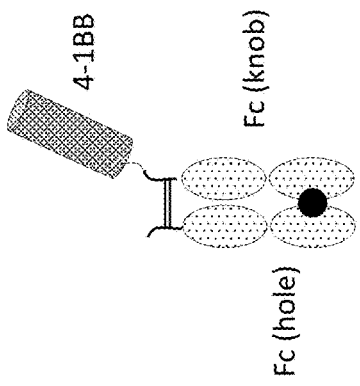

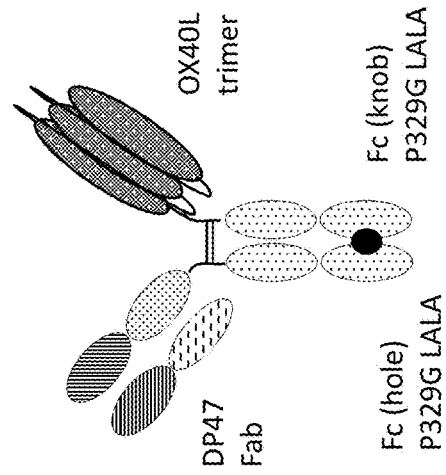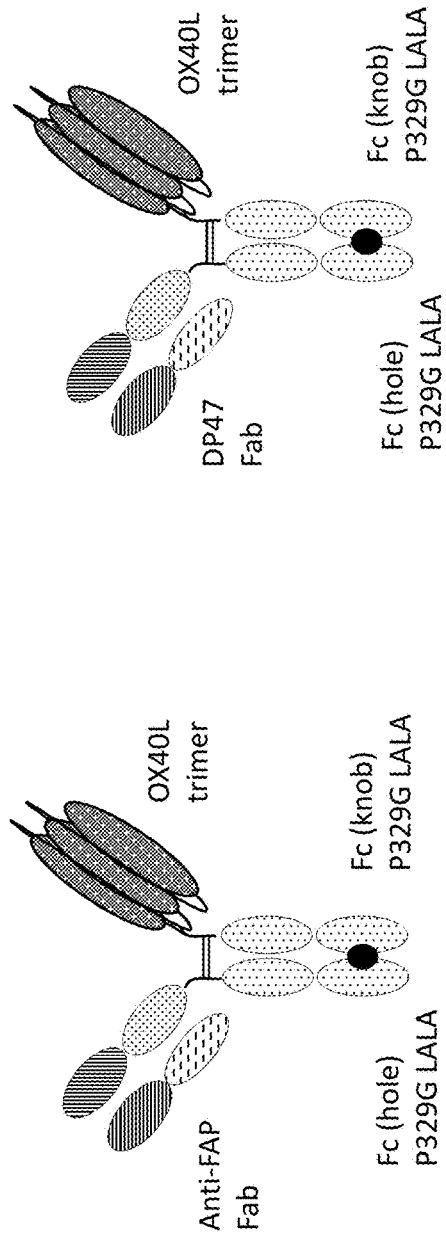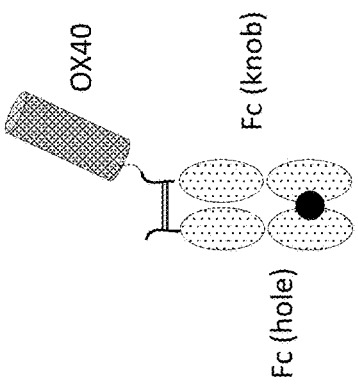

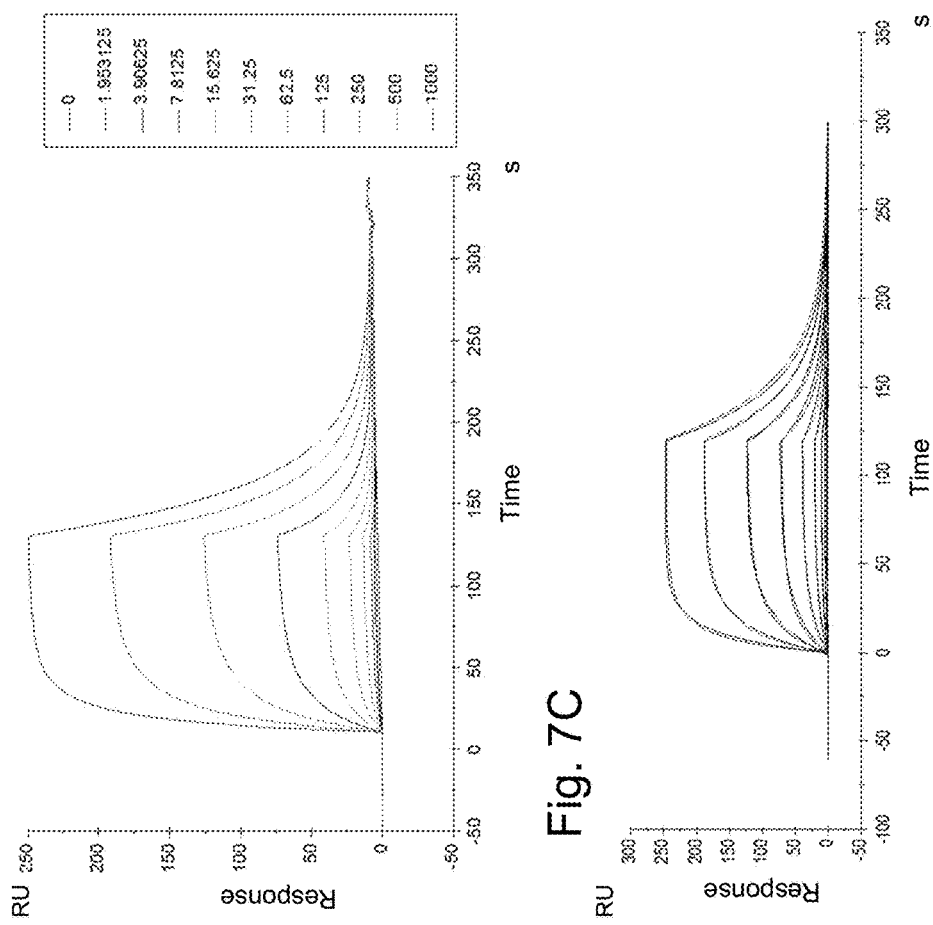
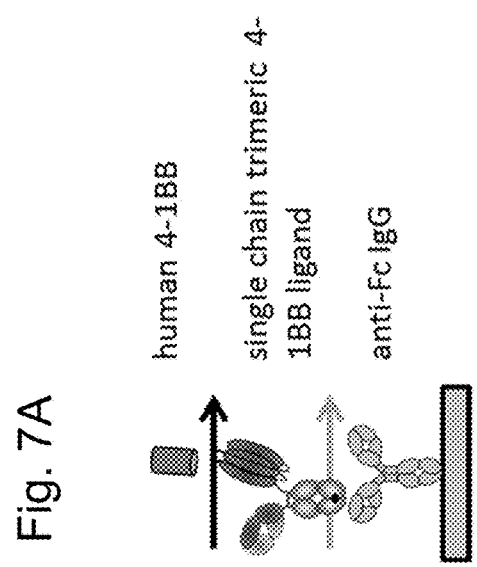
Fig. 7A
human 4-1BB
single chain trimeric 4-1BB ligand
anti-Fc IgG

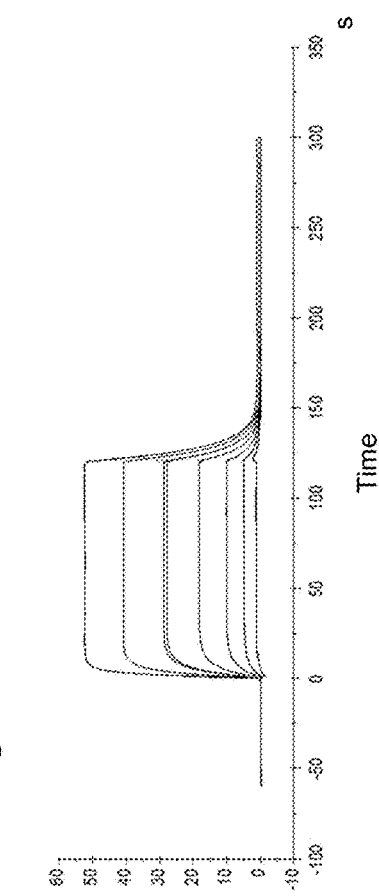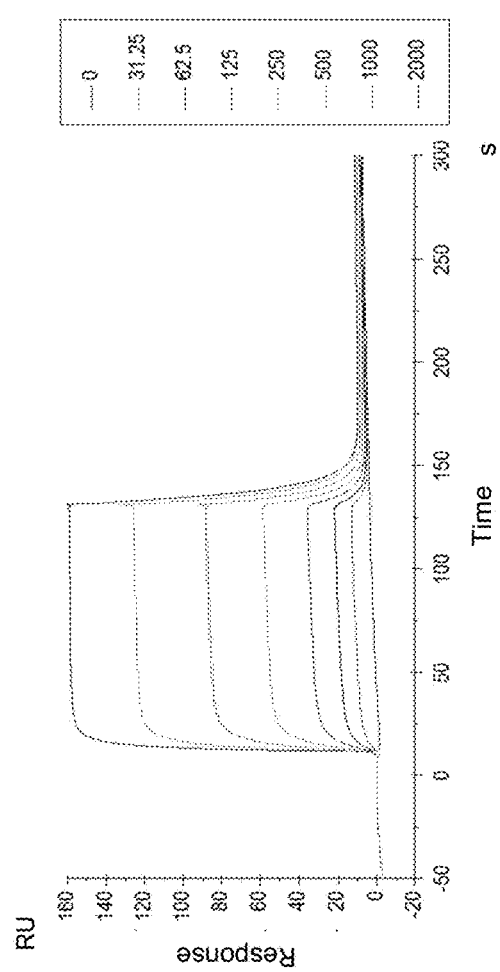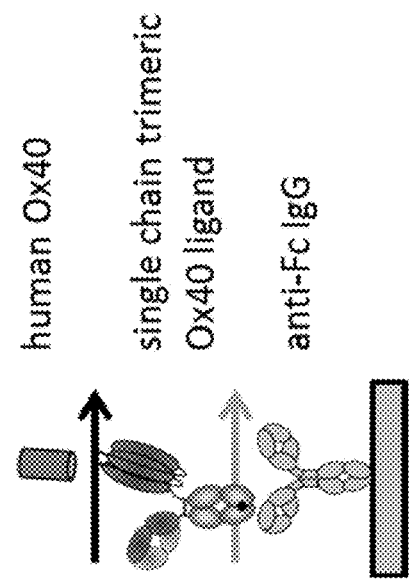

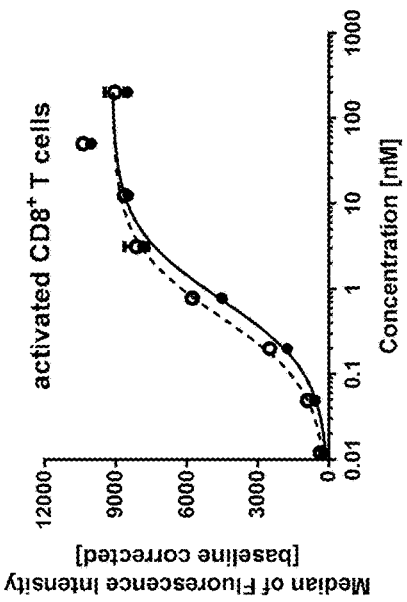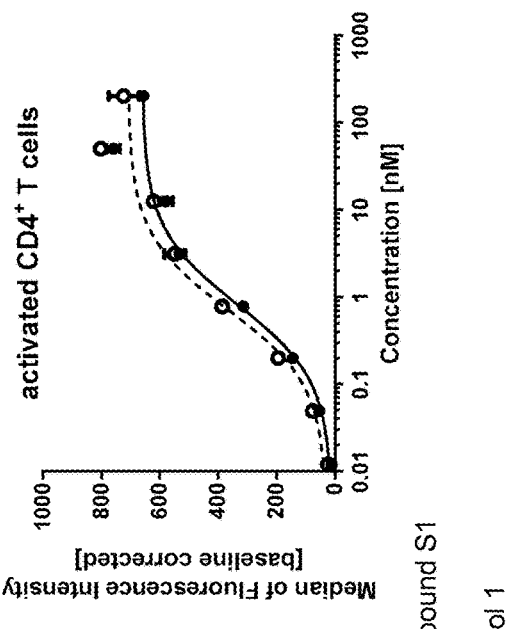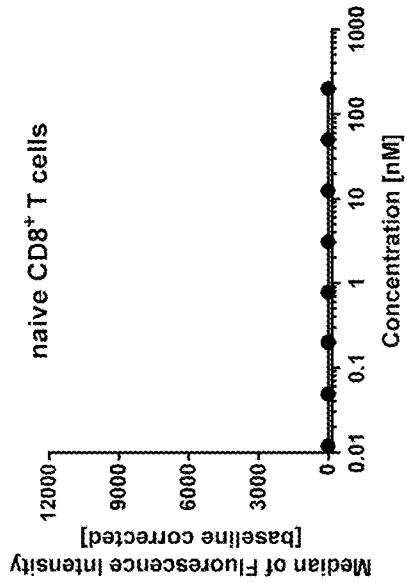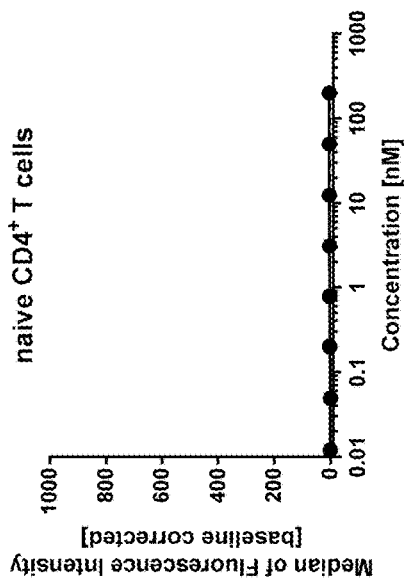

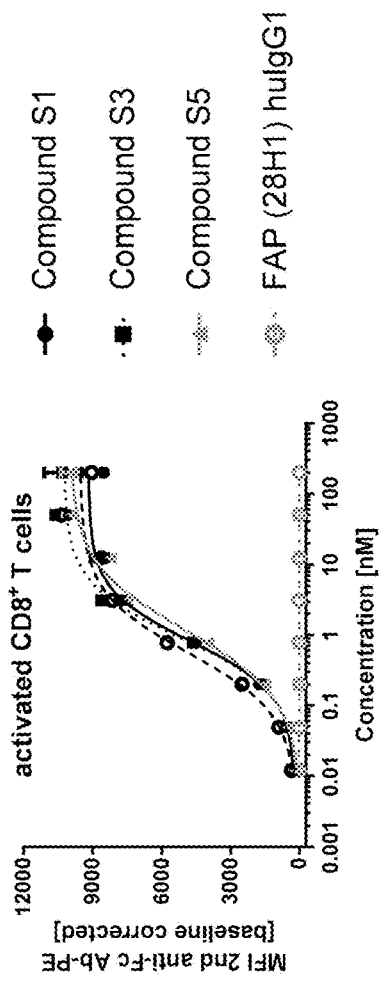
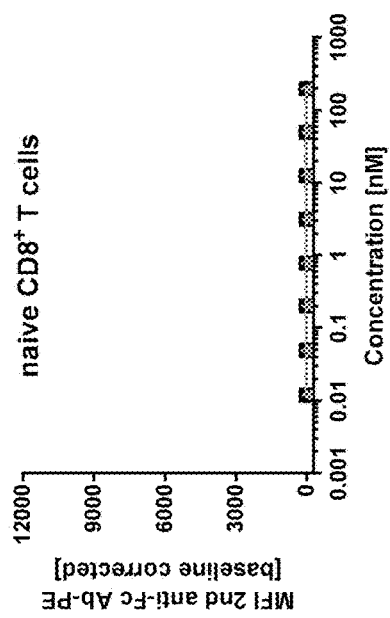
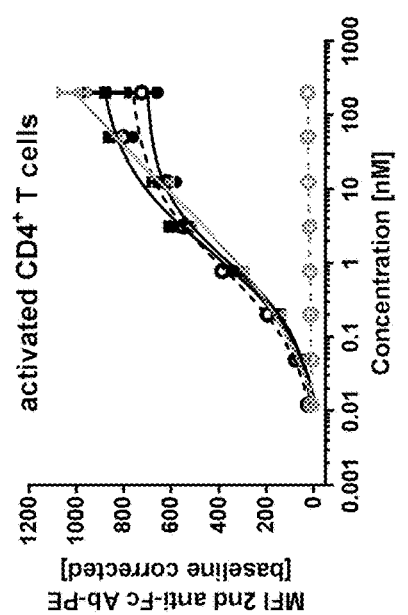
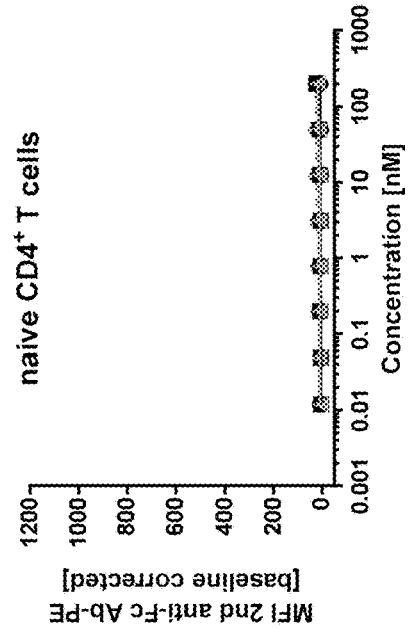
Fig. 11

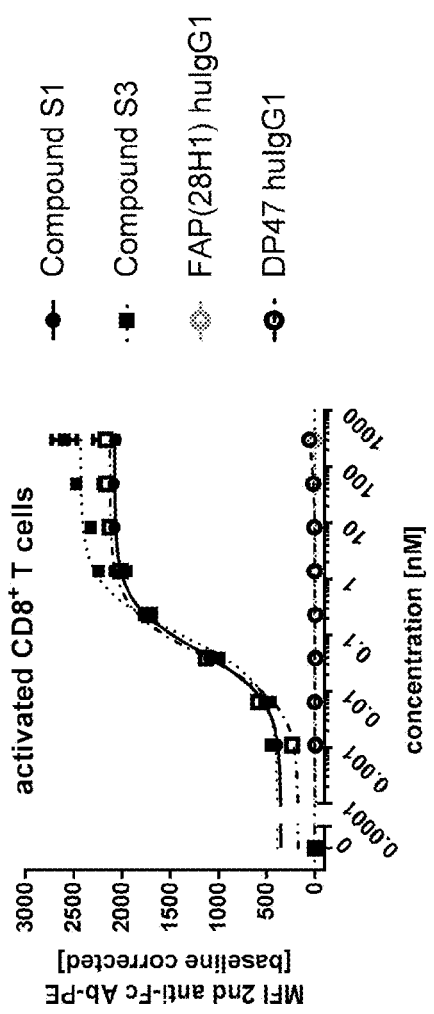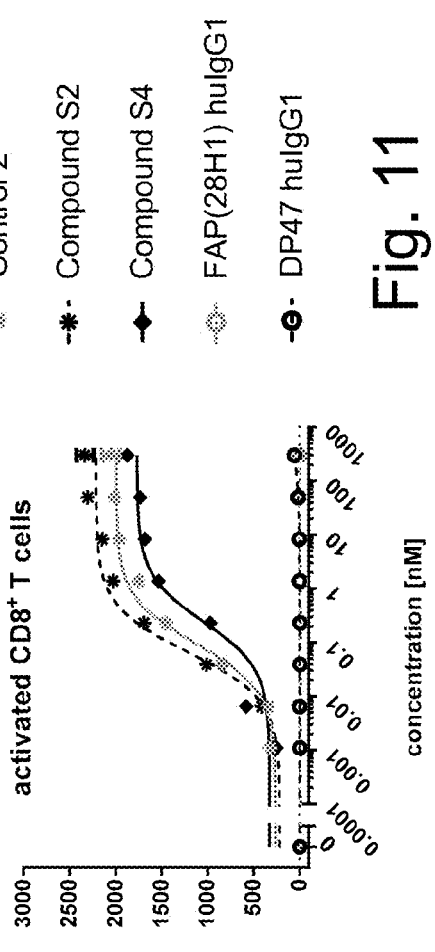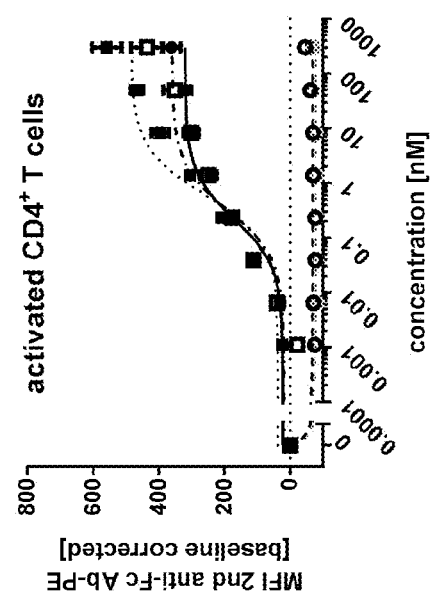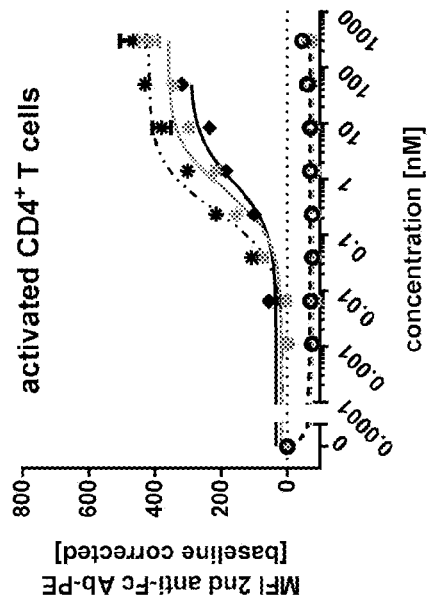
Fig. 11

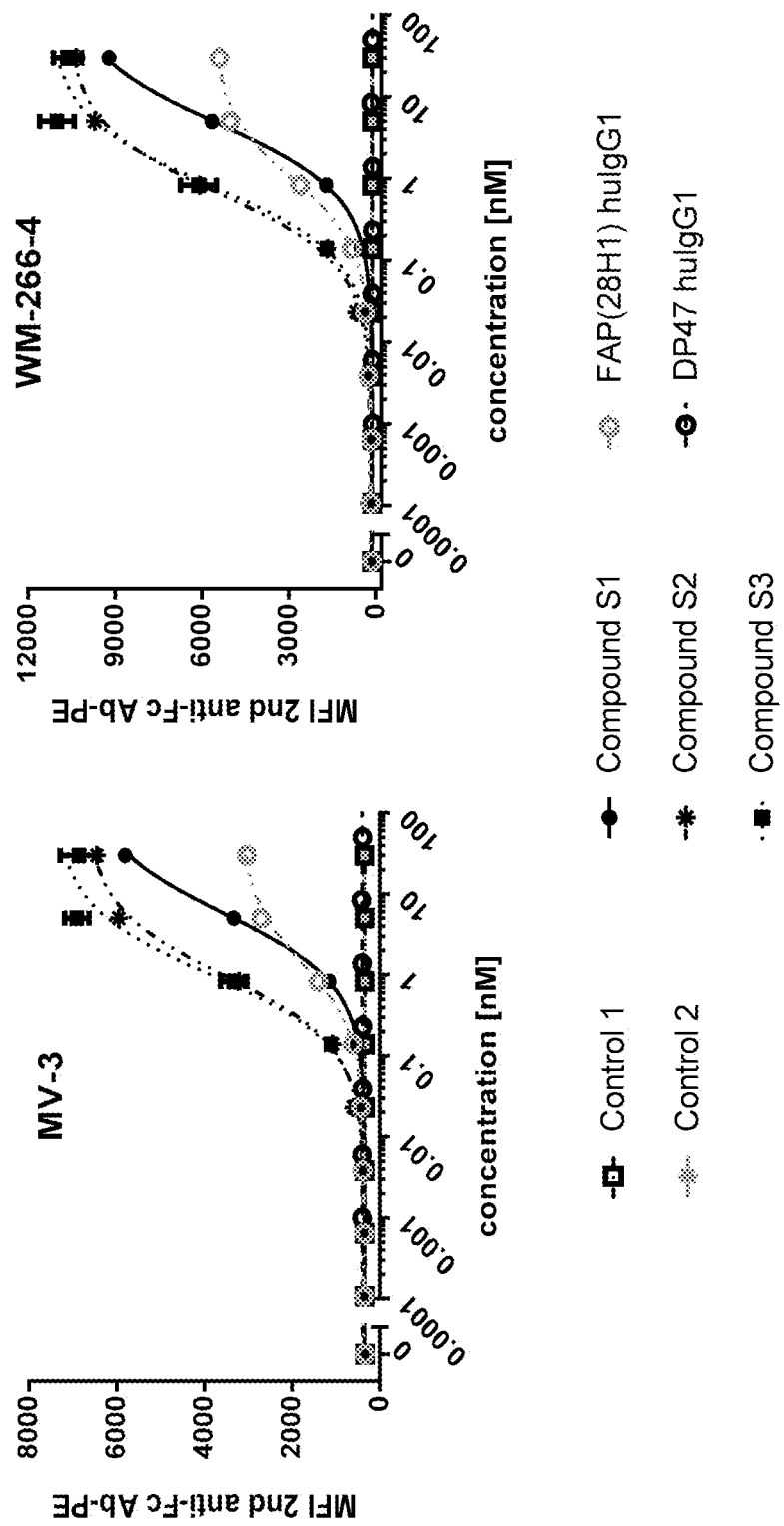

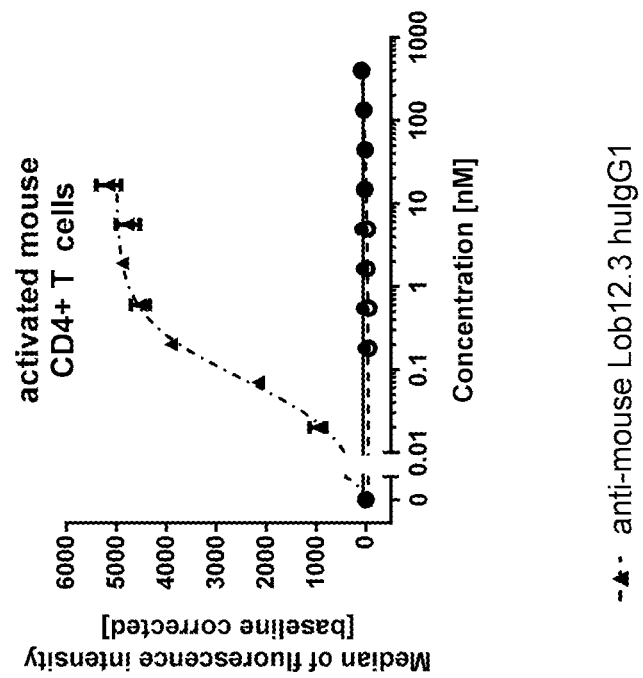
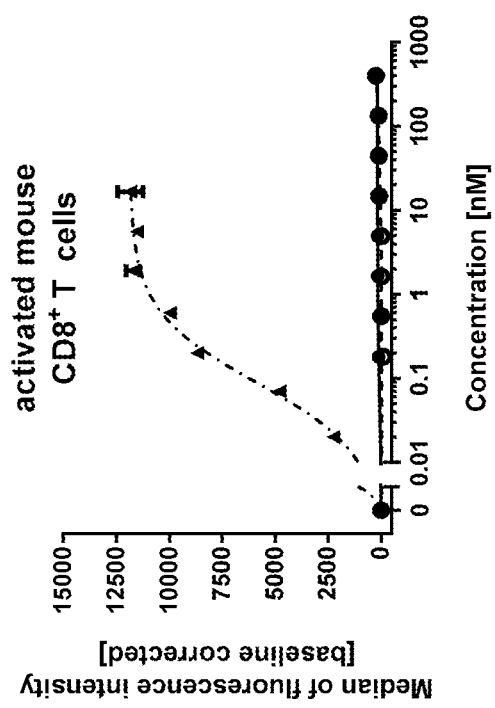

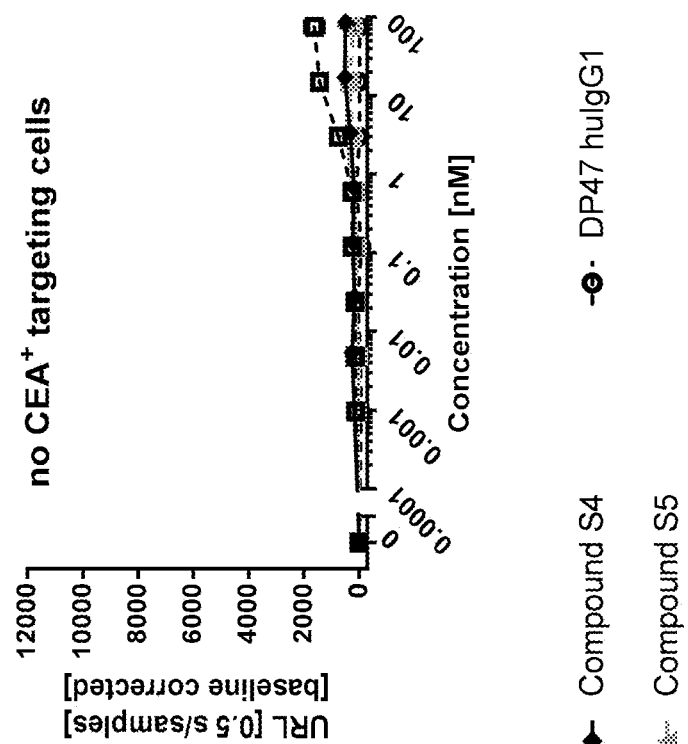
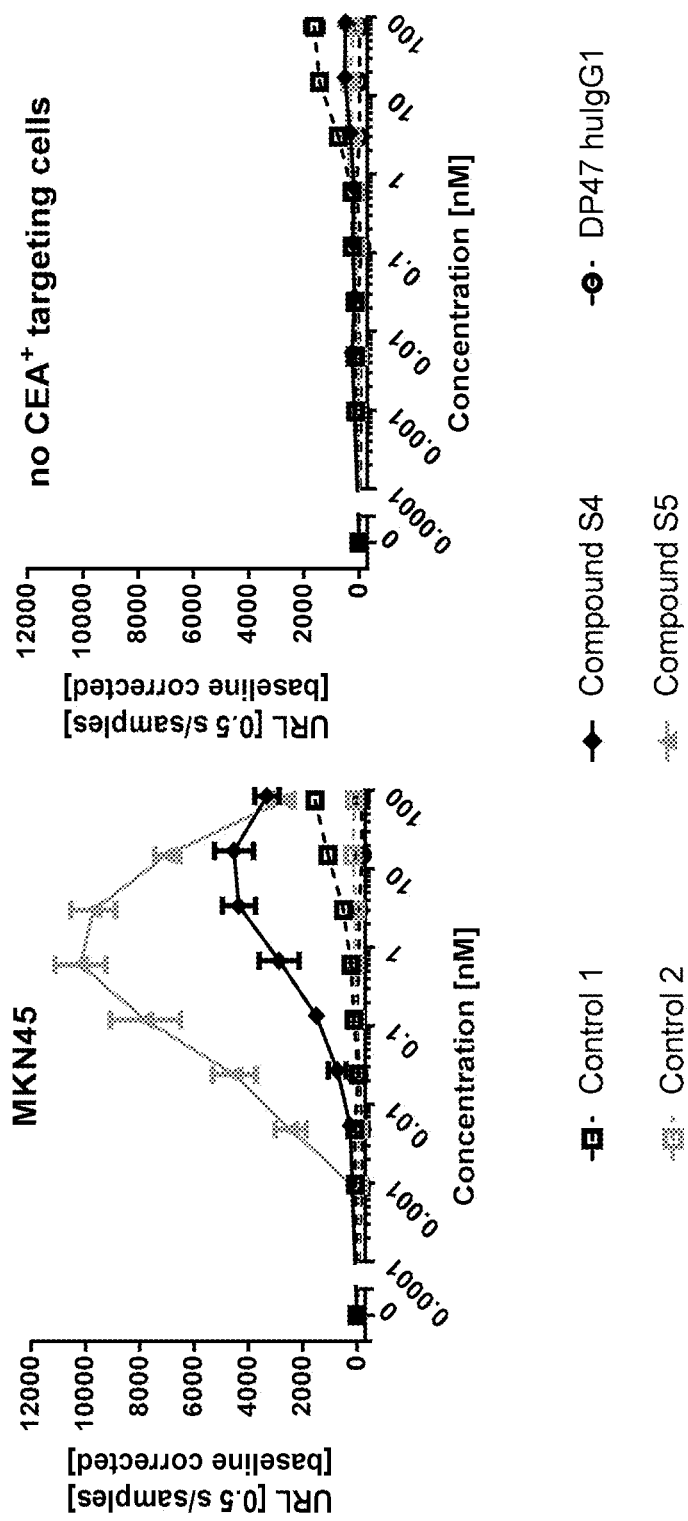
Fig. 20B
Fig. 20A

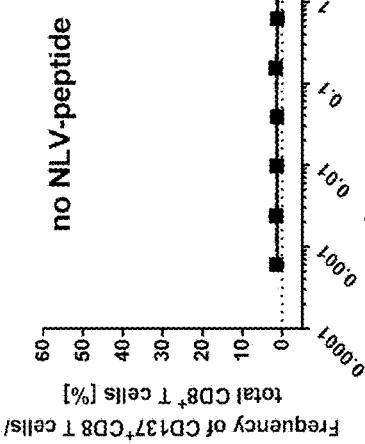
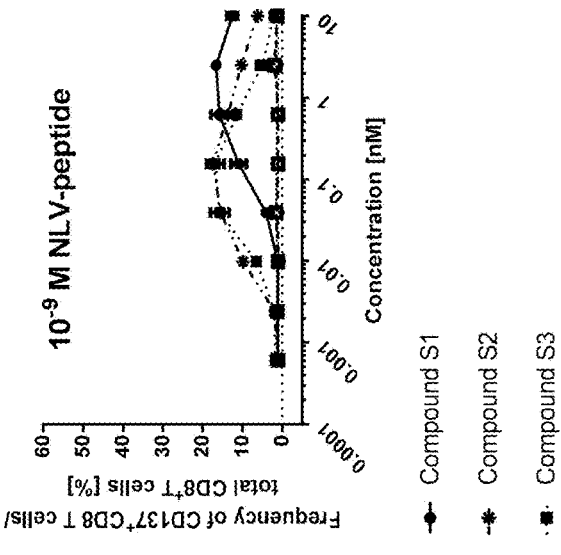
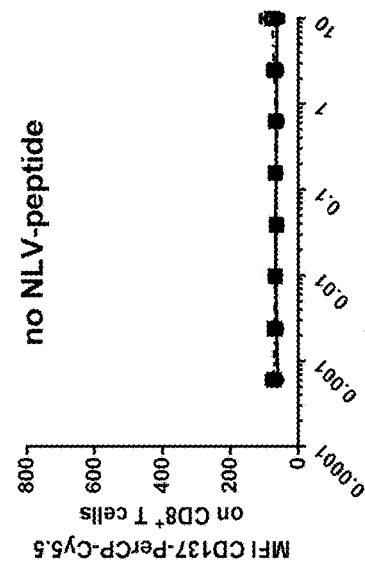
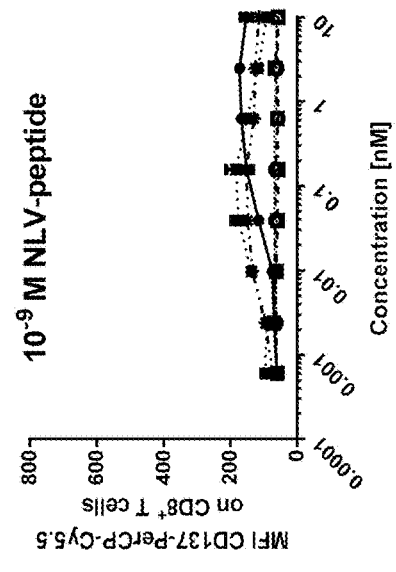

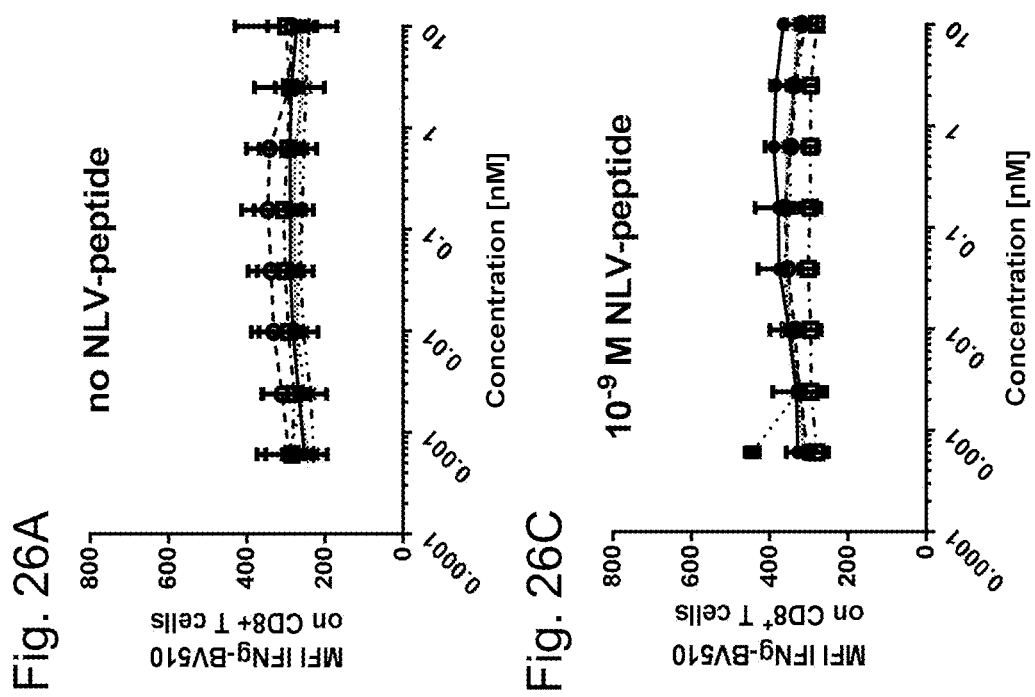

SEQUENCE LISTING

```
<160> NUMBER OF SEQ ID NOS: 183

<210> SEQ ID NO 1
<211> LENGTH: 184
<212> TYPE: PRT
<213> ORGANISM: Homo sapiens

<400> SEQUENCE: 1

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 2
<211> LENGTH: 170
<212> TYPE: PRT
<213> ORGANISM: Homo sapiens

<400> SEQUENCE: 2

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60
```

Leu Arg Arg Val Val Ala Gly Glu Gly Ser Ser Val Ser Leu Ala
65                  70                  75                  80

Leu His Leu Gln Pro Leu Arg Ser Ala Ala Gly Ala Ala Ala Leu Ala
            85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
            115                 120                 125

Gly Val His Leu His Thr Glu Ala Arg Ala Arg His Ala Trp Gln Leu
            130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 3
<211> LENGTH: 175
<212> TYPE: PRT
<213> ORGANISM: Homo sapiens

<400> SEQUENCE: 3

Asp Pro Ala Gly Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
            35                  40                  45

Glu Asp Thr Lys Glu Leu Val Val Ala Lys Ala Gly Val Tyr Tyr Val
50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
            85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 4
<211> LENGTH: 203
<212> TYPE: PRT
<213> ORGANISM: Homo sapiens

<400> SEQUENCE: 4

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
            35                  40                  45

```
Val Leu Leu Ile Asp Gly Pro Leu Ser Trp Tyr Ser Asp Pro Gly Leu
 50                  55                  60

Ala Gly Val Ser Leu Thr Gly Gly Leu Ser Tyr Lys Glu Asp Thr Lys
 65                  70                  75                  80

Glu Leu Val Val Ala Lys Ala Gly Val Tyr Tyr Val Phe Phe Gln Leu
                 85                  90                  95

Glu Leu Arg Arg Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
            195                 200
```

<210> SEQ ID NO 5
<211> LENGTH: 572
<212> TYPE: PRT
<213> ORGANISM: Artificial sequence
<220> FEATURE:
<223> OTHER INFORMATION: trimeric hu 4-1BBL (71-254) connected by (G4S)2 linker

<400> SEQUENCE: 5

```
Arg Glu Gly Pro Glu Leu Ser Pro Asp Asp Pro Ala Gly Leu Leu Asp
  1               5                  10                  15

Leu Arg Gln Gly Met Phe Ala Gln Leu Val Ala Gln Asn Val Leu Leu
                 20                  25                  30

Ile Asp Gly Pro Leu Ser Trp Tyr Ser Asp Pro Gly Leu Ala Gly Val
             35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Ala Gly Glu Gly Ser Gly Ser Val Ser Leu Ala Leu His
                 85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
            195                 200                 205
```

```
Leu Asp Leu Arg Gln Gly Met Phe Ala Gln Leu Val Ala Gln Asn Val
            210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
                260                 265                 270

Leu Arg Arg Val Val Ala Gly Glu Gly Ser Gly Ser Val Ser Leu Ala
            275                 280                 285

Leu His Leu Gln Pro Leu Arg Ser Ala Ala Gly Ala Ala Leu Ala
            290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
                340                 345                 350

Thr Gln Gly Ala Thr Val Leu Gly Leu Phe Arg Val Thr Pro Glu Ile
            355                 360                 365

Pro Ala Gly Leu Pro Ser Pro Arg Ser Glu Gly Gly Gly Ser Gly
370                 375                 380

Gly Gly Gly Ser Arg Glu Gly Pro Glu Leu Ser Pro Asp Asp Pro Ala
385                 390                 395                 400

Gly Leu Leu Asp Leu Arg Gln Gly Met Phe Ala Gln Leu Val Ala Gln
                405                 410                 415

Asn Val Leu Leu Ile Asp Gly Pro Leu Ser Trp Tyr Ser Asp Pro Gly
            420                 425                 430

Leu Ala Gly Val Ser Leu Thr Gly Gly Leu Ser Tyr Lys Glu Asp Thr
            435                 440                 445

Lys Glu Leu Val Val Ala Lys Ala Gly Val Tyr Tyr Val Phe Phe Gln
450                 455                 460

Leu Glu Leu Arg Arg Val Val Ala Gly Glu Gly Ser Gly Ser Val Ser
465                 470                 475                 480

Leu Ala Leu His Leu Gln Pro Leu Arg Ser Ala Ala Gly Ala Ala Ala
                485                 490                 495

Leu Ala Leu Thr Val Asp Leu Pro Pro Ala Ser Ser Glu Ala Arg Asn
                500                 505                 510

Ser Ala Phe Gly Phe Gln Gly Arg Leu Leu His Leu Ser Ala Gly Gln
            515                 520                 525

Arg Leu Gly Val His Leu His Thr Glu Ala Arg Ala Arg His Ala Trp
530                 535                 540

Gln Leu Thr Gln Gly Ala Thr Val Leu Gly Leu Phe Arg Val Thr Pro
545                 550                 555                 560

Glu Ile Pro Ala Gly Leu Pro Ser Pro Arg Ser Glu
                565                 570

<210> SEQ ID NO 6
<211> LENGTH: 133
<212> TYPE: PRT
<213> ORGANISM: Homo sapiens

<400> SEQUENCE: 6

Gln Val Ser His Arg Tyr Pro Arg Ile Gln Ser Ile Lys Val Gln Phe
```

```
                1               5                  10                  15
            Thr Glu Tyr Lys Lys Glu Lys Gly Phe Ile Leu Thr Ser Gln Lys Glu
                            20                  25                  30

Asp Glu Ile Met Lys Val Gln Asn Asn Ser Val Ile Ile Asn Cys Asp
                            35                  40                  45

Gly Phe Tyr Leu Ile Ser Leu Lys Gly Tyr Phe Ser Gln Glu Val Asn
                            50                  55                  60

Ile Ser Leu His Tyr Gln Lys Asp Glu Glu Pro Leu Phe Gln Leu Lys
            65                  70                  75                  80

Lys Val Arg Ser Val Asn Ser Leu Met Val Ala Ser Leu Thr Tyr Lys
                            85                  90                  95

Asp Lys Val Tyr Leu Asn Val Thr Thr Asp Asn Thr Ser Leu Asp Asp
                            100                 105                 110

Phe His Val Asn Gly Gly Glu Leu Ile Leu Ile His Gln Asn Pro Gly
                            115                 120                 125

Glu Phe Cys Val Leu
                            130

<210> SEQ ID NO 7
<211> LENGTH: 132
<212> TYPE: PRT
<213> ORGANISM: Homo sapiens

<400> SEQUENCE: 7

Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
                20                  25                  30

Glu Ile Met Lys Val Gln Asn Asn Ser Val Ile Ile Asn Cys Asp Gly
                35                  40                  45

Phe Tyr Leu Ile Ser Leu Lys Gly Tyr Phe Ser Gln Glu Val Asn Ile
                50                  55                  60

Ser Leu His Tyr Gln Lys Asp Glu Glu Pro Leu Phe Gln Leu Lys Lys
65              70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
                100                 105                 110

His Val Asn Gly Gly Glu Leu Ile Leu Ile His Gln Asn Pro Gly Glu
                115                 120                 125

Phe Cys Val Leu
            130

<210> SEQ ID NO 8
<211> LENGTH: 419
<212> TYPE: PRT
<213> ORGANISM: Artificial sequence
<220> FEATURE:
<223> OTHER INFORMATION: trimeric huOX40L((51-183) connected by (G4S)2
      linker

<400> SEQUENCE: 8

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
```

```
                35                  40                  45
Gly Phe Tyr Leu Ile Ser Leu Lys Gly Tyr Phe Ser Gln Glu Val Asn
 50                  55                  60
Ile Ser Leu His Tyr Gln Lys Asp Glu Glu Pro Leu Phe Gln Leu Lys
 65                  70                  75                  80
Lys Val Arg Ser Val Asn Ser Leu Met Val Ala Ser Leu Thr Tyr Lys
                 85                  90                  95
Asp Lys Val Tyr Leu Asn Val Thr Thr Asp Asn Thr Ser Leu Asp Asp
                100                 105                 110
Phe His Val Asn Gly Gly Glu Leu Ile Leu Ile His Gln Asn Pro Gly
                115                 120                 125
Glu Phe Cys Val Leu Gly Gly Gly Ser Gly Gly Gly Ser Gln
130                 135                 140
Val Ser His Arg Tyr Pro Arg Ile Gln Ser Ile Lys Val Gln Phe Thr
145                 150                 155                 160
Glu Tyr Lys Lys Glu Lys Gly Phe Ile Leu Thr Ser Gln Lys Glu Asp
                165                 170                 175
Glu Ile Met Lys Val Gln Asn Asn Ser Val Ile Ile Asn Cys Asp Gly
                180                 185                 190
Phe Tyr Leu Ile Ser Leu Lys Gly Tyr Phe Ser Gln Glu Val Asn Ile
                195                 200                 205
Ser Leu His Tyr Gln Lys Asp Glu Glu Pro Leu Phe Gln Leu Lys Lys
210                 215                 220
Val Arg Ser Val Asn Ser Leu Met Val Ala Ser Leu Thr Tyr Lys Asp
225                 230                 235                 240
Lys Val Tyr Leu Asn Val Thr Thr Asp Asn Thr Ser Leu Asp Asp Phe
                245                 250                 255
His Val Asn Gly Gly Glu Leu Ile Leu Ile His Gln Asn Pro Gly Glu
                260                 265                 270
Phe Cys Val Leu Gly Gly Gly Ser Gly Gly Gly Ser Gln Val
                275                 280                 285
Ser His Arg Tyr Pro Arg Ile Gln Ser Ile Lys Val Gln Phe Thr Glu
290                 295                 300
Tyr Lys Lys Glu Lys Gly Phe Ile Leu Thr Ser Gln Lys Glu Asp Glu
305                 310                 315                 320
Ile Met Lys Val Gln Asn Asn Ser Val Ile Ile Asn Cys Asp Gly Phe
                325                 330                 335
Tyr Leu Ile Ser Leu Lys Gly Tyr Phe Ser Gln Glu Val Asn Ile Ser
                340                 345                 350
Leu His Tyr Gln Lys Asp Glu Glu Pro Leu Phe Gln Leu Lys Lys Val
                355                 360                 365
Arg Ser Val Asn Ser Leu Met Val Ala Ser Leu Thr Tyr Lys Asp Lys
                370                 375                 380
Val Tyr Leu Asn Val Thr Thr Asp Asn Thr Ser Leu Asp Asp Phe His
385                 390                 395                 400
Val Asn Gly Gly Glu Leu Ile Leu Ile His Gln Asn Pro Gly Glu Phe
                405                 410                 415
Cys Val Leu

<210> SEQ ID NO 9
<211> LENGTH: 5
<212> TYPE: PRT
<213> ORGANISM: Artificial sequence
<220> FEATURE:
```

<223> OTHER INFORMATION: FAP(28H1) CDR-H1

<400> SEQUENCE: 9

Ser His Ala Met Ser
1               5

<210> SEQ ID NO 10
<211> LENGTH: 16
<212> TYPE: PRT
<213> ORGANISM: Artificial sequence
<220> FEATURE:
<223> OTHER INFORMATION: FAP(28H1) CDR-H2

<400> SEQUENCE: 10

Ala Ile Trp Ala Ser Gly Glu Gln Tyr Tyr Ala Asp Ser Val Lys Gly
1               5                   10                  15

<210> SEQ ID NO 11
<211> LENGTH: 8
<212> TYPE: PRT
<213> ORGANISM: Artificial sequence
<220> FEATURE:
<223> OTHER INFORMATION: FAP(28H1) CDR-H3

<400> SEQUENCE: 11

Gly Trp Leu Gly Asn Phe Asp Tyr
1               5

<210> SEQ ID NO 12
<211> LENGTH: 12
<212> TYPE: PRT
<213> ORGANISM: Artificial sequence
<220> FEATURE:
<223> OTHER INFORMATION: FAP(28H1) CDR-L1

<400> SEQUENCE: 12

Arg Ala Ser Gln Ser Val Ser Arg Ser Tyr Leu Ala
1               5                   10

<210> SEQ ID NO 13
<211> LENGTH: 7
<212> TYPE: PRT
<213> ORGANISM: Artificial sequence
<220> FEATURE:
<223> OTHER INFORMATION: FAP(28H1) CDR-L2

<400> SEQUENCE: 13

Gly Ala Ser Thr Arg Ala Thr
1               5

<210> SEQ ID NO 14
<211> LENGTH: 9
<212> TYPE: PRT
<213> ORGANISM: Artificial sequence
<220> FEATURE:
<223> OTHER INFORMATION: FAP(28H1) CDR-L3

<400> SEQUENCE: 14

Gln Gln Gly Gln Val Ile Pro Pro Thr
1               5

<210> SEQ ID NO 15
<211> LENGTH: 809
<212> TYPE: PRT
<213> ORGANISM: Artificial sequence
<220> FEATURE:
<223> OTHER INFORMATION: trimeric hu 4-1BBL(71-254) plus Fc knob chain

<400> SEQUENCE: 15

```
Arg Glu Gly Pro Glu Leu Ser Pro Asp Asp Pro Ala Gly Leu Leu Asp
 1               5                  10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Gln Leu Glu Leu Arg
 65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Leu Ala
290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Ser Gly
370                 375                 380

Gly Gly Gly Ser Arg Glu Gly Pro Glu Leu Ser Pro Asp Asp Pro Ala
385                 390                 395                 400

Gly Leu Leu Asp Leu Arg Gln Gly Met Phe Ala Gln Leu Val Ala Gln
```

```
            405                 410                 415
Asn Val Leu Leu Ile Asp Gly Pro Leu Ser Trp Tyr Ser Asp Pro Gly
            420                 425                 430

Leu Ala Gly Val Ser Leu Thr Gly Gly Leu Ser Tyr Lys Glu Asp Thr
            435                 440                 445

Lys Glu Leu Val Val Ala Lys Ala Gly Val Tyr Tyr Val Phe Phe Gln
            450                 455                 460

Leu Glu Leu Arg Arg Val Val Ala Gly Glu Gly Ser Gly Ser Val Ser
465                 470                 475                 480

Leu Ala Leu His Leu Gln Pro Leu Arg Ser Ala Ala Gly Ala Ala Ala
                485                 490                 495

Leu Ala Leu Thr Val Asp Leu Pro Pro Ala Ser Ser Glu Ala Arg Asn
                500                 505                 510

Ser Ala Phe Gly Phe Gln Gly Arg Leu Leu His Leu Ser Ala Gly Gln
                515                 520                 525

Arg Leu Gly Val His Leu His Thr Glu Ala Arg Ala Arg His Ala Trp
            530                 535                 540

Gln Leu Thr Gln Gly Ala Thr Val Leu Gly Leu Phe Arg Val Thr Pro
545                 550                 555                 560

Glu Ile Pro Ala Gly Leu Pro Ser Pro Arg Ser Glu Gly Ser Pro Gly
                565                 570                 575

Ser Ser Ser Ser Gly Ser Asp Lys Thr His Thr Cys Pro Pro Cys Pro
            580                 585                 590

Ala Pro Glu Ala Ala Gly Gly Pro Ser Val Phe Leu Phe Pro Pro Lys
            595                 600                 605

Pro Lys Asp Thr Leu Met Ile Ser Arg Thr Pro Glu Val Thr Cys Val
            610                 615                 620

Val Val Asp Val Ser His Glu Asp Pro Glu Val Lys Phe Asn Trp Tyr
625                 630                 635                 640

Val Asp Gly Val Glu Val His Asn Ala Lys Thr Lys Pro Arg Glu Glu
                645                 650                 655

Gln Tyr Asn Ser Thr Tyr Arg Val Val Ser Val Leu Thr Val Leu His
                660                 665                 670

Gln Asp Trp Leu Asn Gly Lys Glu Tyr Lys Cys Lys Val Ser Asn Lys
            675                 680                 685

Ala Leu Gly Ala Pro Ile Glu Lys Thr Ile Ser Lys Ala Lys Gly Gln
            690                 695                 700

Pro Arg Glu Pro Gln Val Tyr Thr Leu Pro Pro Cys Arg Asp Glu Leu
705                 710                 715                 720

Thr Lys Asn Gln Val Ser Leu Trp Cys Leu Val Lys Gly Phe Tyr Pro
                725                 730                 735

Ser Asp Ile Ala Val Glu Trp Glu Ser Asn Gly Gln Pro Glu Asn Asn
            740                 745                 750

Tyr Lys Thr Thr Pro Pro Val Leu Asp Ser Asp Gly Ser Phe Phe Leu
            755                 760                 765

Tyr Ser Lys Leu Thr Val Asp Lys Ser Arg Trp Gln Gln Gly Asn Val
            770                 775                 780

Phe Ser Cys Ser Val Met His Glu Ala Leu His Asn His Tyr Thr Gln
785                 790                 795                 800

Lys Ser Leu Ser Leu Ser Pro Gly Lys
            805
```

<210> SEQ ID NO 16

```
<211> LENGTH: 116
<212> TYPE: PRT
<213> ORGANISM: Artificial sequence
<220> FEATURE:
<223> OTHER INFORMATION: FAP(28H1) VH

<400> SEQUENCE: 16
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | His |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Ala | Ile | Trp | Ala | Ser | Gly | Glu | Gln | Tyr | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Lys | Gly | Trp | Leu | Gly | Asn | Phe | Asp | Tyr | Trp | Gly | Gln | Gly | Thr | Leu | Val |
| | | | 100 | | | | | 105 | | | | | 110 | | |
| Thr | Val | Ser | Ser | | | | | | | | | | | | |
| | | | 115 | | | | | | | | | | | | |

```
<210> SEQ ID NO 17
<211> LENGTH: 108
<212> TYPE: PRT
<213> ORGANISM: Artificial sequence
<220> FEATURE:
<223> OTHER INFORMATION: FAP(28H1) VL

<400> SEQUENCE: 17
```

| | | | | | | | | | | | | | | | |
|---|---|---|---|---|---|---|---|---|---|---|---|---|---|---|---|
| Glu | Ile | Val | Leu | Thr | Gln | Ser | Pro | Gly | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Arg | Ser |
| | | | 20 | | | | | 25 | | | | | 30 | | |
| Tyr | Leu | Ala | Trp | Tyr | Gln | Gln | Lys | Pro | Gly | Gln | Ala | Pro | Arg | Leu | Leu |
| | | | 35 | | | | | 40 | | | | | 45 | | |
| Ile | Ile | Gly | Ala | Ser | Thr | Arg | Ala | Thr | Gly | Ile | Pro | Asp | Arg | Phe | Ser |
| | 50 | | | | | 55 | | | | | 60 | | | | |
| Gly | Ser | Gly | Ser | Gly | Thr | Asp | Phe | Thr | Leu | Thr | Ile | Ser | Arg | Leu | Glu |
| 65 | | | | | 70 | | | | | 75 | | | | | 80 |
| Pro | Glu | Asp | Phe | Ala | Val | Tyr | Tyr | Cys | Gln | Gln | Gly | Gln | Val | Ile | Pro |
| | | | | 85 | | | | | 90 | | | | | 95 | |
| Pro | Thr | Phe | Gly | Gln | Gly | Thr | Lys | Val | Glu | Ile | Lys | | | | |
| | | | 100 | | | | | 105 | | | | | | | |

```
<210> SEQ ID NO 18
<211> LENGTH: 446
<212> TYPE: PRT
<213> ORGANISM: Artificial sequence
<220> FEATURE:
<223> OTHER INFORMATION: anti-FAP(28H1) Fc hole chain

<400> SEQUENCE: 18
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | His |
| | | | 20 | | | | | 25 | | | | | 30 | | |

```
Ala Met Ser Trp Val Arg Gln Ala Pro Gly Lys Gly Leu Glu Trp Val
            35                  40                  45
Ser Ala Ile Trp Ala Ser Gly Glu Gln Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Lys Gly Trp Leu Gly Asn Phe Asp Tyr Trp Gly Gln Gly Thr Leu Val
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
    210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Gly Ala Pro Ile Glu Lys Thr Ile Ser
                325                 330                 335
Lys Ala Lys Gly Gln Pro Arg Glu Pro Gln Val Cys Thr Leu Pro Pro
            340                 345                 350
Ser Arg Asp Glu Leu Thr Lys Asn Gln Val Ser Leu Ser Cys Ala Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Val Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445
```

<210> SEQ ID NO 19
<211> LENGTH: 215
<212> TYPE: PRT
<213> ORGANISM: Artificial sequence
<220> FEATURE:
<223> OTHER INFORMATION: anti-FAP(28H1) light chain

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 20
<211> LENGTH: 656
<212> TYPE: PRT
<213> ORGANISM: Artificial sequence
<220> FEATURE:
<223> OTHER INFORMATION: trimeric hu OX40L(51-183) plus Fc knob chain

<400> SEQUENCE: 20

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asp Asn Ser Val Ile Ile Asn Cys Asp
        35                  40                  45

Gly Phe Tyr Leu Ile Ser Leu Lys Gly Tyr Phe Ser Gln Glu Val Asp
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

```
Asp Lys Val Tyr Leu Asn Val Thr Thr Asp Asn Thr Ser Leu Asp Asp
            100                 105                 110
Phe His Val Asn Gly Gly Glu Leu Ile Leu Ile His Gln Asn Pro Gly
        115                 120                 125
Glu Phe Cys Val Leu Gly Gly Gly Ser Gly Gly Gly Ser Gln
    130                 135                 140
Val Ser His Arg Tyr Pro Arg Ile Gln Ser Ile Lys Val Gln Phe Thr
145                 150                 155                 160
Glu Tyr Lys Lys Glu Lys Gly Phe Ile Leu Thr Ser Gln Lys Glu Asp
                165                 170                 175
Glu Ile Met Lys Val Gln Asp Asn Ser Val Ile Ile Asn Cys Asp Gly
            180                 185                 190
Phe Tyr Leu Ile Ser Leu Lys Gly Tyr Phe Ser Gln Glu Val Asp Ile
        195                 200                 205
Ser Leu His Tyr Gln Lys Asp Glu Glu Pro Leu Phe Gln Leu Lys Lys
    210                 215                 220
Val Arg Ser Val Asn Ser Leu Met Val Ala Ser Leu Thr Tyr Lys Asp
225                 230                 235                 240
Lys Val Tyr Leu Asn Val Thr Thr Asp Asn Thr Ser Leu Asp Asp Phe
                245                 250                 255
His Val Asn Gly Gly Glu Leu Ile Leu Ile His Gln Asn Pro Gly Glu
            260                 265                 270
Phe Cys Val Leu Gly Gly Gly Ser Gly Gly Gly Ser Gln Val
        275                 280                 285
Ser His Arg Tyr Pro Arg Ile Gln Ser Ile Lys Val Gln Phe Thr Glu
    290                 295                 300
Tyr Lys Lys Glu Lys Gly Phe Ile Leu Thr Ser Gln Lys Glu Asp Glu
305                 310                 315                 320
Ile Met Lys Val Gln Asp Asn Ser Val Ile Ile Asn Cys Asp Gly Phe
                325                 330                 335
Tyr Leu Ile Ser Leu Lys Gly Tyr Phe Ser Gln Glu Val Asp Ile Ser
            340                 345                 350
Leu His Tyr Gln Lys Asp Glu Glu Pro Leu Phe Gln Leu Lys Lys Val
        355                 360                 365
Arg Ser Val Asn Ser Leu Met Val Ala Ser Leu Thr Tyr Lys Asp Lys
    370                 375                 380
Val Tyr Leu Asn Val Thr Thr Asp Asn Thr Ser Leu Asp Asp Phe His
385                 390                 395                 400
Val Asn Gly Gly Glu Leu Ile Leu Ile His Gln Asn Pro Gly Glu Phe
                405                 410                 415
Cys Val Leu Gly Ser Pro Gly Ser Ser Ser Gly Ser Asp Lys Thr
            420                 425                 430
His Thr Cys Pro Pro Cys Pro Ala Pro Glu Ala Ala Gly Gly Pro Ser
        435                 440                 445
Val Phe Leu Phe Pro Pro Lys Pro Lys Asp Thr Leu Met Ile Ser Arg
    450                 455                 460
Thr Pro Glu Val Thr Cys Val Val Asp Val Ser His Glu Asp Pro
465                 470                 475                 480
Glu Val Lys Phe Asn Trp Tyr Val Asp Gly Val Glu Val His Asn Ala
                485                 490                 495
Lys Thr Lys Pro Arg Glu Glu Gln Tyr Asn Ser Thr Tyr Arg Val Val
            500                 505                 510
Ser Val Leu Thr Val Leu His Gln Asp Trp Leu Asn Gly Lys Glu Tyr
```

```
            515                 520                 525
Lys Cys Lys Val Ser Asn Lys Ala Leu Gly Ala Pro Ile Glu Lys Thr
530                 535                 540

Ile Ser Lys Ala Lys Gly Gln Pro Arg Glu Pro Gln Val Tyr Thr Leu
545                 550                 555                 560

Pro Pro Cys Arg Asp Glu Leu Thr Lys Asn Gln Val Ser Leu Trp Cys
                565                 570                 575

Leu Val Lys Gly Phe Tyr Pro Ser Asp Ile Ala Val Glu Trp Glu Ser
                580                 585                 590

Asn Gly Gln Pro Glu Asn Asn Tyr Lys Thr Thr Pro Pro Val Leu Asp
                595                 600                 605

Ser Asp Gly Ser Phe Phe Leu Tyr Ser Lys Leu Thr Val Asp Lys Ser
                610                 615                 620

Arg Trp Gln Gln Gly Asn Val Phe Ser Cys Ser Val Met His Glu Ala
625                 630                 635                 640

Leu His Asn His Tyr Thr Gln Lys Ser Leu Ser Leu Ser Pro Gly Lys
                645                 650                 655

<210> SEQ ID NO 21
<211> LENGTH: 760
<212> TYPE: PRT
<213> ORGANISM: Homo sapiens

<400> SEQUENCE: 21

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65              70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240
```

-continued

Asp Glu Gln Tyr Pro Arg Thr Ile Asn Ile Pro Tyr Pro Lys Ala Gly
                    245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asp Tyr Ala Lys Tyr Tyr Ala Leu
    450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
    530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
        595                 600                 605

Glu Met Gly Phe Ile Asp Glu Lys Arg Ile Ala Ile Trp Gly Trp Ser
    610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp

```
                    660                 665                 670
Asn Leu Glu His Tyr Lys Asn Ser Thr Val Met Ala Arg Ala Glu Tyr
                675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
                755                 760

<210> SEQ ID NO 22
<211> LENGTH: 748
<212> TYPE: PRT
<213> ORGANISM: Artificial sequence
<220> FEATURE:
<223> OTHER INFORMATION: hu FAP ectodomain + poly-lys-tag + his tag

<400> SEQUENCE: 22

Arg Pro Ser Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
                20                  25                  30

Pro Asn Trp Ile Ser Gly Gln Glu Tyr Leu His Gln Ser Ala Asp Asn
            35                  40                  45

Asn Ile Val Leu Tyr Asn Ile Glu Thr Gly Gln Ser Tyr Thr Ile Leu
        50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
```

```
            260                 265                 270
Val Thr Asp Glu Arg Val Cys Leu Gln Trp Leu Lys Arg Val Gln Asn
            275                 280                 285
Val Ser Val Leu Ser Ile Cys Asp Phe Arg Glu Asp Trp Gln Thr Trp
            290                 295                 300
Asp Cys Pro Lys Thr Gln Glu His Ile Glu Glu Ser Arg Thr Gly Trp
305                 310                 315                 320
Ala Gly Gly Phe Phe Val Ser Thr Pro Val Phe Ser Tyr Asp Ala Ile
                325                 330                 335
Ser Tyr Tyr Lys Ile Phe Ser Asp Lys Asp Gly Tyr Lys His Ile His
                340                 345                 350
Tyr Ile Lys Asp Thr Val Glu Asn Ala Ile Gln Ile Thr Ser Gly Lys
                355                 360                 365
Trp Glu Ala Ile Asn Ile Phe Arg Val Thr Gln Asp Ser Leu Phe Tyr
            370                 375                 380
Ser Ser Asn Glu Phe Glu Glu Tyr Pro Gly Arg Arg Asn Ile Tyr Arg
385                 390                 395                 400
Ile Ser Ile Gly Ser Tyr Pro Pro Ser Lys Lys Cys Val Thr Cys His
                405                 410                 415
Leu Arg Lys Glu Arg Cys Gln Tyr Tyr Thr Ala Ser Phe Ser Asp Tyr
                420                 425                 430
Ala Lys Tyr Tyr Ala Leu Val Cys Tyr Gly Pro Gly Ile Pro Ile Ser
                435                 440                 445
Thr Leu His Asp Gly Arg Thr Asp Gln Glu Ile Lys Ile Leu Glu Glu
            450                 455                 460
Asn Lys Glu Leu Glu Asn Ala Leu Lys Asn Ile Gln Leu Pro Lys Glu
465                 470                 475                 480
Glu Ile Lys Lys Leu Glu Val Asp Glu Ile Thr Leu Trp Tyr Lys Met
                485                 490                 495
Ile Leu Pro Pro Gln Phe Asp Arg Ser Lys Lys Tyr Pro Leu Leu Ile
            500                 505                 510
Gln Val Tyr Gly Gly Pro Cys Ser Gln Ser Val Arg Ser Val Phe Ala
            515                 520                 525
Val Asn Trp Ile Ser Tyr Leu Ala Ser Lys Glu Gly Met Val Ile Ala
            530                 535                 540
Leu Val Asp Gly Arg Gly Thr Ala Phe Gln Gly Asp Lys Leu Leu Tyr
545                 550                 555                 560
Ala Val Tyr Arg Lys Leu Gly Val Tyr Glu Val Glu Asp Gln Ile Thr
                565                 570                 575
Ala Val Arg Lys Phe Ile Glu Met Gly Phe Ile Asp Glu Lys Arg Ile
                580                 585                 590
Ala Ile Trp Gly Trp Ser Tyr Gly Gly Tyr Val Ser Ser Leu Ala Leu
                595                 600                 605
Ala Ser Gly Thr Gly Leu Phe Lys Cys Gly Ile Ala Val Ala Pro Val
            610                 615                 620
Ser Ser Trp Glu Tyr Tyr Ala Ser Val Tyr Thr Glu Arg Phe Met Gly
625                 630                 635                 640
Leu Pro Thr Lys Asp Asp Asn Leu Glu His Tyr Lys Asn Ser Thr Val
                645                 650                 655
Met Ala Arg Ala Glu Tyr Phe Arg Asn Val Asp Tyr Leu Leu Ile His
                660                 665                 670
Gly Thr Ala Asp Asp Asn Val His Phe Gln Asn Ser Ala Gln Ile Ala
            675                 680                 685
```

```
Lys Ala Leu Val Asn Ala Gln Val Asp Phe Gln Ala Met Trp Tyr Ser
            690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
            740                 745
```

<210> SEQ ID NO 23
<211> LENGTH: 2244
<212> TYPE: DNA
<213> ORGANISM: Artificial sequence
<220> FEATURE:
<223> OTHER INFORMATION: DNA hu FAP ectodomain + poly-lys-tag + his tag

<400> SEQUENCE: 23

```
cgcccttcaa gagttcataa ctctgaagaa aatacaatga gagcactcac actgaaggat      60
atttaaatg  gaacattttc ttataaaaca tttttttccaa actggatttc aggacaagaa    120
tatcttcatc aatctgcaga taacaatata gtactttata atattgaaac aggacaatca    180
tataccattt tgagtaatag aaccatgaaa agtgtgaatg cttcaaatta cggcttatca    240
cctgatcggc aatttgtata tctagaaagt gattattcaa agctttggag atactcttac    300
acagcaacat attacatcta tgaccttagc aatggagaat ttgtaagagg aaatgagctt    360
cctcgtccaa ttcagtattt atgctggtcg cctgttggga gtaaattagc atatgtctat    420
caaaacaata tctatttgaa acaaagacca ggagatccac cttttcaaat aacatttaat    480
ggaagagaaa ataaaatatt taatggaatc ccagactggg tttatgaaga ggaaatgctt    540
gctacaaaat atgctctctg gtggtctcct aatggaaaat tttggcata tgcggaattt    600
aatgatacgg atataccagt tattgcctat tcctattatg gcgatgaaca atatcctaga    660
acaataaata ttccataccc aaaggctgga gctaagaatc ccgttgttcg atatttatt    720
atcgatacca cttaccctgc gtatgtaggt ccccaggaag tgcctgttcc agcaatgata    780
gcctcaagtg attattattt cagttggctc acgtgggtta ctgatgaacg agtatgtttg    840
cagtggctaa aaagagtcca gaatgtttcg gtcctgtcta tatgtgactt cagggaagac    900
tggcagacat gggattgtcc aaagacccag gagcatatag aagaaagcag aactggatgg    960
gctggtggat tctttgtttc aacaccagtt ttcagctatg atgccatttc gtactacaaa   1020
atatttagtg acaaggatgg ctacaaacat attcactata tcaaagacac tgtggaaaat   1080
gctattcaaa ttacaagtgg caagtgggag gccataaata tattcagagt aacacaggat   1140
tcactgtttt attctagcaa tgaatttgaa gaatacctg gaagaagaaa catctacaga   1200
attagcattg gaagctatcc tccaagcaag aagtgtgtta cttgccatct aaggaaagaa   1260
aggtgccaat attacacagc aagtttcagc gactacgcca agtactatgc acttgtctgc   1320
tacggcccag gcatccccat ttccacccctt catgatggac gcactgatca agaaattaaa   1380
atcctggaag aaaacaagga attggaaaat gctttgaaaa atatccagct gcctaaagag   1440
gaaattaaga acttgaagt agatgaaatt actttatggt acaagatgat tcttcctcct   1500
caatttgaca gatcaaagaa gtatcccttg ctaattcaag tgtatggtgg tccctgcagt   1560
cagagtgtaa ggtctgtatt tgctgttaat tggatatctt atcttgcaag taaggaaggg   1620
atggtcattg ccttggtgga tggtcgagga acagctttcc aaggtgacaa actcctctat   1680
```

-continued

```
gcagtgtatc gaaagctggg tgtttatgaa gttgaagacc agattacagc tgtcagaaaa    1740
ttcatagaaa tgggtttcat tgatgaaaaa agaatagcca tatggggctg gtcctatgga    1800
ggatacgttt catcactggc ccttgcatct ggaactggtc ttttcaaatg tggtatagca    1860
gtggctccag tctccagctg ggaatattac gcgtctgtct acacagagag attcatgggt    1920
ctcccaacaa aggatgataa tcttgagcac tataagaatt caactgtgat ggcaagagca    1980
gaatatttca gaaatgtaga ctatcttctc atccacggaa cagcagatga taatgtgcac    2040
tttcaaaact cagcacagat tgctaaagct ctggttaatg cacaagtgga tttccaggca    2100
atgtggtact ctgaccagaa ccacggctta tccggcctgt ccacgaacca cttatacacc    2160
cacatgaccc acttcctaaa gcagtgtttc tctttgtcag acggcaaaaa gaaaagaaa    2220 aagggccacc accatcacca tcac                                           2244
```

<210> SEQ ID NO 24
<211> LENGTH: 761
<212> TYPE: PRT
<213> ORGANISM: mus musculus

<400> SEQUENCE: 24

```
Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
                20                  25                  30

Lys Pro Glu Gly Asn Thr Lys Arg Ala Leu Thr Leu Lys Asp Ile Leu
            35                  40                  45

Asn Gly Thr Phe Ser Tyr Lys Thr Tyr Phe Pro Asn Trp Ile Ser Glu
        50                  55                  60

Gln Glu Tyr Leu His Gln Ser Glu Asp Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
                100                 105                 110

Tyr Leu Glu Ser Asp Tyr Ser Lys Leu Trp Arg Tyr Ser Tyr Thr Ala
            115                 120                 125

Thr Tyr Tyr Ile Tyr Asp Leu Gln Asn Gly Glu Phe Val Arg Gly Tyr
        130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Tyr Thr Gly Arg Glu Asn Arg Ile
            180                 185                 190

Phe Asn Gly Ile Pro Asp Trp Val Tyr Glu Glu Met Leu Ala Thr
        195                 200                 205

Lys Tyr Ala Leu Trp Trp Ser Pro Asp Gly Lys Phe Leu Ala Tyr Val
        210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
                245                 250                 255

Ala Lys Asn Pro Val Val Arg Val Phe Ile Val Asp Thr Thr Tyr Pro
                260                 265                 270
```

-continued

His His Val Gly Pro Met Glu Val Pro Val Pro Glu Met Ile Ala Ser
        275                 280                 285

Ser Asp Tyr Tyr Phe Ser Trp Leu Thr Trp Val Ser Ser Glu Arg Val
        290                 295                 300

Cys Leu Gln Trp Leu Lys Arg Val Gln Asn Val Ser Val Leu Ser Ile
305                 310                 315                 320

Cys Asp Phe Arg Glu Asp Trp His Ala Trp Glu Cys Pro Lys Asn Gln
                325                 330                 335

Glu His Val Glu Ser Arg Thr Gly Trp Ala Gly Phe Phe Val
        340                 345                 350

Ser Thr Pro Ala Phe Ser Gln Asp Ala Thr Ser Tyr Tyr Lys Ile Phe
        355                 360                 365

Ser Asp Lys Asp Gly Tyr Lys His Ile His Tyr Ile Lys Asp Thr Val
        370                 375                 380

Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Ser Asn Glu Phe Glu
                405                 410                 415

Gly Tyr Pro Gly Arg Arg Asn Ile Tyr Arg Ile Ser Ile Gly Asn Ser
        420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Tyr Lys Ala Lys Tyr Tyr Ala Leu
        450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                485                 490                 495

Ser Leu Arg Asn Ile Gln Leu Pro Lys Val Glu Ile Lys Lys Leu Lys
        500                 505                 510

Asp Gly Gly Leu Thr Phe Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
        530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
        580                 585                 590

Gly Val Tyr Glu Val Glu Asp Gln Leu Thr Ala Val Arg Lys Phe Ile
        595                 600                 605

Glu Met Gly Phe Ile Asp Glu Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
        660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn

```
              690                 695                 700
Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735

Ser Ser Gly Arg Ser Gln Asn His Leu Tyr Thr His Met Thr His Phe
            740                 745                 750

Leu Lys Gln Cys Phe Ser Leu Ser Asp
        755                 760
```

<210> SEQ ID NO 25
<211> LENGTH: 749
<212> TYPE: PRT
<213> ORGANISM: Artificial sequence
<220> FEATURE:
<223> OTHER INFORMATION: Murine FAP ectodomain + poly-lys-tag + his tag

<400> SEQUENCE: 25

```
Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
            20                  25                  30

Pro Asn Trp Ile Ser Glu Gln Glu Tyr Leu His Gln Ser Glu Asp Asp
        35                  40                  45

Asn Ile Val Phe Tyr Asn Ile Glu Thr Arg Glu Ser Tyr Ile Ile Leu
50                  55                  60

Ser Asn Ser Thr Met Lys Ser Val Asn Ala Thr Asp Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Gln Asn Gly
            100                 105                 110

Glu Phe Val Arg Gly Tyr Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
            180                 185                 190

Lys Phe Leu Ala Tyr Val Glu Phe Asn Asp Ser Asp Ile Pro Ile Ile
        195                 200                 205

Ala Tyr Ser Tyr Tyr Gly Asp Gly Gln Tyr Pro Arg Thr Ile Asn Ile
210                 215                 220

Pro Tyr Pro Lys Ala Gly Ala Lys Asn Pro Val Val Arg Val Phe Ile
225                 230                 235                 240

Val Asp Thr Thr Tyr Pro His His Val Gly Pro Met Glu Val Pro Val
                245                 250                 255

Pro Glu Met Ile Ala Ser Ser Asp Tyr Tyr Phe Ser Trp Leu Thr Trp
            260                 265                 270

Val Ser Ser Glu Arg Val Cys Leu Gln Trp Leu Lys Arg Val Gln Asn
        275                 280                 285

Val Ser Val Leu Ser Ile Cys Asp Phe Arg Glu Asp Trp His Ala Trp
```

-continued

```
            290                 295                 300
Glu Cys Pro Lys Asn Gln Glu His Val Glu Glu Ser Arg Thr Gly Trp
305                 310                 315                 320

Ala Gly Gly Phe Phe Val Ser Thr Pro Ala Phe Ser Gln Asp Ala Thr
                325                 330                 335

Ser Tyr Tyr Lys Ile Phe Ser Asp Lys Asp Gly Tyr Lys His Ile His
                340                 345                 350

Tyr Ile Lys Asp Thr Val Glu Asn Ala Ile Gln Ile Thr Ser Gly Lys
                355                 360                 365

Trp Glu Ala Ile Tyr Ile Phe Arg Val Thr Gln Asp Ser Leu Phe Tyr
370                 375                 380

Ser Ser Asn Glu Phe Glu Gly Tyr Pro Gly Arg Arg Asn Ile Tyr Arg
385                 390                 395                 400

Ile Ser Ile Gly Asn Ser Pro Pro Ser Lys Lys Cys Val Thr Cys His
                405                 410                 415

Leu Arg Lys Glu Arg Cys Gln Tyr Tyr Thr Ala Ser Phe Ser Tyr Lys
                420                 425                 430

Ala Lys Tyr Tyr Ala Leu Val Cys Tyr Gly Pro Gly Leu Pro Ile Ser
                435                 440                 445

Thr Leu His Asp Gly Arg Thr Asp Gln Glu Ile Gln Val Leu Glu Glu
                450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
                485                 490                 495

Ile Leu Pro Pro Gln Phe Asp Arg Ser Lys Lys Tyr Pro Leu Leu Ile
                500                 505                 510

Gln Val Tyr Gly Gly Pro Cys Ser Gln Ser Val Lys Ser Val Phe Ala
                515                 520                 525

Val Asn Trp Ile Thr Tyr Leu Ala Ser Lys Glu Gly Ile Val Ile Ala
                530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Asp Gln Leu Thr
                565                 570                 575

Ala Val Arg Lys Phe Ile Glu Met Gly Phe Ile Asp Glu Glu Arg Ile
                580                 585                 590

Ala Ile Trp Gly Trp Ser Tyr Gly Gly Tyr Val Ser Ser Leu Ala Leu
                595                 600                 605

Ala Ser Gly Thr Gly Leu Phe Lys Cys Gly Ile Ala Val Ala Pro Val
610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
                675                 680                 685

Lys Ala Leu Val Asn Ala Gln Val Asp Phe Gln Ala Met Trp Tyr Ser
                690                 695                 700

Asp Gln Asn His Gly Ile Leu Ser Gly Arg Ser Gln Asn His Leu Tyr
705                 710                 715                 720
```

Thr His Met Thr His Phe Leu Lys Gln Cys Phe Ser Leu Ser Asp Gly
            725                 730                 735

Lys Lys Lys Lys Lys Lys Gly His His His His His
            740                 745

<210> SEQ ID NO 26
<211> LENGTH: 2247
<212> TYPE: DNA
<213> ORGANISM: Artificial sequence
<220> FEATURE:
<223> OTHER INFORMATION: Murine FAP ectodomain + poly-lys-tag + his tag

<400> SEQUENCE: 26

| | | | | | |
|---|---|---|---|---|---|
| cgtccctcaa | gagtttacaa | acctgaagga | aacacaaaga | gagctcttac | cttgaaggat | 60 |
| attttaaatg | gaacattctc | atataaaaca | tattttccca | actggatttc | agaacaagaa | 120 |
| tatcttcatc | aatctgagga | tgataacata | gtattttata | atattgaaac | aagagaatca | 180 |
| tatatcattt | tgagtaatag | caccatgaaa | agtgtgaatg | ctacagatta | tggtttgtca | 240 |
| cctgatcggc | aatttgtgta | tctagaaagt | gattattcaa | agctctggcg | atattcatac | 300 |
| acagcgacat | actacatcta | cgaccttcag | aatggggaat | tgtaagagg | atacgagctc | 360 |
| cctcgtccaa | ttcagtatct | atgctggtcg | cctgttggga | gtaaattagc | atatgtatat | 420 |
| caaaacaata | tttatttgaa | acaaagacca | ggagatccac | cttttcaaat | aacttatact | 480 |
| ggaagagaaa | atagaatatt | taatggaata | ccagactggg | tttatgaaga | ggaaatgctt | 540 |
| gccacaaaat | atgctctttg | gtggtctcca | atggaaaat | ttttggcata | tgtagaattt | 600 |
| aatgattcag | atatccaat | tattgcctat | tcttattatg | gtgatggaca | gtatcctaga | 660 |
| actataaata | ttccatatcc | aaaggctggg | gctaagaatc | cggttgttcg | tgttttatt | 720 |
| gttgacacca | cctaccctca | ccacgtgggc | ccaatggaag | tgccagttcc | agaaatgata | 780 |
| gcctcaagtg | actattattt | cagctggctc | acatgggtgt | ccagtgaacg | agtatgcttg | 840 |
| cagtggctaa | aagagtgca | gaatgtctca | gtcctgtcta | tatgtgattt | cagggaagac | 900 |
| tggcatgcat | gggaatgtcc | aaagaaccag | gagcatgtag | aagaaagcag | aacaggatgg | 960 |
| gctggtggat | tctttgtttc | gacaccagct | tttagccagg | atgccacttc | ttactacaaa | 1020 |
| atatttagcg | acaaggatgg | ttacaaacat | attcactaca | tcaaagacac | tgtggaaaat | 1080 |
| gctattcaaa | ttacaagtgg | caagtgggag | gccatatata | tattccgcgt | aacacaggat | 1140 |
| tcactgtttt | attctagcaa | tgaatttgaa | ggttaccctg | aagaagaaa | catctacaga | 1200 |
| attagcattg | gaaactctcc | tccgagcaag | aagtgtgtta | cttgccatct | aaggaaagaa | 1260 |
| aggtgccaat | attacacagc | aagtttcagc | tacaaagcca | agtactatgc | actcgtctgc | 1320 |
| tatgccctg | gcctccccat | ttccacctc | catgatggcc | gcacagacca | agaaatacaa | 1380 |
| gtattagaag | aaaacaaaga | actggaaaat | tctctgagaa | atatccagct | gcctaaagtg | 1440 |
| gagattaaga | agctcaaaga | cgggggactg | actttctggt | acaagatgat | tctgcctcct | 1500 |
| cagtttgaca | gatcaaagaa | gtacccttg | ctaattcaag | tgtatggtgg | tccttgtagc | 1560 |
| cagagtgtta | agtctgtgtt | tgctgttaat | tggataactt | atctcgcaag | taaggaggg | 1620 |
| atagtcattg | ccctggtaga | tggtcggggc | actgcttcc | aaggtgacaa | attcctgcat | 1680 |
| gccgtgtatc | gaaaactggg | tgtatatgaa | gttgaggacc | agctcacagc | tgtcagaaaa | 1740 |
| ttcatagaaa | tgggtttcat | tgatgaagaa | agaatagcca | tgggggctg | gtcctacgga | 1800 |
| ggttatgttt | catccctggc | ccttgcatct | ggaactggtc | ttttcaaatg | tggcatagca | 1860 |

```
gtggctccag tctccagctg ggaatattac gcatctatct actcagagag attcatgggc   1920
ctcccaacaa aggacgacaa tctcgaacac tataaaaatt caactgtgat ggcaagagca   1980
gaatatttca gaaatgtaga ctatcttctc atccacggaa cagcagatga taatgtgcac   2040
tttcagaact cagcacagat tgctaaagct ttggttaatg cacaagtgga tttccaggcg   2100
atgtggtact ctgaccagaa ccatggtata ttatctgggc gctcccagaa tcatttatat   2160
acccacatga cgcacttcct caagcaatgc ttttctttat cagacggcaa aaagaaaaag   2220
aaaaagggcc accaccatca ccatcac                                       2247
```

<210> SEQ ID NO 27
<211> LENGTH: 748
<212> TYPE: PRT
<213> ORGANISM: Artificial sequence
<220> FEATURE:
<223> OTHER INFORMATION: Cynomolgus FAP ectodomain + poly-lys-tag + his tag

<400> SEQUENCE: 27

```
Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285
```

```
Val Ser Val Leu Ser Ile Cys Asp Phe Arg Glu Asp Trp Gln Thr Trp
    290             295                 300

Asp Cys Pro Lys Thr Gln Glu His Ile Glu Glu Ser Arg Thr Gly Trp
305             310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365

Trp Glu Ala Ile Asn Ile Phe Arg Val Thr Gln Asp Ser Leu Phe Tyr
370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
        450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
        530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
        610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
        690                 695                 700

Asp Gln Asn His Gly Leu Ser Gly Leu Ser Thr Asn His Leu Tyr Thr
```

```
                705                 710                 715                 720
His Met Thr His Phe Leu Lys Gln Cys Phe Ser Leu Ser Asp Gly Lys
                    725                 730                 735

Lys Lys Lys Lys Lys Gly His His His His His
                740                 745

<210> SEQ ID NO 28
<211> LENGTH: 2244
<212> TYPE: PRT
<213> ORGANISM: Artificial sequence
<220> FEATURE:
<223> OTHER INFORMATION: cynomolgus FAP ectodomain + poly-lys-tag + his
      tag

<400> SEQUENCE: 28

Cys Gly Cys Cys Cys Thr Cys Ala Ala Gly Ala Gly Thr Thr Cys
1               5                   10                  15

Ala Thr Ala Ala Cys Thr Cys Thr Gly Ala Ala Gly Ala Ala Ala Ala
                20                  25                  30

Thr Ala Cys Ala Ala Thr Gly Ala Gly Ala Gly Cys Ala Thr Cys
            35                  40                  45

Ala Cys Ala Cys Thr Gly Ala Ala Gly Gly Ala Thr Ala Thr Thr
50                  55                  60

Thr Ala Ala Ala Thr Gly Gly Gly Ala Cys Ala Thr Thr Thr Cys
65                  70                  75                  80

Thr Thr Ala Thr Ala Ala Ala Cys Ala Thr Thr Thr Thr Thr
                85                  90                  95

Cys Cys Ala Ala Ala Cys Thr Gly Gly Ala Thr Thr Cys Ala Gly
                100                 105                 110

Gly Ala Cys Ala Ala Gly Ala Ala Thr Ala Thr Cys Thr Thr Cys Ala
            115                 120                 125

Thr Cys Ala Ala Thr Cys Thr Gly Cys Ala Gly Ala Thr Ala Ala Cys
            130                 135                 140

Ala Ala Thr Ala Thr Ala Gly Thr Ala Cys Thr Thr Thr Ala Thr Ala
145                 150                 155                 160

Ala Thr Ala Thr Thr Gly Ala Ala Ala Cys Ala Gly Gly Ala Cys Ala
                165                 170                 175

Ala Thr Cys Ala Thr Ala Thr Ala Cys Cys Ala Thr Thr Thr Thr Gly
            180                 185                 190

Ala Gly Thr Ala Ala Cys Ala Gly Ala Ala Cys Cys Ala Thr Gly Ala
                195                 200                 205

Ala Ala Ala Gly Thr Gly Thr Gly Ala Ala Thr Gly Cys Thr Thr Cys
            210                 215                 220

Ala Ala Ala Thr Thr Ala Thr Gly Gly Cys Thr Thr Ala Thr Cys Ala
225                 230                 235                 240

Cys Cys Thr Gly Ala Thr Cys Gly Gly Cys Ala Ala Thr Thr Gly
                245                 250                 255

Thr Ala Thr Ala Thr Cys Thr Ala Gly Ala Ala Ala Gly Thr Gly Ala
                260                 265                 270

Thr Thr Ala Thr Thr Cys Ala Ala Ala Gly Cys Thr Thr Gly Gly
            275                 280                 285

Ala Gly Ala Thr Ala Cys Thr Cys Thr Thr Ala Cys Ala Cys Ala Gly
                290                 295                 300

Cys Ala Ala Cys Ala Thr Ala Thr Thr Ala Cys Ala Thr Cys Thr Ala
305                 310                 315                 320
```

-continued

```
Thr Gly Ala Cys Cys Thr Thr Ala Gly Cys Ala Ala Thr Gly Gly Ala
            325                 330                 335

Gly Ala Ala Thr Thr Thr Gly Thr Ala Ala Gly Ala Gly Gly Ala Ala
            340                 345                 350

Ala Thr Gly Ala Gly Cys Thr Thr Cys Cys Thr Cys Gly Thr Cys Cys
            355                 360                 365

Ala Ala Thr Thr Cys Ala Gly Thr Ala Thr Thr Ala Thr Gly Cys
            370                 375             380

Thr Gly Gly Thr Cys Gly Cys Cys Thr Gly Thr Gly Gly Gly Ala
385                 390                 395                 400

Gly Thr Ala Ala Ala Thr Thr Ala Gly Cys Ala Thr Ala Thr Gly Thr
            405                 410                 415

Cys Thr Ala Thr Cys Ala Ala Ala Cys Ala Ala Thr Ala Thr Cys
            420                 425                 430

Thr Ala Thr Thr Thr Gly Ala Ala Cys Ala Ala Ala Gly Ala Cys
            435                 440                 445

Cys Ala Gly Gly Ala Gly Ala Thr Cys Cys Ala Cys Cys Thr Thr Thr
            450                 455                 460

Thr Cys Ala Ala Ala Thr Ala Ala Cys Ala Thr Thr Ala Ala Thr
465                 470                 475                 480

Gly Gly Ala Ala Gly Ala Gly Ala Ala Ala Thr Ala Ala Ala
            485                 490                 495

Thr Ala Thr Thr Thr Ala Ala Thr Gly Gly Ala Ala Thr Cys Cys Cys
            500                 505                 510

Ala Gly Ala Cys Thr Gly Gly Gly Thr Thr Thr Ala Thr Gly Ala Ala
            515                 520                 525

Gly Ala Gly Gly Ala Ala Thr Gly Cys Thr Thr Gly Cys Thr Ala
            530                 535                 540

Cys Ala Ala Ala Thr Ala Thr Gly Cys Thr Cys Thr Cys Thr Gly
545                 550                 555                 560

Gly Thr Gly Gly Thr Cys Thr Cys Cys Thr Ala Ala Thr Gly Gly Ala
            565                 570                 575

Ala Ala Ala Thr Thr Thr Thr Thr Gly Gly Cys Ala Thr Ala Thr Gly
            580                 585                 590

Cys Gly Gly Ala Ala Thr Thr Thr Ala Ala Thr Gly Ala Thr Ala Cys
            595                 600                 605

Ala Gly Ala Thr Ala Thr Ala Cys Cys Ala Gly Thr Thr Ala Thr Thr
            610                 615                 620

Gly Cys Cys Thr Ala Thr Thr Cys Cys Thr Ala Thr Ala Thr Gly
625                 630                 635                 640

Gly Cys Gly Ala Thr Gly Ala Ala Cys Ala Ala Thr Ala Thr Cys Cys
            645                 650                 655

Cys Ala Gly Ala Ala Cys Ala Ala Thr Ala Ala Ala Thr Ala Thr
            660                 665                 670

Cys Cys Ala Thr Ala Cys Cys Ala Ala Ala Gly Gly Cys Cys Gly
            675                 680                 685

Gly Ala Gly Cys Thr Ala Ala Gly Ala Ala Thr Cys Cys Thr Thr Thr
            690                 695                 700

Thr Gly Thr Thr Cys Gly Gly Ala Thr Ala Thr Thr Ala Thr Thr
705                 710                 715                 720

Ala Thr Cys Gly Ala Thr Ala Cys Cys Ala Cys Thr Ala Cys Cys
            725                 730                 735

Cys Thr Gly Cys Gly Thr Ala Thr Gly Thr Ala Gly Gly Thr Cys Cys
```

```
                    740                 745                 750
Cys Cys Ala Gly Gly Ala Ala Gly Thr Gly Cys Cys Thr Gly Thr Thr
                755                 760                 765
Cys Cys Ala Gly Cys Ala Ala Thr Gly Ala Thr Ala Gly Cys Cys Thr
                770                 775                 780
Cys Ala Ala Gly Thr Gly Ala Thr Thr Ala Thr Thr Ala Thr Thr Thr
785                 790                 795                 800
Cys Ala Gly Thr Thr Gly Gly Cys Thr Cys Ala Cys Gly Thr Gly Gly
                805                 810                 815
Gly Thr Thr Ala Cys Thr Gly Ala Thr Gly Ala Ala Cys Gly Ala Gly
                820                 825                 830
Thr Ala Thr Gly Thr Thr Thr Gly Cys Ala Gly Thr Gly Gly Cys Thr
                835                 840                 845
Ala Ala Ala Ala Ala Gly Ala Gly Thr Cys Cys Ala Gly Ala Ala Thr
                850                 855                 860
Gly Thr Thr Thr Cys Gly Gly Thr Cys Thr Thr Gly Thr Cys Thr Ala
865                 870                 875                 880
Thr Ala Thr Gly Thr Gly Ala Thr Thr Cys Ala Gly Gly Ala
                885                 890                 895
Ala Gly Ala Cys Thr Gly Gly Cys Ala Gly Ala Cys Ala Thr Gly Gly
                900                 905                 910
Gly Ala Thr Thr Gly Thr Cys Ala Ala Ala Gly Ala Cys Cys Cys
                915                 920                 925
Ala Gly Gly Ala Gly Cys Ala Thr Ala Thr Ala Gly Ala Ala Gly Ala
                930                 935                 940
Ala Ala Gly Cys Ala Gly Ala Ala Cys Thr Gly Gly Ala Thr Gly Gly
945                 950                 955                 960
Gly Cys Thr Gly Gly Thr Gly Gly Ala Thr Thr Cys Thr Thr Thr Gly
                965                 970                 975
Thr Thr Thr Cys Ala Ala Cys Ala Cys Cys Ala Gly Thr Thr Thr
                980                 985                 990
Cys Ala Gly Cys Thr Ala Thr Gly Ala Thr Gly Cys Cys Ala Thr Thr
                995                 1000                1005
Thr Cys Ala Thr Ala Cys Thr Ala Cys Ala Ala Ala Ala Thr Ala
                1010                1015                1020
Thr Thr Thr Ala Gly Thr Gly Ala Cys Ala Ala Gly Gly Ala Thr
                1025                1030                1035
Gly Gly Cys Thr Ala Cys Ala Ala Ala Cys Ala Thr Ala Thr Thr
                1040                1045                1050
Cys Ala Cys Thr Ala Thr Ala Thr Cys Ala Ala Ala Gly Ala Cys
                1055                1060                1065
Ala Cys Thr Gly Thr Gly Gly Ala Ala Ala Ala Thr Gly Cys Thr
                1070                1075                1080
Ala Thr Thr Cys Ala Ala Ala Thr Thr Ala Cys Ala Ala Gly Thr
                1085                1090                1095
Gly Gly Cys Ala Ala Gly Thr Gly Gly Gly Ala Gly Gly Cys Cys
                1100                1105                1110
Ala Thr Ala Ala Ala Thr Ala Thr Ala Thr Thr Cys Ala Gly Ala
                1115                1120                1125
Gly Thr Ala Ala Cys Ala Cys Ala Gly Gly Ala Thr Thr Cys Ala
                1130                1135                1140
Cys Thr Gly Thr Thr Thr Thr Ala Thr Thr Cys Thr Ala Gly Cys
                1145                1150                1155
```

```
Ala Ala Thr Gly Ala Ala Thr Thr Thr Gly Ala Ala Gly Ala Thr
1160                1165                1170

Thr Ala Cys Cys Cys Thr Gly Gly Ala Ala Gly Ala Ala Gly Ala
1175                1180                1185

Ala Ala Cys Ala Thr Cys Thr Ala Cys Ala Gly Ala Ala Thr Thr
1190                1195                1200

Ala Gly Cys Ala Thr Gly Gly Ala Ala Gly Cys Thr Ala Thr
1205                1210                1215

Cys Cys Thr Cys Cys Ala Ala Gly Cys Ala Ala Gly Ala Ala Gly
1220                1225                1230

Thr Gly Thr Gly Thr Thr Ala Cys Thr Gly Cys Cys Ala Thr
1235                1240                1245

Cys Thr Ala Ala Gly Gly Ala Ala Ala Gly Ala Ala Ala Gly Gly
1250                1255                1260

Thr Gly Cys Cys Ala Ala Thr Ala Thr Thr Ala Cys Ala Cys Ala
1265                1270                1275

Gly Cys Ala Ala Gly Thr Thr Thr Cys Ala Gly Cys Gly Ala Cys
1280                1285                1290

Thr Ala Cys Gly Cys Cys Ala Ala Gly Thr Ala Cys Thr Ala Thr
1295                1300                1305

Gly Cys Ala Cys Thr Thr Gly Thr Cys Thr Gly Cys Thr Ala Thr
1310                1315                1320

Gly Gly Cys Cys Cys Ala Gly Gly Cys Ala Thr Cys Cys Cys Cys
1325                1330                1335

Ala Thr Thr Thr Cys Cys Ala Cys Cys Cys Thr Thr Cys Ala Thr
1340                1345                1350

Gly Ala Cys Gly Gly Ala Cys Gly Cys Ala Cys Thr Gly Ala Thr
1355                1360                1365

Cys Ala Ala Gly Ala Ala Ala Thr Thr Ala Ala Ala Ala Thr Cys
1370                1375                1380

Cys Thr Gly Gly Ala Ala Gly Ala Ala Ala Ala Cys Ala Ala Gly
1385                1390                1395

Gly Ala Ala Thr Thr Gly Gly Ala Ala Ala Ala Thr Gly Cys Thr
1400                1405                1410

Thr Thr Gly Ala Ala Ala Ala Ala Thr Ala Thr Cys Cys Ala Gly
1415                1420                1425

Cys Thr Gly Cys Cys Thr Ala Ala Ala Gly Ala Gly Gly Ala Ala
1430                1435                1440

Ala Thr Thr Ala Ala Gly Ala Ala Ala Cys Thr Thr Gly Ala Ala
1445                1450                1455

Gly Thr Ala Gly Ala Thr Gly Ala Ala Ala Thr Thr Ala Cys Thr
1460                1465                1470

Thr Thr Ala Thr Gly Gly Thr Ala Cys Ala Ala Gly Ala Thr Gly
1475                1480                1485

Ala Thr Thr Cys Thr Thr Cys Cys Thr Cys Cys Thr Cys Ala Ala
1490                1495                1500

Thr Thr Thr Gly Ala Cys Ala Gly Ala Thr Cys Ala Ala Ala Gly
1505                1510                1515

Ala Ala Gly Thr Ala Thr Cys Cys Cys Thr Thr Gly Cys Thr Ala
1520                1525                1530

Ala Thr Thr Cys Ala Ala Gly Thr Gly Thr Ala Thr Gly Gly Thr
1535                1540                1545
```

```
Gly Gly Thr Cys Cys Cys Thr Gly Cys Ala Gly Thr Cys Ala Gly
    1550                1555                1560

Ala Gly Thr Gly Thr Ala Ala Gly Gly Thr Cys Thr Gly Thr Ala
    1565                1570                1575

Thr Thr Thr Gly Cys Thr Gly Thr Thr Ala Ala Thr Thr Gly Gly
    1580                1585                1590

Ala Thr Ala Thr Cys Thr Thr Ala Thr Cys Thr Thr Gly Cys Ala
    1595                1600                1605

Ala Gly Thr Ala Ala Gly Gly Ala Ala Gly Gly Ala Thr Gly
    1610                1615                1620

Gly Thr Cys Ala Thr Thr Gly Cys Cys Thr Thr Gly Gly Thr Gly
    1625                1630                1635

Gly Ala Thr Gly Gly Thr Cys Gly Gly Gly Gly Ala Ala Cys Ala
    1640                1645                1650

Gly Cys Thr Thr Thr Cys Cys Ala Ala Gly Gly Thr Gly Ala Cys
    1655                1660                1665

Ala Ala Ala Cys Thr Cys Cys Thr Gly Thr Ala Thr Gly Cys Ala
    1670                1675                1680

Gly Thr Gly Thr Ala Thr Cys Gly Ala Ala Ala Gly Cys Thr Gly
    1685                1690                1695

Gly Gly Thr Gly Thr Thr Thr Ala Thr Gly Ala Ala Gly Thr Thr
    1700                1705                1710

Gly Ala Ala Gly Ala Cys Cys Ala Gly Ala Thr Thr Ala Cys Ala
    1715                1720                1725

Gly Cys Thr Gly Thr Cys Ala Gly Ala Ala Ala Ala Thr Thr Cys
    1730                1735                1740

Ala Thr Ala Gly Ala Ala Ala Thr Gly Gly Gly Thr Thr Thr Cys
    1745                1750                1755

Ala Thr Thr Gly Ala Thr Gly Ala Ala Ala Ala Ala Ala Gly Ala
    1760                1765                1770

Ala Thr Ala Gly Cys Cys Ala Thr Ala Thr Gly Gly Gly Gly Cys
    1775                1780                1785

Thr Gly Gly Thr Cys Cys Thr Ala Thr Gly Gly Ala Gly Gly Ala
    1790                1795                1800

Thr Ala Thr Gly Thr Thr Thr Cys Ala Thr Cys Ala Cys Thr Gly
    1805                1810                1815

Gly Cys Cys Cys Thr Thr Gly Cys Ala Thr Cys Thr Gly Gly Ala
    1820                1825                1830

Ala Cys Thr Gly Gly Thr Cys Thr Thr Thr Thr Cys Ala Ala Ala
    1835                1840                1845

Thr Gly Thr Gly Gly Gly Ala Thr Ala Gly Cys Ala Gly Thr Gly
    1850                1855                1860

Gly Cys Thr Cys Cys Ala Gly Thr Cys Thr Cys Cys Ala Gly Cys
    1865                1870                1875

Thr Gly Gly Gly Ala Ala Thr Ala Thr Thr Ala Cys Gly Cys Gly
    1880                1885                1890

Thr Cys Thr Gly Thr Cys Thr Ala Cys Ala Cys Ala Gly Ala Gly
    1895                1900                1905

Ala Gly Ala Thr Thr Cys Ala Thr Gly Gly Gly Thr Cys Thr Cys
    1910                1915                1920

Cys Cys Ala Ala Cys Ala Ala Ala Gly Gly Ala Thr Gly Ala Thr
    1925                1930                1935

Ala Ala Thr Cys Thr Thr Gly Ala Gly Cys Ala Cys Thr Ala Thr
```

1940 1945 1950

Ala Ala Gly Ala Ala Thr Thr Cys Ala Ala Cys Thr Gly Thr Gly
1955 1960 1965

Ala Thr Gly Gly Cys Ala Ala Gly Ala Gly Cys Ala Gly Ala Ala
1970 1975 1980

Thr Ala Thr Thr Thr Cys Ala Gly Ala Ala Ala Thr Gly Thr Ala
1985 1990 1995

Gly Ala Cys Thr Ala Thr Cys Thr Thr Cys Thr Cys Ala Thr Cys
2000 2005 2010

Cys Ala Cys Gly Gly Ala Ala Cys Ala Gly Cys Ala Gly Ala Thr
2015 2020 2025

Gly Ala Thr Ala Ala Thr Gly Thr Gly Cys Ala Cys Thr Thr Thr
2030 2035 2040

Cys Ala Ala Ala Ala Cys Thr Cys Ala Gly Cys Ala Cys Ala Gly
2045 2050 2055

Ala Thr Thr Gly Cys Thr Ala Ala Ala Gly Cys Thr Cys Thr Gly
2060 2065 2070

Gly Thr Thr Ala Ala Thr Gly Cys Ala Cys Ala Ala Gly Thr Gly
2075 2080 2085

Gly Ala Thr Thr Thr Cys Cys Ala Gly Gly Cys Ala Ala Thr Gly
2090 2095 2100

Thr Gly Gly Thr Ala Cys Thr Cys Thr Gly Ala Cys Cys Ala Gly
2105 2110 2115

Ala Ala Cys Cys Ala Cys Gly Gly Cys Thr Thr Ala Thr Cys Cys
2120 2125 2130

Gly Gly Cys Cys Thr Gly Thr Cys Cys Ala Cys Gly Ala Ala Cys
2135 2140 2145

Cys Ala Cys Thr Thr Ala Thr Ala Cys Ala Cys Cys Cys Ala Cys
2150 2155 2160

Ala Thr Gly Ala Cys Cys Cys Ala Cys Thr Thr Cys Cys Thr Ala
2165 2170 2175

Ala Ala Gly Cys Ala Gly Thr Gly Thr Thr Thr Cys Thr Cys Thr
2180 2185 2190

Thr Thr Gly Thr Cys Ala Gly Ala Cys Gly Gly Cys Ala Ala Ala
2195 2200 2205

Ala Ala Gly Ala Ala Ala Ala Ala Gly Ala Ala Ala Ala Ala Gly
2210 2215 2220

Gly Gly Cys Cys Ala Cys Cys Ala Cys Cys Ala Thr Cys Ala Cys
2225 2230 2235

Cys Ala Thr Cys Ala Cys
2240

<210> SEQ ID NO 29
<211> LENGTH: 702
<212> TYPE: PRT
<213> ORGANISM: Homo sapiens

<400> SEQUENCE: 29

Met Glu Ser Pro Ser Ala Pro Pro His Arg Trp Cys Ile Pro Trp Gln
1 5 10 15

Arg Leu Leu Leu Thr Ala Ser Leu Leu Thr Phe Trp Asn Pro Pro Thr
20 25 30

Thr Ala Lys Leu Thr Ile Glu Ser Thr Pro Phe Asn Val Ala Glu Gly
35 40 45

Lys Glu Val Leu Leu Val His Asn Leu Pro Gln His Leu Phe Gly
    50              55                  60

Tyr Ser Trp Tyr Lys Gly Glu Arg Val Asp Gly Asn Arg Gln Ile Ile
65              70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                    165                 170                 175

Leu Trp Trp Val Asn Asn Gln Ser Leu Pro Val Ser Pro Arg Leu Gln
                180                 185                 190

Leu Ser Asn Gly Asn Arg Thr Leu Thr Leu Phe Asn Val Thr Arg Asn
            195                 200                 205

Asp Thr Ala Ser Tyr Lys Cys Glu Thr Gln Asn Pro Val Ser Ala Arg
        210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                    245                 250                 255

Leu Ser Cys His Ala Ala Ser Asn Pro Pro Ala Gln Tyr Ser Trp Phe
                260                 265                 270

Val Asn Gly Thr Phe Gln Gln Ser Thr Gln Glu Leu Phe Ile Pro Asn
            275                 280                 285

Ile Thr Val Asn Asn Ser Gly Ser Tyr Thr Cys Gln Ala His Asn Ser
        290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                    325                 330                 335

Asp Glu Asp Ala Val Ala Leu Thr Cys Glu Pro Glu Ile Gln Asn Thr
                340                 345                 350

Thr Tyr Leu Trp Trp Val Asn Asn Gln Ser Leu Pro Val Ser Pro Arg
            355                 360                 365

Leu Gln Leu Ser Asn Asp Asn Arg Thr Leu Thr Leu Leu Ser Val Thr
        370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                    405                 410                 415

Asp Pro Thr Ile Ser Pro Ser Tyr Thr Tyr Tyr Arg Pro Gly Val Asn
                420                 425                 430

Leu Ser Leu Ser Cys His Ala Ala Ser Asn Pro Pro Ala Gln Tyr Ser
            435                 440                 445

Trp Leu Ile Asp Gly Asn Ile Gln Gln His Thr Gln Glu Leu Phe Ile
        450                 455                 460

Ser Asn Ile Thr Glu Lys Asn Ser Gly Leu Tyr Thr Cys Gln Ala Asn

```
            465                 470                 475                 480
        Asn Ser Ala Ser Gly His Ser Arg Thr Thr Val Lys Thr Ile Thr Val
                        485                 490                 495

Ser Ala Glu Leu Pro Lys Pro Ser Ile Ser Ser Asn Asn Ser Lys Pro
                        500                 505                 510

Val Glu Asp Lys Asp Ala Val Ala Phe Thr Cys Glu Pro Glu Ala Gln
                        515                 520                 525

Asn Thr Thr Tyr Leu Trp Trp Val Asn Gly Gln Ser Leu Pro Val Ser
                        530                 535                 540

Pro Arg Leu Gln Leu Ser Asn Gly Asn Arg Thr Leu Thr Leu Phe Asn
        545                 550                 555                 560

Val Thr Arg Asn Asp Ala Arg Ala Tyr Val Cys Gly Ile Gln Asn Ser
                        565                 570                 575

Val Ser Ala Asn Arg Ser Asp Pro Val Thr Leu Asp Val Leu Tyr Gly
                        580                 585                 590

Pro Asp Thr Pro Ile Ile Ser Pro Pro Asp Ser Ser Tyr Leu Ser Gly
                        595                 600                 605

Ala Asn Leu Asn Leu Ser Cys His Ser Ala Ser Asn Pro Ser Pro Gln
        610                 615                 620

Tyr Ser Trp Arg Ile Asn Gly Ile Pro Gln Gln His Thr Gln Val Leu
        625                 630                 635                 640

Phe Ile Ala Lys Ile Thr Pro Asn Asn Asn Gly Thr Tyr Ala Cys Phe
                        645                 650                 655

Val Ser Asn Leu Ala Thr Gly Arg Asn Asn Ser Ile Val Lys Ser Ile
                        660                 665                 670

Thr Val Ser Ala Ser Gly Thr Ser Pro Gly Leu Ser Ala Gly Ala Thr
                        675                 680                 685

Val Gly Ile Met Ile Gly Val Leu Val Gly Val Ala Leu Ile
                        690                 695                 700

<210> SEQ ID NO 30
<211> LENGTH: 2322
<212> TYPE: PRT
<213> ORGANISM: Homo sapiens

<400> SEQUENCE: 30

Met Gln Ser Gly Pro Arg Pro Pro Leu Pro Ala Pro Gly Leu Ala Leu
        1               5                   10                  15

Ala Leu Thr Leu Thr Met Leu Ala Arg Leu Ala Ser Ala Ala Ser Phe
                        20                  25                  30

Phe Gly Glu Asn His Leu Glu Val Pro Val Ala Thr Ala Leu Thr Asp
                        35                  40                  45

Ile Asp Leu Gln Leu Gln Phe Ser Thr Ser Gln Pro Glu Ala Leu Leu
        50                  55                  60

Leu Leu Ala Ala Gly Pro Ala Asp His Leu Leu Leu Gln Leu Tyr Ser
        65                  70                  75                  80

Gly Arg Leu Gln Val Arg Leu Val Leu Gly Gln Glu Glu Leu Arg Leu
                        85                  90                  95

Gln Thr Pro Ala Glu Thr Leu Leu Ser Asp Ser Ile Pro His Thr Val
                        100                 105                 110

Val Leu Thr Val Val Glu Gly Trp Ala Thr Leu Ser Val Asp Gly Phe
                        115                 120                 125

Leu Asn Ala Ser Ser Ala Val Pro Gly Ala Pro Leu Glu Val Pro Tyr
        130                 135                 140
```

-continued

```
Gly Leu Phe Val Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
                260                 265                 270

Leu His Asn Ser Val Pro Val Ala Asp Gly Gln Pro His Glu Val Ser
                275                 280                 285

Val His Ile Asn Ala His Arg Leu Glu Ile Ser Val Asp Gln Tyr Pro
                290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
                420                 425                 430

Thr Ile Ser Pro Leu Val Val Ala Glu Gly Gly Thr Ala Trp Leu Glu
            435                 440                 445

Trp Arg His Val Gln Pro Thr Leu Asp Leu Met Glu Ala Glu Leu Arg
450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
                500                 505                 510

Asp Thr Ser Asp Gln Leu Val Leu Glu Val Ser Val Thr Ala Arg Val
            515                 520                 525

Pro Met Pro Ser Cys Leu Arg Arg Gly Gln Thr Tyr Leu Leu Pro Ile
        530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
```

```
                565                 570                 575
Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
            595                 600                 605

Pro Gly Glu Pro Ala Thr Glu Phe Ser Cys Arg Glu Leu Glu Ala Gly
            610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
            675                 680                 685

Glu Thr Asn Ala Val Gly Gln Asp Val Ser Val Leu Phe Arg Val Thr
            690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
            755                 760                 765

Ile Leu Ser Asn Leu Ser Phe Pro Val Thr Ile Gln Arg Ala Thr Val
770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
            850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Val Val Pro Glu Gly
            900                 905                 910

Gly Glu Gly Val Leu Ser Ala Asp His Leu Phe Val Lys Ser Leu Asn
            915                 920                 925

Ser Ala Ser Tyr Leu Tyr Glu Val Met Glu Arg Pro Arg His Gly Arg
            930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990
```

-continued

```
Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile
    1010                1015                1020

Ser Arg Ile Phe His Val Ala Arg Gly Gly Arg Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly
    1205                1210                1215

Pro Val His Thr Asp Ala Thr Leu Gln Val Thr Ile Ala Leu Glu
    1220                1225                1230

Gly Pro Leu Ala Pro Leu Lys Leu Val Arg His Lys Lys Ile Tyr
    1235                1240                1245

Val Phe Gln Gly Glu Ala Ala Glu Ile Arg Arg Asp Gln Leu Glu
    1250                1255                1260

Ala Ala Gln Glu Ala Val Pro Pro Ala Asp Ile Val Phe Ser Val
    1265                1270                1275

Lys Ser Pro Pro Ser Ala Gly Tyr Leu Val Met Val Ser Arg Gly
    1280                1285                1290

Ala Leu Ala Asp Glu Pro Pro Ser Leu Asp Pro Val Gln Ser Phe
    1295                1300                1305

Ser Gln Glu Ala Val Asp Thr Gly Arg Val Leu Tyr Leu His Ser
    1310                1315                1320

Arg Pro Glu Ala Trp Ser Asp Ala Phe Ser Leu Asp Val Ala Ser
    1325                1330                1335

Gly Leu Gly Ala Pro Leu Glu Gly Val Leu Val Glu Leu Glu Val
    1340                1345                1350

Leu Pro Ala Ala Ile Pro Leu Glu Ala Gln Asn Phe Ser Val Pro
    1355                1360                1365

Glu Gly Gly Ser Leu Thr Leu Ala Pro Pro Leu Leu Arg Val Ser
    1370                1375                1380
```

```
Gly Pro Tyr Phe Pro Thr Leu Leu Gly Leu Ser Leu Gln Val Leu
    1385                1390                1395

Glu Pro Pro Gln His Gly Ala Leu Gln Lys Glu Asp Gly Pro Gln
    1400                1405                1410

Ala Arg Thr Leu Ser Ala Phe Ser Trp Arg Met Val Glu Glu Gln
    1415                1420                1425

Leu Ile Arg Tyr Val His Asp Gly Ser Glu Thr Leu Thr Asp Ser
    1430                1435                1440

Phe Val Leu Met Ala Asn Ala Ser Glu Met Asp Arg Gln Ser His
    1445                1450                1455

Pro Val Ala Phe Thr Val Thr Val Leu Pro Val Asn Asp Gln Pro
    1460                1465                1470

Pro Ile Leu Thr Thr Asn Thr Gly Leu Gln Met Trp Glu Gly Ala
    1475                1480                1485

Thr Ala Pro Ile Pro Ala Glu Ala Leu Arg Ser Thr Asp Gly Asp
    1490                1495                1500

Ser Gly Ser Glu Asp Leu Val Tyr Thr Ile Glu Gln Pro Ser Asn
    1505                1510                1515

Gly Arg Val Val Leu Arg Gly Ala Pro Gly Thr Glu Val Arg Ser
    1520                1525                1530

Phe Thr Gln Ala Gln Leu Asp Gly Gly Leu Val Leu Phe Ser His
    1535                1540                1545

Arg Gly Thr Leu Asp Gly Gly Phe Arg Phe Arg Leu Ser Asp Gly
    1550                1555                1560

Glu His Thr Ser Pro Gly His Phe Phe Arg Val Thr Ala Gln Lys
    1565                1570                1575

Gln Val Leu Leu Ser Leu Lys Gly Ser Gln Thr Leu Thr Val Cys
    1580                1585                1590

Pro Gly Ser Val Gln Pro Leu Ser Ser Gln Thr Leu Arg Ala Ser
    1595                1600                1605

Ser Ser Ala Gly Thr Asp Pro Gln Leu Leu Leu Tyr Arg Val Val
    1610                1615                1620

Arg Gly Pro Gln Leu Gly Arg Leu Phe His Ala Gln Gln Asp Ser
    1625                1630                1635

Thr Gly Glu Ala Leu Val Asn Phe Thr Gln Ala Glu Val Tyr Ala
    1640                1645                1650

Gly Asn Ile Leu Tyr Glu His Glu Met Pro Pro Glu Pro Phe Trp
    1655                1660                1665

Glu Ala His Asp Thr Leu Glu Leu Gln Leu Ser Ser Pro Pro Ala
    1670                1675                1680

Arg Asp Val Ala Ala Thr Leu Ala Val Ala Val Ser Phe Glu Ala
    1685                1690                1695

Ala Cys Pro Gln Arg Pro Ser His Leu Trp Lys Asn Lys Gly Leu
    1700                1705                1710

Trp Val Pro Glu Gly Gln Arg Ala Arg Ile Thr Val Ala Ala Leu
    1715                1720                1725

Asp Ala Ser Asn Leu Leu Ala Ser Val Pro Ser Pro Gln Arg Ser
    1730                1735                1740

Glu His Asp Val Leu Phe Gln Val Thr Gln Phe Pro Ser Arg Gly
    1745                1750                1755

Gln Leu Leu Val Ser Glu Glu Pro Leu His Ala Gly Gln Pro His
    1760                1765                1770

Phe Leu Gln Ser Gln Leu Ala Ala Gly Gln Leu Val Tyr Ala His
```

-continued

```
           1775                1780                1785

Gly Gly Gly Gly Thr Gln Gln Asp Gly Phe His Phe Arg Ala His
           1790                1795                1800

Leu Gln Gly Pro Ala Gly Ala Ser Val Ala Gly Pro Gln Thr Ser
           1805                1810                1815

Glu Ala Phe Ala Ile Thr Val Arg Asp Val Asn Glu Arg Pro Pro
           1820                1825                1830

Gln Pro Gln Ala Ser Val Pro Leu Arg Leu Thr Arg Gly Ser Arg
           1835                1840                1845

Ala Pro Ile Ser Arg Ala Gln Leu Ser Val Val Asp Pro Asp Ser
           1850                1855                1860

Ala Pro Gly Glu Ile Glu Tyr Glu Val Gln Arg Ala Pro His Asn
           1865                1870                1875

Gly Phe Leu Ser Leu Val Gly Gly Leu Gly Pro Val Thr Arg
           1880                1885                1890

Phe Thr Gln Ala Asp Val Asp Ser Gly Arg Leu Ala Phe Val Ala
           1895                1900                1905

Asn Gly Ser Ser Val Ala Gly Ile Phe Gln Leu Ser Met Ser Asp
           1910                1915                1920

Gly Ala Ser Pro Pro Leu Pro Met Ser Leu Ala Val Asp Ile Leu
           1925                1930                1935

Pro Ser Ala Ile Glu Val Gln Leu Arg Ala Pro Leu Glu Val Pro
           1940                1945                1950

Gln Ala Leu Gly Arg Ser Ser Leu Ser Gln Gln Gln Leu Arg Val
           1955                1960                1965

Val Ser Asp Arg Glu Glu Pro Glu Ala Ala Tyr Arg Leu Ile Gln
           1970                1975                1980

Gly Pro Gln Tyr Gly His Leu Leu Val Gly Gly Arg Pro Thr Ser
           1985                1990                1995

Ala Phe Ser Gln Phe Gln Ile Asp Gln Gly Glu Val Val Phe Ala
           2000                2005                2010

Phe Thr Asn Phe Ser Ser Ser His Asp His Phe Arg Val Leu Ala
           2015                2020                2025

Leu Ala Arg Gly Val Asn Ala Ser Ala Val Val Asn Val Thr Val
           2030                2035                2040

Arg Ala Leu Leu His Val Trp Ala Gly Gly Pro Trp Pro Gln Gly
           2045                2050                2055

Ala Thr Leu Arg Leu Asp Pro Thr Val Leu Asp Ala Gly Glu Leu
           2060                2065                2070

Ala Asn Arg Thr Gly Ser Val Pro Arg Phe Arg Leu Leu Glu Gly
           2075                2080                2085

Pro Arg His Gly Arg Val Val Arg Val Pro Arg Ala Arg Thr Glu
           2090                2095                2100

Pro Gly Gly Ser Gln Leu Val Glu Gln Phe Thr Gln Gln Asp Leu
           2105                2110                2115

Glu Asp Gly Arg Leu Gly Leu Glu Val Gly Arg Pro Glu Gly Arg
           2120                2125                2130

Ala Pro Gly Pro Ala Gly Asp Ser Leu Thr Leu Glu Leu Trp Ala
           2135                2140                2145

Gln Gly Val Pro Pro Ala Val Ala Ser Leu Asp Phe Ala Thr Glu
           2150                2155                2160

Pro Tyr Asn Ala Ala Arg Pro Tyr Ser Val Ala Leu Leu Ser Val
           2165                2170                2175
```

```
Pro Glu Ala Ala Arg Thr Glu Ala Gly Lys Pro Glu Ser Ser Thr
    2180            2185                2190

Pro Thr Gly Glu Pro Gly Pro Met Ala Ser Ser Pro Glu Pro Ala
    2195            2200                2205

Val Ala Lys Gly Gly Phe Leu Ser Phe Leu Glu Ala Asn Met Phe
    2210            2215                2220

Ser Val Ile Ile Pro Met Cys Leu Val Leu Leu Leu Ala Leu
    2225            2230                2235

Ile Leu Pro Leu Leu Phe Tyr Leu Arg Lys Arg Asn Lys Thr Gly
    2240            2245                2250

Lys His Asp Val Gln Val Leu Thr Ala Lys Pro Arg Asn Gly Leu
    2255            2260                2265

Ala Gly Asp Thr Glu Thr Phe Arg Lys Val Glu Pro Gly Gln Ala
    2270            2275                2280

Ile Pro Leu Thr Ala Val Pro Gly Gln Gly Pro Pro Gly Gly
    2285            2290                2295

Gln Pro Asp Pro Glu Leu Leu Gln Phe Cys Arg Thr Pro Asn Pro
    2300            2305                2310

Ala Leu Lys Asn Gly Gln Tyr Trp Val
    2315            2320

<210> SEQ ID NO 31
<211> LENGTH: 1210
<212> TYPE: PRT
<213> ORGANISM: Homo sapiens

<400> SEQUENCE: 31

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
```

-continued

```
            210                 215                 220
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640
```

```
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
        660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
        850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe
1010                1015                1020
Phe Ser Ser Pro Ser Thr Ser Arg Thr Pro Leu Leu Ser Ser Leu
    1025                1030                1035
Ser Ala Thr Ser Asn Asn Ser Thr Val Ala Cys Ile Asp Arg Asn
    1040                1045                1050
```

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 32
<211> LENGTH: 556
<212> TYPE: PRT
<213> ORGANISM: Homo sapiens

<400> SEQUENCE: 32

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 33
<211> LENGTH: 297
<212> TYPE: PRT
<213> ORGANISM: Homo sapiens

<400> SEQUENCE: 33

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg

```
                        20                  25                  30
Arg Met Ser Ser Leu Val Gly Pro Thr Gln Ser Phe Phe Met Arg Glu
                35                  40                  45
Ser Lys Thr Leu Gly Ala Val Gln Ile Met Asn Gly Leu Phe His Ile
 50                  55                  60
Ala Leu Gly Gly Leu Leu Met Ile Pro Ala Gly Ile Tyr Ala Pro Ile
 65                  70                  75                  80
Cys Val Thr Val Trp Tyr Pro Leu Trp Gly Gly Ile Met Tyr Ile Ile
                85                  90                  95
Ser Gly Ser Leu Leu Ala Ala Thr Glu Lys Asn Ser Arg Lys Cys Leu
                100                 105                 110
Val Lys Gly Lys Met Ile Met Asn Ser Leu Ser Leu Phe Ala Ala Ile
                115                 120                 125
Ser Gly Met Ile Leu Ser Ile Met Asp Ile Leu Asn Ile Lys Ile Ser
                130                 135                 140
His Phe Leu Lys Met Glu Ser Leu Asn Phe Ile Arg Ala His Thr Pro
145                 150                 155                 160
Tyr Ile Asn Ile Tyr Asn Cys Glu Pro Ala Asn Pro Ser Glu Lys Asn
                165                 170                 175
Ser Pro Ser Thr Gln Tyr Cys Tyr Ser Ile Gln Ser Leu Phe Leu Gly
                180                 185                 190
Ile Leu Ser Val Met Leu Ile Phe Ala Phe Phe Gln Glu Leu Val Ile
                195                 200                 205
Ala Gly Ile Val Glu Asn Glu Trp Lys Arg Thr Cys Ser Arg Pro Lys
                210                 215                 220
Ser Asn Ile Val Leu Leu Ser Ala Glu Glu Lys Lys Glu Gln Thr Ile
225                 230                 235                 240
Glu Ile Lys Glu Glu Val Val Gly Leu Thr Glu Thr Ser Ser Gln Pro
                245                 250                 255
Lys Asn Glu Glu Asp Ile Glu Ile Ile Pro Ile Gln Glu Glu Glu Glu
                260                 265                 270
Glu Glu Thr Glu Thr Asn Phe Pro Glu Pro Pro Gln Asp Gln Glu Ser
                275                 280                 285
Ser Pro Ile Glu Asn Asp Ser Ser Pro
                290                 295

<210> SEQ ID NO 34
<211> LENGTH: 364
<212> TYPE: PRT
<213> ORGANISM: Homo sapiens

<400> SEQUENCE: 34

Met Pro Leu Leu Leu Leu Leu Pro Leu Leu Trp Ala Gly Ala Leu Ala
 1                   5                  10                  15
Met Asp Pro Asn Phe Trp Leu Gln Val Gln Glu Ser Val Thr Val Gln
                20                  25                  30
Glu Gly Leu Cys Val Leu Val Pro Cys Thr Phe Phe His Pro Ile Pro
                35                  40                  45
Tyr Tyr Asp Lys Asn Ser Pro Val His Gly Tyr Trp Phe Arg Glu Gly
                50                  55                  60
Ala Ile Ile Ser Arg Asp Ser Pro Val Ala Thr Asn Lys Leu Asp Gln
 65                  70                  75                  80
Glu Val Gln Glu Glu Thr Gln Gly Arg Phe Arg Leu Leu Gly Asp Pro
                85                  90                  95
```

```
Ser Arg Asn Asn Cys Ser Leu Ser Ile Val Asp Ala Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 35
<211> LENGTH: 205
<212> TYPE: PRT
<213> ORGANISM: Homo sapiens

<400> SEQUENCE: 35

Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110
```

```
Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 36
<211> LENGTH: 233
<212> TYPE: PRT
<213> ORGANISM: Homo sapiens

<400> SEQUENCE: 36

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 37
<211> LENGTH: 244
<212> TYPE: PRT
<213> ORGANISM: Homo sapiens

<400> SEQUENCE: 37
```

Met Gly Ala Leu Gly Leu Glu Gly Arg Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
                35                  40                  45

Gln Asp Gln Gly Gly Leu Val Thr Glu Thr Ala Asp Pro Gly Ala Gln
50                      55                  60

Ala Gln Gln Gly Leu Gly Phe Gln Lys Leu Pro Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
                100                 105                 110

Leu Thr Ser Gly Thr Gln Phe Ser Asp Ala Glu Gly Leu Ala Leu Pro
            115                 120                 125

Gln Asp Gly Leu Tyr Tyr Leu Tyr Cys Leu Val Gly Tyr Arg Gly Arg
130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
                195                 200                 205

Gly Leu Val Gln Leu Arg Arg Gly Glu Arg Val Tyr Val Asn Ile Ser
            210                 215                 220

His Pro Asp Met Val Asp Phe Ala Arg Gly Lys Thr Phe Phe Gly Ala
225                 230                 235                 240

Val Met Val Gly

<210> SEQ ID NO 38
<211> LENGTH: 183
<212> TYPE: PRT
<213> ORGANISM: Homo sapiens

<400> SEQUENCE: 38

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
                50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
            115                 120                 125

```
Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 39
<211> LENGTH: 261
<212> TYPE: PRT
<213> ORGANISM: Homo sapiens

<400> SEQUENCE: 39

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 40
<211> LENGTH: 281
<212> TYPE: PRT
<213> ORGANISM: Homo sapiens

<400> SEQUENCE: 40

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 41
<211> LENGTH: 193
<212> TYPE: PRT
<213> ORGANISM: Homo sapiens

<400> SEQUENCE: 41

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu

```
                        85                  90                  95
Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
                115                 120                 125

Ala Val Gly Ile Cys Ser Pro Ala Ser Arg Ser Ile Ser Leu Leu Arg
                130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 42
<211> LENGTH: 234
<212> TYPE: PRT
<213> ORGANISM: Homo sapiens

<400> SEQUENCE: 42

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
                20                  25                  30

Thr Thr Ser Arg Ser Tyr Phe Tyr Leu Thr Thr Ala Thr Leu Ala Leu
                35                  40                  45

Cys Leu Val Phe Thr Val Ala Thr Ile Met Val Leu Val Val Gln Arg
50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
                100                 105                 110

Leu Ser Trp Asn Lys Asp Gly Ile Leu His Gly Val Arg Tyr Gln Asp
                115                 120                 125

Gly Asn Leu Val Ile Gln Phe Pro Gly Leu Tyr Phe Ile Ile Cys Gln
                130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
                180                 185                 190

Phe Leu Leu Asp Tyr Leu Gln Val Asn Thr Thr Ile Ser Val Asn Val
                195                 200                 205

Asp Thr Phe Gln Tyr Ile Asp Thr Ser Thr Phe Pro Leu Glu Asn Val
                210                 215                 220

Leu Ser Ile Phe Leu Tyr Ser Asn Ser Asp
225                 230

<210> SEQ ID NO 43
<211> LENGTH: 254
<212> TYPE: PRT
```

<213> ORGANISM: Homo sapiens

<400> SEQUENCE: 43

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
                115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
                210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 44
<211> LENGTH: 281
<212> TYPE: PRT
<213> ORGANISM: Homo sapiens

<400> SEQUENCE: 44

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
                35                  40                  45

Tyr Ser Lys Ser Gly Ile Ala Cys Phe Leu Lys Glu Asp Asp Ser Tyr
50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
```

```
                100                 105                 110
Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
            275                 280

<210> SEQ ID NO 45
<211> LENGTH: 317
<212> TYPE: PRT
<213> ORGANISM: Homo sapiens

<400> SEQUENCE: 45

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Pro Ala Pro His Gln Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190
```

Trp Ala Lys Ile Ser Asn Met Thr Phe Ser Asn Gly Lys Leu Ile Val
            195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
            245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
            275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315

<210> SEQ ID NO 46
<211> LENGTH: 249
<212> TYPE: PRT
<213> ORGANISM: Homo sapiens

<400> SEQUENCE: 46

Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 47
<211> LENGTH: 250
<212> TYPE: PRT
<213> ORGANISM: Homo sapiens

<400> SEQUENCE: 47

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 48
<211> LENGTH: 285
<212> TYPE: PRT
<213> ORGANISM: Homo sapiens

<400> SEQUENCE: 48

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

```
Ala Glu Leu Gln Gly His His Ala Glu Lys Leu Pro Ala Gly Ala Gly
                85                  90                  95

Ala Pro Lys Ala Gly Leu Glu Ala Pro Ala Val Thr Ala Gly Leu
            100                 105                 110

Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
            210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
            275                 280                 285

<210> SEQ ID NO 49
<211> LENGTH: 240
<212> TYPE: PRT
<213> ORGANISM: Homo sapiens

<400> SEQUENCE: 49

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
            35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
            130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
```

```
              165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 50
<211> LENGTH: 251
<212> TYPE: PRT
<213> ORGANISM: Homo sapiens

<400> SEQUENCE: 50

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 51
<211> LENGTH: 199
<212> TYPE: PRT
<213> ORGANISM: Homo sapiens

<400> SEQUENCE: 51

Met Thr Leu His Pro Ser Pro Ile Thr Cys Glu Phe Leu Phe Ser Thr
```

```
                1               5                  10                 15
            Ala Leu Ile Ser Pro Lys Met Cys Leu Ser His Leu Glu Asn Met Pro
                        20                  25                 30
            Leu Ser His Ser Arg Thr Gln Gly Ala Gln Arg Ser Ser Trp Lys Leu
                        35                  40                 45
            Trp Leu Phe Cys Ser Ile Val Met Leu Leu Phe Leu Cys Ser Phe Ser
                        50                  55                 60
            Trp Leu Ile Phe Ile Phe Leu Gln Leu Glu Thr Ala Lys Glu Pro Cys
            65                  70                  75                 80
            Met Ala Lys Phe Gly Pro Leu Pro Ser Lys Trp Gln Met Ala Ser Ser
                        85                  90                 95
            Glu Pro Pro Cys Val Asn Lys Val Ser Asp Trp Lys Leu Glu Ile Leu
                        100                 105                110
            Gln Asn Gly Leu Tyr Leu Ile Tyr Gly Gln Val Ala Pro Asn Ala Asn
                        115                 120                125
            Tyr Asn Asp Val Ala Pro Phe Glu Val Arg Leu Tyr Lys Asn Lys Asp
                        130                 135                140
            Met Ile Gln Thr Leu Thr Asn Lys Ser Lys Ile Gln Asn Val Gly Gly
            145                 150                 155                160
            Thr Tyr Glu Leu His Val Gly Asp Thr Ile Asp Leu Ile Phe Asn Ser
                        165                 170                175
            Glu His Gln Val Leu Lys Asn Asn Thr Tyr Trp Gly Ile Ile Leu Leu
                        180                 185                190
            Ala Asn Pro Gln Phe Ile Ser
                        195

<210> SEQ ID NO 52
            <211> LENGTH: 391
            <212> TYPE: PRT
            <213> ORGANISM: Homo sapiens

<400> SEQUENCE: 52

Met Gly Tyr Pro Glu Val Glu Arg Arg Glu Leu Leu Pro Ala Ala Ala
            1               5                  10                 15
            Pro Arg Glu Arg Gly Ser Gln Gly Cys Gly Cys Gly Gly Ala Pro Ala
                        20                  25                 30
            Arg Ala Gly Glu Gly Asn Ser Cys Leu Leu Phe Leu Gly Phe Phe Gly
                        35                  40                 45
            Leu Ser Leu Ala Leu His Leu Leu Thr Leu Cys Cys Tyr Leu Glu Leu
                        50                  55                 60
            Arg Ser Glu Leu Arg Arg Glu Arg Gly Ala Glu Ser Arg Leu Gly Gly
            65                  70                  75                 80
            Ser Gly Thr Pro Gly Thr Ser Gly Thr Leu Ser Ser Leu Gly Gly Leu
                        85                  90                 95
            Asp Pro Asp Ser Pro Ile Thr Ser His Leu Gly Gln Pro Ser Pro Lys
                        100                 105                110
            Gln Gln Pro Leu Glu Pro Gly Glu Ala Ala Leu His Ser Asp Ser Gln
                        115                 120                125
            Asp Gly His Gln Met Ala Leu Leu Asn Phe Phe Phe Pro Asp Glu Lys
                        130                 135                140
            Pro Tyr Ser Glu Glu Glu Ser Arg Arg Val Arg Arg Asn Lys Arg Ser
            145                 150                 155                160
            Lys Ser Asn Glu Gly Ala Asp Gly Pro Val Lys Asn Lys Lys Lys Gly
                        165                 170                175
```

```
Lys Lys Ala Gly Pro Pro Gly Pro Asn Gly Pro Gly Pro Pro Gly
            180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
            210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val His Leu Gln Gly Gln
            245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
            275                 280                 285

Arg Ser Gly Glu Leu Glu Val Leu Val Asp Gly Thr Tyr Phe Ile Tyr
            290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
            325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
            355                 360                 365

Ile Ser Ile Asn Met Ser Lys His Thr Thr Phe Phe Gly Ala Ile Arg
            370                 375                 380

Leu Gly Glu Ala Pro Ala Ser
385                 390

<210> SEQ ID NO 53
<211> LENGTH: 205
<212> TYPE: PRT
<213> ORGANISM: Homo sapiens

<400> SEQUENCE: 53

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Ser Glu Ala Arg
        130                 135                 140

Asn Ser Ala Phe Gly Phe Gln Gly Arg Leu Leu His Leu Ser Ala Gly
145                 150                 155                 160
```

Gln Arg Leu Gly Val His Leu His Thr Glu Ala Arg Ala Arg His Ala
            165                 170                 175

Trp Gln Leu Thr Gln Gly Ala Thr Val Leu Gly Leu Phe Arg Val Thr
        180                 185                 190

Pro Glu Ile Pro Ala Gly Leu Pro Ser Pro Arg Ser Glu
    195                 200                 205

<210> SEQ ID NO 54
<211> LENGTH: 10
<212> TYPE: PRT
<213> ORGANISM: Artificial sequence
<220> FEATURE:
<223> OTHER INFORMATION: Peptide Linker

<400> SEQUENCE: 54

Gly Gly Gly Gly Ser Gly Gly Gly Gly Ser
1               5                   10

<210> SEQ ID NO 55
<211> LENGTH: 10
<212> TYPE: PRT
<213> ORGANISM: Artificial sequence
<220> FEATURE:
<223> OTHER INFORMATION: Peptide linker

<400> SEQUENCE: 55

Ser Gly Gly Gly Gly Ser Gly Gly Gly Gly
1               5                   10

<210> SEQ ID NO 56
<211> LENGTH: 14
<212> TYPE: PRT
<213> ORGANISM: Artificial sequence
<220> FEATURE:
<223> OTHER INFORMATION: Peptide linker

<400> SEQUENCE: 56

Gly Gly Gly Gly Ser Gly Gly Gly Ser Gly Gly Gly Gly
1               5                   10

<210> SEQ ID NO 57
<211> LENGTH: 10
<212> TYPE: PRT
<213> ORGANISM: Artificial sequence
<220> FEATURE:
<223> OTHER INFORMATION: Peptide linker

<400> SEQUENCE: 57

Gly Ser Pro Gly Ser Ser Ser Ser Gly Ser
1               5                   10

<210> SEQ ID NO 58
<211> LENGTH: 20
<212> TYPE: PRT
<213> ORGANISM: Artificial sequence
<220> FEATURE:
<223> OTHER INFORMATION: Peptide linker

<400> SEQUENCE: 58

Gly Gly Gly Gly Ser Gly Gly Gly Gly Ser Gly Gly Gly Gly Ser Gly
1               5                   10                  15

Gly Gly Gly Ser
            20

```
<210> SEQ ID NO 59
<211> LENGTH: 8
<212> TYPE: PRT
<213> ORGANISM: Artificial sequence
<220> FEATURE:
<223> OTHER INFORMATION: Peptide linker

<400> SEQUENCE: 59

Gly Ser Gly Ser Gly Asn Gly Ser
1               5

<210> SEQ ID NO 60
<211> LENGTH: 8
<212> TYPE: PRT
<213> ORGANISM: Artificial sequence
<220> FEATURE:
<223> OTHER INFORMATION: Peptide linker

<400> SEQUENCE: 60

Gly Gly Ser Gly Ser Gly Ser Gly
1               5

<210> SEQ ID NO 61
<211> LENGTH: 6
<212> TYPE: PRT
<213> ORGANISM: Artificial sequence
<220> FEATURE:
<223> OTHER INFORMATION: Peptide linker

<400> SEQUENCE: 61

Gly Gly Ser Gly Ser Gly
1               5

<210> SEQ ID NO 62
<211> LENGTH: 4
<212> TYPE: PRT
<213> ORGANISM: Artificial sequence
<220> FEATURE:
<223> OTHER INFORMATION: Peptide linker

<400> SEQUENCE: 62

Gly Gly Ser Gly
1

<210> SEQ ID NO 63
<211> LENGTH: 8
<212> TYPE: PRT
<213> ORGANISM: Artificial sequence
<220> FEATURE:
<223> OTHER INFORMATION: Peptide linker

<400> SEQUENCE: 63

Gly Gly Ser Gly Asn Gly Ser Gly
1               5

<210> SEQ ID NO 64
<211> LENGTH: 8
<212> TYPE: PRT
<213> ORGANISM: Artificial sequence
<220> FEATURE:
<223> OTHER INFORMATION: Peptide linker

<400> SEQUENCE: 64

Gly Gly Asn Gly Ser Gly Ser Gly
1               5

<210> SEQ ID NO 65
```

```
<211> LENGTH: 6
<212> TYPE: PRT
<213> ORGANISM: Artificial sequence
<220> FEATURE:
<223> OTHER INFORMATION: Peptide linker

<400> SEQUENCE: 65

Gly Gly Asn Gly Ser Gly
1               5

<210> SEQ ID NO 66
<211> LENGTH: 2427
<212> TYPE: DNA
<213> ORGANISM: Artificial sequence
<220> FEATURE:
<223> OTHER INFORMATION: trimeric hu 4-1BBL (71-254) Fc knob chain

<400> SEQUENCE: 66
agagagggcc ctgagctgag ccccgatgat cctgctggac tgctggacct gcggcagggc      60
atgtttgctc agctggtggc ccagaacgtg ctgctgatcg atggccccct gtcctggtac     120
agcgatcctg gactggctgg cgtgtcactg acaggcggcc tgagctacaa agaggacacc     180
aaagaactgg tggtggccaa ggccggcgtg tactacgtgt ctttcagct ggaactgcgg      240
agagtggtgg ccggcgaagg atctggctct gtgtctctgg ccctgcatct gcagcctctg     300
agaagcgctg ctgcgctgc agctctggca ctgacagtgg atctgcctcc tgccagctcc      360
gaggcccgga atagcgcatt tgggtttcaa ggcaggctgc tgcacctgtc tgccggccag     420
aggctgggag tgcatctgca cacagaggcc agggctagac acgcctggca gctgacacag     480
ggcgctacag tgctgggcct gttcagagtg accccccgaga ttccagccgg cctgccttct    540
ccaagaagcg aaggcggagg cggatctggc ggcggaggat ctagagggg acccgaactg      600
tccctgacg atccagccgg ctgctggat ctgagacagg aatgttcgc ccagctggtg        660
gctcagaatg tgctgctgat tgacggacct ctgagctggt actccgaccc agggctggca    720
ggggtgtccc tgactggggg actgtcctac aaagaagata caaagaact ggtggtggct     780
aaagctgggg tgtactatgt gttttttcag ctggaactga ggcgggtggt ggctggggag    840
ggctcaggat ctgtgtccct ggctctgcat ctgcagccac tgcgctctgc tgctggcgca   900
gctgcactgg ctctgactgt ggacctgcca ccagcctcta gcgaggccag aaacagcgcc   960
ttcgggttcc aaggacgcct gctgcatctg agcgccggac agcgcctggg agtgcatctg  1020
catactgaag ccagagcccg gcatgcttgg cagctgactc aggggggcaac tgtgctggga  1080
ctgtttcgcg tgacacctga gatccctgcc ggactgccaa gcctagatc agaaggggc    1140
ggaggaagcg gagggggagg aagtagagaa ggaccagagc tgtctccaga tgaccccgca   1200
ggactgctgg acctgagaca gggcatgttc gcacagctgg tgcccagaa tgtgctgctg   1260
atcgacgggc cactgtcttg gtattccgat cccggcctgg ccggcgtgtc cctgaccggc  1320
ggactgagtt acaaagagga tacaaaagaa ctggtggtgg caaaggcagg ggtgtactat  1380
gtgttctttc agctggaact gagaagggtg gtggccggcg agggaagcgg atcagtgtca  1440
ctggcactgc atctgcagcc cctgagatcc gctgcagggg ccgctgctct ggccctgacc  1500
gtggacctgc ccctgcttc ttccgagct agaaactctg catttgggtt tcaaggacgc   1560
ctgctgcatc tgtcagccgg gcagagactg ggagtgcatc tgcataccga ggctcgcgcc  1620
agacatgcat ggcagctgac ccagggcgcc accgtgctgg gactgtttag agtgactcca  1680
gaaatccccg ctggcctgcc cagcccaaga tccgagggat ctcctggcag cagctctagc  1740
```

| | |
|---|---:|
| ggatccgaca aaactcacac atgcccaccg tgcccagcac ctgaagctgc agggggaccg | 1800 |
| tcagtcttcc tcttcccccc aaaacccaag acaccctca tgatctcccg acccctgag | 1860 |
| gtcacatgcg tggtggtgga cgtgagccac gaagaccctg aggtcaagtt caactggtac | 1920 |
| gtggacggcg tggaggtgca taatgccaag acaaagccgc gggaggagca gtacaacagc | 1980 |
| acgtaccgtg tggtcagcgt cctcaccgtc ctgcaccagg actggctgaa tggcaaggag | 2040 |
| tacaagtgca aggtctccaa caaagccctc ggcgccccca tcgagaaaac catctccaaa | 2100 |
| gccaaagggc agccccgaga accacaggtg tacaccctgc ccccatgccg ggatgagctg | 2160 |
| accaagaacc aggtcagcct gtggtgcctg gtcaaaggct tctatcccag cgacatcgcc | 2220 |
| gtggagtggg agagcaatgg gcagccggag aacaactaca agaccacgcc tcccgtgctg | 2280 |
| gactccgacg gctccttctt cctctacagc aagctcaccg tggacaagag caggtggcag | 2340 |
| caggggaacg tcttctcatg ctccgtgatg catgaggctc tgcacaacca ctacacgcag | 2400 |
| aagagcctct ccctgtctcc gggtaaa | 2427 |

<210> SEQ ID NO 67
<211> LENGTH: 1338
<212> TYPE: DNA
<213> ORGANISM: Artificial sequence
<220> FEATURE:
<223> OTHER INFORMATION: anti-FAP(28H1) Fc hole chain

<400> SEQUENCE: 67

| | |
|---|---:|
| gaagtgcagc tgctggaatc cggcggaggc ctggtgcagc ctggcggatc tctgagactg | 60 |
| tcctgcgccg cctccggctt caccttctcc tcccacgcca tgtcctgggt ccgacaggct | 120 |
| cctggcaaag gcctggaatg ggtgtccgcc atctgggcct ccggcgagca gtactacgcc | 180 |
| gactctgtga agggccggtt caccatctcc cgggacaact ccaagaacac cctgtacctg | 240 |
| cagatgaact ccctgcgggc cgaggacacc gccgtgtact actgtgccaa gggctggctg | 300 |
| ggcaacttcg actactgggg acagggcacc ctggtcaccg tgtccagcgc tagcaccaag | 360 |
| ggcccctccg tgttccccct ggcccccagc agcaagagca ccagcggcgg cacagccgct | 420 |
| ctgggctgcc tggtcaagga ctacttcccc gagcccgtga ccgtgtcctg gaacagcgga | 480 |
| gccctgacct ccggcgtgca caccttcccc gccgtgctgc agagttctgg cctgtatagc | 540 |
| ctgagcagcg tggtcaccgt gccttctagc agcctgggca cccagaccta catctgcaac | 600 |
| gtgaaccaca agcccagcaa caccaaggtg gacaagaagg tggagcccaa gagctgcgac | 660 |
| aaaactcaca catgcccacc gtgcccagca cctgaagctg caggggggacc gtcagtcttc | 720 |
| ctcttccccc caaaacccaa ggacaccctc atgatctccc ggaccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cggcgccccc atcgagaaaa ccatctccaa agccaaaggg | 1020 |
| cagccccgag aaccacaggt gtgcaccctg cccccatccc gggatgagct gaccaagaac | 1080 |
| caggtcagcc tctcgtgcgc agtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctcgtgag caagctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 68
<211> LENGTH: 645
<212> TYPE: DNA
<213> ORGANISM: Artificial sequence
<220> FEATURE:
<223> OTHER INFORMATION: anti-FAP(28H1) light chain

<400> SEQUENCE: 68

```
gagatcgtgc tgacccagtc ccccggcacc ctgtctctga gccctggcga gagagccacc      60
ctgtcctgca gagcctccca gtccgtgtcc cggtcctacc tcgcctggta tcagcagaag     120
cccggccagg cccctcggct gctgatcatc ggcgcctcta ccagagccac cggcatccct     180
gaccggttct ccggctctgg ctccggcacc gacttcaccc tgaccatctc ccggctggaa     240
cccgaggact cgccgtgta ctactgccag cagggccagg tcatccctcc cacctttggc     300
cagggcacca aggtggaaat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                      645
```

<210> SEQ ID NO 69
<211> LENGTH: 1335
<212> TYPE: DNA
<213> ORGANISM: Artificial sequence
<220> FEATURE:
<223> OTHER INFORMATION: anti-DP47 Fc hole chain

<400> SEQUENCE: 69

```
gaggtgcaat gtttggagtc tgggggaggc ttggtacagc ctgggggtc cctgagactc       60
tcctgtgcag cctccggatt cacctttagc agttatgcca tgagctgggt ccgccaggct     120
ccagggaagg gctgagtg gtctcagct attagtggta gtggtggtag cacatactac         180
gcagactccg tgaagggccg gttcaccatc tccagagaca attccaagaa cacgctgtat     240
ctgcagatga acagcctgag agccgaggac acggccgtat attactgtgc gaaaggcagc    300
ggatttgact actggggcca aggaaccctg gtcaccgtct cgagtgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgt gaccgtgcc ctccagcagc ttgggcaccc agacctacat ctgcaacgtg     600
aatcacaagc ccagcaacac caaggtggac aagaaagttg agcccaaatc ttgtgacaaa    660
actcacacat gcccaccgtg cccagcacct gaagctgcag gggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag   960
gtctccaaca aagcccctcgg cgcccccatc gagaaaacca tctccaaagc caaagggcag    1020
ccccgagaac cacaggtgtg caccctgccc ccatcccggg atgagctgac caagaaccag    1080
```

```
gtcagcctct cgtgcgcagt caaaggcttc tatcccagcg acatcgccgt ggagtgggag    1140
agcaatgggc agccggagaa caactacaag accacgcctc ccgtgctgga ctccgacggc    1200
tccttcttcc tcgtgagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                    1335
```

<210> SEQ ID NO 70
<211> LENGTH: 645
<212> TYPE: DNA
<213> ORGANISM: Artificial sequence
<220> FEATURE:
<223> OTHER INFORMATION: anti-DP47 light chain

<400> SEQUENCE: 70

```
gaaatcgtgt taacgcagtc tccaggcacc ctgtctttgt ctccagggga agagccacc     60 ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagtatggta gctcaccgct gacgttcggc   300
caggggacca agtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgt                  645
```

<210> SEQ ID NO 71
<211> LENGTH: 445
<212> TYPE: PRT
<213> ORGANISM: Artificial sequence
<220> FEATURE:
<223> OTHER INFORMATION: anti-DP47 Fc hole chain

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

-continued

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 72
<211> LENGTH: 215
<212> TYPE: PRT
<213> ORGANISM: Artificial sequence
<220> FEATURE:
<223> OTHER INFORMATION: anti-DP47 light chain

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 73
<211> LENGTH: 163
<212> TYPE: PRT
<213> ORGANISM: Homo sapiens

<400> SEQUENCE: 73

Leu Gln Asp Pro Cys Ser Asn Cys Pro Ala Gly Thr Phe Cys Asp Asn
  1               5                  10                  15

Asn Arg Asn Gln Ile Cys Ser Pro Cys Pro Pro Asn Ser Phe Ser Ser
                 20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
 50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln

<210> SEQ ID NO 74
<211> LENGTH: 163
<212> TYPE: PRT
<213> ORGANISM: cynomolgus

<400> SEQUENCE: 74

Leu Gln Asp Leu Cys Ser Asn Cys Pro Ala Gly Thr Phe Cys Asp Asn
```

-continued

```
                1               5                  10                 15
            Asn Arg Ser Gln Ile Cys Ser Pro Cys Pro Asn Ser Phe Ser Ser
                            20                  25                  30

Ala Gly Gly Gln Arg Thr Cys Asp Ile Cys Arg Gln Cys Lys Gly Val
                        35                  40                  45

Phe Lys Thr Arg Lys Glu Cys Ser Ser Thr Ser Asn Ala Glu Cys Asp
            50                  55                  60

Cys Ile Ser Gly Tyr His Cys Leu Gly Ala Glu Cys Ser Met Cys Glu
            65                  70                  75                  80

Gln Asp Cys Lys Gln Gly Gln Glu Leu Thr Lys Lys Gly Cys Lys Asp
                            85                  90                  95

Cys Cys Phe Gly Thr Phe Asn Asp Gln Lys Arg Gly Ile Cys Arg Pro
                        100                 105                 110

Trp Thr Asn Cys Ser Leu Asp Gly Lys Ser Val Leu Val Asn Gly Thr
                        115                 120                 125

Lys Glu Arg Asp Val Val Cys Gly Pro Ser Pro Ala Asp Leu Ser Pro
            130                 135                 140

Gly Ala Ser Ser Ala Thr Pro Pro Ala Pro Ala Arg Glu Pro Gly His
            145                 150                 155                 160

Ser Pro Gln

<210> SEQ ID NO 75
<211> LENGTH: 164
<212> TYPE: PRT
<213> ORGANISM: Mus musculus

<400> SEQUENCE: 75

Val Gln Asn Ser Cys Asp Asn Cys Gln Pro Gly Thr Phe Cys Arg Lys
            1               5                   10                  15

Tyr Asn Pro Val Cys Lys Ser Cys Pro Pro Ser Thr Phe Ser Ser Ile
                            20                  25                  30

Gly Gly Gln Pro Asn Cys Asn Ile Cys Arg Val Cys Ala Gly Tyr Phe
                        35                  40                  45

Arg Phe Lys Lys Phe Cys Ser Ser Thr His Asn Ala Glu Cys Glu Cys
            50                  55                  60

Ile Glu Gly Phe His Cys Leu Gly Pro Gln Cys Thr Arg Cys Glu Lys
            65                  70                  75                  80

Asp Cys Arg Pro Gly Gln Glu Leu Thr Lys Gln Gly Cys Lys Thr Cys
                            85                  90                  95

Ser Leu Gly Thr Phe Asn Asp Gln Asn Gly Thr Gly Val Cys Arg Pro
                        100                 105                 110

Trp Thr Asn Cys Ser Leu Asp Gly Arg Ser Val Leu Lys Thr Gly Thr
                        115                 120                 125

Thr Glu Lys Asp Val Val Cys Gly Pro Pro Val Val Ser Phe Ser Pro
            130                 135                 140

Ser Thr Thr Ile Ser Val Thr Pro Glu Gly Gly Pro Gly Gly His Ser
            145                 150                 155                 160

Leu Gln Val Leu

<210> SEQ ID NO 76
<211> LENGTH: 681
<212> TYPE: DNA
<213> ORGANISM: Artificial sequence
<220> FEATURE:
<223> OTHER INFORMATION: Fc hole chain
```

<400> SEQUENCE: 76

```
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtgcacc ctgcccccat cccgggatga gctgaccaag   420
aaccaggtca gcctctcgtg cgcagtcaaa ggcttctatc ccagcgacat cgccgtggag   480
tgggagagca atgggcagcc ggagaacaac tacaagacca cgcctcccgt gctggactcc   540
gacggctcct tcttcctcgt gagcaagctc accgtggaca agagcaggtg gcagcagggg   600
aacgtcttct catgctccgt gatgcatgag gctctgcaca accactacac gcagaagagc   660
ctctccctgt ctccgggtaa a                                             681
```

<210> SEQ ID NO 77
<211> LENGTH: 1266
<212> TYPE: DNA
<213> ORGANISM: Artificial sequence
<220> FEATURE:
<223> OTHER INFORMATION: human 4-1BB Fc knob chain

<400> SEQUENCE: 77

```
ctgcaggacc cctgcagcaa ctgccctgcc ggcaccttct gcgacaacaa ccggaaccag    60
atctgcagcc cctgcccccc aacagcttc agctctgccg gcggacagcg gacctgcgac   120
atctgcagac agtgcaaggg cgtgttcaga acccggaaag agtgcagcag caccagcaac   180
gccgagtgcg actgcacccc cggcttccat tgtctgggag ccggctgcag catgtgcgag   240
caggactgca gcagggcca ggaactgacc aagaagggct gcaaggactg ctgcttcggc   300
accttcaacg accagaagcg gggcatctgc cggccctgga ccaactgtag cctggacggc   360
aagagcgtgc tggtcaacgg caccaaagaa cgggacgtcg tgtgcggccc cagccctgct   420
gatctgtctc ctggggccag cagcgtgacc cctcctgccc ctgccagaga gcctggccac   480
tctcctcagg tcgacgaaca gttatatttt cagggcggct cacccaaatc tgcagacaaa   540
actcacacat gcccaccgtg cccagcacct gaactcctgg ggggaccgtc agtcttcctc   600
ttccccccaa aacccaagga caccctcatg atctcccgga cccctgaggt cacatgcgtg   660
gtggtggacg tgagccacga agaccctgag gtcaagttca actggtacgt ggacggcgtg   720
gaggtgcata atgccaagac aaagccgcgg gaggagcagt acaacagcac gtaccgtgtg   780
gtcagcgtcc tcaccgtcct gcaccaggac tggctgaatg gcaaggagta caagtgcaag   840
gtctccaaca aagccctccc agcccccatc gagaaaacca tctccaaagc caagggcag   900
ccccgagaac acaggtgta cccctgcccc ccatgccggg atgagctgac caagaaccag   960
gtcagcctgt ggtgcctggt caaaggcttc tatcccagcg acatcgccgt ggagtgggag  1020
agcaatgggc agccggagaa caactacaag accacgcctc ccgtgctgga ctccgacggc  1080
tccttcttcc tctacagcaa gctcaccgtg gacaagagca ggtggcagca ggggaacgtc  1140
ttctcatgct ccgtgatgca tgaggctctg cacaaccact acacgcagaa gagcctctcc  1200
ctgtctccgg gtaaatccgg aggcctgaac gacatcttcg aggcccagaa gattgaatgg  1260
cacgag                                                            1266
```

<210> SEQ ID NO 78
<211> LENGTH: 1266
<212> TYPE: DNA
<213> ORGANISM: Artificial sequence
<220> FEATURE:
<223> OTHER INFORMATION: cynomolgus 4-1BB Fc knob chain

<400> SEQUENCE: 78

| | |
|---|---|
| ttgcaggatc tgtgtagtaa ctgcccagct ggtacattct gtgataataa caggagtcag | 60 |
| atttgcagtc cctgtcctcc aaatagtttc tccagcgcag gtggacaaag gacctgtgac | 120 |
| atatgcaggc agtgtaaagg tgttttcaag accaggaagg agtgttcctc caccagcaat | 180 |
| gcagagtgtg actgcatttc agggtatcac tgcctggggg cagagtgcag catgtgtgaa | 240 |
| caggattgta acaaggtca agaattgaca aaaaaggtt gtaaagactg ttgctttggg | 300 |
| acatttaatg accagaaacg tggcatctgt cgcccctgga caaactgttc tttggatgga | 360 |
| aagtctgtgc ttgtgaatgg gacgaaggag agggacgtgg tctgcggacc atctccagcc | 420 |
| gacctctctc caggagcatc ctctgcgacc ccgcctgccc ctgcgagaga gccaggacac | 480 |
| tctccgcagg tcgacgaaca gttatatttt cagggcggct cacccaaatc tgcagacaaa | 540 |
| actcacacat gcccaccgtg cccagcacct gaactcctgg ggggaccgtc agtcttcctc | 600 |
| ttccccccaa acccaagga caccctcatg atctcccgga cccctgaggt cacatgcgtg | 660 |
| gtggtggacg tgagccacga agaccctgag gtcaagttca actggtacgt ggacggcgtg | 720 |
| gaggtgcata atgccaagac aaagccgcgg gaggagcagt acaacagcac gtaccgtgtg | 780 |
| gtcagcgtcc tcaccgtcct gcaccaggac tggctgaatg gcaaggagta caagtgcaag | 840 |
| gtctccaaca aagccctccc agcccccatc gagaaaacca tctccaaagc caagggcag | 900 |
| ccccgagaac cacaggtgta caccctgccc ccatgccggg atgagctgac caagaaccag | 960 |
| gtcagcctgt ggtgcctggt caaaggcttc tatcccagcg acatcgccgt ggagtgggag | 1020 |
| agcaatgggc agccggagaa caactacaag accacgcctc ccgtgctgga ctccgacggc | 1080 |
| tccttcttcc tctacagcaa gctcaccgtg gacaagagca ggtggcagca ggggaacgtc | 1140 |
| ttctcatgct ccgtgatgca tgaggctctg cacaaccact acacgcagaa gagcctctcc | 1200 |
| ctgtctccgg gtaaatccgg aggcctgaac gacatcttcg aggcccagaa gattgaatgg | 1260 |
| cacgag | 1266 |

<210> SEQ ID NO 79
<211> LENGTH: 1269
<212> TYPE: DNA
<213> ORGANISM: Artificial sequence
<220> FEATURE:
<223> OTHER INFORMATION: Murine 4-1BB Fc knob chain

<400> SEQUENCE: 79

| | |
|---|---|
| gtgcagaaca gctgcgacaa ctgccagccc ggcaccttct gccggaagta caaccccgtg | 60 |
| tgcaagagct gccccccag caccttcagc agcatcggcg ccagcccaa ctgcaacatc | 120 |
| tgcagagtgt gcgccggcta cttccggttc aagaagttct gcagcagcac ccacaacgcc | 180 |
| gagtgcgagt gcatcgaggg cttccactgc ctggcccc agtgcaccag atgcgagaag | 240 |
| gactgcagac ccggccagga actgaccaag cagggctgta agacctgcag cctgggcacc | 300 |
| ttcaacgacc agaacgggac cggcgtgtgc cggccttgga ccaattgcag cctggacggg | 360 |
| agaagcgtgc tgaaaaccgg caccaccgag aaggacgtcg tgtgcggccc tcccgtggtg | 420 |

-continued

```
tccttcagcc ctagcaccac catcagcgtg acccctgaag gcggccctgg cggacactct    480
ctgcaggtcc tggtcgacga acagttatat tttcagggcg gctcacccaa atctgcagac    540
aaaactcaca catgcccacc gtgcccagca cctgaactcc tggggggacc gtcagtcttc    600
ctcttccccc caaaacccaa ggacaccctc atgatctccc ggacccctga ggtcacatgc    660
gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagccccc atcgagaaaa ccatctccaa agccaaaggg    900
cagccccgag aaccacaggt gtacaccctg cccccatgcc gggatgagct gaccaagaac    960
caggtcagcc tgtggtgcct ggtcaaaggc ttctatccca gcgacatcgc cgtggagtgg   1020
gagagcaatg ggcagccgga gaacaactac aagaccacgc tcccgtgct ggactccgac    1080
ggctccttct cctctacag caagctcacc gtggacaaga gcaggtggca gcagggaaac   1140
gtcttctcat gctccgtgat gcatgaggct ctgcacaacc actacacgca gaagagcctc   1200
tccctgtctc cgggtaaatc cggaggcctg aacgacatct cgaggccca aagattgaa    1260
tggcacgag                                                           1269
```

<210> SEQ ID NO 80
<211> LENGTH: 227
<212> TYPE: PRT
<213> ORGANISM: Artificial sequence
<220> FEATURE:
<223> OTHER INFORMATION: Fc hole chain

<400> SEQUENCE: 80

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
210                 215                 220

Pro Gly Lys
225

<210> SEQ ID NO 81
<211> LENGTH: 422
<212> TYPE: PRT
<213> ORGANISM: Artificial sequence
<220> FEATURE:
<223> OTHER INFORMATION: Human 4-1BB Fc knob chain

<400> SEQUENCE: 81

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Asn Ser Phe Ser Ser
        20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Val Asp Glu Gln Leu Tyr Phe Gln Gly Gly Ser Pro Lys
                165                 170                 175

Ser Ala Asp Lys Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
            195                 200                 205

Leu Met Ile Ser Arg Thr Pro Glu Val Thr Cys Val Val Val Asp Val
210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
            275                 280                 285

Pro Ile Glu Lys Thr Ile Ser Lys Ala Lys Gly Gln Pro Arg Glu Pro
290                 295                 300

Gln Val Tyr Thr Leu Pro Pro Cys Arg Asp Glu Leu Thr Lys Asn Gln
305                 310                 315                 320

Val Ser Leu Trp Cys Leu Val Lys Gly Phe Tyr Pro Ser Asp Ile Ala
                325                 330                 335

```
Val Glu Trp Glu Ser Asn Gly Gln Pro Glu Asn Asn Tyr Lys Thr Thr
                340                 345                 350

Pro Pro Val Leu Asp Ser Asp Gly Ser Phe Phe Leu Tyr Ser Lys Leu
            355                 360                 365

Thr Val Asp Lys Ser Arg Trp Gln Gln Gly Asn Val Phe Ser Cys Ser
        370                 375                 380

Val Met His Glu Ala Leu His Asn His Tyr Thr Gln Lys Ser Leu Ser
385                 390                 395                 400

Leu Ser Pro Gly Lys Ser Gly Gly Leu Asn Asp Ile Phe Glu Ala Gln
                405                 410                 415

Lys Ile Glu Trp His Glu
            420

<210> SEQ ID NO 82
<211> LENGTH: 422
<212> TYPE: PRT
<213> ORGANISM: Artificial sequence
<220> FEATURE:
<223> OTHER INFORMATION: Cynomolgus 4-1BB Fc knob chain

<400> SEQUENCE: 82

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Ala Thr Pro Pro Ala Pro Ala Arg Glu Pro Gly His
145                 150                 155                 160

Ser Pro Gln Val Asp Glu Gln Leu Tyr Phe Gln Gly Gly Ser Pro Lys
                165                 170                 175

Ser Ala Asp Lys Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270
```

Asn Gly Lys Glu Tyr Lys Cys Lys Val Ser Asn Lys Ala Leu Pro Ala
            275                 280                 285

Pro Ile Glu Lys Thr Ile Ser Lys Ala Lys Gly Gln Pro Arg Glu Pro
        290                 295                 300

Gln Val Tyr Thr Leu Pro Pro Cys Arg Asp Glu Leu Thr Lys Asn Gln
305                 310                 315                 320

Val Ser Leu Trp Cys Leu Val Lys Gly Phe Tyr Pro Ser Asp Ile Ala
            325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
            355                 360                 365

Thr Val Asp Lys Ser Arg Trp Gln Gln Gly Asn Val Phe Ser Cys Ser
        370                 375                 380

Val Met His Glu Ala Leu His Asn His Tyr Thr Gln Lys Ser Leu Ser
385                 390                 395                 400

Leu Ser Pro Gly Lys Ser Gly Gly Leu Asn Asp Ile Phe Glu Ala Gln
                405                 410                 415

Lys Ile Glu Trp His Glu
            420

<210> SEQ ID NO 83
<211> LENGTH: 423
<212> TYPE: PRT
<213> ORGANISM: Artificial sequence
<220> FEATURE:
<223> OTHER INFORMATION: Murine 4-1BB Fc knob chain

<400> SEQUENCE: 83

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
            85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
130                 135                 140

Ser Thr Thr Ile Ser Val Thr Pro Glu Gly Gly Pro Gly Gly His Ser
145                 150                 155                 160

Leu Gln Val Leu Val Asp Glu Gln Leu Tyr Phe Gln Gly Gly Ser Pro
                165                 170                 175

Lys Ser Ala Asp Lys Thr His Thr Cys Pro Pro Cys Pro Ala Pro Glu
            180                 185                 190

Leu Leu Gly Gly Pro Ser Val Phe Leu Phe Pro Pro Lys Pro Lys Asp
        195                 200                 205

```
Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
290                 295                 300

Pro Gln Val Tyr Thr Leu Pro Pro Cys Arg Asp Glu Leu Thr Lys Asn
305                 310                 315                 320

Gln Val Ser Leu Trp Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys Ser Gly Gly Leu Asn Asp Ile Phe Glu Ala
                405                 410                 415

Gln Lys Ile Glu Trp His Glu
            420

<210> SEQ ID NO 84
<211> LENGTH: 15
<212> TYPE: PRT
<213> ORGANISM: Artificial sequence
<220> FEATURE:
<223> OTHER INFORMATION: Avi tag

<400> SEQUENCE: 84

Gly Leu Asn Asp Ile Phe Glu Ala Gln Lys Ile Glu Trp His Glu
1               5                   10                  15

<210> SEQ ID NO 85
<211> LENGTH: 594
<212> TYPE: DNA
<213> ORGANISM: Artificial sequence
<220> FEATURE:
<223> OTHER INFORMATION: Human 4-1BB his tagged

<400> SEQUENCE: 85
ctgcaggacc cctgcagcaa ctgccctgcc ggcaccttct gcgacaacaa ccggaaccag      60
atctgcagcc cctgccccce caacagcttc agctctgccg gcggacagcg gacctgcgac     120
atctgcagac agtgcaaggg cgtgttcaga acccggaaag agtgcagcag caccagcaac     180
gccgagtgcg actgcacccc cggcttccat tgtctgggag ccggctgcag catgtgcgag     240
caggactgca agcagggcca ggaactgacc aagaagggct gcaaggactg ctgcttcggc     300
accttcaacg accagaagcg gggcatctgc cggccctgga ccaactgtag cctggacggc     360
aagagcgtgc tggtcaacgg caccaaagaa cgggacgtcg tgtgcggccc cagccctgct     420
```

```
gatctgtctc ctggggccag cagcgtgacc cctcctgccc ctgccagaga gcctggccac      480
tctcctcagg tcgacgaaca gttatatttt cagggcggct caggcctgaa cgacatcttc      540
gaggcccaga agatcgagtg gcacgaggct cgagctcacc accatcacca tcac            594
```

<210> SEQ ID NO 86
<211> LENGTH: 198
<212> TYPE: PRT
<213> ORGANISM: Artificial sequence
<220> FEATURE:
<223> OTHER INFORMATION: Human 4-1BB His tagged

<400> SEQUENCE: 86

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Val Asp Glu Gln Leu Tyr Phe Gln Gly Gly Ser Gly Leu
                165                 170                 175

Asn Asp Ile Phe Glu Ala Gln Lys Ile Glu Trp His Glu Ala Arg Ala
            180                 185                 190

His His His His His His
        195
```

<210> SEQ ID NO 87
<211> LENGTH: 1968
<212> TYPE: DNA
<213> ORGANISM: Artificial sequence
<220> FEATURE:
<223> OTHER INFORMATION: trimeric hu OX40L(51-183) Fc knob chain

<400> SEQUENCE: 87

```
caggtgtccc acagataccc cagaatccag agcatcaagg tgcagttcac cgagtacaag      60
aaagagaagg gcttcatcct gaccagccag aaagaggacg agatcatgaa ggtgcaggac     120
aacagcgtga tcatcaactg cgacggcttc tacctgatca gcctgaaggg ctacttcagc     180
caggaagtgg acatcagcct gcactaccag aaggacgagg aacccctgtt ccagctgaag     240
aaagtgcgga gcgtgaacag cctgatggtg gccagcctga cctacaagga caaggtgtac     300
ctgaacgtga ccaccgacaa caccagcctg gacgacttcc acgtgaacgg cggcgagctg     360
atcctgattc accagaaccc cggcgagttc tgcgtgctgg gaggcggagg atctggcgga     420
```

| | |
|---|---|
| ggcggatctc aggtgtcaca ccgctacccc cggattcagt ccattaaggt gcagtttaca | 480 |
| gagtataaga aagaaaaagg ctttattctg acttcccaga aagaagatga gattatgaag | 540 |
| gtgcaggata attctgtgat catcaattgt gatgggtttt atctgatctc cctgaaagga | 600 |
| tactttagtc aggaagtgga tatttctctg cactatcaga aagatgaaga acctctgttc | 660 |
| cagctgaaaa aagtgcgctc cgtgaattct ctgatggtgg cttccctgac atacaaagac | 720 |
| aaagtgtatc tgaatgtgac aacagataat acctccctgg atgatttcca tgtgaatggg | 780 |
| ggggaactga ttctgatcca tcagaaccct ggggaatttt gtgtgctggg cggaggggga | 840 |
| agtggcggcg gaggcagtca ggtgtcccat cggtatccta gaatccagtc tatcaaagtg | 900 |
| cagtttactg agtacaaaaa agagaaagga ttcattctga cctctcagaa agaggacgaa | 960 |
| attatgaagg tgcaggataa cagtgtgatt attaactgtg atgggttcta cctgatttct | 1020 |
| ctgaagggat atttcagtca ggaagtggac atctcactgc attaccagaa ggatgaagaa | 1080 |
| ccactgttcc agctgaagaa agtgcgctct gtgaatagcc tgatggtggc ctctctgact | 1140 |
| tataaggata aggtgtacct gaatgtgaca actgacaata cttctctgga cgactttcat | 1200 |
| gtgaacgggg gagagctgat tctgatccac cagaatccag gcgagttttg tgtgctggga | 1260 |
| agccccggca gcagcagctc tggatccgac aaaactcaca catgcccacc gtgcccagca | 1320 |
| cctgaagctg caggggggacc gtcagtcttc ctcttccccc caaaacccaa ggacaccctc | 1380 |
| atgatctccc ggacccctga ggtcacatgc gtggtggtgg acgtgagcca cgaagaccct | 1440 |
| gaggtcaagt tcaactggta cgtggacggc gtggaggtgc ataatgccaa gacaaagccg | 1500 |
| cgggaggagc agtacaacag cacgtaccgt gtggtcagcg tcctcaccgt cctgcaccag | 1560 |
| gactggctga atggcaagga gtacaagtgc aaggtctcca acaaagccct cggcgccccc | 1620 |
| atcgagaaaa ccatctccaa agccaaaggg cagccccgag aaccacaggt gtacaccctg | 1680 |
| cccccatgcc gggatgagct gaccaagaac caggtcagcc tgtggtgcct ggtcaaaggc | 1740 |
| ttctatccca gcgacatcgc cgtggagtgg gagagcaatg ggcagccgga gaacaactac | 1800 |
| aagaccacgc ctcccgtgct ggactccgac ggctccttct tcctctacag caagctcacc | 1860 |
| gtggacaaga gcaggtggca gcaggggaac gtcttctcat gctccgtgat gcatgaggct | 1920 |
| ctgcacaacc actacacgca gaagagcctc tccctgtctc cgggtaaa | 1968 |

<210> SEQ ID NO 88
<211> LENGTH: 186
<212> TYPE: PRT
<213> ORGANISM: Homo sapiens

<400> SEQUENCE: 88

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
```

```
                    100                 105                 110
Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185

<210> SEQ ID NO 89
<211> LENGTH: 186
<212> TYPE: PRT
<213> ORGANISM: cynomolgus

<400> SEQUENCE: 89

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
    50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
            180                 185

<210> SEQ ID NO 90
<211> LENGTH: 192
<212> TYPE: PRT
<213> ORGANISM: Mus musculus

<400> SEQUENCE: 90

Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
            20                  25                  30

Cys Asp His Thr Arg Asp Thr Leu Cys His Pro Cys Glu Thr Gly Phe
        35                  40                  45

Tyr Asn Glu Ala Val Asn Tyr Asp Thr Cys Lys Gln Cys Thr Gln Cys
```

|  | 50 |  |  | 55 |  |  | 60 |  |  |  |
|---|---|---|---|---|---|---|---|---|---|---|

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
    130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190

<210> SEQ ID NO 91
<211> LENGTH: 1335
<212> TYPE: DNA
<213> ORGANISM: Artificial sequence
<220> FEATURE:
<223> OTHER INFORMATION: Human OX40 Fc knob chain

<400> SEQUENCE: 91
ctgcactgcg tgggcgacac ctaccccagc aacgaccggt gctgccacga gtgcagaccc    60
ggcaacggca tggtgtcccg gtgcagccgg tcccagaaca ccgtgtgcag accttgcggc    120
cctggcttct acaacgacgt ggtgtccagc aagccctgca agccttgtac ctggtgcaac    180
ctgcggagcg gcagcgagcg gaagcagctg tgtaccgcca cccaggatac cgtgtgccgg    240
tgtagagccg gcacccagcc cctggacagc tacaaacccg gcgtggactg cgccccttgc    300
cctcctggcc acttcagccc tggcgacaac caggcctgca gccttggac caactgcacc    360
ctggccggca gcacaccct gcagcccgcc agcaatagca gcgacgccat ctgcgaggac    420
cgggatcctc ctgccacca gcctcaggaa acccagggcc ctcccgccag acccatcacc    480
gtgcagccta cagaggcctg gcccagaacc agcaggggc ctagcaccag acccgtggaa    540
gtgcctggcg gcagagccgt cgacgaacag ttatatttc agggcggctc acccaaatct    600
gcagacaaaa ctcacacatg cccaccgtgc ccagcacctg aactcctggg gggaccgtca    660
gtcttcctct tccccccaaa acccaaggac accctcatga tctcccggac ccctgaggtc    720
acatgcgtgg tggtggacgt gagccacgaa gaccctgagg tcaagttcaa ctggtacgtg    780
gacggcgtgg aggtgcataa tgccaagaca aagccgcggg aggagcagta caacagcacg    840
taccgtgtgg tcagcgtcct caccgtcctg caccaggact ggctgaatgg caaggagtac    900
aagtgcaagg tctccaacaa agccctccca gcccccatcg agaaaaccat ctccaaagcc    960
aaagggcagc cccgagaacc acaggtgtac accctgcccc catgccggga tgagctgacc   1020
aagaaccagg tcagcctgtg tgtgcctggtc aaaggcttct atcccagcga catcgccgtg   1080
gagtgggaga gcaatgggca gccggagaac aactacaaga ccacgcctcc cgtgctggac   1140
tccgacggct ccttcttcct ctacagcaag ctcaccgtgg acaagagcag gtggcagcag   1200
gggaacgtct tctcatgctc cgtgatgcat gaggctctgc acaaccacta cacgcagaag   1260
agcctctccc tgtctccggg taaatccgga ggcctgaacg acatcttcga ggcccagaag   1320

-continued

| attgaatggc acgag | 1335 |

<210> SEQ ID NO 92
<211> LENGTH: 1335
<212> TYPE: DNA
<213> ORGANISM: Artificial sequence
<220> FEATURE:
<223> OTHER INFORMATION: Cynomolgus OX40 Fc knob chain

<400> SEQUENCE: 92

| ctccactgtg tcggggacac ctaccccagc aacgaccggt gctgtcagga gtgcaggcca | 60 |
| ggcaacggga tggtgagccg ctgcaaccgc tcccagaaca cggtgtgccg tccgtgcggg | 120 |
| cccggcttct acaacgacgt ggtcagcgcc aagccctgca aggcctgcac atggtgcaac | 180 |
| ctcagaagtg ggagtgagcg gaaacagccg tgcacggcca cacaggacac agtctgccgc | 240 |
| tgccgggcgg gcacccagcc cctggacagc tacaagcctg gagttgactg tgccccctgc | 300 |
| cctccagggc acttctcccc gggcgacaac caggcctgca gccctggac caactgcacc | 360 |
| ttggccggga agcacaccct gcagccagcc agcaatagct cggacgccat ctgtgaggac | 420 |
| agggaccccc cacccacaca gccccaggag acccagggcc cccgggccag gcccaccact | 480 |
| gtccagccca ctgaagcctg gcccagaacc tcacagagac cctccacccg gccgtggag | 540 |
| gtccccaggg gccctgcggt cgacgaacag ttatatttc agggcggctc acccaaatct | 600 |
| gcagacaaaa ctcacacatg cccaccgtgc ccagcacctg aactcctggg gggaccgtca | 660 |
| gtcttcctct tccccccaaa acccaaggac accctcatga tctcccggac ccctgaggtc | 720 |
| acatgcgtgg tggtggacgt gagccacgaa gaccctgagg tcaagttcaa ctggtacgtg | 780 |
| gacggcgtgg aggtgcataa tgccaagaca aagccgcggg aggagcagta caacagcacg | 840 |
| taccgtgtgg tcagcgtcct caccgtcctg caccaggact ggctgaatgg caaggagtac | 900 |
| aagtgcaagg tctccaacaa agccctccca gcccccatcg agaaaaccat ctccaaagcc | 960 |
| aaagggcagc cccgagaacc acaggtgtac accctgcccc catgccggga tgagctgacc | 1020 |
| aagaaccagg tcagcctgtg tgtgcctggtc aaaggcttct atcccagcga catcgccgtg | 1080 |
| gagtgggaga gcaatgggca gccggagaac aactacaaga ccacgcctcc cgtgctggac | 1140 |
| tccgacggct ccttcttcct ctacagcaag ctcaccgtgg acaagagcag gtggcagcag | 1200 |
| gggaacgtct tctcatgctc cgtgatgcat gaggctctgc acaaccacta cacgcagaag | 1260 |
| agcctctccc tgtctccggg taaatccgga ggcctgaacg acatcttcga ggcccagaag | 1320 |
| attgaatggc acgag | 1335 |

<210> SEQ ID NO 93
<211> LENGTH: 1353
<212> TYPE: DNA
<213> ORGANISM: Artificial sequence
<220> FEATURE:
<223> OTHER INFORMATION: Murine OX40 Fc knob chain

<400> SEQUENCE: 93

| gtgaccgcca gacggctgaa ctgcgtgaag cacacctacc ccagcggcca caagtgctgc | 60 |
| agagagtgcc agcccggcca cggcatggtg tccagatgcg accacacacg ggacaccctg | 120 |
| tgccacccctt gcgagacagg cttctacaac gaggccgtga actacgatac ctgcaagcag | 180 |
| tgcacccagt gcaaccacag aagcggcagc gagctgaagc agaactgcac ccccacccag | 240 |
| gataccgtgt gcagatgcag acccggcacc cagcccgaca ggacagcgg ctacaagctg | 300 |

-continued

```
ggcgtggact gcgtgccctg ccctcctggc cacttcagcc ccggcaacaa ccaggcctgc    360
aagccctgga ccaactgcac cctgagcggc aagcagacca gacacccgc cagcgacagc     420
ctggatgccg tgtgcgagga cagaagcctg ctggccaccc tgctgtggga gacacagcgg    480
cccaccttca gacccaccac cgtgcagagc accaccgtgt ggcccagaac cagcgagctg    540
cccagtcctc ctaccctcgt gacacctgag ggccccgtcg acgaacagtt atattttcag    600
ggcggctcac ccaaatctgc agacaaaact cacacatgcc caccgtgccc agcacctgaa    660
ctcctggggg gaccgtcagt cttcctcttc cccccaaaac ccaaggacac cctcatgatc    720
tcccggaccc ctgaggtcac atgcgtggtg gtggacgtga gccacgaaga ccctgaggtc    780
aagttcaact ggtacgtgga cggcgtggag gtgcataatg ccaagacaaa gccgcgggag    840
gagcagtaca acagcacgta ccgtgtggtc agcgtcctca ccgtcctgca ccaggactgg    900
ctgaatggca aggagtacaa gtgcaaggtc tccaacaaag ccctcccagc ccccatcgag    960
aaaaccatct ccaaagccaa agggcagccc cgagaaccac aggtgtacac cctgcccca    1020
tgccgggatg agctgaccaa gaaccaggtc agcctgtggt gcctggtcaa aggcttctat    1080
cccagcgaca tcgccgtgga gtgggagagc aatgggcagc cggagaacaa ctacaagacc    1140
acgcctcccg tgctggactc cgacggctcc ttcttcctct acagcaagct caccgtggac    1200
aagagcaggt ggcagcaggg gaacgtcttc tcatgctccg tgatgcatga ggctctgcac    1260
aaccactaca cgcagaagag cctctccctg tctccgggta aatccggagg cctgaacgac    1320
atcttcgagg cccagaagat tgaatggcac gag                                 1353
```

<210> SEQ ID NO 94
<211> LENGTH: 445
<212> TYPE: PRT
<213> ORGANISM: Artificial sequence
<220> FEATURE:
<223> OTHER INFORMATION: Human OX40 Fc knob chain

<400> SEQUENCE: 94

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175
```

```
Arg Pro Val Glu Val Pro Gly Gly Arg Ala Val Asp Glu Gln Leu Tyr
            180                 185                 190

Phe Gln Gly Gly Ser Pro Lys Ser Ala Asp Lys Thr His Thr Cys Pro
            195                 200                 205

Pro Cys Pro Ala Pro Glu Leu Leu Gly Gly Pro Ser Val Phe Leu Phe
        210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
                260                 265                 270

Arg Glu Glu Gln Tyr Asn Ser Thr Tyr Arg Val Val Ser Val Leu Thr
            275                 280                 285

Val Leu His Gln Asp Trp Leu Asn Gly Lys Glu Tyr Lys Cys Lys Val
        290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Cys Arg
                325                 330                 335

Asp Glu Leu Thr Lys Asn Gln Val Ser Leu Trp Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Val Leu Asp Ser Asp Gly Ser
370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys Ser Gly Gly Leu
            420                 425                 430

Asn Asp Ile Phe Glu Ala Gln Lys Ile Glu Trp His Glu
        435                 440                 445

<210> SEQ ID NO 95
<211> LENGTH: 445
<212> TYPE: PRT
<213> ORGANISM: Artificial sequence
<220> FEATURE:
<223> OTHER INFORMATION: Cynomolgus OX40 Fc knob chain

<400> SEQUENCE: 95

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95
```

Cys Ala Pro Cys Pro Pro Gly His Phe Ser Pro Gly Asp Asn Gln Ala
                100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala Val Asp Glu Gln Leu Tyr
            180                 185                 190

Phe Gln Gly Gly Ser Pro Lys Ser Ala Asp Lys Thr His Thr Cys Pro
        195                 200                 205

Pro Cys Pro Ala Pro Glu Leu Leu Gly Gly Pro Ser Val Phe Leu Phe
    210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
            260                 265                 270

Arg Glu Glu Gln Tyr Asn Ser Thr Tyr Arg Val Val Ser Val Leu Thr
        275                 280                 285

Val Leu His Gln Asp Trp Leu Asn Gly Lys Glu Tyr Lys Cys Lys Val
    290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Cys Arg
                325                 330                 335

Asp Glu Leu Thr Lys Asn Gln Val Ser Leu Trp Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Val Leu Asp Ser Asp Gly Ser
    370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys Ser Gly Gly Leu
            420                 425                 430

Asn Asp Ile Phe Glu Ala Gln Lys Ile Glu Trp His Glu
        435                 440                 445

<210> SEQ ID NO 96
<211> LENGTH: 451
<212> TYPE: PRT
<213> ORGANISM: Artificial sequence
<220> FEATURE:
<223> OTHER INFORMATION: Murine OX40 Fc knob chain

<400> SEQUENCE: 96

Val Thr Ala Arg Arg Leu Asn Cys Val Lys His Thr Tyr Pro Ser Gly
1               5                   10                  15

-continued

His Lys Cys Cys Arg Glu Cys Gln Pro Gly His Gly Met Val Ser Arg
                20                  25                  30

Cys Asp His Thr Arg Asp Thr Leu Cys His Pro Cys Glu Thr Gly Phe
         35                  40                  45

Tyr Asn Glu Ala Val Asn Tyr Asp Thr Cys Lys Gln Cys Thr Gln Cys
 50                  55                  60

Asn His Arg Ser Gly Ser Glu Leu Lys Gln Asn Cys Thr Pro Thr Gln
 65                  70                  75                  80

Asp Thr Val Cys Arg Cys Arg Pro Gly Thr Gln Pro Arg Gln Asp Ser
                 85                  90                  95

Gly Tyr Lys Leu Gly Val Asp Cys Val Pro Cys Pro Pro Gly His Phe
                100                 105                 110

Ser Pro Gly Asn Asn Gln Ala Cys Lys Pro Trp Thr Asn Cys Thr Leu
            115                 120                 125

Ser Gly Lys Gln Thr Arg His Pro Ala Ser Asp Ser Leu Asp Ala Val
            130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
                180                 185                 190

Val Asp Glu Gln Leu Tyr Phe Gln Gly Gly Ser Pro Lys Ser Ala Asp
            195                 200                 205

Lys Thr His Thr Cys Pro Pro Cys Pro Ala Pro Glu Leu Leu Gly Gly
210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
            275                 280                 285

Val Val Ser Val Leu Thr Val Leu His Gln Asp Trp Leu Asn Gly Lys
290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Cys Arg Asp Glu Leu Thr Lys Asn Gln Val Ser Leu
            340                 345                 350

Trp Cys Leu Val Lys Gly Phe Tyr Pro Ser Asp Ile Ala Val Glu Trp
            355                 360                 365

Glu Ser Asn Gly Gln Pro Glu Asn Asn Tyr Lys Thr Thr Pro Pro Val
370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys Ser Gly Gly Leu Asn Asp Ile Phe Glu Ala Gln Lys Ile Glu

<210> SEQ ID NO 97
<211> LENGTH: 663
<212> TYPE: DNA
<213> ORGANISM: Artificial sequence
<220> FEATURE:
<223> OTHER INFORMATION: Human OX40 His tagged

<400> SEQUENCE: 97

```
ctgcactgcg tgggcgacac ctaccccagc aacgaccggt gctgccacga gtgcagaccc        60
ggcaacggca tggtgtcccg gtgcagccgg tcccagaaca ccgtgtgcag accttgcggc       120
cctggcttct acaacgacgt ggtgtccagc aagccctgca agccttgtac ctggtgcaac       180
ctgcggagcg gcagcgagcg gaagcagctg tgtaccgcca cccaggatac cgtgtgccgg       240
tgtagagccg gcacccagcc cctggacagc tacaaaccccg cgtggactg cgcccccttgc      300
cctcctggcc acttcagccc tggcgacaac caggcctgca agccttggac caactgcacc       360
ctggccggca gcacaccct gcagcccgcc agcaatagca gcgacgccat ctgcgaggac        420
cgggatcctc ctgccaccca gcctcaggaa acccagggcc ctcccgccag acccatcacc       480
gtgcagccta cagaggcctg gcccagaacc agccaggggc ctagcaccag acccgtggaa       540
gtgcctggcg gcagagccgt cgacgaacag ttatattttc agggcggctc aggcctgaac       600
gacatcttcg aggcccagaa gatcgagtgg cacgaggctc gagctcacca ccatcaccat       660
cac                                                                    663
```

<210> SEQ ID NO 98
<211> LENGTH: 221
<212> TYPE: PRT
<213> ORGANISM: Artificial sequence
<220> FEATURE:
<223> OTHER INFORMATION: Human OX40 His tagged

<400> SEQUENCE: 98

Leu His Cys Val Gly Asp Thr Tyr Pro Ser Asn Asp Arg Cys Cys His
 1               5                  10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
        50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

```
Val Gln Pro Thr Glu Ala Trp Pro Arg Thr Ser Gln Gly Pro Ser Thr
                165                 170                 175

Arg Pro Val Glu Val Pro Gly Gly Arg Ala Val Asp Glu Gln Leu Tyr
            180                 185                 190

Phe Gln Gly Gly Ser Gly Leu Asn Asp Ile Phe Glu Ala Gln Lys Ile
        195                 200                 205

Glu Trp His Glu Ala Arg Ala His His His His His His
    210                 215                 220

<210> SEQ ID NO 99
<211> LENGTH: 178
<212> TYPE: PRT
<213> ORGANISM: Homo sapiens

<400> SEQUENCE: 99

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 100
<211> LENGTH: 164
<212> TYPE: PRT
<213> ORGANISM: Homo sapiens

<400> SEQUENCE: 100

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
```

```
                    85                  90                  95
Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
            115                 120                 125

Gly Val His Leu His Thr Glu Ala Arg Ala Arg His Ala Trp Gln Leu
            130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 101
<211> LENGTH: 169
<212> TYPE: PRT
<213> ORGANISM: Homo sapiens

<400> SEQUENCE: 101

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 102
<211> LENGTH: 197
<212> TYPE: PRT
<213> ORGANISM: Homo sapiens

<400> SEQUENCE: 102

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80
```

```
Glu Leu Val Val Ala Lys Ala Gly Val Tyr Tyr Val Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
            115                 120                 125

Ala Leu Thr Val Asp Leu Pro Pro Ala Ser Ser Glu Ala Arg Asn Ser
        130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
            195

<210> SEQ ID NO 103
<211> LENGTH: 555
<212> TYPE: PRT
<213> ORGANISM: Artificial sequence
<220> FEATURE:
<223> OTHER INFORMATION: trimeric hu 4-1BBL (71-248) connected by (G4S)2
      linker

<400> SEQUENCE: 103

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Glu Gly Gly Gly Gly Ser Gly Gly Gly Gly Ser Arg Glu Gly
            180                 185                 190

Pro Glu Leu Ser Pro Asp Asp Pro Ala Gly Leu Leu Asp Leu Arg Gln
        195                 200                 205

Gly Met Phe Ala Gln Leu Val Ala Gln Asn Val Leu Leu Ile Asp Gly
    210                 215                 220

Pro Leu Ser Trp Tyr Ser Asp Pro Gly Leu Ala Gly Val Ser Leu Thr
```

```
            225                 230                 235                 240
Gly Gly Leu Ser Tyr Lys Glu Asp Thr Lys Glu Leu Val Val Ala Lys
                245                 250                 255
Ala Gly Val Tyr Tyr Val Phe Phe Gln Leu Glu Leu Arg Arg Val Val
                260                 265                 270
Ala Gly Glu Gly Ser Gly Ser Val Ser Leu Ala Leu His Leu Gln Pro
                275                 280                 285
Leu Arg Ser Ala Ala Gly Ala Ala Leu Ala Leu Thr Val Asp Leu
    290                 295                 300
Pro Pro Ala Ser Ser Glu Ala Arg Asn Ser Ala Phe Gly Phe Gln Gly
305                 310                 315                 320
Arg Leu Leu His Leu Ser Ala Gly Gln Arg Leu Gly Val His Leu His
                325                 330                 335
Thr Glu Ala Arg Ala Arg His Ala Trp Gln Leu Thr Gln Gly Ala Thr
                340                 345                 350
Val Leu Gly Leu Phe Arg Val Thr Pro Glu Ile Pro Ala Gly Leu Gly
                355                 360                 365
Gly Gly Gly Ser Gly Gly Gly Ser Arg Glu Gly Pro Glu Leu Ser
    370                 375                 380
Pro Asp Asp Pro Ala Gly Leu Leu Asp Leu Arg Gln Gly Met Phe Ala
385                 390                 395                 400
Gln Leu Val Ala Gln Asn Val Leu Leu Ile Asp Gly Pro Leu Ser Trp
                405                 410                 415
Tyr Ser Asp Pro Gly Leu Ala Gly Val Ser Leu Thr Gly Gly Leu Ser
                420                 425                 430
Tyr Lys Glu Asp Thr Lys Glu Leu Val Val Ala Lys Ala Gly Val Tyr
                435                 440                 445
Tyr Val Phe Phe Gln Leu Glu Leu Arg Arg Val Val Ala Gly Glu Gly
                450                 455                 460
Ser Gly Ser Val Ser Leu Ala Leu His Leu Gln Pro Leu Arg Ser Ala
465                 470                 475                 480
Ala Gly Ala Ala Ala Leu Ala Leu Thr Val Asp Leu Pro Pro Ala Ser
                485                 490                 495
Ser Glu Ala Arg Asn Ser Ala Phe Gly Phe Gln Gly Arg Leu Leu His
                500                 505                 510
Leu Ser Ala Gly Gln Arg Leu Gly Val His Leu His Thr Glu Ala Arg
                515                 520                 525
Ala Arg His Ala Trp Gln Leu Thr Gln Gly Ala Thr Val Leu Gly Leu
                530                 535                 540
Phe Arg Val Thr Pro Glu Ile Pro Ala Gly Leu
545                 550                 555

<210> SEQ ID NO 104
<211> LENGTH: 5
<212> TYPE: PRT
<213> ORGANISM: Artificial Sequence
<220> FEATURE:
<223> OTHER INFORMATION: FAP(4B9) CDR-H1

<400> SEQUENCE: 104

Ser Tyr Ala Met Ser
1               5

<210> SEQ ID NO 105
<211> LENGTH: 17
<212> TYPE: PRT
```

```
<213> ORGANISM: Artificial Sequence
<220> FEATURE:
<223> OTHER INFORMATION: FAP(4B9) CDR-H2

<400> SEQUENCE: 105

Ala Ile Ile Gly Ser Gly Ala Ser Thr Tyr Tyr Ala Asp Ser Val Lys
1               5                   10                  15
Gly

<210> SEQ ID NO 106
<211> LENGTH: 8
<212> TYPE: PRT
<213> ORGANISM: Artificial Sequence
<220> FEATURE:
<223> OTHER INFORMATION: FAP(4B9) CDR-H3

<400> SEQUENCE: 106

Gly Trp Phe Gly Gly Phe Asn Tyr
1               5

<210> SEQ ID NO 107
<211> LENGTH: 12
<212> TYPE: PRT
<213> ORGANISM: Artificial Sequence
<220> FEATURE:
<223> OTHER INFORMATION: FAP(4B9) CDR-L1

<400> SEQUENCE: 107

Arg Ala Ser Gln Ser Val Thr Ser Ser Tyr Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: FAP(4B9) CDR-L2

<400> SEQUENCE: 108

Val Gly Ser Arg Arg Ala Thr
1               5

<210> SEQ ID NO 109
<211> LENGTH: 9
<212> TYPE: PRT
<213> ORGANISM: Artificial Sequence
<220> FEATURE:
<223> OTHER INFORMATION: FAP(4B9) CDR-L3

<400> SEQUENCE: 109

Gln Gln Gly Ile Met Leu Pro Pro Thr
1               5

<210> SEQ ID NO 110
<211> LENGTH: 117
<212> TYPE: PRT
<213> ORGANISM: Artificial Sequence
<220> FEATURE:
<223> OTHER INFORMATION: FAP(4B9) VH

<400> SEQUENCE: 110

Glu Val Gln Leu Leu Glu Ser Gly Gly Gly Leu Val Gln Pro Gly Gly
1               5                   10                  15
Ser Leu Arg Leu Ser Cys Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ala Ile Ile Gly Ser Gly Ala Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 111
<211> LENGTH: 108
<212> TYPE: PRT
<213> ORGANISM: Artificial Sequence
<220> FEATURE:
<223> OTHER INFORMATION: FAP(4B9) VL

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 112
<211> LENGTH: 5
<212> TYPE: PRT
<213> ORGANISM: Artificial Sequence
<220> FEATURE:
<223> OTHER INFORMATION: CEA(sm9b) CDR-H1

<400> SEQUENCE: 112

Asp Ser Tyr Met His
1               5

<210> SEQ ID NO 113
<211> LENGTH: 17
<212> TYPE: PRT
<213> ORGANISM: Artificial Sequence
<220> FEATURE:
<223> OTHER INFORMATION: CEA(sm9b) CDR-H2

<400> SEQUENCE: 113

Trp Ile Asp Pro Glu Asn Gly Asp Thr Glu Tyr Ala Pro Lys Phe Gln
1               5                   10                  15

Gly

<210> SEQ ID NO 114

```
<211> LENGTH: 11
<212> TYPE: PRT
<213> ORGANISM: Artificial Sequence
<220> FEATURE:
<223> OTHER INFORMATION: CEA(sm9b) CDR-H3

<400> SEQUENCE: 114

Gly Thr Pro Thr Gly Pro Tyr Tyr Phe Asp Tyr
1               5                   10

<210> SEQ ID NO 115
<211> LENGTH: 10
<212> TYPE: PRT
<213> ORGANISM: Artificial Sequence
<220> FEATURE:
<223> OTHER INFORMATION: CEA(sm9b) CDR-L1

<400> SEQUENCE: 115

Ser Ala Ser Ser Ser Val Pro Tyr Met His
1               5                   10

<210> SEQ ID NO 116
<211> LENGTH: 7
<212> TYPE: PRT
<213> ORGANISM: Artificial Sequence
<220> FEATURE:
<223> OTHER INFORMATION: CEA(sm9b) CDR-L2

<400> SEQUENCE: 116

Ser Thr Ser Asn Leu Ala Ser
1               5

<210> SEQ ID NO 117
<211> LENGTH: 9
<212> TYPE: PRT
<213> ORGANISM: Artificial Sequence
<220> FEATURE:
<223> OTHER INFORMATION: CEA(sm9b) CDR-L3

<400> SEQUENCE: 117

Gln Gln Arg Ser Ser Tyr Pro Leu Thr
1               5

<210> SEQ ID NO 118
<211> LENGTH: 120
<212> TYPE: PRT
<213> ORGANISM: Artificial Sequence
<220> FEATURE:
<223> OTHER INFORMATION: CEA(sm9b) VH

<400> SEQUENCE: 118

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Cys Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
```

```
                  100                 105                 110
Gly Thr Leu Val Thr Val Ser Ser
            115                 120

<210> SEQ ID NO 119
<211> LENGTH: 106
<212> TYPE: PRT
<213> ORGANISM: Artificial Sequence
<220> FEATURE:
<223> OTHER INFORMATION: CEA(sm9b) VL

<400> SEQUENCE: 119

Glu Asn Val Leu Thr Gln Ser Pro Ser Ser Met Ser Val Ser Val Gly
1               5                   10                  15

Asp Arg Val Thr Ile Ala Cys Ser Ala Ser Ser Ser Val Pro Tyr Met
                20                  25                  30

His Trp Leu Gln Gln Lys Pro Gly Lys Ser Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Asp Tyr Ser Leu Thr Ile Ser Ser Val Gln Pro Glu
65                  70                  75                  80

Asp Ala Ala Thr Tyr Tyr Cys Gln Gln Arg Ser Ser Tyr Pro Leu Thr
                85                  90                  95

Phe Gly Cys Gly Thr Lys Leu Glu Ile Lys
                100                 105

<210> SEQ ID NO 120
<211> LENGTH: 5
<212> TYPE: PRT
<213> ORGANISM: Artificial Sequence
<220> FEATURE:
<223> OTHER INFORMATION: CD19 (8B8-018) CDR-H1

<400> SEQUENCE: 120

Asp Tyr Ile Met His
1               5

<210> SEQ ID NO 121
<211> LENGTH: 17
<212> TYPE: PRT
<213> ORGANISM: Artificial Sequence
<220> FEATURE:
<223> OTHER INFORMATION: CD19 (8B8-018) CDR-H2

<400> SEQUENCE: 121

Tyr Ile Asn Pro Tyr Asn Asp Gly Ser Lys Tyr Thr Glu Lys Phe Gln
1               5                   10                  15

Gly

<210> SEQ ID NO 122
<211> LENGTH: 12
<212> TYPE: PRT
<213> ORGANISM: Artificial Sequence
<220> FEATURE:
<223> OTHER INFORMATION: CD19 (8B8-018) CDR-H3

<400> SEQUENCE: 122

Gly Thr Tyr Tyr Tyr Gly Ser Ala Leu Phe Asp Tyr
1               5                   10

<210> SEQ ID NO 123
```

```
<211> LENGTH: 16
<212> TYPE: PRT
<213> ORGANISM: Artificial Sequence
<220> FEATURE:
<223> OTHER INFORMATION: CD19 (8B8-018) CDR-L1

<400> SEQUENCE: 123

Lys Ser Ser Gln Ser Leu Glu Asn Pro Asn Gly Asn Thr Tyr Leu Asn
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: CD19 (8B8-018) CDR-L2

<400> SEQUENCE: 124

Arg Val Ser Lys Arg Phe Ser
1               5

<210> SEQ ID NO 125
<211> LENGTH: 9
<212> TYPE: PRT
<213> ORGANISM: Artificial Sequence
<220> FEATURE:
<223> OTHER INFORMATION: CD19 (8B8-018) CDR-L3

<400> SEQUENCE: 125

Leu Gln Leu Thr His Val Pro Tyr Thr
1               5

<210> SEQ ID NO 126
<211> LENGTH: 121
<212> TYPE: PRT
<213> ORGANISM: Artificial Sequence
<220> FEATURE:
<223> OTHER INFORMATION: CD19 (8B8-018) VH

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Ala Leu Phe Asp Tyr Trp Gly
                100                 105                 110

Gln Gly Thr Thr Val Thr Val Ser Ser
            115                 120

<210> SEQ ID NO 127
<211> LENGTH: 112
<212> TYPE: PRT
<213> ORGANISM: Artificial Sequence
<220> FEATURE:
<223> OTHER INFORMATION: CD19 (8B8-018) VL
```

<400> SEQUENCE: 127

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Asn Pro
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Thr His Val Pro Tyr Thr Phe Gly Gln Gly Thr Lys Leu Glu Ile Lys
            100                 105                 110

<210> SEQ ID NO 128
<211> LENGTH: 5
<212> TYPE: PRT
<213> ORGANISM: Artificial Sequence
<220> FEATURE:
<223> OTHER INFORMATION: CD19 (8B8-2B11) CDR-H1

<400> SEQUENCE: 128

Asp Tyr Ile Met His
1               5

<210> SEQ ID NO 129
<211> LENGTH: 17
<212> TYPE: PRT
<213> ORGANISM: Artificial Sequence
<220> FEATURE:
<223> OTHER INFORMATION: CD19 (8B8-2B11) CDR-H2

<400> SEQUENCE: 129

Tyr Ile Asn Pro Tyr Asn Asp Gly Ser Lys Tyr Thr Glu Lys Phe Gln
1               5                   10                  15

Gly

<210> SEQ ID NO 130
<211> LENGTH: 12
<212> TYPE: PRT
<213> ORGANISM: Artificial Sequence
<220> FEATURE:
<223> OTHER INFORMATION: CD19 (8B8-2B11) CDR-H3

<400> SEQUENCE: 130

Gly Thr Tyr Tyr Tyr Gly Pro Gln Leu Phe Asp Tyr
1               5                   10

<210> SEQ ID NO 131
<211> LENGTH: 16
<212> TYPE: PRT
<213> ORGANISM: Artificial Sequence
<220> FEATURE:
<223> OTHER INFORMATION: CD19 (8B8-2B11) CDR-L1

<400> SEQUENCE: 131

Lys Ser Ser Gln Ser Leu Glu Thr Ser Thr Gly Thr Thr Tyr Leu Asn
1               5                   10                  15

<210> SEQ ID NO 132

```
<211> LENGTH: 7
<212> TYPE: PRT
<213> ORGANISM: Artificial Sequence
<220> FEATURE:
<223> OTHER INFORMATION: CD19 (8B8-2B11) CDR-L2

<400> SEQUENCE: 132

Arg Val Ser Lys Arg Phe Ser
1               5

<210> SEQ ID NO 133
<211> LENGTH: 9
<212> TYPE: PRT
<213> ORGANISM: Artificial Sequence
<220> FEATURE:
<223> OTHER INFORMATION: CD19 (8B8-2B11) CDR-L3

<400> SEQUENCE: 133

Leu Gln Leu Leu Glu Asp Pro Tyr Thr
1               5

<210> SEQ ID NO 134
<211> LENGTH: 121
<212> TYPE: PRT
<213> ORGANISM: Artificial Sequence
<220> FEATURE:
<223> OTHER INFORMATION: CD19 (8B8-2B11) VH

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser
        115                 120

<210> SEQ ID NO 135
<211> LENGTH: 112
<212> TYPE: PRT
<213> ORGANISM: Artificial Sequence
<220> FEATURE:
<223> OTHER INFORMATION: CD19 (8B8-2B11) VL

<400> SEQUENCE: 135

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Leu
                 85                  90                  95

Leu Glu Asp Pro Tyr Thr Phe Gly Gln Gly Thr Lys Leu Glu Ile Lys
            100                 105                 110
```

<210> SEQ ID NO 136
<211> LENGTH: 5
<212> TYPE: PRT
<213> ORGANISM: Artificial Sequence
<220> FEATURE:
<223> OTHER INFORMATION: Peptide linker G4S

<400> SEQUENCE: 136

```
Gly Gly Gly Gly Ser
1               5
```

<210> SEQ ID NO 137
<211> LENGTH: 1341
<212> TYPE: DNA
<213> ORGANISM: Artificial Sequence
<220> FEATURE:
<223> OTHER INFORMATION: nucleotide sequence of anti-FAP(4B9) Fc hole chain

<400> SEQUENCE: 137

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg gttcaccatc agcggggaca cagcaagaa cacccctgtac     240
ctgcagatga acagcctgcg ggccgaggac accgccgtgt actactgcgc caagggatgg     300
ttcggcggct tcaactactg gggacagggc accctggtca cagtgtccag cgctagcacc     360
aagggcccct ccgtgttccc cctggcccc agcagcaaga gcaccagcgg cggcacagcc     420
gctctgggct gcctggtcaa ggactacttc cccgagcccg tgaccgtgtc ctggaacagc     480
ggagccctga cctccggcgt gcacaccttc cccgccgtgc tgcagagttc tggcctgtat     540
agcctgagca gcgtggtcac cgtgccttct agcagcctgg gcacccagac ctacatctgc     600
aacgtgaacc acaagcccag caacaccaag gtggacaaga aggtggagcc caagagctgc     660
gacaaaactc acacatgccc accgtgccca gcacctgaag ctgcagggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020
gggcagcccc gagaaccaca ggtgtgcacc ctgccccat cccgggatga gctgaccaag    1080
aaccaggtca gcctctcgtg cgcagtcaaa ggcttctatc ccagcgacat cgccgtggag    1140
tgggagagca atgggcagcc ggagaacaac tacaagacca cgcctcccgt gctggactcc    1200
gacggctcct tcttcctcgt gagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 138
<211> LENGTH: 3084
<212> TYPE: DNA
<213> ORGANISM: Artificial Sequence
<220> FEATURE:
<223> OTHER INFORMATION: nucleotide sequence of anti-FAP(4B9) Fc knob
      chain fused to trimeric hu 4-1BBL (71-254)

<400> SEQUENCE: 138

```
gaggtgcagc tgctcgaaag cggcggagga ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcatcggct ctggcgccag cacctactac     180
gccgacagcg tgaagggccg cgttcaccatc agcagggaca cagcaagaa cacccctgtac     240
ctgcagatga acagcctgcg ggccgaggac accgccgtgt actactgcgc caagggatgg     300
ttcggcggct tcaactactg gggacagggc accctggtca cagtgtccag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaag ctgcagggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcggcgcc cccatcgaga aaaccatctc caaagccaaa    1020
gggcagcccc gagaaccaca ggtgtacacc ctgcccccct gcagagatga gctgaccaag    1080
aaccaggtgt ccctgtggtg cctcgtgaag ggcttctacc cctccgatat cgccgtggaa    1140
tgggagagca cggccagcc cgagaacaac tacaagacca cccccctgt gctggacagc    1200
gacggctcat tcttcctgta ctccaagctg accgtggaca gagccggtg gcagcagggc    1260
aacgtgttca gctgcagcgt gatgcacgag gccctgcaca accactacac ccagaagtcc    1320
ctgagcctga gcctggcggg aggcggagga tctggcgggg aggatctag agagggcct    1380
gagctgtccc ccgatgatcc tgctggactg ctggacctgc ggcagggcat gtttgctcag    1440
ctggtggccc agaacgtgct gctgatcgac ggccctctga gctggtacag cgatcctgga    1500
ctggctggcg tgtcactgac aggcggcctg agctacaaag aggacaccaa agaactggtg    1560
gtggccaagg ccggcgtgta ctacgtgttc tttcagctgg aactgcggag agtggtggcc    1620
ggcgagggat ctggatctgt gtctctggcc ctgcatctgc agcccctgag atcagctgct    1680
ggcgctgctg ctctggctct gacagtggat ctgcctcctg ccagcagcga ggcccggaat    1740
agcgcatttg gtttcaagg caggctgctg cacctgtctg ccggcagag ctgggagtg    1800
catctgcaca cagaagccag agccaggcac gcttggcagc tgacacaggg cgctacagtg    1860
ctgggcctgt tcagagtgac ccccgagatt ccagccggcc tgccttctcc aagaagcgaa    1920
ggcggcggag gctccggagg aggcggctct agagaaggac tgaactgag cccagacgac    1980
cccgcagggc tgctggatct gagacaggga atgttcgccc agctggtggc tcagaatgtg    2040
```

```
ctgctgattg atggacccct gtcctggtac tccgacccag ggctggcagg ggtgtccctg    2100
actggcggac tgtcttacaa agaagataca aagaactgg tggtggctaa agctggggtg     2160
tactatgtgt tttttcagct ggaactgagg cgggtggtgg ctggggaagg cagtggctct    2220
gtgtccctgg cactgcatct gcagcctctg cgcagtgctg caggcgcagc cgcactggca    2280
ctgactgtgg acctgccccc agcttccagc gaggctagaa acagcgcctt cgggtttcaa    2340
ggacgcctgc tgcatctgag cgccggacag cgcctgggag tgcatctgca tactgaggct    2400
agggccagac atgcctggca gctgacccag ggggcaactg tgctgggact gtttcgcgtg    2460
acacctgaga tccccgctgg cctgccaagc cctagatcag aaggcggagg gggatcaggg    2520
ggaggcggat ccagagaggg ccctgagctg agccccgatg atcctgctgg actgctggac    2580
ctgcggcagg gcatgtttgc tcagctggtg gcccagaacg tgctgctgat cgatggcccc    2640
ctgtcctggt acagcgatcc tggactggct ggcgtgtcac tgacaggcgg cctgagctac    2700
aaagaggaca ccaaagaact ggtggtggcc aaggccggcg tgtactacgt gttctttcag    2760
ctggaactgc ggagagtggt ggccggcgaa ggatctggct ctgtgtctct ggccctgcat    2820
ctgcagcctc tgagaagcgc tgctggcgct gcagctctgg cactgacagt ggatctgcct    2880
cctgccagct ccgaggcccg gaatagcgca tttgggtttc aaggcaggct gctgcacctg    2940
tctgccggcc agaggctggg agtgcatctg cacacagagg ccagggctag acacgcctgg    3000
cagctgacac agggcgctac agtgctgggc ctgttcagag tgaccccga gattccagcc    3060 ggcctgcctt ctccaagaag cgaa                                           3084

<210> SEQ ID NO 139
<211> LENGTH: 645
<212> TYPE: DNA
<213> ORGANISM: Artificial Sequence
<220> FEATURE:
<223> OTHER INFORMATION: nucleotide sequence of anti-FAP(4B9) light
      chain

<400> SEQUENCE: 139
gagatcgtgc tgacccagtc ccccggcacc ctgtctctga gccctggcga gagagccacc      60
ctgtcctgca gagcctccca gtccgtgacc tcctcctacc tcgcctggta tcagcagaag     120
cccggccagg cccctcggct gctgatcaac gtgggcagtc ggagagccac cggcatccct     180
gaccggttct ccggctctgg ctccggcacc gacttcaccc tgaccatctc ccggctggaa     240
cccgaggact tcgccgtgta ctactgccag cagggcatca tgctgccccc cacctttggc     300
cagggcacca aggtggaaat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgt                     645

<210> SEQ ID NO 140
<211> LENGTH: 447
<212> TYPE: PRT
<213> ORGANISM: Artificial Sequence
<220> FEATURE:
<223> OTHER INFORMATION: anti-FAP(4B9) Fc hole chain

<400> SEQUENCE: 140
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
            325                 330                 335

Ser Lys Ala Lys Gly Gln Pro Arg Glu Pro Gln Val Cys Thr Leu Pro
        340                 345                 350

Pro Ser Arg Asp Glu Leu Thr Lys Asn Gln Val Ser Leu Ser Cys Ala
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
            405                 410                 415

```
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 141
<211> LENGTH: 1028
<212> TYPE: PRT
<213> ORGANISM: Artificial Sequence
<220> FEATURE:
<223> OTHER INFORMATION: anti-FAP(4B9) Fc knob chain fused to trimeric 4
      hu 4-1BBL (71-254)

<400> SEQUENCE: 141

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ile Gly Ser Gly Ala Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Trp Phe Gly Gly Phe Asn Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Gly Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Ser Arg Glu Gly Pro Glu Leu Ser Pro
    450                 455                 460

Asp Asp Pro Ala Gly Leu Leu Asp Leu Arg Gln Gly Met Phe Ala Gln
465                 470                 475                 480

Leu Val Ala Gln Asn Val Leu Leu Ile Asp Gly Pro Leu Ser Trp Tyr
            485                 490                 495

Ser Asp Pro Gly Leu Ala Gly Val Ser Leu Thr Gly Gly Leu Ser Tyr
            500                 505                 510

Lys Glu Asp Thr Lys Glu Leu Val Val Ala Lys Ala Gly Val Tyr Tyr
            515                 520                 525

Val Phe Phe Gln Leu Glu Leu Arg Arg Val Val Ala Gly Glu Gly Ser
            530                 535                 540

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
            565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
            595                 600                 605

Arg His Ala Trp Gln Leu Thr Gln Gly Ala Thr Val Leu Gly Leu Phe
            610                 615                 620

Arg Val Thr Pro Glu Ile Pro Ala Gly Leu Pro Ser Pro Arg Ser Glu
625                 630                 635                 640

Gly Gly Gly Gly Ser Gly Gly Gly Ser Arg Glu Gly Pro Glu Leu
            645                 650                 655

Ser Pro Asp Asp Pro Ala Gly Leu Leu Asp Leu Arg Gln Gly Met Phe
            660                 665                 670

Ala Gln Leu Val Ala Gln Asn Val Leu Leu Ile Asp Gly Pro Leu Ser
            675                 680                 685

Trp Tyr Ser Asp Pro Gly Leu Ala Gly Val Ser Leu Thr Gly Gly Leu
            690                 695                 700

Ser Tyr Lys Glu Asp Thr Lys Glu Leu Val Val Ala Lys Ala Gly Val
705                 710                 715                 720

Tyr Tyr Val Phe Phe Gln Leu Glu Leu Arg Arg Val Val Ala Gly Glu
            725                 730                 735

Gly Ser Gly Ser Val Ser Leu Ala Leu His Leu Gln Pro Leu Arg Ser
            740                 745                 750
```

-continued

Ala Ala Gly Ala Ala Ala Leu Ala Leu Thr Val Asp Leu Pro Pro Ala
              755                 760                 765

Ser Ser Glu Ala Arg Asn Ser Ala Phe Gly Phe Gln Gly Arg Leu Leu
770                 775                 780

His Leu Ser Ala Gly Gln Arg Leu Gly Val His Leu His Thr Glu Ala
785                 790                 795                 800

Arg Ala Arg His Ala Trp Gln Leu Thr Gln Gly Ala Thr Val Leu Gly
                805                 810                 815

Leu Phe Arg Val Thr Pro Glu Ile Pro Ala Gly Leu Pro Ser Pro Arg
            820                 825                 830

Ser Glu Gly Gly Gly Gly Ser Gly Gly Gly Ser Arg Glu Gly Pro
        835                 840                 845

Glu Leu Ser Pro Asp Asp Pro Ala Gly Leu Leu Asp Leu Arg Gln Gly
    850                 855                 860

Met Phe Ala Gln Leu Val Ala Gln Asn Val Leu Leu Ile Asp Gly Pro
865                 870                 875                 880

Leu Ser Trp Tyr Ser Asp Pro Gly Leu Ala Gly Val Ser Leu Thr Gly
                885                 890                 895

Gly Leu Ser Tyr Lys Glu Asp Thr Lys Glu Leu Val Val Ala Lys Ala
            900                 905                 910

Gly Val Tyr Tyr Val Phe Phe Gln Leu Glu Leu Arg Arg Val Val Ala
        915                 920                 925

Gly Glu Gly Ser Gly Ser Val Ser Leu Ala Leu His Leu Gln Pro Leu
    930                 935                 940

Arg Ser Ala Ala Gly Ala Ala Ala Leu Ala Leu Thr Val Asp Leu Pro
945                 950                 955                 960

Pro Ala Ser Ser Glu Ala Arg Asn Ser Ala Phe Gly Phe Gln Gly Arg
                965                 970                 975

Leu Leu His Leu Ser Ala Gly Gln Arg Leu Gly Val His Leu His Thr
            980                 985                 990

Glu Ala Arg Ala Arg His Ala Trp Gln Leu Thr Gln Gly Ala Thr Val
        995                 1000                1005

Leu Gly Leu Phe Arg Val Thr Pro Glu Ile Pro Ala Gly Leu Pro
    1010                1015                1020

Ser Pro Arg Ser Glu
    1025

<210> SEQ ID NO 142
<211> LENGTH: 215
<212> TYPE: PRT
<213> ORGANISM: Artificial Sequence
<220> FEATURE:
<223> OTHER INFORMATION: anti-FAP(4B9) light chain

<400> SEQUENCE: 142

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
        100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 143
<211> LENGTH: 1350
<212> TYPE: DNA
<213> ORGANISM: Artificial Sequence
<220> FEATURE:
<223> OTHER INFORMATION: nucleotide sequence of anti-CEA(sm9b) Fc hole
      chain

<400> SEQUENCE: 143

```
caagtgaagc tggagcagag cggcgccgaa gtcgtgaaac ccggggcttc cgtcaagctc      60
tcttgcaagg catcaggatt caacatcaaa gacagctaca tgcactggct gaggcagggc     120
cctggtcagt gccttgagtg gattggctgg atcgatccag agaatggcga caccgaatat     180
gcccccaagt tcaaggaaa ggctacattc accactgata catccgcaaa caccgcctac     240
ctgggtctct caagtctgcg ccctgaggac actgctgtgt attactgtaa tgagggcacc     300
ccaacagggc cctactattt tgactactgg ggacagggca ccttggttac agtgagctcc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaagc tcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc ccatcgagaa aaccatctcc    1020
aaagccaaag ggcagccccg agaaccacag gtgtgcaccc tgcccccatc ccgggatgag    1080
ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260
```

```
cagcagggga acgtcttctc atgctccgtg atgcatgagg ctctgcacaa ccactacacg    1320
cagaagagcc tctccctgtc tccgggtaaa                                     1350

<210> SEQ ID NO 144
<211> LENGTH: 3093
<212> TYPE: DNA
<213> ORGANISM: Artificial Sequence
<220> FEATURE:
<223> OTHER INFORMATION: nucleotide sequence of anti-CEA(sm9b) Fc knob
      chain fused to trimeric hu 4-1BBL (71-254)

<400> SEQUENCE: 144
caagtgaagc tggagcagag cggcgccgaa gtcgtgaaac ccggggcttc cgtcaagctc      60
tcttgcaagg catcaggatt caacatcaaa gacagctaca tgcactggct gaggcagggc     120
cctggtcagt gccttgagtg gattggctgg atcgatccag agaatggcga caccgaatat     180
gcccccaagt tcaaggaaa ggctacattc accactgata catccgcaaa caccgcctac      240
ctgggtctct caagtctgcg ccctgaggac actgctgtgt attactgtaa tgagggcacc     300
ccaacagggc cctactattt tgactactgg ggacagggca ccttggttac agtgagctcc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaagc tgcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc catcgagaa aaccatctcc     1020 aaagccaaag ggcagccccg agaaccacag gtgtacaccc tgccccctg cagagatgag    1080 ctgaccaaga accaggtgtc cctgtggtgc ctcgtgaagg gcttctaccc ctccgatatc    1140
gccgtggaat gggagagcaa cggccagccc gagaacaact acaagaccac ccccctgtg    1200 ctggacagcg acggctcatt cttcctgtac tccaagctga ccgtggacaa gagccggtgg    1260
cagcagggca acgtgttcag ctgcagcgtg atgcacgagg ccctgcacaa ccactacacc    1320
cagaagtccc tgagcctgag ccctggcgga ggcggaggat ctggcggggg aggatctaga    1380
gagggccctg agctgtcccc cgatgatcct gctggactgc tggacctgcg gcagggcatg    1440
tttgctcagc tggtggccca gaacgtgctg ctgatcgacg ccctctgag ctggtacagc    1500 gatcctggac tggctggcgt gtcactgaca ggcggcctga gctacaaaga ggacaccaaa    1560
gaactggtgg tggccaaggc cggcgtgtac tacgtgttct ttcagctgga actgcggaga    1620
gtggtggccg cgagggatc tggatctgtg tctctggccc tgcatctgca gcccctgaga    1680
tcagctgctg gcgctgctgc tctggctctg acagtggatc tgcctcctgc cagcagcgag    1740
gcccggaata gcgcatttgg gtttcaaggc aggctgctgc acctgtctgc cggccagagg    1800
ctgggagtgc atctgcacac agaagccaga gccaggcacg cttggcagct gacacaggc     1860 gctacagtgc tgggcctgtt cagagtgacc cccgagattc agccggcct gccttctcca    1920
```

```
agaagcgaag gcggcggagg ctccggagga ggcggctcta gagaaggacc tgaactgagc    1980
ccagacgacc ccgcagggct gctggatctg agacaggaa tgttcgccca gctggtggct    2040
cagaatgtgc tgctgattga tggacccctg tcctggtact ccgacccagg gctggcaggg    2100
gtgtccctga ctggcggact gtcttacaaa gaagatacaa agaactggt ggtggctaaa    2160 gctggggtgt actatgtgtt ttttcagctg gaactgaggc gggtggtggc tggggaaggc    2220
agtggctctg tgtccctggc actgcatctg cagcctctgc gcagtgctgc aggcgcagcc    2280
gcactggcac tgactgtgga cctgccccca gcttccagcg aggctagaaa cagcgccttc    2340
gggtttcaag gacgcctgct gcatctgagc gccggacagc gcctgggagt gcatctgcat    2400
actgaggcta gggccagaca tgcctggcag ctgacccagg gggcaactgt gctgggactg    2460
tttcgcgtga cacctgagat ccccgctggc ctgccaagcc ctagatcaga aggcggaggg    2520
ggatcagggg gaggcggatc cagagagggc cctgagctga gccccgatga tcctgctgga    2580
ctgctggacc tgcggcaggg catgtttgct cagctggtgg cccagaacgt gctgctgatc    2640
gatggccccc tgtcctggta cagcgatcct ggactggctg gcgtgtcact gacaggcggc    2700
ctgagctaca aagaggacac caaagaactg gtggtggcca aggccggcgt gtactacgtg    2760
ttctttcagc tggaactgcg gagagtggtg gccggcgaag atctggctc tgtgtctctg    2820 gccctgcatc tgcagcctct gagaagcgct gctggcgctg cagctctggc actgacagtg    2880
gatctgcctc ctgccagctc cgaggcccgg aatagcgcat ttgggtttca aggcaggctg    2940
ctgcacctgt ctgccggcca gaggctggga gtgcatctgc acacagaggc cagggctaga    3000
cacgcctggc agctgacaca gggcgctaca gtgctgggcc tgttcagagt gaccccccgag    3060 attccagccg gcctgccttc tccaagaagc gaa                                  3093
```

<210> SEQ ID NO 145
<211> LENGTH: 639
<212> TYPE: DNA
<213> ORGANISM: Artificial Sequence
<220> FEATURE:
<223> OTHER INFORMATION: nucleotide sequence of anti-CEA(sm9b) light chain

<400> SEQUENCE: 145

```
gagaacgtgc tgacccagag cccctcctct atgtcagtca gcgtgggcga cagggtcaca      60
atcgcctgct ccgcttctag tagcgtgcct acatgcact ggctccagca gaagccaggg     120
aaatccccca gctgcttat ttattctacc tcaaatctgg caagcggagt tcctagcaga     180
ttctctggca gtggtagcgg gactgattac tccctcacaa tctcaagtgt gcagccagaa     240
gacgccgcta cctattactg tcaacagcgc agctcctacc ccctgacttt tggctgtggc     300
accaagttgg agattaaacg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639
```

<210> SEQ ID NO 146
<211> LENGTH: 450
<212> TYPE: PRT
<213> ORGANISM: Artificial Sequence
<220> FEATURE:
<223> OTHER INFORMATION: anti-CEA(sm9b) Fc hole chain

<400> SEQUENCE: 146

```
Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Cys Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 147
<211> LENGTH: 1031
<212> TYPE: PRT
<213> ORGANISM: Artificial Sequence
<220> FEATURE:
<223> OTHER INFORMATION: anti-CEA(sm9b) Fc knob chain fused to trimeric
      hu 4-1BBL (71-254)

<400> SEQUENCE: 147

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Cys Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

-continued

```
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Cys Arg Asp Glu Leu Thr Lys Asn Gln Val Ser Leu
                355                 360                 365
Trp Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Gly Gly Gly Ser Gly Gly Gly Ser Arg Glu Gly Pro Glu
450                 455                 460
Leu Ser Pro Asp Pro Ala Gly Leu Leu Asp Leu Arg Gln Gly Met
465                 470                 475                 480
Phe Ala Gln Leu Val Ala Gln Asn Val Leu Leu Ile Asp Gly Pro Leu
                485                 490                 495
Ser Trp Tyr Ser Asp Pro Gly Leu Ala Gly Val Ser Leu Thr Gly Gly
                500                 505                 510
Leu Ser Tyr Lys Glu Asp Thr Lys Glu Leu Val Val Ala Lys Ala Gly
                515                 520                 525
Val Tyr Tyr Val Phe Phe Gln Leu Glu Leu Arg Arg Val Val Ala Gly
                530                 535                 540
Glu Gly Ser Gly Ser Val Ser Leu Ala Leu His Leu Gln Pro Leu Arg
545                 550                 555                 560
Ser Ala Ala Gly Ala Ala Ala Leu Ala Leu Thr Val Asp Leu Pro Pro
                565                 570                 575
Ala Ser Ser Glu Ala Arg Asn Ser Ala Phe Gly Phe Gln Gly Arg Leu
                580                 585                 590
Leu His Leu Ser Ala Gly Gln Arg Leu Gly Val His Leu His Thr Glu
                595                 600                 605
Ala Arg Ala Arg His Ala Trp Gln Leu Thr Gln Gly Ala Thr Val Leu
610                 615                 620
Gly Leu Phe Arg Val Thr Pro Glu Ile Pro Ala Gly Leu Pro Ser Pro
625                 630                 635                 640
Arg Ser Glu Gly Gly Gly Ser Gly Gly Gly Ser Arg Glu Gly
                645                 650                 655
Pro Glu Leu Ser Pro Asp Asp Pro Ala Gly Leu Leu Asp Leu Arg Gln
                660                 665                 670
Gly Met Phe Ala Gln Leu Val Ala Gln Asn Val Leu Leu Ile Asp Gly
                675                 680                 685
Pro Leu Ser Trp Tyr Ser Asp Pro Gly Leu Ala Gly Val Ser Leu Thr
                690                 695                 700
Gly Gly Leu Ser Tyr Lys Glu Asp Thr Lys Glu Leu Val Val Ala Lys
705                 710                 715                 720
```

```
Ala Gly Val Tyr Tyr Val Phe Phe Gln Leu Glu Leu Arg Arg Val Val
            725                 730                 735

Ala Gly Glu Gly Ser Gly Ser Val Ser Leu Ala Leu His Leu Gln Pro
        740                 745                 750

Leu Arg Ser Ala Ala Gly Ala Ala Leu Ala Leu Thr Val Asp Leu
    755                 760                 765

Pro Pro Ala Ser Ser Glu Ala Arg Asn Ser Ala Phe Gly Phe Gln Gly
770                 775                 780

Arg Leu Leu His Leu Ser Ala Gly Gln Arg Leu Gly Val His Leu His
785                 790                 795                 800

Thr Glu Ala Arg Ala Arg His Ala Trp Gln Leu Thr Gln Gly Ala Thr
                805                 810                 815

Val Leu Gly Leu Phe Arg Val Thr Pro Glu Ile Pro Ala Gly Leu Pro
                820                 825                 830

Ser Pro Arg Ser Glu Gly Gly Gly Ser Gly Gly Gly Ser Arg
        835                 840                 845

Glu Gly Pro Glu Leu Ser Pro Asp Asp Pro Ala Gly Leu Leu Asp Leu
    850                 855                 860

Arg Gln Gly Met Phe Ala Gln Leu Val Ala Gln Asn Val Leu Leu Ile
865                 870                 875                 880

Asp Gly Pro Leu Ser Trp Tyr Ser Asp Pro Gly Leu Ala Gly Val Ser
                885                 890                 895

Leu Thr Gly Gly Leu Ser Tyr Lys Glu Asp Thr Lys Glu Leu Val Val
            900                 905                 910

Ala Lys Ala Gly Val Tyr Tyr Val Phe Phe Gln Leu Glu Leu Arg Arg
        915                 920                 925

Val Val Ala Gly Glu Gly Ser Gly Ser Val Ser Leu Ala Leu His Leu
    930                 935                 940

Gln Pro Leu Arg Ser Ala Ala Gly Ala Ala Leu Ala Leu Thr Val
945                 950                 955                 960

Asp Leu Pro Pro Ala Ser Ser Glu Ala Arg Asn Ser Ala Phe Gly Phe
                965                 970                 975

Gln Gly Arg Leu Leu His Leu Ser Ala Gly Gln Arg Leu Gly Val His
            980                 985                 990

Leu His Thr Glu Ala Arg Ala Arg His Ala Trp Gln Leu Thr Gln Gly
        995                 1000                1005

Ala Thr Val Leu Gly Leu Phe Arg Val Thr Pro Glu Ile Pro Ala
    1010                1015                1020

Gly Leu Pro Ser Pro Arg Ser Glu
    1025                1030

<210> SEQ ID NO 148
<211> LENGTH: 213
<212> TYPE: PRT
<213> ORGANISM: Artificial Sequence
<220> FEATURE:
<223> OTHER INFORMATION: anti-CEA(sm9b) light chain

<400> SEQUENCE: 148

Glu Asn Val Leu Thr Gln Ser Pro Ser Ser Met Ser Val Ser Val Gly
1               5                   10                  15

Asp Arg Val Thr Ile Ala Cys Ser Ala Ser Ser Ser Val Pro Tyr Met
            20                  25                  30

His Trp Leu Gln Gln Lys Pro Gly Lys Ser Pro Lys Leu Leu Ile Tyr
        35                  40                  45
```

Ser Thr Ser Asn Leu Ala Ser Gly Val Pro Ser Arg Phe Ser Gly Ser
        50                  55                  60

Gly Ser Gly Thr Asp Tyr Ser Leu Thr Ile Ser Ser Val Gln Pro Glu
65                  70                  75                  80

Asp Ala Ala Thr Tyr Tyr Cys Gln Gln Arg Ser Ser Tyr Pro Leu Thr
                85                  90                  95

Phe Gly Cys Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 149
<211> LENGTH: 1353
<212> TYPE: DNA
<213> ORGANISM: Artificial Sequence
<220> FEATURE:
<223> OTHER INFORMATION: nucleotide sequence of anti- CD19(8B8-018) Fc
      hole chain

<400> SEQUENCE: 149
caggtccagc tggtgcagtc cggcgccgag gtcaagaaac ccggggcttc tgtgaaggtt      60
tcatgcaagg caagcggata caccttcacc gactatatca tgcattgggt caggcaggcc    120
cctggccaag gtctcgaatg gatgggctac attaacccat ataatgatgg ctccaaatac    180
accgagaagt tcagggaag agtcactatg acatctgaca ccagtatcag cactgcttac    240
atggagctgt cccgccttcg gtctgatgac accgcagtgt attactgtgc caggggcaca    300
tattactacg gctcagctct gttcgactat tgggggcagg gaaccacagt aaccgtgagc    360
tccgctagca ccaagggccc ctccgtgttc cccctggccc cagcagcaa gagcaccagc    420 ggcggcacag ccgctctggg ctgcctggtc aaggactact cccccagcc cgtgaccgtg    480 tcctggaaca gcggagccct gacctccggc gtgcacacct tcccgccgt gctgcagagt    540 tctggcctgt atagcctgag cagcgtggtc accgtgcctt ctagcagcct gggcacccag    600
acctacatct gcaacgtgaa ccacaagccc agcaacacca aggtggacaa gaaggtggag    660
cccaagagct gcgacaaaac tcacacatgc ccaccgtgcc cagcacctga gctgcaggg    720 ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca gtgcaaggt ctccaacaaa gccctcggcg cccccatcga gaaaaccatc   1020

```
tccaaagcca aagggcagcc ccgagaacca caggtgtgca ccctgccccc atcccgggat    1080
gagctgacca agaaccaggt cagcctctcg tgcgcagtca aaggcttcta tcccagcgac    1140
atcgccgtgg agtgggagag caatgggcag ccggagaaca actacaagac cacgcctccc    1200
gtgctggact ccgacggctc cttcttcctc gtgagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353

<210> SEQ ID NO 150
<211> LENGTH: 3096
<212> TYPE: DNA
<213> ORGANISM: Artificial Sequence
<220> FEATURE:
<223> OTHER INFORMATION: nucleotide sequence of anti- CD19(8B8-018) Fc
      knob chain fused to trimeric hu 4-1BBL (71-254)

<400> SEQUENCE: 150
caggtccagc tggtgcagtc cggcgccgag gtcaagaaac ccggggcttc tgtgaaggtt      60
tcatgcaagg caagcggata caccttcacc gactatatca tgcattgggt caggcaggcc    120
cctggccaag gtctcgaatg gatgggctac attaacccat ataatgatgg ctccaaatac    180
accgagaagt ttcagggaag agtcactatg acatctgaca ccagtatcag cactgcttac    240
atggagctgt cccgccttcg gtctgatgac accgcagtgt attactgtgc aggggcaca    300 tattactacg gctcagctct gttcgactat tgggggcagg gaaccacagt aaccgtgagc    360
tccgctagca ccaagggccc atcggtcttc cccctggcac cctcctccaa gagcacctct    420
gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga agctgcaggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca gtgcaaggt ctccaacaaa gccctcggcg cccccatcga gaaaaccatc   1020
tccaaagcca aagggcagcc ccgagaacca caggtgtaca ccctgccccc tgcagagat    1080 gagctgacca agaaccaggt gtccctgtgg tgcctcgtga agggcttcta cccctccgat    1140
atcgccgtgg aatgggagag caacggccag ccggagaaca actacaagac cacccccct    1200 gtgctggaca cgacggctc attcttcctg tactccaagc tgaccgtgga caagagccgg    1260
tggcagcagg gcaacgtgtt cagctgcagc gtgatgcacg aggccctgca caaccactac    1320
acccagaagt ccctgagcct gagccctggc ggaggcggag gatctggcgg gggaggatct    1380
agagagggcc ctgagctgtc ccccgatgat cctgctggac tgctggacct gcggcagggc    1440
atgtttgctc agctggtggc ccagaacgtg ctgctgatcg acggccctct gagctggtac    1500
agcgatcctg gactggctgg cgtgtcactg acaggcggcc tgagctacaa agaggacacc    1560
aaagaactgg tggtggccaa ggccggcgtg tactacgtgt tctttcagct ggaactgcgg    1620
agagtggtgg ccggcgaggg atctggatct gtgtctctgg ccctgcatct gcagcccctg    1680
```

| | |
|---|---|
| agatcagctg ctggcgctgc tgctctggct ctgacagtgg atctgcctcc tgccagcagc | 1740 |
| gaggcccgga atagcgcatt tgggtttcaa ggcaggctgc tgcacctgtc tgccggccag | 1800 |
| aggctgggag tgcatctgca cacagaagcc agagccaggc acgcttggca gctgacacag | 1860 |
| ggcgctacag tgctgggcct gttcagagtg acccccgaga ttccagccgg cctgccttct | 1920 |
| ccaagaagcg aaggcggcgg aggctccgga ggaggcggct ctagagaagg acctgaactg | 1980 |
| agcccagacg accccgcagg gctgctggat ctgagacagg gaatgttcgc ccagctggtg | 2040 |
| gctcagaatg tgctgctgat tgatggaccc ctgtcctggt actccgaccc agggctggca | 2100 |
| ggggtgtccc tgactggcgg actgtcttac aaagaagata caaaagaact ggtggtggct | 2160 |
| aaagctgggg tgtactatgt gttttttcag ctggaactga ggcgggtggt ggctggggaa | 2220 |
| ggcagtggct ctgtgtccct ggcactgcat ctgcagcctc tgcgcagtgc tgcaggcgca | 2280 |
| gccgcactgg cactgactgt ggacctgccc ccagcttcca gcgaggctag aaacagcgcc | 2340 |
| ttcgggtttc aaggacgcct gctgcatctg agcgccggac agcgcctggg agtgcatctg | 2400 |
| catactgagg ctagggccag acatgcctgg cagctgaccc aggggcaac tgtgctggga | 2460 |
| ctgtttcgcg tgacacctga tccccgct ggcctgccaa gccctagatc agaaggcgga | 2520 |
| gggggatcag ggggaggcgg atccagagag ggccctgagc tgagcccga tgatcctgct | 2580 |
| ggactgctgg acctgcggca gggcatgttt gctcagctgg tggcccagaa cgtgctgctg | 2640 |
| atcgatggcc cctgtcctg gtacagcgat cctggactgg ctggcgtgtc actgacaggc | 2700 |
| ggcctgagct acaaagagga caccaaagaa ctggtggtgg ccaaggccgg cgtgtactac | 2760 |
| gtgttctttc agctggaact gcggagagtg gtggccggcg aaggatctgg ctctgtgtct | 2820 |
| ctggccctgc atctgcagcc tctgagaagc gctgctggcg ctgcagctct ggcactgaca | 2880 |
| gtggatctgc ctcctgccag ctccgaggcc cggaatagcg catttgggtt tcaaggcagg | 2940 |
| ctgctgcacc tgtctgccgg ccagaggctg ggagtgcatc tgcacacaga ggccagggct | 3000 |
| agacacgcct ggcagctgac acagggcgct acagtgctgg gcctgttcag agtgaccccc | 3060 |
| gagattccag ccggcctgcc ttctccaaga agcgaa | 3096 |

<210> SEQ ID NO 151
<211> LENGTH: 657
<212> TYPE: DNA
<213> ORGANISM: Artificial Sequence
<220> FEATURE:
<223> OTHER INFORMATION: nucleotide sequence of anti- CD19(8B8-018) light chain

<400> SEQUENCE: 151

| | |
|---|---|
| gacatcgtca tgacccagac accctgtcc ctctctgtga cccctggcca gccagcctca | 60 |
| attagctgca gtcctctca agtctggag accccaatg gaacactta ccttaattgg | 120 |
| tatctgcaga aacccggaca atcccctcaa ctcctgatct acagggtctc taagagattc | 180 |
| tcaggcgtgc cagatcgctt tagcggttcc ggtctggca cagacttcac cttgaagatt | 240 |
| agtcgggttg aagctgagga tgtgggagtc tattactgtc tgcagctcac tcatgtgccc | 300 |
| tacacctttg gtcagggcac aaaactggaa atcaagcgga ccgtggccgc tcccctcgtg | 360 |
| ttcatcttcc caccctccga cgagcagctg aagtccggca ccgccagcgt ggtgtgcctg | 420 |
| ctgaacaact tctaccccg cgaggccaag gtgcagtgga aggtggacaa cgccctgcag | 480 |
| tccggcaact cccaggaatc cgtgaccgag caggactcca aggacagcac ctactccctg | 540 |
| tcctccaccc tgaccctgtc caaggccgac tacgagaagc acaaggtgta cgcctgcgaa | 600 |

```
gtgacccacc agggcctgtc cagccccgtg accaagtcct tcaaccgggg cgagtgc            657
```

<210> SEQ ID NO 152
<211> LENGTH: 451
<212> TYPE: PRT
<213> ORGANISM: Artificial Sequence
<220> FEATURE:
<223> OTHER INFORMATION: anti- CD19(8B8-018) Fc hole chain

<400> SEQUENCE: 152

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Ser Ala Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
```

```
                355                 360                 365
Leu Ser Cys Ala Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
        450

<210> SEQ ID NO 153
<211> LENGTH: 1032
<212> TYPE: PRT
<213> ORGANISM: Artificial Sequence
<220> FEATURE:
<223> OTHER INFORMATION: anti- CD19(8B8-018) Fc knob chain fused to
      trimeric hu 4-1BBL (71-254)

<400> SEQUENCE: 153

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Ile Met His Trp Val Arg Gln Ala Pro Gly Gln Gly Leu Glu Trp Met
            35                  40                  45
Gly Tyr Ile Asn Pro Tyr Asn Asp Gly Ser Lys Tyr Thr Glu Lys Phe
        50                  55                  60
Gln Gly Arg Val Thr Met Thr Ser Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Thr Tyr Tyr Tyr Gly Ser Ala Leu Phe Asp Tyr Trp Gly
                100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Arg Glu Gly Pro
    450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
            500                 505                 510

Gly Leu Ser Tyr Lys Glu Asp Thr Lys Glu Leu Val Val Ala Lys Ala
        515                 520                 525

Gly Val Tyr Tyr Val Phe Phe Gln Leu Glu Leu Arg Arg Val Val Ala
    530                 535                 540

Gly Glu Gly Ser Gly Ser Val Ser Leu Ala Leu His Leu Gln Pro Leu
545                 550                 555                 560

Arg Ser Ala Ala Gly Ala Ala Leu Ala Leu Thr Val Asp Leu Pro
                565                 570                 575

Pro Ala Ser Ser Glu Ala Arg Asn Ser Ala Phe Gly Phe Gln Gly Arg
            580                 585                 590

Leu Leu His Leu Ser Ala Gly Gln Arg Leu Gly Val His Leu His Thr
        595                 600                 605

Glu Ala Arg Ala Arg His Ala Trp Gln Leu Thr Gln Gly Ala Thr Val
    610                 615                 620

Leu Gly Leu Phe Arg Val Thr Pro Glu Ile Pro Ala Gly Leu Pro Ser
625                 630                 635                 640

Pro Arg Ser Glu Gly Gly Gly Ser Gly Gly Gly Ser Arg Glu
                645                 650                 655

Gly Pro Glu Leu Ser Pro Asp Asp Pro Ala Gly Leu Leu Asp Leu Arg
            660                 665                 670

Gln Gly Met Phe Ala Gln Leu Val Ala Gln Asn Val Leu Leu Ile Asp
```

675                 680                 685

Gly Pro Leu Ser Trp Tyr Ser Asp Pro Gly Leu Ala Gly Val Ser Leu
    690                 695                 700

Thr Gly Gly Leu Ser Tyr Lys Glu Asp Thr Lys Glu Leu Val Val Ala
705                 710                 715                 720

Lys Ala Gly Val Tyr Tyr Val Phe Phe Gln Leu Glu Leu Arg Arg Val
                725                 730                 735

Val Ala Gly Glu Gly Ser Gly Ser Val Ser Leu Ala Leu His Leu Gln
            740                 745                 750

Pro Leu Arg Ser Ala Ala Gly Ala Ala Leu Ala Leu Thr Val Asp
            755                 760                 765

Leu Pro Pro Ala Ser Ser Glu Ala Arg Asn Ser Ala Phe Gly Phe Gln
770                 775                 780

Gly Arg Leu Leu His Leu Ser Ala Gly Gln Arg Leu Gly Val His Leu
785                 790                 795                 800

His Thr Glu Ala Arg Ala Arg His Ala Trp Gln Leu Thr Gln Gly Ala
                805                 810                 815

Thr Val Leu Gly Leu Phe Arg Val Thr Pro Glu Ile Pro Ala Gly Leu
            820                 825                 830

Pro Ser Pro Arg Ser Glu Gly Gly Gly Ser Gly Gly Gly Ser
        835                 840                 845

Arg Glu Gly Pro Glu Leu Ser Pro Asp Pro Ala Gly Leu Leu Asp
850                 855                 860

Leu Arg Gln Gly Met Phe Ala Gln Leu Val Ala Gln Asn Val Leu Leu
865                 870                 875                 880

Ile Asp Gly Pro Leu Ser Trp Tyr Ser Asp Pro Gly Leu Ala Gly Val
                885                 890                 895

Ser Leu Thr Gly Gly Leu Ser Tyr Lys Glu Asp Thr Lys Glu Leu Val
            900                 905                 910

Val Ala Lys Ala Gly Val Tyr Tyr Val Phe Phe Gln Leu Glu Leu Arg
        915                 920                 925

Arg Val Val Ala Gly Glu Gly Ser Gly Ser Val Ser Leu Ala Leu His
930                 935                 940

Leu Gln Pro Leu Arg Ser Ala Ala Gly Ala Ala Ala Leu Ala Leu Thr
945                 950                 955                 960

Val Asp Leu Pro Pro Ala Ser Ser Glu Ala Arg Asn Ser Ala Phe Gly
                965                 970                 975

Phe Gln Gly Arg Leu Leu His Leu Ser Ala Gly Gln Arg Leu Gly Val
            980                 985                 990

His Leu His Thr Glu Ala Arg Ala  Arg His Ala Trp Gln Leu Thr Gln
        995                 1000                 1005

Gly Ala  Thr Val Leu Gly Leu  Phe Arg Val Thr Pro  Glu Ile Pro
        1010                 1015                 1020

Ala Gly  Leu Pro Ser Pro Arg  Ser Glu
        1025                 1030

<210> SEQ ID NO 154
<211> LENGTH: 219
<212> TYPE: PRT
<213> ORGANISM: Artificial Sequence
<220> FEATURE:
<223> OTHER INFORMATION: anti- CD19(8B8-018) light chain

<400> SEQUENCE: 154

Asp Ile Val Met Thr Gln Thr Pro Leu Ser Leu Ser Val Thr Pro Gly

```
              1               5              10              15
            Gln Pro Ala Ser Ile Ser Cys Lys Ser Ser Gln Ser Leu Glu Asn Pro
                             20                  25                  30

Asn Gly Asn Thr Tyr Leu Asn Trp Tyr Leu Gln Lys Pro Gly Gln Ser
                         35                  40                  45

Pro Gln Leu Leu Ile Tyr Arg Val Ser Lys Arg Phe Ser Gly Val Pro
                     50                  55                  60

Asp Arg Phe Ser Gly Ser Gly Ser Gly Thr Asp Phe Thr Leu Lys Ile
             65                  70                  75                  80

Ser Arg Val Glu Ala Glu Asp Val Gly Val Tyr Tyr Cys Leu Gln Leu
                             85                  90                  95

Thr His Val Pro Tyr Thr Phe Gly Gln Gly Thr Lys Leu Glu Ile Lys
                            100                 105                 110

Arg Thr Val Ala Ala Pro Ser Val Phe Ile Phe Pro Pro Ser Asp Glu
                        115                 120                 125

Gln Leu Lys Ser Gly Thr Ala Ser Val Val Cys Leu Leu Asn Asn Phe
                    130                 135                 140

Tyr Pro Arg Glu Ala Lys Val Gln Trp Lys Val Asp Asn Ala Leu Gln
            145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
                210                 215
```

<210> SEQ ID NO 155
<211> LENGTH: 1353
<212> TYPE: DNA
<213> ORGANISM: Artificial Sequence
<220> FEATURE:
<223> OTHER INFORMATION: nucleotide sequence of anti- CD19(8B8-2B11) Fc hole chain

<400> SEQUENCE: 155

```
caggtgcaat tggttcaatc tggtgctgaa gtaaaaaaac cgggcgcttc cgttaaagtg      60
agctgcaaag catctggtta caccttcact gactatatca tgcactgggt tcgtcaggcc     120
ccgggccagg gtctggagtg gatgggctac attaacccat acaacgacgg ttccaaatat     180
accgagaaat tccagggccg cgtcacgatg accagcgaca cttctatctc caccgcgtac     240
atggaactgt ctagactgcg ttctgacgac accgctgttt actattgtgc acgcggtacc     300
tactactacg gtccacagct gtttgattac tggggccaag gtaccacggt gaccgtaagc     360
tctgctagca ccaagggccc ctccgtgttc cccctggccc ccagcagcaa gagcaccagc     420
ggcggcacag ccgctctggg ctgcctggtc aaggactact cccccgagcc cgtgaccgtg     480
tcctggaaca gcggagccct gacctccggc gtgcacacct cccccgccgt gctgcagagt     540
tctggcctgt atagcctgag cagcgtggtc accgtgcctt ctagcagcct gggcacccag     600
acctacatct gcaacgtgaa ccacaagccc agcaacacca aggtggacaa gaaggtggag     660
cccaagagct gcgacaaaac tcacacatgc ccaccgtgcc cagcacctga gctgcaggg     720
ggaccgtcag tcttcctctt ccccccaaaa cccaaggaca cctcatgat ctcccggacc     780
cctgaggtca catgcgtggt ggtggacgtg agccacgaag accctgaggt caagttcaac     840
```

```
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcggcg ccccatcga gaaaaccatc      1020 tccaaagcca aagggcagcc ccgagaacca caggtgtgca ccctgccccc atcccgggat      1080
gagctgacca agaaccaggt cagcctctcg tgcgcagtca aaggcttcta tcccagcgac      1140
atcgccgtgg agtgggagag caatgggcag ccggagaaca actacaagac cacgcctccc      1200
gtgctggact ccgacggctc cttcttcctc gtgagcaagc tcaccgtgga cagagcagg      1260 tggcagcagg ggaacgtctt ctcatgctcc gtgatgcatg aggctctgca caaccactac      1320
acgcagaaga gcctctccct gtctccgggt aaa                                  1353

<210> SEQ ID NO 156
<211> LENGTH: 3096
<212> TYPE: DNA
<213> ORGANISM: Artificial Sequence
<220> FEATURE:
<223> OTHER INFORMATION: nucleotide sequence of anti- CD19(8B8-2B11) Fc
      knob chain fused to trimeric hu 4-1BBL (71-254)

<400> SEQUENCE: 156
caggtgcaat tggttcaatc tggtgctgaa gtaaaaaaac cgggcgcttc cgttaaagtg       60
agctgcaaag catctggtta caccttcact gactatatca tgcactgggt tcgtcaggcc      120
ccgggccagg gtctggagtg gatgggctac attaacccat acaacgacgg ttccaaatat      180
accgagaaat tccagggccg cgtcacgatg accagcgaca cttctatctc caccgcgtac      240
atggaactgt ctagactgcg ttctgacgac accgctgttt actattgtgc acgcggtacc      300
tactactacg gtccacagct gtttgattac tggggccaag gtaccacggt gaccgtaagc      360
tctgctagca ccaagggccc atcggtcttc cccctggcac cctcctccaa gagcacctct      420
gggggcacag cggccctggg ctgcctggtc aaggactact ccccgaaccc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gaaagttgag      660
cccaaatctt gtgacaaaac tcacacatgc ccaccgtgcc cagcacctga gctgcaggg      720 ggaccgtcag tcttcctctt ccccccaaaa cccaaggaca cctcatgat ctcccggacc      780 cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcggcg ccccatcga gaaaaccatc      1020 tccaaagcca aagggcagcc ccgagaacca caggtgtaca ccctgccccc ctgcagagat      1080
gagctgacca agaaccaggt gtccctgtgg tgcctcgtga gggcttcta cccctccgat      1140 atcgccgtgg aatgggagag caacggccag cccgagaaca actacaagac caccccccct      1200
gtgctggaca cgacggctc attcttcctg tactccaagc tgaccgtgga cagagccgg      1260 tggcagcagg gcaacgtgtt cagctgcagc gtgatgcacg aggccctgca caaccactac      1320
acccagaagt ccctgagcct gagccctggc ggaggcggag gatctggcgg gggaggatct      1380
agagagggcc ctgagctgtc ccccgatgat cctgctggac tgctggacct gcggcagggc      1440
atgtttgctc agctggtggc ccagaacgtg ctgctgatcg acggccctct gagctggtac      1500
```

```
agcgatcctg gactggctgg cgtgtcactg acaggcggcc tgagctacaa agaggacacc    1560
aaagaactgg tggtggccaa ggccggcgtg tactacgtgt tctttcagct ggaactgcgg    1620
agagtggtgg ccggcgaggg atctggatct gtgtctctgg ccctgcatct gcagcccctg    1680
agatcagctg ctggcgctgc tgctctggct ctgacagtgg atctgcctcc tgccagcagc    1740
gaggcccgga atagcgcatt tgggtttcaa ggcaggctgc tgcacctgtc tgccggccag    1800
aggctgggag tgcatctgca cacagaagcc agagccaggc acgcttggca gctgacacag    1860
ggcgctacag tgctgggcct gttcagagtg accccgaga ttccagccgg cctgccttct    1920
ccaagaagcg aaggcggcgg aggctccgga ggaggcggct ctagagaagg acctgaactg    1980
agcccagacg accccgcagg gctgctggat ctgagacagg aatgttcgc ccagctggtg    2040 gctcagaatg tgctgctgat tgatggaccc ctgtcctggt actccgaccc agggctggca    2100
ggggtgtccc tgactggcgg actgtcttac aaagaagata caaagaact ggtggtggct    2160 aaagctgggg tgtactatgt gttttttcag ctggaactga gcggtggt ggctggggaa    2220 ggcagtggct ctgtgtccct ggcactgcat ctgcagcctc tgcgcagtgc tgcaggcgca    2280
gccgcactgg cactgactgt ggacctgccc ccagcttcca gcgaggctag aaacagcgcc    2340
ttcgggtttc aaggacgcct gctgcatctg agcgccggac agcgcctggg agtgcatctg    2400
catactgagg ctagggccag acatgcctgg cagctgaccc aggggcaac tgtgctggga    2460 ctgtttcgcg tgacacctga tccccgct ggcctgccaa gccctagatc agaaggcgga    2520
gggggatcag ggggaggcgg atccagagag ggccctgagc tgagccccga tgatcctgct    2580
ggactgctgg acctgcggca gggcatgttt gctcagctgg tgcccagaa cgtgctgctg    2640 atcgatggcc cctgtcctg gtacagcgat cctggactgg ctggcgtgtc actgacaggc    2700
ggcctgagct acaaagagga caccaaagaa ctggtggtgg ccaaggccgg cgtgtactac    2760 gtgttcttc agctgaact gcggagagtg gtggccggcg aaggatctgg ctctgtgtct    2820
ctggccctgc atctgcagcc tctgagaagc gctgctggcg ctgcagctct ggcactgaca    2880
gtggatctgc ctcctgccag ctccgaggcc cggaatagcg catttgggtt tcaaggcagg    2940
ctgctgcacc tgtctgccgg ccagaggctg ggagtgcatc tgcacacaga ggccaggct    3000 agacacgcct ggcagctgac acagggcgct acagtgctgg gcctgttcag agtgaccccc    3060
gagattccag ccggcctgcc ttctccaaga agcgaa                              3096
```

<210> SEQ ID NO 157
<211> LENGTH: 657
<212> TYPE: DNA
<213> ORGANISM: Artificial Sequence
<220> FEATURE:
<223> OTHER INFORMATION: nucleotide sequence of anti- CD19(8B8-2B11)
      light chain

<400> SEQUENCE: 157

```
gatattgtca tgactcaaac tccactgtct ctgtccgtga ccccgggtca gccagcgagc      60
atttcttgca aatccagcca atctctggaa acctccaccg gcaccacgta cctgaactgg     120
tatctccaga aaccgggtca gagcccgcag ctgctgatct accgtgtatc taagcgcttc     180
tccggcgttc ctgatcgttt cagcggttct ggatccggca ccgactttac tctgaaaatc     240
agccgtgtgg aagctgaaga cgttggcgtc tactattgtc tgcagctgct ggaagatcca     300
tacaccttcg gtcaaggaac gaaactgaa attaaacgta cggtggctgc accatctgtc     360
ttcatcttcc cgccatctga tgagcagttg aaatctggaa ctgcctctgt tgtgtgcctg     420
```

```
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 158
<211> LENGTH: 451
<212> TYPE: PRT
<213> ORGANISM: Artificial Sequence
<220> FEATURE:
<223> OTHER INFORMATION: anti-CD19(8B8-2B11) Fc hole chain

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Gly Ala Pro Ile
            325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 159
<211> LENGTH: 1032
<212> TYPE: PRT
<213> ORGANISM: Artificial Sequence
<220> FEATURE:
<223> OTHER INFORMATION: anti- CD19(8B8-2B11) Fc knob chain fused to
      trimeric hu 4-1BBL (71-254)

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Pro Gln Leu Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Glu Ala Ala Gly
225                 230                 235                 240

Gly Pro Ser Val Phe Leu Phe Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Arg Glu Gly Pro
    450                 455                 460

Glu Leu Ser Pro Asp Asp Pro Ala Gly Leu Leu Asp Leu Arg Gln Gly
465                 470                 475                 480

Met Phe Ala Gln Leu Val Ala Gln Asn Val Leu Leu Ile Asp Gly Pro
                485                 490                 495

Leu Ser Trp Tyr Ser Asp Pro Gly Leu Ala Gly Val Ser Leu Thr Gly
            500                 505                 510

Gly Leu Ser Tyr Lys Glu Asp Thr Lys Glu Leu Val Val Ala Lys Ala
            515                 520                 525

Gly Val Tyr Tyr Val Phe Phe Gln Leu Glu Leu Arg Arg Val Val Ala
        530                 535                 540

Gly Glu Gly Ser Gly Ser Val Ser Leu Ala Leu His Leu Gln Pro Leu
545                 550                 555                 560

Arg Ser Ala Ala Gly Ala Ala Ala Leu Ala Leu Thr Val Asp Leu Pro
            565                 570                 575

Pro Ala Ser Ser Glu Ala Arg Asn Ser Ala Phe Gly Phe Gln Gly Arg
                580                 585                 590

Leu Leu His Leu Ser Ala Gly Gln Arg Leu Gly Val His Leu His Thr
        595                 600                 605

Glu Ala Arg Ala Arg His Ala Trp Gln Leu Thr Gln Gly Ala Thr Val
        610                 615                 620

Leu Gly Leu Phe Arg Val Thr Pro Glu Ile Pro Ala Gly Leu Pro Ser
625                 630                 635                 640
```

```
Pro Arg Ser Glu Gly Gly Gly Ser Gly Gly Gly Ser Arg Glu
            645                 650                 655

Gly Pro Glu Leu Ser Pro Asp Asp Pro Ala Gly Leu Leu Asp Leu Arg
        660                 665                 670

Gln Gly Met Phe Ala Gln Leu Val Ala Gln Asn Val Leu Leu Ile Asp
        675                 680                 685

Gly Pro Leu Ser Trp Tyr Ser Asp Pro Gly Leu Ala Gly Val Ser Leu
        690                 695                 700

Thr Gly Gly Leu Ser Tyr Lys Glu Asp Thr Lys Glu Leu Val Val Ala
705                 710                 715                 720

Lys Ala Gly Val Tyr Tyr Val Phe Phe Gln Leu Glu Leu Arg Arg Val
                725                 730                 735

Val Ala Gly Glu Gly Ser Gly Ser Val Ser Leu Ala Leu His Leu Gln
            740                 745                 750

Pro Leu Arg Ser Ala Ala Gly Ala Ala Ala Leu Ala Leu Thr Val Asp
        755                 760                 765

Leu Pro Pro Ala Ser Ser Glu Ala Arg Asn Ser Ala Phe Gly Phe Gln
        770                 775                 780

Gly Arg Leu Leu His Leu Ser Ala Gly Gln Arg Leu Gly Val His Leu
785                 790                 795                 800

His Thr Glu Ala Arg Ala Arg His Ala Trp Gln Leu Thr Gln Gly Ala
                805                 810                 815

Thr Val Leu Gly Leu Phe Arg Val Thr Pro Glu Ile Pro Ala Gly Leu
            820                 825                 830

Pro Ser Pro Arg Ser Glu Gly Gly Gly Ser Gly Gly Gly Ser
        835                 840                 845

Arg Glu Gly Pro Glu Leu Ser Pro Asp Asp Pro Ala Gly Leu Leu Asp
850                 855                 860

Leu Arg Gln Gly Met Phe Ala Gln Leu Val Ala Gln Asn Val Leu Leu
865                 870                 875                 880

Ile Asp Gly Pro Leu Ser Trp Tyr Ser Asp Pro Gly Leu Ala Gly Val
                885                 890                 895

Ser Leu Thr Gly Gly Leu Ser Tyr Lys Glu Asp Thr Lys Glu Leu Val
            900                 905                 910

Val Ala Lys Ala Gly Val Tyr Tyr Val Phe Phe Gln Leu Glu Leu Arg
        915                 920                 925

Arg Val Val Ala Gly Glu Gly Ser Gly Ser Val Ser Leu Ala Leu His
        930                 935                 940

Leu Gln Pro Leu Arg Ser Ala Ala Gly Ala Ala Ala Leu Ala Leu Thr
945                 950                 955                 960

Val Asp Leu Pro Pro Ala Ser Ser Glu Ala Arg Asn Ser Ala Phe Gly
                965                 970                 975

Phe Gln Gly Arg Leu Leu His Leu Ser Ala Gly Gln Arg Leu Gly Val
            980                 985                 990

His Leu His Thr Glu Ala Arg Ala Arg His Ala Trp Gln Leu Thr Gln
        995                 1000                1005

Gly Ala Thr Val Leu Gly Leu Phe Arg Val Thr Pro Glu Ile Pro
    1010                1015                1020

Ala Gly Leu Pro Ser Pro Arg Ser Glu
    1025                1030

<210> SEQ ID NO 160
<211> LENGTH: 219
<212> TYPE: PRT
```

<213> ORGANISM: Artificial Sequence
<220> FEATURE:
<223> OTHER INFORMATION: anti- CD19(8B8-2B11) light chain

<400> SEQUENCE: 160

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 161
<211> LENGTH: 6
<212> TYPE: PRT
<213> ORGANISM: Artificial Sequence
<220> FEATURE:
<223> OTHER INFORMATION: HVR-L1 anti-CD19(8B8)

<400> SEQUENCE: 161

```
Asn Ser Asn Gly Asn Thr
1               5
```

<210> SEQ ID NO 162
<211> LENGTH: 4
<212> TYPE: PRT
<213> ORGANISM: Artificial Sequence
<220> FEATURE:
<223> OTHER INFORMATION: HVR-H2 anti-CD19(8B8)

<400> SEQUENCE: 162

```
Lys Phe Asn Gly
1
```

<210> SEQ ID NO 163
<211> LENGTH: 681
<212> TYPE: DNA
<213> ORGANISM: Artificial Sequence

```
<220> FEATURE:
<223> OTHER INFORMATION: Nucleotide sequence of Fc hole chain with HYRF
      mutation

<400> SEQUENCE: 163
gacaaaactc acacatgccc accgtgccca gcacctgaag ctgcagggggg accgtcagtc      60 ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
tgcaaggtct ccaacaaagc cctcggcgcc cccatcgaga aaaccatctc caaagccaaa     360
gggcagcccc gagaaccaca ggtgtgcacc ctgcccccat cccgggatga gctgaccaag     420
aaccaggtca gcctctcgtg cgcagtcaaa ggcttctatc cagcgacat cgccgtggag      480 tgggagagca atgggcagcc ggagaacaac tacaagacca cgcctcccgt gctggactcc     540
gacggctcct tcttcctcgt gagcaagctc accgtggaca agagcaggtg gcagcagggg     600
aacgtcttct catgctccgt gatgcatgag gctctgcaca accgcttcac gcagaagagc     660 ctctcccctgt ctccgggtaa a                                              681

<210> SEQ ID NO 164
<211> LENGTH: 1602
<212> TYPE: DNA
<213> ORGANISM: Artificial Sequence
<220> FEATURE:
<223> OTHER INFORMATION: Nucleotide sequence of human CD19 antigen Fc
      knob chain avi tag

<400> SEQUENCE: 164
cccgaggaac ccctggtcgt gaaggtggaa gagggcgaca atgccgtgct gcagtgcctg      60
aagggcacct ccgatggccc tacccagcag ctgacctggt ccagagagag ccccctgaag     120 ccccttcctga agctgtctct gggcctgcct ggcctgggca tccatatgag gcctctggcc    180
atctggctgt tcatcttcaa cgtgtcccag cagatgggcg gcttctacct gtgtcagcct     240 ggcccccat ctgagaaggc ttggcagcct ggctggaccg tgaacgtgga aggatccggc      300
gagctgttcc ggtggaacgt gtccgatctg ggcggcctgg gatgcggcct gaagaacaga     360
tctagcgagg gccccagcag ccccagcggc aaactgatga gccccaagct gtacgtgtgg     420
gccaaggaca gacccgagat ctgggagggc gagcctcctt gcctgccccc tagagacagc     480
ctgaaccaga gcctgagcca ggacctgaca atggcccctg gcagcacact gtggctgagc     540
tgtggcgtgc cacccgactc tgtgtctaga ggccctctga gctggaccca cgtgcaccct     600
aagggcccta gagcctgct gagcctgaa ctgaaggacg acaggcccgc cagagatatg       660
tgggtcatgg aaaccggcct gctgctgcct agagccacag cccaggatgc cggcaagtac     720
tactgccaca gaggcaacct gaccatgagc ttccacctgg aaatcaccgc cagacccgtg     780
ctgtggcact ggctgctgag aacaggcggc tggaaggtcg acgctagcgg tggtagtccg     840
acacctccga cacccggggg tggttctgca gacaaaactc acacatgccc accgtgccca     900
gcacctgaag ccgcagggggg accgtcagtc ttcctcttcc ccccaaaacc caaggacacc     960
ctcatgatct cccggacccc tgaggtcaca tgcgtggtgg tggacgtgag ccacgaagac    1020
cctgaggtca agttcaactg gtacgtggac ggcgtggagg tgcataatgc caagacaaag    1080
ccgcgggagg agcagtacaa cagcacgtac cgtgtggtca gcgtcctcac cgtcctgcac    1140
```

| | |
|---|---|
| caggactggc tgaatggcaa ggagtacaag tgcaaggtct ccaacaaagc cctcggagcc | 1200 |
| cccatcgaga aaaccatctc caaagccaaa gggcagcccc gagaaccaca ggtgtacacc | 1260 |
| ctgcccccat gccgggatga gctgaccaag aaccaggtca gcctgtggtg cctggtcaaa | 1320 |
| ggcttctatc ccagcgacat cgccgtggag tgggagagca atgggcagcc ggagaacaac | 1380 |
| tacaagacca cgcctcccgt gctggactcc gacggctcct tcttcctcta cagcaagctc | 1440 |
| accgtggaca agagcaggtg gcagcagggg aacgtcttct catgctccgt gatgcatgag | 1500 |
| gctctgcaca accactacac gcagaagagc ctctccctgt ctccgggtaa atccggaggc | 1560 |
| ctgaacgaca tcttcgaggc ccagaagatt gaatggcacg ag | 1602 |

```
<210> SEQ ID NO 165
<211> LENGTH: 227
<212> TYPE: PRT
<213> ORGANISM: Artificial Sequence
<220> FEATURE:
<223> OTHER INFORMATION: Fc hole chain with HYRF mutation

<400> SEQUENCE: 165
```

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

```
<210> SEQ ID NO 166
<211> LENGTH: 534
<212> TYPE: PRT
<213> ORGANISM: Artificial Sequence
<220> FEATURE:
<223> OTHER INFORMATION: human CD19 antigen Fc knob chain avi tag
```

```
<400> SEQUENCE: 166

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270

Val Asp Ala Ser Gly Ser Pro Thr Pro Thr Pro Gly Gly Gly
        275                 280                 285

Ser Ala Asp Lys Thr His Thr Cys Pro Pro Cys Pro Ala Pro Glu Ala
    290                 295                 300

Ala Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Lys Phe Asn Trp Tyr Val Asp Gly Val
            340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
    370                 375                 380

Asn Gly Lys Glu Tyr Lys Cys Lys Val Ser Asn Lys Ala Leu Gly Ala
385                 390                 395                 400

Pro Ile Glu Lys Thr Ile Ser Lys Ala Lys Gly Gln Pro Arg Glu Pro
                405                 410                 415
```

Gln Val Tyr Thr Leu Pro Pro Cys Arg Asp Glu Leu Thr Lys Asn Gln
                420                 425                 430

Val Ser Leu Trp Cys Leu Val Lys Gly Phe Tyr Pro Ser Asp Ile Ala
            435                 440                 445

Val Glu Trp Glu Ser Asn Gly Gln Pro Glu Asn Asn Tyr Lys Thr Thr
        450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
            500                 505                 510

Leu Ser Pro Gly Lys Ser Gly Gly Leu Asn Asp Ile Phe Glu Ala Gln
        515                 520                 525

Lys Ile Glu Trp His Glu
    530

<210> SEQ ID NO 167
<211> LENGTH: 1605
<212> TYPE: DNA
<213> ORGANISM: Artificial Sequence
<220> FEATURE:
<223> OTHER INFORMATION: Nucleotide sequence of cynomolgus CD19 antigen
      Fc knob chain avi tag

<400> SEQUENCE: 167

```
ccccaggaac ccctggtcgt gaaggtggaa gagggcgaca atgccgtgct ccagtgcctg      60
gaaggcacct ccgatggccc tacacagcag ctcgtgtggt gcagagacag ccccttcgag     120
cccttcctga acctgtctct gggcctgcct ggcatgggca tcagaatggg ccctctgggc     180
atctggctgc tgatcttcaa cgtgtccaac cagaccggcg gcttctacct gtgtcagcct     240
ggcctgccaa gcgagaaggc ttggcagcct ggatggaccg tgtccgtgga aggatctggc     300
gagctgttcc ggtggaacgt gtccgatctg gcggcctgga tgcggcct aagaacaga      360 agcagcgagg gcctagcag ccccagcggc aagctgaata gcagccagct gtacgtgtgg     420
gccaaggaca gacccgagat gtgggagggc gagcctgtgt gtggccccc tagagatagc     480 ctgaaccaga gcctgagcca ggacctgaca atggcccctg cagcacact gtggctgagc     540 tgtggcgtgc acccgactc tgtgtccaga ggccctctga gctggacaca cgtgcggcca     600
aagggcccta gagcagcct gctgagcctg aactgaagg acgaccggcc cgaccgggat     660
atgtgggtgg tggatacagg cctgctgctg accagagcca cagcccagga tgccggcaag     720
tactactgcc acagaggcaa ctggaccaag agcttttacc tggaaatcac cgccagaccc     780
gccctgtggc actggctgct gagaatcgga ggctggaagg tcgacgctag cggtggtagt     840
ccgacacctc cgacacccgg gggtggttct gcagacaaaa ctcacacatg cccaccgtgc     900
ccagcacctg aagccgcagg gggaccgtca gtcttcctct ccccccaaa acccaaggac     960 accctcatga tctcccggac ccctgaggtc acatgcgtgg tggtggacgt gagccacgaa    1020
gaccctgagg tcaagttcaa ctggtacgtg gacggcgtgg aggtgcataa tgccaagaca    1080
aagccgcggg aggagcagta acagcacg taccgtgtgg tcagcgtcct caccgtcctg    1140
caccaggact ggctgaatgg caaggagtac aagtgcaagg tctccaacaa agccctcgga    1200
gcccccatcg agaaaaccat ctccaaagcc aagggcagc ccgagaacc acaggtgtac    1260 accctgcccc catgccggga tgagctgacc aagaaccagg tcagcctgtg gtgcctggtc    1320
```

```
aaaggcttct atcccagcga catcgccgtg gagtgggaga gcaatgggca gccggagaac    1380
aactacaaga ccacgcctcc cgtgctggac tccgacggct ccttcttcct ctacagcaag    1440
ctcaccgtgg acaagagcag gtggcagcag gggaacgtct tctcatgctc cgtgatgcat    1500
gaggctctgc acaaccacta cacgcagaag agcctctccc tgtctccggg taaatccgga    1560
ggcctgaacg acatcttcga ggcccagaag attgaatggc acgag                    1605
```

<210> SEQ ID NO 168
<211> LENGTH: 535
<212> TYPE: PRT
<213> ORGANISM: Artificial Sequence
<220> FEATURE:
<223> OTHER INFORMATION: cynomolgus CD19 antigen Fc knob chain avi tag

<400> SEQUENCE: 168

```
Pro Gln Glu Pro Leu Val Val Lys Val Glu Glu Gly Asp Asn Ala Val
1               5                   10                  15

Leu Gln Cys Leu Glu Gly Thr Ser Asp Gly Pro Thr Gln Gln Leu Val
            20                  25                  30

Trp Cys Arg Asp Ser Pro Phe Glu Pro Phe Leu Asn Leu Ser Leu Gly
        35                  40                  45

Leu Pro Gly Met Gly Ile Arg Met Gly Pro Leu Gly Ile Trp Leu Leu
    50                  55                  60

Ile Phe Asn Val Ser Asn Gln Thr Gly Gly Phe Tyr Leu Cys Gln Pro
65                  70                  75                  80

Gly Leu Pro Ser Glu Lys Ala Trp Gln Pro Gly Trp Thr Val Ser Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Asn Ser Ser Gln Leu Tyr Val Trp Ala Lys Asp Arg
    130                 135                 140

Pro Glu Met Trp Glu Gly Glu Pro Val Cys Gly Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val Arg Pro Lys Gly Pro Lys Ser Ser Leu Leu
        195                 200                 205

Ser Leu Glu Leu Lys Asp Asp Arg Pro Asp Arg Asp Met Trp Val Val
    210                 215                 220

Asp Thr Gly Leu Leu Leu Thr Arg Ala Thr Ala Gln Asp Ala Gly Lys
225                 230                 235                 240

Tyr Tyr Cys His Arg Gly Asn Trp Thr Lys Ser Phe Tyr Leu Glu Ile
                245                 250                 255

Thr Ala Arg Pro Ala Leu Trp His Trp Leu Leu Arg Ile Gly Gly Trp
            260                 265                 270

Lys Val Asp Ala Ser Gly Gly Ser Pro Thr Pro Thr Pro Gly Gly
        275                 280                 285

Gly Ser Ala Asp Lys Thr His Thr Cys Pro Pro Cys Pro Ala Pro Glu
    290                 295                 300

Ala Ala Gly Gly Pro Ser Val Phe Leu Phe Pro Pro Lys Pro Lys Asp
```

```
                305                 310                 315                 320
            Thr Leu Met Ile Ser Arg Thr Pro Glu Val Thr Cys Val Val Asp
                            325                 330                 335

Val Ser His Glu Asp Pro Glu Val Lys Phe Asn Trp Tyr Val Asp Gly
                            340                 345                 350

Val Glu Val His Asn Ala Lys Thr Lys Pro Arg Glu Glu Gln Tyr Asn
                            355                 360                 365

Ser Thr Tyr Arg Val Val Ser Val Leu Thr Val Leu His Gln Asp Trp
                370                 375                 380

Leu Asn Gly Lys Glu Tyr Lys Cys Lys Val Ser Asn Lys Ala Leu Gly
            385                 390                 395                 400

Ala Pro Ile Glu Lys Thr Ile Ser Lys Ala Lys Gly Gln Pro Arg Glu
                            405                 410                 415

Pro Gln Val Tyr Thr Leu Pro Pro Cys Arg Asp Glu Leu Thr Lys Asn
                            420                 425                 430

Gln Val Ser Leu Trp Cys Leu Val Lys Gly Phe Tyr Pro Ser Asp Ile
                            435                 440                 445

Ala Val Glu Trp Glu Ser Asn Gly Gln Pro Glu Asn Asn Tyr Lys Thr
                450                 455                 460

Thr Pro Pro Val Leu Asp Ser Asp Gly Ser Phe Phe Leu Tyr Ser Lys
            465                 470                 475                 480

Leu Thr Val Asp Lys Ser Arg Trp Gln Gln Gly Asn Val Phe Ser Cys
                            485                 490                 495

Ser Val Met His Glu Ala Leu His Asn His Tyr Thr Gln Lys Ser Leu
                            500                 505                 510

Ser Leu Ser Pro Gly Lys Ser Gly Gly Leu Asn Asp Ile Phe Glu Ala
                            515                 520                 525

Gln Lys Ile Glu Trp His Glu
                            530                 535

<210> SEQ ID NO 169
<211> LENGTH: 363
<212> TYPE: DNA
<213> ORGANISM: Artificial Sequence
<220> FEATURE:
<223> OTHER INFORMATION: Nucleotide sequence CD19 (8B8) VH Parental
      clone

<400> SEQUENCE: 169
gaggtccagc tgcagcagtc tggacctgag ctggtaaagc ctggggcttc agtgaagatg       60
gcctgcaagg cttctggata cacattcact gactatatta tgcactgggt gaagcagaag      120
actgggcagg gccttgagtg gattggatat attaatcctt acaatgatgg ttctaagtac      180
actgagaagt tcaacggcaa ggccacactg acttcagaca atcttccat acagcctac        240 atggagctca gcagcctgac ctctgaggac tctgcggtct attactgtgc aagagggacc      300
tattattatg gtagcgccct ctttgactac tggggccaag gcaccactct cacagtctcc      360
tcg                                                                    363

<210> SEQ ID NO 170
<211> LENGTH: 336
<212> TYPE: DNA
<213> ORGANISM: Artificial Sequence
<220> FEATURE:
<223> OTHER INFORMATION: Nucleotide sequence CD19 (8B8) VL Parental
      clone

<400> SEQUENCE: 170
```

-continued

```
gatgctgtga tgacccaaac tccactctcc ctgcctgtca gtcttggaga tcaagcctcc      60
atctcttgca ggtctagtca gagccttgaa aacagtaatg aaacaccta tttgaactgg      120 tacctccaga aaccaggcca gtctccacaa ctcctgatct acagggtttc caaacgattt     180
tctggggtcc tagacaggtt cagtggtagt ggatcaggga cagatttcac actgaaaatc     240
agcagagtgg aggctgagga tttgggagtt tatttctgcc tacaacttac acatgtcccg    300
tacacgttcg gaggggggac caagctggaa ataaaa                                336
```

<210> SEQ ID NO 171
<211> LENGTH: 94
<212> TYPE: DNA
<213> ORGANISM: Artificial Sequence
<220> FEATURE:
<223> OTHER INFORMATION: 43-45: 40% Y, 6% A/S/T/G/P/D/N/E/Q/V, 49-51: 40% N, 6% A/S/T/Y/G/P/D/E/Q/V, 55-57: 25% S/T/Q/E, 61-63: 25% S/T/Q/E
<220> FEATURE:
<221> NAME/KEY: misc_feature
<222> LOCATION: (43)..(45)
<223> OTHER INFORMATION: n is a, c, g or t
<220> FEATURE:
<221> NAME/KEY: misc_feature
<222> LOCATION: (49)..(51)
<223> OTHER INFORMATION: n is a, c, g or t
<220> FEATURE:
<221> NAME/KEY: misc_feature
<222> LOCATION: (55)..(57)
<223> OTHER INFORMATION: n is a, c, g or t
<220> FEATURE:
<221> NAME/KEY: misc_feature
<222> LOCATION: (61)..(63)
<223> OTHER INFORMATION: n is a, c, g or t

<400> SEQUENCE: 171

```
cagctgcggg ctctgacccg gtttctggag ataccagttc agnnncgtnn ngccnnngga      60
nnnttccaga gattggctgg atttgcaaga aatg                                   94
```

<210> SEQ ID NO 172
<211> LENGTH: 99
<212> TYPE: DNA
<213> ORGANISM: Artificial Sequence
<220> FEATURE:
<223> OTHER INFORMATION: 40-42: 30% R, 20% E, 5% A/S/T/Y/G/P/D/N/Q/V. 49-51: 30% K, 20% S, 5% A/N/T/Y/G/P/D/E/Q/V, 55-57: 40% F, 5% A/S/T/Y/G/P/D/E/Q/V/I/L,
<220> FEATURE:
<221> NAME/KEY: misc_feature
<222> LOCATION: (40)..(42)
<223> OTHER INFORMATION: n is a, c, g or t
<220> FEATURE:
<221> NAME/KEY: misc_feature
<222> LOCATION: (49)..(51)
<223> OTHER INFORMATION: n is a, c, g or t
<220> FEATURE:
<221> NAME/KEY: misc_feature
<222> LOCATION: (55)..(57)
<223> OTHER INFORMATION: n is a, c, g or t
<220> FEATURE:
<221> NAME/KEY: misc_feature
<222> LOCATION: (58)..(60)
<223> OTHER INFORMATION: n is a, c, g or t
<220> FEATURE:
<221> NAME/KEY: misc_feature
<222> LOCATION: (67)..(69)
<223> OTHER INFORMATION: n is a, c, g or t

<400> SEQUENCE: 172

```
ctccagaaac cgggtcagag cccgcagctg ctgatctacn nngtatctnn ncgcnnnnnn      60
```

```
ggcgttnnng atcgtttcag cggttctgga tccggcacc                              99
```

<210> SEQ ID NO 173
<211> LENGTH: 99
<212> TYPE: DNA
<213> ORGANISM: Artificial Sequence
<220> FEATURE:
<223> OTHER INFORMATION: 40-42: 52% H, 4% G/A/S/P/T/N/Y/D/E/Q/V/I,
      46-48: 30% I, 15% Y, 5% G/A/S/T/P/N/H/D/E/Q/V, 49-51: 52% Y, 4%
      G/A/S/P/T/N/H/D/E/Q/V/I, 52-54: 30% D, 15% G, 5%
      A/S/P/Y/N/H/D/E/Q/V/I, 55-57: 52% T, 4% G/A/S/P/Y/N/H/D/E/Q/V/I,
      61-63: 52% T, 4% G/A/S/P/Y/N/H/D/E/
<220> FEATURE:
<221> NAME/KEY: misc_feature
<222> LOCATION: (40)..(42)
<223> OTHER INFORMATION: n is a, c, g or t
<220> FEATURE:
<221> NAME/KEY: misc_feature
<222> LOCATION: (46)..(48)
<223> OTHER INFORMATION: n is a, c, g or t
<220> FEATURE:
<221> NAME/KEY: misc_feature
<222> LOCATION: (49)..(51)
<223> OTHER INFORMATION: n is a, c, g or t
<220> FEATURE:
<221> NAME/KEY: misc_feature
<222> LOCATION: (52)..(54)
<223> OTHER INFORMATION: n is a, c, g or t
<220> FEATURE:
<221> NAME/KEY: misc_feature
<222> LOCATION: (55)..(57)
<223> OTHER INFORMATION: n is a, c, g or t
<220> FEATURE:
<221> NAME/KEY: misc_feature
<222> LOCATION: (61)..(63)
<223> OTHER INFORMATION: n is a, c, g or t

<400> SEQUENCE: 173

```
catccactcc agaccctggc ccggggcctg acgaacccan nncatnnnnn nnnnnnngaa        60
nnngtaacca gatgctttgc agctcacttt aacggaagc                              99
```

<210> SEQ ID NO 174
<211> LENGTH: 99
<212> TYPE: DNA
<213> ORGANISM: Artificial Sequence
<220> FEATURE:
<223> OTHER INFORMATION: 34-36: 45% Y, 5% others, 40-42: 52% N, 4%
      others, 46-48: 40% Y,5% others, 49-51: 30% N, 15% S, 5% others,
      52-54: 30% D, 15% G,5% others,  55-57: 52% G, 4% others, 61-63:
      30% K, 15% N, 4% others, 70-72: 30% E, 15% Q, 5% others
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (40)..(42)
<223> OTHER INFORMATION: n is a, c, g or t
<220> FEATURE:
<221> NAME/KEY: misc_feature
<222> LOCATION: (46)..(48)
<223> OTHER INFORMATION: n is a, c, g or t
<220> FEATURE:
<221> NAME/KEY: misc_feature
<222> LOCATION: (49)..(51)
<223> OTHER INFORMATION: n is a, c, g or t
<220> FEATURE:
<221> NAME/KEY: misc_feature
<222> LOCATION: (52)..(54)
<223> OTHER INFORMATION: n is a, c, g or t
<220> FEATURE:
<221> NAME/KEY: misc_feature
<222> LOCATION: (55)..(57)
<223> OTHER INFORMATION: n is a, c, g or t
<220> FEATURE:

-continued

```
<221> NAME/KEY: misc_feature
<222> LOCATION: (61)..(63)
<223> OTHER INFORMATION: n is a, c, g or t
<220> FEATURE:
<221> NAME/KEY: misc_feature
<222> LOCATION: (70)..(72)
<223> OTHER INFORMATION: n is a, c, g or t

<400> SEQUENCE: 174
caggccccgg gccagggtct ggagtggatg ggcnnnattn nnccannnnn nnnnnnntcc      60
nnntataccn nnaaattcca gggccgcgtc acgatgacc                            99

<210> SEQ ID NO 175
<211> LENGTH: 33
<212> TYPE: DNA
<213> ORGANISM: Artificial Sequence
<220> FEATURE:
<223> OTHER INFORMATION: CD19 H3 reverse constant

<400> SEQUENCE: 175
cgtcaccggt tcggggaagt agtccttgac cag                                  33

<210> SEQ ID NO 176
<211> LENGTH: 26
<212> TYPE: DNA
<213> ORGANISM: Artificial Sequence
<220> FEATURE:
<223> OTHER INFORMATION: LMB3

<400> SEQUENCE: 176
caggaaacag ctatgaccat gattac                                          26

<210> SEQ ID NO 177
<211> LENGTH: 33
<212> TYPE: DNA
<213> ORGANISM: Artificial Sequence
<220> FEATURE:
<223> OTHER INFORMATION: CD19 L1 forward constant

<400> SEQUENCE: 177
tggtatctcc agaaaccggg tcagagcccg cag                                  33

<210> SEQ ID NO 178
<211> LENGTH: 84
<212> TYPE: DNA
<213> ORGANISM: Artificial Sequence
<220> FEATURE:
<223> OTHER INFORMATION: 34-36: 52% Y, 4% others, 37-39: 52% P, 4%
      others, 40-42: 42% V,10% L, 4% others, 43-45: 52% H, 4% others,
      46-48: 42% T, 10% I, 4% others, 49-51: 45% L, 11% G, 4% others
<220> FEATURE:
<221> NAME/KEY: misc_feature
<222> LOCATION: (34)..(36)
<223> OTHER INFORMATION: n is a,c,g or t
<220> FEATURE:
<221> NAME/KEY: misc_feature
<222> LOCATION: (37)..(39)
<223> OTHER INFORMATION: n is a,c,g or t
<220> FEATURE:
<221> NAME/KEY: misc_feature
<222> LOCATION: (40)..(42)
<223> OTHER INFORMATION: n is a,c,g or t
<220> FEATURE:
<221> NAME/KEY: misc_feature
<222> LOCATION: (43)..(45)
<223> OTHER INFORMATION: n is a,c,g or t
<220> FEATURE:
<221> NAME/KEY: misc_feature
<222> LOCATION: (46)..(48)
<223> OTHER INFORMATION: n is a,c,g or t
```

```
<220> FEATURE:
<221> NAME/KEY: misc_feature
<222> LOCATION: (49)..(51)
<223> OTHER INFORMATION: n is a,c,g or t

<400> SEQUENCE: 178
tttaatttcc agtttagttc cttgaccgaa ggtnnnnnnn nnnnnnnnnn nctgcagaca      60
atagtagacg ccaacgtctt cagc                                            84

<210> SEQ ID NO 179
<211> LENGTH: 35
<212> TYPE: DNA
<213> ORGANISM: Artificial Sequence
<220> FEATURE:
<223> OTHER INFORMATION: CD19 L3 forward constant

<400> SEQUENCE: 179
accttcggtc aaggaactaa actggaaatt aaacg                                35

<210> SEQ ID NO 180
<211> LENGTH: 107
<212> TYPE: DNA
<213> ORGANISM: Artificial Sequence
<220> FEATURE:
<223> OTHER INFORMATION: pos. 59-61: 50% L, 3.8% others, 62-64: 50% A,
      4.2% others, 65-67:50% S, 4.2% others, 68-70: 50% G, 4.2% others,
      71-73: 50% Y, 4.2%others, 74-76: 50% Y, 4.2% others, 77-79: 50% Y,
      4.2% others, 80-82: 50% T, 4.2% others, 83-85: 50% G, 4.2% others.
<220> FEATURE:
<221> NAME/KEY: misc_feature
<222> LOCATION: (54)..(58)
<223> OTHER INFORMATION: n is a, c, g or t
<220> FEATURE:
<221> NAME/KEY: misc_feature
<222> LOCATION: (59)..(61)
<223> OTHER INFORMATION: n is a, c, g or t
<220> FEATURE:
<221> NAME/KEY: misc_feature
<222> LOCATION: (62)..(64)
<223> OTHER INFORMATION: n is a, c, g or t
<220> FEATURE:
<221> NAME/KEY: misc_feature
<222> LOCATION: (65)..(67)
<223> OTHER INFORMATION: n is a, c, g or t
<220> FEATURE:
<221> NAME/KEY: misc_feature
<222> LOCATION: (68)..(70)
<223> OTHER INFORMATION: n is a, c, g or t
<220> FEATURE:
<221> NAME/KEY: misc_feature
<222> LOCATION: (71)..(73)
<223> OTHER INFORMATION: n is a, c, g or t
<220> FEATURE:
<221> NAME/KEY: misc_feature
<222> LOCATION: (74)..(76)
<223> OTHER INFORMATION: n is a, c, g or t
<220> FEATURE:
<221> NAME/KEY: misc_feature
<222> LOCATION: (77)..(79)
<223> OTHER INFORMATION: n is a, c, g or t
<220> FEATURE:
<221> NAME/KEY: misc_feature
<222> LOCATION: (80)..(82)
<223> OTHER INFORMATION: n is a, c, g or t

<400> SEQUENCE: 180
ttggtgctag cagagcttac ggtcaccgtg gtaccttggc cccagtaatc aaannnnnnn      60
nnnnnnnnnn nnnnnnnnnn gcgtgcacaa tagtaaacag cggtgtc                   107

<210> SEQ ID NO 181
<211> LENGTH: 3078
```

<212> TYPE: DNA
<213> ORGANISM: Artificial Sequence
<220> FEATURE:
<223> OTHER INFORMATION: nucleotide sequence of DP47 Fc knob fused to trimeric hu 4-1BBL (71-254)

<400> SEQUENCE: 181

| | | | | | |
|---|---|---|---|---|---|
| gaggtgcaat | tgttggagtc | tgggggaggc | ttggtacagc | ctggggggtc | cctgagactc | 60 |
| tcctgtgcag | cctccggatt | cacctttagc | agttatgcca | tgagctgggt | ccgccaggct | 120 |
| ccagggaagg | ggctggagtg | ggtctcagct | attagtggta | gtggtggtag | cacatactac | 180 |
| gcagactccg | tgaagggccg | gttcaccatc | tccagagaca | attccaagaa | cacgctgtat | 240 |
| ctgcagatga | acagcctgag | agccgaggac | acggccgtat | attactgtgc | gaaaggcagc | 300 |
| ggatttgact | actggggcca | aggaaccctg | gtcaccgtct | cgagtgctag | caccaagggc | 360 |
| ccatcggtct | tccccctggc | accctcctcc | aagagcacct | ctggggcac | agcggccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcaccc | agacctacat | ctgcaacgtg | 600 |
| aatcacaagc | ccagcaacac | caaggtggac | aagaaagttg | agcccaaatc | ttgtgacaaa | 660 |
| actcacacat | gcccaccgtg | cccagcacct | gaagctgcag | ggggaccgtc | agtcttcctc | 720 |
| ttccccccaa | aacccaagga | caccctcatg | atctcccgga | cccctgaggt | cacatgcgtg | 780 |
| gtggtggacg | tgagccacga | agaccctgag | gtcaagttca | actggtacgt | ggacggcgtg | 840 |
| gaggtgcata | atgccaagac | aaagccgcgg | gaggagcagt | acaacagcac | gtaccgtgtg | 900 |
| gtcagcgtcc | tcaccgtcct | gcaccaggac | tggctgaatg | gcaaggagta | caagtgcaag | 960 |
| gtctccaaca | aagccctcgg | cgccccatc | gagaaaacca | tctccaaagc | caagggcag | 1020 |
| ccccgagaac | cacaggtgta | caccctgccc | cctgcagag | atgagctgac | caagaaccag | 1080 |
| gtgtccctgt | ggtgcctcgt | gaagggcttc | taccctccg | atatcgccgt | ggaatgggag | 1140 |
| agcaacggcc | agcccgagaa | caactacaag | accacccccc | ctgtgctgga | cagcgacggc | 1200 |
| tcattcttcc | tgtactccaa | gctgaccgtg | gacaagagcc | ggtggcagca | gggcaacgtg | 1260 |
| ttcagctgca | gcgtgatgca | cgaggccctg | cacaaccact | acacccagaa | gtccctgagc | 1320 |
| ctgagccctg | gcgaggcgg | aggatctggc | ggggaggat | ctagagaggg | ccctgagctg | 1380 |
| tcccccgatg | atcctgctgg | actgctggac | ctgcggcagg | gcatgtttgc | tcagctggtg | 1440 |
| gcccagaacg | tgctgctgat | cgacggcccc | tgagctggt | acagcgatcc | tggactggct | 1500 |
| ggcgtgtcac | tgacaggcgg | cctgagctac | aaagaggaca | ccaaagaact | ggtggtggcc | 1560 |
| aaggccggcg | tgtactacgt | gttctttcag | ctggaactgc | ggagagtggt | ggccggcgag | 1620 |
| ggatctggat | ctgtgtctct | ggccctgcat | ctgcagcccc | tgagatcagc | tgctggcgct | 1680 |
| gctgctctgg | ctctgacagt | ggatctgcct | cctgccagca | gcgaggcccg | gaatagcgca | 1740 |
| tttgggtttc | aaggcaggct | gctgcacctg | tctgccggcc | agaggctggg | agtgcatctg | 1800 |
| cacacagaag | ccagagccag | gcacgcttgg | cagctgacac | agggcgctac | agtgctgggc | 1860 |
| ctgttcagag | tgacccccga | gattccagcc | ggcctgcctt | ctccaagaag | cgaaggcggc | 1920 |
| ggaggctccg | gaggaggcgg | ctctagagaa | ggacctgaac | tgagcccaga | cgaccccgca | 1980 |
| gggctgctgg | atctgagaca | gggaatgttc | gcccagctgg | tggctcagaa | tgtgctgctg | 2040 |
| attgatggac | cctgtcctg | gtactccgac | ccagggctgg | caggggtgtc | cctgactggc | 2100 |
| ggactgtctt | acaaagaaga | tacaaaagaa | ctggtggtgg | ctaaagctgg | ggtgtactat | 2160 |

-continued

```
gtgttttttc agctggaact gaggcgggtg gtggctgggg aaggcagtgg ctctgtgtcc    2220
ctggcactgc atctgcagcc tctgcgcagt gctgcaggcg cagccgcact ggcactgact    2280
gtggacctgc ccccagcttc cagcgaggct agaaacagcg ccttcgggtt tcaaggacgc    2340
ctgctgcatc tgagcgccgg acagcgcctg ggagtgcatc tgcatactga ggctagggcc    2400
agacatgcct ggcagctgac ccaggggggca actgtgctgg gactgtttcg cgtgacacct    2460
gagatccccg ctggcctgcc aagccctaga tcagaaggcg gagggggatc aggggggaggc    2520 ggatccagag agggccctga gctgagcccc gatgatcctg ctggactgct ggacctgcgg    2580
cagggcatgt ttgctcagct ggtggcccag aacgtgctgc tgatcgatgg ccccctgtcc    2640
tggtacagcg atcctggact ggctggcgtg tcactgacag gcggcctgag ctacaaagag    2700
gacaccaaag aactggtggt ggccaaggcc ggcgtgtact acgtgttctt tcagctggaa    2760
ctgcggagag tggtggccgg cgaaggatct ggctctgtgt ctctggccct gcatctgcag    2820
cctctgagaa gcgctgctgg cgctgcagct ctggcactga cagtggatct gcctcctgcc    2880
agctccgagg cccggaatag cgcatttggg tttcaaggca ggctgctgca cctgtctgcc    2940
ggccagaggc tgggagtgca tctgcacaca gaggccaggg ctagacacgc ctggcagctg    3000
acacagggcg ctacagtgct gggcctgttc agagtgaccc ccgagattcc agccggcctg    3060
ccttctccaa gaagcgaa                                                 3078
```

<210> SEQ ID NO 182
<211> LENGTH: 1026
<212> TYPE: PRT
<213> ORGANISM: Artificial Sequence
<220> FEATURE:
<223> OTHER INFORMATION: DP47 Fc knob fused to trimeric hu 4-1BBL (71-254)

<400> SEQUENCE: 182

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
    195                 200                 205
Val Asp Lys Lys Val Glu Pro Lys Ser Cys Asp Lys Thr His Thr Cys
    210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Gly Ala Pro Ile Glu Lys Thr Ile Ser Lys
                325                 330                 335
Ala Lys Gly Gln Pro Arg Glu Pro Gln Val Tyr Thr Leu Pro Pro Cys
            340                 345                 350
Arg Asp Glu Leu Thr Lys Asn Gln Val Ser Leu Trp Cys Leu Val Lys
                355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Gly Gly Gly Gly
                435                 440                 445
Ser Gly Gly Gly Gly Ser Arg Glu Gly Pro Glu Leu Ser Pro Asp Asp
        450                 455                 460
Pro Ala Gly Leu Leu Asp Leu Arg Gln Gly Met Phe Ala Gln Leu Val
465                 470                 475                 480
Ala Gln Asn Val Leu Leu Ile Asp Gly Pro Leu Ser Trp Tyr Ser Asp
                485                 490                 495
Pro Gly Leu Ala Gly Val Ser Leu Thr Gly Gly Leu Ser Tyr Lys Glu
            500                 505                 510
Asp Thr Lys Glu Leu Val Val Ala Lys Ala Gly Val Tyr Tyr Val Phe
            515                 520                 525
Phe Gln Leu Glu Leu Arg Arg Val Val Ala Gly Glu Gly Ser Gly Ser
        530                 535                 540
Val Ser Leu Ala Leu His Leu Gln Pro Leu Arg Ser Ala Ala Gly Ala
545                 550                 555                 560
Ala Ala Leu Ala Leu Thr Val Asp Leu Pro Pro Ala Ser Ser Glu Ala
                565                 570                 575
Arg Asn Ser Ala Phe Gly Phe Gln Gly Arg Leu Leu His Leu Ser Ala
            580                 585                 590
Gly Gln Arg Leu Gly Val His Leu His Thr Glu Ala Arg Ala Arg His
        595                 600                 605
```

Ala Trp Gln Leu Thr Gln Gly Ala Thr Val Leu Gly Leu Phe Arg Val
    610                 615                 620

Thr Pro Glu Ile Pro Ala Gly Leu Pro Ser Pro Arg Ser Glu Gly Gly
625                 630                 635                 640

Gly Gly Ser Gly Gly Gly Ser Arg Glu Gly Pro Glu Leu Ser Pro
            645                 650                 655

Asp Asp Pro Ala Gly Leu Leu Asp Leu Arg Gln Gly Met Phe Ala Gln
            660                 665                 670

Leu Val Ala Gln Asn Val Leu Leu Ile Asp Gly Pro Leu Ser Trp Tyr
        675                 680                 685

Ser Asp Pro Gly Leu Ala Gly Val Ser Leu Thr Gly Leu Ser Tyr
    690                 695                 700

Lys Glu Asp Thr Lys Glu Leu Val Ala Lys Ala Gly Val Tyr Tyr
705                 710                 715                 720

Val Phe Phe Gln Leu Glu Leu Arg Arg Val Val Ala Gly Glu Gly Ser
                725                 730                 735

Gly Ser Val Ser Leu Ala Leu His Leu Gln Pro Leu Arg Ser Ala Ala
            740                 745                 750

Gly Ala Ala Ala Leu Ala Leu Thr Val Asp Leu Pro Pro Ala Ser Ser
        755                 760                 765

Glu Ala Arg Asn Ser Ala Phe Gly Phe Gln Gly Arg Leu Leu His Leu
770                 775                 780

Ser Ala Gly Gln Arg Leu Gly Val His Leu His Thr Glu Ala Arg Ala
785                 790                 795                 800

Arg His Ala Trp Gln Leu Thr Gln Gly Ala Thr Val Leu Gly Leu Phe
                805                 810                 815

Arg Val Thr Pro Glu Ile Pro Ala Gly Leu Pro Ser Pro Arg Ser Glu
            820                 825                 830

Gly Gly Gly Gly Ser Gly Gly Gly Ser Arg Glu Gly Pro Glu Leu
        835                 840                 845

Ser Pro Asp Asp Pro Ala Gly Leu Leu Asp Leu Arg Gln Gly Met Phe
850                 855                 860

Ala Gln Leu Val Ala Gln Asn Val Leu Leu Ile Asp Gly Pro Leu Ser
865                 870                 875                 880

Trp Tyr Ser Asp Pro Gly Leu Ala Gly Val Ser Leu Thr Gly Leu
            885                 890                 895

Ser Tyr Lys Glu Asp Thr Lys Glu Leu Val Ala Lys Ala Gly Val
        900                 905                 910

Tyr Tyr Val Phe Phe Gln Leu Glu Leu Arg Arg Val Val Ala Gly Glu
    915                 920                 925

Gly Ser Gly Ser Val Ser Leu Ala Leu His Leu Gln Pro Leu Arg Ser
930                 935                 940

Ala Ala Gly Ala Ala Ala Leu Ala Leu Thr Val Asp Leu Pro Pro Ala
945                 950                 955                 960

Ser Ser Glu Ala Arg Asn Ser Ala Phe Gly Phe Gln Gly Arg Leu Leu
                965                 970                 975

His Leu Ser Ala Gly Gln Arg Leu Gly Val His Leu His Thr Glu Ala
            980                 985                 990

Arg Ala Arg His Ala Trp Gln Leu Thr Gln Gly Ala Thr Val Leu Gly
        995                 1000                1005

Leu Phe Arg Val Thr Pro Glu Ile Pro Ala Gly Leu Pro Ser Pro
    1010                1015                1020

Arg Ser Glu

```
<210> SEQ ID NO 183
<211> LENGTH: 9
<212> TYPE: PRT
<213> ORGANISM: Artificial Sequence
<220> FEATURE:
<223> OTHER INFORMATION: CMV derived peptide

<400> SEQUENCE: 183

Asn Leu Val Pro Met Val Ala Thr Val
1               5
```

TUMOR NECROSIS FACTOR (TNF) FAMILY LIGAND TRIMER-CONTAINING ANTIGEN BINDING MOLECULES

CROSS REFERENCE TO RELATED APPLICATIONS

This application claims priority to European Patent Application No. EP 15161880.8 now withdrawn, filed Mar. 31, 2015, the disclosure of which is incorporated herein by reference in its entirety

SEQUENCE LISTING

The present application contains a Sequence Listing which has been submitted in ASCII format via EFS-Web and is hereby incorporated by reference in its entirety. Said ASCII copy, created on Mar. 29, 2016, is named P32693-US_ST25.txt and is 412,194 bytes in size.

FIELD OF THE INVENTION

The invention relates to novel TNF family ligand trimer-containing antigen binding molecules comprising (a) at least one moiety capable of specific binding to a target cell antigen, (b) a polypeptide comprising three ectodomains of a TNF ligand family member or fragments thereof that are connected to each other by a peptide linker, and (c) a Fc domain composed of a first and a second subunit capable of stable association. The invention further relates to methods of producing these molecules and to methods of using the same.

BACKGROUND

Ligands interacting with molecules of the TNF (tumor necrosis factor) receptor superfamily have pivotal roles in the organization and function of the immune system. While regulating normal functions such as immune responses, hematopoiesis and morphogenesis, the TNF family ligands (also called cytokines) play a role in tumorgenesis, transplant rejection, septic shock, viral replication, bone resorption, rheumatoid arthritis and diabetes (Aggarwal, 2003). Their diverse and important role in immunity has made them interesting for the development of cancer immunotherapeutics (Bremer, 2013). The TNF ligand family comprises 18 genes encoding 19 type II (i.e. intracellular N terminus and extracellular C-terminus) transmembrane proteins, characterized by the presence of a conserved C-terminal domain coined the 'TNF homology domain' (THD). This domain is responsible for receptor binding and is thus critical for the biological activity of the TNF ligand family members. The sequence identity between family members is ~20-30% (Bodmer, 2002). Members of the TNF ligand family exert their biological function as self-assembling, noncovalent trimers (Banner et al, 1993). Thus, the TNF family ligands form a trimer that is able to bind to and to activate the corresponding receptors of TNFR superfamily. Some members of the TNF ligand family have costimulatory effects on T-cells, meaning that they sustain T-cell responses after initial T cell activation (Watts, 2005). 4-1BBL, OX40L, GITRL, CD70, CD30L and LIGHT belong to this group of costimulatory TNF family ligands.

Among several costimulatory molecules, the tumor necrosis factor (TNF) receptor family member OX40 (CD134) plays a key role in the survival and homeostasis of effector and memory T cells (Croft et al., 2009). OX40 (CD134) regulates immune responses against infections, tumors and self-antigens and its expression has been demonstrated on the surface of T-cells, NKT-cells and NK-cells as well as neutrophils (Baumann et al., 2004) and shown to be strictly inducible or strongly upregulated in response to various stimulatory signals. Combined with T-cell receptor triggering, OX40 engagement on T-cells by its natural ligand or agonistic antibodies leads to synergistic activation of the PI3K and NFκB signalling pathways (Song et al., 2008). In turn, this results in enhanced proliferation, increased cytokine receptor and cytokine production and better survival of activated T-cells.

4-1BB (CD137), a member of the TNF receptor superfamily, has been first identified as a molecule whose expression is induced by T-cell activation (Kwon and Weissman, 1989). Subsequent studies demonstrated expression of 4-1BB in T- and B-lymphocytes (Snell et al., 2011; Zhang et al., 2010), NK-cells (Lin et al., 2008), NKT-cells (Kim et al., 2008), monocytes (Kienzle and von Kempis, 2000; Schwarz et al., 1995), neutrophils (Heinisch et al., 2000), mast (Nishimoto et al., 2005) and dendritic cells as well as cells of non-hematopoietic origin such as endothelial and smooth muscle cells (Broll et al., 2001; Olofsson et al., 2008). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002; von Kempis et al., 1997; Zhang et al., 2010).

Expression of 4-1BB ligand (4-1BBL or CD137L) is more restricted and is observed on professional antigen presenting cells (APC) such as B-cells, dendritic cells (DCs) and macrophages. Inducible expression of 4-1BBL is characteristic for T-cells, including both αβ and γδ T-cell subsets, and endothelial cells (reviewed in Shao and Schwarz, 2011).

CD137 signaling is known to stimulate IFNγ secretion and proliferation of NK cells (Buechele et al., 2012; Lin et al., 2008; Melero et al., 1998) as well as to promote DC activation as indicated by their increased survival and capacity to secret cytokines and upregulate co-stimulatory molecules (Choi et al., 2009; Futagawa et al., 2002; Wilcox et al., 2002). However, CD137 is best characterized as a co-stimulatory molecule which modulates TCR-induced activation in both the CD4+ and CD8+ subsets of T-cells. In combination with TCR triggering, agonistic 4-1BB-specific antibodies enhance proliferation of T-cells, stimulate lymphokine secretion and decrease sensitivity of T-lymphocytes to activation-induced cells death (reviewed in (reviewed in Snell et al., 2011).

In line with these co-stimulatory effects of 4-1BB antibodies on T-cells in vitro, their administration to tumor bearing mice leads to potent anti-tumor effects in many experimental tumor models (Melero et al., 1997; Narazaki et al., 2010). However, 4-1BB usually exhibits its potency as an anti-tumor agent only when administered in combination with other immunomodulatory compounds (Curran et al., 2011; Guo et al., 2013; Morales-Kastresana et al., 2013; Teng et al., 2009; Wei et al., 2013), chemotherapeutic reagents (Ju et al., 2008; Kim et al., 2009), tumor-specific vaccination (Cuadros et al., 2005; Lee et al., 2011) or radiotherapy (Shi and Siemann, 2006). In vivo depletion experiments demonstrated that CD8+ T-cells play the most critical role in anti-tumoral effect of 4-1BB-specific antibodies. However, depending on the tumor model or combination therapy, which includes anti-4-1BB, contributions of other types of cells such as DCs, NK-cells or CD4+ T-cells have been reported (Melero et al., 1997; Murillo et al., 2009; Narazaki et al., 2010; Stagg et al., 2011).

In addition to their direct effects on different lymphocyte subsets, 4-1BB agonists can also induce infiltration and retention of activated T-cells in the tumor through 4-1BB-mediated upregulation of intercellular adhesion molecule 1 (ICAM1) and vascular cell adhesion molecule 1 (VCAM1) on tumor vascular endothelium (Palazon et al., 2011).

4-1BB triggering may also reverse the state of T-cell anergy induced by exposure to soluble antigen that may contribute to disruption of immunological tolerance in the tumor micro-environment or during chronic infections (Wilcox et al., 2004).

It appears that the immunomodulatory properties of 4-1BB agonistic antibodies in vivo require the presence of the wild type Fc-portion on the antibody molecule thereby implicating Fc-receptor binding as an important event required for the pharmacological activity of such reagents as has been described for agonistic antibodies specific to other apoptosis-inducing or immunomodulatory members of the TNFR-superfamily (Li and Ravetch, 2011; Teng et al., 2009). However, systemic administration of 4-1BB-specific agonistic antibodies with the functionally active Fc domain also induces expansion of CD8+ T-cells associated with liver toxicity (Dubrot et al., 2010) that is diminished or significantly ameliorated in the absence of functional Fc-receptors in mice. In human clinical trials (ClinicalTrials.gov, NCT00309023), Fc-competent 4-1BB agonistic antibodies (BMS-663513) administered once every three weeks for 12 weeks induced stabilization of the disease in patients with melanoma, ovarian or renal cell carcinoma. However, the same antibody given in another trial (NCT00612664) caused grade 4 hepatitis leading to termination of the trial (Simeone and Ascierto, 2012).

Collectively, the available pre-clinical and clinical data clearly demonstrate that there is a high clinical need for effective 4-1BB agonists. However, new generation drug candidates should not only effectively engage 4-1BB on the surface of hematopoietic and endothelial cells but also be capable of achieving that through mechanisms other than binding to Fc-receptors in order to avoid uncontrollable side effects. The latter may be accomplished through preferential binding to and oligomerization on tumor-specific or tumor-associated moieties.

Fusion proteins composed of one extracellular domain of a 4-1BB ligand and a single chain antibody fragment (Mueller et al., 2008; Hornig et al., 2012, Kermer et al., 2014) or a single 4-1BB ligand fused to the C-terminus of a heavy chain (Zhang et al, 2007) have been made. EP 1 736 482 A1 relates to recombinant 4-1BBL polypeptides comprising the whole extracellular domain of native 4-1BBL and a cross-linkable peptide domain. WO 2010/010051 discloses the generation of fusion proteins that consist of three TNF ligand ectodomains linked to each other and fused to an antibody part.

However, there is a need of new antigen binding molecules that combine a moiety capable of preferred binding to tumor-specific or tumor-associated targets with a moiety capable of forming a costimulatory TNF family ligand trimer and that possess sufficient stability to be pharmaceutically useful. The antigen binding molecules of the present invention comprise both and therefore may be able to trigger TNF receptors not only effectively, but also very selectively at the desired site thereby reducing side effects.

SUMMARY OF THE INVENTION

This invention provides a TNF family ligand trimer-containing antigen binding molecule comprising (a) at least one moiety capable of specific binding to a target cell antigen,
(b) a polypeptide comprising three ectodomains of a TNF ligand family member or fragments thereof that are connected to each other, optionally by peptide linkers, and
(c) a Fc domain composed of a first and a second subunit capable of stable association.

In one aspect, the invention provides a TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association.

In another aspect, the TNF family ligand trimer containing antigen binding molecule comprises
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association, wherein the polypeptide comprising the three ectodomains of a TNF ligand family member or fragments thereof that are connected to each other by peptide linkers is fused to the N- or C-terminal amino acid of one of the two subunits of the Fc domain, optionally through a peptide linker.

In a particular aspect, the TNF family ligand trimer-containing antigen binding molecule comprises (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, wherein the TNF ligand family member costimulates human T-cell activation. Thus, the TNF ligand family member is a costimulatory TNF family ligand. In particular, the costimulatory TNF family ligand is selected from the group consisting of 4-1BBL, OX40L, GITRL, CD70, CD30L and LIGHT, more particularly the costimulatory TNF family ligand is selected from 4-1BBL and OX40L.

In one aspect, the TNF ligand family member is 4-1BBL.

In a further aspect, the ectodomain of a TNF ligand family member comprises the amino acid sequence selected from the group consisting of SEQ ID NO:1, SEQ ID NO: 2, SEQ ID NO:3, SEQ ID NO:4, SEQ ID NO:99, SEQ ID NO: 100, SEQ ID NO:101 and SEQ ID NO:102, particularly the amino acid sequence of SEQ ID NO:1 or SEQ ID NO:99.

In a particular aspect, the ectodomain of a TNF ligand family member or fragment thereof comprises the amino acid sequence selected from the group consisting of SEQ ID NO:1, SEQ ID NO:2, SEQ ID NO:3 and SEQ ID NO:4, particularly the amino acid sequence of SEQ ID NO:1.

In a further aspect, the TNF family ligand trimer-containing antigen binding molecule of the invention comprises
(a) at least one moiety capable of specific binding to a target cell antigen and
(b) a polypeptide comprising the amino acid sequence of SEQ ID NO:5 or SEQ ID NO:103, and
(c) a Fc domain composed of a first and a second subunit capable of stable association. More particularly, the polypeptide comprises the amino acid sequence of SEQ ID NO:5.

In another aspect, the TNF ligand family member is OX40L.

In a particular aspect, the ectodomain of a TNF ligand family member comprises the amino acid sequence selected from the group consisting of SEQ ID NO:6 and SEQ ID NO:7, particularly the amino acid sequence of SEQ ID NO:6.

In a further aspect, the TNF family ligand trimer-containing antigen binding molecule of the invention comprises
(a) at least one moiety capable of specific binding to a target cell antigen and
(b) a polypeptide comprising the amino acid sequence of SEQ ID NO:8, and
(c) a Fc domain composed of a first and a second subunit capable of stable association.

In one aspect, the invention relates to the TNF family ligand trimer-containing antigen binding molecule as described herein before, wherein the polypeptide comprising three ectodomains of a TNF ligand family member or fragments thereof is fused at the C-terminal amino acid to the N-terminal amino acid of one of the subunits of the Fc domain. In particular, provided is a TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other by a peptide linkers and
(c) a Fc domain composed of a first and a second subunit capable of stable association,
wherein the polypeptide comprising three ectodomains of a TNF ligand family member or fragments thereof is fused at the C-terminal amino acid to the N-terminal amino acid of a CH2 domain in the Fc domain.

In another aspect, In another aspect, the TNF family ligand trimer-containing antigen binding molecule is one, wherein the polypeptide comprising three ectodomains of a TNF ligand family member or fragments thereof is fused at the N-terminal amino acid to a C-terminal amino acid of one of the subunits of the Fc domain, e.g. the polypeptide comprising three ectodomains of a TNF ligand family member or fragments thereof is fused at the N-terminal amino acid to the C-terminal amino acid of a CH3 domain in the Fc domain.

In another aspect, the invention relates to a TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association,
wherein the moiety capable of specific binding to a target cell antigen is not fused to the polypeptide comprising three ectodomains of a TNF ligand family member or fragments thereof.

In a further aspect, the invention provides a TNF family ligand trimer-containing antigen binding molecule as defined herein before, wherein the moiety capable of specific binding to a target cell antigen is selected from the group consisting of an antibody, an antibody fragment and a scaffold antigen binding protein.

In one aspect, the invention provides a TNF family ligand trimer-containing antigen binding molecule as defined herein before, wherein the moiety capable of specific binding to a target cell antigen is an antibody.

In another aspect, the invention provides a TNF family ligand trimer-containing antigen binding molecule as defined herein before, wherein the moiety capable of specific binding to a target cell antigen is an antibody fragment. In particular, the antibody fragment is selected from the group consisting of a Fab molecule, a crossover Fab molecule, a single chain Fab molecule, a Fv molecule, a scFv molecule, a single domain antibody, and aVH.

In a further aspect, the invention provides a TNF family ligand trimer-containing antigen binding molecule as defined herein before, wherein the moiety capable of specific binding to a target cell antigen is a scaffold antigen binding protein.

Thus, in a further aspect, the invention relates to a TNF family ligand trimer-containing antigen binding molecule as defined herein before, wherein the moiety capable of specific binding to a target cell antigen is selected from the group consisting of an antibody fragment, a Fab molecule, a crossover Fab molecule, a single chain Fab molecule, a Fv molecule, a scFv molecule, a single domain antibody, an aVH and a scaffold antigen binding protein.

In a particular aspect, the invention is concerned with a TNF family ligand trimer-containing antigen binding molecule as defined above, wherein the moiety capable of specific binding to a target cell antigen is a Fab molecule capable of specific binding to a target cell antigen.

In another aspect, provided is a TNF family ligand trimer-containing antigen binding molecule of the invention, wherein the target cell antigen is selected from the group consisting of Fibroblast Activation Protein (FAP), Carcinoembryonic Antigen (CEA), Melanoma-associated Chondroitin Sulfate Proteoglycan (MCSP), Epidermal Growth Factor Receptor (EGFR), CD19, CD20 and CD33.

In a particular aspect, the target cell antigen is Fibroblast Activation Protein (FAP). In one aspect, the invention provides a TNF family ligand trimer-containing antigen binding molecule as described herein before, wherein the moiety capable of specific binding to FAP comprises
(a) a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, or
(b) a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

In one aspect, the moiety capable of specific binding to FAP comprises a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14. In another particular aspect, the moiety capable of specific binding to FAP comprises a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

In a further aspect, the moiety capable of specific binding to FAP comprises a variable heavy chain comprising an amino acid sequence of SEQ ID NO:16 and a variable light chain comprising an amino acid sequence of SEQ ID NO:17 or wherein the moiety capable of specific binding to FAP comprises a variable heavy chain comprising an amino acid sequence of SEQ ID NO:110 and a variable light chain comprising an amino acid sequence of SEQ ID NO:111.

In another aspect, the target cell antigen is CEA. In one aspect, the invention provides a TNF family ligand trimer-containing antigen binding molecule as described herein before, wherein the moiety capable of specific binding to CEA comprises a VH domain comprising (i) CDR-H1 comprising the amino acid sequence of SEQ ID NO:112, (ii) CDR-H2 comprising the amino acid sequence of SEQ ID NO:113 and (iii) CDR-H3 comprising the amino acid sequence of SEQ ID NO:114, and a VL domain comprising (iv) CDR-L1 comprising the amino acid sequence of SEQ ID NO:115, (v) CDR-L2 comprising the amino acid sequence of SEQ ID NO:116 and (vi) CDR-L3 comprising the amino acid sequence of SEQ ID NO:117. In particular, the moiety capable of specific binding to CEA comprises a variable heavy chain comprising an amino acid sequence of SEQ ID NO:118 and a variable light chain comprising an amino acid sequence of SEQ ID NO:119.

In yet another aspect, the target cell antigen is CD19. In one aspect, the invention provides a TNF family ligand trimer-containing antigen binding molecule as described herein before, wherein the moiety capable of specific binding to CD19 comprises (a) a VH domain comprising (i) CDR-H1 comprising the amino acid sequence of SEQ ID NO:120, (ii) CDR-H2 comprising the amino acid sequence of SEQ ID NO:121 and (iii) CDR-H3 comprising the amino acid sequence of SEQ ID NO:122, and a VL domain comprising (iv) CDR-L1 comprising the amino acid sequence of SEQ ID NO:123, (v) CDR-L2 comprising the amino acid sequence of SEQ ID NO:124 and (vi) CDR-L3 comprising the amino acid sequence of SEQ ID NO:125, or (b) a VH domain comprising (i) CDR-H1 comprising the amino acid sequence of SEQ ID NO:128, (ii) CDR-H2 comprising the amino acid sequence of SEQ ID NO:129 and (iii) CDR-H3 comprising the amino acid sequence of SEQ ID NO:130, and a VL domain comprising (iv) CDR-L1 comprising the amino acid sequence of SEQ ID NO:131, (v) CDR-L2 comprising the amino acid sequence of SEQ ID NO:132 and (vi) CDR-L3 comprising the amino acid sequence of SEQ ID NO:133. In particular, the moiety capable of specific binding to CD19 comprises a variable heavy chain comprising an amino acid sequence of SEQ ID NO:126 and a variable light chain comprising an amino acid sequence of SEQ ID NO:127 or wherein the moiety capable of specific binding to FAP comprises a variable heavy chain comprising an amino acid sequence of SEQ ID NO:134 and a variable light chain comprising an amino acid sequence of SEQ ID NO:135.

In a further aspect, provided is a TNF family ligand trimer-containing antigen binding molecule as described herein before, wherein the Fc domain composed of a first and a second subunit capable of stable association is an IgG, particularly an IgG1 Fc domain or an IgG4 Fc domain. In particular, the Fc domain composed of a first and a second subunit capable of stable association is an IgG1 Fc domain.

In another aspect, the invention is concerned with a TNF family ligand trimer-containing antigen binding molecule as defined herein before, comprising
(c) an Fc domain composed of a first and a second subunit capable of stable association, wherein the Fc domain comprises one or more amino acid substitution that reduces binding to an Fc receptor, in particular towards Fcγ receptor.

In particular, the Fc domain comprises amino acid substitutions at positions 234 and 235 (EU numbering) and/or 329 (EU numbering). More particularly, provided is a trimeric TNF family ligand-containing antigen binding molecule according to the invention which comprises an Fc domain with the amino acid substitutions L234A, L235A and P329G (EU numbering) in the IgG heavy chains.

In a particular aspect, the invention provides a TNF family ligand trimer-containing antigen binding molecule as described herein before, wherein the Fc domain is an IgG1 Fc domain and comprises amino acid substitutions at positions 234 and 235 (EU numbering) and 329 (EU numbering) of the IgG heavy chains.

In another aspect, provided is a monovalent TNF family ligand trimer-containing antigen binding molecule as described herein before, comprising one moiety capable of specific binding to a target cell antigen.

In particular, the TNF family ligand trimer-containing antigen binding molecule of the invention comprising (c) an Fc domain composed of a first and a second subunit capable of stable association further comprises (a) a Fab molecule capable of specific binding to a target cell antigen, wherein the Fab heavy chain is fused at the C-terminus to the N-terminus of a CH2 domain in the Fc domain.

Furthermore, the invention provides a TNF family ligand trimer-containing antigen binding molecule as described herein before, wherein the antigen binding molecule comprises
(a) a heavy chain and a light chain, both comprising a Fab molecule capable of specific binding to a target cell antigen, and
(b) a fusion protein comprising the amino acid sequence of SEQ ID NO:15.

In another aspect, provided is a TNF family ligand trimer-containing antigen binding molecule as described hereinbefore, wherein the antigen binding molecule comprises
(a) a heavy chain and a light chain, both comprising a Fab molecule capable of specific binding to a target cell antigen, and
(b) the fusion protein comprising the amino acid sequence of SEQ ID NO:20.

In a further aspect, the TNF family ligand trimer-containing antigen binding molecule comprises
(i) a first heavy chain comprising the VH domain of a Fab molecule capable of specific binding to a target cell antigen,
(ii) a light chain comprising the VL domain of a Fab molecule capable of specific binding to a target cell antigen, and
(iii) a second heavy chain comprising the amino acid sequence of SEQ ID NO:5 or SEQ ID NO:103 or SEQ ID NO:8.

In a particular aspect, the TNF family ligand trimer-containing antigen binding molecule comprises (i) a first heavy chain comprising a VH domain comprising an amino acid sequence of SEQ ID NO:16 or a VH domain comprising an amino acid sequence of SEQ ID NO:110, (ii) a light chain comprising a VL domain comprising an amino acid sequence of SEQ ID NO:17 or a VL domain comprising an amino acid sequence of SEQ ID NO:111, and (iii) a second heavy chain comprising the amino acid sequence of SEQ ID NO:5 or SEQ ID NO:103 or SEQ ID NO:8. In another aspect, TNF family ligand trimer-containing antigen binding molecule comprises (i) a first heavy chain comprising a VH domain comprising an amino acid sequence of SEQ ID NO:118, (ii) a light chain comprising a VL domain comprising an amino acid sequence of SEQ ID NO:119, and (iii) a second heavy chain comprising the amino acid sequence of SEQ ID NO:5 or SEQ ID NO:103 or SEQ ID NO:8. In a further aspect, the TNF family ligand trimer-containing antigen binding molecule comprises (i) a first heavy chain comprising a VH domain comprising an amino acid sequence of SEQ ID NO:126 or a VH domain comprising an amino acid sequence of SEQ ID NO:134, (ii) a light chain comprising a VL domain comprising an amino acid sequence of SEQ ID NO:127 or a VL domain comprising an amino acid sequence of SEQ ID NO:135, and (iii) a second heavy chain comprising the amino acid sequence of SEQ ID NO:5 or SEQ ID NO:103 or SEQ ID NO:8.

In another aspect, provided is a bivalent TNF family ligand trimer-containing antigen binding molecule, comprising two moieties capable of specific binding to a target cell antigen.

In one aspect, the TNF family ligand trimer-containing antigen binding molecule comprises
(i) a first heavy chain comprising a VH domain of a Fab molecule capable of specific binding to a target cell antigen,
(ii) two light chains comprising each the VL domain of a Fab molecule capable of specific binding to a target cell antigen, and
(iii) a second heavy chain comprising a VH domain of a Fab molecule capable of specific binding to a target cell antigen and the amino acid sequence of SEQ ID NO:5 or SEQ ID NO:103 or SEQ ID NO:8.

In a particular aspect, the TNF family ligand trimer-containing antigen binding molecule comprises (i) a first heavy chain comprising a VH domain comprising an amino acid sequence of SEQ ID NO:16 or a VH domain comprising an amino acid sequence of SEQ ID NO:110, (ii) two light chains comprising each a VL domain comprising an amino acid sequence of SEQ ID NO:17 or a VL domain comprising an amino acid sequence of SEQ ID NO:111, and (iii) a second heavy chain comprising a VH domain comprising an amino acid sequence of SEQ ID NO:16 or a VH domain comprising an amino acid sequence of SEQ ID NO:110 and the amino acid sequence of SEQ ID NO:5 or SEQ ID NO:103 or SEQ ID NO:8. In another aspect, the TNF family ligand trimer-containing antigen binding molecule comprises (i) a first heavy chain comprising a VH domain comprising an amino acid sequence of SEQ ID NO:118, (ii) two light chains comprising each a VL domain comprising an amino acid sequence of SEQ ID NO:119, and (iii) a second heavy chain comprising a VH domain comprising an amino acid sequence of SEQ ID NO:118 and the amino acid sequence of SEQ ID NO:5 or SEQ ID NO:103 or SEQ ID NO:8. In yet another aspect, the TNF family ligand trimer-containing antigen binding molecule comprises (i) a first heavy chain comprising a VH domain comprising an amino acid sequence of SEQ ID NO:126 or a VH domain comprising an amino acid sequence of SEQ ID NO:134, (ii) two light chains comprising a VL domain comprising an amino acid sequence of SEQ ID NO:127 or a VL domain comprising an amino acid sequence of SEQ ID NO:135, and (iii) a second heavy chain comprising a VH domain comprising an amino acid sequence of SEQ ID NO:126 or a VH domain comprising an amino acid sequence of SEQ ID NO:134 and the amino acid sequence of SEQ ID NO:5 or SEQ ID NO:103 or SEQ ID NO:8.

In a particular aspect, provided is a TNF family ligand trimer-containing antigen binding molecule as described herein before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:5.

More particularly, provided is a TNF family ligand trimer-containing antigen binding molecule as described herein before, wherein the antigen binding molecule comprises
(i) a heavy chain comprising the amino acid sequence of SEQ ID NO:18,
(ii) a light chain comprising the amino acid sequence of SEQ ID NO:19, and
(iii) a fusion protein comprising the amino acid sequence of SEQ ID NO:15.

In a particular aspect, provided is a TNF family ligand trimer-containing antigen binding molecule as described herein before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:8.

More particularly, provided is a TNF family ligand trimer-containing antigen binding molecule as described herein before, wherein the antigen binding molecule comprises
(i) a heavy chain comprising the amino acid sequence of SEQ ID NO:18,
(ii) a light chain comprising the amino acid sequence of SEQ ID NO:19, and
(iii) a fusion protein comprising the amino acid sequence of SEQ ID NO:20.

According to another aspect of the invention, there is provided an isolated polynucleotide encoding a TNF family ligand trimer-containing antigen binding molecule as defined herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the TNF family ligand trimer-containing antigen binding molecule of the invention, comprising the steps of (i) culturing the host cell of the invention under conditions suitable for expression of the antigen binding molecule, and (ii) recovering the antigen binding molecule. The invention also encompasses a TNF family ligand trimer-containing antigen binding molecule produced by the method of the invention.

The invention further provides a pharmaceutical composition comprising the TNF family ligand trimer-containing antigen binding molecule of the invention and at least one pharmaceutically acceptable excipient.

Also encompassed by the invention is the TNF family ligand trimer-containing antigen binding molecule of the invention, or the pharmaceutical composition of the invention, for use as a medicament. In one aspect, provided is a TNF family ligand trimer-containing antigen binding molecule of the invention, or the pharmaceutical composition of the invention, for use in the treatment of a disease in an individual in need thereof. In a specific embodiment, provided is the TNF family ligand trimer-containing antigen binding molecule of the invention, or the pharmaceutical composition of the invention, for use in the treatment of cancer.

Also provided is the use of the TNF family ligand trimer-containing antigen binding molecule of the invention for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the TNF family ligand trimer-containing antigen binding molecule of the invention in a pharmaceutically acceptable form. In a specific embodiment, the disease is cancer. In any of the above embodiments the individual is preferably a mammal, particularly a human.

BRIEF DESCRIPTION OF THE DRAWINGS

FIG. 1A shows a polypeptide comprising three ectodomains of 4-1BBL that are connected to each other by peptide linkers (GGGGSGGGGS (SEQ ID NO:54) and FIG. 1B shows a polypeptide comprising three ectodomains of OX40L that are connected to each other by peptide linkers (GGGGSGGGGS (SEQ ID NO:54).

FIGS. 3A-3C show representative examples of the TNF ligand trimer-containing antigen binding molecules of the invention. A representative example of the TNF ligand trimer-containing antigen binding molecule of the invention is a FAP-targeted trimeric 4-1BB ligand Fc (kih) P329G LALA fusion antigen binding molecule as shown in FIG. 3A. Its preparation is described in Examples 1.1 and 1.3. FIG. 3B shows the "untargeted" variant (control 1) comprising a DP47 Fab molecule and the single chain trimeric 4-1BB ligand Fc (kih) P329G LALA fusion antigen binding molecule as prepared in Example 2. FIG. 3C is a drawing of the monomeric 4-1BB Fc(kih) construct as prepared in Example 4.

FIGS. 4A-4C show representative examples of the TNF ligand trimer-containing antigen binding molecules of the invention, Another example of the TNF ligand trimer-containing antigen binding molecule of the invention is a FAP-targeted trimeric OX40 ligand Fc (kih) P329G LALA fusion antigen binding molecule as shown in FIG. 4A. Its preparation is described in Example 6. FIG. 4B shows the "untargeted" variant comprising a DP47 Fab molecule and the single chain trimeric OX40 ligand Fc (kih) P329G LALA fusion molecule as prepared in Example 7. FIG. 4C is a drawing of the monomeric OX40 Fc(kih) construct as prepared in Example 8.

In FIG. 5A the setup of the assay is shown, 4-1BB Fc (kih) is immobilized on a SA chip. FIG. 5B shows binding to human 4-1BB Fc (kih), FIG. 5C binding to cynomolgus 4-1BB Fc (kih) and FIG. 5D binding to murine 4-1BB Fc (kih).

FIG. 6A shows binding to human 4-1BB Fc (kih), FIG. 6B binding to cynomolgus 4-1BB Fc (kih) and FIG. 6C binding to murine 4-1BB Fc (kih).

FIGS. 7A-E illustrate the binding of recombinant human 4-1BB to FAP-targeted 4-1BB ligand trimer-containing Fc (kih) fusion antigen binding molecule (compound S1). In FIG. 7A the setup of the affinity measurement is shown. FIGS. 7B and 7C show the binding of human 4-1BB avi-His tag to the FAP-targeted 4-1BB ligand trimer-containing Fc (kih) fusion antigen binding molecule (FAP-targeted single chain trimeric 4-1BBL) and FIGS. 7D and 7E show the binding of human 4-1BB avi-His tag to DP47 containing 4-1BB ligand trimer-containing Fc (kih) fusion antigen binding molecule (DP47-containing single chain trimeric 4-1BBL molecule).

In FIG. 8A the setup of the assay is shown, OX40 Fc (kih) is immobilized on a SA chip. FIG. 8B shows binding to human OX40 Fc (kih), FIG. 8C binding to cynomolgus OX40 Fc (kih) and FIG. 8D binding to murine OX40 Fc (kih).

FIG. 9A shows binding to human OX40 Fc (kih), FIG. 9B binding to cynomolgus OX40 Fc (kih) and FIG. 9C binding to murine OX40 Fc (kih).

FIGS. 10A-C show the binding of recombinant human OX40 to FAP-targeted OX40 ligand trimer-containing Fc (kih) fusion antigen binding molecule (Compound S10). In FIG. 10A the setup of the affinity measurement is shown. In FIG. 10B the binding of human OX40 avi-His tag to the FAP-targeted OX40 ligand trimer-containing Fc (kih) fusion antigen binding molecule (FAP-targeted single chain OX40 ligand) is shown and FIG. 10C illustrates the binding of human 4-1BB avi-His tag to DP47-containing OX40 ligand trimer-containing Fc (kih) fusion molecule (DP47-containing single chain trimeric OX40L).

Figure 1A:
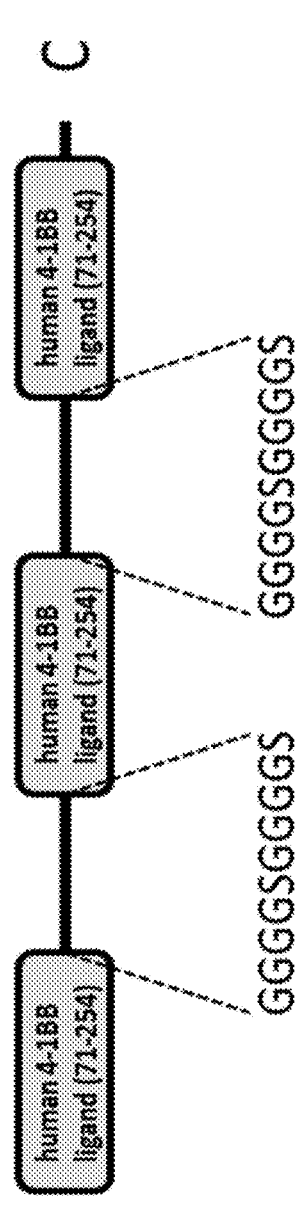
FIGS. 1A and 1B show polypeptides comprising three ectodomains of a TNF ligand family member or fragments thereof that are connected to each other by peptide linkers (GGGGSGGGGS (SEQ ID NO:54).

4-1BB and OX40 are not expressed on resting (naïve) human PBMCs (FIGS. 11A, 11C, 11E and 11G, FIGS. 12A and 12C). After activation of human PBMCs 4-1BB and OX40 are up-regulated on CD4$^+$ and CD8$^+$ T cells whereas human CD8$^+$ T cells (FIGS. 11B, 11F, 11K and 11M and 12B) show a 10 times higher 4-1BB but a 4 times lower OX40 upregulation than on CD4+ T cells (FIGS. 11D, 11H, 11J and 11L and 12D). As shown, FAP-targeted single chain trimeric 4-1BBL or OX40L Fc(kih) fusion antigen binding molecules (filled circle) and DP47-containing ("untargeted") single chain trimeric 4-1BBL and OX40L (open circle, dotted line) show a similar binding to activated CD4+ and CD8+ T cells but no binding to naïve human T cells. Therefore independent of FAP- or DP47-binding, both single chain trimeric 4-1BBL and single chain trimeric OX40L show similar binding to human 4-1BB or OX40 expressing cells. In the absence of human 4-1BB or OX40 expressing cells no binding can be observed (resting, naïve cells). Shown is the binding as median of fluorescence intensity (MFI) of red macrophytic algae Phycoerythrin (R-PE)- or Fluorescein isothiocyanate (FITC)-conjugated anti-human IgG Fcγ-specific goat IgG F(ab')$_2$ fragment which is used as secondary detection antibody. MFI was measured by flow cytometry and baseline corrected by subtracting the MFI of the blank control. The x-axis shows the concentration of FAP- or DP47-containing single chain trimeric 4-1BBL or OX40L Fc(kih) fusion molecules.

FIGS. 11A-D relate to the binding of FAP-targeted 4-1BB ligand trimer-containing Fc(kih) fusion antigen binding molecule (Compound S1, filled circles) or DP47-containing 4-1BB ligand trimer-containing Fc(kih) fusion molecule (Control 1, open circles) to resting (naïve) or activated human PMBCs. Specifically, the binding to resting (naïve) or activated human CD8+ T cells is shown in the upper two graphs and to resting (naïve) or activated human CD4+ T cells in the two graphs below, respectively.

FIGS. 11E-H show the binding of monovalent targeted single chain trimeric 4-1BB ligand Fc (kih) fusion antigen binding molecules to resting and activated human T cells. 4-1BB is not expressed on resting (naïve) CD4 or CD8 T cells isolated from the blood of healthy donors. After activation 4-1BB is upregulated on CD4+ (see graph right below) and CD8+ (see graph right above) T cells whereas CD8+ T cells show a 5-10 times higher 4-1BB expression than CD4+ T cells (depending on the donor). As shown, all monovalent targeted single chain trimeric 4-1BBL Fc (kih) fusion molecules bound similar to 4-1BB+ human T cells, independent of their targeting. Shown is on the y-axis the mean of fluorescence intensity (MFI) of the R-PE-conjugated anti-human IgG Fcγ fragment-specific F(ab')$_2$ goat IgG fragment. On the x-axis the tested concentration of the different targeted single chain trimeric 4-1BB ligand Fc (kih) fusion antigen binding molecules (compounds S1, S3 and S5) are indicated. Values were baseline corrected by subtracting the MFI of blank control.

In FIGS. 11J-M it is shown the binding of monovalent versus bivalent targeted single chain trimeric 4-1BB ligand Fc (kih) fusion antigen binding molecules to activated human T cells. After activation 4-1BB is upregulated on CD4+ (left hand side) and CD8+(right hand side) T cells. As shown, all monovalent and bivalent targeted single chain trimeric 4-1BBL Fc (kih) fusion antigen binding molecules bound similar to 4-1BB+ human T cells, independent of their targeting. Shown is on the y-axis the mean of fluorescence intensity (MFI) of the R-PE-conjugated anti-human IgG Fcγ fragment-specific F(ab')2 goat IgG fragment. On the x-axis the tested concentration of the different targeted single chain trimeric 4-1BB ligand Fc (kih) fusion antigen binding molecules (Compounds S1, S3, S2 and S4) are indicated. Values were baseline corrected by subtracting the MFI of blank control.

Figure 12A:
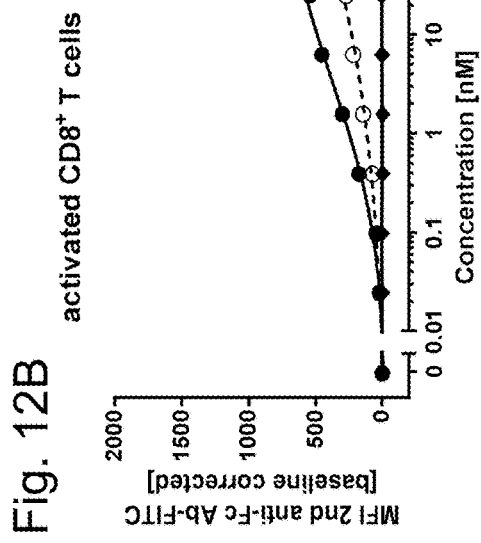
Figure 12B:
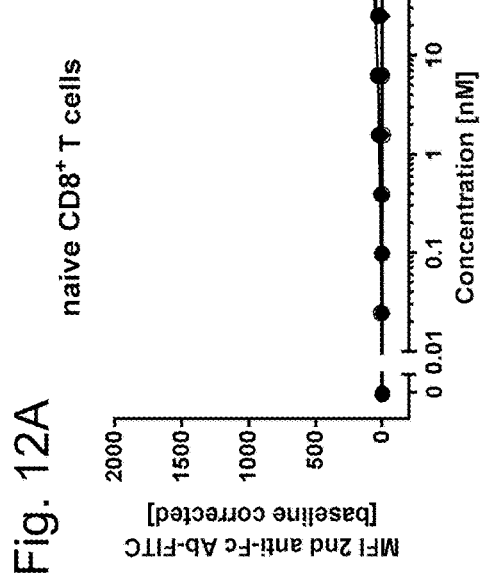
Figure 12C:
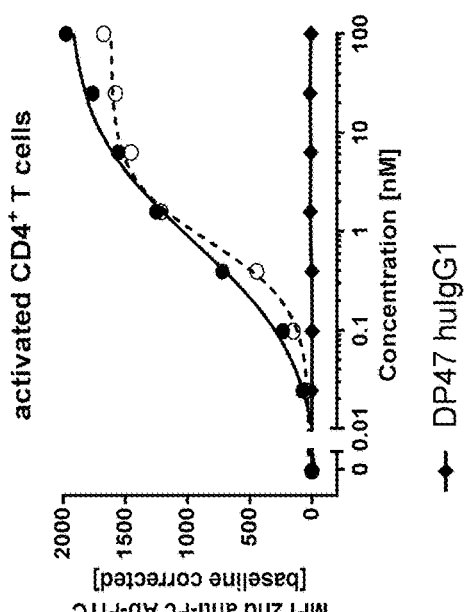
Figure 12D:
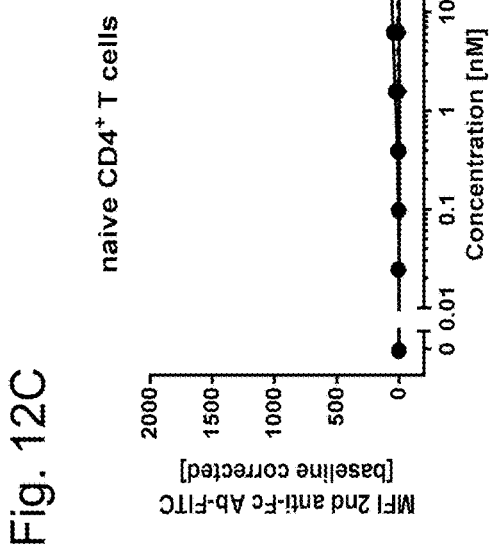

FIGS. 12A-D show the binding of FAP-targeted OX40 ligand trimer-containing Fc(kih) fusion antigen binding molecule (Compound S10, filled circles) or DP47-containing OX40 ligand trimer-containing Fc(kih) fusion molecule (DP47 single chain OX40L trimer, Control 3, open circles) to resting (naïve) or activated human PMBCs. Specifically, the binding to resting (naïve) or activated human CD8+ T cells is shown in FIGS. 12A and 12B, respectively, and to resting (naïve) or activated human CD4+ T cells in FIGS. 12C and 12D, respectively. The binding of DP47 human IgG1 P329G LALA is symbolized by the filled diamonds (negative control).

Figure 13A:
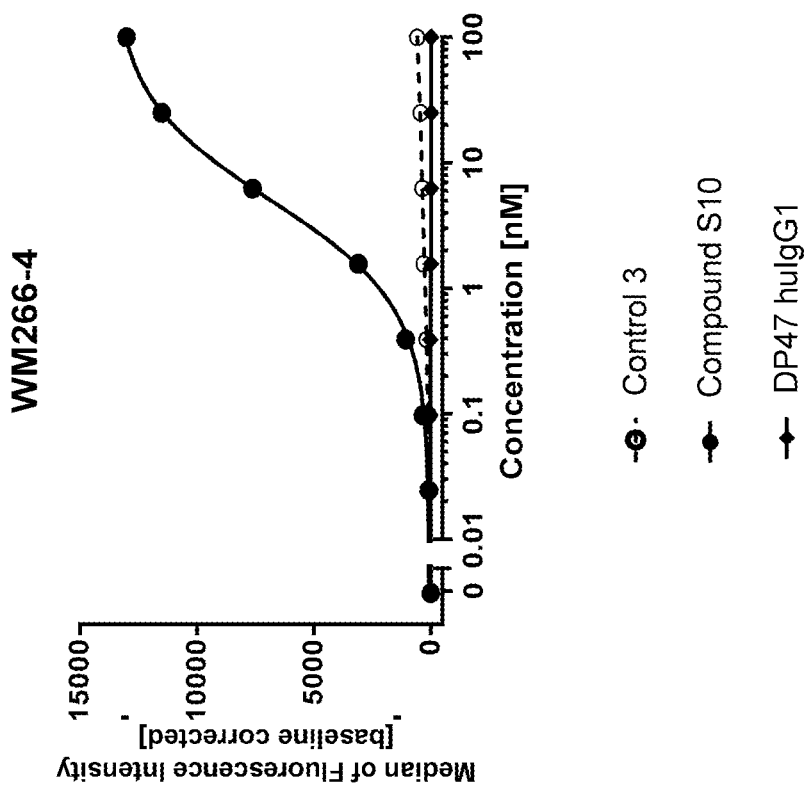
Figure 13B:
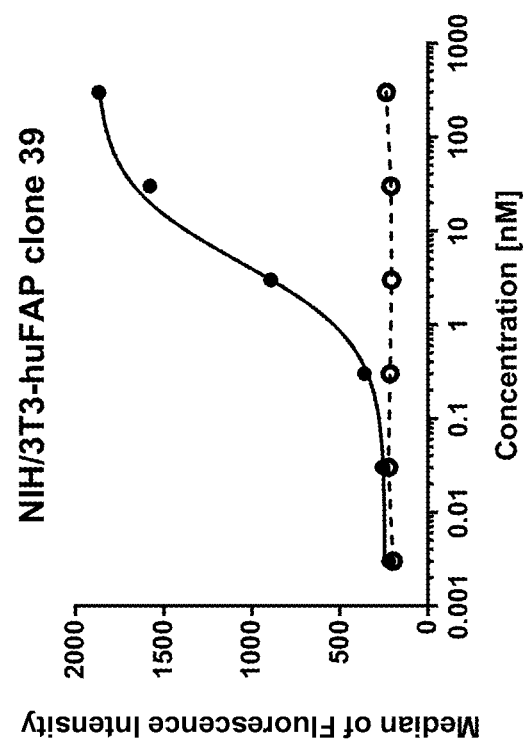

FIGS. 13A-E shows the binding of single chain TNF ligand trimer-containing Fc(kih) fusion antigen binding molecules (compound S1 and S10, respectively) to transgenic modified mouse embryonic fibroblast NIH/3T3-huFAP clone 39 (FIG. 13A) or to fibroblast activation protein (FAP)-expressing human WM266-4 cell line (FIG. 13B). These cells express high levels of human fibroblast activation protein (huFAP). Shown is the binding as median of fluorescence intensity (MFI) of Fluorescein isothiocyanate (FITC)-labeled anti-human IgG Fcγ-specific goat IgG F(ab')2 fragment which is used as secondary detection antibody. MFI was measured by flow cytometry. The x-axis shows the concentration of FAP-targeted or DP47-targeted ("untargeted") single chain trimeric 4-1BBL or OX40L antigen binding molecule. In FIG. 13A it is shown that only the FAP-targeted single chain trimeric 4-1BBL molecule (Compound S1, filled circles), but not the DP47-containing single chain trimeric 4-1BBL antigen binding molecule (open circles, dotted line) binds to NIH/3T3-huFAP clone 39 cells, FIG. 13B demonstrates that only the FAP-targeted single chain trimeric OX40L antigen binding molecule (Compound S10, filled circles), but not the DP47-containing single chain trimeric OX40 antigen binding molecule (open circles, dotted line) binds to WM266-4 cells. As a negative control DP47 human IgG1 P329G LALA symbolized by the filled diamonds did also not bind.

In FIGS. 13C and 13D it is shown the binding of monovalent versus bivalent FAP (4B9 or 28H1)-targeted single chain trimeric 4-1BB ligand Fc (kih) fusion antigen binding molecules to FAP-expressing tumor cells. As shown, the FAP (4B9)-targeted molecules show the strongest binding to FAP with a lower $EC_{50}$ value. With the strong FAP (4B9) binder we see only very small differences in MFI or $EC_{50}$ between the monovalent and the bivalent targeted single chain trimeric 4-1BB ligand (kih) fusion antigen molecules (compounds S3 and S2, respectively). This is different for the weaker FAP-binder 28H1 (compound S1). Here a bivalent binding (shown with the bivalent binding FAP (28H1)-targeted huIgG1 P329G LALA) gives a lower MFI. DP47-untargeted molecules do not bind to the FAP+ tumor cells and are therefore truly untargeted. Shown is on the y-axis the mean of fluorescence intensity (MFI) of the R-PE-conjugated anti-human IgG Fcγ fragment-specific F(ab')2 goat IgG fragment. On the x-axis the tested concentration of the different targeted single chain trimeric 4-1BB ligand Fc (kih) fusion antigen binding molecules are indicated.

Figure 13E:
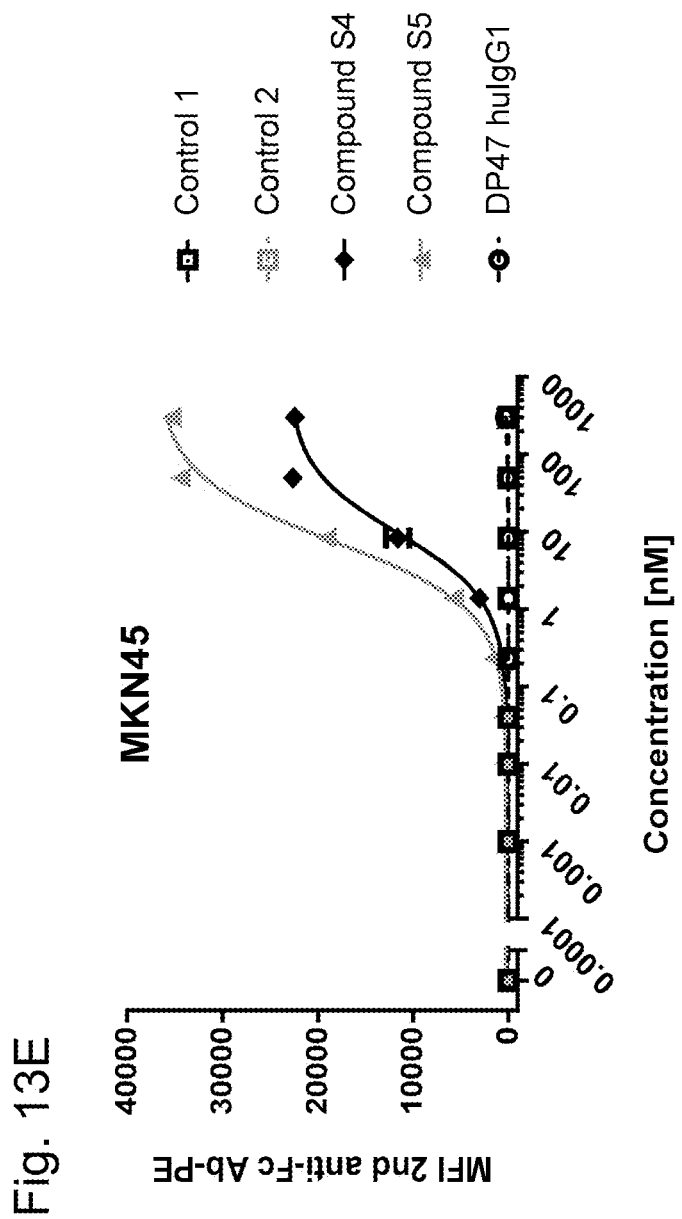

FIG. 13E shows the binding of monovalent versus bivalent CEA-targeted single chain trimeric 4-1BB ligand Fc (kih) fusion antigen binding molecules to a CEA-expressing tumor cell line. The binding of the bivalent CEA-targeted single chain trimeric 4-1BB ligand Fc (kih) fusion antigen binding molecule (compound S4) gives a lower MFI than that of the monovalent CEA-targeted single chain trimeric 4-1BB ligand Fc (kih) fusion antigen binding molecule (compound S5). This can be explained by the occupation of two CEA-molecules on the surface of the tumor cell at the same time. The DP47-untargeted molecules (Control 1 and 2, respectively) do not bind to the CEA+MKN45 tumor cells and are therefore truly untargeted. Shown is on the y-axis the mean of fluorescence intensity (MFI) of the PE-conjugated anti-human IgG Fcγ fragment-specific F(ab')2 goat IgG fragment. On the x-axis the tested concentration of the different targeted single chain trimeric 4-1BB ligand Fc (kih) fusion antigen binding molecules are indicated.

In FIGS. 14A and 14B it is shown that FAP-targeted 4-1BB ligand trimer-containing Fc(kih) fusion antigen binding molecules (compound 51, filled circles) or DP47-containing 4-1BB ligand trimer-containing Fc(kih) fusion antigen binding molecules (Control 1; open circles) do not bind to mouse 4-1BB expressing activated mouse splenocytes. An anti-mouse CD137-specific human IgG1 P329G LALA antibody (clone Lob12.3) was used as positive control (triangles). The binding is characterized by plotting the MFI of R-PE-labeled anti-human IgG Fcγ-specific goat IgG F(ab')$_2$ fragment that is used as secondary detection antibody versus the concentration in nM of the tested primary 4-1BBL trimer antigen binding molecules. MFI was measured by flow cytometry and baseline corrected by subtracting the MFI of the blank control.

Figure 15:
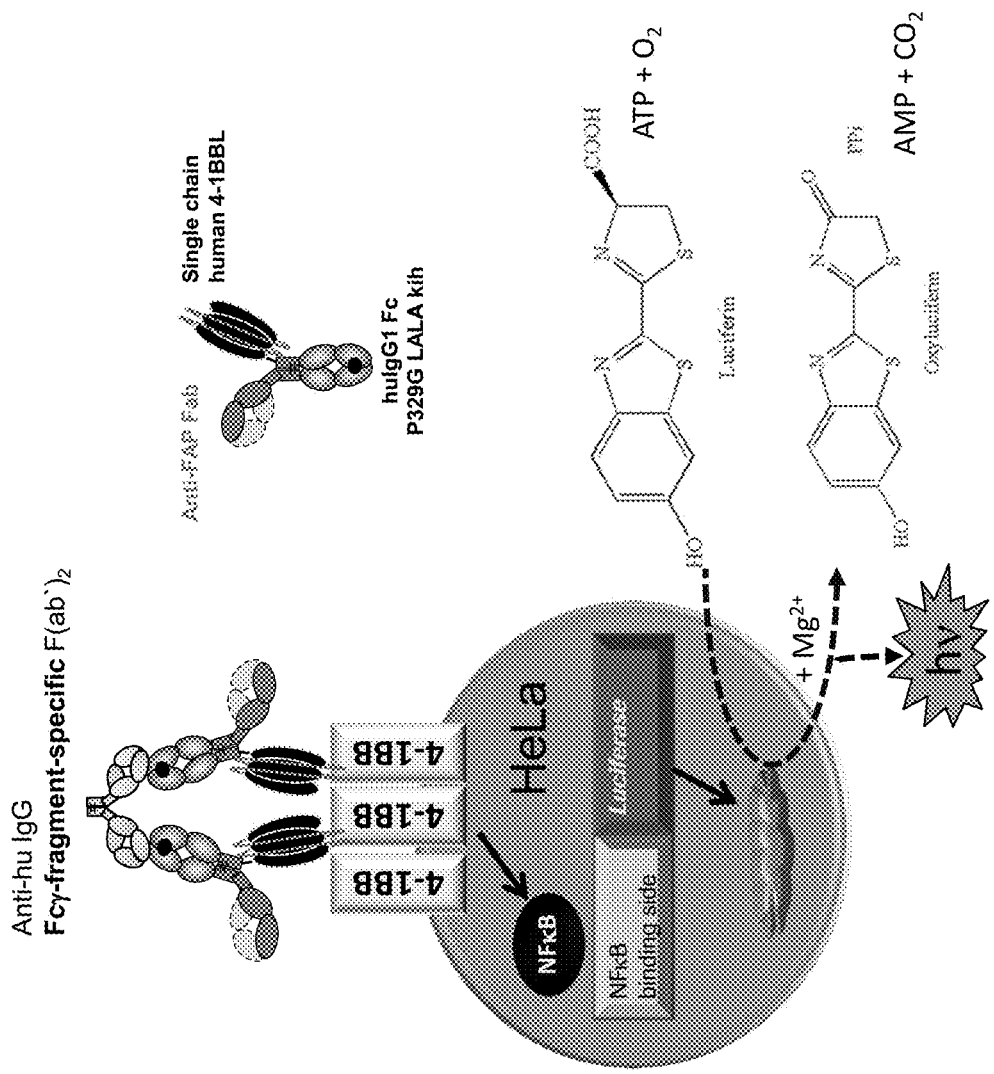

The scheme in FIG. 15 illustrates the general principal of the NFκB activity assay described in Example 11.1.2. using a reporter cell line. The ratio of anti-hu IgG1 Fcγ-specific antibody to human 4-1BB ligand trimer-containing Fc(kih) fusion antigen binding molecules was 1 to 4.

Figure 16:
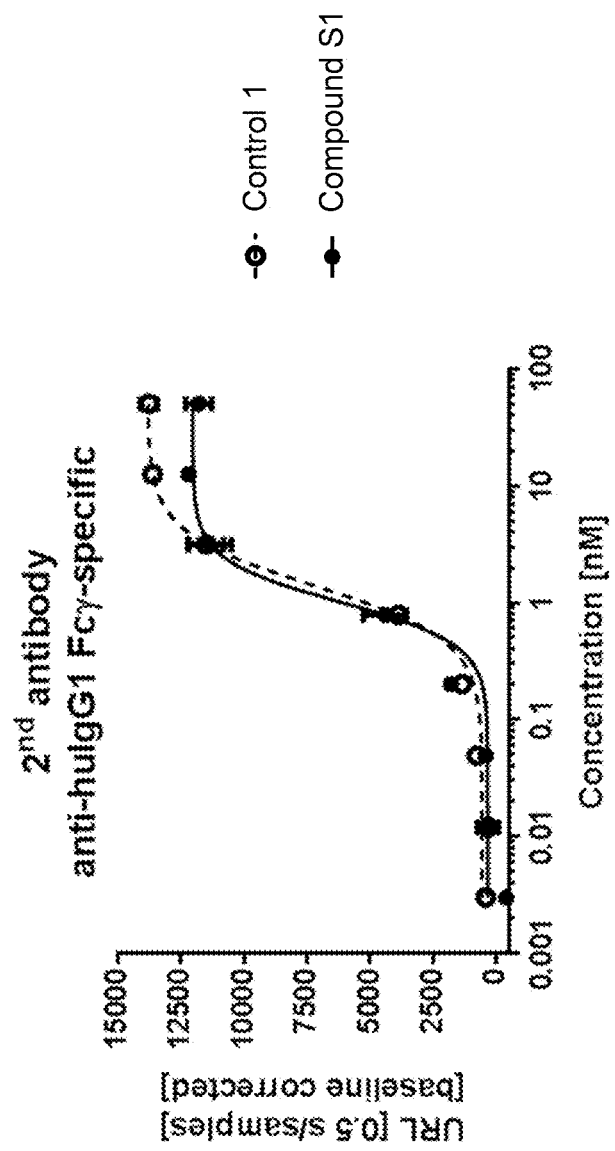

In FIG. 16 it is shown the activation of NFκB signaling pathway in the reporter cell line by secondary-antibody-crosslinked FAP-targeted single chain trimeric 4-1BBL antigen binding molecules (Compound 51, filled circles) or secondary-antibody-crosslinked DP47-containing single chain trimeric 4-1BBL molecules (Control 1, open circle, dotted line). The reporter cells were cultured for 6 hours in the presence of single chain 4-1BBL trimer-containing antigen binding molecules at the indicated concentrations together with crosslinking secondary poly-clonal anti-hu-IgG1 Fcγ-specific goat IgG F(ab)$_2$ fragment in a 1 to 4 ratio. Luciferase activity was assessed as described in Example 11.1.1. Activity is characterized by blotting the units of released light (URL) measured during 0.5 s versus the concentration in nM of tested single chain human 4-1BBL trimer antigen binding molecules. URLs are emitted due to luciferase-mediated oxidation of luciferin to oxyluciferin.

Figure 17:
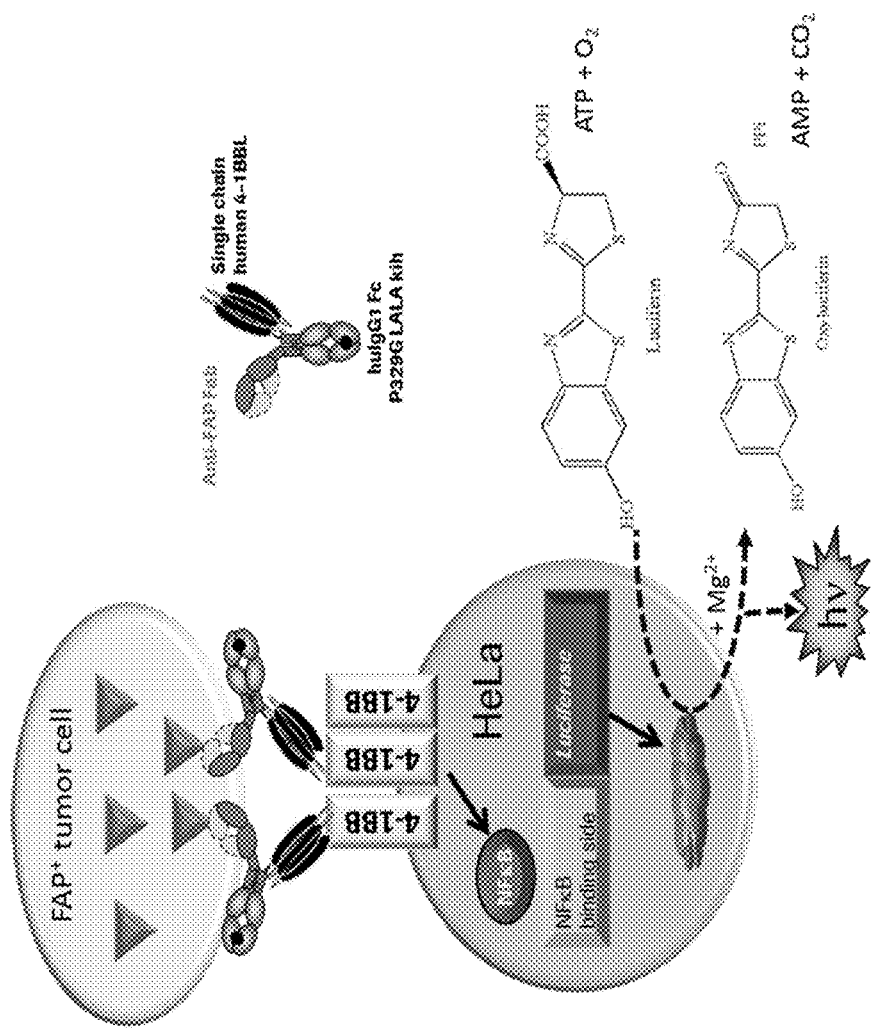

The scheme in FIG. 17 illustrates the general principal of the NFκB-mediated luciferase-activity assay as described in Example 11.1.3. using HeLa-hu4-1BB-NFkB-luc clone 26 as reporter cell line. The used ratio of FAP-expressing tumor cells to human 4-1BB expressing reporter cells was 5 to 1.

Figure 18A:
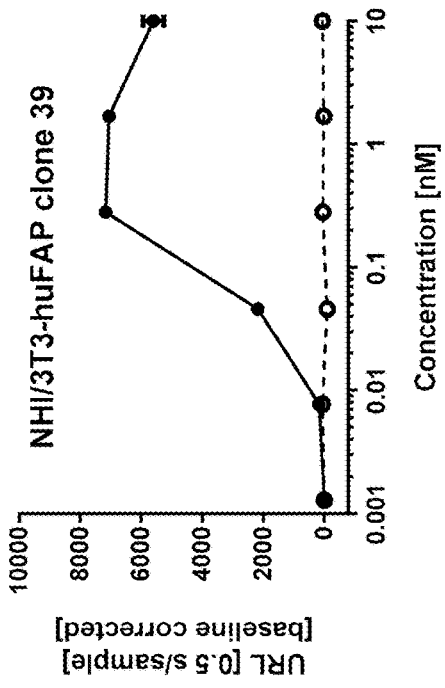
Figure 18B:
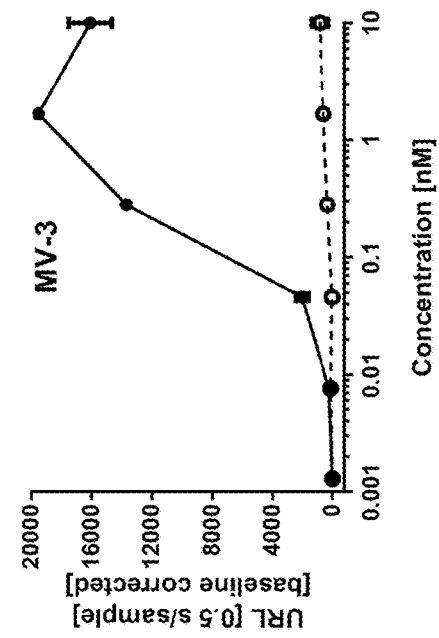
Figure 18C:
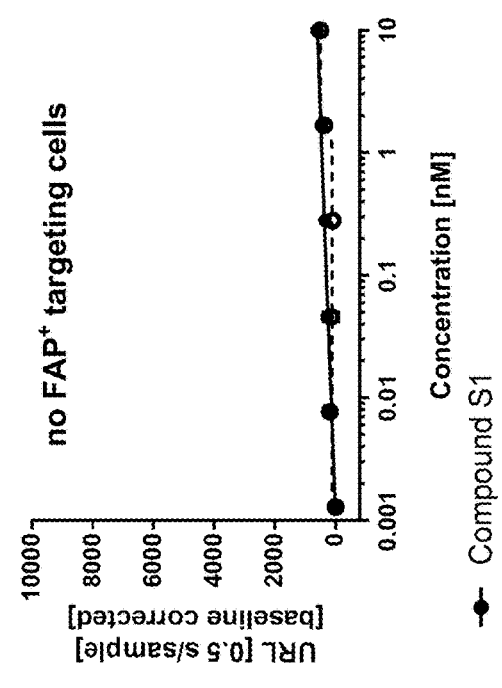
Figure 18D:
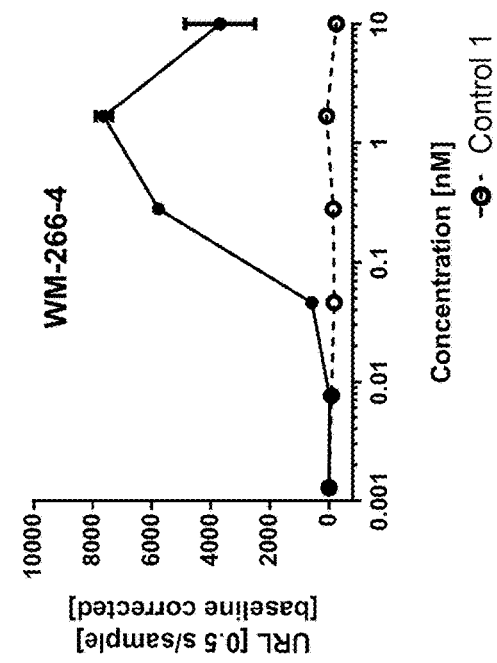

FIGS. 18A-D show the activation of the NFκB signaling pathway in the reporter cells via FAP-expressing tumor cell line crosslinked FAP-targeted single chain trimeric 4-1BBL Fc(kih) fusion antigen binding molecules (Compound S1, filled circles). The data for not-crosslinked DP47-containing single chain trimeric 4-1BBL molecules is shown as a negative control (Control 1, open circles, dotted line). The reporter cells were cultured for 6 hours in the presence of titrated FAP-targeted or DP47-containing single chain trimeric 4-1BBL molecules and crosslinking FAP$^+$ tumor cell lines. The ratio between reporter cells and FAP-expressing tumor cells was 1 to 5. NFκB-mediated luciferase activity is characterized by blotting the units of released light (URL) measured during 0.5 s versus the concentration in nM of tested single chain trimeric 4-1BBL antigen binding molecules. URLs are emitted due to luciferase-mediated oxidation of luciferin to oxyluciferin. Values are baseline corrected by subtracting the URLs of the blank control. FIG. 18A shows the activation with MV3 cell line as target cells, cell line NIH/3T3-human FAP clone 39 was used as target cells in FIG. 18B. FIG. 18C shows the activation with WM-266-4 cell lines as target cells and FIG. 18D shows the measured data if no FAP$^+$ targeting cells are present.

Figure 19A:
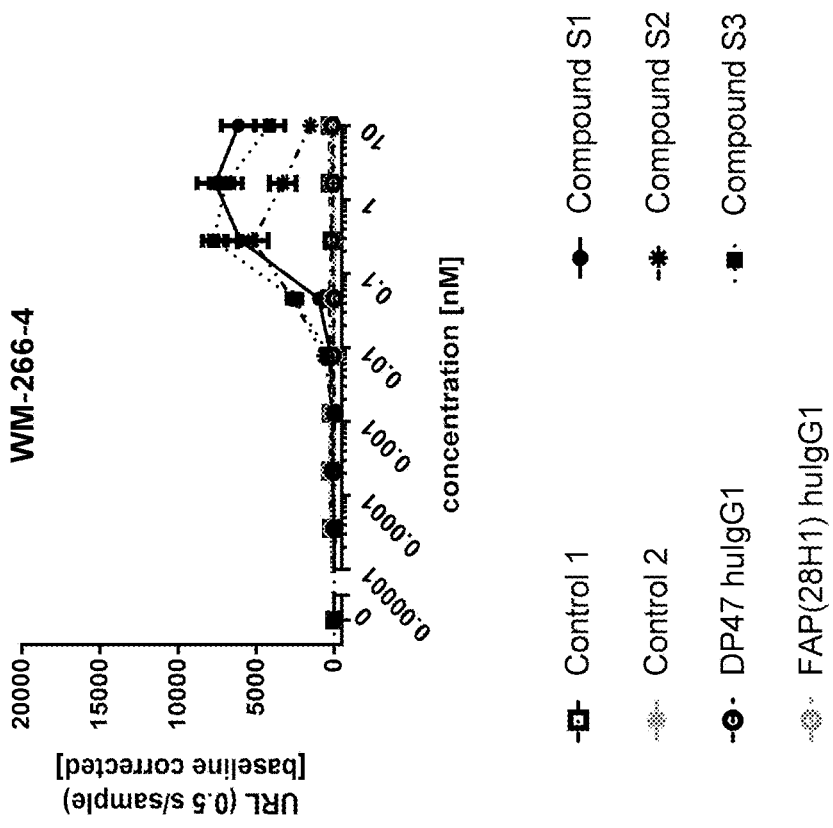
Figure 19B:
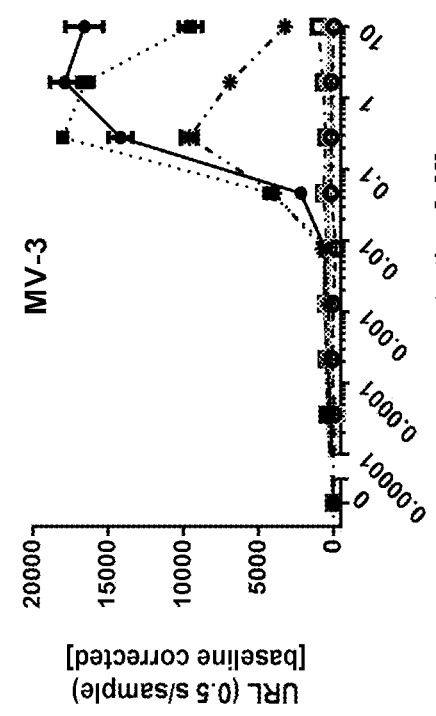
Figure 19C:
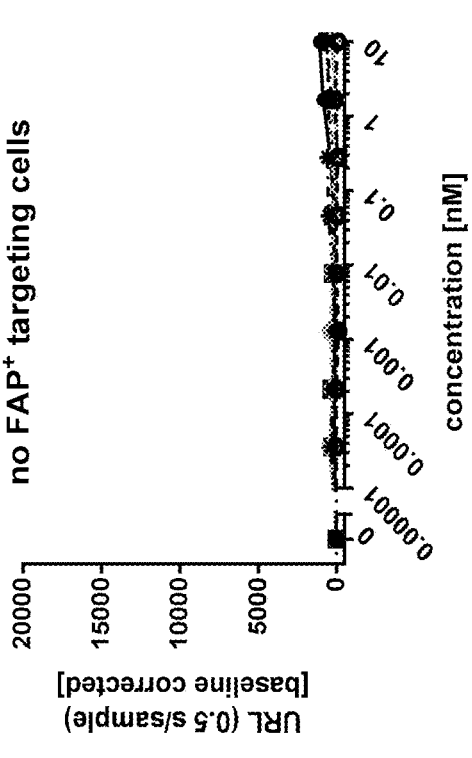

FIGS. 19A-C show the activation of NK-κB via 4-1BB activation mediated by FAP-targeted crosslinking of single chain trimeric 4-1BB ligand Fc (kih) fusion antigen binding molecules. Shown is the activation of NF-κB signaling pathway in the HeLa-hu4-1BB-NFkB-luc clone 26 reporter cells via FAP-expressing tumor cell line crosslinked FAP-targeted single chain trimeric 4-1BB ligand Fc (kih) fusion molecules. DP47-untargeted single chain trimeric 4-1BB ligand Fc (kih) fusion molecules do not induce NK-κB activation (Controls 1 and 2). Monovalent FAP-targeted single chain trimeric 4-1BB ligand Fc (kih) fusion antigen binding molecules (Compounds S1 and S3) induce a stronger NF-κB activation than bivalent FAP-targeted single chain trimeric 4-1BB ligand Fc (kih) fusion molecule (Compound S2). The HeLa-hu4-1BB-NF-κB-luc reporter cells were cultured for 6 hours in the presence of titrated FAP-targeted or DP47-untargeted single chain trimeric 4-1BB ligand Fc (kih) fusion antigen binding molecules and cross-linking FAP$^+$ tumor cell lines. The ratio between reporter cells and FAP-expressing tumor cells was 1:5. NF-κB-mediated luciferase activity is characterized by blotting the units of released light (URL) measured during 0.5 s versus the concentration in nM of tested single chain trimeric 4-1BB ligands. URLs are emitted due to luciferase-mediated oxidation of luciferin to oxyluciferin. Values are baseline corrected by subtracting the URLs of the blank control. FIG. 19A shows the activation with MV3 cell line as target cells and FIG. 19B the activation with WM-266-4 cell lines as target cells. FIG. 19C shows the measured data if no FAP$^+$ targeting cells are present.

In FIGS. 20A-B it is shown the activation of NF-κB signaling pathway in the HeLa-hu4-1BB-NFkB-luc clone 26 reporter cells via CEA-expressing tumor cell line crosslinked CEA (sm9b)-targeted single chain trimeric 4-1BB ligand Fc (kih) fusion antigen binding molecules (Compounds S4 and S5). DP47-untargeted single chain trimeric 4-1BB ligand Fc (kih) fusion molecules do not induce NK-κB activation (Control 1 and 2). Monovalent CEA (sm9b)-targeted single chain trimeric 4-1BB ligand Fc (kih) fusion antigen molecules (compound S5) induce a stronger NF-κB activation than bivalent CEA (sm9b)-targeted single chain trimeric 4-1BB ligand Fc (kih) fusion antigen binding molecules (compound S4). The HeLa-hu4-1BB-NF-κB-luc reporter cells were cultured for 6 hours in the presence of titrated CEA (Sm9b)-targeted or DP47-untargeted single chain trimeric 4-1BB ligand Fc (kih) fusion molecules and crosslinking CEA$^+$ MKN45 tumor cell line. The ratio between reporter cells and CEA-expressing MKN45 tumor cells was 1:5. NF-κB-mediated luciferase activity is characterized by blotting the units of released light (URL) measured during 0.5 s versus the concentration in nM of tested single chain trimeric 4-1BB ligands. URLs are emitted due to luciferase-mediated oxidation of luciferin to oxyluciferin. Values are baseline corrected by subtracting the URLs of the blank control. FIG. 20A shows the activation with MKN45 cell line as target cells and FIG. 20B shows the measured data if no CEA$^+$ targeting cells are present.

Figure 21B:
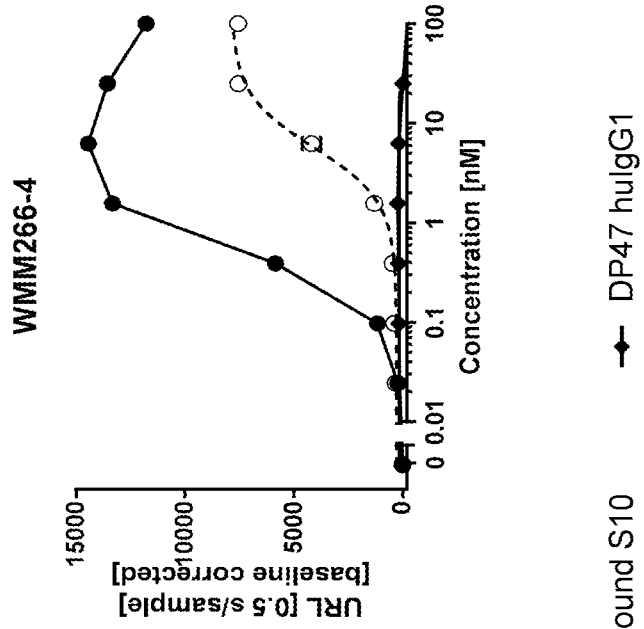
Figure 21A:
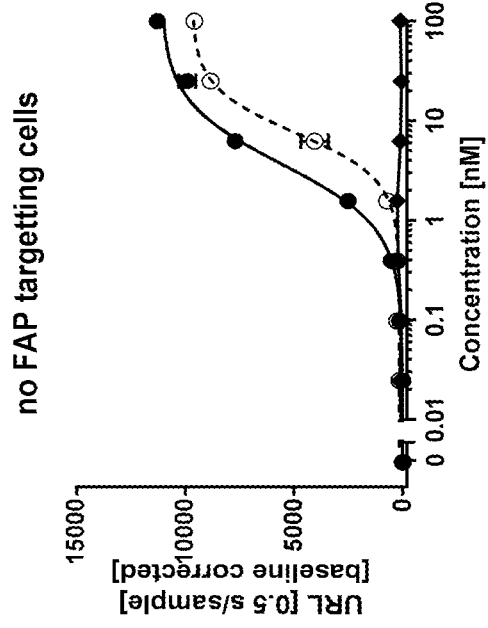

FIG. 21B shows the activation of the NFκB signaling pathway in the HeLa-huOX40-NFkB-luc1 reporter cells via FAP-expressing WM266-4 tumor cell line crosslinking FAP-targeted single chain trimeric OX40L molecules (filled circles, Compounds S10). Not crosslinked DP47-containing single chain trimeric OX40L molecules (open circle, dotted line, Control 3) are shown as a negative control. The reporter cells were cultured for 6 hours in the presence of titrated FAP-targeted or DP47-containing single chain trimeric OX40L molecules and crosslinking FAP⁺ tumor cell lines. The ratio between reporter cells and FAP-expressing tumor cells was 1 to 2.5. NFκB-mediated luciferase activity is characterized by blotting the units of released light (URL) measured during 0.5 s versus the concentration in nM of tested single chain trimeric OX40L antigen binding molecules. URLs are emitted due to luciferase-mediated oxidation of luciferin to oxyluciferin. Values are baseline corrected by subtracting the URLs of the blank control. As shown in FIG. 21A, FAP-targeted single chain trimeric OX40L molecules (Compound S10, filled circles) and DP47-containing single chain trimeric OX40L antigen binding molecules (Control 3) already induce a certain amount of NFκB activation if no FAP⁺ targeting cells are present and thus no cross-linking happened.

Figure 22:
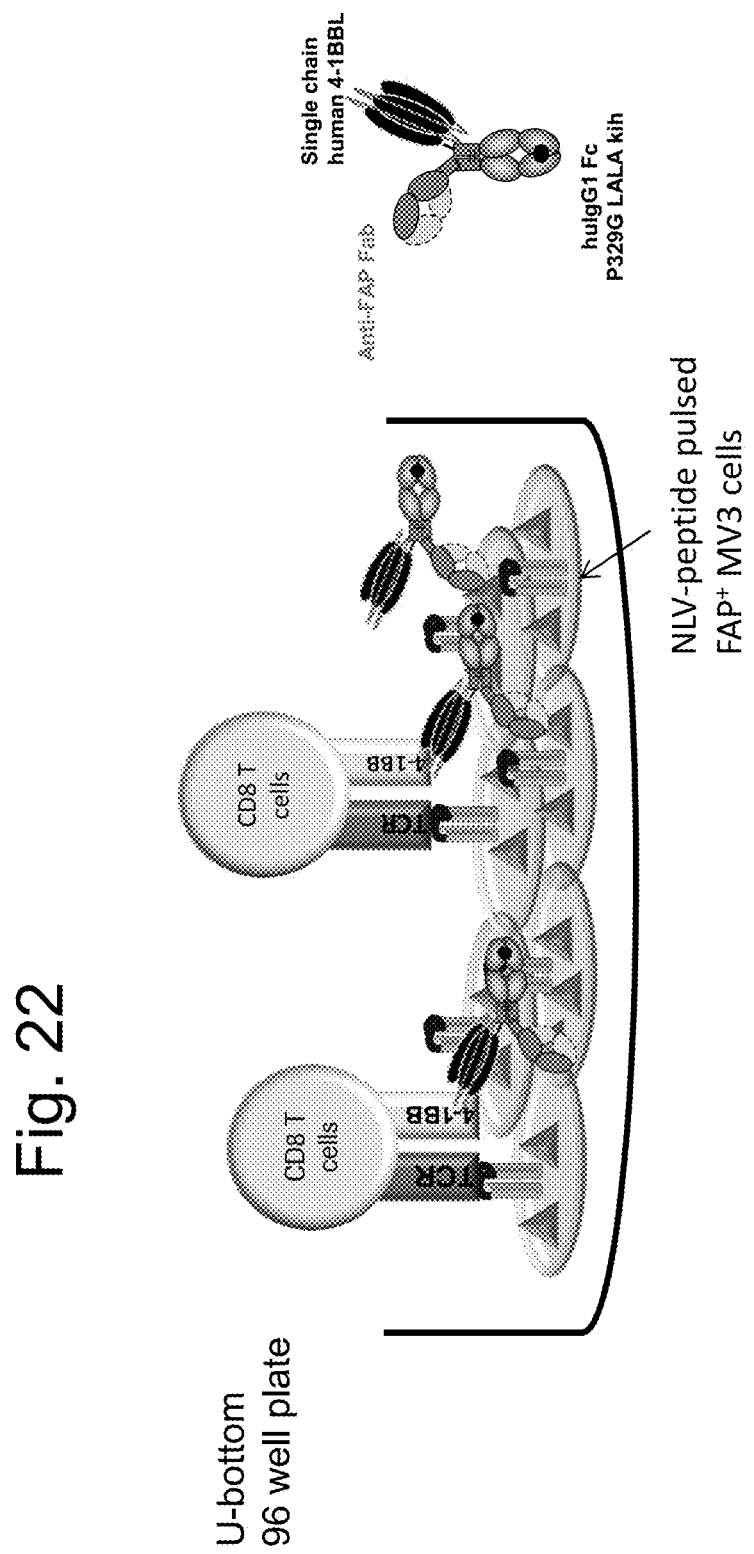
Figure 23A:
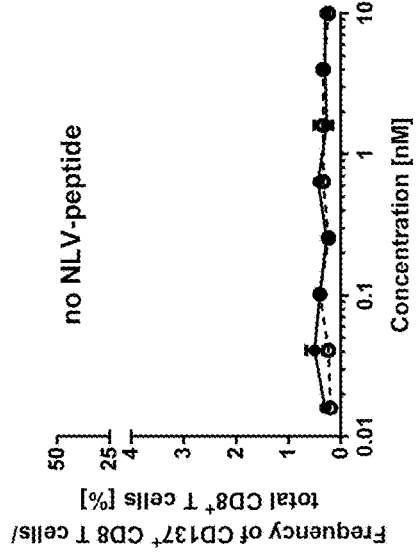
Figure 23B:
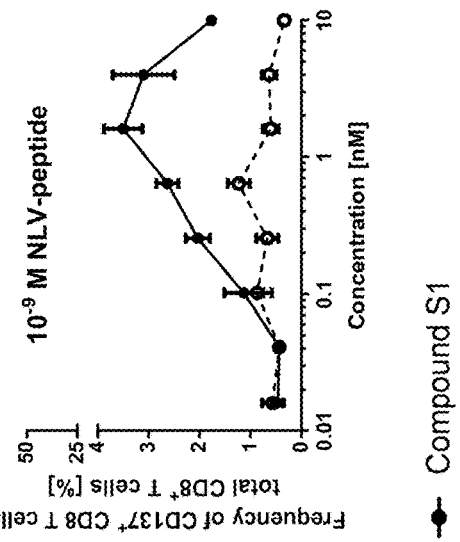
Figure 23C:
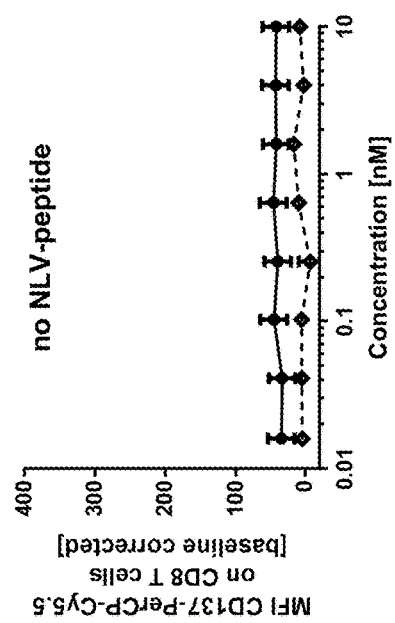
Figure 23D:
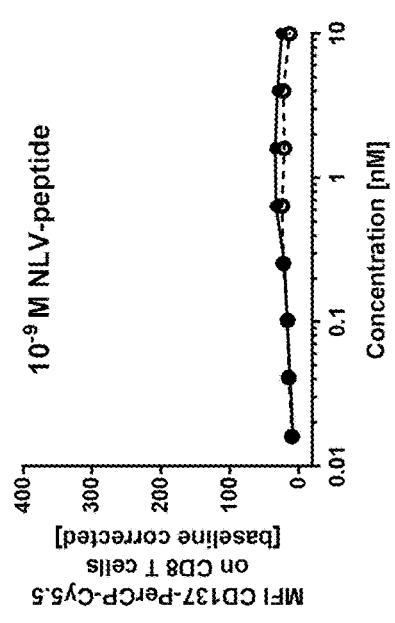
Figure 23F:
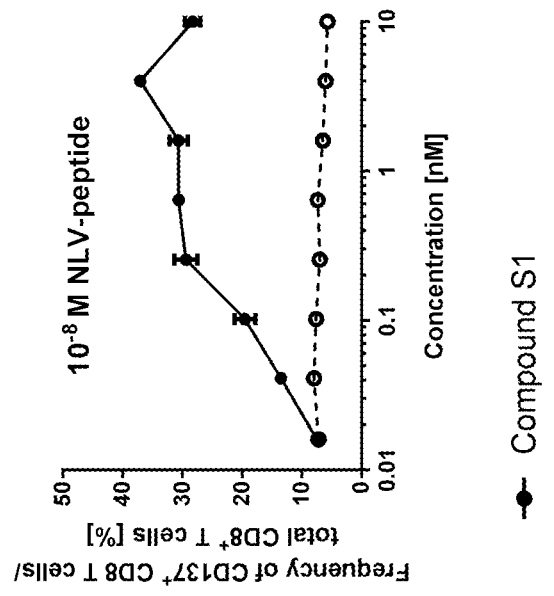
Figure 23E:
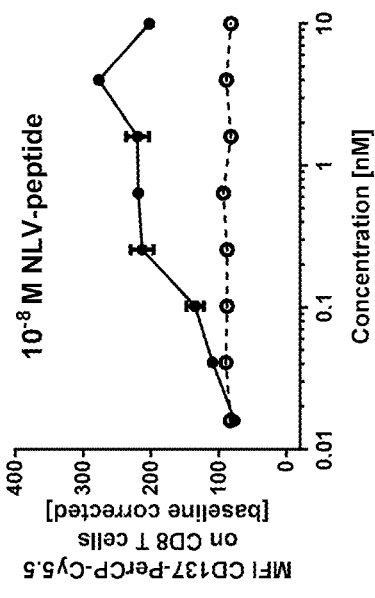
Figure 24A:
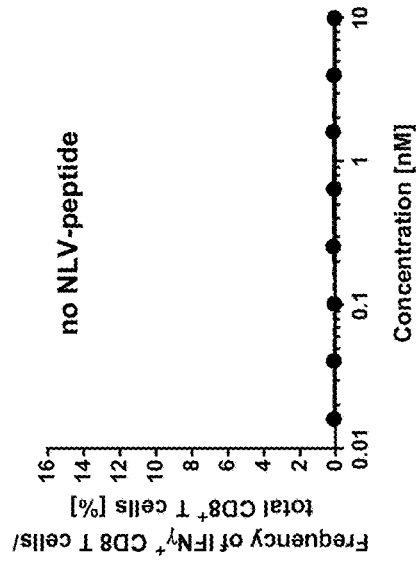
Figure 24B:
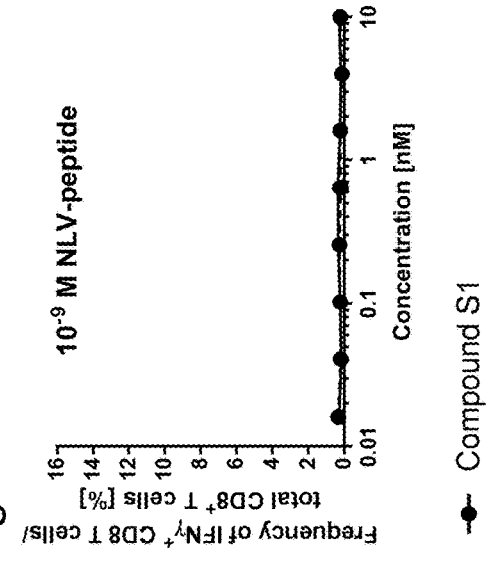
Figure 24C:
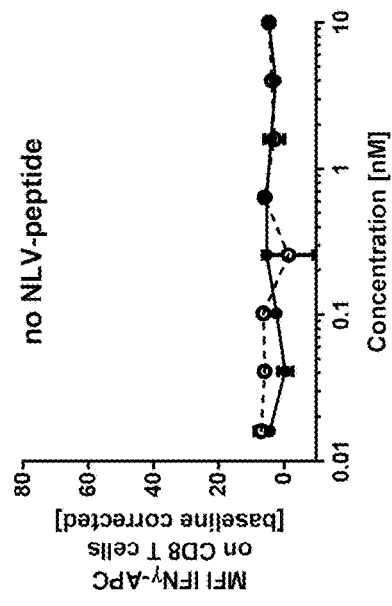
Figure 24D:
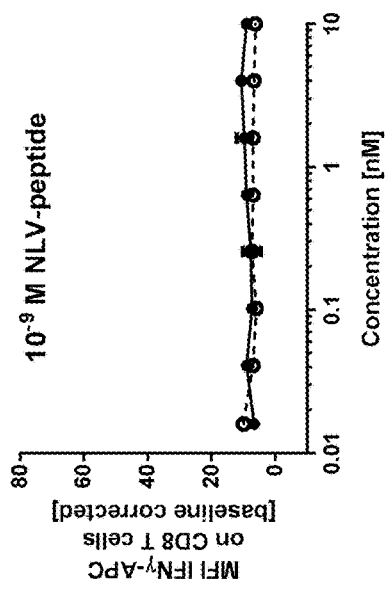
Figures 24E, 24F:
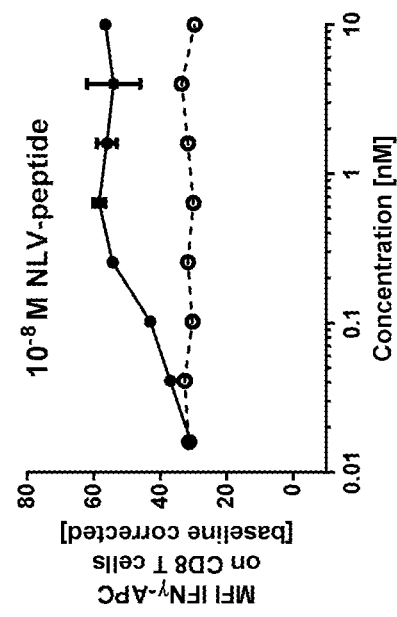
Figure 25F:
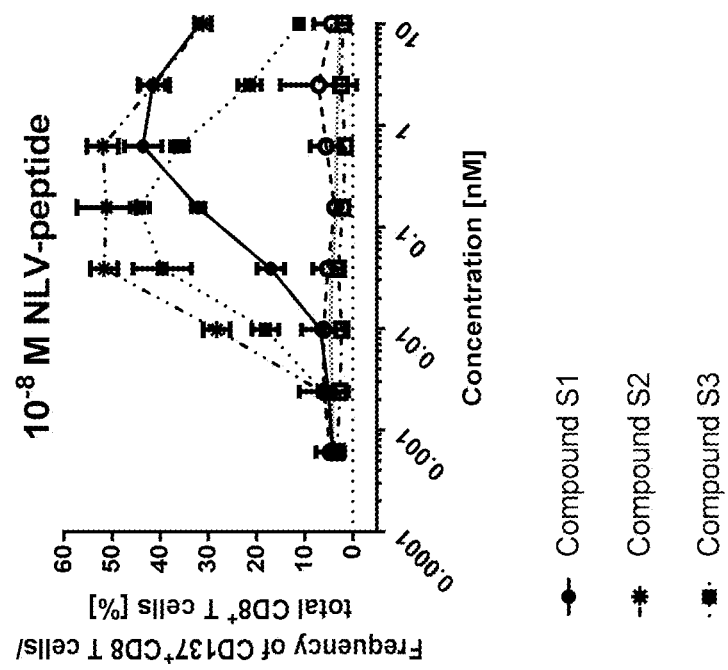
Figure 25E:
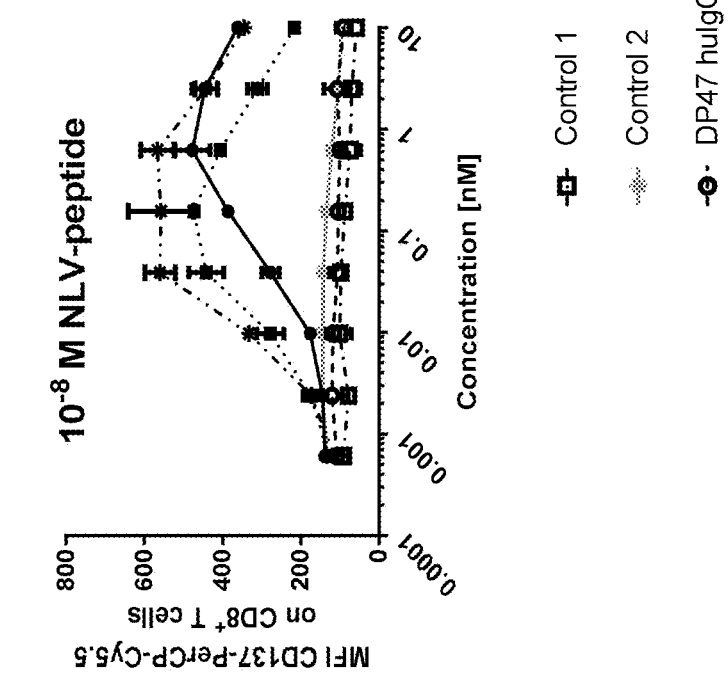
Figure 26E:
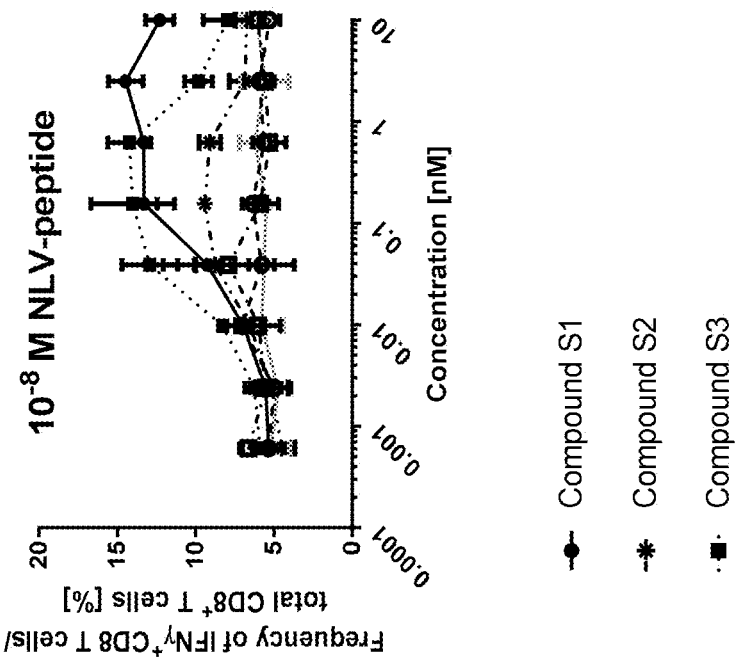
Figure 26F:
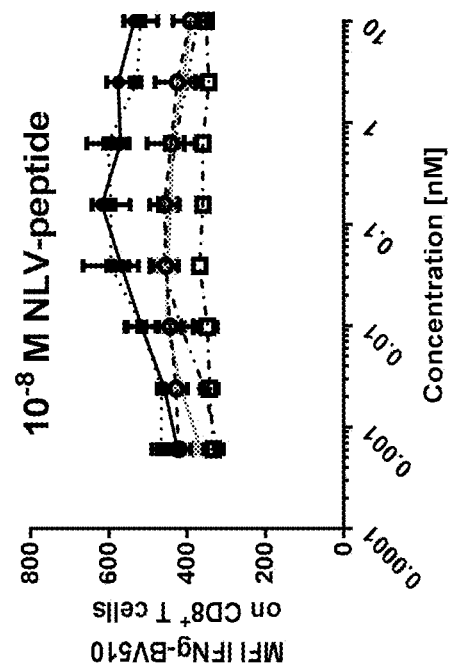
Figure 27A:
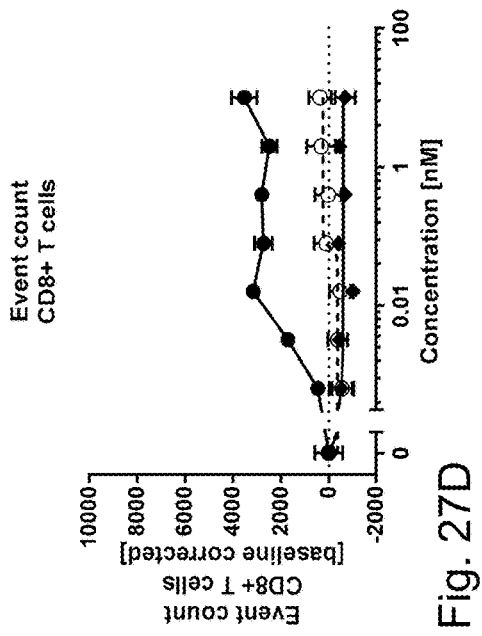
Figure 27C:
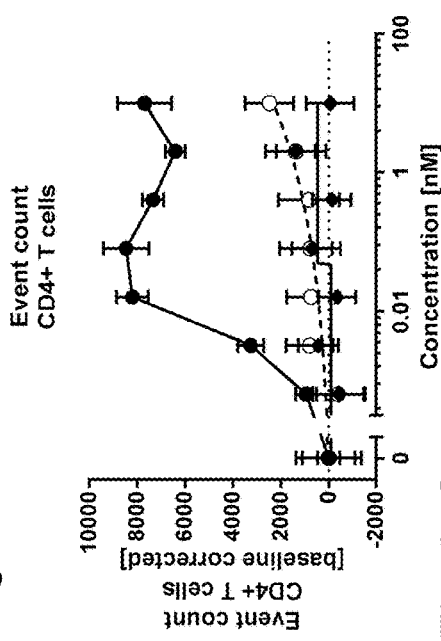
Figure 27B:
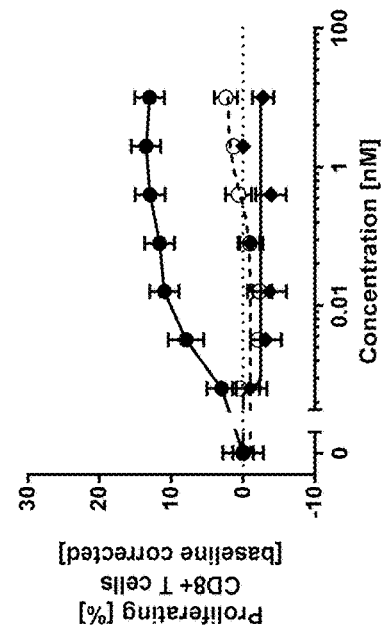
Figure 27D:
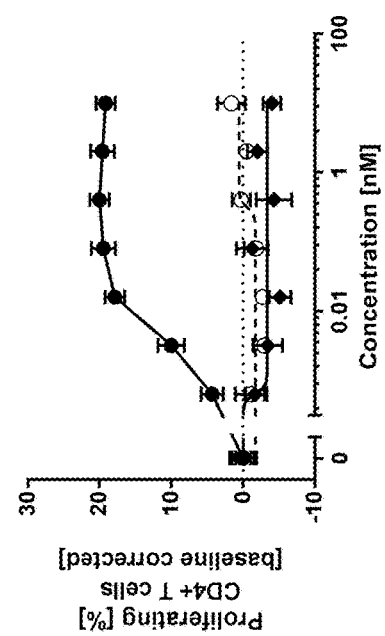
Figure 27E:
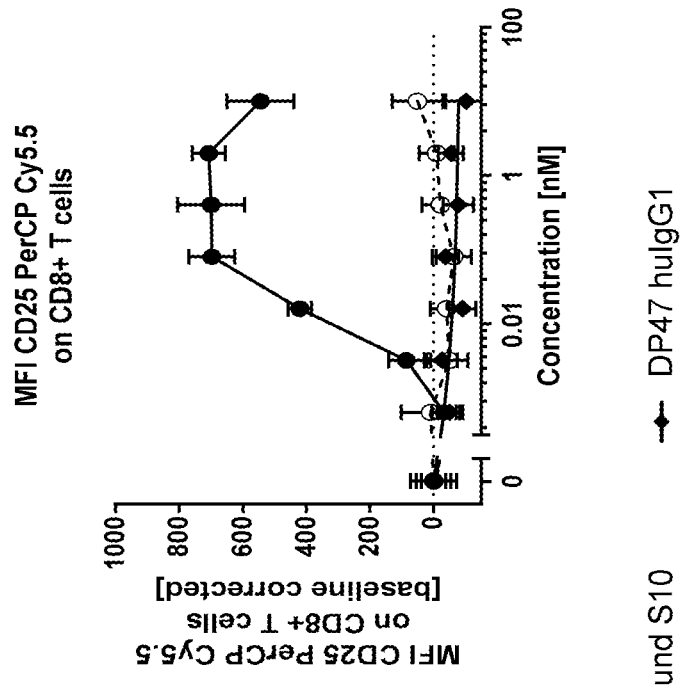
Figure 27F:
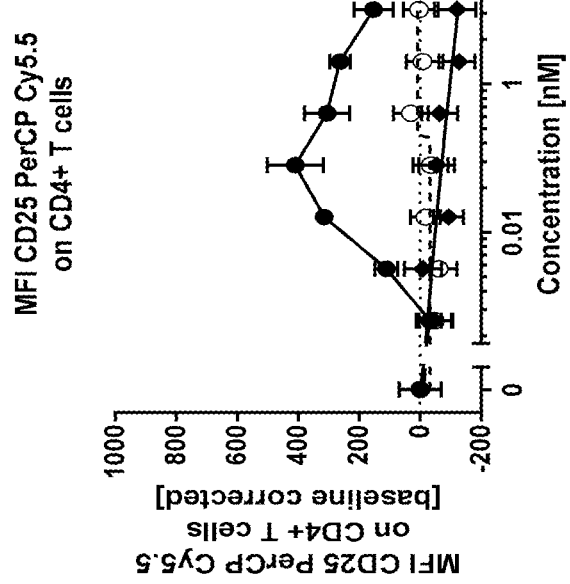

The scheme in FIG. 22 illustrates the general principal of the antigen-specific CD8⁺ T-cell activation assay described in Example 10.2.2.

FIGS. 23A-F and 24A-F show the effect of single chain trimeric 4-1BBL antigen binding molecules on CD137 expression (FIGS. 23A-F) of NLV-specific CD8⁺ T cells on IFNγ secretion of NLV-specific CD8⁺ T cells (FIGS. 24A-F). Prolonged IFNγ secretion and CD137 expression of NLV-specific CD8⁺ T cells is strictly dependent on simultaneous activation of T-cells via recognition of NLV-HLA-A2 complexes (signal 1, Figures A and B) and 4-1BB-triggering by FAP-targeted single chain trimeric 4-1BBL antigen binding molecules (signal 2, Figures C to F). Filled circles: FAP-targeted single chain trimeric 4-1BBL molecules (compound S1); open circles: DP47-containing single chain trimeric 4-1BBL molecules (control 3). The effect of 4-1BB upregulation is shown in FIGS. 23A to 23F, whereas the effect of INFγ expression of CD8⁺ T cells is presented in FIGS. 24A to 24F. Shown is always the median of fluorescence intensity (left panels) and the frequency in percentage of positive cells in the total CD8⁺ T cell population (right panels).

In FIGS. 25A-F and 26A-F is shown the prolonged IFNγ secretion and CD137 expression of NLV-specific CD8⁺ T cells that is strictly dependent on simultaneous activation of T-cells via recognition of NLV-HLA-A2 complexes (signal 1, Figures A and B) and 4-1BB-triggering by FAP-targeted single chain trimeric 4-1BB ligand (signal 2, Figures C to F). The effect of 4-1BB upregulation is shown in FIGS. 25A to 25F, whereas the effect of INFγ expression is shown in FIGS. 26A to 26F. Shown is always the median of fluorescence intensity (left panels) and the frequency in percentage of positive cells in the total CD8+ T cell population (right panels) versus the used concentration of monovalent or bivalent FAP (28H1 or 4B9)-targeted or DP47-untargeted single chain trimeric 4-1BB ligand (kih) fusion antigen binding molecules.

FIGS. 27A-F demonstrate that costimulation with DP47-containing trimeric single chain OX40L molecules (open circle, dotted line, Control 3) only slightly promoted proliferation and induced an enhanced activated phenotype (CD25 expression) in human CD4⁺ (left side) and CD8⁺ T cells (right side) stimulated suboptimally with anti-human CD3 antibody. Hyper-crosslinking of the FAP-targeted trimeric single chain OX40L molecules by the present NIH/3T3-huFAP clone 39 cells strongly increased this effect (filled circle, Compound S10). Shown is either the event count, the percentage of proliferating (CFSE-low) cells or the MFI of CD25-PerCPCy5.5 on vital CD4⁺ and CD8⁺ T cells. Baseline values of blank samples containing only anti-human CD3 (clone V9, huIgG1), resting human PBMC and NIH/3T3-huFAP clone 39) were subtracted from test compound samples. Thus the enhancing effect of OX40L co-stimulation but not the effect of suboptimal anti-CD3 stimulation per se is shown here.

Figure 28A:
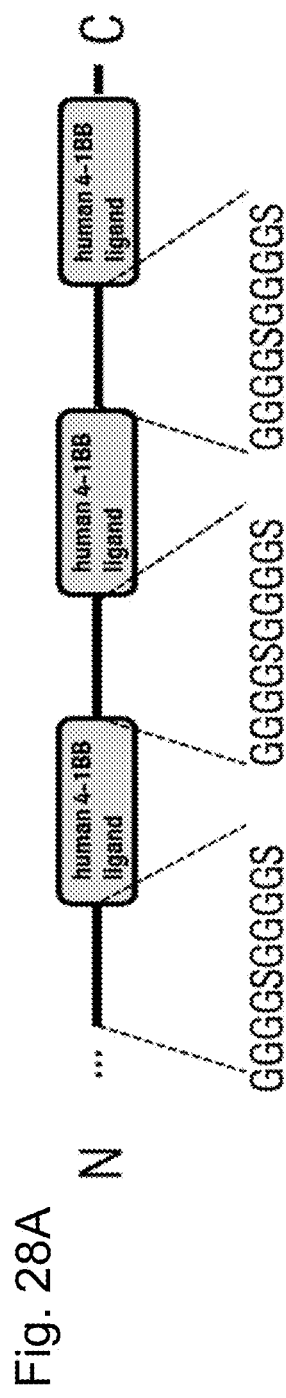

FIG. 28A shows a polypeptide comprising three ectodomains of 4-1BBL that are connected to each other by peptide linkers (GGGGSGGGGS (SEQ ID NO:54).

Figure 28B:
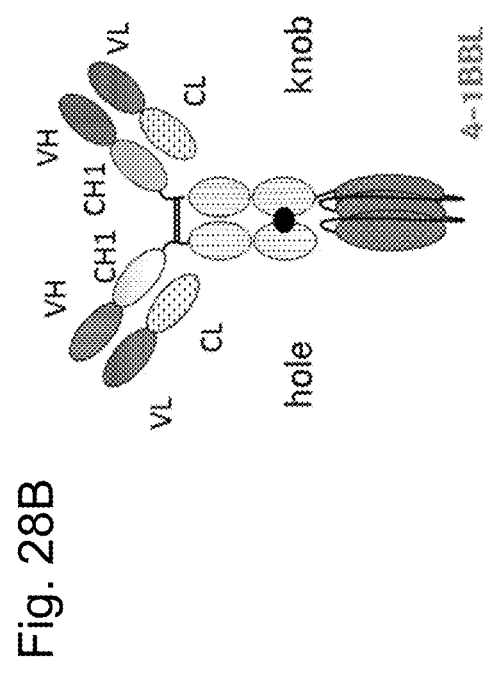

FIG. 28B shows a representative example of a bivalent TNF ligand trimer-containing antigen binding molecule of the invention comprising the polypeptide of FIG. 28A. The three TNF ligands are symbolized by the grey areas at the bottom. The white areas with black points symbolize the Fc part, the thick black point stands for the knob-into-hole modification.

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

As used herein, the term "moiety capable of specific binding to a target cell antigen" refers to a polypeptide molecule that specifically binds to an antigenic determinant. In one aspect, the antigen binding moiety is able to activate signaling through its target cell antigen. In a particular aspect, the antigen binding moiety is able to direct the entity to which it is attached (e.g. the TNF family ligand trimer) to a target site, for example to a specific type of tumor cell or tumor stroma bearing the antigenic determinant. Moieties capable of specific binding to a target cell antigen include antibodies and fragments thereof as further defined herein. In addition, moieties capable of specific binding to a target cell antigen include scaffold antigen binding proteins as further defined herein, e.g. binding domains which are based on designed repeat proteins or designed repeat domains (see e.g. WO 2002/020565).

In relation to an antibody or fragment thereof, the term "moiety capable of specific binding to a target cell antigen" refers to the part of the molecule that comprises the area which specifically binds to and is complementary to part or all of an antigen. A moiety capable of specific antigen binding may be provided, for example, by one or more antibody variable domains (also called antibody variable regions). Particularly, a moiety capable of specific antigen binding comprises an antibody light chain variable region (VL) and an antibody heavy chain variable region (VH).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ(IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPINs®) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (ANTICALIN®), a Protein A-derived molecule such as Z-domain of Protein A (AFFIBODY®), an A-domain (Avimer/Maxibody), a serum transferrin (trans-body); a designed ankyrin repeat protein (DARPIN®), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (AFFILIN® molecules); a kunitz type domain of human protease inhibitors, microbodies such as the proteins from the knottin family, peptide aptamers and fibronectin (adnectin).

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. ANTICALINs® are between 160-180 amino acids in size, and are derived from lipocalins. For further details see Biochim Biophys Acta 1482: 337-350 (2000), U.S. Pat. No. 7,250,297B1 and US20070224633.

An AFFIBODY® is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1.

Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPINs®) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domains were derived from the variable domain of the antibody heavy chain from camelids (nanobodies or $V_H$H fragments). Furthermore, the term single-domain antibody includes an autonomous human heavy chain variable domain (aVH) or $V_{NAR}$ fragments derived from sharks.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataBl and conotoxin and knottins. The microproteins have a loop which can be engineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIACORE® instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, e.g. from $10^{-8}$M to $10^{-13}$M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "target cell antigen" as used herein refers to an antigenic determinant presented on the surface of a target cell, for example a cell in a tumor such as a cancer cell or a cell of the tumor stroma. In certain embodiments, the target cell antigen is an antigen on the surface of a tumor cell. In one embodiment, target cell antigen is selected from the group consisting of Fibroblast Activation Protein (FAP), Carcinoembryonic Antigen (CEA), Melanoma-associated Chondroitin Sulfate Proteoglycan (MCSP), Epidermal Growth Factor Receptor (EGFR), CD19, CD20 and CD33. In particular, the target cell antigen is Fibroblast Activation Protein (FAP).

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP which results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt (uniprot.org) accession no. Q12884 (version 149, SEQ ID NO:21), or NCBI (ncbi.nlm.nih.gov/) RefSeq NP_004451.2. The extracellular domain (ECD) of human FAP extends from amino acid position 26 to 760. The amino acid and nucleotide sequences of a His-tagged human FAP ECD is shown in SEQ ID NOs 22 and 23, respectively. The amino acid sequence of mouse FAP is shown in UniProt accession no. P97321 (version 126, SEQ ID NO:24), or NCBI RefSeq NP_032012.1. The extracellular domain (ECD) of mouse FAP extends from amino acid position 26 to 761. SEQ ID NOs 25 and 26 show the amino acid and nucleotide sequences, respectively, of a His-tagged mouse FAP ECD. SEQ ID NOs 27 and 28 show the amino acid and nucleotide sequences, respectively, of a His-tagged cynomolgus FAP ECD. Preferably, an anti-FAP binding molecule of the invention binds to the extracellular domain of FAP. Exemplary anti-FAP binding molecules are described in International Patent Application No. WO 2012/020006 A2.

The term "Carcinoembroynic antigen (CEA)", also known as Carcinoembryonic antigen-related cell adhesion molecule 5 (CEACAMS), refers to any native CEA from any vertebrate source, including mammals such as primates (e.g. humans) non-human primates (e.g. cynomolgus monkeys) and rodents (e.g. mice and rats), unless otherwise indicated. The amino acid sequence of human CEA is shown in UniProt accession no. P06731 (version 151, SEQ ID NO:29). CEA has long been identified as a tumor-associated antigen (Gold and Freedman, J Exp Med., 121:439-462, 1965; Berinstein N. L., J Clin Oncol., 20:2197-2207, 2002). Originally classified as a protein expressed only in fetal tissue, CEA has now been identified in several normal adult tissues. These tissues are primarily epithelial in origin, including cells of the gastrointestinal, respiratory, and urogential tracts, and cells of colon, cervix, sweat glands, and prostate (Nap et al., Tumour Biol., 9(2-3):145-53, 1988; Nap et al., Cancer Res., 52(8):2329-23339, 1992). Tumors of epithelial origin, as well as their metastases, contain CEA as a tumor associated antigen. While the presence of CEA itself does not indicate transformation to a cancerous cell, the distribution of CEA is indicative. In normal tissue, CEA is generally expressed on the apical surface of the cell (Hammarstrom S., Semin Cancer Biol. 9(2):67-81 (1999)), making it inaccessible to antibody in the blood stream. In contrast to normal tissue, CEA tends to be expressed over the entire surface of cancerous cells (Hammarstrom S., Semin Cancer Biol. 9(2):67-81 (1999)). This change of expression pattern makes CEA accessible to antibody binding in cancerous cells. In addition, CEA expression increases in cancerous cells. Furthermore, increased CEA expression promotes increased intercellular adhesions, which may lead to metastasis (Marshall J., Semin Oncol., 30(a Suppl. 8):30-6, 2003). The prevalence of CEA expression in various tumor entities is generally very high. In concordance with published data, own analyses performed in tissue samples confirmed its high prevalence, with approximately 95% in colorectal carcinoma (CRC), 90% in pancreatic cancer, 80% in gastric cancer, 60% in non-small cell lung cancer (NSCLC, where it is co-expressed with HER3), and 40% in breast cancer; low expression was found in small cell lung cancer and glioblastoma. CEA is readily cleaved from the cell surface and shed into the blood stream from tumors, either directly or via the lymphatics. Because of this property, the level of serum CEA has been used as a clinical marker for diagnosis of cancers and screening for recurrence of cancers, particularly colorectal cancer (Goldenberg D M., The International Journal of Biological Markers, 7:183-188, 1992; Chau I., et al., J Clin Oncol., 22:1420-1429, 2004; Flamini et al., Clin Cancer Res; 12(23):6985-6988, 2006).

The term "Melanoma-associated Chondroitin Sulfate Proteoglycan (MCSP)", also known as Chondroitin Sulfate Proteoglycan 4 (CSPG4) refers to any native MCSP from any vertebrate source, including mammals such as primates (e.g. humans) non-human primates (e.g. cynomolgus monkeys) and rodents (e.g. mice and rats), unless otherwise indicated. The amino acid sequence of human MCSP is shown in UniProt accession no. Q6UVK1 (version 103, SEQ ID NO:30). The term "Epidermal Growth Factor Receptor (EGFR)", also named Proto-oncogene c-ErbB-1 or Receptor tyrosine-protein kinase erbB-1, refers to any native EGFR from any vertebrate source, including mammals such as primates (e.g. humans) non-human primates (e.g. cynomolgus monkeys) and rodents (e.g. mice and rats), unless otherwise indicated. The amino acid sequence of human EGFR is shown in UniProt accession no. P00533 (version 211, SEQ ID NO:31).

The term "CD19" refers to B-lymphocyte antigen CD19, also known as B-lymphocyte surface antigen B4 or T-cell surface antigen Leu-12 and includes any native CD19 from any vertebrate source, including mammals such as primates (e.g. humans) non-human primates (e.g. cynomolgus monkeys) and rodents (e.g. mice and rats), unless otherwise indicated. The amino acid sequence of human CD19 is shown in Uniprot accession no. P15391 (version 160, SEQ ID NO:32). The term encompasses "full-length" unprocessed human CD19 as well as any form of human CD19 that results from processing in the cell as long as the antibody as reported herein binds thereto. CD19 is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD19 is expressed by most pre-B acute lymphoblastic leukemias (ALL), non-Hodgkin's lymphomas, B cell chronic lymphocytic leukemias (CLL), prolymphocytic leukemias, hairy cell leukemias, common acute lymphocytic leukemias, and some Null-acute lymphoblastic leukemias. The expression of CD19 on plasma cells further suggests it may be expressed on differentiated B cell tumors such as multiple myeloma. Therefore, the CD19 antigen is a target for immunotherapy in the treatment of non-Hodgkin's lymphoma, chronic lymphocytic leukemia and/or acute lymphoblastic leukemia.

"CD20" refers to B-lymphocyte antigen CD20, also known as membrane-spanning 4-domains subfamily A member 1 (MS4A1), B-lymphocyte surface antigen B1 or Leukocyte surface antigen Leu-16, and includes any native CD20 from any vertebrate source, including mammals such as primates (e.g. humans) non-human primates (e.g. cynomolgus monkeys) and rodents (e.g. mice and rats), unless otherwise indicated. The amino acid sequence of human CD20 is shown in Uniprot accession no. P11836 (version 149, SEQ ID NO:33). "CD33" refers to Myeloid cell surface antigen CD33, also known as SIGLEC3 or gp67, and includes any native CD33 from any vertebrate source, including mammals such as primates (e.g. humans) non-human primates (e.g. cynomolgus monkeys) and rodents (e.g. mice and rats), unless otherwise indicated. The amino acid sequence of human CD33 is shown in Uniprot accession no. P20138 (version 157, SEQ ID NO:34).

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgA_1$, and $IgA_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). The numbering is according to EU index of Kabat et al, Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "TNF ligand family member" or "TNF family ligand" refers to a proinflammatory cytokine. Cytokines in general, and in particular the members of the TNF ligand family, play a crucial role in the stimulation and coordination of the immune system. At present, nineteen cyctokines have been identified as members of the TNF (tumour necrosis factor) ligand superfamily on the basis of sequence, functional, and structural similarities. All these ligands are type II transmembrane proteins with a C-terminal extracellular domain (ectodomain), N-terminal intracellular domain and a single transmembrane domain. The C-terminal extracellular domain, known as TNF homology domain (THD), has 20-30% amino acid identity between the superfamily members and is responsible for binding to the receptor. The TNF ectodomain is also responsible for the TNF ligands to form trimeric complexes that are recognized by their specific receptors.

Members of the TNF ligand family are selected from the group consisting of Lymphotoxin a (also known as LTA or TNFSF1), TNF (also known as TNFSF2), LTβ (also known as TNFSF3), OX40L (also known as TNFSF4), CD40L (also known as CD154 or TNFSF5), FasL (also known as CD95L, CD178 or TNFSF6), CD27L (also known as CD70 or TNFSF7), CD30L (also known as CD153 or TNFSF8), 4-1BBL (also known as TNFSF9), TRAIL (also known as APO2L, CD253 or TNFSF10), RANKL (also known as CD254 or TNFSF11), TWEAK (also known as TNFSF12), APRIL (also known as CD256 or TNFSF13), BAFF (also known as CD257 or TNFSF13B), LIGHT (also known as CD258 or TNFSF14), TL1A (also known as VEGI or TNFSF15), GITRL (also known as TNFSF18), EDA-A1 (also known as ectodysplasin A1) and EDA-A2 (also known as ectodysplasin A2). The term refers to any native TNF family ligand from any vertebrate source, including mammals such as primates (e.g. humans), non-human primates (e.g. cynomolgus monkeys) and rodents (e.g. mice and rats), unless otherwise indicated. In specific embodiments of the invention, the TNF ligand family member is selected from the group consisting of 4-1BBL, OX40L, GITRL, CD70, CD30L, CD40L and LIGHT. In a particular embodiment, the TNF ligand family member is selected from 4-1BBL and OX40L.

Further information, in particular sequences, of the TNF ligand family members may be obtained from publically accessible databases such as Uniprot (uniprot.org). For instance, the human TNF ligands have the following amino acid sequences: human Lymphotoxin a (UniProt accession no. P01374, SEQ ID NO:35), human TNF (UniProt accession no. P01375, SEQ ID NO:36), human Lymphotoxin β (UniProt accession no. Q06643, SEQ ID NO:37), human OX40L (UniProt accession no. P23510, SEQ ID NO:38), human CD40L (UniProt accession no. P29965, SEQ ID NO:39), human FasL (UniProt accession no. P48023, SEQ ID NO:40), human CD27L (UniProt accession no. P32970, SEQ ID NO:41), human CD30L (UniProt accession no. P32971, SEQ ID NO:42), 4-1BBL (UniProt accession no. P41273, SEQ ID NO:43), TRAIL (UniProt accession no. P50591, SEQ ID NO:44), RANKL (UniProt accession no. 014788, SEQ ID NO:45), TWEAK (UniProt accession no. 043508, SEQ ID NO:46), APRIL (UniProt accession no. 075888, SEQ ID NO:47), BAFF (UniProt accession no. Q9Y275, SEQ ID NO:48), LIGHT (UniProt accession no. 043557, SEQ ID NO:49), TL1A (UniProt accession no. 095150, SEQ ID NO:50), GITRL (UniProt accession no. Q9UNG2, SEQ ID NO:51) and ectodysplasin A (UniProt accession no. Q92838, SEQ ID NO:52).

An "ectodomain" is the domain of a membrane protein that extends into the extracellular space (i.e. the space outside the target cell). Ectodomains are usually the parts of proteins that initiate contact with surfaces, which leads to signal transduction. The ectodomain of TNF ligand family member as defined herein thus refers to the part of the TNF ligand protein that extends into the extracellular space (the extracellular domain), but also includes shorter parts or fragments thereof that are responsible for the trimerization and for the binding to the corresponding TNF receptor. The term "ectodomain of a TNF ligand family member or a fragment thereof" thus refers to the extracellular domain of the TNF ligand family member that forms the extracellular domain or to parts thereof that are still able to bind to the receptor (receptor binding domain).

The term "costimulatory TNF ligand family member" or "costimulatory TNF family ligand" refers to a subgroup of TNF ligand family members, which are able to costimulate proliferation and cytokine production of T-cells. These TNF family ligands can costimulate TCR signals upon interaction with their corresponding TNF receptors and the interaction with their receptors leads to recruitment of TNFR-associated factors (TRAF), which initiate signalling cascades that result in T-cell activation. Costimulatory TNF family ligands are selected from the group consisting of 4-1BBL, OX40L, GITRL, CD70, CD30L and LIGHT, more particularly the costimulatory TNF ligand family member is selected from 4-1BBL and OX40L.

As described herein before, 4-1BBL is a type II transmembrane protein and one member of the TNF ligand family. Complete or full length 4-1BBL having the amino acid sequence of SEQ ID NO:43 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:53) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL), SEQ ID NO:2 (amino acids 85-254 of human 4-1BBL), SEQ ID NO:99 (amino acids 71-248 of human 4-1BBL), SEQ ID NO:100 (amino acids 85-248 of human 4-1BBL), SEQ ID NO:101 (amino acids 80-248 of human 4-1BBL) and SEQ ID NO:102 (amino acids 52-254 of human 4-1BBL), but also other fragments of the ectodomain capable of trimerization are included herein.

As described herein before, OX40L is another type II transmembrane protein and a further member of the TNF ligand family. Complete or full length human OX40L has the amino acid sequence of SEQ ID NO:38. The amino acids 51-183 of the human OX40L sequence (SEQ ID NO:6) form the extracellular domain of OX40L, but even fragments thereof that are able to form the trimers. In specific embodiments of the invention, the term "ectodomain of OX40L or a fragment thereof" refers to a polypeptide having an amino acid sequence selected from SEQ ID NO:6 (amino acids 51-183 of human OX40L) or SEQ ID NO:7 (amino acids 52-183 of human OX40L), but also other fragments of the ectodomain capable of trimerization are included herein.

The term "peptide linker" refers to a peptide comprising one or more amino acids. A peptide linker comprises 1 to 44 amino acids, more particularly 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:136), GGGGSGGGGS (SEQ ID NO:54), SGGGGSGGGG (SEQ ID NO:55) and GGGGSGGGGSGGGG (SEQ ID NO:56), but also include the sequences GSPGSSSSGS (SEQ ID NO:57), GSGSGSGS (SEQ ID NO:58), GSGSGNGS (SEQ ID NO:59), GGSGSGSG (SEQ ID NO:60), GGSGSG (SEQ ID NO:61), GGSG (SEQ ID NO:62), GGSGNGSG (SEQ ID NO:63), GGNGSGSG (SEQ ID NO:64) and GGNGSG (SEQ ID NO:65). Peptide linkers of particular interest are $((G4S)_1$ or GGGGS (SEQ ID NO:136), $(G_4S)_2$ or GGGGSGGGGS (SEQ ID NO:54) and GSPGSSSSGS (SEQ ID NO:57), more particularly $(G_4S)_2$ or GGGGSGGGGS (SEQ ID NO:54) and GSPGSSSSGS (SEQ ID NO:57).

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "single chain fusion protein" as used herein refers to a single chain polypeptide composed of one or two ectodomains of said TNF ligand family member fused to a part of antigen binding moiety or Fc part. The fusion may occur by directly linking the N or C-terminal amino acid of the antigen binding moiety via a peptide linker to the C- or N-terminal amino acid of the ectodomain of said TNF ligand family member.

By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the TNF ligand trimer-containing antigen binding molecules provided herein are contemplated. For example, it may be desirable to improve the binding affinity and/or other biological properties of the TNF ligand trimer-containing antigen binding molecules. Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include TNF family ligand trimer-containing antigen binding molecule with an N-terminal methionyl residue. Other insertional variants of the molecule include the fusion to the N- or C-terminus to a polypeptide which increases the serum half-life of the TNF ligand trimer-containing antigen binding molecules.

In certain embodiments, the TNF family ligand trimer-containing antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the TNF ligand trimer-containing antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in TNF family ligand trimer-containing antigen binding molecule may be made in order to create variants with certain improved properties. In one aspect, variants of TNF family ligand trimer-containing antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the TNF family ligand trimer-containing antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the TNF family ligand trimer-containing antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the TNF family ligand trimer-containing antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

In another aspect, immunoconjugates of the TNF family ligand trimer-containing antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, carcinoma, lymphoma, blastoma, sarcoma, leukemia, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer (CRC), pancreatic cancer, breast cancer, triple-negative breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, melanoma, multiple myeloma, B-cell cancer (lymphoma), chronic lymphocytic leukemia (CLL), acute lymphoblastic leukemia (ALL), hairy cell leukemia, chronic myeloblastic leukemia, including refractory versions of any of the above cancers, or a combination of one or more of the above cancers.

TNF Family Ligand Trimer-Containing Antigen Binding Molecules of the Invention

The invention provides novel TNF family ligand trimer-containing antigen binding molecules with particularly advantageous properties such as producibility, stability, binding affinity, biological activity, targeting efficiency and reduced toxicity.

Thus, the invention relates to a TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other, optionally by peptide linkers, and
(c) a Fc domain composed of a first and a second subunit capable of stable association.

In one aspect, the invention provides a TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association.

In another aspect, the TNF family ligand trimer containing antigen binding molecule comprises
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association, wherein the polypeptide comprising the three ectodomains of a TNF ligand family member or fragments thereof that are connected to each other by peptide linkers is fused to the N- or C-terminal amino acid of one of the two subunits of the Fc domain, optionally through a peptide linker.

In a particular aspect, the TNF family ligand trimer-containing antigen binding molecule comprises (a) at least one moiety capable of specific binding to a target cell antigen,
(b) a polypeptide comprising three ectodomains of a TNF ligand family member or fragments thereof that are connected to each other by peptide linkers and (c) a Fc domain composed of a first and a second subunit capable of stable association, wherein the TNF ligand family member costimulates human T-cell activation. Thus, the TNF ligand family member is a costimulatory TNF family ligand. In particular, the costimulatory TNF family ligand is selected from the group consisting of 4-1BBL, OX40L, GITRL, CD70, CD30L and LIGHT, more particularly the costimulatory TNF family ligand is selected from 4-1BBL and OX40L.

In one aspect, the TNF ligand family member is 4-1BBL.

In a further aspect, the ectodomain of a TNF ligand family member comprises the amino acid sequence selected from the group consisting of SEQ ID NO:1, SEQ ID NO: 2, SEQ ID NO:3, SEQ ID NO:4, SEQ ID NO:99, SEQ ID NO: 100, SEQ ID NO:101 and SEQ ID NO:102, particularly the amino acid sequence of SEQ ID NO:1 or SEQ ID NO:99.

In a particular aspect, the ectodomain of a TNF ligand family member or fragment thereof comprises the amino acid sequence selected from the group consisting of SEQ ID NO:1, SEQ ID NO:2, SEQ ID NO:3 and SEQ ID NO:4, particularly the amino acid sequence of SEQ ID NO:1.

In a further aspect, the TNF family ligand trimer-containing antigen binding molecule of the invention comprises
(a) at least one moiety capable of specific binding to a target cell antigen and
(b) a polypeptide comprising the amino acid sequence of SEQ ID NO:5 or SEQ ID NO:103, and
(c) a Fc domain composed of a first and a second subunit capable of stable association. More particularly, the polypeptide comprises the amino acid sequence of SEQ ID NO:5.

In another aspect, the TNF ligand family member is OX40L.

In another aspect, the ectodomain of a TNF ligand family member comprises the amino acid sequence selected from the group consisting of SEQ ID NO:6 and SEQ ID NO:7, particularly the amino acid sequence of SEQ ID NO:6.

In a further aspect, the TNF family ligand trimer-containing antigen binding molecule of the invention comprises
(a) at least one moiety capable of specific binding to a target cell antigen and (b) a polypeptide comprising the amino acid sequence of SEQ ID NO:8 and (c) a Fc domain composed of a first and a second subunit capable of stable association.

In one aspect, the TNF family ligand trimer-containing antigen binding molecule comprises (a) at least one moiety capable of specific binding to a target cell antigen, (b) a polypeptide comprising three ectodomains of a TNF ligand family member or fragments thereof that are connected to each other and (c) a Fc domain composed of a first and a second subunit capable of stable association, wherein the three ectodomains of a TNF ligand family member or fragments thereof are linked to each other directly, or with a suitable chemical linker, such as a disulfide, ester or ether bridge.

In another aspect, the TNF family ligand trimer-containing antigen binding molecule comprises (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, wherein the three ectodomains of a TNF ligand family member or fragments thereof are linked to each other by peptide linkers that are the same or different and are selected from the group consisting of GGGGSGGGGS (SEQ ID NO:54), SGGGGSGGGG (SEQ ID NO:55) and GGGGSGGGGSGGGG (SEQ ID NO:56), but also include the sequences GSPGSSSSGS (SEQ ID NO:57), GSGSGSGS (SEQ ID NO:58), GSGSGNGS (SEQ ID NO:59), GGSGSGSG (SEQ ID NO:60), GGSGSG (SEQ ID NO:61), GGSG (SEQ ID NO:62), GGSGNGSG (SEQ ID NO:63), GGNGSGSG (SEQ ID NO:64) and GGNGSG (SEQ ID NO:65). In particular, the peptide linkers are the same and are selected from the group consisting of $(G_4S)_2$ (SEQ ID NO:54) and GSPGSSSSGS (SEQ ID NO:57). More particularly, the invention relates to a TNF family ligand trimer-containing antigen binding molecule as defined above, wherein the three ectodomains of a TNF ligand family member or fragments thereof are connected to each other by $(G_4S)_2$ (SEQ ID NO:54) linkers.

In another aspect, the TNF family ligand trimer-containing antigen binding molecule of the invention comprises (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, wherein the polypeptide comprising three ectodomains of a TNF ligand family member or fragments thereof is fused at the C-terminal amino acid to the N-terminal amino acid of one of the subunits of the Fc domain. In a particular aspect, the polypeptide comprising three ectodomains of a TNF ligand family member or fragments thereof is fused at the C-terminal amino acid to the N-terminal amino acid of a CH2 domain in the Fc domain. In a further aspect, the polypeptide comprising three ectodomains of a TNF ligand family member or fragments thereof is connected at the C-terminal amino acid by a peptide linker to the N-terminal amino acid of the Fc domain.

In another aspect, the TNF family ligand trimer-containing antigen binding molecule of the invention comprises (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, wherein the polypeptide comprising three ectodomains of a TNF ligand family member or fragments thereof is fused at the N-terminal amino acid to the C-terminal amino acid of the Fc domain. In a particular aspect, the polypeptide comprising three ectodomains of a TNF ligand family member or fragments thereof is fused at the N-terminal amino acid to the C-terminal amino acid of a CH3 domain in the Fc domain. In a further aspect, the polypeptide comprising three ectodomains of a TNF ligand family member or fragments thereof is connected at the N-terminal amino acid by a peptide linker to the C-terminal amino acid of the Fc domain.

In another aspect, the TNF family ligand trimer-containing antigen binding molecule comprises (a) at least one moiety capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association, wherein the moiety capable of specific binding to a target cell antigen is not fused to the polypeptide comprising three ectodomains of a TNF ligand family member or fragments thereof.

In a further aspect, the invention provides a TNF family ligand trimer-containing antigen binding molecule as defined herein before, wherein the moiety capable of specific binding to a target cell antigen is selected from the group consisting of an antibody, an antibody fragment and a scaffold antigen binding protein.

In one aspect, the invention provides a TNF family ligand trimer-containing antigen binding molecule as defined herein before, wherein the moiety capable of specific binding to a target cell antigen is an antibody.

In another aspect, the invention provides a TNF family ligand trimer-containing antigen binding molecule as defined herein before, wherein the moiety capable of specific binding to a target cell antigen is an antibody fragment. In particular, the antibody fragment is selected from the group consisting of a Fab molecule, a crossover Fab molecule, a single chain Fab molecule, a Fv molecule, a scFv molecule, a single domain antibody, and aVH.

In a further aspect, the invention provides a TNF family ligand trimer-containing antigen binding molecule as defined herein before, wherein the moiety capable of specific binding to a target cell antigen is a scaffold antigen binding protein.

Thus, in a further aspect, the invention relates to a TNF family ligand trimer-containing antigen binding molecule as defined herein before, wherein the moiety capable of specific binding to a target cell antigen is selected from the group consisting of an antibody fragment, a Fab molecule, a crossover Fab molecule, a single chain Fab molecule, a Fv molecule, a scFv molecule, a single domain antibody, an aVH and a scaffold antigen binding protein. Thus, in a particular aspect, the invention provides a TNF family ligand trimer-containing antigen binding molecule comprising (a) at least one antibody fragment capable of specific binding to a target cell antigen which is selected from the group consisting of a Fab molecule, a crossover Fab molecule, a single chain Fab molecule, a Fv molecule, a scFv molecule, a single domain antibody, an aVH and a scaffold antigen binding protein, (b) a polypeptide comprising three ectodomains of a TNF ligand family member or fragments thereof that are connected to each other by peptide linkers and (c) a Fc domain composed of a first and a second subunit capable of stable association. In one aspect, the TNF family ligand trimer-containing antigen binding molecule comprising (a) one antibody fragment capable of specific binding to a target cell antigen which is selected from the group consisting of a Fab molecule, a crossover Fab molecule, a single chain Fab molecule, a Fv molecule, a scFv molecule, a single domain antibody, an aVH and a scaffold antigen binding protein.

In a particular aspect, the invention is concerned with a TNF family ligand trimer-containing antigen binding molecule as defined above, wherein the moiety capable of specific binding to a target cell antigen is a Fab molecule capable of specific binding to a target cell antigen. Thus, the invention provides a TNF family ligand trimer-containing antigen binding molecule comprising (a) at least one Fab molecule capable of specific binding to a target cell antigen, (b) a polypeptide comprising three ectodomains of a TNF ligand family member or fragments thereof that are connected to each other by peptide linkers and (c) a Fc domain composed of a first and a second subunit capable of stable association.

In another aspect, provided is a TNF family ligand trimer-containing antigen binding molecule of the invention, wherein the target cell antigen is selected from the group consisting of Fibroblast Activation Protein (FAP), Carcinoembryonic Antigen (CEA), Melanoma-associated Chondroitin Sulfate Proteoglycan (MCSP), Epidermal Growth Factor Receptor (EGFR), CD19, CD20 and CD33.

In a further aspect, provided is a TNF family ligand trimer-containing antigen binding molecule as described herein before, wherein the Fc domain composed of a first and a second subunit capable of stable association is an IgG Fc domain, particularly an IgG1 Fc domain or an IgG4 Fc domain. In particular, the Fc domain composed of a first and a second subunit capable of stable association is an IgG1 Fc domain. In a particular aspect, the Fc domain comprises a modification promoting the association of the first and second subunit of the Fc domain.

Fc Domain Modifications Reducing Fc Receptor Binding and/or Effector Function

The Fc domain of the TNF family ligand trimer-containing antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. The Fc domain thus favorably contributes to the pharmacokinetic parameters (PK data) of the antigen binding molecules, such as clearance, volume of distribution or elimination half-time ($t_{1/2}$). At the same time it may, however, lead to undesirable targeting of the bispecific antibodies of the invention to cells expressing Fc receptors rather than to the preferred antigen-bearing cells. Accordingly, in particular aspects, the Fc domain of the TNF family ligand trimer-containing antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of a TNF family ligand trimer-containing antigen binding molecule provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In one aspect, the invention is concerned with a TNF family ligand trimer-containing antigen binding molecule as defined herein before, comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association, wherein the Fc domain comprises one or more amino acid substitution that reduces binding to an Fc receptor, in particular towards Fcγ receptor.

In one aspect, the Fc domain of the TNF family ligand trimer-containing antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is a trimeric TNF family ligand-containing antigen binding molecule according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions. "EU numbering" refers to the numbering according to EU index of Kabat et al, Sequences of Proteins of Immunological Interest, 5th Ed. Public Health Service, National Institutes of Health, Bethesda, Md., 1991.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In a particular aspect, the Fc domain comprises a modification promoting the association of the first and second subunit of the Fc domain.

Fc Domain Modifications Promoting Heterodimerization

The Fc domain comprises different moieties, fused to one or the other of the two subunits of the Fc domain that are typically comprised in two non-identical polypetide chains ("heavy chains"). Recombinant co-expression of these polypeptides and subsequent dimerization leads to several possible combinations of the two polypeptides. To improve the yield and purity of the TNF family ligand trimer-containing antigen binding molecules in recombinant production, it will thus be advantageous to introduce in the Fc domain of the TNF family ligand trimer-containing antigen binding molecules of the invention a modification promoting the association of the desired polypeptides.

Accordingly, the Fc domain of the TNF family ligand trimer-containing antigen binding molecules of the invention comprises a modification promoting the association of the first and the second subunit of the Fc domain. The site of most extensive protein-protein interaction between the two subunits of a human IgG Fc domain is in the CH3 domain of the Fc domain. Thus, said modification is particularly in the CH3 domain of the Fc domain.

In a specific aspect, said modification is a so-called "knob-into-hole" modification, comprising a "knob" modification in one of the two subunits of the Fc domain and a "hole" modification in the other one of the two subunits of the Fc domain. Thus, in a particular aspect, the invention relates to a TNF family ligand trimer-containing antigen binding molecule as described herein before which comprises an IgG molecule, wherein the Fc part of the first heavy chain comprises a first dimerization module and the Fc part of the second heavy chain comprises a second dimerization module allowing a heterodimerization of the two heavy chains of the IgG molecule and the first dimerization module comprises knobs and the second dimerization module comprises holes according to the knob into hole technology.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular aspect, in the CH3 domain of the first subunit of the Fc domain of the TNF family ligand trimer-containing antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). More particularly, in the second subunit of the Fc domain additionally the threonine residue at position 366 is replaced with a serine residue (T366S) and the leucine residue at position 368 is replaced with an alanine residue (L368A). More particularly, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). The introduction of these two cysteine residues results in the formation of a disulfide bridge between the two subunits of the Fc domain. The disulfide bridge further stabilizes the dimer (Carter, J Immunol Methods 248, 7-15 (2001)).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Particular TNF Family Ligand Trimer-Containing Antigen Binding Molecules

In another aspect, provided is a monovalent TNF family ligand trimer-containing antigen binding molecule as described herein before, comprising one moiety capable of specific binding to a target cell antigen.

In particular, the TNF family ligand trimer-containing antigen binding molecule of the invention comprising (c) an Fc domain composed of a first and a second subunit capable of stable association further comprises (a) a Fab molecule capable of specific binding to a target cell antigen, wherein the Fab heavy chain is fused at the C-terminus to the N-terminus of a CH2 domain in the Fc domain.

Furthermore, the invention provides a TNF family ligand trimer-containing antigen binding molecule as described herein before, wherein the antigen binding molecule comprises
(a) a heavy chain and a light chain, both comprising a Fab molecule capable of specific binding to a target cell antigen, and
(b) a fusion protein comprising the amino acid sequence of SEQ ID NO:15.

In a further aspect, the TNF family ligand trimer-containing antigen binding molecule comprises
(i) a first heavy chain comprising the VH domain of a Fab molecule capable of specific binding to a target cell antigen,
(ii) a light chain comprising the VL domain of a Fab molecule capable of specific binding to a target cell antigen, and
(iii) a second heavy chain comprising the amino acid sequence of SEQ ID NO:5 or SEQ ID NO:103 or SEQ ID NO:8.

In a particular aspect, the TNF family ligand trimer-containing antigen binding molecule comprises (i) a first heavy chain comprising a VH domain comprising an amino acid sequence of SEQ ID NO:16 or a VH domain comprising an amino acid sequence of SEQ ID NO:110, (ii) a light chain comprising a VL domain comprising an amino acid sequence of SEQ ID NO:17 or a VL domain comprising an amino acid sequence of SEQ ID NO:111, and (iii) a second heavy chain comprising the amino acid sequence of SEQ ID NO:5 or SEQ ID NO:103 or SEQ ID NO:8. In another aspect, TNF family ligand trimer-containing antigen binding molecule comprises (i) a first heavy chain comprising a VH domain comprising an amino acid sequence of SEQ ID NO:118, (ii) a light chain comprising a VL domain comprising an amino acid sequence of SEQ ID NO:119, and (iii) a second heavy chain comprising the amino acid sequence of SEQ ID NO:5 or SEQ ID NO:103 or SEQ ID NO:8. In a further aspect, the TNF family ligand trimer-containing antigen binding molecule comprises (i) a first heavy chain comprising a VH domain comprising an amino acid sequence of SEQ ID NO:126 or a VH domain comprising an amino acid sequence of SEQ ID NO:134, (ii) a light chain comprising a VL domain comprising an amino acid sequence of SEQ ID NO:127 or a VL domain comprising an amino acid sequence of SEQ ID NO:135, and (iii) a second heavy chain comprising the amino acid sequence of SEQ ID NO:5 or SEQ ID NO:103 or SEQ ID NO:8.

In another aspect, provided is a bivalent TNF family ligand trimer-containing antigen binding molecule, comprising two moieties capable of specific binding to a target cell antigen.

In one aspect, the TNF family ligand trimer-containing antigen binding molecule comprises
(i) a first heavy chain comprising a VH domain or a VL domain of a Fab molecule capable of specific binding to a target cell antigen,
(ii) two light chains comprising each a VL domain or a VH domain of a Fab molecule capable of specific binding to a target cell antigen, and
(iii) a second heavy chain comprising a VH domain or a VL domain of a Fab molecule capable of specific binding to a target cell antigen and the amino acid sequence of SEQ ID NO:5 or SEQ ID NO:103 or SEQ ID NO:8.

In one aspect, the TNF family ligand trimer-containing antigen binding molecule comprises
(i) a first heavy chain comprising a VH domain of a Fab molecule capable of specific binding to a target cell antigen,
(ii) two light chains comprising each the VL domain of a Fab molecule capable of specific binding to a target cell antigen, and
(iii) a second heavy chain comprising a VH domain of a Fab molecule capable of specific binding to a target cell antigen and the amino acid sequence of SEQ ID NO:5 or SEQ ID NO:103 or SEQ ID NO:8.

In a particular aspect, the TNF family ligand trimer-containing antigen binding molecule comprises (i) a first heavy chain comprising a VH domain comprising an amino acid sequence of SEQ ID NO:16 or a VH domain comprising an amino acid sequence of SEQ ID NO:110, (ii) two light chains comprising each a VL domain comprising an amino acid sequence of SEQ ID NO:17 or a VL domain comprising an amino acid sequence of SEQ ID NO:111, and (iii) a second heavy chain comprising a VH domain comprising an amino acid sequence of SEQ ID NO:16 or a VH domain comprising an amino acid sequence of SEQ ID NO:110 and the amino acid sequence of SEQ ID NO:5 or SEQ ID NO:103 or SEQ ID NO:8. In another aspect, the TNF family ligand trimer-containing antigen binding molecule comprises (i) a first heavy chain comprising a VH domain comprising an amino acid sequence of SEQ ID NO:118, (ii) two light chains comprising each a VL domain comprising an amino acid sequence of SEQ ID NO:119, and (iii) a second heavy chain comprising a VH domain comprising an amino acid sequence of SEQ ID NO:118 and the amino acid sequence of SEQ ID NO:5 or SEQ ID NO:103 or SEQ ID NO:8. In yet another aspect, the TNF family ligand trimer-containing antigen binding molecule comprises (i) a first heavy chain comprising a VH domain comprising an amino acid sequence of SEQ ID NO:126 or a VH domain comprising an amino acid sequence of SEQ ID NO:134, (ii) two light chains comprising a VL domain comprising an amino acid sequence of SEQ ID NO:127 or a VL domain comprising an amino acid sequence of SEQ ID NO:135, and (iii) a second heavy chain comprising a VH domain comprising an amino acid sequence of SEQ ID NO:126 or a VH domain comprising an amino acid sequence of SEQ ID NO:134 and the amino acid sequence of SEQ ID NO:5 or SEQ ID NO:103 or SEQ ID NO:8.

In one aspect, provided is a TNF family ligand trimer-containing antigen binding molecule according to the invention, wherein the antigen binding molecule comprises
(a) a heavy chain comprising a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a light chain comprising a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, and
(b) a fusion protein comprising the amino acid sequence of SEQ ID NO:15.

In a further aspect, the invention provides a TNF family ligand trimer-containing antigen binding molecule according to the invention, wherein the antigen binding molecule comprises
(a) a moiety capable of specific binding to FAP comprising a VH domain comprising the amino acid sequence of SEQ ID NO:16 and a VL domain comprising the amino acid sequence of SEQ ID NO:17 and
(b) a fusion protein comprising the amino acid sequence of SEQ ID NO:15.

In a particular aspect, provided is a TNF family ligand trimer-containing antigen binding molecule as described herein before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:5.

In a particular aspect, provided is a TNF family ligand trimer-containing antigen binding molecule as described herein before, wherein the antigen binding molecule comprises
(i) a heavy chain comprising the amino acid sequence of SEQ ID NO:16,
(ii) a light chain comprising the amino acid sequence of SEQ ID NO:17, and
(iii) a fusion protein comprising the amino acid sequence of SEQ ID NO:15.

In another aspect, provided is a TNF family ligand trimer-containing antigen binding molecule as described hereinbefore, wherein the antigen binding molecule comprises
(a) a heavy chain and a light chain, both comprising a Fab molecule capable of specific binding to a target cell antigen, and
(b) the fusion protein comprising the amino acid sequence of SEQ ID NO:20.

In one aspect, provided is a TNF family ligand trimer-containing antigen binding molecule according to the invention, wherein the antigen binding molecule comprises
(a) a heavy chain comprising a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a light chain comprising a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, and
(b) a fusion protein comprising the amino acid sequence of SEQ ID NO:20.

In a further aspect, the invention provides a TNF family ligand trimer-containing antigen binding molecule according to the invention, wherein the antigen binding molecule comprises
(a) a moiety capable of specific binding to FAP comprising a VH domain comprising the amino acid sequence of SEQ ID NO:16 and a VL domain comprising the amino acid sequence of SEQ ID NO:17 and
(b) a fusion protein comprising the amino acid sequence of SEQ ID NO:20.

In a particular aspect, provided is a TNF family ligand trimer-containing antigen binding molecule as described herein before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:8.

In a particular aspect, provided is a TNF family ligand trimer-containing antigen binding molecule as described herein before, wherein the antigen binding molecule comprises
(i) a heavy chain comprising the amino acid sequence of SEQ ID NO:16,
(ii) a light chain comprising the amino acid sequence of SEQ ID NO:17, and
(iii) a fusion protein comprising the amino acid sequence of SEQ ID NO:20.

TNF Family Ligand Trimer-Containing Antigen Binding Molecules, Wherein the Target Cell Antigen is FAP In a particular aspect, the target cell antigen is Fibroblast Activation Protein (FAP). In one aspect, the invention provides a TNF family ligand trimer-containing antigen binding molecule as described herein before, wherein the moiety capable of specific binding to FAP comprises
(a) a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, or
(b) a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

In one aspect, the moiety capable of specific binding to FAP comprises a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14. In another particular aspect, the moiety capable of specific binding to FAP comprises a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

In a further aspect, the moiety capable of specific binding to FAP comprises a heavy chain variable region comprising an amino acid sequence that is at least about 95%, 96%, 97%, 98%, 99% or 100% identical to the amino acid sequence of SEQ ID NO:16 and a light chain variable region comprising an amino acid sequence that is at least about 95%, 96%, 97%, 98%, 99% or 100% identical to the amino acid sequence of SEQ ID NO:17. In a particular aspect, the moiety capable of specific binding to FAP comprises a heavy chain variable region comprising the amino acid sequence of SEQ ID NO:16 and a light chain variable region comprising the amino acid sequence of SEQ ID NO:17. In a specific aspect, the moiety capable of specific binding to FAP comprises a VH domain consisting of amino acid sequence of SEQ ID NO:16 and a VL domain consisting of the amino acid sequence of SEQ ID NO:17.

In a further particular aspect, the TNF family ligand trimer-containing antigen binding molecule of the invention comprises a heavy chain comprising the amino acid sequence of SEQ ID NO:18 and a light chain comprising the amino acid sequence of SEQ ID NO:19. In a specific aspect, the TNF family ligand trimer-containing antigen binding molecule comprises a heavy chain consisting of amino acid sequence of SEQ ID NO:18 and a light chain consisting of the amino acid sequence of SEQ ID NO:19.

In another aspect, the moiety capable of specific binding to FAP comprises a heavy chain variable region comprising an amino acid sequence that is at least about 95%, 96%, 97%, 98%, 99% or 100% identical to the amino acid sequence of SEQ ID NO:110 and a light chain variable region comprising an amino acid sequence that is at least about 95%, 96%, 97%, 98%, 99% or 100% identical to the amino acid sequence of SEQ ID NO:111. In a particular aspect, the moiety capable of specific binding to FAP comprises a heavy chain variable region comprising the amino acid sequence of SEQ ID NO:110 and a light chain variable region comprising the amino acid sequence of SEQ ID NO:111. In a specific aspect, the moiety capable of specific binding to FAP comprises a VH domain consisting of amino acid sequence of SEQ ID NO:110 and a VL domain consisting of the amino acid sequence of SEQ ID NO:111.

In one aspect, provided is a monovalent TNF family ligand trimer-containing antigen binding molecule as described herein before, comprising one moiety capable of specific binding to FAP.

In a particular aspect, provided is a TNF family ligand trimer-containing antigen binding molecule as described herein before, wherein the antigen binding molecule comprises
(i) a variable heavy chain comprising the amino acid sequence of SEQ ID NO:18,
(ii) a variable light chain comprising the amino acid sequence of SEQ ID NO:19, and
(iii) a fusion protein comprising the amino acid sequence of SEQ ID NO:15.

In a further particular aspect, provided is a TNF family ligand trimer-containing antigen binding molecule as described herein before, wherein the antigen binding molecule comprises
(i) a variable heavy chain comprising the amino acid sequence of SEQ ID NO:140,
(ii) a variable light chain comprising the amino acid sequence of SEQ ID NO:142, and
(iii) a fusion protein comprising the amino acid sequence of SEQ ID NO:15.

In another particular aspect, provided is a TNF family ligand trimer-containing antigen binding molecule as described herein before, wherein the antigen binding molecule comprises
(i) a variable heavy chain comprising the amino acid sequence of SEQ ID NO:18,
(ii) a variable light chain comprising the amino acid sequence of SEQ ID NO:19, and
(iii) a fusion protein comprising the amino acid sequence of SEQ ID NO:20.

In another aspect, provided is a bivalent TNF family ligand trimer-containing antigen binding molecule as described herein before, comprising two moieties capable of specific binding to FAP.

In a particular aspect, provided is a TNF family ligand trimer-containing antigen binding molecule as described herein before, wherein the antigen binding molecule comprises
(i) a variable heavy chain comprising the amino acid sequence of SEQ ID NO:140,
(ii) a variable light chain comprising the amino acid sequence of SEQ ID NO:142, and
(iii) a fusion protein comprising the amino acid sequence of SEQ ID NO:141.

TNF Family Ligand Trimer-Containing Antigen Binding Molecules, Wherein the Target Cell Antigen is CEA In another aspect, the target cell antigen is CEA. In one aspect, the invention provides a TNF family ligand trimer-containing antigen binding molecule as described herein before, wherein the moiety capable of specific binding to CEA comprises a VH domain comprising (i) CDR-H1 comprising the amino acid sequence of SEQ ID NO:112, (ii) CDR-H2 comprising the amino acid sequence of SEQ ID NO:113 and (iii) CDR-H3 comprising the amino acid sequence of SEQ ID NO:114, and a VL domain comprising (iv) CDR-L1 comprising the amino acid sequence of SEQ ID NO:115, (v) CDR-L2 comprising the amino acid sequence of SEQ ID NO:116 and (vi) CDR-L3 comprising the amino acid sequence of SEQ ID NO:117.

In a further aspect, the moiety capable of specific binding to CEA comprises a heavy chain variable region comprising an amino acid sequence that is at least about 95%, 96%, 97%, 98%, 99% or 100% identical to the amino acid sequence of SEQ ID NO:118 and a light chain variable region comprising an amino acid sequence that is at least about 95%, 96%, 97%, 98%, 99% or 100% identical to the amino acid sequence of SEQ ID NO:119. In a particular aspect, the moiety capable of specific binding to CEA comprises a heavy chain variable region comprising the amino acid sequence of SEQ ID NO:118 and a light chain variable region comprising the amino acid sequence of SEQ ID NO:119. In a specific aspect, the moiety capable of specific binding to FAP comprises a VH domain consisting of amino acid sequence of SEQ ID NO:118 and a VL domain consisting of the amino acid sequence of SEQ ID NO:119.

In one aspect, provided is a monovalent TNF family ligand trimer-containing antigen binding molecule as described herein before, comprising one moiety capable of specific binding to CEA.

In a particular aspect, provided is a TNF family ligand trimer-containing antigen binding molecule as described herein before, wherein the antigen binding molecule comprises
(i) a variable heavy chain comprising the amino acid sequence of SEQ ID NO:146,
(ii) a variable light chain comprising the amino acid sequence of SEQ ID NO:148, and
(iii) a fusion protein comprising the amino acid sequence of SEQ ID NO:15.

In another aspect, provided is a bivalent TNF family ligand trimer-containing antigen binding molecule as described herein before, comprising two moieties capable of specific binding to CEA.

In a particular aspect, provided is a TNF family ligand trimer-containing antigen binding molecule as described herein before, wherein the antigen binding molecule comprises
(i) a variable heavy chain comprising the amino acid sequence of SEQ ID NO:146,
(ii) a variable light chain comprising the amino acid sequence of SEQ ID NO:148, and
(iii) a fusion protein comprising the amino acid sequence of SEQ ID NO:147.

TNF Family Ligand Trimer-Containing Antigen Binding Molecules, Wherein the Target Cell Antigen is CD19

In yet another aspect, the target cell antigen is CD19. In one aspect, the invention provides a TNF family ligand trimer-containing antigen binding molecule as described herein before, wherein the moiety capable of specific binding to CD19 comprises (a) a VH domain comprising (i) CDR-H1 comprising the amino acid sequence of SEQ ID NO:120, (ii) CDR-H2 comprising the amino acid sequence of SEQ ID NO:121 and (iii) CDR-H3 comprising the amino acid sequence of SEQ ID NO:122, and a VL domain comprising (iv) CDR-L1 comprising the amino acid sequence of SEQ ID NO:123, (v) CDR-L2 comprising the amino acid sequence of SEQ ID NO:124 and (vi) CDR-L3 comprising the amino acid sequence of SEQ ID NO:125, or (b) a VH domain comprising (i) CDR-H1 comprising the amino acid sequence of SEQ ID NO:128, (ii) CDR-H2 comprising the amino acid sequence of SEQ ID NO:129 and (iii) CDR-H3 comprising the amino acid sequence of SEQ ID NO:130, and a VL domain comprising (iv) CDR-L1 comprising the amino acid sequence of SEQ ID NO:131, (v) CDR-L2 comprising the amino acid sequence of SEQ ID NO:132 and (vi) CDR-L3 comprising the amino acid sequence of SEQ ID NO:133.

In a further aspect, the moiety capable of specific binding to CD19 comprises a heavy chain variable region comprising an amino acid sequence that is at least about 95%, 96%, 97%, 98%, 99% or 100% identical to the amino acid sequence of SEQ ID NO:126 and a light chain variable region comprising an amino acid sequence that is at least about 95%, 96%, 97%, 98%, 99% or 100% identical to the amino acid sequence of SEQ ID NO:127. In another aspect, the moiety capable of specific binding to CD19 comprises a heavy chain variable region comprising an amino acid sequence that is at least about 95%, 96%, 97%, 98%, 99% or 100% identical to the amino acid sequence of SEQ ID NO:134 and a light chain variable region comprising an amino acid sequence that is at least about 95%, 96%, 97%, 98%, 99% or 100% identical to the amino acid sequence of SEQ ID NO:135. In a particular aspect, the moiety capable of specific binding to CD19 comprises a heavy chain variable region comprising the amino acid sequence of SEQ ID NO:126 and a light chain variable region comprising the amino acid sequence of SEQ ID NO:127. In a specific aspect, the moiety capable of specific binding to FAP comprises a VH domain consisting of amino acid sequence of SEQ ID NO:118 and a VL domain consisting of the amino acid sequence of SEQ ID NO:119. In another particular aspect, moiety capable of specific binding to CD19 comprises a variable heavy chain comprising an amino acid sequence of SEQ ID NO:134 and a variable light chain comprising an amino acid sequence of SEQ ID NO:135. In a specific aspect, the moiety capable of specific binding to FAP comprises a VH domain consisting of amino acid sequence of SEQ ID NO:134 and a VL domain consisting of the amino acid sequence of SEQ ID NO:135.

In one aspect, provided is a monovalent TNF family ligand trimer-containing antigen binding molecule as described herein before, comprising one moiety capable of specific binding to CD19.

In a particular aspect, provided is a TNF family ligand trimer-containing antigen binding molecule as described herein before, wherein the antigen binding molecule comprises
(i) a variable heavy chain comprising the amino acid sequence of SEQ ID NO:152,
(ii) a variable light chain comprising the amino acid sequence of SEQ ID NO:154, and
(iii) a fusion protein comprising the amino acid sequence of SEQ ID NO:15.

In a further particular aspect, provided is a TNF family ligand trimer-containing antigen binding molecule as described herein before, wherein the antigen binding molecule comprises
(i) a variable heavy chain comprising the amino acid sequence of SEQ ID NO:158,
(ii) a variable light chain comprising the amino acid sequence of SEQ ID NO:160, and
(iii) a fusion protein comprising the amino acid sequence of SEQ ID NO:15.

In another aspect, provided is a bivalent TNF family ligand trimer-containing antigen binding molecule as described herein before, comprising two moieties capable of specific binding to CD19.

In a particular aspect, provided is a TNF family ligand trimer-containing antigen binding molecule as described herein before, wherein the antigen binding molecule comprises
(i) a variable heavy chain comprising the amino acid sequence of SEQ ID NO:152,
(ii) a variable light chain comprising the amino acid sequence of SEQ ID NO:154, and
(iii) a fusion protein comprising the amino acid sequence of SEQ ID NO:153.

In a further particular aspect, provided is a TNF family ligand trimer-containing antigen binding molecule as described herein before, wherein the antigen binding molecule comprises (i) a variable heavy chain comprising the amino acid sequence of SEQ ID NO:158,
(ii) a variable light chain comprising the amino acid sequence of SEQ ID NO:160, and
(iii) a fusion protein comprising the amino acid sequence of SEQ ID NO:159.

Polynucleotides

The invention further provides isolated polynucleotides encoding a TNF family ligand trimer-containing antigen binding molecule as described herein or a fragment thereof.

The isolated polynucleotides encoding TNF ligand trimer-containing antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire TNF family ligand trimer-containing antigen binding molecule according to the invention as described herein. In other embodiments, the isolated polynucleotide encodes a polypeptide comprised in the TNF family ligand trimer-containing antigen binding molecule according to the invention as described herein.

In one aspect, the present invention is directed to an isolated polynucleotide encoding a TNF family ligand trimer-containing antigen binding molecule, wherein the polynucleotide comprises (a) a sequence that encodes a moiety capable of specific binding to a target cell antigen, (b) a sequence that encodes polypeptide comprising three ectodomains of a TNF ligand family member or fragments thereof that are connected to each other by peptide linkers and (c) a sequence that encodes a Fc domain composed of a first and a second subunit capable of stable association.

In another aspect, provided is an isolated polynucleotide encoding a 4-1BB ligand trimer-containing antigen binding molecule, wherein the polynucleotide comprises (a) a sequence that encodes a moiety capable of specific binding to a target cell antigen, (b) a sequence that encodes polypeptide comprising three ectodomains of 4-1BBL or fragments thereof that are connected to each other by peptide linkers and (c) a sequence that encodes a Fc domain composed of a first and a second subunit capable of stable association.

In a further aspect, the invention is directed to an isolated polynucleotide comprising a sequence that encodes a polypeptide comprising three 4-1BBL fragments comprising an amino acid sequence that is at least about 90%, 95%, 98% or 100% identical to an amino acid sequence shown in SEQ ID NO:1, SEQ ID NO: 2, SEQ ID NO:3, SEQ ID NO:4, SEQ ID NO:99, SEQ ID NO: 100, SEQ ID NO:101 and SEQ ID NO:102. In one aspect, provided is an isolated polynucleotide comprising a sequence that encodes a polypeptide comprising the amino acid sequence of SEQ ID NO:5 or SEQ ID NO:103.

In another aspect, provided is an isolated polynucleotide encoding a OX40 ligand trimer-containing antigen binding molecule, wherein the polynucleotide comprises (a) a sequence that encodes a moiety capable of specific binding to a target cell antigen, (b) a sequence that encodes polypeptide comprising three ectodomains of OX40L or fragments thereof that are connected to each other by peptide linkers and (c) a sequence that encodes a Fc domain composed of a first and a second subunit capable of stable association.

In a further aspect, the invention is directed to an isolated polynucleotide comprising a sequence that encodes a polypeptide comprising three OX40L fragments comprising an amino acid sequence that is at least about 90%, 95%, 98% or 100% identical to an amino acid sequence shown in SEQ ID NO:6 or SEQ ID NO:7. In one aspect, provided is an isolated polynucleotide comprising a sequence that encodes a polypeptide comprising the amino acid sequence of SEQ ID NO:8.

In another aspect, provided is an isolated polynucleotide encoding a TNF family ligand trimer-containing antigen binding molecule, wherein the polynucleotide comprises (a) a sequence that encodes a moiety capable of specific binding to a target cell antigen, (b) a sequence that encodes a polypeptide comprising three ectodomains of a TNF ligand family member or fragments thereof that are connected to each other by peptide linkers and that is fused at the C-terminal amino acid to the N-terminal amino acid of a CH2 domain in the Fc domain (c) a sequence that encodes a Fc domain composed of a first and a second subunit capable of stable association. In a further aspect, provided is an isolated polynucleotide encoding a TNF family ligand trimer-containing antigen binding molecule, wherein the polynucleotide comprises (a) a sequence that encodes a moiety capable of specific binding to a target cell antigen, (b) a sequence that encodes a polypeptide comprising three ectodomains of a TNF ligand family member or fragments thereof that are connected to each other by peptide linkers is fused at the N-terminal amino acid to the C-terminal amino acid of a CH3 domain in the Fc domain and (c) a sequence that encodes a Fc domain composed of a first and a second subunit capable of stable association.

In one aspect, the invention is directed to an isolated polynucleotide that comprises a sequence that encodes an IgG1 Fc domain. In a particular aspect, the isolated polynucleotide comprises a sequence that encodes an Fc domain with amino acid substitutions at positions 234, 235 and/or 329 (EU numbering).

In another aspect, the invention is directed to an isolated polynucleotide that comprises a sequence that is at least about 80%, 85%, 90%, 95%, 96%, 97%, 98%, or 99% identical to a nucleic acid sequence as shown in SEQ ID NO:66. In a further aspect, provided is an isolated polynucleotide that comprises a sequence that is at least about 80%, 85%, 90%, 95%, 96%, 97%, 98%, or 99% identical to a nucleic acid sequence as shown in SEQ ID NO:87.

In a further aspect, the invention is directed to an isolated polynucleotide encoding a TNF family ligand trimer-containing antigen binding molecule, wherein the polynucleotide comprises sequences encoding a heavy chain and a light chain, both comprising a Fab molecule capable of specific binding to a target cell antigen, and the nucleic acid sequence of SEQ ID NO:66. In a further aspect, the invention is directed to an isolated polynucleotide encoding a TNF family ligand trimer-containing antigen binding molecule, wherein the polynucleotide comprises sequences encoding a heavy chain and a light chain, both comprising a Fab molecule capable of specific binding to a target cell antigen, and the nucleic acid sequence of SEQ ID NO:87.

In one aspect, provided is an isolated polynucleotide encoding a 4-1BBL trimer-containing antigen binding molecule, wherein the polynucleotide comprises sequences encoding (a) a heavy chain comprising a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a light chain comprising a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, and (b) a polypeptide comprising the amino acid sequence of SEQ ID NO:5.

In another aspect, provided is an isolated polynucleotide encoding a 4-1BBL trimer-containing antigen binding molecule, wherein the polynucleotide comprises sequences encoding (a) a heavy chain comprising a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a light chain comprising a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109, and (b) a polypeptide comprising the amino acid sequence of SEQ ID NO:5.

In a further aspect, provided is an isolated polynucleotide encoding a 4-1BBL trimer-containing antigen binding molecule, wherein the polynucleotide comprises sequences encoding (a) a heavy chain comprising a VH domain comprising (i) CDR-H1 comprising the amino acid sequence of SEQ ID NO:112, (ii) CDR-H2 comprising the amino acid sequence of SEQ ID NO:113 and (iii) CDR-H3 comprising the amino acid sequence of SEQ ID NO:114, and a light chain comprising a VL domain comprising (iv) CDR-L1 comprising the amino acid sequence of SEQ ID NO:115, (v) CDR-L2 comprising the amino acid sequence of SEQ ID NO:116 and (vi) CDR-L3 comprising the amino acid sequence of SEQ ID NO:117, and (b) a polypeptide comprising the amino acid sequence of SEQ ID NO:5.

In yet another aspect, provided is an isolated polynucleotide encoding a 4-1BBL trimer-containing antigen binding molecule, wherein the polynucleotide comprises sequences encoding (a) a heavy chain comprising a VH domain comprising (i) CDR-H1 comprising the amino acid sequence of SEQ ID NO:120, (ii) CDR-H2 comprising the amino acid sequence of SEQ ID NO:121 and (iii) CDR-H3 comprising the amino acid sequence of SEQ ID NO:122, and a light chain comprising a VL domain comprising (iv) CDR-L1 comprising the amino acid sequence of SEQ ID NO:123, (v) CDR-L2 comprising the amino acid sequence of SEQ ID NO:124 and (vi) CDR-L3 comprising the amino acid sequence of SEQ ID NO:125, and (b) a polypeptide comprising the amino acid sequence of SEQ ID NO:5.

In a further aspect, provided is an isolated polynucleotide encoding a 4-1BBL trimer-containing antigen binding molecule, wherein the polynucleotide comprises sequences encoding (a) a heavy chain comprising a VH domain comprising (i) CDR-H1 comprising the amino acid sequence of SEQ ID NO:128, (ii) CDR-H2 comprising the amino acid sequence of SEQ ID NO:129 and (iii) CDR-H3 comprising the amino acid sequence of SEQ ID NO:130, and a light chain comprising a VL domain comprising (iv) CDR-L1 comprising the amino acid sequence of SEQ ID NO:131, (v) CDR-L2 comprising the amino acid sequence of SEQ ID NO:132 and (vi) CDR-L3 comprising the amino acid sequence of SEQ ID NO:133, and (b) a polypeptide comprising the amino acid sequence of SEQ ID NO:5.

In a further aspect, the invention provides an isolated polynucleotide encoding a 4-1BBL trimer-containing antigen binding molecule, wherein the polynucleotide comprises sequences encoding (a) a moiety capable of specific binding to FAP comprising a VH domain consisting of amino acid sequence of SEQ ID NO:16 and a VL domain consisting of the amino acid sequence of SEQ ID NO:17 and b) a polypeptide comprising the amino acid sequence of SEQ ID NO:5.

In a particular aspect, the invention provides an isolated polynucleotide encoding a 4-1BBL trimer-containing antigen binding molecule, wherein the polynucleotide comprises sequences encoding (i) a heavy chain comprising the amino acid sequence of SEQ ID NO:16, (ii) a light chain comprising the amino acid sequence of SEQ ID NO:17, and (iii) a fusion protein comprising the amino acid sequence of SEQ ID NO:15.

In a further aspect, the invention provides an isolated polynucleotide encoding a 4-1BBL trimer-containing antigen binding molecule, wherein the polynucleotide comprises sequences encoding (a) a moiety capable of specific binding to FAP comprising a VH domain consisting of amino acid sequence of SEQ ID NO:110 and a VL domain consisting of the amino acid sequence of SEQ ID NO:111 and b) a polypeptide comprising the amino acid sequence of SEQ ID NO:5.

In a particular aspect, the invention provides an isolated polynucleotide encoding a 4-1BBL trimer-containing antigen binding molecule, wherein the polynucleotide comprises sequences encoding (i) a heavy chain comprising the amino acid sequence of SEQ ID NO:110, (ii) a light chain comprising the amino acid sequence of SEQ ID NO:111, and (iii) a fusion protein comprising the amino acid sequence of SEQ ID NO:15.

In another aspect, provided is an isolated polynucleotide encoding a OX40L trimer-containing antigen binding molecule, wherein the polynucleotide comprises sequences encoding (a) a heavy chain comprising a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a light chain comprising a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, and (b) a polypeptide comprising the amino acid sequence of SEQ ID NO:8.

In a further aspect, the invention provides an isolated polynucleotide encoding a OX40L trimer-containing antigen binding molecule, wherein the polynucleotide comprises sequences encoding (a) a moiety capable of specific binding to FAP comprising a VH domain consisting of amino acid sequence of SEQ ID NO:16 and a VL domain consisting of the amino acid sequence of SEQ ID NO:17 and b) a polypeptide comprising the amino acid sequence of SEQ ID NO:8.

In a particular aspect, the invention provides an isolated polynucleotide encoding a OX40L trimer-containing antigen binding molecule, wherein the polynucleotide comprises sequences encoding (i) a heavy chain comprising the amino acid sequence of SEQ ID NO:16, (ii) a light chain comprising the amino acid sequence of SEQ ID NO:17, and (iii) a fusion protein comprising the amino acid sequence of SEQ ID NO:20.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

TNF family ligand trimer-containing antigen binding molecules of the invention may be obtained, for example, by solid-state peptide synthesis (e.g. Merrifield solid phase synthesis) or recombinant production. For recombinant production one or more polynucleotide encoding the TNF family ligand trimer-containing antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the TNF family ligand trimer-containing antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the TNF family ligand trimer-containing antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the TNF family ligand trimer-containing antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the TNF family ligand trimer-containing antigen binding molecule or polypeptide fragments thereof is desired, DNA encoding a signal sequence may be placed upstream of the nucleic acid encoding a TNF family ligand trimer-containing antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a TNF family ligand trimer-containing antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a TNF family ligand trimer-containing antigen binding molecule of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as $E.$ $coli$, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of $Spodoptera$ $frugiperda$ cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a TNF family ligand trimer-containing antigen binding molecule of the invention or polypeptide fragments thereof is provided, wherein the method comprises culturing a host cell comprising polynucleotides encoding the TNF family ligand trimer-containing antigen binding molecule of the invention or polypeptide fragments thereof, as provided herein, under conditions suitable for expression of the TNF family ligand trimer-containing antigen binding molecule of the invention or polypeptide fragments thereof, and recovering the TNF family ligand trimer-containing antigen binding molecule of the invention or polypeptide fragments thereof from the host cell (or host cell culture medium).

In the TNF family ligand trimer-containing antigen binding molecule of the invention, the components (at least one moiety capable of specific binding to a target cell antigen, one polypeptide comprising three ectodomains of a TNF ligand family member or fragments thereof and a Fc domain) are not all genetically fused to each other. The polypeptides are designed such that its components (three ectodomains of a TNF ligand family member or fragments thereof and other components such as CH2 and CH3 of the Fc domain) are fused to each other directly or through a linker sequence. The composition and length of the linker may be determined in accordance with methods well known in the art and may be tested for efficacy. Examples of linker sequences between different components of the antigen binding molecules of the invention are found in the sequences provided herein. Additional sequences may also be included to incorporate a cleavage site to separate the individual components of the fusion protein if desired, for example an endopeptidase recognition sequence.

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to a target cell antigen (e.g. Fab fragments) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

TNF ligand trimer-containing antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the TNF ligand trimer-containing antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the TNF ligand trimer-containing antigen binding molecule or fragments thereof can be determined by any of a variety of well-known analytical methods including gel electrophoresis, high pressure liquid chromatography, and the like. For example, the TNF ligand trimer-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity Assays

The affinity of the TNF family ligand trimer-containing antigen binding molecule provided herein for the corresponding TNF receptor can be determined in accordance with the methods set forth in the Examples by surface plasmon resonance (SPR), using standard instrumentation such as a BIACORE® instrument (GE Healthcare), and receptors or target proteins such as may be obtained by recombinant expression. The affinity of the TNF family ligand trimer-containing antigen binding molecule for the target cell antigen can also be determined by surface plasmon resonance (SPR), using standard instrumentation such as a BIACORE® instrument (GE Healthcare), and receptors or target proteins such as may be obtained by recombinant expression. A specific illustrative and exemplary embodiment for measuring binding affinity is described in Example 4. According to one aspect, $K_D$ is measured by surface plasmon resonance using a BIACORE® T100 machine (GE Healthcare) at 25° C.

2. Binding Assays and Other Assays

Binding of the TNF family ligand trimer-containing antigen binding molecule provided herein to the corresponding receptor expressing cells may be evaluated using cell lines expressing the particular receptor or target antigen, for example by flow cytometry (FACS). In one aspect, fresh peripheral blood mononuclear cells (PBMCs) expressing the TNF receptor are used in the binding assay. These cells are used directly after isolation (naïve PMBCs) or after stimulation (activated PMBCs). In another aspect, activated mouse splenocytes (expressing the TNF receptor molecule) were used to demonstrate the binding of the TNF family ligand trimer-containing antigen binding molecule of the invention to the corresponding TNF receptor expressing cells.

In a further aspect, cancer cell lines expressing the target cell antigen, for example FAP, were used to demonstrate the binding of the antigen binding molecules to the target cell antigen.

In another aspect, competition assays may be used to identify an antigen binding molecule that competes with a specific antibody or antigen binding molecule for binding to the target or TNF receptor, respectively. In certain embodiments, such a competing antigen binding molecule binds to the same epitope (e.g., a linear or a conformational epitope) that is bound by a specific anti-target antibody or a specific anti-TNF receptor antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

3. Activity Assays

In one aspect, assays are provided for identifying TNF family ligand trimer-containing antigen binding molecules that bind to a specific target cell antigen and to a specific TNF receptor having biological activity. Biological activity may include, e.g., agonistic signalling through the TNF receptor on cells expressing the target cell antigen. TNF family ligand trimer-containing antigen binding molecules identified by the assays as having such biological activity in vitro are also provided.

In certain aspects, a TNF family ligand trimer-containing antigen binding molecule of the invention is tested for such biological activity. Assays for detecting the biological activity of the molecules of the invention are those described in Example 6. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition the biological activity of such complexes can be assessed by evaluating their effects on survival, proliferation and lymphokine secretion of various lymphocyte subsets such as NK cells, NKT-cells or γ6 T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the TNF family ligand trimer-containing antigen binding molecules provided herein, e.g., for use in any of the below therapeutic methods. In one embodiment, a pharmaceutical composition comprises any of the TNF family ligand trimer-containing antigen binding molecules provided herein and at least one pharmaceutically acceptable excipient. In another embodiment, a pharmaceutical composition comprises any of the TNF family ligand trimer-containing antigen binding molecules provided herein and at least one additional therapeutic agent, e.g., as described below.

Pharmaceutical compositions of the present invention comprise a therapeutically effective amount of one or more TNF family ligand trimer-containing antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one TNF family ligand trimer-containing antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the TNF family ligand trimer-containing antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The TNF family ligand trimer-containing antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the TNF family ligand trimer-containing antigen binding molecules provided herein may be used in therapeutic methods.

For use in therapeutic methods, TNF family ligand trimer-containing antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, TNF family ligand trimer-containing antigen binding molecules of the invention for use as a medicament are provided. In further aspects, TNF family ligand trimer-containing antigen binding molecules of the invention for use in treating a disease, in particular for use in the treatment of cancer, are provided. In certain aspects, TNF family ligand trimer-containing antigen binding molecules of the invention for use in a method of treatment are provided. In one aspect, the invention provides a TNF family ligand trimer-containing antigen binding molecule as described herein for use in the treatment of a disease in an individual in need thereof. In certain aspects, the invention provides a TNF family ligand trimer-containing antigen binding molecule for use in a method of treating an individual having a disease comprising administering to the individual a therapeutically effective amount of the fusion protein. In certain aspects, the disease to be treated is cancer. Examples of cancers include solid tumors, bladder cancer, renal cell carcinoma, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer, melanoma, B-cell lymphoma, B-cell leukemia, non-Hodgkin lymphoma and acute lymphoblastic leukemia. Thus, a TNF family ligand trimer-containing antigen binding molecule as described herein for use in the treatment of cancer is provided. The subject, patient, or "individual" in need of treatment is typically a mammal, more specifically a human.

In another aspect, provided is a TNF family ligand trimer-containing antigen binding molecule as described herein for use in the treatment of infectious diseases, in particular for the treatment of viral infections. In a further aspect, provided is a TNF family ligand trimer-containing antigen binding molecule as described herein for use in the treatment of autoimmune diseases such as for example Lupus disease.

In one aspect, provided is a TNF family ligand trimer-containing antigen binding molecule according to the invention for use in treating head and neck squamous cell carcinoma (HNSCC), breast cancer, colorectal cancer (CRC), pancreatic cancer (PAC), gastric cancer, non-small-cell lung carcinoma (NSCLC) and Mesothelioma, wherein the target cell antigen is FAP.

In a further aspect, the invention relates to the use of a TNF family ligand trimer-containing antigen binding molecule in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Thus, in one aspect, the invention relates to the use of a TNF family ligand trimer-containing antigen binding molecule of the invention in the manufacture or preparation of a medicament for the treatment of cancer. Examples of cancers include solid tumors, bladder cancer, renal cell carcinoma, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer, melanoma, B-cell lymphoma, B-cell leukemia, non-Hodgkin lymphoma and acute lymphoblastic leukemia. Other cell proliferation disorders that can be treated using a TNF family ligand trimer-containing antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan may recognize that in some cases the TNF family ligand trimer-containing antigen binding molecule may not provide a cure but may only provide partial benefit. In some aspects, a physiological change having some benefit is also considered therapeutically beneficial. Thus, in some aspects, an amount of TNF family ligand trimer-containing antigen binding molecule that provides a physiological change is considered an "effective amount" or a "therapeutically effective amount".

In a further aspect, the invention relates to the use of a TNF family ligand trimer-containing antigen binding molecule as described herein in the manufacture or preparation of a medicament for the treatment of infectious diseases, in particular for the treatment of viral infections or for the treatment of autoimmune diseases, for example Lupus disease.

In a further aspect, the invention provides a method for treating a disease in an individual, comprising administering to said individual a therapeutically effective amount of a TNF family ligand trimer-containing antigen binding molecule of the invention. In one aspect a composition is administered to said individual, comprising a fusion protein of the invention in a pharmaceutically acceptable form. In certain aspects, the disease to be treated is a proliferative disorder. In a particular aspect, the disease is cancer. In another aspect, the disease is an infectious disease or an autoimmune disease. In certain aspects, the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a TNF family ligand trimer-containing antigen binding molecule of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The TNF family ligand trimer-containing antigen binding molecule is suitably administered to the patient at one time or over a series of treatments. Depending on the type and severity of the disease, about 1 µg/kg to 15 mg/kg (e.g. 0.1 mg/kg-10 mg/kg) of TNF family ligand trimer-containing antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The TNF family ligand trimer-containing antigen binding molecules of the invention will generally be used in an amount effective to achieve the intended purpose. For use to treat or prevent a disease condition, the TNF family ligand trimer-containing antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the TNF family ligand trimer-containing antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the TNF family ligand trimer-containing antigen binding molecule may not be related to plasma concentration. One skilled in the art will be able to optimize therapeutically effective local dosages without undue experimentation.

A therapeutically effective dose of the TNF family ligand trimer-containing antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. TNF family ligand trimer-containing antigen binding molecules that exhibit large therapeutic indices are preferred. In one embodiment, the TNF family ligand trimer-containing antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The TNF family ligand trimer-containing antigen binding molecules of the invention may be administered in combination with one or more other agents in therapy. For instance, a fusion protein of the invention may be coadministered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The TNF family ligand trimer-containing antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the TNF family ligand trimer-containing antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a TNF ligand trimer-containing antigen binding molecule of the invention.

The label or package insert indicates that the composition is used for treating the condition of choice. Moreover, the article of manufacture may comprise (a) a first container with a composition contained therein, wherein the composition comprises a TNF ligand trimer-containing antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C (Sequences):

| SEQ ID NO: | Name | Sequence |
|---|---|---|
| 1 | Human (hu) 4-1BBL (71-254) | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSE |
| 2 | hu 4-1BBL (85-254) | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGLPSPRSE |
| 3 | hu 4-1BBL (80-254) | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGLPSPRSE |
| 4 | hu 4-1BBL (52-254) | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGLPSPRSE |
| 5 | trimeric hu 4-1BBL (71-254) connected by (G4S)$_2$ linker | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM FAQLVAQNVLLIDGPLSWYSDPGLAGVSLTGGLSYK EDTKELVVAKAGVYYVFFQLELRRVVAGEGSGSVSL |

TABLE C-continued (Sequences):

| SEQ ID NO: | Name | Sequence |
|---|---|---|
| | | ALHLQPLRSAAGAAALALTVDLPPASSEARNSAFGF QGRLLHLSAGQRLGVHLHTEARARHAWQLTQGATV LGLFRVTPEIPAGLPSPRSEGGGGSGGGGSREGPELSP DDPAGLLDLRQGMFAQLVAQNVLLIDGPLSWYSDP GLAGVSLTGGLSYKEDTKELVVAKAGVYYVFFQLEL RRVVAGEGSGSVSLALHLQPLRSAAGAAALALTVDL PPASSEARNSAFGFQGRLLHLSAGQRLGVHLHTEAR ARHAWQLTQGATVLGLFRVTPEIPAGLPSPRSE |
| 6 | hu OX40L (51-183) | QVSHRYPRIQSIKVQFTEYKKEKGFILTSQKEDEIMK VQNNSVIINCDGFYLISLKGYFSQEVNISLHYQKDEEP LFQLKKVRSVNSLMVASLTYKDKVYLNVTTDNTSL DDFHVNGGELILIHQNPGEFCVL |
| 7 | hu OX40L (52-183) | VSHRYPRIQSIKVQFTEYKKEKGFILTSQKEDEIMKV QNNSVIINCDGFYLISLKGYFSQEVNISLHYQKDEEPL FQLKKVRSVNSLMVASLTYKDKVYLNVTTDNTSLD DFHVNGGELILIHQNPGEFCVL |
| 8 | trimeric hu OX40L (51-183) connected by (G4S)$_2$ linker | QVSHRYPRIQSIKVQFTEYKKEKGFILTSQKEDEIMK VQNNSVIINCDGFYLISLKGYFSQEVNISLHYQKDEEP LFQLKKVRSVNSLMVASLTYKDKVYLNVTTDNTSL DDFHVNGGELILIHQNPGEFCVLGGGGSGGGGSQVS HRYPRIQSIKVQFTEYKKEKGFILTSQKEDEIMKVQN NSVIINCDGFYLISLKGYFSQEVNISLHYQKDEEPLFQ LKKVRSVNSLMVASLTYKDKVYLNVTTDNTSLDDF HVNGGELILIHQNPGEFCVLGGGGSGGGGSQVSHRY PRIQSIKVQFTEYKKEKGFILTSQKEDEIMKVQNNSVI INCDGFYLISLKGYFSQEVNISLHYQKDEEPLFQLKK VRSVNSLMVASLTYKDKVYLNVTTDNTSLDDFHVN GGELILIHQNPGEFCVL |
| 9 | FAP(28H1) CDR-H1 | SHAMS |
| 10 | FAP(28H1) CDR-H2 | AIWASGEQYYADSVKG |
| 11 | FAP(28H1) CDR-H3 | GWLGNFDY |
| 12 | FAP(28H1) CDR-L1 | RASQSVSRSYLA |
| 13 | FAP(28H1) CDR-L2 | GASTRAT |
| 14 | FAP(28H1) CDR-L3 | QQGQVIPPT |
| 15 | trimeric hu 4-1BBL (71-254) Fc knob chain | See Table 1 |
| 16 | FAP(28H1) VH | EVQLLESGGGLVQPGGSLRLSCAASGFTFSSHA MSWVRQAPGKGLEWVSAIWASGEQYYADSVK GRFTISRDNSKNTLYLQMNSLRAEDTAVYYCAK GWLGNFDYWGQGTLVTVSS |
| 17 | FAP(28H1) VL | EIVLTQSPGTLSLSPGERATLSCRASQSVSRSYLA WYQQKPGQAPRLLIIGASTRATGIPDRFSGSGSG TDFTLTISRLEPEDFAVYYCQQGQVIPPTFGQGT KVEIK |
| 18 | FAP(28H1) Fc hole chain | See Table 1 |
| 19 | FAP(28H1) light chain | See Table 1 |
| 20 | trimeric hu OX40L (51-183)-Fc knob chain | See Table 27 |
| 21 | Human (hu) FAP | UniProt no. Q12884 |
| 22 | hu FAP ectodomain + poly-lys-tag + his$_6$-tag | RPSRVHNSEENTMRALTLKDILNGTFSYKTFFPNWIS GQEYLHQSADNNIVLYNIETGQSYTILSNRTMKSVNA SNYGLSPDRQFVYLESDYSKLWRYSYTATYYIYDLS NGEFVRGNELPRPIQYLCWSPVGSKLAYVYQNNIYL KQRPGDPPFQITFNGRENKIFNGIPDWVYEEEMLATK YALWWSPNGKFLAYAEFNDTDIPVIAYSYYGDEQYP RTINIPYPKAGAKNPVVRIFIIDTTYPAYVGPQEVPVP AMIASSDYYFSWLTWVTDERVCLQWLKRVQNVSVL SICDFREDWQTWDCPKTQEHIEESRTGWAGGFFVST |

TABLE C-continued (Sequences):

| SEQ ID NO: | Name | Sequence |
|---|---|---|
| | | PVFSYDAISYYKIFSDKDGYKHIHYIKDTVENAIQITS GKWEAINIFRVTQDSLFYSSNEFEEYPGRRNIYRISIGS YPPSKKCVTCHLRKERCQYYTASFSDYAKYYALVCY GPGIPISTLHDGRTDQEIKILEENKELENALKNIQLPKE EIKKLEVDEITLWYKMILPPQFDRSKKYPLLIQVYGG PCSQSVRSVFAVNWISYLASKEGMVIALVDGRGTAF QGDKLLYAVYRKLGVYEVEDQITAVRKFIEMGFIDE KRIAIWGWSYGGYVSSLALASGTGLFKCGIAVAPVSS WEYYASVYTERFMGLPTKDDNLEHYKNSTVMARAE YFRNVDYLLIHGTADDNVHFQNSAQIAKALVNAQV DFQAMWYSDQNHGLSGLSTNHLYTHMTHFLKQCFS LSDGKKKKKKGHHHHHH |
| 23 | nucleotide sequence hu FAP ectodomain + poly-lys-tag + his$_6$-tag | CGCCCTTCAAGAGTTCATAACTCTGAAGAAAATAC AATGAGAGCACTCACACTGAAGGATATTTTAAATG GAACATTTTCTTATAAAACATTTTTTCCAAACTGGA TTTCAGGACAAGAATATCTTCATCAATCTGCAGAT AACAATATAGTACTTTATAATATTGAAACAGGACA ATCATATACCATTTTGAGTAATAGAACCATGAAAA GTGTGAATGCTTCAAATTACGGCTTATCACCTGAT CGGCAATTTGTATATCTAGAAAGTGATTATTCAAA GCTTTGGAGATACTCTTACACAGCAACATATTACA TCTATGACCTTAGCAATGGAGAATTTGTAAGAGGA AATGAGCTTCCTCGTCCAATTCAGTATTTATGCTGG TCGCCTGTTGGGAGTAAATTAGCATATGTCTATCA AAACAATATCTATTTGAAACAAAGACCAGGAGAT CCACCTTTTCAAATAACATTTAATGGAAGAGAAAA TAAAATATTTAATGGAATCCCAGACTGGGTTTATG AAGAGGAAATGCTTGCTACAAAATATGCTCTCTGG TGGTCTCCTAATGGAAAATTTTTGGCATATGCGGA ATTTAATGATACGGATATACCAGTTATTGCCTATTC CTATTATGGCGATGAACAATATCCTAGAACAATAA ATATTCCATACCCAAAGGCTGGAGCTAAGAATCCC GTTGTTCGGATATTTATTATCGATACCACTTACCCT GCGTATGTAGGTCCCCAGGAAGTGCCTGTTCCAGC AATGATAGCCTCAAGTGATTATTATTTCAGTTGGC TCACGTGGGTTACTGATGAACGAGTATGTTTGCAG TGGCTAAAAAGAGTCCAGAATGTTTCGGTCCTGTC TATATGTGACTTCAGGGAAGACTGGCAGACATGGG ATTGTCCAAAGACCCAGGAGCATATAGAAGAAAG CAGAACTGGATGGGCTGGTGGATTCTTTGTTTCAA CACCAGTTTTCAGCTATGATGCCATTTCGTACTACA AAATATTTAGTGACAAGGATGGCTACAAACATATT CACTATATCAAAGACACTGTGGAAAATGCTATTCA AATTACAAGTGGCAAGTGGGAGGCCATAAATATA TTCAGAGTAACACAGGATTCACTGTTTTATTCTAG CAATGAATTTGAAGAATACCCTGGAAGAAGAAAC ATCTACAGAATTAGCATTGGAAGCTATCCTCCAAG CAAGAAGTGTGTTACTTGCCATCTAAGGAAAGAAA GGTGCCAATATTACACAGCAAGTTTCAGCGACTAC GCCAAGTACTATGCACTTGTCTGCTACGGCCCAGG CATCCCCATTTCCACCCTTCATGATGGACGCACTG ATCAAGAAATTAAAATCCTGGAAGAAAACAAGGA ATTGGAAAATGCTTTGAAAAATATCCAGCTGCCTA AAGAGGAAATTAAGAAACTTGAAGTAGATGAAAT TACTTTATGGTACAAGATGATTCTTCCTCCTCAATT TGACAGATCAAAGAAGTATCCCTTGCTAATTCAAG TGTATGGTGGTCCCTGCAGTCAGAGTGTAAGGTCT GTATTTGCTGTTAATTGGATATCTTATCTTGCAAGT AAGGAAGGGATGGTCATTGCCTTGGTGGATGGTCG AGGAACAGCTTTCCAAGGTGACAAACTCCTCTATG CAGTGTATCGAAAGCTGGGTGTTTATGAAGTTGAA GACCAGATTACAGCTGTCAGAAAATTCATAGAAAT GGGTTTCATTGATGAAAAAGAATAGCCATATGGG GCTGGTCCTATGGAGGATACGTTTCATCACTGGCC CTTGCATCTGGAACTGGTCTTTTCAAATGTGGTATA GCAGTGGCTCCAGTCTCCAGCTGGGAATATTACGC GTCTGTCTACACAGAGAGATTCATGGGTCTCCCAA CAAAGGATGATAATCTTGAGCACTATAAGAATTCA ACTGTGATGGCAAGAGCAGAATATTTCAGAAATGT AGACTATCTTCTCATCCACGGAACAGCAGATGATA ATGTGCACTTTCAAAACTCAGCACAGATTGCTAAA GCTCTGGTTAATGCACAAGTGGATTTCCAGGCAAT GTGGTACTCTGACCAGAACCACGGCTTATCCGGCC TGTCCACGAACCACTTATACACCCACATGACCCAC |

TABLE C-continued (Sequences):

| SEQ ID NO: | Name | Sequence |
|---|---|---|
| | | TTCCTAAAGCAGTGTTTCTCTTTGTCAGACGGCAA |
| | | AAAGAAAAAGAAAAAGGGCCACCACCATCACCAT |
| | | CAC |
| 24 | mouse FAP | UniProt no. P97321 |
| 25 | Murine FAP ectodomain + poly-lys-tag + his$_6$-tag | RPSRVYKPEGNTKRALTLKDILNGTFSYKTYFPNWIS EQEYLHQSEDDNIVFYNIETRESYIILSNSTMKSVNAT DYGLSPDRQFVYLESDYSKLWRYSYTATYYIYDLQN GEFVRGYELPRPIQYLCWSPVGSKLAYVYQNNIYLK QRPGDPPFQITYTGRENRIFNGIPDWVYEEEMLATKY ALWWSPDGKFLAYVEFNDSDIPIIAYSYYGDGQYPR TINIPYPKAGAKNPVVRVFIVDTTYPHHVGPMEVPVP EMIASSDYYFSWLTWVSSERVCLQWLKRVQNVSVL SICDFREDWHAWECPKNQEHVEESRTGWAGGFFVST PAFSQDATSYYKIFSDKDGYKHIHYIKDTVENAIQITS GKWEAIYIFRVTQDSLFYSSNEFEGYPGRRNIYRISIG NSPPSKKCVTCHLRKERCQYYTASFSYKAKYYALVC YGPGLPISTLHDGRTDQEIQVLEENKELENSLRNIQLP KVEIKKLKDGGLTFWYKMILPPQFDRSKKYPLLIQVY GGPCSQSVKSVFAVNWITYLASKEGIVIALVDGRGTA FQGDKFLHAVYRKLGVYEVEDQLTAVRKFIEMGPID EERIAIWGWSYGGYVSSLALASGTGLFKCGIAVAPVS SWEYYASIYSERFMGLPTKDDNLEHYKNSTVMARA EYFRNVDYLLIHGTADDNVHFQNSAQIAKALVNAQV DFQAMWYSDQNHGILSGRSQNHLYTHMTHFLKQCF SLSDGKKKKKGHHHHHH |
| 26 | nucleotide sequence Murine FAP ectodomain + poly-lys-tag + his$_6$-tag | CGTCCCTCAAGAGTTTACAAACCTGAAGGAAACAC AAAGAGAGCTCTTACCTTGAAGGATATTTTAAATG GAACATTCTCATATAAAACATATTTTCCCAACTGG ATTTCAGAACAAGAATATCTTCATCAATCTGAGGA TGATAACATAGTATTTTATAATATTGAAACAAGAG AATCATATATCATTTTGAGTAATAGCACCATGAAA AGTGTGAATGCTACAGATTATGGTTTGTCACCTGA TCGGCAATTTGTGTATCTAGAAAGTGATTATTCAA AGCTCTGGCGATATTCATACACAGCGACATACTAC ATCTACGACCTTCAGAATGGGGAATTTGTAAGAGG ATACGAGCTCCCTCGTCCAATTCAGTATCTATGCT GGTCGCCTGTTGGGAGTAAATTAGCATATGTATAT CAAAACAATATTTATTTGAAACAAAGACCAGGAG ATCCACCTTTTCAAATAACTTATACTGGAAGAGAA AATAGAATATTTAATGGAATACCAGACTGGGTTTA TGAAGAGGAAATGCTTGCCACAAAATATGCTCTTT GGTGGTCTCCAGATGGAAAATTTTTGGCATATGTA GAATTTAATGATTCAGATATACCAATTATTGCCTA TTCTTATTATGGTGATGGACAGTATCCTAGAACTA TAAATATTCCATATCCAAAGGCTGGGGCTAAGAAT CCGGTTGTTCGTGTTTTTATTGTTGACACCACCTAC CCTCACCACGTGGGCCCAATGGAAGTGCCAGTTCC AGAAATGATAGCCTCAAGTGACTATTATTTCAGCT GGCTCACATGGGTGTCCAGTGAACGAGTATGCTTG CAGTGGCTAAAAAGAGTGCAGAATGTCTCAGTCCT GTCTATATGTGATTTCAGGGAAGACTGGCATGCAT GGGAATGTCCAAAGAACCAGGAGCATGTAGAAGA AAGCAGAACAGGATGGGCTGGTGGATTCTTTGTTT CGACACCAGCTTTTAGCCAGGATGCCACTTCTTAC TACAAAATATTTAGCGACAAGGATGGTTACAAACA TATTCACTACATCAAAGACACTGTGGAAAATGCTA TTCAAATTACAAGTGGCAAGTGGGAGGCCATATAT ATATTCCGCGTAACACAGGATTCACTGTTTTATTCT AGCAATGAATTTGAAGGTTACCCTGGAAGAAGAA ACATCTACAGAATTAGCATTGGAAACTCTCCTCCG AGCAAGAAGTGTGTTACTTGCCATCTAAGGAAAGA AAGGTGCCAATATTACACAGCAAGTTTCAGCTACA AAGCCAAGTACTATGCACTCGTCTGCTATGGCCCT GGCCTCCCCATTTCCACCCTCCATGATGGCCGCAC AGACCAAGAAATACAAGTATTAGAAGAAAACAAA GAACTGGAAAATTCTCTGAGAAATATCCAGCTGCC TAAAGTGGAGATTAAGAAGCTCAAAGACGGGGGA CTGACTTTCTGGTACAAGATGATTCTGCCTCCTCAG TTTGACAGATCAAAGAAGTACCCTTTGCTAATTCA AGTGTATGGTGGTCCTTGTAGCCAGAGTGTTAAGT CTGTGTTTGCTGTTAATTGGATAACTTATCTCGCAA GTAAGGAGGGGATAGTCATTGCCCTGGTAGATGGT |

TABLE C-continued (Sequences):

| SEQ ID NO: Name | Sequence |
|---|---|
| | CGGGGCACTGCTTTCCAAGGTGACAAATTCCTGCA TGCCGTGTATCGAAAACTGGGTGTATATGAAGTTG AGGACCAGCTCACAGCTGTCAGAAAATTCATAGA AATGGGTTTCATTGATGAAGAAAGAATAGCCATAT GGGGCTGGTCCTACGGAGGTTATGTTTCATCCCTG GCCCTTGCATCTGGAACTGGTCTTTTCAAATGTGG CATAGCAGTGGCTCCAGTCTCCAGCTGGGAATATT ACGCATCTATCTACTCAGAGAGATTCATGGGCCTC CCAACAAAGGACGACAATCTCGAACACTATAAAA ATTCAACTGTGATGGCAAGAGCAGAATATTTCAGA AATGTAGACTATCTTCTCATCCACGGAACAGCAGA TGATAATGTGCACTTTCAGAACTCAGCACAGATTG CTAAAGCTTTGGTTAATGCACAAGTGGATTTCCAG GCGATGTGGTACTCTGACCAGAACCATGGTATATT ATCTGGGCGCTCCCAGAATCATTTATATACCCACA TGACGCACTTCCTCAAGCAATGCTTTTCTTTATCAG ACGGCAAAAGAAAAAGAAAAAGGGCCACCACCA TCACCATCAC |
| 27 Cynomolgus FAP ectodomain + poly-lys-tag + his$_6$-tag | RPPRVHNSEENTMRALTLKDILNGTFSYKTFFPNWIS GQEYLHQSADNNIVLYNIETGQSYTILSNRTMKSVNA SNYGLSPDRQFVYLESDYSKLWRYSYTATYYIYDLS NGEFVRGNELPRPIQYLCWSPVGSKLAYVYQNNIYL KQRPGDPPFQITFNGRENKIFNGIPDWVYEEEMLATK YALWWSPNGKFLAYAEFNDTDIPVIAYSYYGDEQYP RTINIPYPKAGAKNPFVRIFIIDTTYPAYVGPQEVPVP AMIASSDYYFSWLTWVTDERVCLQWLKRVQNVSVL SICDFREDWQTWDCPKTQEHIEESRTGWAGGFFVST PVFSYDAISYYKIFSDKDGYKHIHYIKDTVENAIQITS GKWEAINIFRVTQDSLFYSSNEFEDYPGRRNIYRISIG SYPPSKKCVTCHLRKERCQYYTASFSDYAKYYALVC YGPGIPISTLHDGRTDQEIKILEENKELENALKNIQLP KEEIKKLEVDEITLWYKMILPPQFDRSKKYPLLIQVY GGPCSQSVRSVFAVNWISYLASKEGMVIALVDGRGT AFQGDKLLYAVYRKLGVYEVEDQITAVRKFIEMGFI DEKRIAIWGWSYGGYVSSLALASGTGLFKCGIAVAP VSSWEYYASVYTERFMGLPTKDDNLEHYKNSTVMA RAEYFRNVDYLLIHGTADDNVHFQNSAQIAKALVNA QVDFQAMWYSDQNHGLSGLSTNHLYTHMTHFLKQ CFSLSDGKKKKKKGHHHHHH |
| 28 nucleotide sequence Cynomolgus FAP ectodomain + poly-lys-tag + his$_6$-tag | CGCCCTCCAAGAGTTCATAACTCTGAAGAAAATAC AATGAGAGCACTCACACTGAAGGATATTTTAAATG GGACATTTTCTTATAAAACATTTTTTCCAAACTGGA TTTCAGGACAAGAATATCTTCATCAATCTGCAGAT AACAATATAGTACTTTATAATATTGAAACAGGACA ATCATATACCATTTTGAGTAACAGAACCATGAAAA GTGTGAATGCTTCAAATTATGGCTTATCACCTGAT CGGCAATTTGTATATCTAGAAAGTGATTATTCAAA GCTTTGGAGATACTCTTACACAGCAACATATTACA TCTATGACCTTAGCAATGGAGAATTTGTAAGAGGA AATGAGCTTCCTCGTCCAATTCAGTATTTATGCTGG TCGCCTGTTGGGAGTAAATTAGCATATGTCTATCA AAACAATATCTATTTGAAACAAAGACCAGGAGAT CCACCTTTTCAAATAACATTTAATGGAAGAGAAAA TAAAATATTTAATGGAATCCCAGACTGGGTTTATG AAGAGGAAATGCTTGCTACAAAATATGCTCTCTGG TGGTCTCCTAATGGAAAATTTTTGGCATATGCGGA ATTTAATGATACAGATATACCAGTTATTGCCTATTC CTATTATGGCGATGAACAATATCCCAGAACAATAA ATATTCCATACCCAAAGGCCGGAGCTAAGAATCCT TTTGTTCGGATATTTATTATCGATACCACTTACCCT GCGTATGTAGGTCCCCAGGAAGTGCCTGTTCCAGC AATGATAGCCTCAAGTGATTATTATTTCAGTTGGC TCACGTGGGTTACTGATGAACGAGTATGTTTGCAG TGGCTAAAAAGAGTCCAGAATGTTTCGGTCTTGTC TATATGTGATTTCAGGGAAGACTGGCAGACATGGG ATTGTCCAAAGACCCAGGAGCATATAGAAGAAAG CAGAACTGGATGGGCTGGTGGATTCTTTGTTTCAA CACCAGTTTTCAGCTATGATGCCATTTCATACTACA AAATATTTAGTGACAAGGATGGCTACAAACATATT CACTATATCAAAGACACTGTGGAAAATGCTATTCA AATTACAAGTGGCAAGTGGGAGGCCATAAATATA TTCAGAGTAACACAGGATTCACTGTTTTATTCTAG CAATGAATTTGAAGATTACCCTGGAAGAAGAAAC |

TABLE C-continued (Sequences):

| SEQ ID NO: | Name | Sequence |
|---|---|---|
| | | ATCTACAGAATTAGCATTGGAAGCTATCCTCCAAG CAAGAAGTGTGTTACTTGCCATCTAAGGAAAGAAA GGTGCCAATATTACACAGCAAGTTTCAGCGACTAC GCCAAGTACTATGCACTTGTCTGCTATGGCCCAGG CATCCCCATTTCCACCCTTCATGACGGACGCACTG ATCAAGAAATTAAAATCCTGGAAGAAAACAAGGA ATTGGAAAATGCTTTGAAAAATATCCAGCTGCCTA AAGAGGAAATTAAGAAACTTGAAGTAGATGAAAT TACTTTATGGTACAAGATGATTCTTCCTCCTCAATT TGACAGATCAAAGAAGTATCCCTTGCTAATTCAAG TGTATGGTGGTCCCTGCAGTCAGAGTGTAAGGTCT GTATTTGCTGTTAATTGGATATCTTATCTTGCAAGT AAGGAAGGGATGGTCATTGCCTTGGTGGATGGTCG GGGAACAGCTTTCCAAGGTGACAAACTCCTGTATG CAGTGTATCGAAAGCTGGGTGTTTATGAAGTTGAA GACCAGATTACAGCTGTCAGAAAATTCATAGAAAT GGGTTTCATTGATGAAAAAGAATAGCCATATGGG GCTGGTCCTATGGAGGATATGTTTCATCACTGGCC CTTGCATCTGGAACTGGTCTTTTCAAATGTGGGAT AGCAGTGGCTCCAGTCTCCAGCTGGGAATATTACG CGTCTGTCTACACAGAGAGATTCATGGGTCTCCCA ACAAAGGATGATAATCTTGAGCACTATAAGAATTC AACTGTGATGGCAAGAGCAGAATATTTCAGAAAT GTAGACTATCTTCTCATCCACGGAACAGCAGATGA TAATGTGCACTTTCAAAACTCAGCACAGATTGCTA AAGCTCTGGTTAATGCACAAGTGGATTTCCAGGCA ATGTGGTACTCTGACCAGAACCACGGCTTATCCGG CCTGTCCACGAACCACTTATACACCCACATGACCC ACTTCCTAAAGCAGTGTTTCTCTTTGTCAGACGGC AAAAAGAAAAGAAAAAGGGCCACCACCATCACC ATCAC |
| 29 | human CEA | UniProt no. P06731 |
| 30 | human MCSP | UniProt no. Q6UVK1 |
| 31 | human EGFR | UniProt no. P00533 |
| 32 | human CD19 | UniProt no. P15391 |
| 33 | human CD20 | Uniprot no. P11836 |
| 34 | human CD33 | UniProt no. P20138 |
| 35 | human Lymphotoxin α | UniProt no. P01374 |
| 36 | human TNF | UniProt no. P01375 |
| 37 | human Lymphotoxin β | UniProt no. Q06643 |
| 38 | human OX40L | UniProt no. P23510 |
| 39 | human CD40L | UniProt no. P29965 |
| 40 | human FasL | UniProt no. P48023 |
| 41 | human CD27L | UniProt no. P32970 |
| 42 | human CD30L | UniProt no. P32971 |
| 43 | human 4-1BBL | UniProt no. P41273 |
| 44 | human TRAIL | UniProt no. P50591 |
| 45 | human RANKL | UniProt no. O14788 |
| 46 | human TWEAK | UniProt no. O43508 |
| 47 | human APRIL | UniProt no. O75888 |
| 48 | human BAFF | UniProt no. Q9Y275 |
| 49 | human LIGHT | UniProt no. O43557 |
| 50 | human TL1A | UniProt no. O95150 |

TABLE C-continued (Sequences):

| SEQ ID NO: | Name | Sequence |
|---|---|---|
| 51 | human GITRL | UniProt no. Q9UNG2 |
| 52 | human ectodysplasin A | UniProt no. Q92838 |
| 53 | hu 4-1BBL (50-254) | ACPWAVSGARASPGSAASPRLREGPELSPDDPAGLL DLRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSEAR NSAFGFQGRLLHLSAGQRLGVHLHTEARARHAWQL TQGATVLGLFRVTPEIPAGLPSPRSE |
| 54 | Peptide linker (G4S)$_2$ | GGGGSGGGGS |
| 55 | Peptide linker (SG4)$_2$ | SGGGGSGGGG |
| 56 | Peptide linker G4(SG4)$_2$ | GGGGSGGGGSGGGG |
| 57 | Peptide linker | GSPGSSSSGS |
| 58 | Peptide linker (G4S)$_4$ | GGGGSGGGGSGGGGSGGGGS |
| 59 | Peptide linker | GSGSGNGS |
| 60 | Peptide linker | GGSGSGSG |
| 61 | Peptide linker | GGSGSG |
| 62 | Peptide linker | GGSG |
| 63 | Peptide linker | GGSGNGSG |
| 64 | Peptide linker | GGNGSGSG |
| 65 | Peptide linker | GGNGSG |
| 66 | nucleotide sequence trimeric hu 4-1BBL (71-254) Fc knob chain | See Table 1 |
| 67 | nucleotide sequence FAP(28H1) Fc hole chain | See Table 1 |
| 68 | nucleotide sequence FAP(28H1) light chain | See Table 1 |
| 69 | nucleotide sequence DP47 Fc hole chain | See Table 19 |
| 70 | Nucleotide sequence DP47 light chain | See Table 19 |
| 71 | DP47 Fc hole chain | See Table 19 |
| 72 | DP47 light chain | See Table 19 |
| 73 | Human 4-1BB ECD | Uniprot No. Q07011, aa 24-186 |
| 74 | Cynomolgus 4-1BB ECD | aa 24-186 |
| 75 | Murine 4-1BB ECD | Uniprot No. P20334, aa 24-187 |
| 76 | nucleotide sequence Fc hole chain | See Table 24 |
| 77 | nucleotide sequence human 4-1BB Fc knob chain | See Table 24 |
| 78 | nucleotide sequence cynomolgus 4-1BB Fc knob chain | See Table 24 |
| 79 | nucleotide sequence murine 4-1BB Fc knob chain | See Table 24 |

TABLE C-continued (Sequences):

| SEQ ID NO: | Name | Sequence |
|---|---|---|
| 80 | Fc hole chain | See Table 24 |
| 81 | human 4-1BB Fc knob chain | See Table 24 |
| 82 | cynomolgus 4-1BB Fc knob chain | See Table 24 |
| 83 | murine 4-1BB Fc knob chain | See Table 24 |
| 84 | Avi tag | GLNDIFEAQKIEWHE |
| 85 | nucleotide sequence Human 4-1BB His | See Table 25 |
| 86 | Human 4-1BB His | See Table 25 |
| 87 | nucleotide sequence trimeric hu OX40L (51-183) Fc knob chain | See Table 27 |
| 88 | Human OX40 ECD | Uniprot No. P43489, aa 29-214 |
| 89 | Cynomolgus OX40 ECD | aa 29-214 |
| 90 | Murine OX40 ECD | Uniprot No. P47741, aa 10-211 |
| 91 | nucleotide sequence human OX40 Fc knob chain | See Table 30 |
| 92 | nucleotide sequence cynomolgus OX40 Fc knob chain | See Table 30 |
| 93 | nucleotide sequence murine OX40 Fc knob chain | See Table 30 |
| 94 | human OX40 Fc knob chain | See Table 30 |
| 95 | cynomolgus OX40 Fc knob chain | See Table 30 |
| 96 | murine OX40 Fc knob chain | See Table 30 |
| 97 | nucleotide sequence human OX40 His | See Table 31 |
| 98 | human OX40 His | See Table 31 |
| 99 | Human (hu) 4-1BBL (71-248) | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGL |
| 100 | hu 4-1BBL (85-248) | LDLRQGMFAQLVAQNVLLIDGPLSWYSDPGLAGVSL TGGLSYKEDTKELVVAKAGVYYVFFQLELRRVVAG EGSGSVSLALHLQPLRSAAGAAALALTVDLPPASSEA RNSAFGFQGRLLHLSAGQRLGVHLHTEARARHAWQ LTQGATVLGLFRVTPEIPAGL |
| 101 | hu 4-1BBL (80-248) | DPAGLLDLRQGMFAQLVAQNVLLIDGPLSWYSDPGL AGVSLTGGLSYKEDTKELVVAKAGVYYVFFQLELRR VVAGEGSGSVSLALHLQPLRSAAGAAALALTVDLPP ASSEARNSAFGFQGRLLHLSAGQRLGVHLHTEARAR HAWQLTQGATVLGLFRVTPEIPAGL |
| 102 | hu 4-1BBL (52-248) | PWAVSGARASPGSAASPRLREGPELSPDDPAGLLDLR QGMFAQLVAQNVLLIDGPLSWYSDPGLAGVSLTGGL SYKEDTKELVVAKAGVYYVFFQLELRRVVAGEGSG SVSLALHLQPLRSAAGAAALALTVDLPPASSEARNSA FGFQGRLLHLSAGQRLGVHLHTEARARHAWQLTQG ATVLGLFRVTPEIPAGL |

TABLE C-continued (Sequences):

| SEQ ID NO: | Name | Sequence |
|---|---|---|
| 103 | trimeric hu 4-1BBL (71-248) connected by (G4S)2 linker | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLE GGGGSGGGGSREGPELSPDDPAGLLDLRQGMFAQLV AQNVLLIDGPLSWYSDPGLAGVSLTGGLSYKEDTKE LVVAKAGVYYVFFQLELRRVVAGEGSGSVSLALHL QPLRSAAGAAALALTVDLPPASSEARNSAFGFQGRL LHLSAGQRLGVHLHTEARARHAWQLTQGATVLGLF RVTPEIPAGLGGGGSGGGGSREGPELSPDDPAGLLDL RQGMFAQLVAQNVLLIDGPLSWYSDPGLAGVSLTG GLSYKEDTKELVVAKAGVYYVFFQLELRRVVAGEG SGSVSLALHLQPLRSAAGAAALALTVDLPPASSEARN SAFGFQGRLLHLSAGQRLGVHLHTEARARHAWQLT QGATVLGLFRVTPEIPAGL |
| 104 | FAP(4B9) CDR-H1 | SYAMS |
| 105 | FAP(4B9) CDR-H2 | AIIGSGASTYYADSVKG |
| 106 | FAP(4B9) CDR-H3 | GWFGGFNY |
| 107 | FAP(4B9) CDR-L1 | RASQSVTSSYLA |
| 108 | FAP(4B9) CDR-L2 | VGSRRAT |
| 109 | FAP(4B9) CDR-L3 | QQGIMLPPT |
| 110 | FAP(4B9) VH | EVQLLESGGGLVQPGGSLRLSCAASGFTFSSYAMSW VRQAPGKGLEWVSAIIGSGASTYYADSVKGRFTISRD NSKNTLYLQMNSLRAEDTAVYYCAKGWFGGFNYW GQGTLVTVSS |
| 111 | FAP(4B9) VL | EIVLTQSPGTLSLSPGERATLSCRASQSVTSSYLAWY QQKPGQAPRLLINVGSRRATGIPDRFSGSGSGTDFTL TISRLEPEDFAVYYCQQGIMLPPTFGQGTKVEIK |
| 112 | CEA(sm9b) CDR-H1 | DSYMH |
| 113 | CEA(sm9b) CDR-H2 | WIDPENGDTEYAPKFQG |
| 114 | CEA(sm9b) CDR-H3 | GTPTGPYYFDY |
| 115 | CEA(sm9b) CDR-L1 | SASSSVPYMH |
| 116 | CEA(sm9b) CDR-L2 | STSNLAS |
| 117 | CEA(sm9b) CDR-L3 | QQRSSYPLT |
| 118 | CEA(sm9b) VH | QVKLEQSGAEVVKPGASVKLSCKASGFNIKDSYMH WLRQGPGQCLEWIGWIDPENGDTEYAPKFQGKATFT TDTSANTAYLGLSSLRPEDTAVYYCNEGTPTGPYYF DYWGQGTLVTVSS |
| 119 | CEA(sm9b) VL | ENVLTQSPSSMSVSVGDRVTIACSASSSVPYMHWLQ QKPGKSPKLLIYSTSNLASGVPSRFSGSGSGTDYSLTI SSVQPEDAATYYCQQRSSYPLTFGCGTKLEIK |
| 120 | CD19 (8B8-018) CDR-H1 | DYIMH |
| 121 | CD19 (8B8-018) CDR-H2 | YINPYNDGSKYTEKFQG |
| 122 | CD19 (8B8-018) CDR-H3 | GTYYYGSALFDY |
| 123 | CD19 (8B8-018) CDR-L1 | KSSQSLENPNGNTYLN |
| 124 | CD19 (8B8-018) CDR-L2 | RVSKRFS |
| 125 | CD19 (8B8-018) CDR-L3 | LQLTHVPYT |

TABLE C-continued (Sequences):

| SEQ ID NO: | Name | Sequence |
|---|---|---|
| 126 | CD19 (8B8-018) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 127 | CD19 (8B8-018) VL | DIVMTQTPLSLSVTPGQPASISCKSSQSLENPNGNTYL NWYLQKPGQSPQLLIYRVSKRFSGVPDRFSGSGSGTD FTLKISRVEAEDVGVYYCLQLTHVPYTFGQGTKLEIK |
| 128 | CD19 (8B8-2B11) CDR-H1 | DYIMH |
| 129 | CD19 (8B8-2B11) CDR-H2 | YINPYNDGSKYTEKFQG |
| 130 | CD19 (8B8-2B11) CDR-H3 | GTYYYGPQLFDY |
| 131 | CD19 (8B8-2B11) CDR-L1 | KSSQSLETSTGTTYLN |
| 132 | CD19 (8B8-2B11) CDR-L2 | RVSKRFS |
| 133 | CD19 (8B8-2B11) CDR-L3 | LQLLEDPYT |
| 134 | CD19 (8B8-2B11) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSS |
| 135 | CD19 (8B8-2B11) VL | DIVMTQTPLSLSVTPGQPASISCKSSQSLETSTGTTYL NWYLQKPGQSPQLLIYRVSKRFSGVPDRFSGSGSGTD FTLKISRVEAEDVGVYYCLQLLEDPYTFGQGTKLEIK |
| 136 | G4S | GGGGS |
| 137 | nucleotide sequence of anti-FAP(4B9) Fc hole chain | Table 3 |
| 138 | nucleotide sequence of anti-FAP(4B9) Fc knob chain fused to trimeric hu 4-1BBL (71-254) | Table 3 |
| 139 | nucleotide sequence of anti-FAP(4B9) light chain | Table 3 |
| 140 | anti-FAP(4B9) Fc hole chain | Table 3 |
| 141 | anti-FAP(4B9) Fc knob chain fused to trimeric hu 4-1BBL (71-254) | Table 3 |
| 142 | anti-FAP(4B9) light chain | Table 3 |
| 143 | nucleotide sequence of anti-CEA(sm9b) Fc hole chain | Table 5 |
| 144 | nucleotide sequence of anti-CEA(sm9b) Fc knob chain fused to trimeric hu 4-1BBL (71-254) | Table 5 |
| 145 | nucleotide sequence of anti-CEA(sm9b) light chain | Table 5 |
| 146 | anti-CEA(sm9b) Fc hole chain | Table 5 |
| 147 | anti-CEA(sm9b) Fc knob chain fused to trimeric hu 4-1BBL (71-254) | Table 5 |
| 148 | anti-CEA(sm9b) light chain | Table 5 |
| 149 | nucleotide sequence of anti-CD19(8B8-018) Fc hole chain | Table 7 |

TABLE C-continued (Sequences):

| SEQ ID NO: | Name | Sequence |
|---|---|---|
| 150 | nucleotide sequence of anti-CD19(8B8-018) Fc knob chain fused to trimeric hu 4-1BBL (71-254) | Table 7 |
| 151 | nucleotide sequence of anti-CD19(8B8-018) light chain | Table 7 |
| 152 | anti-CD19(8B8-018) Fc hole chain | Table 7 |
| 153 | anti-CD19(8B8-018) Fc knob chain fused to trimeric hu 4-1BBL (71-254) | Table 7 |
| 154 | anti-CD19(8B8-018) light chain | Table 7 |
| 155 | nucleotide sequence of anti-CD19(8B8-2B11) Fc hole chain | Table 8 |
| 156 | nucleotide sequence of anti-CD19(8B8-2B11) Fc knob chain fused to trimeric hu 4-1BBL (71-254) | Table 8 |
| 157 | nucleotide sequence of anti-CD19(8B8-2B11) light chain | Table 8 |
| 158 | anti-CD19(8B8-2B11) Fc hole chain | Table 8 |
| 159 | anti-CD19(8B8-2B11) Fc knob chain fused to trimeric hu 4-1BBL (71-254) | Table 8 |
| 160 | anti-CD19(8B8-2B11) light chain | Table 8 |
| 161 | HVR-L1 anti-CD19(8B8) | NSNGNT |
| 162 | HVR-H2 anti-CD19(8B8) | KFNG |
| 163 | Nucleotide sequence of Fc hole chain with HYRF mutation | Table 13 |
| 164 | Nucleotide sequence of human CD19 antigen Fc knob chain avi tag | Table 13 |
| 165 | Fc hole chain with HYRF mutation | Table 13 |
| 166 | human CD19 antigen Fc knob chain avi tag | Table 13 |
| 167 | Nucleotide sequence of cynomolgus CD19 antigen Fc knob chain avi tag | Table 13 |
| 168 | cynomolgus CD19 antigen Fc knob chain avi tag | Table 13 |
| 169 | Nucleotide sequence CD19 (8B8) VH Parental clone | GAGGTCCAGCTGCAGCAGTCTGGACCTGAGCTGGT AAAGCCTGGGGCTTCAGTGAAGATGGCCTGCAAG GCTTCTGGATACACATTCACTGACTATATTATGCA CTGGGTGAAGCAGAAGACTGGGCAGGGCCTTGAG TGGATTGGATATATTAATCCTTACAATGATGGTTCT AAGTACACTGAGAAGTTCAACGGCAAGGCCACAC TGACTTCAGACAAATCTTCCATCACAGCCTACATG GAGCTCAGCAGCCTGACCTCTGAGGACTCTGCGGT CTATTACTGTGCAAGAGGGACCTATTATTATGGTA |

TABLE C-continued (Sequences):

| SEQ ID NO: | Name | Sequence |
|---|---|---|
| | | GCGCCCTCTTTGACTACTGGGGCCAAGGCACCACTCTCACAGTCTCCTCG |
| 170 | Nucleotide sequence CD19 (8B8) VL Parental clone | GATGCTGTGATGACCCAAACTCCACTCTCCCTGCCTGTCAGTCTTGGAGATCAAGCCTCCATCTCTTGCAGGTCTAGTCAGAGCCTTGAAAACAGTAATGGAAACACCTATTTGAACTGGTACCTCCAGAAACCAGGCCAGTCTCCACAACTCCTGATCTACAGGGTTTCCAAACGATTTTCTGGGGTCCTAGACAGGTTCAGTGGTAGTGGATCAGGGACAGATTTCACACTGAAAATCAGCAGAGTGGAGGCTGAGGATTTGGGAGTTTATTTCTGCCTACAACTTACACATGTCCCGTACACGTTCGGAGGGGGGACCAAGCTGGAAATAAAA |
| 171 | CD19 L1 reverse random | see Table 15 |
| 172 | CD19 L2 forward random | see Table 15 |
| 173 | CD19 H1 reverse random | see Table 15 |
| 174 | CD19 H2 forward random | see Table 15 |
| 175 | CD19 H3 reverse constant | see Table 15 |
| 176 | LMB3 | see Table 15 |
| 177 | CD19 L1 forward constant | see Table 16 |
| 178 | CD19 L3 reverse random | see Table 16 |
| 179 | CD19 L3 forward constant | see Table 16 |
| 180 | CD19 H3 reverse random | see Table 16 |
| 181 | nucleotide sequence of DP47 Fc knob fused to trimeric hu 4-1BBL (71-254) | see Table 21 |
| 182 | DP47 Fc knob fused to trimeric hu 4-1BBL (71-254) | see Table 21 |
| 183 | CMV-derived peptide | NLVPMVATV |

In the following specific embodiments of the invention are listed:

A TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other, optionally by peptide linkers, and
(c) a Fc domain composed of a first and a second subunit capable of stable association.

The TNF family ligand trimer-containing antigen binding molecule comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association.

The TNF family ligand trimer-containing antigen binding molecule as described before, comprising
(a) at least one moiety capable of specific binding to a target cell antigen,
(b) a polypeptide comprising three ectodomains of a TNF ligand family member or fragments thereof that are connected to each other by peptide linkers and
(c) a Fc domain composed of a first and a second subunit capable of stable association, wherein the polypeptide comprising the three ectodomains of a TNF ligand family member or fragments thereof that are connected to each other by peptide linkers is fused to the N- or C-terminal amino acid of one of the two subunits of the Fc domain, optionally through a peptide linker.

The TNF family ligand trimer-containing antigen binding molecule as described before, wherein the TNF ligand family member costimulates human T-cell activation.

The TNF family ligand trimer-containing antigen binding molecule as described before, wherein the TNF ligand family member is selected from 4-1BBL and OX40L.

The TNF family ligand trimer-containing antigen binding molecule as described before, wherein the TNF ligand family member is 4-1BBL.

The TNF family ligand trimer-containing antigen binding molecule as described before, wherein the ectodomain of a TNF ligand family member comprises the amino acid sequence selected from the group consisting of SEQ ID NO:1, SEQ ID NO: 2, SEQ ID NO:3, SEQ ID NO:4, SEQ ID NO:99, SEQ ID NO: 100, SEQ ID NO:101 and SEQ ID NO:102, particularly the amino acid sequence of SEQ ID NO:1 or SEQ ID NO:99.

The TNF family ligand trimer-containing antigen binding molecule as described before, wherein the ectodomain of a TNF ligand family member comprises the amino acid sequence selected from the group consisting of SEQ ID NO:1, SEQ ID NO: 2, SEQ ID NO:3 and SEQ ID NO:4, particularly the amino acid sequence of SEQ ID NO:1.

The TNF family ligand trimer-containing antigen binding molecule as described before, comprising
(a) at least one moiety capable of specific binding to a target cell antigen and
(b) a polypeptide comprising the amino acid sequence of SEQ ID NO:5 or SEQ ID NO:103, and
(c) a Fc domain composed of a first and a second subunit capable of stable association.

The TNF family ligand trimer-containing antigen binding molecule as described before, comprising
(a) at least one moiety capable of specific binding to a target cell antigen and
(b) a polypeptide comprising the amino acid sequence of SEQ ID NO:5 and
(c) a Fc domain composed of a first and a second subunit capable of stable association.

The TNF family ligand trimer-containing antigen binding molecule as described before, wherein the TNF ligand family member is OX40L.

The TNF family ligand trimer-containing antigen binding molecule as described before, wherein the ectodomain of a TNF ligand family member comprises the amino acid sequence selected from the group consisting of SEQ ID NO:6 and SEQ ID NO:7, particularly the amino acid sequence of SEQ ID NO:6.

The TNF family ligand trimer-containing antigen binding molecule as described before, comprising
(a) at least one moiety capable of specific binding to a target cell antigen and
(b) a polypeptide comprising the amino acid sequence of SEQ ID NO:8, and
(c) a Fc domain composed of a first and a second subunit capable of stable association.

The TNF family ligand trimer-containing antigen binding molecule as described before, wherein the polypeptide comprising three ectodomains of a TNF ligand family member or fragments thereof is fused at the C-terminal amino acid to the N-terminal amino acid of one of the subunits of the Fc domain.

The TNF family ligand trimer-containing antigen binding molecule as described before, wherein the polypeptide comprising three ectodomains of a TNF ligand family member or fragments thereof is fused at the N-terminal amino acid to a C-terminal amino acid of one of the subunits of the Fc domain.

The TNF family ligand trimer-containing antigen binding molecule as described before, wherein the moiety capable of specific binding to a target cell antigen is selected from the group consisting of an antibody fragment, a Fab molecule, a crossover Fab molecule, a single chain Fab molecule, a Fv molecule, a scFv molecule, a single domain antibody, an aVH and a scaffold antigen binding protein.

The TNF family ligand trimer-containing antigen binding molecule as described before, wherein the moiety capable of specific binding to a target cell antigen is a Fab molecule capable of specific binding to a target cell antigen.

The TNF family ligand trimer-containing antigen binding molecule as described before, wherein the target cell antigen is selected from the group consisting of Fibroblast Activation Protein (FAP), Melanoma-associated Chondroitin Sulfate Proteoglycan (MCSP), Epidermal Growth Factor Receptor (EGFR), Carcinoembryonic Antigen (CEA), CD19, CD20 and CD33.

The TNF family ligand trimer-containing antigen binding molecule as described before, wherein the target cell antigen is Fibroblast Activation Protein (FAP).

The TNF family ligand trimer-containing antigen binding molecule as described before, wherein the moiety capable of specific binding to FAP comprises a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14.

The TNF family ligand trimer-containing antigen binding molecule as described before, wherein the moiety capable of specific binding to FAP comprises a VH domain domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

The TNF family ligand trimer-containing antigen binding molecule as described herein before, wherein the moiety capable of specific binding to FAP comprises a variable heavy chain comprising an amino acid sequence of SEQ ID NO:16 and a variable light chain comprising an amino acid sequence of SEQ ID NO:17 or wherein the moiety capable of specific binding to FAP comprises a variable heavy chain comprising an amino acid sequence of SEQ ID NO:110 and a variable light chain comprising an amino acid sequence of SEQ ID NO:111.

The TNF family ligand trimer-containing antigen binding molecule of any one of claims 1 to 15, wherein the target cell antigen is CEA.

The TNF family ligand trimer-containing antigen binding molecule as described herein before, wherein the moiety capable of specific binding to CEA comprises a VH domain comprising (i) CDR-H1 comprising the amino acid sequence of SEQ ID NO:112, (ii) CDR-H2 comprising the amino acid sequence of SEQ ID NO:113 and (iii) CDR-H3 comprising the amino acid sequence of SEQ ID NO:114, and a VL domain comprising (iv) CDR-L1 comprising the amino acid sequence of SEQ ID NO:115, (v) CDR-L2 comprising the amino acid sequence of SEQ ID NO:116 and (vi) CDR-L3 comprising the amino acid sequence of SEQ ID NO:117.

The TNF family ligand trimer-containing antigen binding molecule as described herein before, wherein the moiety capable of specific binding to CEA comprises a variable heavy chain comprising an amino acid sequence of SEQ ID NO:118 and a variable light chain comprising an amino acid sequence of SEQ ID NO:119.

The TNF family ligand trimer-containing antigen binding molecule as described herein before, wherein the target cell antigen is CD19.

The TNF family ligand trimer-containing antigen binding molecule as described herein before, wherein the moiety capable of specific binding to CD19 comprises
(a) a VH domain comprising (i) CDR-H1 comprising the amino acid sequence of SEQ ID NO:120, (ii) CDR-H2 comprising the amino acid sequence of SEQ ID NO:121 and (iii) CDR-H3 comprising the amino acid sequence of SEQ ID NO:122, and a VL domain comprising (iv) CDR-L1 comprising the amino acid sequence of SEQ ID NO:123, (v) CDR-L2 comprising the amino acid sequence of SEQ ID NO:124 and (vi) CDR-L3 comprising the amino acid sequence of SEQ ID NO:125, or
(b) a VH domain comprising (i) CDR-H1 comprising the amino acid sequence of SEQ ID NO:128, (ii) CDR-H2 comprising the amino acid sequence of SEQ ID NO:129 and (iii) CDR-H3 comprising the amino acid sequence of SEQ ID NO:130, and a VL domain comprising (iv) CDR-L1 comprising the amino acid sequence of SEQ ID NO:131, (v) CDR-L2 comprising the amino acid sequence of SEQ ID NO:132 and (vi) CDR-L3 comprising the amino acid sequence of SEQ ID NO:133.

The TNF family ligand trimer-containing antigen binding molecule as described herein before, wherein the moiety capable of specific binding to CD19 comprises a variable heavy chain comprising an amino acid sequence of SEQ ID NO:126 and a variable light chain comprising an amino acid sequence of SEQ ID NO:127 or wherein the moiety capable of specific binding to FAP comprises a variable heavy chain comprising an amino acid sequence of SEQ ID NO:134 and a variable light chain comprising an amino acid sequence of SEQ ID NO:135.

The TNF family ligand trimer-containing antigen binding molecule as described before, wherein the Fc domain is an IgG, particularly an IgG1 Fc domain or an IgG4 Fc domain.

The TNF family ligand trimer-containing antigen binding molecule as described before, wherein the Fc domain is an IgG1 Fc domain and comprises amino acid substitutions at positions 234 and 235 (EU numbering) and/or 329 (EU numbering) of the IgG heavy chains.

The TNF family ligand trimer-containing antigen binding molecule as described herein before, comprising one moiety capable of specific binding to a target cell antigen.

The TNF family ligand trimer-containing antigen binding molecule as described herein before, wherein the antigen binding molecule comprises
(i) a first heavy chain comprising the VH domain of a Fab molecule capable of specific binding to a target cell antigen,
(ii) a light chain comprising the VL domain of a Fab molecule capable of specific binding to a target cell antigen, and
(iii) a second heavy chain comprising the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:16 or a VH domain comprising an amino acid sequence of SEQ ID NO:110,
(ii) a light chain comprising a VL domain comprising an amino acid sequence of SEQ ID NO:17 or a VL domain comprising an amino acid sequence of SEQ ID NO:111, and
(iii) a second heavy chain comprising the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:118,
(ii) a light chain comprising a VL domain comprising an amino acid sequence of SEQ ID NO:119, and
(iii) a second heavy chain comprising the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:126 or a VH domain comprising an amino acid sequence of SEQ ID NO:134,
(ii) a light chain comprising a VL domain comprising an amino acid sequence of SEQ ID NO:127 or a VL domain comprising an amino acid sequence of SEQ ID NO:135, and
(iii) a second heavy chain comprising the amino acid sequence of SEQ ID NO:5 or SEQ ID NO:103 or SEQ ID NO:8.

The TNF family ligand trimer-containing antigen binding molecule as described herein before, comprising two moieties capable of specific binding to a target cell antigen.

The TNF family ligand trimer-containing antigen binding molecule as described herein before, wherein the antigen binding molecule comprises
(i) a first heavy chain comprising a VH domain of a Fab molecule capable of specific binding to a target cell antigen,
(ii) two light chains comprising each the VL domain of a Fab molecule capable of specific binding to a target cell antigen, and
(iii) a second heavy chain comprising a VH domain of a Fab molecule capable of specific binding to a target cell antigen and the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:16 or a VH domain comprising an amino acid sequence of SEQ ID NO:110, (ii) two light chains comprising each a VL domain comprising an amino acid sequence of SEQ ID NO:17 or a VL domain comprising an amino acid sequence of SEQ ID NO:111, and
(iii) a second heavy chain comprising a VH domain comprising an amino acid sequence of SEQ ID NO:16 or a VH domain comprising an amino acid sequence of SEQ ID NO:110 and the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:118,
(ii) two light chains comprising each a VL domain comprising an amino acid sequence of SEQ ID NO:119, and
(iii) a second heavy chain comprising a VH domain comprising an amino acid sequence of SEQ ID NO:118 and the amino acid sequence of SEQ ID NO:5 or SEQ ID NO:103 or SEQ ID NO:8.

The TNF family ligand trimer-containing antigen binding molecule as described herein before, wherein the antigen binding molecule comprises
(i) a first heavy chain comprising a VH domain comprising an amino acid sequence of SEQ ID NO:126 or a VH domain comprising an amino acid sequence of SEQ ID NO:134,
(ii) two light chains comprising a VL domain comprising an amino acid sequence of SEQ ID NO:127 or a VL domain comprising an amino acid sequence of SEQ ID NO:135, and
(iii) a second heavy chain comprising a VH domain comprising an amino acid sequence of SEQ ID NO:126 or a VH domain comprising an amino acid sequence of SEQ ID NO:134 and the amino acid sequence of SEQ ID NO:5 or SEQ ID NO:103 or SEQ ID NO:8.

The TNF family ligand trimer-containing antigen binding molecule as described before, wherein the antigen binding molecule comprises
(a) a heavy chain and a light chain, both comprising a Fab molecule capable of specific binding to a target cell antigen, and
(b) a fusion protein comprising a Fc domain and a polypeptide comprising the amino acid sequence of SEQ ID NO:5.

The TNF family ligand trimer-containing antigen binding molecule as described before, wherein the antigen binding molecule comprises
(a) a heavy chain and a light chain, both comprising a Fab molecule capable of specific binding to a target cell antigen, and
(b) the fusion protein comprising the amino acid sequence of SEQ ID NO:15.

The TNF family ligand trimer-containing antigen binding molecule as described before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:5.

The TNF family ligand trimer-containing antigen binding molecule as described before, wherein the antigen binding molecule comprises
(a) a heavy chain and a light chain, both comprising a Fab molecule capable of specific binding to a target cell antigen, and
(b) a fusion protein comprising a Fc domain and a polypeptide comprising the amino acid sequence of SEQ ID NO:8.

The TNF family ligand trimer-containing antigen binding molecule as described before, wherein the antigen binding molecule comprises
(a) a heavy chain and a light chain, both comprising a Fab molecule capable of specific binding to a target cell antigen, and
(b) the fusion protein comprising the amino acid sequence of SEQ ID NO:20.

The TNF family ligand trimer-containing antigen binding molecule as described before, wherein the antigen binding molecule comprises
(i) a variable heavy chain comprising the amino acid sequence of SEQ ID NO:16,
(ii) a variable light chain comprising the amino acid sequence of SEQ ID NO:17, and
(iii) a polypeptide comprising the amino acid sequence of SEQ ID NO:8.

An isolated polynucleotide encoding the TNF family ligand trimer-containing antigen binding molecule as described before.

A vector, particularly an expression vector, comprising the isolated polynucleotide as described before.

A host cell comprising the isolated polynucleotide as described before or the vector as described before.

A method for producing the TNF family ligand trimer-containing antigen binding molecule as described before, comprising the steps of
(i) culturing the host cell of as described before under conditions suitable for expression of the antigen binding molecule, and
(ii) recovering the antigen binding molecule.

A pharmaceutical composition comprising the TNF family ligand trimer-containing antigen binding molecule as described before and at least one pharmaceutically acceptable excipient.

The TNF family ligand trimer-containing antigen binding molecule as described before, or the pharmaceutical composition as described before, for use as a medicament.

The TNF family ligand trimer-containing antigen binding molecule as described before, or the pharmaceutical composition as described before, for use in the treatment of cancer.

Use of the TNF family ligand trimer-containing antigen binding molecule as described before for the manufacture of a medicament for the treatment of cancer.

A method of treating a disease in an individual, comprising administering to said individual a therapeutically effective amount of a composition comprising TNF family ligand trimer-containing antigen binding molecule as described before in a pharmaceutically acceptable form.

The method of treating a disease as described before, wherein said disease is cancer.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKGEL® G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Example 1

Preparation and Purification of Targeted Single Chain 4-1BB Ligand Trimer-Containing Fc Fusion Antigen Binding Molecules 1.1. Monovalent FAP(28H1)-Targeted Single Chain 4-1BB Ligand Trimer-Containing Fc (Kih) Fusion Antigen Binding Molecule (Compound S1)

The DNA sequence encoding part of the ectodomain (amino acids 71-254 or 71-248) of human 4-1BB ligand was synthetized according to UniProt Accession No. P41273 (SEQ ID NO:43).

A polypeptide comprising three ectodomains of 4-1BB ligand, each separated by a $(G_4S)_2$ linker (SEQ ID NO:54), was cloned as described in FIG. 1A: human 4-1BB ligand, $(G_4S)_2$ connector, human 4-1BB ligand, $(G_4S)_2$ (SEQ ID NO:54) connector, human 4-1BB ligand.

The polypeptide encoding the single chain trimeric 4-1BB ligand was subcloned in frame with the human IgG1 heavy chain CH2 and CH3 domains on the knob (Merchant, Zhu et al., 1998), using a linker (GSPGSSSSGS) of SEQ ID NO:57.

The variable region of heavy and light chain DNA sequences encoding a binder specific for fibroblast activation protein (FAP), clone 28H1, were subcloned in frame with either the constant heavy chain of the hole (Carter, 2001) or the constant light chain of human IgG1. The generation and preparation of the FAP binders is described in WO 2012/020006 A2, which is incorporated herein by reference.

The Pro329Gly, Leu234Ala and Leu235Ala mutations were introduced in the constant region of the knob and hole heavy chains to abrogate binding to Fc gamma receptors according to the method described in International Patent Appl. Publ. No. WO 2012/130831 A1.

Combination of the single chain ligand-Fc knob chain containing the S354C/T366W mutations, with the targeted anti-FAP-Fc hole chain containing the Y349C/T366S/

L368A/Y407V mutations and the anti-FAP light chain, allows generation of a heterodimer, which includes a single chain 4-1BB ligand trimer and a FAP binding Fab (FIGS. 3A-C).

Table 1 shows, respectively, the cDNA and amino acid sequences of the FAP(28H1)-targeted single chain 4-1BB ligand trimer-containing Fc (kih) fusion antigen binding molecule.

TABLE 1

Sequences of FAP(28H1)-targeted human 4-1BB ligand trimer-containing Fc (kih) fusion molecule (FAP single chain 4-1BBL trimer) (compound S1)

| SEQ ID NO: | Description | Sequence |
|---|---|---|
| 66 | nucleotide sequence of trimeric hu 4-1BBL (71-254)-Fc knob chain | AGAGAGGGCCCTGAGCTGAGCCCCGATGATCCTGCTGG ACTGCTGGACCTGCGGCAGGGCATGTTTGCTCAGCTGGT GGCCCAGAACGTGCTGCTGATCGATGGCCCCCTGTCCTG GTACAGCGATCCTGGACTGGCTGGCGTGTCACTGACAGG CGGCCTGAGCTACAAAGAGGACACCAAAGAACTGGTGG TGGCCAAGGCCGGCGTGTACTACGTGTTCTTTCAGCTGG AACTGCGGAGAGTGGTGGCCGGCGAAGGATCTGGCTCT GTGTCTCTGGCCCTGCATCTGCAGCCTCTGAGAAGCGCT GCTGGCGCTGCAGCTCTGGCACTGACAGTGGATCTGCCT CCTGCCAGCTCCGAGGCCCGGAATAGCGCATTTGGGTTT CAAGGCAGGCTGCTGCACCTGTCTGCCGGCCAGAGGCT GGGAGTGCATCTGCACACAGAGGCCAGGGCTAGACACG CCTGGCAGCTGACACAGGGCGCTACAGTGCTGGGCCTG TTCAGAGTGACCCCCGAGATTCCAGCCGGCCTGCCTTCT CCAAGAAGCGAAGGCGGAGGCGGATCTGGCGGCGGAG GATCTAGAGAGGGACCCGAACTGTCCCCTGACGATCCA GCCGGGCTGCTGGATCTGAGACAGGGAATGTTCGCCCA GCTGGTGGCTCAGAATGTGCTGCTGATTGACGGACCTCT GAGCTGGTACTCCGACCCAGGGCTGGCAGGGGTGTCCC TGACTGGGGGACTGTCCTACAAAGAAGATACAAAAGAA CTGGTGGTGGCTAAAGCTGGGGTGTACTATGTGTTTTTT CAGCTGGAACTGAGGCGGGTGGTGGCTGGGGAGGGCTC AGGATCTGTGTCCCTGGCTCTGCATCTGCAGCCACTGCG CTCTGCTGCTGGCGCAGCTGCACTGGCTCTGACTGTGGA CCTGCCACCAGCCTCTAGCGAGGCCAGAAACAGCGCCT TCGGGTTCCAAGGACGCCTGCTGCATCTGAGCGCCGGAC AGCGCCTGGGAGTGCATCTGCATACTGAAGCCAGAGCC CGGCATGCTTGGCAGCTGACTCAGGGGGCAACTGTGCTG GGACTGTTTCGCGTGACACCTGAGATCCCTGCCGGACTG CCAAGCCCTAGATCAGAAGGGGGCGGAGGAAGCGGAG GGGGAGGAAGTAGAGAAGGACCAGAGCTGTCTCCAGAT GACCCCGCAGGACTGCTGGACCTGAGACAGGGCATGTT CGCACAGCTGGTGGCCCAGAATGTGCTGCTGATCGACG GGCCACTGTCTTGGTATTCCGATCCCGGCCTGGCCGGCG TGTCCCTGACCGGCGGACTGAGTTACAAAGAGGATACA AAAGAACTGGTGGTGGCAAAGGCAGGGGTGTACTATGT GTTCTTTCAGCTGGAACTGAGAAGGGTGGTGGCCGGCG AGGGAAGCGGATCAGTGTCACTGGCACTGCATCTGCAG CCCCTGAGATCCGCTGCAGGGGCCGCTGCTCTGGCCCTG ACCGTGGACCTGCCCCCTGCTTCTTCCGAGGCTAGAAAC TCTGCATTTGGGTTTCAAGGACGCCTGCTGCATCTGTCA GCCGGGCAGAGACTGGGAGTGCATCTGCATACCGAGGC TCGCGCCAGACATGCATGGCAGCTGACCCAGGGCGCCA CCGTGCTGGGACTGTTTAGAGTGACTCCAGAAATCCCCG CTGGCCTGCCCAGCCCAAGATCCGAGGGATCTCCTGGCA GCAGCTCTAGCGGATCCGACAAAACTCACACATGCCCA CCGTGCCCAGCACCTGAAGCTGCAGGGGGACCGTCAGT CTTCCTCTTCCCCCCAAAACCCAAGGACACCCTCATGAT CTCCCGGACCCCTGAGGTCACATGCGTGGTGGTGGACGT GAGCCACGAAGACCCTGAGGTCAAGTTCAACTGGTACG TGGACGGCGTGGAGGTGCATAATGCCAAGACAAAGCCG CGGGAGGAGCAGTACAACAGCACGTACCGTGTGGTCAG CGTCCTCACCGTCCTGCACCAGGACTGGCTGAATGGCAA GGAGTACAAGTGCAAGGTCTCCAACAAAGCCCTCGGCG CCCCCATCGAGAAAACCATCTCCAAAGCCAAAGGGCAG CCCCGAGAACCACAGGTGTACACCCTGCCCCCATGCCG GGATGAGCTGACCAAGAACCAGGTCAGCCTGTGGTGCC TGGTCAAAGGCTTCTATCCCAGCGACATCGCCGTGGAGT GGGAGAGCAATGGGCAGCCGGAGAACAACTACAAGAC CACGCCTCCCGTGCTGGACTCCGACGGCTCCTTCTTCCT CTACAGCAAGCTCACCGTGGACAAGAGCAGGTGGCAGC AGGGGAACGTCTTCTCATGCTCCGTGATGCATGAGGCTC TGCACAACCACTACACGCAGAAGAGCCTCTCCCTGTCTC CGGGTAAA |
| 67 | anti-FAP (28H1) Fc hole chain | GAAGTGCAGCTGCTGGAATCCGGCGGAGGCCTGGTGCA GCCTGGCGGATCTCTGAGACTGTCCTGCGCCGCCTCCGG |

TABLE 1-continued

Sequences of FAP(28H1)-targeted human 4-1BB ligand trimer-containing Fc (kih) fusion molecule (FAP single chain 4-1BBL trimer) (compound S1)

| SEQ ID NO: | Description | Sequence |
|---|---|---|
| | | CTTCACCTTCTCCTCCCACGCCATGTCCTGGGTCCGACA
GGCTCCTGGCAAAGGCCTGGAATGGGTGTCCGCCATCTG
GGCCTCCGGCGAGCAGTACTACGCCGACTCTGTGAAGG
GCCGGTTCACCATCTCCCGGGACAACTCCAAGAACACCC
TGTACCTGCAGATGAACTCCCTGCGGGCCGAGGACACC
GCCGTGTACTACTGTGCCAAGGGCTGGCTGGGCAACTTC
GACTACTGGGGACAGGGCACCCTGGTCACCGTGTCCAG
CGCTAGCACCAAGGGCCCCTCCGTGTTCCCCCTGGCCCC
CAGCAGCAAGAGCACCAGCGGCGGCACAGCCGCTCTGG
GCTGCCTGGTCAAGGACTACTTCCCCGAGCCCGTGACCG
TGTCCTGGAACAGCGGAGCCCTGACCTCCGGCGTGCAC
ACCTTCCCCGCCGTGCTGCAGAGTTCTGGCCTGTATAGC
CTGAGCAGCGTGGTCACCGTGCCTTCTAGCAGCCTGGGC
ACCCAGACCTACATCTGCAACGTGAACCACAAGCCCAG
CAACACCAAGGTGGACAAGAAGGTGGAGCCCAAGAGCT
GCGACAAAACTCACACATGCCCACCGTGCCCAGCACCT
GAAGCTGCAGGGGACCGTCAGTCTTCCTCTTCCCCCCA
AAACCCAAGGACACCCTCATGATCTCCCGGACCCCTGA
GGTCACATGCGTGGTGGTGGACGTGAGCCACGAAGACC
CTGAGGTCAAGTTCAACTGGTACGTGGACGGCGTGGAG
GTGCATAATGCCAAGACAAAGCCGCGGGAGGAGCAGTA
CAACAGCACGTACCGTGTGGTCAGCGTCCTCACCGTCCT
GCACCAGGACTGGCTGAATGGCAAGGAGTACAAGTGCA
AGGTCTCCAACAAAGCCCTCGGCGCCCCCATCGAGAAA
ACCATCTCCAAAGCCAAAGGGCAGCCCCGAGAACCACA
GGTGTGCACCCTGCCCCCATCCCGGGATGAGCTGACCAA
GAACCAGGTCAGCCTCTCGTGCGCAGTCAAAGGCTTCTA
TCCCAGCGACATCGCCGTGGAGTGGGAGAGCAATGGGC
AGCCGGAGAACAACTACAAGACCACGCCTCCCGTGCTG
GACTCCGACGGCTCCTTCTTCCTCGTGAGCAAGCTCACC
GTGGACAAGAGCAGGTGGCAGCAGGGGAACGTCTTCTC
ATGCTCCGTGATGCATGAGGCTCTGCACAACCACTACAC
GCAGAAGAGCCTCTCCCTGTCTCCGGGTAAA |
| 68 | anti-FAP(28H1) light chain | GAGATCGTGCTGACCCAGTCCCCCGGCACCCTGTCTCTG
AGCCCTGGCGAGAGAGCCACCCTGTCCTGCAGAGCCTC
CCAGTCCGTGTCCCGGTCCTACCTCGCCTGGTATCAGCA
GAAGCCCGGCCAGGCCCCTCGGCTGCTGATCATCGGCG
CCTCTACCAGAGCCACCGGCATCCCTGACCGGTTCTCCG
GCTCTGGCTCCGGCACCGACTTCACCCTGACCATCTCCC
GGCTGGAACCCGAGGACTTCGCCGTGTACTACTGCCAGC
AGGGCCAGGTCATCCCTCCCACCTTTGGCCAGGGCACCA
AGGTGGAAATCAAGCGTACGGTGGCTGCACCATCTGTCT
TCATCTTCCCGCCATCTGATGAGCAGTTGAAATCTGGAA
CTGCCTCTGTTGTGTGCCTGCTGAATAACTTCTATCCCAG
AGAGGCCAAAGTACAGTGGAAGGTGGATAACGCCCTCC
AATCGGGTAACTCCCAGGAGAGTGTCACAGAGCAGGAC
AGCAAGGACAGCACCTACAGCCTCAGCAGCACCCTGAC
GCTGAGCAAAGCAGACTACGAGAAACACAAAGTCTACG
CCTGCGAAGTCACCCATCAGGGCCTGAGCTCGCCCGTCA
CAAAGAGCTTCAACAGGGGAGAGTGT |
| 15 | trimeric hu 4-1BBL (71-254)-Fc knob chain | REGPELSPDDPAGLLDLRQGMFAQLVAQNVLLIDGPLSWY
SDPGLAGVSLTGGLSYKEDTKELVVAKAGVYYVFFQLELR
RVVAGEGSGSVSLALHLQPLRSAAGAAALALTVDLPPASS
EARNSAFGFQGRLLHLSAGQRLGVHLHTEARARHAWQLT
QGATVLGLFRVTPEIPAGLPSPRSEGGGGSGGGGSREGPEL
SPDDPAGLLDLRQGMFAQLVAQNVLLIDGPLSWYSDPGLA
GVSLTGGLSYKEDTKELVVAKAGVYYVFFQLELRRVVAG
EGSGSVSLALHLQPLRSAAGAAALALTVDLPPASSEARNS
AFGFQGRLLHLSAGQRLGVHLHTEARARHAWQLTQGATV
LGLFRVTPEIPAGLPSPRSEGGGGSGGGGSREGPELSPDDPA
GLLDLRQGMFAQLVAQNVLLIDGPLSWYSDPGLAGVSLTG
GLSYKEDTKELVVAKAGVYYVFFQLELRRVVAGEGSGSV
SLALHLQPLRSAAGAAALALTVDLPPASSEARNSAFGFQG
RLLHLSAGQRLGVHLHTEARARHAWQLTQGATVLGLFRV
TPEIPAGLPSPRSEGSPGSSSSGSDKTHTCPPCPAPEAAGGPS
VFLFPPKPKDTLMISRTPEVTCVVVDVSHEDPEVKFNWYV
DGVEVHNAKTKPREEQYNSTYRVVSVLTVLHQDWLNGKE
YKCKVSNKALGAPIEKTISKAKGQPREPQVYTLPPCRDELT
KNQVSLWCLVKGFYPSDIAVEWESNGQPENNYKTTPPVLD
SDGSFFLYSKLTVDKSRWQQGNVFSCSVMHEALHNHYTQ
KSLSLSPGK |

TABLE 1-continued

Sequences of FAP(28H1)-targeted human 4-1BB ligand trimer-containing Fc (kih) fusion molecule (FAP single chain 4-1BBL trimer) (compound S1)

| SEQ ID NO: | Description | Sequence |
|---|---|---|
| 18 | anti-FAP(28H1) Fc hole chain | EVQLLESGGGLVQPGGSLRLSCAASGFTFSSHAMSWVRQA PGKGLEWVSAIWASGEQYYADSVKGRFTISRDNSKNTLYL QMNSLRAEDTAVYYCAKGWLGNFDYWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKKVEPKSCDKTHTCPPCPAPEAAGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALGAPIEKTISKAKGQPREPQVCTLPPSRDELTKN QVSLSCAVKGFYPSDIAVEWESNGQPENNYKTTPPVLDSD GSFFLVSKLTVDKSRWQQGNVFSCSVMHEALHNHYTQKS LSLSPGK |
| 19 | anti-FAP (28H1) light chain | EIVLTQSPGTLSLSPGERATLSCRASQSVSRSYLAWYQQKP GQAPRLLIIGASTRATGIPDRFSGSGSGTDFTLTISRLEPEDF AVYYCQQGQVIPPTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC |

The targeted single chain TNF ligand trimer-containing Fc (kih) fusion antigen binding molecule encoding sequences were cloned into a plasmid vector driving expression of the insert from an MPSV promoter and containing a synthetic polyA sequence located at the 3' end of the CDS. In addition, the vector contained an EBV OriP sequence for episomal maintenance of the plasmid.

The targeted single chain 4-1BBL-containing Fc (kih) fusion antigen binding molecule was produced by co-transfecting HEK293-EBNA cells with the mammalian expression vectors using polyethylenimine. The cells were transfected with the corresponding expression vectors at a 1:1:1 ratio ("vector knob chain":"vector hole chain":"vector light chain").

For production in 500 mL shake flasks, 400 million HEK293 EBNA cells were seeded 24 hours before transfection. For transfection cells were centrifuged for 5 minutes at 210×g, and the supernatant was replaced by pre-warmed CD CHO medium. Expression vectors were mixed in 20 mL CD CHO medium to a final amount of 200 µg DNA. After addition of 540 µL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection 1 mM valproic acid and 7% Feed with supplements were added. After culturing for 7 days, the supernatant was collected by centrifugation for 15 minutes at 210×g. The solution was sterile filtered (0.22 µm filter), supplemented with sodium azide to a final concentration of 0.01% (w/v), and kept at 4° C.

The targeted 4-1BBL trimer-containing Fc (kih) fusion antigen binding molecule was purified from cell culture supernatants by affinity chromatography using Protein A, followed by size exclusion chromatography. For affinity chromatography, the supernatant was loaded on a HITRAP® ProteinA HP column (CV=5 mL, GE Healthcare) and equilibrated with 20 mM sodium phosphate, 20 mM sodium citrate, 0.5 M sodium chloride, 0.01% (v/v) TWEEN® 20 (polysorbate 20) containing buffer (pH 7.5). Unbound protein was removed by washing with at least 10 column volumes of the same buffer. The bound protein was eluted using a linear pH gradient over 20 column volumes to 100% of 20 mM sodium citrate, 0.5 M sodium chloride, 0.01% (v/v) TWEEN® 20 (polysorbate 20) containing buffer (pH 2.5). The column was then washed with 10 column volumes of 20 mM sodium citrate, 0.5 M sodium chloride, 0.01% TWEEN® 20 (polysorbate 20) buffer (pH 2.5).

The pH of the collected fractions was adjusted by adding 1/40 (v/v) of 2M Tris, pH8.0. The protein was concentrated prior to loading on a HILOAD® Superdex 200 column (GE Healthcare) equilibrated with 20 mM Histidine, 150 mM sodium chloride, 0.01% (v/v) TWEEN® 20 (polysorbate 20) solution of pH 6.0.

The protein concentration was determined by measuring the optical density (OD) at 280 nm, using a molar extinction coefficient calculated on the basis of the amino acid sequence. Purity and molecular weight of the targeted TNF ligand trimer-containing Fc (kih) fusion antigen binding molecule was analyzed by SDS-PAGE in the presence and absence of a reducing agent (5 mM 1,4-dithiotreitol) and staining with Coomassie SIMPLYBLUE™ SafeStain (Invitrogen USA). The aggregate content of samples was analyzed using a TSKGEL® G3000 SW XL analytical size-exclusion column (Tosoh) equilibrated in 25 mM $K_2HPO_4$, 125 mM NaCl, 200 mM L-Arginine Monohydrocloride, 0.02% (w/v) $NaN_3$, pH 6.7 running buffer at 25° C.

Table 2 summarizes the yield and final monomer content of the FAP-targeted 4-1BBL trimer-containing Fc (kih) fusion antigen binding molecule.

TABLE 2

Summary of the production of the FAP-targeted 4-1BBL trimer-containing Fc (kih) fusion antigen binding molecule

| Construct | Yield [mg/l] | Monomer [%] (SEC) | LC/MS (non red) |
|---|---|---|---|
| FAP-targeted 4-1BBL trimer-containing Fc (kih) fusion | 14 | 100 | Theoretical*: 157358.6 Da |

TABLE 2-continued

Summary of the production of the FAP-targeted 4-1BBL trimer-containing Fc (kih) fusion antigen binding molecule

| Construct | Yield [mg/l] | Monomer [%] (SEC) | LC/MS (non red) |
|---|---|---|---|
| antigen binding molecule (FAP-targeted single chain 4-1BBL trimer) Compound S1 | | | Experimental: 157384 Da * without terminal lysines |

1.2. Bivalent FAP(4B9)-Targeted Single Chain 4-1BB Ligand Trimer-Containing Fc (Kih) Fusion Antigen Binding Molecule (Compound S2)

A polypeptide containing three ectodomains of 4-1BB ligand (71-254 or 71-248, synthetized according to P41273), separated by $(G_4S)_2$ linkers (SEQ ID NO:54) was subcloned in frame at the C-terminus of human IgG1 Fc knob chain (Merchant, Zhu et al., 1998), as depicted in FIG. 28A: human IgG1 Fc knob, $(G_4S)_2$ (SEQ ID NO:54) connector, human 4-1BB ligand, $(G_4S)_2$ (SEQ ID NO:54) connector, human 4-1BB ligand, $(G_4S)_2$ (SEQ ID NO:54) connector, human 4-1BB ligand.

The variable region of heavy and light chain DNA sequences encoding a binder specific for fibroblast activation protein (FAP), clone 4B9, were subcloned in frame with either the constant heavy chain of the hole, the knob or the constant light chain of human IgG1. The generation and preparation of the FAP binders is described in WO 2012/020006 A2, which is incorporated herein by reference.

The Pro329Gly, Leu234Ala and Leu235Ala mutations have been introduced in the constant region of the knob and hole heavy chains to abrogate binding to Fc gamma receptors as described in WO 2012/130831 A1.

Combination of the anti-FAP huIgG1 hole chain containing the Y349C/T366S/L368A/Y407V mutations, the anti-FAP huIgG1 knob trimeric ligand chain containing the S354C/T366W mutations and the anti-FAP light chain allows generation of a heterodimer, which includes an assembled trimeric 4-1BB ligand and two FAP binding Fabs (FIG. 28B).

Table 3 shows, respectively, the cDNA and amino acid sequences of the bivalent FAP-targeted single chain 4-1BB ligand trimer-containing Fc (kih) fusion antigen binding molecule.

TABLE 3

Sequences of bivalent FAP(4B9)-targeted single chain 4-1BBL(71-254) trimer-containing Fc (kih) fusion antigen binding molecule (Compound S2)

| SEQ ID NO: | Description | Sequence |
|---|---|---|
| 137 | nucleotide sequence of anti-FAP(4B9) Fc hole chain | GAGGTGCAGCTGCTCGAAAGCGGCGGAGGACTGGTGCA GCCTGGCGGCAGCCTGAGACTGTCTTGCGCCGCCAGCG GCTTCACCTTCAGCAGCTACGCCATGAGCTGGGTCCGCC AGGCCCCTGGCAAGGGACTGGAATGGGTGTCCGCCATC ATCGGCTCTGGCGCCAGCACCTACTACGCCGACAGCGTG AAGGGCCGGTTCACCATCAGCCGGGACAACAGCAAGAA CACCCTGTACCTGCAGATGAACAGCCTGCGGGCCGAGG ACACCGCCGTGTACTACTGCGCCAAGGGATGGTTCGGC GGCTTCAACTACTGGGGACAGGGCACCCTGGTCACAGT GTCCAGCGCTAGCACCAAGGGCCCCTCCGTGTTCCCCCT GGCCCCCAGCAGCAAGAGCACCAGCGGCGGCACAGCCG CTCTGGGCTGCCTGGTCAAGGACTACTTCCCCGAGCCCG TGACCGTGTCCTGGAACAGCGGAGCCCTGACCTCCGGC GTGCACACCTTCCCCGCCGTGCTGCAGAGTTCTGGCCTG TATAGCCTGAGCAGCGTGGTCACCGTGCCTTCTAGCAGC CTGGGCACCCAGACCTACATCTGCAACGTGAACCACAA GCCCAGCAACACCAAGGTGGACAAGAAGGTGGAGCCCA AGAGCTGCGACAAAACTCACACATGCCCACCGTGCCCA GCACCTGAAGCTGCAGGGGGACCGTCAGTCTTCCTCTTC CCCCCAAAACCCAAGGACACCCTCATGATCTCCCGGACC CCTGAGGTCACATGCGTGGTGGTGGACGTGAGCCACGA AGACCCTGAGGTCAAGTTCAACTGGTACGTGGACGGCG TGGAGGTGCATAATGCCAAGACAAAGCCGCGGGAGGAG CAGTACAACAGCACGTACCGTGTGGTCAGCGTCCTCACC GTCCTGCACCAGGACTGGCTGAATGGCAAGGAGTACAA GTGCAAGGTCTCCAACAAAGCCCTCGGCGCCCCCATCG AGAAAACCATCTCCAAAGCCAAAGGGCAGCCCCGAGAA CCACAGGTGTGCACCCTGCCCCCATCCCGGGATGAGCTG ACCAAGAACCAGGTCAGCCTCTCGTGCGCAGTCAAAGG CTTCTATCCCAGCGACATCGCCGTGGAGTGGGAGAGCA ATGGGCAGCCGGAGAACAACTACAAGACCACGCCTCCC GTGCTGGACTCCGACGGCTCCTTCTTCCTCGTGAGCAAG CTCACCGTGGACAAGAGCAGGTGGCAGCAGGGGAACGT CTTCTCATGCTCCGTGATGCATGAGGCTCTGCACAACCA CTACACGCAGAAGAGCCTCTCCCTGTCTCCGGGTAAA |
| 138 | nucleotide sequence of anti-FAP(4B9) Fc knob chain fused to trimeric hu 4-1BBL (71-254) | GAGGTGCAGCTGCTCGAAAGCGGCGGAGGACTGGTGCA GCCTGGCGGCAGCCTGAGACTGTCTTGCGCCGCCAGCG GCTTCACCTTCAGCAGCTACGCCATGAGCTGGGTCCGCC AGGCCCCTGGCAAGGGACTGGAATGGGTGTCCGCCATC ATCGGCTCTGGCGCCAGCACCTACTACGCCGACAGCGTG AAGGGCCGGTTCACCATCAGCCGGGACAACAGCAAGAA |

TABLE 3-continued

Sequences of bivalent FAP(4B9)-targeted single chain
4-1BBL(71-254) trimer-containing Fc (kih) fusion antigen
binding molecule (Compound S2)

| SEQ ID NO: | Description | Sequence |
|---|---|---|
| | | CACCCTGTACCTGCAGATGAACAGCCTGCGGGCCGAGG |
| | | ACACCGCCGTGTACTACTGCGCCAAGGGATGGTTCGGC |
| | | GGCTTCAACTACTGGGGACAGGGCACCCTGGTCACAGT |
| | | GTCCAGCGCTAGCACCAAGGGCCCATCGGTCTTCCCCCT |
| | | GGCACCCTCCTCCAAGAGCACCTCTGGGGGCACAGCGG |
| | | CCCTGGGCTGCCTGGTCAAGGACTACTTCCCCGAACCGG |
| | | TGACGGTGTCGTGGAACTCAGGCGCCCTGACCAGCGGC |
| | | GTGCACACCTTCCCGGCTGTCCTACAGTCCTCAGGACTC |
| | | TACTCCCTCAGCAGCGTGGTGACCGTGCCCTCCAGCAGC |
| | | TTGGGCACCCAGACCTACATCTGCAACGTGAATCACAA |
| | | GCCCAGCAACACCAAGGTGGACAAGAAAGTTGAGCCCA |
| | | AATCTTGTGACAAAACTCACACATGCCCACCGTGCCCAG |
| | | CACCTGAAGCTGCAGGGGGACCGTCAGTCTTCCTCTTCC |
| | | CCCCAAAACCCAAGGACACCCTCATGATCTCCCGGACCC |
| | | CTGAGGTCACATGCGTGGTGGTGGACGTGAGCCACGAA |
| | | GACCCTGAGGTCAAGTTCAACTGGTACGTGGACGGCGT |
| | | GGAGGTGCATAATGCCAAGACAAAGCCGCGGGAGGAGC |
| | | AGTACAACAGCACGTACCGTGTGGTCAGCGTCCTCACCG |
| | | TCCTGCACCAGGACTGGCTGAATGGCAAGGAGTACAAG |
| | | TGCAAGGTCTCCAACAAAGCCCTCGGCGCCCCCATCGA |
| | | GAAAACCATCTCCAAAGCCAAAGGGCAGCCCCGAGAAC |
| | | CACAGGTGTACACCCTGCCCCCCTGCAGAGATGAGCTG |
| | | ACCAAGAACCAGGTGTCCCTGTGGTGCCTCGTGAAGGG |
| | | CTTCTACCCCTCCGATATCGCCGTGGAATGGGAGAGCAA |
| | | CGGCCAGCCCGAGAACAACTACAAGACCACCCCCCCTG |
| | | TGCTGGACAGCGACGGCTCATTCTTCCTGTACTCCAAGC |
| | | TGACCGTGGACAAGAGCCGGTGGCAGCAGGGCAACGTG |
| | | TTCAGCTGCAGCGTGATGCACGAGGCCCTGCACAACCA |
| | | CTACACCCAGAAGTCCCTGAGCCTGAGCCCTGGCGGAG |
| | | GCGGAGGATCTGGCGGGGGAGGATCTAGAGAGGGCCCT |
| | | GAGCTGTCCCCCGATGATCCTGCTGGACTGCTGGACCTG |
| | | CGGCAGGGCATGTTTGCTCAGCTGGTGGCCCAGAACGTG |
| | | CTGCTGATCGACGGCCCTCTGAGCTGGTACAGCGATCCT |
| | | GGACTGGCTGGCGTGTCACTGACAGGCGGCCTGAGCTA |
| | | CAAAGAGGACACCAAAGAACTGGTGGTGGCCAAGGCCG |
| | | GCGTGTACTACGTGTTCTTTCAGCTGGAACTGCGGAGAG |
| | | TGGTGGCCGGCGAGGGATCTGGATCTGTGTCTCTGGCCC |
| | | TGCATCTGCAGCCCCTGAGATCAGCTGCTGGCGCTGCTG |
| | | CTCTGGCTCTGACAGTGGATCTGCCTCCTGCCAGCAGCG |
| | | AGGCCCGGAATAGCGCATTTGGGTTTCAAGGCAGGCTG |
| | | CTGCACCTGTCTGCCGGCCAGAGGCTGGGAGTGCATCTG |
| | | CACACAGAAGCCAGAGCCAGGCACGCTTGGCAGCTGAC |
| | | ACAGGGCGCTACAGTGCTGGGCCTGTTCAGAGTGACCC |
| | | CCGAGATTCCAGCCGGCCTGCCTTCTCCAAGAAGCGAA |
| | | GGCGGCGAGGCTCCGGAGGAGGCGGCTCTAGAGAAGG |
| | | ACCTGAACTGAGCCCAGACGACCCCGCAGGGCTGCTGG |
| | | ATCTGAGACAGGGAATGTTCGCCCAGCTGGTGGCTCAG |
| | | AATGTGCTGCTGATTGATGGACCCCTGTCCTGGTACTCC |
| | | GACCCAGGGCTGGCAGGGGTGTCCCTGACTGGCGGACT |
| | | GTCTTACAAAGAAGATACAAAAGAACTGGTGGTGGCTA |
| | | AAGCTGGGGTGTACTATGTGTTTTTTCAGCTGGAACTGA |
| | | GGCGGGTGGTGGCTGGGGAAGGCAGTGGCTCTGTGTCC |
| | | CTGGCACTGCATCTGCAGCCTCTGCGCAGTGCTGCAGGC |
| | | GCAGCCGCACTGGCACTGACTGTGGACCTGCCCCCAGCT |
| | | TCCAGCGAGGCTAGAAACAGCGCCTTCGGGTTTCAAGG |
| | | ACGCCTGCTGCATCTGAGCGCCGGACAGCGCCTGGGAG |
| | | TGCATCTGCATACTGAGGCTAGGGCCAGACATGCCTGGC |
| | | AGCTGACCCAGGGGCAACTGTGCTGGGACTGTTTCGCG |
| | | TGACACCTGAGATCCCCGCTGGCCTGCCAAGCCCTAGAT |
| | | CAGAAGGCGGAGGGGATCAGGGGGAGGCGGATCCAG |
| | | AGAGGGCCCTGAGCTGAGCCCCGATGATCCTGCTGGAC |
| | | TGCTGGACCTGCGGCAGGGCATGTTTGCTCAGCTGGTGG |
| | | CCCAGAACGTGCTGCTGATCGATGGCCCCCTGTCCTGGT |
| | | ACAGCGATCCTGGACTGGCTGGCGTGTCACTGACAGGC |
| | | GGCCTGAGCTACAAAGAGGACACCAAAGAACTGGTGGT |
| | | GGCCAAGGCCGGCGTGTACTACGTGTTCTTTCAGCTGGA |
| | | ACTGCGGAGAGTGGTGGCCGGCGAAGGATCTGGCTCTG |
| | | TGTCTCTGGCCCTGCATCTGCAGCCTCTGAGAAGCGCTG |
| | | CTGGCGCTGCAGCTCTGGCACTGACAGTGGATCTGCCTC |
| | | CTGCCAGCTCCGAGGCCCGGAATAGCGCATTTGGGTTTC |
| | | AAGGCAGGCTGCTGCACCTGTCTGCCGGCCAGAGGCTG |
| | | GGAGTGCATCTGCACACAGAGGCCAGGGCTAGACACGC |
| | | CTGGCAGCTGACACAGGGCGCTACAGTGCTGGGCCTGTT |

TABLE 3-continued

Sequences of bivalent FAP(4B9)-targeted single chain
4-1BBL(71-254) trimer-containing Fc (kih) fusion antigen
binding molecule (Compound S2)

| SEQ ID NO: | Description | Sequence |
|---|---|---|
| | | CAGAGTGACCCCCGAGATTCCAGCCGGCCTGCCTTCTCC<br>AAGAAGCGAA |
| 139 | nucleotide sequence of anti-FAP(4B9) light chain | GAGATCGTGCTGACCCAGTCCCCCGGCACCCTGTCTCTG<br>AGCCCTGGCGAGAGAGCCACCCTGTCCTGCAGAGCCTC<br>CCAGTCCGTGACCTCCTCCTACCTCGCCTGGTATCAGCA<br>GAAGCCCGGCCAGGCCCCTCGGCTGCTGATCAACGTGG<br>GCAGTCGGAGAGCCACCGGCATCCCTGACCGGTTCTCCG<br>GCTCTGGCTCCGGCACCGACTTCACCCTGACCATCTCCC<br>GGCTGGAACCCGAGGACTTCGCCGTGTACTACTGCCAGC<br>AGGGCATCATGCTGCCCCCCACCTTTGGCCAGGGCACCA<br>AGGTGGAAATCAAGCGTACGGTGGCTGCACCATCTGTCT<br>TCATCTTCCCGCCATCTGATGAGCAGTTGAAATCTGGAA<br>CTGCCTCTGTTGTGTGCCTGCTGAATAACTTCTATCCCAG<br>AGAGGCCAAAGTACAGTGGAAGGTGGATAACGCCCTCC<br>AATCGGGTAACTCCCAGGAGAGTGTCACAGAGCAGGAC<br>AGCAAGGACAGCACCTACAGCCTCAGCAGCACCCTGAC<br>GCTGAGCAAAGCAGACTACGAGAAACACAAAGTCTACG<br>CCTGCGAAGTCACCCATCAGGGCCTGAGCTCGCCCGTCA<br>CAAAGAGCTTCAACAGGGGAGAGTGT |
| 140 | anti-FAP(4B9) Fc hole chain | EVQLLESGGGLVQPGGSLRLSCAASGFTFSSYAMSWVRQA<br>PGKGLEWVSAIIGSGASTYYADSVKGRFTISRDNSKNTLYL<br>QMNSLRAEDTAVYYCAKGWFGGFNYWGQGTLVTVSSAS<br>TKGPSVFPLAPSSKSTSGGTAALGCLVKDYFPEPVTVSWNS<br>GALTSGVHTFPAVLQSSGLYSLSSVVTVPSSSLGTQTYICN<br>VNHKPSNTKVDKKVEPKSCDKTHTCPPCPAPEAAGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALGAPIEKTISKAKGQPREPQVCTLPPSRDELTKN<br>QVSLSCAVKGFYPSDIAVEWESNGQPENNYKTTPPVLDSD<br>GSFFLVSKLTVDKSRWQQGNVFSCSVMHEALHNHYTQKS<br>LSLSPGK |
| 141 | anti-FAP(4B9) Fc knob chain fused to trimeric 4 hu 4-1BBL (71-254) | EVQLLESGGGLVQPGGSLRLSCAASGFTFSSYAMSWVRQA<br>PGKGLEWVSAIIGSGASTYYADSVKGRFTISRDNSKNTLYL<br>QMNSLRAEDTAVYYCAKGWFGGFNYWGQGTLVTVSSAS<br>TKGPSVFPLAPSSKSTSGGTAALGCLVKDYFPEPVTVSWNS<br>GALTSGVHTFPAVLQSSGLYSLSSVVTVPSSSLGTQTYICN<br>VNHKPSNTKVDKKVEPKSCDKTHTCPPCPAPEAAGGPSVF<br>LFPPKPKDTLMISRTPEVTCVVVDVSHEDPEVKFNWYVDG<br>VEVHNAKTKPREEQYNSTYRVVSVLTVLHQDWLNGKEYK<br>CKVSNKALGAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKS<br>LSLSPGGGGGSGGGGSREGPELSPDDPAGLLDLRQGMFAQ<br>LVAQNVLLIDGPLSWYSDPGLAGVSLTGGLSYKEDTKELV<br>VAKAGVYYVFFQLELRRVVAGEGSGSVSLALHLQPLRSAA<br>GAAALALTVDLPPASSEARNSAFGFQGRLLHLSAGQRLGV<br>HLHTEARARHAWQLTQGATVLGLFRVTPEIPAGLPSPRSEG<br>GGGSGGGGSREGPELSPDDPAGLLDLRQGMFAQLVAQNV<br>LLIDGPLSWYSDPGLAGVSLTGGLSYKEDTKELVVAKAGV<br>YYVFFQLELRRVVAGEGSGSVSLALHLQPLRSAAGAAALA<br>LTVDLPPASSEARNSAFGFQGRLLHLSAGQRLGVHLHTEA<br>RARHAWQLTQGATVLGLFRVTPEIPAGLPSPRSEGGGGSG<br>GGGSREGPELSPDDPAGLLDLRQGMFAQLVAQNVLLIDGP<br>LSWYSDPGLAGVSLTGGLSYKEDTKELVVAKAGVYYVFF<br>QLELRRVVAGEGSGSVSLALHLQPLRSAAGAAALALTVDL<br>PPASSEARNSAFGFQGRLLHLSAGQRLGVHLHTEARARHA<br>WQLTQGATVLGLFRVTPEIPAGLPSPRSE |
| 142 | anti-FAP(4B9) light chain | EIVLTQSPGTLSLSPGERATLSCRASQSVTSSYLAWYQQKP<br>GQAPRLLINVGSRRATGIPDRFSGSGSGTDFTLTISRLEPEDF<br>AVYYCQQGIMLPPTFGQGTKVEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSS<br>PVTKSFNRGEC |

1.3. Monovalent FAP(4B9)-Targeted Single Chain 4-1BB Ligand Trimer-Containing Fc (Kih) Fusion Antigen Binding Molecule (Compound S3)

A polypeptide containing three ectodomains of 4-1BB ligand (71-254 or 71-248, synthetized according to P41273), separated by $(G_4S)_2$ (SEQ ID NO:54) linkers was subcloned as depicted in FIG. 1A: human 4-1BB ligand, $(G_4S)_2$ (SEQ ID NO:54) connector, human 4-1BB ligand, $(G_4S)_2$ (SEQ ID NO:54) connector, human 4-1BB ligand.

The polypeptide encoding the single chain trimeric 4-1BB ligand was subcloned in frame with the human IgG1 heavy chain CH2 and CH3 domains on the knob (Merchant, Zhu et al, 1998), using a linker (GSPGSSSSGS) of SEQ ID NO:57.

The variable region of heavy and light chain DNA sequences encoding a binder specific for fibroblast activation protein (FAP), clone 4B9, were subcloned in frame with either the constant heavy chain of the hole, the knob or the constant light chain of human IgG1. The generation and preparation of the FAP binder is described in WO 2012/020006 A2, which is incorporated herein by reference.

The Pro329Gly, Leu234Ala and Leu235Ala mutations have been introduced in the constant region of the knob and hole heavy chains to abrogate binding to Fc gamma receptors as described in WO 2012/130831 A1.

Combination of the single chain ligand-Fc knob chain containing the S354C/T366W mutations, with the targeted anti-FAP-Fc hole chain containing the Y349C/T366S/L368A/Y407V mutations and the anti-FAP light chain, allows generation of a heterodimer, which includes a single chain 4-1BB ligand trimer and a FAP binding Fab (FIG. 3A).

Table 4 shows, respectively, the cDNA and amino acid sequences of the monovalent FAP(4B9)-targeted single chain 4-1BB ligand trimer-containing Fc (kih) fusion antigen binding molecule.

TABLE 4

Sequences of monovalent FAP(4B9)-targeted single chain 4-1BBL(71-254) trimer containing Fc (kih) fusion antigen binding molecule (Compound S3)

| SEQ ID NO: | Description | Sequence |
|---|---|---|
| 137 | nucleotide sequence of anti-FAP(4B9) Fc hole chain | see Table 3 |
| 66 | nucleotide sequence of trimeric hu 4-1BBL (71-254) Fc knob chain | see Table 1 |
| 139 | nucleotide sequence of anti-FAP(4B9) light chain | see Table 3 |
| 140 | anti-FAP(4B9) Fc hole chain | see Table 3 |
| 15 | trimeric hu 4-1BBL (71-254) Fc knob chain | see Table 1 |
| 142 | anti-FAP(4B9) light chain | see Table 3 |

1.4. Bivalent CEA-Targeted Single Chain 4-1BB Ligand Trimer-Containing Fc (Kih) Fusion Antigen Binding Molecule (Compound S4)

The molecule was prepared as described in 1.2 for the bivalent FAP(4B9)-targeted construct, with the only difference that the anti-FAP binder was replaced by an anti-CEA binder.

The variable region of heavy and light chain DNA sequences encoding a binder specific for carcinoembryonic antigen (CEA), clone sm9b, were subcloned in frame with either the constant heavy chain of the hole, the knob or the constant light chain of human IgG1. The clone sm9b is further described in US 2005/0147614, Graff et al. 2004 and WO 2014/004694 A1 which are incorporated herein by reference.

The Pro329Gly, Leu234Ala and Leu235Ala mutations have been introduced in the constant region of the knob and hole heavy chains to abrogate binding to Fc gamma receptors as described in WO 2012/130831 A1.

Combination of the anti-CEA huIgG1 hole chain containing the Y349C/T366S/L368A/Y407V mutations, the anti-CEA huIgG1 knob trimeric ligand chain containing the S354C/T366W mutations and the anti-CEA light chain allows generation of a heterodimer, which includes an assembled trimeric 4-1BB ligand and two CEA binding Fabs (FIG. 28B).

Table 5 shows, respectively, the cDNA and amino acid sequences of the bivalent CEA(sm9b)-targeted single chain 4-1BB ligand trimer-containing Fc (kih) fusion antigen binding molecule.

TABLE 5

Sequences of bivalent CEA(sm9b)-targeted single chain 4-1BBL(71-254) trimer-containing Fc (kih) fusion antigen binding molecule (Compound S4)

| SEQ ID NO: | Description | Sequence |
|---|---|---|
| 143 | nucleotide sequence of anti-CEA(sm9b) Fc hole chain | CAAGTGAAGCTGGAGCAGAGCGGCGCCGAAGTCGTGAA<br>ACCCGGGGCTTCCGTCAAGCTCTCTTGCAAGGCATCAGG<br>ATTCAACATCAAAGACAGCTACATGCACTGGCTGAGGC<br>AGGGCCCTGGTCAGTGCCTTGAGTGGATTGGCTGGATCG<br>ATCCAGAGAATGGCGACACCGAATATGCCCCCAAGTTT<br>CAAGGAAAGGCTACATTCACCACTGATACATCCGCAAA<br>CACCGCCTACCTGGGTCTCTCAAGTCTGCGCCCTGAGGA<br>CACTGCTGTGTATTACTGTAATGAGGGCACCCCAACAGG<br>GCCCTACTATTTTGACTACTGGGGACAGGGCACCTTGGT<br>TACAGTGAGCTCCGCTAGCACCAAGGGCCCATCGGTCTT<br>CCCCCTGGCACCCTCCTCCAAGAGCACCTCTGGGGGCAC<br>AGCGGCCCTGGGCTGCCTGGTCAAGGACTACTTCCCCGA<br>ACCGGTGACGGTGTCGTGGAACTCAGGCGCCCTGACCA<br>GCGGCGTGCACACCTTCCCGGCTGTCCTACAGTCCTCAG<br>GACTCTACTCCCTCAGCAGCGTGGTGACCGTGCCCTCCA<br>GCAGCTTGGGCACCCAGACCTACATCTGCAACGTGAATC |

TABLE 5-continued

Sequences of bivalent CEA(sm9b)-targeted single chain
4-1BBL(71-254) trimer-containing Fc (kih) fusion antigen
binding molecule (Compound S4)

| SEQ ID NO: | Description | Sequence |
|---|---|---|
| | | ACAAGCCCAGCAACACCAAGGTGGACAAGAAAGTTGAG<br>CCCAAATCTTGTGACAAAACTCACACATGCCCACCGTGC<br>CCAGCACCTGAAGCTGCAGGGGACCGTCAGTCTTCCTC<br>TTCCCCCCAAAACCCAAGGACACCCTCATGATCTCCCGG<br>ACCCCTGAGGTCACATGCGTGGTGGTGGACGTGAGCCA<br>CGAAGACCCTGAGGTCAAGTTCAACTGGTACGTGGACG<br>GCGTGGAGGTGCATAATGCCAAGACAAAGCCGCGGGAG<br>GAGCAGTACAACAGCACGTACCGTGTGGTCAGCGTCCT<br>CACCGTCCTGCACCAGGACTGGCTGAATGGCAAGGAGT<br>ACAAGTGCAAGGTCTCCAACAAAGCCCTCGGCGCCCCC<br>ATCGAGAAAACCATCTCCAAAGCCAAAGGGCAGCCCCG<br>AGAACCACAGGTGTGCACCCTGCCCCCATCCCGGGATG<br>AGCTGACCAAGAACCAGGTCAGCCTCTCGTGCGCAGTC<br>AAAGGCTTCTATCCCAGCGACATCGCCGTGGAGTGGGA<br>GAGCAATGGGCAGCCGGAGAACAACTACAAGACCACGC<br>CTCCCGTGCTGGACTCCGACGGCTCCTTCTTCCTCGTGA<br>GCAAGCTCACCGTGGACAAGAGCAGGTGGCAGCAGGGG<br>AACGTCTTCTCATGCTCCGTGATGCATGAGGCTCTGCAC<br>AACCACTACACGCAGAAGAGCCTCTCCCTGTCTCCGGGT<br>AAA |
| 144 | nucleotide sequence of anti-CEA(sm9b) Fc knob chain fused to trimeric hu 4-1BBL (71-254) | CAAGTGAAGCTGGAGCAGAGCGGCGCCGAAGTCGTGAA<br>ACCCGGGGCTTCCGTCAAGCTCTCTTGCAAGGCATCAGG<br>ATTCAACATCAAAGACAGCTACATGCACTGGCTGAGGC<br>AGGGCCCTGGTCAGTGCCTTGAGTGGATTGGCTGGATCG<br>ATCCAGAGAATGGCGACACCGAATATGCCCCCAAGTTT<br>CAAGGAAAGGCTACATTCACCACTGATACATCCGCAAA<br>CACCGCCTACCTGGGTCTCTCAAGTCTGCGCCCTGAGGA<br>CACTGCTGTGTATTACTGTAATGAGGGCACCCCAACAGG<br>GCCCTACTATTTTGACTACTGGGGACAGGGCACCTTGGT<br>TACAGTGAGCTCCGCTAGCACCAAGGGCCCATCGGTCTT<br>CCCCCTGGCACCCTCCTCCAAGAGCACCTCTGGGGGCAC<br>AGCGGCCCTGGGCTGCCTGGTCAAGGACTACTTCCCCGA<br>ACCGGTGACGGTGTCGTGGAACTCAGGCGCCCTGACCA<br>GCGGCGTGCACACCTTCCCGGCTGTCCTACAGTCCTCAG<br>GACTCTACTCCCTCAGCAGCGTGGTGACCGTGCCCTCCA<br>GCAGCTTGGGCACCCAGACCTACATCTGCAACGTGAATC<br>ACAAGCCCAGCAACACCAAGGTGGACAAGAAAGTTGAG<br>CCCAAATCTTGTGACAAAACTCACACATGCCCACCGTGC<br>CCAGCACCTGAAGCTGCAGGGGACCGTCAGTCTTCCTC<br>TTCCCCCCAAAACCCAAGGACACCCTCATGATCTCCCGG<br>ACCCCTGAGGTCACATGCGTGGTGGTGGACGTGAGCCA<br>CGAAGACCCTGAGGTCAAGTTCAACTGGTACGTGGACG<br>GCGTGGAGGTGCATAATGCCAAGACAAAGCCGCGGGAG<br>GAGCAGTACAACAGCACGTACCGTGTGGTCAGCGTCCT<br>CACCGTCCTGCACCAGGACTGGCTGAATGGCAAGGAGT<br>ACAAGTGCAAGGTCTCCAACAAAGCCCTCGGCGCCCCC<br>ATCGAGAAAACCATCTCCAAAGCCAAAGGGCAGCCCCG<br>AGAACCACAGGTGTACACCCTGCCCCCCTGCAGAGATG<br>AGCTGACCAAGAACCAGGTCAGCCTGTGGTGCCTCGTGA<br>AGGGCTTCTACCCCTCCGATATCGCCGTGGAATGGGAGA<br>GCAACGGCCAGCCCGAGAACAACTACAAGACCACCCCC<br>CCTGTGCTGGACAGCGACGGCTCATTCTTCCTGTACTCC<br>AAGCTGACCGTGGACAAGAGCCGGTGGCAGCAGGGCAA<br>CGTGTTCAGCTGCAGCGTGATGCACGAGGCCCTGCACA<br>ACCACTACACCCAGAAGTCCCTGAGCCTGAGCCCTGGC<br>GGAGGCGGAGGATCTGGCGGGGGAGGATCTAGAGAGG<br>GCCCTGAGCTGTCCCCCGATGATCCTGCTGGACTGCTGG<br>ACCTGCGGCAGGGCATGTTTGCTCAGCTGGTGGCCCAGA<br>ACGTGCTGCTGATCGACGGCCCTCTGAGCTGGTACAGCG<br>ATCCTGGACTGGCTGGCGTGTCACTGACAGGCGGCCTGA<br>GCTACAAAGAGGACACCAAAGAACTGGTGGTGGCCAAG<br>GCCGGCGTGTACTACGTGTTCTTTCAGCTGGAACTGCGG<br>AGAGTGGTGGCCGGCGAGGGATCTGGATCTGTGTCTCTG<br>GCCCTGCATCTGCAGCCCCTGAGATCAGCTGCTGGCGCT<br>GCTGCTCTGGCTCTGACAGTGGATCTGCCTCCTGCCAGC<br>AGCGAGGCCCGGAATAGCGCATTTGGGTTTCAAGGCAG<br>GCTGCTGCACCTGTCTGCCGGCCAGAGGCTGGGAGTGC<br>ATCTGCACACAGAAGCAGAGCCAGGCACGCTTGGCAG<br>CTGACACAGGGCGCTACAGTGCTGGGCCTGTTCAGAGTG<br>ACCCCCGAGATTCCAGCCGGCCTGCCTTCTCCAAGAAGC<br>GAAGGCGGCGGAGGCTCCGGAGGAGGCGGCTCTAGAGA<br>AGGACCTGAACTGAGCCCAGACGACCCCGCAGGGCTGC |

TABLE 5-continued

Sequences of bivalent CEA(sm9b)-targeted single chain
4-1BBL(71-254) trimer-containing Fc (kih) fusion antigen
binding molecule (Compound S4)

| SEQ ID NO: | Description | Sequence |
|---|---|---|
| | | TGGATCTGAGACAGGGAATGTTCGCCCAGCTGGTGGCTC AGAATGTGCTGCTGATTGATGGACCCCTGTCCTGGTACT CCGACCCAGGGCTGGCAGGGGTGTCCCTGACTGGCGGA CTGTCTTACAAAGAAGATACAAAAGAACTGGTGGTGGC TAAAGCTGGGGTGTACTATGTGTTTTTTCAGCTGGAACT GAGGCGGGTGGTGGCTGGGGAAGGCAGTGGCTCTGTGT CCCTGGCACTGCATCTGCAGCCTCTGCGCAGTGCTGCAG GCGCAGCCGCACTGGCACTGACTGTGGACCTGCCCCCA GCTTCCAGCGAGGCTAGAAACAGCGCCTTCGGGTTTCAA GGACGCCTGCTGCATCTGAGCGCCGGACAGCGCCTGGG AGTGCATCTGCATACTGAGGCTAGGGCCAGACATGCCTG GCAGCTGACCCAGGGGGCAACTGTGCTGGGACTGTTTCG CGTGACACCTGAGATCCCCGCTGGCCTGCCAAGCCCTAG ATCAGAAGGCGGAGGGGATCAGGGGGAGGCGGATCC AGAGAGGGCCCTGAGCTGAGCCCCGATGATCCTGCTGG ACTGCTGGACCTGCGGCAGGGCATGTTTGCTCAGCTGGT GGCCCAGAACGTGCTGCTGATCGATGGCCCCCTGTCCTG GTACAGCGATCCTGGACTGGCTGGCGTGTCACTGACAGG CGGCCTGAGCTACAAAGAGGACACCAAAGAACTGGTGG TGGCCAAGGCCGGCGTGTACTACGTGTTCTTTCAGCTGG AACTGCGGAGAGTGGTGGCCGGCGAAGGATCTGGCTCT GTGTCTCTGGCCCTGCATCTGCAGCCTCTGAGAAGCGCT GCTGGCGCTGCAGCTCTGGCACTGACAGTGGATCTGCCT CCTGCCAGCTCCGAGGCCCGGAATAGCGCATTTGGGTTT CAAGGCAGGCTGCTGCACCTGTCTGCCGGCCAGAGGCT GGGAGTGCATCTGCACACAGAGGCCAGGGCTAGCACAG CCTGGCAGCTGACACAGGGCGCTACAGTGCTGGGCCTG TTCAGAGTGACCCCCGAGATTCCAGCCGGCCTGCCTTCT CCAAGAAGCGAA |
| 145 | nucleotide sequence of anti-CEA(sm9b) light chain | GAGAACGTGCTGACCCAGAGCCCCTCCTCTATGTCAGTC AGCGTGGGCGACAGGGTCACAATCGCCTGCTCCGCTTCT AGTAGCGTGCCTTACATGCACTGGTCCAGCAGAAGCC AGGGAAATCCCCCAAGCTGCTTATTTATTCTACCTCAAA TCTGGCAAGCGGAGTTCCTAGCAGATTCTCTGGCAGTGG TAGCGGGACTGATTACTCCCTCACAATCTCAAGTGTGCA GCCAGAAGACGCCGCTACCTATTACTGTCAACAGCGCA GCTCCTACCCCCTGACTTTTGGCTGTGGCACCAAGTTGG AGATTAAACGTACGGTGGCTGCACCATCTGTCTTCATCT TCCCGCCATCTGATGAGCAGTTGAAATCTGGAACTGCCT CTGTTGTGTGCCTGCTGAATAACTTCTATCCCAGAGAGG CCAAAGTACAGTGGAAGGTGGATAACGCCCTCCAATCG GGTAACTCCCAGGAGAGTGTCACAGAGCAGGACAGCAA GGACAGCACCTACAGCCTCAGCAGCACCCTGACGCTGA GCAAAGCAGACTACGAGAAACACAAAGTCTACGCCTGC GAAGTCACCCATCAGGGCCTGAGCTCGCCCGTCACAAA GAGCTTCAACAGGGGAGAGTGT |
| 146 | anti-CEA(sm9b) Fc hole chain | QVKLEQSGAEVVKPGASVKLSCKASGFNIKDSYMHWLRQ GPGQCLEWIGWIDPENGDTEYAPKFQGKATFTTDTSANTA YLGLSSLRPEDTAVYYCNEGTPTGPYYFDYWGQGTLVTVS SASTKGPSVFPLAPSSKSTSGGTAALGCLVKDYFPEPVTVS WNSGALTSGVHTFPAVLQSSGLYSLSSVVTVPSSSLGTQTY ICNVNHKPSNTKVDKKVEPKSCDKTHTCPPCPAPEAAGGP SVFLFPPKPKDTLMISRTPEVTCVVVDVSHEDPEVKFNWY VDGVEVHNAKTKPREEQYNSTYRVVSVLTVLHQDWLNG KEYKCKVSNKALGAPIEKTISKAKGQPREPQVCTLPPSRDE LTKNQVSLSCAVKGFYPSDIAVEWESNGQPENNYKTTPPV LDSDGSFFLVSKLTVDKSRWQQGNVFSCSVMHEALHNHY TQKSLSLSPGK |
| 147 | anti-CEA(sm9b) Fc knob chain fused to trimeric hu 4-1BBL (71-254) | QVKLEQSGAEVVKPGASVKLSCKASGFNIKDSYMHWLRQ GPGQCLEWIGWIDPENGDTEYAPKFQGKATFTTDTSANTA YLGLSSLRPEDTAVYYCNEGTPTGPYYFDYWGQGTLVTVS SASTKGPSVFPLAPSSKSTSGGTAALGCLVKDYFPEPVTVS WNSGALTSGVHTFPAVLQSSGLYSLSSVVTVPSSSLGTQTY ICNVNHKPSNTKVDKKVEPKSCDKTHTCPPCPAPEAAGGP SVFLFPPKPKDTLMISRTPEVTCVVVDVSHEDPEVKFNWY VDGVEVHNAKTKPREEQYNSTYRVVSVLTVLHQDWLNG KEYKCKVSNKALGAPIEKTISKAKGQPREPQVYTLPPCRDE LTKNQVSLWCLVKGFYPSDIAVEWESNGQPENNYKTTPPV LDSDGSFFLYSKLTVDKSRWQQGNVFSCSVMHEALHNHY TQKSLSLSPGGGGGSGGGGSREGPELSPDDPAGLLDLRQG |

TABLE 5-continued

Sequences of bivalent CEA(sm9b)-targeted single chain
4-1BBL(71-254) trimer-containing Fc (kih) fusion antigen
binding molecule (Compound S4)

| SEQ ID NO: | Description | Sequence |
|---|---|---|
|  |  | MFAQLVAQNVLLIDGPLSWYSDPGLAGVSLTGGLSYKEDT<br>KELVVAKAGVYYVFFQLELRRVVAGEGSGSVSLALHLQPL<br>RSAAGAAALALTVDLPPASSEARNSAFGFQGRLLHLSAGQ<br>RLGVHLHTEARARHAWQLTQGATVLGLFRVTPEIPAGLPS<br>PRSEGGGGSGGGGSREGPELSPDDPAGLLDLRQGMFAQLV<br>AQNVLLIDGPLSWYSDPGLAGVSLTGGLSYKEDTKELVVA<br>KAGVYYVFFQLELRRVVAGEGSGSVSLALHLQPLRSAAGA<br>AALALTVDLPPASSEARNSAFGFQGRLLHLSAGQRLGVHL<br>HTEARARHAWQLTQGATVLGLFRVTPEIPAGLPSPRSEGG<br>GGSGGGGSREGPELSPDDPAGLLDLRQGMFAQLVAQNVL<br>LIDGPLSWYSDPGLAGVSLTGGLSYKEDTKELVVAKAGVY<br>YVFFQLELRRVVAGEGSGSVSLALHLQPLRSAAGAAALAL<br>TVDLPPASSEARNSAFGFQGRLLHLSAGQRLGVHLHTEAR<br>ARHAWQLTQGATVLGLFRVTPEIPAGLPSPRSE |
| 148 | anti-CEA(sm9b) light chain | ENVLTQSPSSMSVSVGDRVTIACSASSSVPYMHWLQQKPG<br>KSPKLLIYSTSNLASGVPSRFSGSGSGTDYSLTISSVQPEDA<br>ATYYCQQRSSYPLTFGCGTKLEIKRTVAAPSVFIFPPSDEQL<br>KSGTASVVCLLNNFYPREAKVQWKVDNALQSGNSQESVT<br>EQDSKDSTYSLSSTLTLSKADYEKHKVYACEVTHQGLSSP<br>VTKSFNRGEC |

1.5. Monovalent CEA(sm9b)-Targeted Single Chain 4-1BB Ligand Trimer-Containing Fc (Kih) Fusion Antigen Binding Molecule (Compound S5)

The molecule was prepared as described in 1.3 for the monovalent FAP-targeted construct, with the only difference that the anti-FAP binder was replaced by an anti-CEA binder.

The variable region of heavy and light chain DNA sequences encoding a binder specific for fibroblast activation protein (CEA), clone sm9b, were subcloned in frame with either the constant heavy chain of the hole (Carter, 2001) or the constant light chain of human IgG1.

Figure 2A:
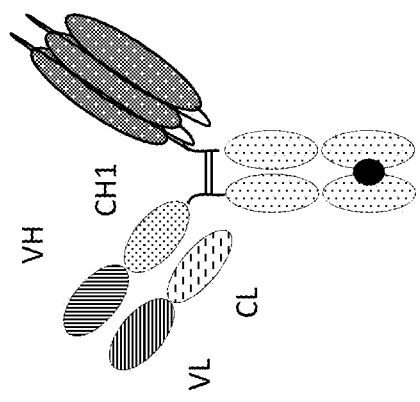
FIGS. 2A and 2B schematically show variants (2A) and (2B) of the monovalent TNF ligand trimer-containing antigen binding molecules of the invention. The three TNF ligands are symbolized by the grey areas with white points. The white areas with black points symbolize the Fc part, the thick black point stands for the knob-into-hole modification.
Figure 2B:
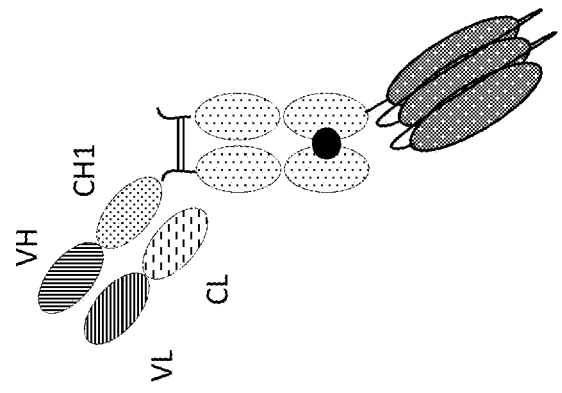

Combination of the anti-CEA huIgG1 hole chain containing the Y349C/T366S/L368A/Y407V mutations, the single chain ligand huIgG1 knob chain containing the S354C/T366W mutations and the anti-CEA light chain allows generation of a heterodimer, which includes an assembled trimeric 4-1BB ligand and one CEA binding Fab (FIG. 2A).

Table 6 shows, respectively, the cDNA and amino acid sequences of the monovalent CEA(sm9b)-targeted single chain 4-1BB ligand trimer-containing Fc (kih) fusion antigen binding molecule.

TABLE 6

Sequences of monovalent CEA(sm9b)-targeted single chain 4-1BBL(71-254) trimer-containing Fc (kih) fusion antigen binding molecule (Compound S5)

| SEQ ID NO: | Description | Sequence |
|---|---|---|
| 143 | nucleotide sequence of anti-CEA(sm9b) Fc hole chain | see Table 5 |
| 66 | nucleotide sequence of trimeric hu 4-1BBL (71-254) Fc knob chain | see Table 1 |
| 145 | nucleotide sequence of anti-CEA(sm9b) light chain | see Table 5 |
| 146 | anti-CEA(sm9b) Fc hole chain | see Table 5 |
| 15 | trimeric hu 4-1BBL (71-254) Fc knob chain | see Table 1 |
| 148 | anti-CEA(sm9b) light chain | see Table 5 |

1.6. Bivalent CD19-Targeted Single Chain 4-1BB Ligand Trimer-Containing Fc (Kih) Fusion Antigen Binding Molecules (Compound S6 and S7)

The molecules are prepared as described in 1.2 for the bivalent FAP(4B9)-targeted construct, with the only difference that the anti-FAP binder is replaced by anti-CD19 binders. The generation of the CD19 clones is described in Example 1.8.

The variable region of heavy and light chain DNA sequences encoding a binder specific for CD19, i.e. clones 8B8-018 and 8B8-2B11, are subcloned in frame with either the constant heavy chain of the hole, the knob or the constant light chain of human IgG1.

Combination of the anti-CD19 hu IgG1 hole chain containing the Y349C/T366S/L368A/Y407V mutations, the anti-CD19 hu IgG1 knob trimeric ligand chain containing the S354C/T366W mutations and the anti-CD19 light chain allows generation of a heterodimer, which includes an assembled trimeric 4-1BB ligand and two CD19 binding Fabs (FIG. 28B). The Pro329Gly, Leu234Ala and Leu235Ala mutations are introduced in the constant region of the knob and hole heavy chains to abrogate binding to Fc gamma receptors as described in WO 2012/130831 A1.

Table 7 shows, respectively, the cDNA and amino acid sequences of the bivalent CD19(8B8-018)-targeted single chain 4-1BB ligand trimer-containing Fc (kih) fusion antigen binding molecule.

TABLE 7

Sequences of bivalent CD19(8B8-018)-targeted single chain
4-1BBL(71-254) trimer-containing Fc (kih) fusion antigen
binding molecule (Compound S6)

| SEQ ID NO: | Description | Sequence |
|---|---|---|
| 149 | nucleotide sequence of anti-CD19(8B8-018) Fc hole chain | CAGGTCCAGCTGGTGCAGTCCGGCGCCGAGGTCAAGAA ACCCGGGGCTTCTGTGAAGGTTTCATGCAAGGCAAGCG GATACACCTTCACCGACTATATCATGCATTGGGTCAGGC AGGCCCCTGGCCAAGGTCTCGAATGGATGGGCTACATTA ACCCATATAATGATGGCTCCAAATACACCGAGAAGTTTC AGGGAAGAGTCACTATGACATCTGACACCAGTATCAGC ACTGCTTACATGGAGCTGTCCCGCCTTCGGTCTGATGAC ACCGCAGTGTATTACTGTGCCAGGGGCACATATTACTAC GGCTCAGCTCTGTTCGACTATTGGGGCAGGGAACCACA GTAACCGTGAGCTCCGCTAGCACCAAGGGCCCCTCCGTG TTCCCCCTGGCCCCCAGCAGCAAGAGCACCAGCGGCGG CACAGCCGCTCTGGGCTGCCTGGTCAAGGACTACTTCCC CGAGCCCGTGACCGTGTCCTGGAACAGCGGAGCCCTGA CCTCCGGCGTGCACACCTTCCCCGCCGTGCTGCAGAGTT CTGGCCTGTATAGCCTGAGCAGCGTGGTCACCGTGCCTT CTAGCAGCCTGGGCACCCAGACCTACATCTGCAACGTG AACCACAAGCCCAGCAACACCAAGGTGGACAAGAAGGT GGAGCCCAAGAGCTGCGACAAAACTCACACATGCCCAC CGTGCCCAGCACCTGAAGCTGCAGGGGGACCGTCAGTC TTCCTCTTCCCCCCAAAACCCAAGGACACCCTCATGATC TCCCGGACCCCTGAGGTCACATGCGTGGTGGTGGACGTG AGCCACGAAGACCCTGAGGTCAAGTTCAACTGGTACGT GGACGGCGTGGAGGTGCATAATGCCAAGACAAAGCCGC GGGAGGAGCAGTACAACAGCACGTACCGTGTGGTCAGC GTCCTCACCGTCCTGCACCAGGACTGGCTGAATGGCAAG GAGTACAAGTGCAAGGTCTCCAACAAAGCCCTCGGCGC CCCCATCGAGAAAACCATCTCCAAAGCCAAAGGGCAGC CCCGAGAACCACAGGTGTGCACCCTGCCCCCATCCCGG GATGAGCTGACCAAGAACCAGGTCAGCCTCTCGTGCGC AGTCAAAGGCTTCTATCCCAGCGACATCGCCGTGGAGTG GGAGAGCAATGGGCAGCCGGAGAACAACTACAAGACC ACGCCTCCCGTGCTGGACTCCGACGGCTCCTTCTTCCTC GTGAGCAAGCTCACCGTGGACAAGAGCAGGTGGCAGCA GGGGAACGTCTTCTCATGCTCCGTGATGCATGAGGCTCT GCACAACCACTACACGCAGAAGAGCCTCTCCCTGTCTCC GGGTAAA |
| 150 | nucleotide sequence of anti-CD19(8B8-018) Fc knob chain fused to trimeric hu4-1BBL (71-254) | CAGGTCCAGCTGGTGCAGTCCGGCGCCGAGGTCAAGAA ACCCGGGGCTTCTGTGAAGGTTTCATGCAAGGCAAGCG GATACACCTTCACCGACTATATCATGCATTGGGTCAGGC AGGCCCCTGGCCAAGGTCTCGAATGGATGGGCTACATTA ACCCATATAATGATGGCTCCAAATACACCGAGAAGTTTC AGGGAAGAGTCACTATGACATCTGACACCAGTATCAGC ACTGCTTACATGGAGCTGTCCCGCCTTCGGTCTGATGAC ACCGCAGTGTATTACTGTGCCAGGGGCACATATTACTAC GGCTCAGCTCTGTTCGACTATTGGGGCAGGGAACCACA GTAACCGTGAGCTCCGCTAGCACCAAGGGCCCATCGGT CTTCCCCCTGGCACCCTCCTCCAAGAGCACCTCTGGGGG CACAGCGGCCCTGGGCTGCCTGGTCAAGGACTACTTCCC CGAACCGGTGACGGTGTCGTGGAACTCAGGCGCCCTGA CCAGCGGCGTGCACACCTTCCCGGCTGTCCTACAGTCCT CAGGACTCTACTCCCTCAGCAGCGTGGTGACCGTGCCCT CCAGCAGCTTGGGCACCCAGACCTACATCTGCAACGTG AATCACAAGCCCAGCAACACCAAGGTGGACAAGAAAGT TGAGCCCAAATCTTGTGACAAAACTCACACATGCCCACC GTGCCCAGCACCTGAAGCTGCAGGGGGACCGTCAGTCT TCCTCTTCCCCCCAAAACCCAAGGACACCCTCATGATCT CCCGGACCCCTGAGGTCACATGCGTGGTGGTGGACGTG AGCCACGAAGACCCTGAGGTCAAGTTCAACTGGTACGT GGACGGCGTGGAGGTGCATAATGCCAAGACAAAGCCGC GGGAGGAGCAGTACAACAGCACGTACCGTGTGGTCAGC GTCCTCACCGTCCTGCACCAGGACTGGCTGAATGGCAAG GAGTACAAGTGCAAGGTCTCCAACAAAGCCCTCGGCGC CCCCATCGAGAAAACCATCTCCAAAGCCAAAGGGCAGC CCCGAGAACCACAGGTGTACACCCTGCCCCCCTGCAGA GATGAGCTGACCAAGAACCAGGTGTCCCTGTGGTGCCTC GTGAAGGGCTTCTACCCCTCCGATATCGCCGTGGAATGG GAGAGCAACGGCCAGCCCGAGAACAACTACAAGACCAC CCCCCCTGTGCTGGACAGCGACGGCTCATTCTTCCTGTA CTCCAAGCTGACCGTGGACAAGAGCCGGTGGCAGCAGG GCAACGTGTTCAGCTGCAGCGTGATGCACGAGGCCCTG CACAACCACTACACCCAGAAGTCCCTGAGCCTGAGCCCT GGCGGAGGCGGAGGATCTGGCGGGGGAGGATCTAGAGA |

TABLE 7-continued

Sequences of bivalent CD19(8B8-018)-targeted single chain 4-1BBL(71-254) trimer-containing Fc (kih) fusion antigen binding molecule (Compound S6)

| SEQ ID NO: | Description | Sequence |
|---|---|---|
|  |  | GGGCCCTGAGCTGTCCCCCGATGATCCTGCTGGACTGCT<br>GGACCTGCGGCAGGGCATGTTTGCTCAGCTGGTGGCCCA<br>GAACGTGCTGCTGATCGACGGCCCTCTGAGCTGGTACAG<br>CGATCCTGGACTGGCTGGCGTGTCACTGACAGGCGGCCT<br>GAGCTACAAAGAGGACACCAAAGAACTGGTGGTGGCCA<br>AGGCCGGCGTGTACTACGTGTTCTTTCAGCTGGAACTGC<br>GGAGAGTGGTGGCCGGCGAGGGATCTGGATCTGTGTCT<br>CTGGCCCTGCATCTGCAGCCCTGAGATCAGCTGCTGGC<br>GCTGCTGCTCTGGCTCTGACAGTGGATCTGCCTCCTGCC<br>AGCAGCGAGGCCCGGAATAGCGCATTTGGGTTTCAAGG<br>CAGGCTGCTGCACCTGTCTGCCGGCCAGAGGCTGGGAG<br>TGCATCTGCACACAGAAGCCAGAGCCAGGCACGCTTGG<br>CAGCTGACACAGGGCGCTACAGTGCTGGGCCTGTTCAG<br>AGTGACCCCCGAGATTCCAGCCGGCCTGCCTTCTCCAAG<br>AAGCGAAGGCGGCGGAGGCTCCGGAGGAGGCGGCTCTA<br>GAGAAGGACCTGAACTGAGCCCAGACGACCCCGCAGGG<br>CTGCTGGATCTGAGACAGGGAATGTTCGCCCAGCTGGTG<br>GCTCAGAATGTGCTGCTGATTGATGGACCCCTGTCCTGG<br>TACTCCGACCCAGGGCTGGCAGGGGTGTCCCTGACTGGC<br>GGACTGTCTTACAAAGAAGATACAAAAGAACTGGTGGT<br>GGCTAAAGCTGGGGTGTACTATGTGTTTTTTCAGCTGGA<br>ACTGAGGCGGGTGGTGGCTGGGGAAGGCAGTGGCTCTG<br>TGTCCCTGGCACTGCATCTGCAGCCTCTGCGCAGTGCTG<br>CAGGCGCAGCCGCACTGGCACTGACTGTGGACCTGCCC<br>CCAGCTTCCAGCGAGGCTAGAAACAGCGCCTTCGGGTTT<br>CAAGGACGCCTGCTGCATCTGAGCGCCGGACAGCGCCT<br>GGGAGTGCATCTGCATACTGAGGCTAGGGCCAGACATG<br>CCTGGCAGCTGACCCAGGGGGCAACTGTGCTGGGACTG<br>TTTCGCGTGACACCTGAGATCCCCGCTGGCCTGCCAAGC<br>CCTAGATCAGAAGGCGGAGGGGGATCAGGGGGAGGCG<br>GATCCAGAGAGGGCCCTGAGCTGAGCCCCGATGATCCT<br>GCTGGACTGCTGGACCTGCGGCAGGGCATGTTTGCTCAG<br>CTGGTGGCCCAGAACGTGCTGCTGATCGATGGCCCCCTG<br>TCCTGGTACAGCGATCCTGGACTGGCTGGCGTGTCACTG<br>ACAGGCGGCCTGAGCTACAAAGAGGACACCAAAGAACT<br>GGTGGTGGCCAAGGCCGGCGTGTACTACGTGTTCTTTCA<br>GCTGGAACTGCGGAGAGTGGTGGCCGGCGAAGGATCTG<br>GCTCTGTGTCTCTGGCCCTGCATCTGCAGCCTCTGAGAA<br>GCGCTGCTGGCGCTGCAGCTCTGGCACTGACAGTGGATC<br>TGCCTCCTGCCAGCTCCGAGGCCCGGAATAGCGCATTTG<br>GGTTTCAAGGCAGGCTGCTGCACCTGTCTGCCGGCCAGA<br>GGCTGGGAGTGCATCTGCACACAGAGGCCAGGGCTAGA<br>CACGCCTGGCAGCTGACACAGGGCGCTACAGTGCTGGG<br>CCTGTTCAGAGTGACCCCCGAGATTCCAGCCGGCCTGCC<br>TTCTCCAAGAAGCGAA |
| 151 | nucleotide sequence of anti-CD19(8B8-018) light chain | GACATCGTCATGACCCAGACACCCCTGTCCCTCTCTGTG<br>ACCCCTGGCCAGCCAGCCTCAATTAGCTGCAAGTCCTCT<br>CAAAGTCTGGAGAACCCCAATGGGAACACTTACCTTAAT<br>TGGTATCTGCAGAAACCCGGACAATCCCCTCAACTCCTG<br>ATCTACAGGGTCTCTAAGAGATTCTCAGGCGTGCCAGAT<br>CGCTTTAGCGGTTCCGGGTCTGGCACAGACTTCACCTTG<br>AAGATTAGTCGGGTTGAAGCTGAGGATGTGGGAGTCTA<br>TTACTGTCTGCAGCTCACTCATGTGCCCTACACCTTTGGT<br>CAGGGCACAAAACTGGAGATCAAGCGGACCGTGGCCGC<br>TCCCTCCGTGTTCATCTTCCCACCCTCCGACGAGCAGCT<br>GAAGTCCGGCACCGCCAGCGTGGTGTGCCTGCTGAACA<br>ACTTCTACCCCCGCGAGGCCAAGGTGCAGTGGAAGGTG<br>GACAACGCCCTGCAGTCCGGCAACTCCCAGGAATCCGT<br>GACCGAGCAGGACTCCAAGGACAGCACCTACTCCCTGT<br>CCTCCACCCTGACCCTGTCCAAGGCCGACTACGAGAAGC<br>ACAAGGTGTACGCCTGCGAAGTGACCCACCAGGGCCTG<br>TCCAGCCCCGTGACCAAGTCCTTCAACCGGGGCGAGTGC |
| 152 | anti-CD19(8B8-018) Fc hole chain | QVQLVQSGAEVKKPGASVKVSCKASGYTFTDYIMHWVRQ<br>APGQGLEWMGYINPYNDGSKYTEKFQGRVTMTSDTSISTA<br>YMELSRLRSDDTAVYYCARGTYYYGSALFDYWGQGTTVT<br>VSSASTKGPSVFPLAPSSKSTSGGTAALGCLVKDYFPEPVT<br>VSWNSGALTSGVHTFPAVLQSSGLYSLSSVVTVPSSSLGTQ<br>TYICNVNHKPSNTKVDKKVEPKSCDKTHTCPPCPAPEAAG<br>GPSVFLFPPKPKDTLMISRTPEVTCVVVDVSHEDPEVKFNW<br>YVDGVEVHNAKTKPREEQYNSTYRVVSVLTVLHQDWLN<br>GKEYKCKVSNKALGAPIEKTISKAKGQPREPQVCTLPPSRD |

TABLE 7-continued

Sequences of bivalent CD19(8B8-018)-targeted single chain 4-1BBL(71-254) trimer-containing Fc (kih) fusion antigen binding molecule (Compound S6)

| SEQ ID NO: | Description | Sequence |
|---|---|---|
|  |  | ELTKNQVSLSCAVKGFYPSDIAVEWESNGQPENNYKTTPP VLDSDGSFFLVSKLTVDKSRWQQGNVFSCSVMHEALHNH YTQKSLSLSPGK |
| 153 | anti-CD19(8B8-018) Fc knob chain fused to trimeric hu 4-1BBL (71-254) | QVQLVQSGAEVKKPGASVKVSCKASGYTFTDYIMHWVRQ APGQGLEWMGYINPYNDGSKYTEKFQGRVTMTSDTSISTA YMELSRLRSDDTAVYYCARGTYYYGSALFDYWGQGTTVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLN GKEYKCKVSNKALGAPIEKTISKAKGQPREPQVYTLPPCRD ELTKNQVSLWCLVKGFYPSDIAVEWESNGQPENNYKTTPP VLDSDGSFFLYSKLTVDKSRWQQGNVFSCSVMHEALHNH YTQKSLSLSPGGGGGSGGGGSREGPELSPDDPAGLLDLRQ GMFAQLVAQNVLLIDGPLSWYSDPGLAGVSLTGGLSYKED TKELVVAKAGVYYVFFQLELRRVVAGEGSGSVSLALHLQP LRSAAGAAALALTVDLPPASSEARNSAFGFQGRLLHLSAG QRLGVHLHTEARARHAWQLTQGATVLGLFRVTPEIPAGLP SPRSEGGGGSGGGGSREGPELSPDDPAGLLDLRQGMFAQL VAQNVLLIDGPLSWYSDPGLAGVSLTGGLSYKEDTKELVV AKAGVYYVFFQLELRRVVAGEGSGSVSLALHLQPLRSAAG AAALALTVDLPPASSEARNSAFGFQGRLLHLSAGQRLGVH LHTEARARHAWQLTQGATVLGLFRVTPEIPAGLPSPRSEGG GGSGGGGSREGPELSPDDPAGLLDLRQGMFAQLVAQNVL LIDGPLSWYSDPGLAGVSLTGGLSYKEDTKELVVAKAGVY YVFFQLELRRVVAGEGSGSVSLALHLQPLRSAAGAAALAL TVDLPPASSEARNSAFGFQGRLLHLSAGQRLGVHLHTEAR ARHAWQLTQGATVLGLFRVTPEIPAGLPSPRSE |
| 154 | anti-CD19(8B8-018) light chain | DIVMTQTPLSLSVTPGQPASISCKSSQSLENPNGNTYLNWY LQKPGQSPQLLIYRVSKRFSGVPDRFSGSGSGTDFTLKISRV EAEDVGVYYCLQLTHVPYTFGQGTKLEIKRTVAAPSVFIFP PSDEQLKSGTASVVCLLNNFYPREAKVQWKVDNALQSGN SQESVTEQDSKDSTYSLSSTLTLSKADYEKHKVYACEVTH QGLSSPVTKSFNRGEC |

Table 8 shows, respectively, the cDNA and amino acid sequences of the bivalent CD19(8B8-2B11)-targeted single chain 4-1BB ligand trimer-containing Fc (kih) fusion antigen binding molecule.

TABLE 8

Sequences of bivalent CD19(8B8-2B11)-targeted single chain 4-1BBL(71-254) trimer-containing Fc (kih) fusion antigen binding molecule (Compound S7)

| SEQ ID NO: | Description | Sequence |
|---|---|---|
| 155 | nucleotide sequence of anti-CD19(8B8-2B11) Fc hole chain | CAGGTGCAATTGGTTCAATCTGGTGCTGAAGTAAAAAA ACCGGGCGCTTCCGTTAAAGTGAGCTGCAAAGCATCTGG TTACACCTTCACTGACTATATCATGCACTGGGTTCGTCA GGCCCCGGGCCAGGGTCTGGAGTGGATGGGCTACATTA ACCCATACAACGACGGTTCCAAATATACCGAGAAATTC CAGGGCCGCGTCACGATGACCAGCGACACTTCTATCTCC ACCGCGTACATGGAACTGTCTAGACTGCGTTCTGACGAC ACCGCTGTTTACTATTGTGCACGCGGTACCTACTACTAC GGTCCACAGCTGTTTGATTACTGGGGCCAAGGTACCACG GTGACCGTAAGCTCTGCTAGCACCAAGGGCCCCTCCGTG TTCCCCCTGGCCCCCAGCAGCAAGAGCACCAGCGGCGG CACAGCCGCTCTGGGCTGCCTGGTCAAGGACTACTTCCC CGAGCCCGTGACCGTGTCCTGGAACAGCGGAGCCCTGA CCTCCGGCGTGCACACCTTCCCCGCCGTGCTGCAGAGTT CTGGCCTGTATAGCCTGAGCAGCGTGGTCACCGTGCCTT CTAGCAGCCTGGGCACCCAGACCTACATCTGCAACGTG AACCACAAGCCCAGCAACACCAAGGTGGACAAGAAGGT GGAGCCCAAGAGCTGCGACAAAACTCACACATGCCCAC |

TABLE 8-continued

Sequences of bivalent CD19(8B8-2B11)-targeted single
chain 4-1BBL(71-254) trimer-containing Fc (kih) fusion
antigen binding molecule (Compound S7)

| SEQ ID NO: | Description | Sequence |
|---|---|---|
| | | CGTGCCCAGCACCTGAAGCTGCAGGGGGACCGTCAGTC<br>TTCCTCTTCCCCCCAAAACCCAAGGACACCCTCATGATC<br>TCCCGGACCCCTGAGGTCACATGCGTGGTGGTGGACGTG<br>AGCCACGAAGACCCTGAGGTCAAGTTCAACTGGTACGT<br>GGACGGCGTGGAGGTGCATAATGCCAAGACAAAGCCGC<br>GGGAGGAGCAGTACAACAGCACGTACCGTGTGGTCAGC<br>GTCCTCACCGTCCTGCACCAGGACTGGCTGAATGGCAAG<br>GAGTACAAGTGCAAGGTCTCCAACAAAGCCCTCGGCGC<br>CCCCATCGAGAAACCATCTCCAAAGCCAAAGGGCAGC<br>CCCGAGAACCACAGGTGTGCACCCTGCCCCCATCCCGG<br>GATGAGCTGACCAAGAACCAGGTCAGCCTCTCGTGCGC<br>AGTCAAAGGCTTCTATCCCAGCGACATCGCCGTGGAGTG<br>GGAGAGCAATGGGCAGCCGGAGAACAACTACAAGACC<br>ACGCCTCCCGTGCTGGACTCCGACGGCTCCTTCTTCCTC<br>GTGAGCAAGCTCACCGTGGACAAGAGCAGGTGGCAGCA<br>GGGGAACGTCTTCTCATGCTCCGTGATGCATGAGGCTCT<br>GCACAACCACTACACGCAGAAGAGCCTCTCCCTGTCTCC<br>GGGTAAA |
| 156 | nucleotide sequence of anti-CD19(8B8-2B11) Fc knob chain fused to trimeric hu4-1BBL (71-254) | CAGGTGCAATTGGTTCAATCTGGTGCTGAAGTAAAAAA<br>ACCGGGCGCTTCCGTTAAAGTGAGCTGCAAAGCATCTGG<br>TTACACCTTCACTGACTATATCATGCACTGGGTTCGTCA<br>GGCCCCGGGCCAGGGTCTGGAGTGGATGGGCTACATTA<br>ACCCATACAACGACGGTTCCAAATATACCGAGAAATTC<br>CAGGGCCGCGTCACGATGACCAGCGACACTTCTATCTCC<br>ACCGCGTACATGGAACTGTCTAGACTGCGTTCTGACGAC<br>ACCGCTGTTTACTATTGTGCACGCGGTACCTACTACTAC<br>GGTCCACAGCTGTTTGATTACTGGGGCCAAGGTACCACG<br>GTGACCGTAAGCTCTGCTAGCACCAAGGGCCCATCGGTC<br>TTCCCCCTGGCACCCTCCTCCAAGAGCACCTCTGGGGGC<br>ACAGCGGCCCTGGGCTGCCTGGTCAAGGACTACTTCCCC<br>GAACCGGTGACGGTGTCGTGGAACTCAGGCGCCCTGAC<br>CAGCGGCGTGCACACCTTCCCGGCTGTCCTACAGTCCTC<br>AGGACTCTACTCCCTCAGCAGCGTGGTGACCGTGCCCTC<br>CAGCAGCTTGGGCACCCAGACCTACATCTGCAACGTGA<br>ATCACAAGCCCAGCAACACCAAGGTGGACAAGAAAGTT<br>GAGCCCAAATCTTGTGACAAAACTCACACATGCCCACC<br>GTGCCCAGCACCTGAAGCTGCAGGGGGACCGTCAGTCT<br>TCCTCTTCCCCCCAAAACCCAAGGACACCCTCATGATCT<br>CCCGGACCCCTGAGGTCACATGCGTGGTGGTGGACGTG<br>AGCCACGAAGACCCTGAGGTCAAGTTCAACTGGTACGT<br>GGACGGCGTGGAGGTGCATAATGCCAAGACAAAGCCGC<br>GGGAGGAGCAGTACAACAGCACGTACCGTGTGGTCAGC<br>GTCCTCACCGTCCTGCACCAGGACTGGCTGAATGGCAAG<br>GAGTACAAGTGCAAGGTCTCCAACAAAGCCCTCGGCGC<br>CCCCATCGAGAAACCATCTCCAAAGCCAAAGGGCAGC<br>CCCGAGAACCACAGGTGTACACCCTGCCCCCCTGCAGA<br>GATGAGCTGACCAAGAACCAGGTGTCCCTGTGGTGCCTC<br>GTGAAGGGCTTCTACCCCTCCGATATCGCCGTGGAATGG<br>GAGAGCAACGGCCAGCCCGAGAACAACTACAAGACCAC<br>CCCCCCTGTGCTGGACAGCGACGGCTCATTCTTCCTGTA<br>CTCCAAGCTGACCGTGGACAAGAGCCGGTGGCAGCAGG<br>GCAACGTGTTCAGCTGCAGCGTGATGCACGAGGCCCTG<br>CACAACCACTACACCCAGAAGTCCCTGAGCCTGAGCCCT<br>GGCGGAGGCGGAGGATCTGGCGGGGGAGGATCTAGAGA<br>GGGCCCTGAGCTGTCCCCCGATGATCCTGCTGGACTGCT<br>GGACCTGCGGCAGGGCATGTTTGCTCAGCTGGTGGCCCA<br>GAACGTGCTGCTGATCGACGGCCCTCTGAGCTGGTACAG<br>CGATCCTGGACTGGCTGGCGTGTCACTGACAGGCGGCCT<br>GAGCTACAAAGAGGACACCAAAGAACTGGTGGTGGCCA<br>AGGCCGGCGTGTACTACGTGTTCTTTCAGCTGGAACTGC<br>GGAGAGTGGTGGCCGGCGAGGGATCTGGATCTGTGTCT<br>CTGGCCCTGCATCTGCAGCCCCTGAGATCAGCTGCTGGC<br>GCTGCTGCTCTGGCTCTGACAGTGGATCTGCCTCCTGCC<br>AGCAGCGAGGCCCGGAATAGCGCATTTGGGTTTCAAGG<br>CAGGCTGCTGCACCTGTCTGCCGGCCAGAGGCTGGGAG<br>TGCATCTGCACACAGAAGCCAGAGCCAGGCACGCTTGG<br>CAGCTGACACAGGGCGCTACAGTGCTGGGCCTGTTCAG<br>AGTGACCCCCGAGATTCCAGCCGGCCTGCCTTCTCCAAG<br>AAGCGAAGGCGGCGAGGCTCCGGAGGAGGCGGCTCTA<br>GAGAAGGACCTGAACTGAGCCCAGACGACCCCGCAGGG<br>CTGCTGGATCTGAGACAGGGAATGTTCGCCCAGCTGGTG<br>GCTCAGAATGTGCTGCTGATTGATGGACCCCTGTCCTGG |

TABLE 8-continued

Sequences of bivalent CD19(8B8-2B11)-targeted single
chain 4-1BBL(71-254) trimer-containing Fc (kih) fusion
antigen binding molecule (Compound S7)

| SEQ ID NO: | Description | Sequence |
|---|---|---|
| | | TACTCCGACCCAGGGCTGGCAGGGGTGTCCCTGACTGGC GGACTGTCTTACAAAGAAGATACAAAAGAACTGGTGGT GGCTAAAGCTGGGGTGTACTATGTGTTTTTTCAGCTGGA ACTGAGGCGGGTGGTGGCTGGGGAAGGCAGTGGCTCTG TGTCCCTGGCACTGCATCTGCAGCCTCTGCGCAGTGCTG CAGGCGCAGCCGCACTGGACTGTGGACCTGCCC CCAGCTTCCAGCGAGGCTAGAAACAGCGCCTTCGGGTTT CAAGGACGCCTGCTGCATCTGAGCGCCGGACAGCGCCT GGGAGTGCATCTGCATACTGAGGCTAGGGCCAGACATG CCTGGCAGCTGACCCAGGGGGCAACTGTGCTGGGACTG TTTCGCGTGACACCTGAGATCCCCGCTGGCCTGCCAAGC CCTAGATCAGAAGGCGGAGGGGATCAGGGGGAGGCG GATCCAGAGAGGGCCCTGAGCTGAGCCCCGATGATCCT GCTGGACTGCTGGACCTGCGGCAGGGCATGTTTGCTCAG CTGGTGGCCCAGAACGTGCTGCTGATCGATGGCCCCCTG TCCTGGTACAGCGATCCTGGACTGGCTGGCGTGTCACTG ACAGGCGGCCTGAGCTACAAAGAGGACACCAAAGAACT GGTGGTGGCCAAGGCCGGCGTGTACTACGTGTTCTTTCA GCTGGAACTGCGGAGAGTGGTGGCCGGCGAAGGATCTG GCTCTGTGTCTCTGGCCCTGCATCTGCAGCCTCTGAGAA GCGCTGCTGGCGCTGCAGCTCTGGCACTGACAGTGGATC TGCCTCCTGCCAGCTCCGAGGCCCGGAATAGCGCATTTG GGTTTCAAGGCAGGCTGCTGCACCTGTCTGCCGGCCAGA GGCTGGGAGTGCATCTGCACACAGAGGCCAGGGCTAGA CACGCCTGGCAGCTGACACAGGGCGCTACAGTGCTGGG CCTGTTCAGAGTGACCCCCGAGATTCCAGCCGGCCTGCC TTCTCCAAGAAGCGAA |
| 157 | nucleotide sequence of anti-CD19(8B8-2B11) light chain | GATATTGTCATGACTCAAACTCCACTGTCTCTGTCCGTG ACCCCGGGTCAGCCAGCGAGCATTTCTTGCAAATCCAGC CAATCTCTGGAAACCTCCACCGGCACCACGTACCTGAAC TGGTATCTCCAGAAACCGGGTCAGAGCCCGCAGCTGCT GATCTACCGTGTATCTAAGCGCTTCTCCGGCGTTCCTGA TCGTTTCAGCGGTTCTGGATCCGGCACCGACTTTACTCT GAAAATCAGCCGTGTGGAAGCTGAAGACGTTGGCGTCT ACTATTGTCTGCAGCTGCTGGAAGATCCATACACCTTCG GTCAAGGAACGAAACTGGAAATTAAACGTACGGTGGCT GCACCATCTGTCTTCATCTTCCCGCCATCTGATGAGCAG TTGAAATCTGGAACTGCCTCTGTTGTGTGCCTGCTGAAT AACTTCTATCCCAGAGAGGCCAAAGTACAGTGGAAGGT GGATAACGCCCTCCAATCGGGTAACTCCCAGGAGAGTG TCACAGAGCAGGACAGCAAGGACAGCACCTACAGCCTC AGCAGCACCCTGACGCTGAGCAAAGCAGACTACGAGAA ACACAAAGTCTACGCCTGCGAAGTCACCCATCAGGGCC TGAGCTCGCCCGTCACAAAGAGCTTCAACAGGGGAGAG TGT |
| 158 | anti-CD19(8B8-2B11) Fc hole chain | QVQLVQSGAEVKKPGASVKVSCKASGYTFTDYIMHWVRQ APGQGLEWMGYINPYNDGSKYTEKFQGRVTMTSDTSISTA YMELSRLRSDDTAVYYCARGTYYYGPQLFDYWGQGTTVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLN GKEYKCKVSNKALGAPIEKTISKAKGQPREPQVCTLPPSRD ELTKNQVSLSCAVKGFYPSDIAVEWESNGQPENNYKTTPP VLDSDGSFFLVSKLTVDKSRWQQGNVFSCSVMHEALHNH YTQKSLSLSPGK |
| 159 | anti-CD19(8B8-2B11) Fc knob chain fused to trimeric hu 4-1BBL (71-254) | QVQLVQSGAEVKKPGASVKVSCKASGYTFTDYIMHWVRQ APGQGLEWMGYINPYNDGSKYTEKFQGRVTMTSDTSISTA YMELSRLRSDDTAVYYCARGTYYYGPQLFDYWGQGTTVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKVEPKSCDKTHTCPPCPAPEAAG GPSVFLFPPKPKDTLMISRTPEVTCVVVDVSHEDPEVKFNW YVDGVEVHNAKTKPREEQYNSTYRVVSVLTVLHQDWLN GKEYKCKVSNKALGAPIEKTISKAKGQPREPQVYTLPPCRD ELTKNQVSLWCLVKGFYPSDIAVEWESNGQPENNYKTTPP VLDSDGSFFLYSKLTVDKSRWQQGNVFSCSVMHEALHNH YTQKSLSLSPGGGGSGGGGSREGPELSPDDPAGLLDLRQ GMFAQLVAQNVLLIDGPLSWYSDPGLAGVSLTGGLSYKED |

TABLE 8-continued

Sequences of bivalent CD19(8B8-2B11)-targeted single chain 4-1BBL(71-254) trimer-containing Fc (kih) fusion antigen binding molecule (Compound S7)

| SEQ ID NO: | Description | Sequence |
|---|---|---|
|  |  | TKELVVAKAGVYYVFFQLELRRVVAGEGSGSVSLALHLQP LRSAAGAAALALTVDLPPASSEARNSAFGFQGRLLHLSAG QRLGVHLHTEARARHAWQLTQGATVLGLFRVTPEIPAGLP SPRSEGGGGSGGGGSREGPELSPDDPAGLLDLRQGMFAQL VAQNVLLIDGPLSWYSDPGLAGVSLTGGLSYKEDTKELVV AKAGVYYVFFQLELRRVVAGEGSGSVSLALHLQPLRSAAG AAALALTVDLPPASSEARNSAFGFQGRLLHLSAGQRLGVH LHTEARARHAWQLTQGATVLGLFRVTPEIPAGLPSPRSEGG GGSGGGGSREGPELSPDDPAGLLDLRQGMFAQLVAQNVL LIDGPLSWYSDPGLAGVSLTGGLSYKEDTKELVVAKAGVY YVFFQLELRRVVAGEGSGSVSLALHLQPLRSAAGAAALAL TVDLPPASSEARNSAFGFQGRLLHLSAGQRLGVHLHTEAR ARHAWQLTQGATVLGLFRVTPEIPAGLPSPRSE |
| 160 | anti-CD19(8B8-2B11) light chain | DIVMTQTPLSLSVTPGQPASISCKSSQSLETSTGTTYLNWYL QKPGQSPQLLIYRVSKRFSGVPDRFSGSGSGTDFTLKISRVE AEDVGVYYCLQLLEDPYTFGQGTKLEIKRTVAAPSVFIFPP SDEQLKSGTASVVCLLNNFYPREAKVQWKVDNALQSGNS QESVTEQDSKDSTYSLSSTLTLSKADYEKHKVYACEVTHQ GLSSPVTKSFNRGEC |

1.7. Monovalent CD19-Targeted Single Chain 4-1BB Ligand Trimer-Containing Fc (Kih) Fusion Antigen Binding Molecules (Compound S8 and S9)

The molecules are prepared as described in 1.3 for the monovalent FAP-targeted construct, with the only difference that the anti-FAP binder is replaced by an anti-CD19 binder.

The variable region of heavy and light chain DNA sequences encoding a binder specific for CD19, i.e. clones 8B8-018 or 8B8-2B11, are subcloned in frame with either the constant heavy chain of the hole (Carter, 2001) or the constant light chain of human IgG1.

Combination of the anti-CD19 hu IgG1 hole chain containing the Y349C/T366S/L368A/Y407V mutations, the single chain ligand hu IgG1 knob chain containing the S354C/T366W mutations and the anti-CD19 light chain allows generation of a heterodimer, which includes an assembled trimeric 4-1BB ligand and one CD19 binding Fab (FIG. 2A).

Table 9 shows, respectively, the cDNA and amino acid sequences of the monovalent CD19(8B8-018)-targeted single chain 4-1BB ligand trimer-containing Fc (kih) fusion antigen binding molecule.

TABLE 9

Sequences of monovalent CD19(8B8-018)-targeted single chain 4-1BBL(71-254) trimer-containing Fc (kih) fusion antigen binding molecule (Compound S8)

| SEQ ID NO: | Description | Sequence |
|---|---|---|
| 149 | nucleotide sequence of anti-CD19(8B8-018) Fc hole chain | see Table 7 |
| 66 | nucleotide sequence of trimeric hu 4-1BBL (71-254) Fc knob chain | see Table 1 |
| 151 | nucleotide sequence of anti-CD19(8B8-018) light chain | see Table 7 |
| 152 | anti-CD19(8B8-018) Fc hole chain | see Table 7 |
| 15 | trimeric hu 4-1BBL (71-254) Fc knob chain | see Table 1 |
| 154 | anti-CD19(8B8-018) light chain | see Table 7 |

Table 10 shows, respectively, the cDNA and amino acid sequences of the monovalent CD19(8B8-2B11)-targeted single chain 4-1BB ligand trimer-containing Fc (kih) fusion antigen binding molecule.

TABLE 10

Sequences of monovalent CD19(8B8-2B11)-targeted single chain 4-1BBL(71-254) trimer-containing Fc (kih) fusion antigen binding molecule (Compound S9)

| SEQ ID NO: | Description | Sequence |
|---|---|---|
| 155 | nucleotide sequence of anti-CD19(8B8-2B11) Fc hole chain | see Table 8 |
| 66 | nucleotide sequence of trimeric hu 4-1BBL (71-254) Fc knob chain | see Table 1 |
| 157 | nucleotide sequence of anti-CD19(8B8-2B11) light chain | see Table 8 |
| 158 | anti-CD19(8B8-2B11) Fc hole chain | see Table 8 |
| 15 | trimeric hu 4-1BBL (71-254) Fc knob chain | see Table 1 |
| 160 | anti-CD19(8B8-2B11) light chain | see Table 8 |

1.8. Generation of Anti-CD19 Binders 8B8-018 and 8B8-2B11

1.8.1 Generation of Anti-CD19 Clone 8B8-018 a) Immunization and Generation of Mouse Anti-Human CD19 Antibodies (Hybridomas)

Balb/c mice were immunized six times and boosted with CD19-transfected HEK293 cells (mean receptor density 35,000 per cell). The immune response was monitored by testing serum samples with a CD19-cell-ELISA on human CD19-transfected NIH-3T3 cells. Spleen cells from mice with sufficient titers of anti-human CD19 antibody were used for immortalization by fusion with mouse myeloma cell line P3X63 Ag8.653. Three fusions were carried out and hybridoma supernatants screened by cell-ELISA on human CD19-transfected NIH-3T3 cells and FACS binding assay using Daudi (CD19+) and CD19-cells for anti-human CD19 specific antibodies (see Example 1 of WO 2011/147834).

b) Hybridoma Screening and Cell Biological Functional Evaluation of Anti-CD19 Antibodies A cell ELISA was applied for screening of hybridomas, and to identify those hybridomas that secrete antibodies against human-CD19. NIH3T3 cells transfected with human-CD19 were used as positive cells; non-transfected NIH3T3 cells were used as negative control cells. For the assessment of the positive hybridomas the OD ratio between transfected and non-transfected NIH3T3 cells was quantified.

Culture Medium: DMEM high glucose (4.5 mg/ml), 10% FCS, Na-Pyruvate, NEAA, Glutamine
Antibodies positive control: anti CD19 monoclonal antibody (IgG1) Pharmingen Cat#555409 c=1 mg/ml
Detection antibody: Goat anti-Mouse IgG (H+L) HRP Conjugate Bio-Rad Cat#170-06516
Dilution 1: 2000 in 1×ELISA Blocking Reagent
Other reagents: Fibronectin Roche Cat#838039 c=1 mg/ml
Glutardialdehyde: 25% stock solution//Grade Agar Scientific #R102 final concentration: 0.05% in PBS
ELISA Blocking Reagent: 10× stock solution//Roche Cat#1112589
TMB substrate: Roche Cat#11432559
Stop Solution: 1 M H2SO4
BioRad Cat#170-6516 Dilution 1: 2000 in 1×ELISA Blocking Reagent Day 1:
Fibronectin coating: 5 µg/cm$^2$ in PBS; 96 well plate=32 cm$^2$; 160 µg/plate in 6 ml
PBS, 50 µl/well
incubate 45 min at RT, aspirate coating solution
Seed 1.25×104 cells/well in 50 µl culture medium in a 96 well plate
incubate 40 hours at 37° C.
add to upper half of the plate: NIH3T3 cells expressing CD19
add to lower half of the plate: non-transfected NIH3T3 cells Day 3:
Addition of positive control antibody or samples (supernatant or mouse serum) in 50 µl culture medium
incubate for 2 h at 4° C.
Remove medium, fix cells with 100 µl Glutardialdehyde (0.05% in PBS)
Wash two times with 200 µl PBS
Addition of detection antibody 1:2000, 50 µl/well
incubate 2 h at RT
wash three times with 200 µl PBS
add 50 µl TMB, incubate for 30 min. at RT,
stop by addition of 25 µl M H2SO4; read extinction at 450 nm/620 nm
Calculation of results: ratio OD NIH3T3 CD19:OD NIH3T3 non-transfected The selected antibody demonstrated specific binding to CD19 transfected NIH3T3 cells as compared to untransfected NIH3T3 cells (see Example 2 of WO 2011/147834).

c) Humanization of Anti-CD19 Antibody

The CD19 binding specificity of the murine antibody was transferred onto a human acceptor framework to eliminate potential immunogenicity issues arising from sequence stretches that the human body will recognize as foreign. This was done by engrafting the entire complementary determining regions (CDR) of the murine (donor) antibody onto a human (acceptor) antibody framework, and is called CDR-grafting or antibody humanization.

The murine amino acid sequence was aligned with a collection of human germ-line antibody V genes, and sorted according to sequence identity and homology. Before selecting one particular acceptor sequence, the so-called canonical loop structures of the donor antibody have to be determined (Morea, V., et al., Methods, Vol 20, Issue 3 (2000) 267-279). These canonical loop structures are determined by the type of residues present at the so-called canonical positions. These positions lie (partially) outside of the CDR regions, and have to be kept functionally equivalent in the final construct in order to retain the CDR conformation of the parental (donor) antibody. The human germ-line sequence VBASE_VH1_1 was chosen as the acceptor for the heavy chain and sequence VBASE_VK2_5 was chosen for the light chain.

It was found that the wild-type humanized anti-human CD19 antibody 8B8 has three deamidation hotspots in the HVR-L1: NSNGNT (SEQ ID NO: 161). Additionally it was found that in the HVR-H2 a further deamidation hotspot is present: KFNG (SEQ ID NO: 162). To address the deamidation hotspot in the HVR-H2 an N (Asn) to Q (Gln) point mutation at position 64 (numbering according to Kabat) has been introduced. To address the deamidation hotspots in the light chain and to obtain a humanized anti-human CD19 antibody with improved deamidation stability a single mutation at position 27e from S (serine) to P (proline) (numbering according to Kabat) was introduced. Thus, clone 8B8-018 with the CDRs as shown in Table 18 below was generated.

TABLE 11

Comparison of 8B8-018 with humanized wild-type CD19 antibody 8B8

| variant → <br> ↓parameter | wt 8B8 | 8B8-018 |
|---|---|---|
| $K_D$ (BIAcore) [nM] | 5 | 6 |
| $t_{1/2}$ [min] | — | 43.6 |
| human CD19 binding after pH 7.4 incubation [%] | 46 | 95 |
| human CD19 binding after pH 6.0 incubation [%] | 90 | 99 |
| SEC main peak after incubation [%] | >95 | >95 |

Additionally, 8B8-018 maintains the cross-reactivity to cynomolgus CD19 as shown in the following Table 12.

| EC50 [µg/ml] | wt 8B8 | 8B8-018 |
|---|---|---|
| huCD19 ECD | 0.087 | 0.084 |
| cyCD19 ECD | 0.313 | 0.255 |

1.8.2 Preparation, Purification and Characterization of CD19 Antigen Fc Fusion for Phage Display Campaign In order to express and purify the human and cynomolgus CD19 ectodomain in a monomeric state (human CD19 see SEQ ID NO:32), the respective DNA fragment was fused to a human IgG1 Fc gene segment containing the "knob" mutations (human: SEQ ID NO: 163; cynomolgus: SEQ ID NO: 165) and was transfected with an "Fc-hole" (SEQ ID NO: 76) counterpart (Merchant et al., 1998). An IgA cleavage site (PTPPTP) was introduced between the antigen ectodomain and the Fc knob chain. An Avi tag for directed biotinylation was introduced at the C-terminus of the antigen-Fc knob chain and mutations H435R and Y436F were introduced in the Fc hole for purification purposes (Jendeberg L. et al., J. Immunological methods, 1997). Combination of the antigen-Fc knob chain containing the S354C/T366W mutations (human: SEQ ID NO: 164; cynomolgus: SEQ ID NO: 166), with a Fc hole chain containing the Y349C/T366S/L368A/Y407V mutations (SEQ ID NO: 80) allows generation of a heterodimeric Fc fusion fragment which includes a single copy of the CD19 ectodomain (in analogy to the 4-1BB construct in FIG. 3C). Table 13 lists the cDNA and amino acid sequences of the antigen Fc-fusion construct.

TABLE 13 cDNA and Amino acid sequences of monomeric human and cynomolgus CD19 antigen Fc(kih) fusion molecule

| SEQ ID NO: | Antigen | Sequence |
|---|---|---|
| 163 | Nucleotide sequence of Fc hole chain with HYRF mutation | GACAAAACTCACACATGCCCACCGTGCCCAGCACCTGAAG CTGCAGGGGGACCGTCAGTCTTCCTCTTCCCCCCAAAACCC AAGGACACCCTCATGATCTCCCGGACCCCTGAGGTCACATG CGTGGTGGTGGACGTGAGCCACGAAGACCCTGAGGTCAAG TTCAACTGGTACGTGGACGGCGTGGAGGTGCATAATGCCA AGACAAAGCCGCGGGAGGAGCAGTACAACAGCACGTACC GTGTGGTCAGCGTCCTCACCGTCCTGCACCAGGACTGGCTG AATGGCAAGGAGTACAAGTGCAAGGTCTCCAACAAAGCCC TCGGCGCCCCCATCGAGAAAACCATCTCCAAAGCCAAAGG GCAGCCCCGAGAACCACAGGTGTGCACCCTGCCCCCATCC CGGGATGAGCTGACCAAGAACCAGGTCAGCCTCTCGTGCG CAGTCAAAGGCTTCTATCCCAGCGACATCGCCGTGGAGTG GGAGAGCAATGGGCAGCCGGAGAACAACTACAAGACCAC GCCTCCCGTGCTGGACTCCGACGGCTCCTTCTTCCTCGTGA GCAAGCTCACCGTGGACAAGAGCAGGTGGCAGCAGGGGA ACGTCTTCTCATGCTCCGTGATGCATGAGGCTCTGCACAAC CGCTTCACGCAGAAGAGCCTCTCCCTGTCTCCGGGTAAA |
| 164 | Nucleotide sequence of human CD19 antigen Fc knob chain avi tag | CCCGAGGAACCCCTGGTCGTGAAGGTGGAAGAGGGCGACA ATGCCGTGCTGCAGTGCCTGAAGGGCACCTCCGATGGCCCT ACCCAGCAGCTGACCTGGTCCAGAGAGAGCCCCCTGAAGC CCTTCCTGAAGCTGTCTCTGGGCCTGCCTGGCCTGGGCATC CATATGAGGCCTCTGGCCATCTGGCTGTTCATCTTCAACGT GTCCCAGCAGATGGGCGGCTTCTACCTGTGTCAGCCTGGCC CCCCATCTGAGAAGGCTTGGCAGCCTGGCTGGACCGTGAA CGTGGAAGGATCCGGCGAGCTGTTCCGGTGGAACGTGTCC GATCTGGGCGGCCTGGGATGCGGCCTGAAGAACAGATCTA GCGAGGGCCCCAGCAGCCCCAGCGGCAAACTGATGAGCCC CAAGCTGTACGTGTGGGCCAAGGACAGACCCGAGATCTGG GAGGGCGAGCCTCCTTGCCTGCCCCCTAGAGACAGCCTGA ACCAGAGCCTGAGCCAGGACCTGACAATGGCCCCTGGCAG CACACTGTGGCTGAGCTGTGGCGTGCCCACCCGACTCTGTGT CTAGAGGCCCTCTGAGCTGGACCCACGTGCACCCTAAGGG CCCTAAGAGCCTGCTGAGCCTGGAACTGAAGGACGACAGG CCCGCCAGAGATATGTGGGTCATGGAAACCGGCCTGCTGC TGCCTAGAGCCACAGCCCAGGATGCCGGCAAGTACTACTG CCACAGAGGCAACCTGACCATGAGCTTCCACCTGGAAATC ACCGCCAGACCCGTGCTGTGGCACTGGCTGCTGAGAACAG GCGGCTGGAAGGTCGACGCTAGCGGTGGTAGTCCGACACC TCCGACACCCGGGGGTGGTTCTGCAGACAAAACTCACACA TGCCCACCGTGCCCAGCACCTGAAGCGCAGGGGGACCGT CAGTCTTCCTCTTCCCCCCAAAACCCAAGGACACCCTCATG ATCTCCCGGACCCCTGAGGTCACATGCGTGGTGGTGGACGT GAGCCACGAAGACCCTGAGGTCAAGTTCAACTGGTACGTG GACGGCGTGGAGGTGCATAATGCCAAGACAAAGCCGCGGG AGGAGCAGTACAACAGCACGTACCGTGTGGTCAGCGTCCT CACCGTCCTGCACCAGGACTGGCTGAATGGCAAGGAGTAC AAGTGCAAGGTCTCCAACAAAGCCCTCGGAGCCCCCATCG AGAAAACCATCTCCAAAGCCAAAGGGCAGCCCCGAGAACC ACAGGTGTACACCCTGCCCCCATGCCGGGATGAGCTGACC AAGAACCAGGTCAGCCTGTGGTGCCTGGTCAAAGGCTTCT ATCCCAGCGACATCGCCGTGGAGTGGGAGAGCAATGGGCA GCCGGAGAACAACTACAAGACCACGCCTCCCGTGCTGGAC TCCGACGGCTCCTTCTTCCTCTACAGCAAGCTCACCGTGGA CAAGAGCAGGTGGCAGCAGGGGAACGTCTTCTCATGCTCC GTGATGCATGAGGCTCTGCACAACCACTACACGCAGAAGA GCCTCTCCCTGTCTCCGGGTAAATCCGGAGGCCTGAACGAC ATCTTCGAGGCCCAGAAGATTGAATGGCACGAG |
| 165 | Fc hole chain with HYRF mutation | DKTHTCPPCPAPEAAGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALGAPIEKTISKAKGQPREP QVCTLPPSRDELTKNQVSLSCAVKGFYPSDIAVEWESNGQPE NNYKTTPPVLDSDGSFFLVSKLTVDKSRWQQGNVFSCSVMHE ALHNRFTQKSLSLSPGK |
| 166 | human CD19 antigen Fc knob chain | PEEPLVVKVEEGDNAVLQCLKGTSDGPTQQLTWSRESPLKPF LKLSLGLPGLGIHMRPLAIWLFIFNVSQQMGGFYLCQPGPPSE KAWQPGWTVNVEGSGELFRWNVSDLGGLGCGLKNRSSEGPS |

TABLE 13-continued cDNA and Amino acid sequences of monomeric
human and cynomolgus CD19 antigen Fc(kih)
fusion molecule

| SEQ ID NO: | Antigen | Sequence |
|---|---|---|
| | avi tag | SPSGKLMSPKLYVWAKDRPEIWEGEPPCLPPRDSLNQSLSQDL<br>TMAPGSTLWLSCGVPPDSVSRGPLSWTHVHPKGPKSLLSLEL<br>KDDRPARDMWVMETGLLLPRATAQDAGKYYCHRGNLTMSF<br>HLEITARPVLWHWLLRTGGWKVDASGGSPTPPTPGGGSADK<br>THTCPPCPAPEAAGGPSVFLFPPKPKDTLMISRTPEVTCVVVD<br>VSHEDPEVKFNWYVDGVEVHNAKTKPREEQYNSTYRVVSVL<br>TVLHQDWLNGKEYKCKVSNKALGAPIEKTISKAKGQPREPQV<br>YTLPPCRDELTKNQVSLWCLVKGFYPSDIAVEWESNGQPENN<br>YKTTPPVLDSDGSFFLYSKLTVDKSRWQQGNVFSCSVMHEAL<br>HNHYTQKSLSLSPGKSGGLNDIFEAQKIEWHE |
| 167 | Nucleotide sequence of cynomolgus CD19 antigen Fc knob chain avi tag | CCCCAGGAACCCCTGGTCGTGAAGGTGGAAGAGGGCGACA<br>ATGCCGTGCTCCAGTGCCTGGAAGGCACCTCCGATGGCCCT<br>ACACAGCAGCTCGTGTGGTGCAGAGACAGCCCCTTCGAGC<br>CCTTCCTGAACCTGTCTCTGGGCCTGCCTGGCATGGGCATC<br>AGAATGGGCCCTCTGGGCATCTGGCTGCTGATCTTCAACGT<br>GTCCAACCAGACCGGCGGCTTCTACCTGTGTCAGCCTGGCC<br>TGCCAAGCGAGAAGGCTTGGCAGCCTGGATGGACCGTGTC<br>CGTGGAAGGATCTGGCGAGCTGTTCCGGTGGAACGTGTCC<br>GATCTGGGCGGCCTGGATGCGGCCTGAAGAACAGAAGCA<br>GCGAGGGCCCTAGCAGCCCCAGCGGCAAGCTGAATAGCAG<br>CCAGCTGTACGTGTGGGCCAAGGACAGACCCGAGATGTGG<br>GAGGGCGAGCCTGTGTGTGGCCCCCCTAGAGATAGCCTGA<br>ACCAGAGCCTGAGCCAGGACCTGACAATGGCCCCTGGCAG<br>CACACTGTGGCTGAGCTGTGGCGTGCCACCCGACTCTGTGT<br>CCAGAGGCCCTCTGAGCTGGACACACGTGCGGCCAAAGGG<br>CCCTAAGAGCAGCCTGCTGAGCCTGGAACTGAAGGACGAC<br>CGGCCCGACCGGGATATGTGGGTGGTGGATACAGGCCTGC<br>TGCTGACCAGAGCCACAGCCCAGGATGCCGGCAAGTACTA<br>CTGCCACAGAGGCAACTGGACCAAGAGCTTTTACCTGGAA<br>ATCACCGCCAGACCCGCCCTGTGGCACTGGCTGCTGAGAAT<br>CGGAGGCTGGAAGGTCGACGCTAGCGGTGGTAGTCCGACA<br>CCTCCGACACCCGGGGGTGGTTCTGCAGACAAAACTCACA<br>CATGCCCACCGTGCCCAGCACCTGAAGCCGCAGGGGACC<br>GTCAGTCTTCCTCTTCCCCCCAAAACCCAAGGACACCCTCA<br>TGATCTCCCGGACCCCTGAGGTCACATGCGTGGTGGTGGAC<br>GTGAGCCACGAAGACCCTGAGGTCAAGTTCAACTGGTACG<br>TGGACGGCGTGGAGGTGCATAATGCCAAGACAAAGCCGCG<br>GGAGGAGCAGTACAACAGCACGTACCGTGTGGTCAGCGTC<br>CTCACCGTCCTGCACCAGGACTGGCTGAATGGCAAGGAGT<br>ACAAGTGCAAGGTCTCCAACAAAGCCCTCGGAGCCCCCAT<br>CGAGAAAACCATCTCCAAAGCCAAAGGGCAGCCCCGAGAA<br>CCACAGGTGTACACCCTGCCCCCATGCCGGGATGAGCTGA<br>CCAAGAACCAGGTCAGCCTGTGGTGCCTGGTCAAAGGCTT<br>CTATCCCAGCGACATCGCCGTGGAGTGGGAGAGCAATGGG<br>CAGCCGGAGAACAACTACAAGACCACGCCTCCCGTGCTGG<br>ACTCCGACGGCTCCTTCTTCCTCTACAGCAAGCTCACCGTG<br>GACAAGAGCAGGTGGCAGCAGGGGAACGTCTTCTCATGCT<br>CCGTGATGCATGAGGCTCTGCACAACCACTACACGCAGAA<br>GAGCCTCTCCCTGTCTCCGGGTAAATCCGGAGGCCTGAACG<br>ACATCTTCGAGGCCCAGAAGATTGAATGGCACGAG |
| 168 | cynomolgus CD19 antigen Fc knob chain avi tag | PQEPLVVKVEEGDNAVLQCLEGTSDGPTQQLVWCRDSPFEPF<br>LNLSLGLPGMGIRMGPLGIWLLIFNVSNQTGGFYLCQPGLPSE<br>KAWQPGWTVSVEGSGELFRWNVSDLGGLGCGLKNRSSEGPS<br>SPSGKLNSSQLYVWAKDRPEMWEGEPVCGPPRDSLNQSLSQD<br>LTMAPGSTLWLSCGVPPDSVSRGPLSWTHVRPKGPKSSLLSLE<br>LKDDRPDRDMWVVDTGLLLTRATAQDAGKYYCHRGNWTKS<br>FYLEITARPALWHWLLRIGGWKVDASGGSPTPPTPGGGSADK<br>THTCPPCPAPEAAGGPSVFLFPPKPKDTLMISRTPEVTCVVVD<br>VSHEDPEVKFNWYVDGVEVHNAKTKPREEQYNSTYRVVSVL<br>TVLHQDWLNGKEYKCKVSNKALGAPIEKTISKAKGQPREPQV<br>YTLPPCRDELTKNQVSLWCLVKGFYPSDIAVEWESNGQPENN<br>YKTTPPVLDSDGSFFLYSKLTVDKSRWQQGNVFSCSVMHEAL<br>HNHYTQKSLSLSPGKSGGLNDIFEAQKIEWHE |

For the production of the monomeric antigen/Fc fusion molecules, exponentially growing suspension CHO cells were co-transfected with two plasmids encoding the two components of fusion protein (knob and hole chains) using standard methods.

Secreted protein was purified from cell culture supernatant by affinity chromatography using Protein A, followed by size exclusion chromatography. For affinity chromatography, the supernatant was loaded on a MABSELECT SURE® column volume (CV)=5-15 mL, resin from GE Healthcare) equilibrated with Sodium Phosphate (20 mM), Sodium Citrate (20 mM), 0.5M sodium chloride buffer (pH 7.5). Unbound protein was removed by washing with at least 6 column volumes of the same buffer. The bound protein was eluted using a linear gradient; step 1, 10 CV from 0 to 60% elution buffer (20 mM sodium citrate, 500 mM Sodium chloride buffer (pH 2.5)); step 2, 2 CV from 60 to 100% elution buffer. For the linear gradient an additional 2 column volumes step elution with 100% elution buffer was applied.

The pH of collected fractions was adjusted by adding 1/40 (v/v) of 2M Tris, pH8.0. The protein was concentrated and filtered prior to loading on a HILOAD® Superdex 200 column (GE Healthcare) equilibrated with 2 mM MOPS, 150 mM sodium chloride, 0.02% (w/v) sodium azide solution of pH 7.4.

Table 14 summarizes the yield and final monomer content of monomeric human and cynomolgus CD19 antigen Fc(kih) fusion protein.

TABLE 14

Biochemical analysis of monomeric human and cynomolgus CD19 antigen Fc(kih) fusion protein

| Construct | Monomer [%] (SEC) | Yield [mg/l] |
|---|---|---|
| monomeric human CD19 Fc(kih) fusion protein | 91 | 0.2 |
| monomeric cynomolgus CD19 Fc(kih) fusion protein | 95 | 3.56 |

Part of the purified antigen was in vitro biotinylated using the BirA biotin-protein ligase standard reaction kit (Avidity, Cat. # BirA500) according to the manufacturer's instructions. The biotinylation degree for the human CD19-containing fusion was 94%, for the respective cynomolgus CD19 construct 100%. The biotinylated protein was then used for selection, screening and characterization of affinity-matured 8B8-derived clones devoid of the de-amidation hotspots N27d and N28. Two phage display libraries were generated in which a) both asparagine residues at positions 27d and 28 were eliminated and b) additional CDRs of heavy and light chain were randomized in order to select for 8B8 variants with an improved affinity.

1.8.3 Generation of 8B8 Affinity Maturation Libraries Devoid of CDR-L1 Hotspots

Generation of affinity-matured 8B8-derived antibodies without the de-amidation sites N27d and N28, located in CDR-L1, was carried out by phage display using standard protocols (Silacci et al, 2005). In a first step, the VL and VH DNA sequences of the humanized parental clone 8B8 (SEQ ID NO: 169 and SEQ ID NO: 170) were cloned into a phagemid which was then used as a template for randomization. In a next step, two libraries were generated for the selection of favourable clones by phage display. In order to eliminate the above-mentioned hotspot positions, a LCDR1 randomization primer (SEQ ID NO: 171) that only allowed amino acids S T Q E at positions 27d and 28 was used for both libraries. Maturation library 1 was randomized in CDR1 and 2 of both the light and the heavy chain, while maturation library 2 was randomized in CDR1 and 3 of the light chain and in CDR3 of the heavy chain. For the generation of the maturation library 1, randomized in CDR1 and 2 of both the light and the heavy chain, three fragments were assembled by "splicing by overlapping extension" (SOE) PCR and cloned into the phage vector. The following primer combinations were used to generate the library fragments: fragment 1 (LMB3 (SEQ ID NO: 176) and CD19 L1 reverse random (SEQ ID NO: 171), fragment 2 (CD19 L2 forward random (SEQ ID NO: 172) and CD19 H1 reverse random (SEQ ID NO: 173), and fragment 3 (CD19 H2 forward random (SEQ ID NO: 174) and CD19 H3 reverse constant (SEQ ID NO: 175) (Table 15). After assembly of sufficient amounts of full length randomized fragment, it was digested with NcoI/NheI alongside with identically treated acceptor phagemid vector. A 3-fold molar excess of library insert was ligated with 10 μg of phagemid vector. Purified ligations were used for 20 transformations resulting in 2×10 exp9 transformants. Phagemid particles displaying the 8B8 affinity maturation library were rescued and purified by PEG/NaCl purification to be used for selections.

The generation of the second library, randomized in CDR1 and 3 of the light chain and in CDR3 of the heavy chain, was done similarly. The following primer combinations were used to generate the library fragments: fragment 1 (LMB3 (SEQ ID NO: 176) and CD19 L1 reverse random (SEQ ID NO: 171), fragment 2 (CD19 L1 forward constant (SEQ ID NO 177) and CD19 L3 reverse random (SEQ ID NO 178), and fragment 3 (CD19 L3 forward constant (SEQ ID NO: 179) and CD19 H3 reverse random (SEQ ID NO: 180) (Table 16). After assembly of sufficient amounts of full length randomized fragment, it was digested with NcoI/KpnI alongside with identically treated acceptor phagemid vector. A 3-fold molar excess of library insert was ligated with 20 ug of phagemid vector. Purified ligations were used for 40 transformations resulting in 2×10 exp9 transformants. Phagemid particles displaying the 8B8 affinity maturation library were rescued and purified by PEG/NaCl purification to be used for selections.

TABLE 15

Primers for 8B8 affinity maturation and hotspot removal library L1_L2/H1_H2

| SEQ ID | Name | Sequence |
|---|---|---|
| 171 | CD19 L1 reverse random | CAG CTG CGG GCT CTG ACC CGG TTT CTG GAG ATA CCA GTT CAG 1 CGT 2 GCC 3 GGA 4 TTC CAG AGA TTG GCT GGA TTT GCA AGA AAT G<br>1: 40% Y, 6% A/S/T/G/P/D/N/E/Q/V, 2: 40% N, 6% A/S/T/Y/G/P/D/E/Q/V, 3: 25% S/T/Q/E, 4: 25% S/T/Q/E |
| 172 | CD19 L2 forward random | CTC CAG AAA CCG GGT CAG AGC CCG CAG CTG CTG ATC TAC 5 GTA TCT 6 CGC 7 8 GGC GTT 9 GAT CGT TTC AGC GGT TCT GGA TCC GGC ACC<br>5: 30% R, 20% E, 5% A/S/T/Y/G/P/D/N/Q/V. 6: 30% K, 20% S, 5% A/N/T/Y/G/P/D/E/Q/V, 7: 40% F, 5% A/S/T/Y/G/P/D/E/Q/V/I/L, 8: 40% S, 6.6% A/T/Y/G/P/D/E/Q/V, 9: 50% P, 50% L |

TABLE 15-continued

Primers for 8B8 affinity maturation and hotspot removal
library L1_L2/H1_H2

| SEQ ID | Name | Sequence |
|---|---|---|
| 173 | CD19 H1 reverse random | CAT CCA CTC CAG ACC CTG GCC CGG GGC CTG ACG AAC CCA 10 CAT 11 12 13 14 GAA 15 GTA ACC AGA TGC TTT GCA GCT CAC TTT AAC GGA AGC<br>10: 52% H, 4% G/A/S/P/T/N/Y/D/E/Q/V/I, 11: 30% I, 15% Y, 5% G/A/S/T/P/N/H/D/E/Q/V, 12: 52% Y, 4% G/A/S/P/T/N/H/D/E/Q/V/I, 13: 30% D, 15% Q 5% A/S/P/Y/N/H/D/E/Q/V/I, 14: 52% T, 4% G/A/S/P/Y/N/H/D/E/Q/V/I, 15: 52% T, 4% G/A/S/P/Y/N/H/D/E/Q/V/I |
| 174 | CD19 H2 forward random | CAG GCC CCG GGC CAG GGT CTG GAG TGG ATG GGC 16 ATT 17 CCA 18 19 20 21 TCC 22 TAT ACC 23 AAA TTC CAG GGC CGC GTC ACG ATG ACC<br>16: 45% Y, 5% A/S/P/T/N/H/D/E/Q/V/I, 17: 52% N, 4% G/A/S/P/Y/T/H/D/E/Q/V/I, 18: 40% Y, 5% G/A/S/P/T/N/H/D/E/Q/V/I, 19: 30% N, 15% S, 5% G/A/T/P/Y/N/H/D/E/Q/V/I, 20: 30% D, 15% G, 5% A/S/T/P/Y/N/H/D/E/Q/V/I, 21: 52% Q 4% N/A/S/P/Y/T/H/D/E/Q/V/I, 22: 30% K, 15% N, 4% G/A/S/P/Y/T/H/D/E/Q/V/I, 23: 30% E, 15% Q, 5% G/A/S/T/P/Y/N/H/D/V/I |
| 175 | CD19 H3 reverse constant | CGTCACCGGTTCGGGGAAGTAGTCCTTGACCAG |
| 176 | LMB3 | CAGGAAACAGCTATGACCATGATTAC |

TABLE 16

Primers for 8B8 affinity maturation and hotspot removal
library L1_L3/H3

| SEQ ID | Name | Sequence |
|---|---|---|
| 177 | CD19 L1 forward constant | TGGTATCTCCAGAAACCGGGTCAGAGCCCGCAG |
| 171 | CD19 L1 reverse random | See Table 15 |
| 178 | CD19 L3 reverse random | TTT AAT TTC CAG TTT AGT TCC TTG ACC GAA GGT 24 25 26 27 28 29 CTG CAG ACA ATA GTA GAC GCC AAC GTC TTC AGC<br>24: 52% Y, 4% G/A/S/T/N/P/D/E/Q/V/L/I, 25: 52% P, 4% G/A/S/T/Y/N/H/D/E/Q/V/I, 26: 42% V, 10% L, 4% G/A/S/T/Y/N/P/D/E/Q/V/I, 27: 52% H, 4% G/A/S/T/Y/N/P/D/E/Q/V/I, 28: 42% T, 10% I, 4% G/A/S/T/Y/N/P/D/E/Q/V/L, 29: 45% L, 11% G, 4% A/S/T/Y/N/P/D/E/Q/V/I |
| 179 | CD19 L3 forward constant | ACCTTCGGTCAAGGAACTAAACTGGAAATTAAACG |
| 180 | CD19 H3 reverse random | TT GGT GCT AGC AGA GCT TAC GGT CAC CGT GGT ACC TTG GCC CCA GTA ATC AAA 30 31 32 33 34 35 36 37 38 GCG TGC ACA ATA GTA AAC AGC GGT GTC<br>30: 50% L, 3.8% G/A/S/T/P/H/Y/N/D/E/Q/V/I, 31: 50% A, 4.2% G/S/T/P/H/Y/N/D/E/Q/V/I, 32: 50% S, 4.2% G/A/T/P/H/Y/N/D/E/Q/V/I, 33: 50% G, 4.2% S/A/T/P/H/Y/N/D/E/Q/V/I, 34: 50% Y, 4.2% G/A/T/P/H/Y/N/D/E/Q/V/I, 35: 50% Y, 4.2% G/A/T/P/H/S/N/D/E/Q/V/I, 36: 50% Y, 4.2% |

TABLE 16-continued

Primers for 8B8 affinity maturation and hotspot removal library L1_L3/H3

| SEQ ID | Name | Sequence |
|---|---|---|
| | | G/A/T/P/H/S/N/D/E/Q/V/I, 37: 50% T, 4.2%<br>G/A/Y/P/H/S/N/D/E/Q/V/I, 38: 50% G, 4.2%<br>Y/A/T/P/H/S/N/D/E/Q/V/I |
| 176 | LMB3 | See Table 15 |

1.8.4 Selection of Affinity Matured 8B8-Derived Clones Devoid of CDR-L1 Hotspots N27d and N28

For the selection of affinity-matured clones devoid of the CDR-L1 hotspots N27d and N28, two selection approaches by phage display were performed:

In the first approach, the selection was executed on human CD19-Fc fusion protein using both phage display libraries. Panning rounds were performed in solution according to the following pattern: 1. binding of ~$10^{12}$ phagemid particles to 30 nM biotinylated CD19-Fc protein for 0.5 h in a total volume of 1 ml, 2. capture of biotinylated CD19-Fc protein and specifically bound phage particles by addition of 5.4× $10^7$ streptavidin-coated magnetic beads for 10 min, 3. washing of beads using 5×1 ml PBS/-TWEEN® 20 (polysorbate 20) and 5×1 ml PBS, 4. elution of phage particles by addition of 1 ml 100 mM TEA for 10 min and neutralization by adding 500 ul 1M Tris/HCl pH 7.4, 5. re-infection of exponentially growing E. coli TG1 bacteria, and 6. infection with helperphage VCSM13 and subsequent PEG/NaCl precipitation of phagemid particles to be used in subsequent selection rounds. Selections were carried out over 3 rounds using decreasing antigen concentrations (30×$10^{-9}$M, 10×$10^{-9}$M, and 3×$10^{-9}$M). In round 2 and 3, capture of antigen:phage complexes was performed using neutravidin plates instead of streptavidin beads. Neutravidin plates were washed with 5×PBS/TWEEN® 20 (polysorbate 20) and 5×PBS. In round 3, the neutravidin plate was incubated overnight in 2 liters PBS for an "off-rate" selection before phage was eluted from the plate. Furthermore, cynomolgus CD19-Fc protein was used in round 2 in order to enrich cross-reactive binders.

In the second selection approach, the phage panning was executed on cells transiently expressing either the human or cynomolgus CD19 ECD on the cell surface. For the transient transfection of HEK cells, expression plasmids were generated that harbor the DNA sequences (from 5' to 3') for the following protein segments: A Flag tag, a SNAP tag, the CD19 ECD of either human or cynomolgus origin, and the transmembrane region of the Platelet-derived growth factor receptor (PDGFR) (SEQ ID NOs: 227 and 228). The expression of the respective proteins (SEQ ID NOs: 229 and 230) on the cell surface was confirmed by flow cytometry using an anti-Flag antibody for detection. Both libraries were exposed in the first selection round to cells either expressing the human or cynomolgus CD19 ECD-containing protein fusion. For the subsequent panning rounds, the species of the CD19 ECD was alternated accordingly. Cells transiently transfected with an irrelevant membrane protein were used for pre-clearing.

Panning rounds were performed according to the following pattern:
1. Transfection of HEK cells with constructs expressing either CD19 ECD or an irrelevant transmembrane protein according to the standard procedure described before,
2. Incubation of the cells for total 48h at 37° C. in an incubator with a 5% $CO_2$ atmosphere,
3. Isolation of cells by centrifugation (3 min at 250×g) and re-suspension of 1×10E7 CD19 ECD-positive cells and 1×10E7 negative cells in PBS/5% BSA, respectively,
4. Pre-clearing of unspecific phage by incubating the phage library with 1×107 CD19-negative cells for 60 min at 4° C. using a gently rotating tube rotator,
5. Centrifugation of cells at 250×g for 3 min and transfer of supernatant into a fresh tube and addition of 1×10E7 CD19-positive cells and incubation for 60 min at 4° C. by gentle rotation on a tube rotator,
6. Washing of cells by centrifugation for 1 min at 250×g, aspiration of the supernatant, and re-suspension in 1 ml PBS (8 times),
7. Phage elution with 1 ml 100 mM TEA, incubation for 5 min at RT, and neutralization of the eluate with 500 ul 1M Tris-HCl, pH7.6,
8. re-infection of exponentially growing E. coli TG1 bacteria, and
9. infection with helperphage VCSM13 and subsequent PEG/NaCl precipitation of phagemid particles to be used in subsequent selection rounds. Selections were carried out over 3 rounds.

For both selection approaches, specific binders were identified by ELISA as follows: 100 ul of 30 nM biotinylated CD19-Fc protein per well were coated on neutravidin plates. Fab-containing bacterial supernatants were added and binding Fabs were detected via their Flag-tags using an anti-Flag/HRP secondary antibody.

Clones that were ELISA-positive on recombinant human CD19 were further tested in a cell-based ELISA using cells that were transiently transfected with the human CD19 ECD-containing expression plasmid (SEQ ID NO: 227). This analysis was performed as follows: 48 h after transfection, HEK cells were harvested and centrifuged at 250×g for 5 min. Cells were then re suspended in ice-cold PBS BSA 2% to 4×$10^6$ cells/ml and incubated for 20 min on ice to block unspecific binding sites. 4×$10^5$ cells in 100 ul were distributed to each well of a 96 well plate and centrifuged at 250×g and 4° C. for 3 min. Supernatant was aspirated off and 50 ul bacterial supernatant containing soluble Fab fragments was diluted with 50 ul ice-cold PBS/BSA 2%, added to the plate, mixed with the cells and incubated for 1 h at 4° C. Afterwards, cells were washed 3 times with ice cold PBS before 100 ul PBS BSA 2% per well containing a 1:2000 dilution of anti-Fab-HRP antibody were added. After an incubation time of 1 h, cells were washed again 3 times with ice-cold PBS. For the development, 100 ul "1-step ultra TMB-ELISA" substrate was added per well. After an incubation time of 10 minutes, supernatant was transferred to a new 96-well plate containing 40 ul $H_2SO_4$ 1M per well and absorbance was measured 450 nM. Clones exhibiting significant signals over background were subjected to a kinetic screening experiment by SPR-analysis using ProteOn XPR36.

1.8.5 Identification of Affinity-Matured 8B8-Derived Variants by SPR

In order to further characterize the ELISA-positive clones, the off-rate was measured by surface plasmon resonance and compared with the parental humanized clone 8B8.

For this experiment, 7000 RU of polyclonal anti-human Fab antibody were immobilized on all 6 channels of a GLM chip by Amine coupling (NaAcetate pH4.5, 25 µl/min, 240s) (vertical orientation). Each antibody-containing bacterial supernatant was filtered and 2-fold diluted with PBS, and then injected for 360s at 25 µl/minute to achieve immobilization levels of between 100 and 400 response units (RU) in vertical orientation. Injection of monomeric CD19-Fc: For one-shot kinetics measurements, injection direction was changed to horizontal orientation, three-fold dilution series of purified monomeric CD19-Fc (varying concentration ranges between 150 and 6 nM) were injected simultaneously at 50 µl/min along separate channels 1-4, with association times of 180 s, and dissociation times of 300 s. A human IgG Fc fragment (150 nM) was injected in channel 5 as a negative control for specific binding to the affinity matured CD19 variants along with a PBS injection in the 6th channel to provide an "in-line" blank for referencing. Regeneration was performed by two pulses of 10 mM glycine pH 1.5 and 50 mM NaOH for 30s at 90 ul/min (horizontal orientation). Dissociation rate constants ($k_{off}$) were calculated using a simple one-to-one Langmuir binding model in ProteOn Manager v3.1 software by simultaneously fitting the sensorgrams. Clones expressing Fabs with the slowest dissociation rate constants were identified. The variable domains of the corresponding phagemids were sequenced. Importantly, both asparagine residue in CDR-L1 (position 27d and 28) were replaced by a serine or a threonine, demonstrating that both de-amidation sites were removed.

TABLE 17

Dissociation constants of parental 8B8 and selected clone 2B11 obtained in screening analysis with bacterial supernatant

| clone | Dissociation constant kd (1/s) |
|---|---|
| Parental 8B8 | 3.01E−4 |
| 2B11 | 4.37E−6 |

Table 18 shows the amino acid sequences of the CDRs and variable regions VH and VL of clones 8B8-018 and 8B8-2B11, respectively.

TABLE 18

Sequences of of the CDRs and variable regions VH and VL of clones 8B8-018 and 8B8-2B11

| SEQ ID NO: | Description | Sequence |
|---|---|---|
| 120 | CD19 (8B8-018) CDR-H1 | DYIMH |
| 121 | CD19 (8B8-018) CDR-H2 | YINPYNDGSKYTEKFQG |
| 122 | CD19 (8B8-018) CDR-H3 | GTYYYGSALFDY |
| 123 | CD19 (8B8-018) CDR-L1 | KSSQSLENPNGNTYLN |
| 124 | CD19 (8B8-018) CDR-L2 | RVSKRFS |
| 125 | CD19 (8B8-018) CDR-L3 | LQLTHVPYT |
| 126 | CD19 (8B8-018) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 127 | CD19 (8B8-018) VL | DIVMTQTPLSLSVTPGQPASISCKSSQSLENPNGNTYL NWYLQKPGQSPQLLIYRVSKRFSGVPDRFSGSGSGTD FTLKISRVEAEDVGVYYCLQLTHVPYTFGQGTKLEIK |
| 128 | CD19 (8B8-2B11) CDR-H1 | DYIMH |
| 129 | CD19 (8B8-2B11) CDR-H2 | YINPYNDGSKYTEKFQG |
| 130 | CD19 (8B8-2B11) CDR-H3 | GTYYYGPQLFDY |
| 131 | CD19 (8B8-2B11) CDR-L1 | KSSQSLETSTGTTYLN |
| 132 | CD19 (8B8-2B11) CDR-L2 | RVSKRFS |
| 133 | CD19 (8B8-2B11) CDR-L3 | LQLLEDPYT |
| 134 | CD19 (8B8-018) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSS |
| 135 | CD19 (8B8-018) VL | DIVMTQTPLSLSVTPGQPASISCKSSQSLETSTGTTYL NWYLQKPGQSPQLLIYRVSKRFSGVPDRFSGSGSGTD FTLKISRVEAEDVGVYYCLQLLEDPYTFGQGTKLEIK |

Example 2

Preparation and Purification of "Untargeted" Single Chain 4-1BB Ligand Trimer-Containing Fc Fusion Antigen Binding Molecules The polypeptide chain coding for the single chain trimeric ligand (FIG. 1A) was used to prepare untargeted (germline control, DP47) 4-1BB ligand trimer-containing Fc fusion antigen binding molecules (for example the monovalent control shown in FIG. 3B), as described above for the FAP-targeted construct.

The variable region of heavy and light chain DNA sequences of the FAP binder, were replaced with those of a germline control (DP47) and subcloned in frame with either the constant heavy chain of the hole or the constant light chain of human IgG1.

The untargeted single chain 4-1BB ligand trimer-containing Fc (kih) fusion antigen binding molecules were produced as described above for the FAP-targeted construct. The cells were transfected with the corresponding expression vectors at a 1:1:1 ratio ("vector trimeric ligand-knob chain":"vector DP47 Fab-hole chain":"vector DP47 light chain").

Table 19 shows, respectively, the cDNA and amino acid sequences of the monovalent DP47-containing 4-1BB ligand trimer-containing Fc (kih) fusion antigen binding molecule.

TABLE 19

Sequences of monovalent DP47-containing single chain 4-1BB ligand trimer-containing Fc (kih) fusion antigen binding molecule (DP47 single chain 4-1BBL trimer) (Control 1)

| SEQ ID NO: | Description | Sequence |
|---|---|---|
| 66 | nucleotide sequence of trimeric hu 4-1BBL (71-254) - Fc knob chain | see Table 1 |
| 69 | nucleotide sequence of DP47 Fc hole chain | GAGGTGCAATTGTTGGAGTCTGGGGGAGGCTTGGTAC<br>AGCCTGGGGGGTCCCTGAGACTCTCCTGTGCAGCCTCC<br>GGATTCACCTTTAGCAGTTATGCCATGAGCTGGGTCCG<br>CCAGGCTCCAGGGAAGGGGCTGGAGTGGGTCTCAGCT<br>ATTAGTGGTAGTGGTGGTAGCACATACTACGCAGACTC<br>CGTGAAGGGCCGGTTCACCATCTCCAGAGACAATTCCA<br>AGAACACGCTGTATCTGCAGATGAACAGCCTGAGAGC<br>CGAGGACACGGCCGTATATTACTGTGCGAAAGGCAGC<br>GGATTTGACTACTGGGGCCAAGGAACCCTGGTCACCGT<br>CTCGAGTGCTAGCACCAAGGGCCCATCGGTCTTCCCCC<br>TGGCACCCTCCTCCAAGAGCACCTCTGGGGGCACAGCG<br>GCCCTGGGCTGCCTGGTCAAGGACTACTTCCCCGAACC<br>GGTGACGGTGTCGTGGAACTCAGGCGCCCTGACCAGC<br>GGCGTGCACACCTTCCCGGCTGTCCTACAGTCCTCAGG<br>ACTCTACTCCCTCAGCAGCGTGGTGACCGTGCCCTCCA<br>GCAGCTTGGGCACCCAGACCTACATCTGCAACGTGAAT<br>CACAAGCCCAGCAACACCAAGGTGGACAAGAAAGTTG<br>AGCCCAAATCTTGTGACAAAACTCACACATGCCCACCG<br>TGCCCAGCACCTGAAGCTGCAGGGGGACCGTCAGTCTT<br>CCTCTTCCCCCCAAAACCCAAGGACACCCTCATGATCT<br>CCCGGACCCCTGAGGTCACATGCGTGGTGGTGGACGTG<br>AGCCACGAAGACCCTGAGGTCAAGTTCAACTGGTACG<br>TGGACGGCGTGGAGGTGCATAATGCCAAGACAAAGCC<br>GCGGGAGGAGCAGTACAACAGCACGTACCGTGTGGTC<br>AGCGTCCTCACCGTCCTGCACCAGGACTGGCTGAATGG<br>CAAGGAGTACAAGTGCAAGGTCTCCAACAAAGCCCTC<br>GGCGCCCCCATCGAGAAAACCATCTCCAAAGCCAAAG<br>GGCAGCCCCGAGAACCACAGGTGTGCACCCTGCCCCC<br>ATCCCGGGATGAGCTGACCAAGAACCAGGTCAGCCTC<br>TCGTGCGCAGTCAAAGGCTTCTATCCCAGCGACATCGC<br>CGTGGAGTGGGAGAGCAATGGGCAGCCGGAGAACAAC<br>TACAAGACCACGCCTCCCGTGCTGGACTCCGACGGCTC<br>CTTCTTCCTCGTGAGCAAGCTCACCGTGGACAAGAGCA<br>GGTGGCAGCAGGGGAACGTCTTCTCATGCTCCGTGATG<br>CATGAGGCTCTGCACAACCACTACACGCAGAAGAGCC<br>TCTCCCTGTCTCCGGGTAAA |
| 70 | nucleotide sequence of DP47 light chain | GAAATCGTGTTAACGCAGTCTCCAGGCACCCTGTCTTT<br>GTCTCCAGGGGAAAGAGCCACCCTCTCTTGCAGGGCCA<br>GTCAGAGTGTTAGCAGCAGCTACTTAGCCTGGTACCAG<br>CAGAAACCTGGCCAGGCTCCCAGGCTCCTCATCTATGG<br>AGCATCCAGCAGGGCCACTGGCATCCCAGACAGGTTC<br>AGTGGCAGTGGATCCGGGACAGACTTCACTCTCACCAT<br>CAGCAGACTGGAGCCTGAAGATTTTGCAGTGTATTACT<br>GTCAGCAGTATGGTAGCTCACCGCTGACGTTCGGCCAG<br>GGGACCAAAGTGGAAATCAAACGTACGGTGGCTGCAC<br>CATCTGTCTTCATCTTCCCGCCATCTGATGAGCAGTTGA<br>AATCTGGAACTGCCTCTGTTGTGTGCCTGCTGAATAAC |

TABLE 19-continued

Sequences of monovalent DP47-containing single chain 4-1BB ligand trimer-containing Fc (kih) fusion antigen binding molecule (DP47 single chain 4-1BBL trimer) (Control 1)

| SEQ ID NO: | Description | Sequence |
|---|---|---|
| | | TTCTATCCCAGAGAGGCCAAAGTACAGTGGAAGGTGG<br>ATAACGCCCTCCAATCGGGTAACTCCCAGGAGAGTGTC<br>ACAGAGCAGGACAGCAAGGACAGCACCTACAGCCTCA<br>GCAGCACCCTGACGCTGAGCAAAGCAGACTACGAGAA<br>ACACAAAGTCTACGCCTGCGAAGTCACCCATCAGGGC<br>CTGAGCTCGCCCGTCACAAAGAGCTTCAACAGGGGAG<br>AGTGT |
| 15 | trimeric hu 4-1BBL (71-254) - Fc knob chain | see Table 1 |
| 71 | DP47 Fc hole chain | EVQLLESGGGLVQPGGSLRLSCAASGFTFSSYAMSWVRQ<br>APGKGLEWVSAISGSGGSTYYADSVKGRFTISRDNSKNTL<br>YLQMNSLRAEDTAVYYCAKGSGFDYWGQGTLVTVSSAS<br>TKGPSVFPLAPSSKSTSGGTAALGCLVKDYFPEPVTVSWN<br>SGALTSGVHTFPAVLQSSGLYSLSSVVTVPSSSLGTQTYIC<br>NVNHKPSNTKVDKKVEPKSCDKTHTCPPCPAPEAAGGPS<br>VFLFPPKPKDTLMISRTPEVTCVVVDVSHEDPEVKFNWY<br>VDGVEVHNAKTKPREEQYNSTYRVVSVLTVLHQDWLNG<br>KEYKCKVSNKALGAPIEKTISKAKGQPREPQVCTLPPSRD<br>ELTKNQVSLSCAVKGFYPSDIAVEWESNGQPENNYKTTP<br>PVLDSDGSFFLVSKLTVDKSRWQQGNVFSCSVMHEALH<br>NHYTQKSLSLSPGK |
| 72 | DP47 light chain | EIVLTQSPGTLSLSPGERATLSCRASQSVSSSYLAWYQQK<br>PGQAPRLLIYGASSRATGIPDRFSGSGSGTDFTLTISRLEPE<br>DFAVYYCQQYGSSPLTFGQGTKVEIKRTVAAPSVFIFPPS<br>DEQLKSGTASVVCLLNNFYPREAKVQWKVDNALQSGNS<br>QESVTEQDSKDSTYSLSSTLTLSKADYEKHKVYACEVTH<br>QGLSSPVTKSFNRGEC |

Table 20 summarizes the yield and final monomer content of the DP47-containing single chain 4-1BB ligand trimer-containing Fc (kih) fusion molecule.

TABLE 20

Summary of the production of DP47-containing 4-1BBL trimer-containing Fc (kih) fusion molecule

| Construct | Monomer [%] (SEC) | Yield [mg/l] | LC/MS (non red) |
|---|---|---|---|
| DP47-containing 4-1BBL trimer-containing Fc (kih) fusion molecule | 100 | 8 | Theoretical*: 156912.9 Da Experimental: |
| (DP47 single chain 4-1BBL trimer) Control 1 | | | 156937.5 Da * without terminal lysines |

Table 21 shows, respectively, the cDNA and amino acid sequences of the bivalent DP47-containing 4-1BB ligand trimer-containing Fc (kih) fusion antigen binding molecule (Control 2).

TABLE 21

Sequences of bivalent DP47-containing single chain 4-1BB ligand trimer-containing Fc (kih) fusion antigen binding molecule (DP47 single chain 4-1BBL trimer) (Control 2)

| SEQ ID NO: | Description | Sequence |
|---|---|---|
| 69 | nucleotide sequence of DP47 Fc hole chain | see Table 19 |
| 181 | nucleotide sequence of DP47 Fc knob fused to trimeric hu 4-1BBL (71-254) | GAGGTGCAATTGTTGGAGTCTGGGGGAGGCTTGGTAC<br>AGCCTGGGGGGTCCCTGAGACTCTCCTGTGCAGCCTCC<br>GGATTCACCTTTAGCAGTTATGCCATGAGCTGGGTCCG<br>CCAGGCTCCAGGGAAGGGGCTGGAGTGGGTCTCAGCT<br>ATTAGTGGTAGTGGTGGTAGCACATACTACGCAGACTC |

TABLE 21-continued

Sequences of bivalent DP47-containing single chain 4-1BB ligand trimer-containing Fc (kih) fusion antigen binding molecule (DP47 single chain 4-1BBL trimer) (Control 2)

| SEQ ID NO: Description | Sequence |
| --- | --- |
| | CGTGAAGGGCCGGTTCACCATCTCCAGAGACAATTCCA |
| | AGAACACGCTGTATCTGCAGATGAACAGCCTGAGAGC |
| | CGAGGACACGGCCGTATATTACTGTGCGAAAGGCAGC |
| | GGATTTGACTACTGGGGCCAAGGAACCCTGGTCACCGT |
| | CTCGAGTGCTAGCACCAAGGGCCCATCGGTCTTCCCCC |
| | TGGCACCCTCCTCCAAGAGCACCTCTGGGGGCACAGCG |
| | GCCCTGGGCTGCCTGGTCAAGGACTACTTCCCCGAACC |
| | GGTGACGGTGTCGTGGAACTCAGGCGCCCTGACCAGC |
| | GGCGTGCACACCTTCCCGGCTGTCCTACAGTCCTCAGG |
| | ACTCTACTCCCTCAGCAGCGTGGTGACCGTGCCCTCCA |
| | GCAGCTTGGGCACCCAGACCTACATCTGCAACGTGAAT |
| | CACAAGCCCAGCAACACCAAGGTGGACAAGAAAGTTG |
| | AGCCCAAATCTTGTGACAAAACTCACACATGCCCACCG |
| | TGCCCAGCACCTGAAGCTGCAGGGGACCGTCAGTCTT |
| | CCTCTTCCCCCCAAAACCCAAGGACACCCTCATGATCT |
| | CCCGGACCCCTGAGGTCACATGCGTGGTGGTGGACGTG |
| | AGCCACGAAGACCCTGAGGTCAAGTTCAACTGGTACG |
| | TGGACGGCGTGGAGGTGCATAATGCCAAGACAAAGCC |
| | GCGGGAGGAGCAGTACAACAGCACGTACCGTGTGGTC |
| | AGCGTCCTCACCGTCCTGCACCAGGACTGGCTGAATGG |
| | CAAGGAGTACAAGTGCAAGGTCTCCAACAAAGCCCTC |
| | GGCGCCCCCATCGAGAAAACCATCTCCAAAGCCAAAG |
| | GGCAGCCCCGAGAACCACAGGTGTACACCCTGCCCCC |
| | CTGCAGAGATGAGCTGACCAAGAACCAGGTGTCCCTG |
| | TGGTGCCTCGTGAAGGGCTTCTACCCCTCCGATATCGC |
| | CGTGGAATGGGAGAGCAACGGCCAGCCCGAGAACAAC |
| | TACAAGACCACCCCCCCTGTGCTGGACAGCGACGGCTC |
| | ATTCTTCCTGTACTCCAAGCTGACCGTGGACAAGAGCC |
| | GGTGGCAGCAGGGCAACGTGTTCAGCTGCAGCGTGAT |
| | GCACGAGGCCCTGCACAACCACTACACCCAGAAGTCC |
| | CTGAGCCTGAGCCCTGGCGGAGGCGGAGGATCTGGCG |
| | GGGGAGGATCTAGAGAGGGCCCTGAGCTGTCCCCCGA |
| | TGATCCTGCTGGACTGCTGGACCTGCGGCAGGGCATGT |
| | TTGCTCAGCTGGTGGCCCAGAACGTGCTGCTGATCGAC |
| | GGCCCTCTGAGCTGGTACAGCGATCCTGGACTGGCTGG |
| | CGTGTCACTGACAGGCGGCCTGAGCTACAAAGAGGAC |
| | ACCAAAGAACTGGTGGTGGCCAAGGCCGGCGTGTACT |
| | ACGTGTTCTTTCAGCTGGAACTGCGGAGAGTGGTGGCC |
| | GGCGAGGGATCTGGATCTGTGTCTCTGGCCCTGCATCT |
| | GCAGCCCCTGAGATCAGCTGCTGGCGCTGCTGCTCTGG |
| | CTCTGACAGTGGATCTGCCTCCTGCCAGCAGCGAGGCC |
| | CGGAATAGCGCATTTGGGTTTCAAGGCAGGCTGCTGCA |
| | CCTGTCTGCCGGCCAGAGGCTGGGAGTGCATCTGCACA |
| | CAGAAGCCAGAGCCAGGCACGCTTGGCAGCTGACACA |
| | GGGCGCTACAGTGCTGGGCCTGTTCAGAGTGACCCCCG |
| | AGATTCCAGCCGGCCTGCCTTCTCCAAGAAGCGAAGGC |
| | GGCGGAGGCTCCGGAGGAGGCGGCTCTAGAGAAGGAC |
| | CTGAACTGAGCCCAGACGACCCCGCAGGGCTGCTGGA |
| | TCTGAGACAGGGAATGTTCGCCCAGCTGGTGGCTCAGA |
| | ATGTGCTGCTGATTGATGGACCCCTGTCCTGGTACTCC |
| | GACCCAGGGCTGGCAGGGGTGTCCCTGACTGGCGGAC |
| | TGTCTTACAAAGAAGATACAAAAGAACTGGTGGTGGC |
| | TAAAGCTGGGGTGTACTATGTGTTTTTTCAGCTGGAAC |
| | TGAGGCGGGTGGTGGCTGGGGAAGGCAGTGGCTCTGT |
| | GTCCCTGGCACTGCATCTGCAGCCTCTGCGCAGTGCTG |
| | CAGGCGCAGCCGCACTGGCACTGACTGTGGACCTGCCC |
| | CCAGCTTCCAGCGAGGCTAGAAACAGCGCCTTCGGGTT |
| | TCAAGGACGCCTGCTGCATCTGAGCGCCGGACAGCGC |
| | CTGGGAGTGCATCTGCATACTGAGGCTAGGGCCAGAC |
| | ATGCCTGGCAGCTGACCCAGGGGGCAACTGTGCTGGG |
| | ACTGTTTCGCGTGACACCTGAGATCCCCGCTGGCCTGC |
| | CAAGCCCTAGATCAGAAGGCGGAGGGGATCAGGGGG |
| | AGGCGGATCCAGAGAGGGCCCTGAGCTGAGCCCCGAT |
| | GATCCTGCTGGACTGCTGGACCTGCGCAGGGCATGTT |
| | TGCTCAGCTGGTGGCCCAGAACGTGCTGCTGATCGATG |
| | GCCCCCTGTCCTGGTACAGCGATCCTGGACTGGCTGGC |
| | GTGTCACTGACAGGCGGCCTGAGCTACAAAGAGGACA |
| | CCAAAGAACTGGTGGTGGCCAAGGCCGGCGTGTACTA |
| | CGTGTTCTTTCAGCTGGAACTGCGGAGAGTGGTGGCCG |
| | GCGAAGGATCTGGCTCTGTGTCTCTGGCCCTGCATCTG |
| | CAGCCTCTGAGAAGCGCTGCTGGCGCTGCAGCTCTGGC |
| | ACTGACAGTGGATCTGCCTCCTGCCAGCTCCGAGGCCC |
| | GGAATAGCGCATTTGGGTTTCAAGGCAGGCTGCTGCAC |

TABLE 21-continued

Sequences of bivalent DP47-containing single chain 4-1BB ligand trimer-containing Fc (kih) fusion antigen binding molecule (DP47 single chain 4-1BBL trimer) (Control 2)

| SEQ ID NO: | Description | Sequence |
|---|---|---|
| | | CTGTCTGCCGGCCAGAGGCTGGGAGTGCATCTGCACAC AGAGGCCAGGGCTAGACACGCCTGGCAGCTGACACAG GGCGCTACAGTGCTGGGCCTGTTCAGAGTGACCCCCGA GATTCCAGCCGGCCTGCCTTCTCCAAGAAGCGAA |
| 70 | nucleotide sequence of DP47 light chain | see Table 19 |
| 71 | DP47 Fc hole chain | see Table 19 |
| 182 | DP47 Fc knob fused to trimeric hu 4-1BBL (71-254) | EVQLLESGGGLVQPGGSLRLSCAASGFTFSSYAMSWVRQ APGKGLEWVSAISGSGGSTYYADSVKGRFTISRDNSKNTL YLQMNSLRAEDTAVYYCAKGSGFDYWGQGTLVTVSSAS TKGPSVFPLAPSSKSTSGGTAALGCLVKDYFPEPVTVSWN SGALTSGVHTFPAVLQSSGLYSLSSVVTVPSSSLGTQTYIC NVNHKPSNTKVDKKVEPKSCDKTHTCPPCPAPEAAGGPS VFLFPPKPKDTLMISRTPEVTCVVVDVSHEDPEVKFNWY VDGVEVHNAKTKPREEQYNSTYRVVSVLTVLHQDWLNG KEYKCKVSNKALGAPIEKTISKAKGQPREPQVYTLPPCRD ELTKNQVSLWCLVKGFYPSDIAVEWESNGQPENNYKTTP PVLDSDGSFFLYSKLTVDKSRWQQGNVFSCSVMHEALH NHYTQKSLSLSPGGGGSGGGGSREGPELSPDDPAGLLD LRQGMFAQLVAQNVLLIDGPLSWYSDPGLAGVSLTGGLS YKEDTKELVVAKAGVYYVFFQLELRRVVAGEGSGSVSL ALHLQPLRSAAGAAALALTVDLPPASSEARNSAFGFQGR LLHLSAGQRLGVHLHTEARARHAWQLTQGATVLGLFRV TPEIPAGLPSPRSEGGGGSGGGGSREGPELSPDDPAGLLDL RQGMFAQLVAQNVLLIDGPLSWYSDPGLAGVSLTGGLSY KEDTKELVVAKAGVYYVFFQLELRRVVAGEGSGSVSLA LHLQPLRSAAGAAALALTVDLPPASSEARNSAFGFQGRL LHLSAGQRLGVHLHTEARARHAWQLTQGATVLGLFRVT PEIPAGLPSPRSEGGGGSGGGGSREGPELSPDDPAGLLDLR QGMFAQLVAQNVLLIDGPLSWYSDPGLAGVSLTGGLSY KEDTKELVVAKAGVYYVFFQLELRRVVAGEGSGSVSLA LHLQPLRSAAGAAALALTVDLPPASSEARNSAFGFQGRL LHLSAGQRLGVHLHTEARARHAWQLTQGATVLGLFRVT PEIPAGLPSPRSE |
| 72 | DP47 light chain | see Table 19 |

Example 3

Production of Targeted Single Chain 4-1BB Ligand Trimer-Containing Fc (Kih) Fusion Antigen Binding Molecules and their Controls The encoding sequences of the targeted and untargeted trimeric 4-1BB ligand Fc (kih) fusion antigen binding molecules as described herein before were cloned into a plasmid vector, which drives expression of the insert from an MPSV promoter and contains a synthetic polyA sequence located at the 3' end of the CDS. In addition, the vector contains an EBV OriP sequence for episomal maintenance of the plasmid.

The targeted and untargeted single chain trimeric 4-1BB ligand Fc (kih) fusion antigen binding molecules were produced by co-transfecting HEK293-EBNA cells with the mammalian expression vectors using polyethylenimine. The cells were transfected with the corresponding expression vectors in a 1:1:1 ratio ("vector knob chain":"vector hole chain":"vector light chain").

For production in 500 mL shake flasks, 300 million HEK293 EBNA cells were seeded 24 hours before transfection. For transfection cells were centrifuged for 10 minutes at 210×g, and the supernatant was replaced by 20 mL pre-warmed CD CHO medium. Expression vectors (200 µg of total DNA) were mixed in 20 mL CD CHO medium. After addition of 540 µL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of Excell medium supplemented with 6 mM L-Glutamine, 5 g/L PEPSOY and 1.2 mM valproic acid was added and cells were cultured for 24 hours. One day after transfection 12% Feed were added. After culturing for 7 days, the supernatant was collected by centrifugation for 30-40 minutes at least 400×g. The solution was sterile filtered (0.22 µm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a MABSELECT SURE® column (CV=5-15 mL, resin from GE Healthcare) equilibrated with Sodium Phosphate (20 mM), Sodium Citrate (20 mM) buffer (pH 7.5). Unbound protein was removed by washing with at least 6 column volumes of the same buffer. The bound protein was eluted using either a linear gradient (20 CV) or a step elution (8 CV) with 20 mM sodium citrate, 100 mM Sodium chloride, 100 mM Glycine buffer (pH 3.0). For the linear gradient an additional 4 column volumes step elution was applied.

The pH of collected fractions was adjusted by adding 1/10 (v/v) of 0.5M sodium phosphate, pH8.0. The protein was concentrated prior to loading on a HILOAD® Superdex 200 column (GE Healthcare) equilibrated with 20 mM histidine, 140 mM sodium chloride, 0.01% (v/v) TWEEN® 20 (polysorbate 20) solution of pH 6.0.

The protein concentration was determined by measuring the optical density (OD) at 280 nm, using a molar extinction coefficient calculated on the basis of the amino acid sequence. Purity and molecular weight of the targeted trimeric 4-1BB ligand Fc (kih) fusion was analyzed by SDS-PAGE in the presence and absence of a reducing agent (5 mM 1,4-dithiotreitol) and staining with Coomassie SIMPLYBLUE™ SafeStain (Invitrogen USA) or CE-SDS using Caliper LabChip GXII (Perkin Elmer). The aggregate content of samples was analyzed using a TSKGEL® G3000 SW XL analytical size-exclusion column (Tosoh) equilibrated in 25 mM $K_2HPO_4$, 125 mM NaCl, 200 mM L-Arginine Monohydrocloride, 0.02% (w/v) $NaN_3$, pH 6.7 running buffer at 25° C.

Table 22 summarizes the yield and final monomer content of the targeted and untargeted single chain trimeric 4-1BB ligand Fc (kih) fusion antigen binding molecules.

TABLE 22

Biochemical analysis of targeted and untargeted single chain 4-1BB ligand trimer-containing Fc (kih) fusion antigen binding molecules

| Construct | Monomer [%] (SEC) | Yield [mg/l] |
|---|---|---|
| Bivalent FAP(4B9) targeted single chain trimeric 4-1BB ligand Fc (kih) fusion antigen binding molecule Compound S2 | 92.2 | 2.7 |
| Bivalent CEA(sm9b) targeted single chain trimeric 4-1BB ligand Fc (kih) fusion antigen binding molecule Compound S4 | 98.9 | 3.9 |
| Bivalent untargeted trimeric 4-1BB single chain ligand Fc fusion as control antigen binding molecule Control 2 | 89 | 2.0 |
| Monovalent FAP(4B9) targeted single chain trimeric 4-1BB ligand Fc (kih) fusion antigen binding molecule Compound S3 | 97.5 | 21.2 |
| Monovalent CEA(sm9b) targeted single chain trimeric 4-1BB ligand Fc (kih) fusion antigen binding molecule Compound S5 | 94.5 | 4.7 |

Example 4

Preparation, Purification and Characterization of 4-1BB

DNA sequences encoding the ectodomains of human, mouse or cynomolgus 4-1BB (Table 23) were subcloned in frame with the human IgG1 heavy chain CH2 and CH3 domains on the knob (Merchant et al., 1998). An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of the 4-1BB ectodomain containing chain, thus creating a monomeric form of Fc-linked antigen (FIG. 3C). Table 24 lists the cDNA and amino acid sequences of monomeric antigen Fc(kih) fusion molecules as depicted in FIG. 3C.

TABLE 23

Amino acid numbering of antigen ectodomains (ECD) and their origin

| SEQ ID NO: | Construct | Origin | ECD |
|---|---|---|---|
| 73 | human 4-1BB ECD | Synthetized according to Q07011 | aa 24-186 |
| 74 | cynomolgus 4-1BB ECD | isolated from cynomolgus blood | aa 24-186 |
| 75 | murine 4-1BB ECD | Synthetized according to P20334 | aa 24-187 |

TABLE 24 cDNA and Amino acid sequences of monomeric antigen
Fc(kih) fusion molecules (produced by combination of
one Fc hole chain with one antigen Fc knob chain)

| SEQ ID NO: | Antigen | Sequence |
| --- | --- | --- |
| 76 | Nucleotide sequence Fc hole chain | GACAAAACTCACACATGCCCACCGTGCCCAGCACCTGA ACTCCTGGGGGGACCGTCAGTCTTCCTCTTCCCCCCAAA ACCCAAGGACACCCTCATGATCTCCCGGACCCCTGAGGT CACATGCGTGGTGGTGGACGTGAGCCACGAAGACCCTG AGGTCAAGTTCAACTGGTACGTGGACGGCGTGGAGGTG CATAATGCCAAGACAAAGCCGCGGGAGGAGCAGTACAA CAGCACGTACCGTGTGGTCAGCGTCCTCACCGTCCTGCA CCAGGACTGGCTGAATGGCAAGGAGTACAAGTGCAAGG TCTCCAACAAAGCCCTCCCAGCCCCCATCGAGAAAACC ATCTCCAAAGCCAAGGGCAGCCCCGAGAACCACAGGT GTGCACCCTGCCCCCATCCCGGGATGAGCTGACCAAGA ACCAGGTCAGCCTCTCGTGCGCAGTCAAAGGCTTCTATC CCAGCGACATCGCCGTGGAGTGGGAGAGCAATGGGCAG CCGGAGAACAACTACAAGACCACGCCTCCCGTGCTGGA CTCCGACGGCTCCTTCTTCCTCGTGAGCAAGCTCACCGT GGACAAGAGCAGGTGGCAGCAGGGGAACGTCTTCTCAT GCTCCGTGATGCATGAGGCTCTGCACAACCACTACACGC AGAAGAGCCTCTCCCTGTCTCCGGGTAAA |
| 77 | Nucleotide sequence human 4-1BB antigen Fc knob chain | CTGCAGGACCCCTGCAGCAACTGCCCTGCCGGCACCTTC TGCGACAACAACCGGAACCAGATCTGCAGCCCCTGCCC CCCCAACAGCTTCAGCTCTGCCGGCGGACAGCGGACCT GCGACATCTGCAGACAGTGCAAGGGCGTGTTCAGAACC CGGAAAGAGTGCAGCAGCACCAGCAACGCCGAGTGCGA CTGCACCCCCGGCTTCCATTGTCTGGGAGCCGGCTGCAG CATGTGCGAGCAGGACTGCAAGCAGGGCCAGGAACTGA CCAAGAAGGGCTGCAAGGACTGCTGCTTCGGCACCTTC AACGACCAGAAGCGGGGCATCTGCCGGCCCTGGACCAA CTGTAGCCTGGACGGCAAGAGCGTGCTGGTCAACGGCA CCAAAGAACGGGACGTCGTGTGCGGCCCCAGCCCTGCT GATCTGTCTCCTGGGGCCAGCAGCGTGACCCCTCCTGCC CCTGCCAGAGAGCCTGGCCACTCTCCTCAGGTCGACGAA CAGTTATATTTTCAGGGCGGCTCACCCAAATCTGCAGAC AAAACTCACACATGCCCACCGTGCCCAGCACCTGAACTC CTGGGGGGACCGTCAGTCTTCCTCTTCCCCCCAAAACCC AAGGACACCCTCATGATCTCCCGGACCCCTGAGGTCACA TGCGTGGTGGTGGACGTGAGCCACGAAGACCCTGAGGT CAAGTTCAACTGGTACGTGGACGGCGTGGAGGTGCATA ATGCCAAGACAAAGCCGCGGGAGGAGCAGTACAACAGC ACGTACCGTGTGGTCAGCGTCCTCACCGTCCTGCACCAG GACTGGCTGAATGGCAAGGAGTACAAGTGCAAGGTCTC CAACAAAGCCCTCCCAGCCCCCATCGAGAAAACCATCT CCAAAGCCAAAGGGCAGCCCCGAGAACCACAGGTGTAC ACCCTGCCCCCATGCGGGATGAGCTGACCAAGAACCA GGTCAGCCTGTGGTGCCTGGTCAAAGGCTTCTATCCCAG CGACATCGCCGTGGAGTGGGAGAGCAATGGGCAGCCGG AGAACAACTACAAGACCACGCCTCCCGTGCTGGACTCC GACGGCTCCTTCTTCCTCTACAGCAAGCTCACCGTGGAC AAGAGCAGGTGGCAGCAGGGGAACGTCTTCTCATGCTC CGTGATGCATGAGGCTCTGCACAACCACTACACGCAGA AGAGCCTCTCCCTGTCTCCGGGTAAATCCGGAGGCCTGA ACGACATCTTCGAGGCCCAGAAGATTGAATGGCACGAG |
| 78 | Nucleotide sequence cynomolgus 4-1BB antigen Fc knob chain | TTGCAGGATCTGTGTAGTAACTGCCCAGCTGGTACATTC TGTGATAATAACAGGAGTCAGATTTGCAGTCCCTGTCCT CCAAATAGTTTCTCCAGCGCAGGTGGACAAAGGACCTGT GACATATGCAGGCAGTGTAAAGGTGTTTTCAAGACCAG GAAGGAGTGTTCCTCCACCAGCAATGCAGAGTGTGACT GCATTTCAGGGTATCACTGCCTGGGGGCAGAGTGCAGC ATGTGTGAACAGGATTGTAAACAAGGTCAAGAATTGAC AAAAAAAGGTTGTAAAGACTGTTGCTTTGGGACATTTAA TGACCAGAAACGTGGCATCTGTCGCCCCTGGACAAACT GTTCTTTGGATGGAAAGTCTGTGCTTGTGAATGGGACGA AGGAGAGGGACGTGGTCTGCGGACCATCTCCAGCCGAC CTCTCTCCAGGAGCATCCTCTGCGACCCCGCCTGCCCCT GCGAGAGAGCCAGGACACTCTCCGCAGGTCGACGAACA GTTATATTTTCAGGGCGGCTCACCCAAATCTGCAGACAA AACTCACACATGCCCACCGTGCCCAGCACCTGAACTCCT GGGGGGACCGTCAGTCTTCCTCTTCCCCCCAAAACCCAA GGACACCCTCATGATCTCCCGGACCCCTGAGGTCACATG CGTGGTGGTGGACGTGAGCCACGAAGACCCTGAGGTCA AGTTCAACTGGTACGTGGACGGCGTGGAGGTGCATAAT GCCAAGACAAAGCCGCGGGAGGAGCAGTACAACAGCA CGTACCGTGTGGTCAGCGTCCTCACCGTCCTGCACCAGG |

TABLE 24-continued cDNA and Amino acid sequences of monomeric antigen
Fc(kih) fusion molecules (produced by combination of
one Fc hole chain with one antigen Fc knob chain)

| SEQ ID NO: | Antigen | Sequence |
|---|---|---|
| | | ACTGGCTGAATGGCAAGGAGTACAAGTGCAAGGTCTCC<br>AACAAAGCCCTCCCAGCCCCCATCGAGAAAACCATCTC<br>CAAAGCCAAAGGGCAGCCCCGAGAACCACAGGTGTACA<br>CCCTGCCCCCATGCCGGGATGAGCTGACCAAGAACCAG<br>GTCAGCCTGTGGTGCCTGGTCAAAGGCTTCTATCCCAGC<br>GACATCGCCGTGGAGTGGGAGAGCAATGGGCAGCCGGA<br>GAACAACTACAAGACCACGCCTCCCGTGCTGGACTCCG<br>ACGGCTCCTTCTTCCTCTACAGCAAGCTCACCGTGGACA<br>AGAGCAGGTGGCAGCAGGGGAACGTCTTCTCATGCTCC<br>GTGATGCATGAGGCTCTGCACAACCACTACACGCAGAA<br>GAGCCTCTCCCTGTCTCCGGGTAAATCCGGAGGCCTGAA<br>CGACATCTTCGAGGCCCAGAAGATTGAATGGCACGAG |
| 79 | murine 4-1BB<br>antigen Fc knob<br>chain | GTGCAGAACAGCTGCGACAACTGCCAGCCCGGCACCTT<br>CTGCCGGAAGTACAACCCCGTGTGCAAGAGCTGCCCCC<br>CCAGCACCTTCAGCAGCATCGGCGGCCAGCCCAACTGC<br>AACATCTGCAGAGTGTGCGCCGGCTACTTCCGGTTCAAG<br>AAGTTCTGCAGCAGCACCCACAACGCCGAGTGCGAGTG<br>CATCGAGGGCTTCCACTGCCTGGGCCCCCAGTGCACCAG<br>ATGCGAGAAGGACTGCAGACCCGGCCAGGAACTGACCA<br>AGCAGGGCTGTAAGACCTGCAGCCTGGGCACCTTCAAC<br>GACCAGAACGGGACCGGCGTGTGCCGGCCTTGGACCAA<br>TTGCAGCCTGGACGGGAGAAGCGTGCTGAAAACCGGCA<br>CCACCGAGAAGGACGTCGTGTGCGGCCCTCCCGTGGTGT<br>CCTTCAGCCCTAGCACCACCATCAGCGTGACCCCTGAAG<br>GCGGCCCTGGCGGACACTCTCTGCAGGTCCTGGTCGACG<br>AACAGTTATATTTTCAGGGCGGCTCACCCAAATCTGCAG<br>ACAAAACTCACACATGCCCACCGTGCCCAGCACCTGAA<br>CTCCTGGGGGGACCGTCAGTCTTCCTCTTCCCCCCAAAA<br>CCCAAGGACACCCTCATGATCTCCCGGACCCCTGAGGTC<br>ACATGCGTGGTGGTGGACGTGAGCCACGAAGACCCTGA<br>GGTCAAGTTCAACTGGTACGTGGACGGCGTGGAGGTGC<br>ATAATGCCAAGACAAAGCCGCGGGAGGAGCAGTACAAC<br>AGCACGTACCGTGTGGTCAGCGTCCTCACCGTCCTGCAC<br>CAGGACTGGCTGAATGGCAAGGAGTACAAGTGCAAGGT<br>CTCCAACAAAGCCCTCCCAGCCCCCATCGAGAAAACCA<br>TCTCCAAAGCCAAAGGGCAGCCCCGAGAACCACAGGTG<br>TACACCCTGCCCCCATGCCGGGATGAGCTGACCAAGAA<br>CCAGGTCAGCCTGTGGTGCCTGGTCAAAGGCTTCTATCC<br>CAGCGACATCGCCGTGGAGTGGGAGAGCAATGGGCAGC<br>CGGAGAACAACTACAAGACCACGCCTCCCGTGCTGGAC<br>TCCGACGGCTCCTTCTTCCTCTACAGCAAGCTCACCGTG<br>GACAAGAGCAGGTGGCAGCAGGGGAACGTCTTCTCATG<br>CTCCGTGATGCATGAGGCTCTGCACAACCACTACACGCA<br>GAAGAGCCTCTCCCTGTCTCCGGGTAAATCCGGAGGCCT<br>GAACGACATCTTCGAGGCCCAGAAGATTGAATGGCACG<br>AG |
| 80 | Fc hole chain | DKTHTCPPCPAPELLGGPSVFLFPPKPKDTLMISRTPEVTCV<br>VVDVSHEDPEVKFNWYVDGVEVHNAKTKPREEQYNSTYR<br>VVSVLTVLHQDWLNGKEYKCKVSNKALPAPIEKTISKAKG<br>QPREPQVCTLPPSRDELTKNQVSLSCAVKGFYPSDIAVEWE<br>SNGQPENNYKTTPPVLDSDGSFFLVSKLTVDKSRWQQGNV<br>FSCSVMHEALHNHYTQKSLSLSPGK |
| 81 | human 4-1BB<br>antigen Fc knob<br>chain | LQDPCSNCPAGTFCDNNRNQICSPCPPNSFSSAGGQRTCDI<br>CRQCKGVFRTRKECSSTSNAECDCTPGFHCLGAGCSMCEQ<br>DCKQGQELTKKGCKDCCFGTFNDQKRGICRPWTNCSLDG<br>KSVLVNGTKERDVVCGPSPADLSPGASSVTPPAPAREPGHS<br>PQVDEQLYFQGGSPKSADKTHTCPPCPAPELLGGPSVFLFP<br>PKPKDTLMISRTPEVTCVVVDVSHEDPEVKFNWYVDGVE<br>VHNAKTKPREEQYNSTYRVVSVLTVLHQDWLNGKEYKCK<br>VSNKALPAPIEKTISKAKGQPREPQVYTLPPCRDELTKNQV<br>SLWCLVKGFYPSDIAVEWESNGQPENNYKTTPPVLDSDGS<br>FFLYSKLTVDKSRWQQGNVFSCSVMHEALHNHYTQKSLS<br>LSPGKSGGLNDIFEAQKIEWHE |
| 82 | cynomolgus 4-<br>1BB antigen<br>Fc knob chain | LQDLCSNCPAGTFCDNNRSQICSPCPPNSFSSAGGQRTCDIC<br>RQCKGVFKTRKECSSTSNAECDCISGYHCLGAECSMCEQD<br>CKQGQELTKKGCKDCCFGTFNDQKRGICRPWTNCSLDGK<br>SVLVNGTKERDVVCGPSPADLSPGASSATPPAPAREPGHSP<br>QVDEQLYFQGGSPKSADKTHTCPPCPAPELLGGPSVFLFPP<br>KPKDTLMISRTPEVTCVVVDVSHEDPEVKFNWYVDGVEV<br>HNAKTKPREEQYNSTYRVVSVLTVLHQDWLNGKEYKCKV |

TABLE 24-continued cDNA and Amino acid sequences of monomeric antigen Fc(kih) fusion molecules (produced by combination of one Fc hole chain with one antigen Fc knob chain)

| SEQ ID NO: | Antigen | Sequence |
|---|---|---|
| | | SNKALPAPIEKTISKAKGQPREPQVYTLPPCRDELTKNQVS<br>LWCLVKGFYPSDIAVEWESNGQPENNYKTTPPVLDSDGSF<br>FLYSKLTVDKSRWQQGNVFSCSVMHEALHNHYTQKSLSL<br>SPGKSGGLNDIFEAQKIEWHE |
| 83 | murine 4-1BB antigen Fc knob chain | VQNSCDNCQPGTFCRKYNPVCKSCPPSTFSSIGGQPNCNIC<br>RVCAGYFRFKKFCSSTHNAECECIEGFHCLGPQCTRCEKDC<br>RPGQELTKQGCKTCSLGTFNDQNGTGVCRPWTNCSLDGR<br>SVLKTGTTEKDVVCGPPVVSFSPSTTISVTPEGGPGGHSLQ<br>VLVDEQLYFQGGSPKSADKTHTCPPCPAPELLGGPSVFLFP<br>PKPKDTLMISRTPEVTCVVVDVSHEDPEVKFNWYVDGVE<br>VHNAKTKPREEQYNSTYRVVSVLTVLHQDWLNGKEYKCK<br>VSNKALPAPIEKTISKAKGQPREPQVYTLPPCRDELTKNQV<br>SLWCLVKGFYPSDIAVEWESNGQPENNYKTTPPVLDSDGS<br>FFLYSKLTVDKSRWQQGNVFSCSVMHEALHNHYTQKSLS<br>LSPGKSGGLNDIFEAQKIEWHE |

All 4-1BB-Fc-fusion encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob":"Fc hole":"BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 µg of vector DNA. After addition of 540 µL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed were added to the culture. After 7 days of culturing, the cell supernatant was collected by spinning down cells for 15 min at 210 g. The solution was sterile filtered (0.22 µm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HITRAP® ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate, 0.5 M sodium chloride containing buffer (pH 7.5). The bound protein was eluted using a linear pH-gradient of sodium chloride (from 0 to 500 mM) created over 20 column volumes of 20 mM sodium citrate, 0.01% (v/v) TWEEN® 20 (polysorbate 20), pH 3.0. The column was then washed with 10 column volumes of 20 mM sodium citrate, 500 mM sodium chloride, 0.01% (v/v) TWEEN® 20 (polysorbate 20), pH 3.0.

The pH of collected fractions was adjusted by adding 1/40 (v/v) of 2M Tris, pH8.0. The protein was concentrated and filtered prior to loading on a HILOAD® Superdex 200 column (GE Healthcare) equilibrated with 2 mM MOPS, 150 mM sodium chloride, 0.02% (w/v) sodium azide solution of pH 7.4.

For affinity determination to the human receptor, the ectodomain of human 4-1BB was also subcloned in frame with an avi (GLNDIFEAQKIEWHE, SEQ ID NO:84) and a hexahistidine tag. Protein production was performed as described above for the Fc-fusion protein. Secreted proteins were purified from cell culture supernatants by chelating chromatography, followed by size exclusion chromatography. The first chromatographic step was performed on a Ni-NTA SUPERFLOW™ Cartridge (5 ml, Qiagen) equilibrated in 20 mM sodium phosphate, 500 nM sodium chloride, pH 7.4. Elution was performed by applying a gradient over 12 column volume from 5% to 45% of elution buffer (20 mM sodium phosphate, 500 nM sodium chloride, 500 mM Imidazole, pH 7.4). The protein was concentrated and filtered prior to loading on a HILOAD® Superdex 75 column (GE Healthcare) equilibrated with 2 mM MOPS, 150 mM sodium chloride, 0.02% (w/v) sodium azide solution of pH 7.4.

TABLE 25

Sequences of monomeric human 4-1BB His molecule

| SEQ ID NO: | antigen | Sequence |
|---|---|---|
| 85 | nucleotide sequence | CTGCAGGACCCCTGCAGCAACTGCCCTGCCGGCACCTTCTG<br>CGACAACAACCGGAACCAGATCTGCAGCCCCTGCCCCCCC |

TABLE 25-continued

Sequences of monomeric human 4-1BB His molecule

| SEQ ID NO: | antigen | Sequence |
|---|---|---|
|  | human 4-1BB His | AACAGCTTCAGCTCTGCCGGCGGACAGCGGACCTGCGACA TCTGCAGACAGTGCAAGGGCGTGTTCAGAACCCGGAAAGA GTGCAGCAGCACCAGCAACGCCGAGTGCGACTGCACCCCC GGCTTCCATTGTCTGGGAGCCGGCTGCAGCATGTGCGAGC AGGACTGCAAGCAGGGCCAGGAACTGACCAAGAAGGGCT GCAAGGACTGCTGCTTCGGCACCTTCAACGACCAGAAGCG GGGCATCTGCCGGCCCTGGACCAACTGTAGCCTGGACGGC AAGAGCGTGCTGGTCAACGGCACCAAAGAACGGGACGTCG TGTGCGGCCCCAGCCCTGCTGATCTGTCTCCTGGGGCCAGC AGCGTGACCCCTCCTGCCCCTGCCAGAGAGCCTGGCCACTC TCCTCAGGTCGACGAACAGTTATATTTTCAGGGCGGCTCAG GCCTGAACGACATCTTCGAGGCCCAGAAGATCGAGTGGCA CGAGGCTCGAGCTCACCACCATCACCATCAC |
| 86 | human 4-1BB His | LQDPCSNCPAGTFCDNNRNQICSPCPPNSFSSAGGQRTCDICR QCKGVFRTRKECSSTSNAECDCTPGFHCLGAGCSMCEQDCK QGQELTKKGCKDCCFGTFNDQKRGICRPWTNCSLDGKSVLV NGTKERDVVCGPSPADLSPGASSVTPPAPAREPGHSPQVDEQL YFQGGSGLNDIFEAQKIEWHEARAHHHHHH |

Example 5

Biochemical Characterization of FAP-Targeted Single Chain 4-1BB Ligand Trimer-Containing Fc Fusion Antigen Binding Molecule by Surface Plasmon Resonance Binding of FAP-targeted single chain 4-1BB ligand trimer-containing Fc (kih) fusion antigen binding molecule to recombinant 4-1BB was assessed by surface plasmon resonance (SPR). All SPR experiments were performed on a BIACORE® T100 instrument at 25° C. with HBS-EP as a running buffer (0.01 M HEPES pH 7.4, 0.15 M NaCl, 3 mM EDTA, 0.005% Surfactant P20, Biacore, Freiburg/ Germany).

Figure 5B:
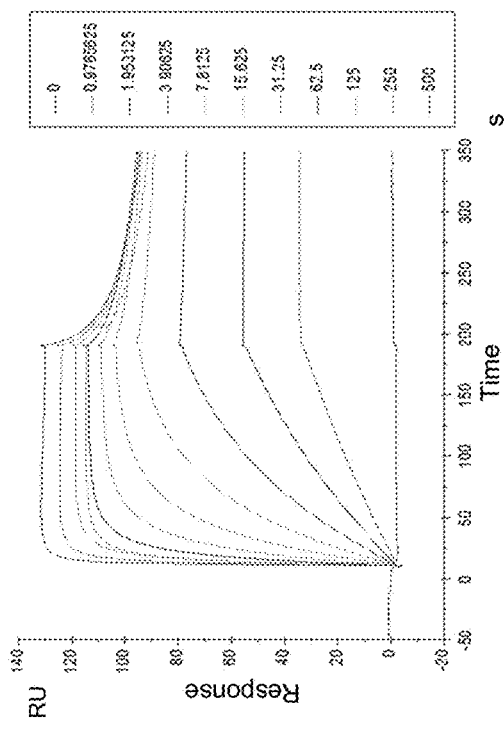
FIGS. 5A-D show the binding of FAP-targeted 4-1BB ligand trimer-containing Fc (kih) fusion molecule (compound 51) to recombinant 4-1BB Fc (kih) receptor as assessed by surface plasmon resonance.
Figure 5D:
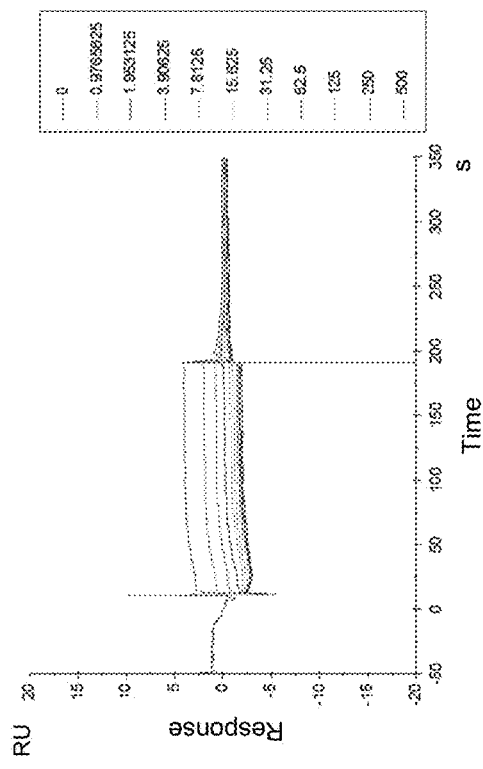
Figure 5A:
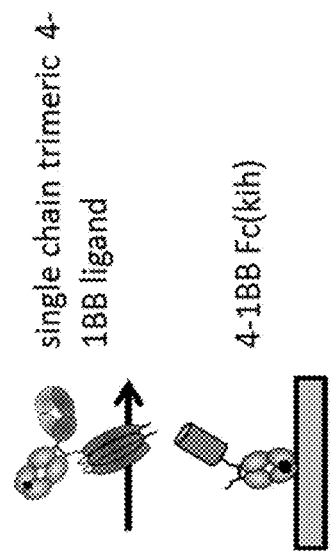
Figure 5C:
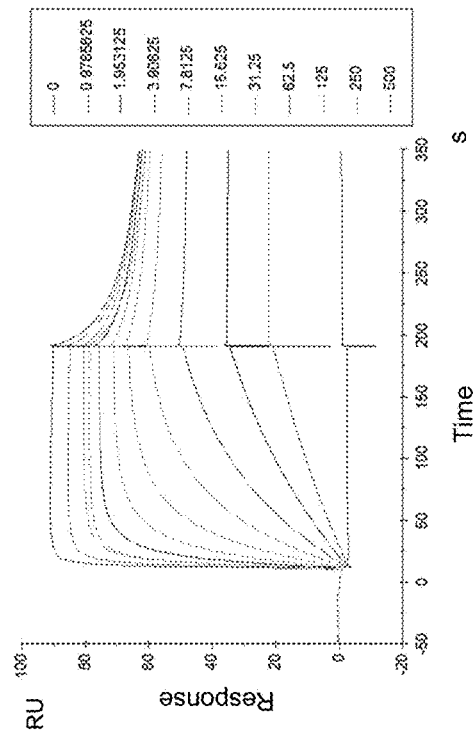
Figure 6A:
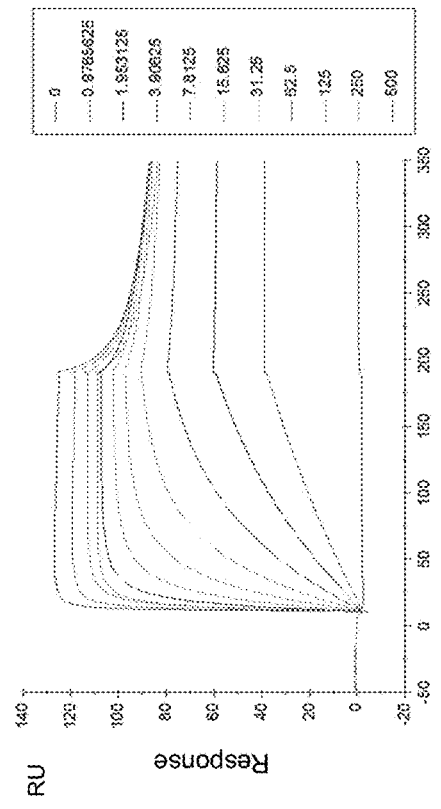
FIGS. 6A-C show the binding of DP47 containing 4-1BB ligand trimer-containing Fc (kih) fusion antigen binding molecule (Control 1) to recombinant 4-1BB Fc kih receptor. 4-1BB Fc (kih) is immobilized on a SA chip.
Figure 6C:
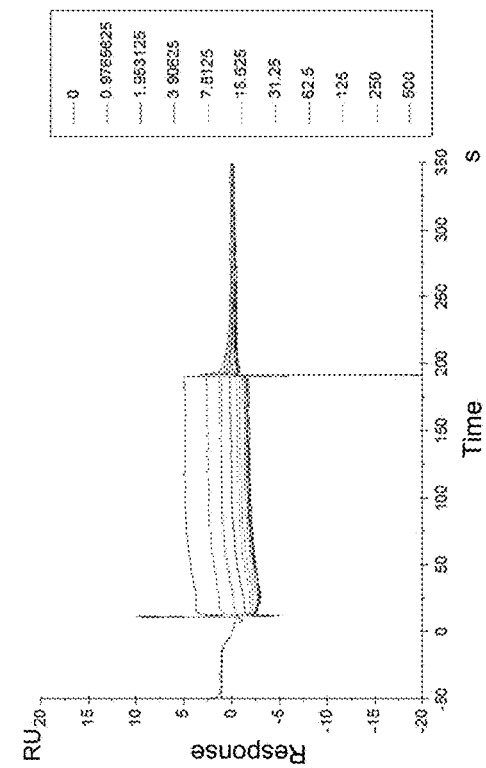
Figure 6B:
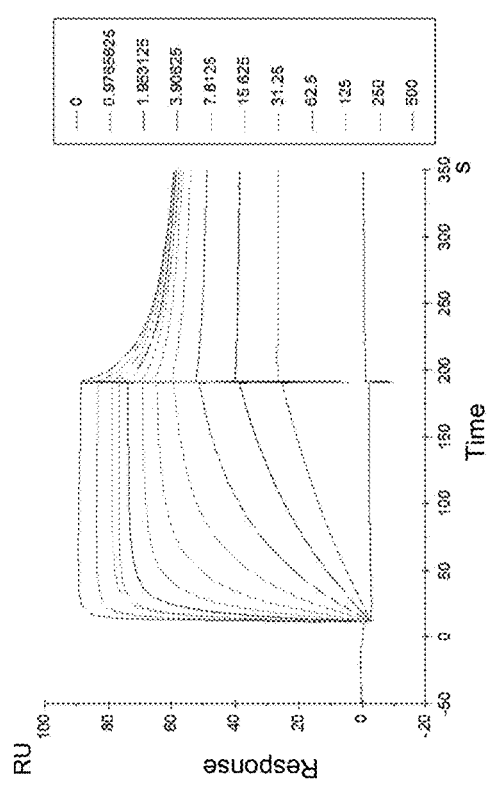
Figure 7D:
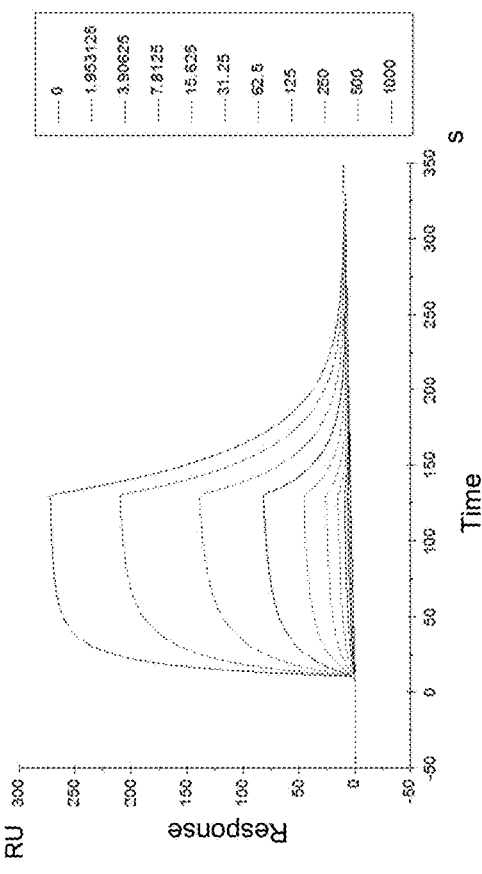
Figure 7E:
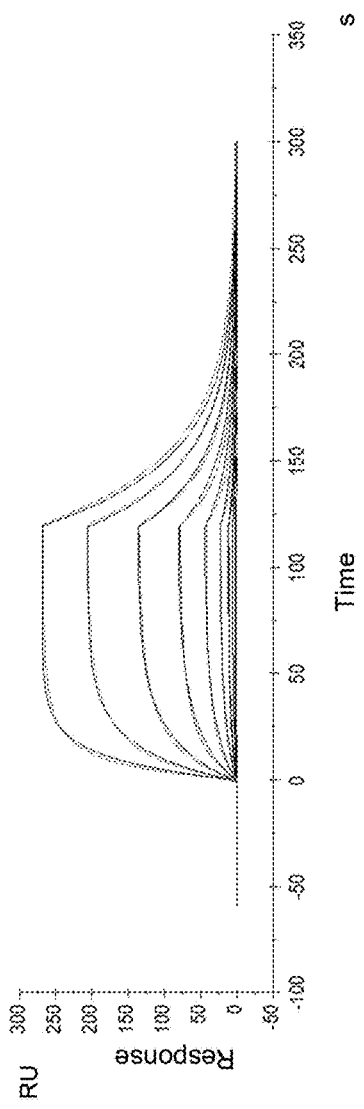

The avidity of the interaction between the FAP-targeted or "untargeted" 4-1BB ligand trimer-containing Fc (kih) fusion antigen binding molecules and recombinant 4-1BB (human, cyno and murine) was determined as illustrated in FIG. 5A. The data demonstrated that all variants of 4-1BB ligand trimer-containing Fc (kih) fusion antigen binding molecules (see for example the curves for FAP (28H1) single chain 4-1BBL trimer (Compound S1) in FIGS. 5A-D, and for the "untargeted" DP47 single chain 4-1BBL trimer (Control A) in FIGS. 6A-C) bind with comparable avidities to human and cynomolgus 4-1BB but negligibly to the mouse homolog.

Recombinant biotinylated human, cynomolgus and murine 4-1BB Fc(kih) fusion molecules were directly coupled on a SA chip using the standard coupling instruction (Biacore, Freiburg/Germany). The immobilization level was about 30 resonance units (RU). FAP-targeted 4-1BB ligand trimer-containing Fc (kih) fusion antigen binding molecule (Compound S1), or the DP47-containing control, was passed at a concentration range from 0.9 to 500 nM with a flow of 30 µL/minutes through the flow cells over 180 seconds. The dissociation was monitored for 180 seconds. Bulk refractive index differences were corrected for by subtracting the response obtained on a reference empty flow cell.

For affinity measurement (FIGS. 7A-E), direct coupling of around 7200 resonance units (RU) of the anti-human Fc specific antibody was performed on a CM5 chip at pH 5.0 using the standard amine coupling kit (GE Healthcare). FAP-targeted or untargeted single chain 4-1BB ligand trimer-containing Fc (kih) fusion antigen binding molecule at 50 nM was captured with a flow rate of 30 µL/min for 60 seconds on flow cell 2. A dilution series (1.95 to 1000 nM) of hu4-1BB avi His was passed on both flow cells at 30 µL/min for 120 seconds to record the association phase. The dissociation phase was monitored for 180 seconds and triggered by switching from the sample solution to HBS-EP. The chip surface was regenerated after every cycle using a double injection of 60 seconds 3M $MgCl_2$. Bulk refractive index differences were corrected for by subtracting the response obtained on the reference flow cell 1. For the interaction between targeted single chain trimeric 4-1BB ligand Fc(kih) fusion antigen binding molecule and hu4-1BB avi His, the affinity constants were derived from the rate constants by fitting to a 1:1 Langmuir binding using the Biaeval software (GE Healthcare). Dissociation constants can be found in Table 26.

TABLE 26

Fittings to 1:1 Langmuir binding and Affinity constants

| Ligand | Analyte | ka (1/Ms) | kd (1/s) | KD (M) |
|---|---|---|---|---|
| FAP single chain 4-1BBL trimer Compound S1 | Hu 4-1BB avi His | 6.2E+04 | 3.3E−02 | 5.4E−07 |
| DP47 single chain 4-1BBL trimer Control 1 | Hu 4-1BB avi His | 6.2E+04 | 3.3E−02 | 5.2E−07 |

Example 6

Preparation and Purification of Targeted Single Chain OX40 Ligand Trimer-Containing Fc Fusion Antigen Binding Molecules The DNA sequence encoding part of the ectodomain (amino acids 51-183) of human OX40 ligand was synthetized according to UniProt Accession No. P23510 (SEQ ID NO:38). Two Asn-linked glycosylation sites (N90 and N114) were replaced by aspartic acid (Asp) by mutagenesis.

Figure 1B:
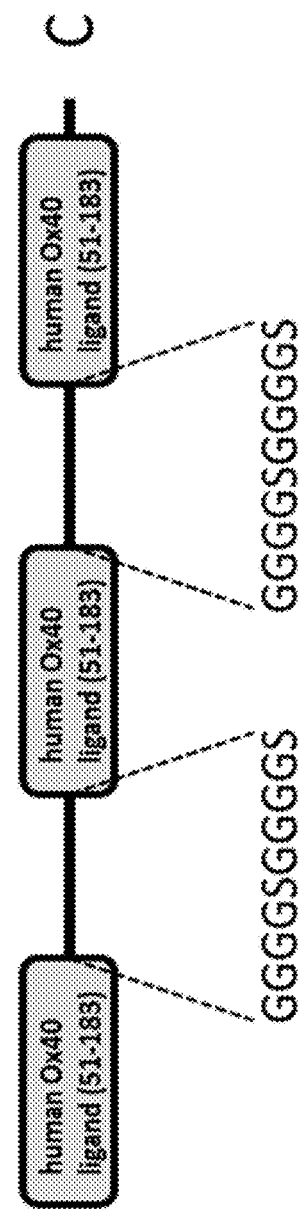

A polypeptide containing three ectodomains of OX40 ligand, separated by $(G_4S)_2$ (SEQ ID NO:54) linkers, was cloned as described in FIG. 1B: human OX40 ligand, (G$_4$S)$_2$ (SEQ ID NO:54) connector, human OX40 ligand, (G$_4$S)$_2$ (SEQ ID NO:54) connector, human OX40 ligand.

The polypeptide encoding the single chain trimeric OX40 ligand was subcloned in frame with the human IgG1 heavy chain CH2 and CH3 domains on the knob (Merchant, Zhu et al. 1998), using a linker (GSPGSSSSGS) of SEQ ID NO:57.

The variable region of heavy and light chain DNA sequences encoding a binder specific for fibroblast activation protein (FAP) were subcloned in frame with either the constant heavy chain of the hole (Carter, 2001) or the constant light chain of human IgG1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831 A1.

Combination of the single chain ligand-Fc knob chain containing the S354C/T366W mutations, with the targeted anti-FAP-Fc hole chain containing the Y349C/T366S/L368A/Y407V mutations and the anti-FAP light chain, allows generation of a heterodimer, which includes a single chain trimeric OX40 ligand and a FAP binding Fab (FIG. 4A).

Table 27 shows, respectively, the cDNA and amino acid sequences of the FAP-targeted single chain OX40 ligand trimer-containing Fc (kih) fusion antigen binding molecule. The polypeptide encoding the single chain trimeric OX40 ligand was subcloned in frame with the human IgG1 heavy chain CH2 and CH3 domains on the knob (Merchant, Zhu et al. 1998), using a linker (GSPGSSSSGS) of SEQ ID NO:57.

TABLE 27

Sequences of FAP(28H1)-targeted human OX40 ligand trimer-containing Fc (kih) fusion molecule (FAP single chain OX40L trimer) (Compound S10)

| SEQ ID NO: | Description | Sequence |
| --- | --- | --- |
| 87 | nucleotide sequence of trimeric hu OX40L (51-183)-Fc knob chain | CAGGTGTCCCACAGATACCCCAGAATCCAGAGCATCAA GGTGCAGTTCACCGAGTACAAGAAAGAGAAGGGCTTCA TCCTGACCAGCCAGAAAGAGGACGAGATCATGAAGGTG CAGGACAACAGCGTGATCATCAACTGCGACGGCTTCTA CCTGATCAGCCTGAAGGGCTACTTCAGCCAGGAAGTGG ACATCAGCCTGCACTACCAGAAGGACGAGGAACCCCTG TTCCAGCTGAAGAAAGTGCGGAGCGTGAACAGCCTGAT GGTGGCCAGCCTGACCTACAAGGACAAGGTGTACCTGA ACGTGACCACCGACAACACCAGCCTGGACGACTTCCAC GTGAACGGCGGCGAGCTGATCCTGATTCACCAGAACCC CGGCGAGTTCTGCGTGCTGGGAGGCGGAGGATCTGGCG GAGGCGGATCTCAGGTGTCACACCGCTACCCCCGGATTC AGTCCATTAAGGTGCAGTTTACAGAGTATAAGAAAGAA AAAGGCTTTATTCTGACTTCCCAGAAAGAAGATGAGATT ATGAAGGTGCAGGATAATTCTGTGATCATCAATTGTGAT GGGTTTTATCTGATCTCCCTGAAAGGATACTTTAGTCAG GAAGTGGATATTTCTCTGCACTATCAGAAAGATGAAGA ACCTCTGTTCCAGCTGAAAAAAGTGCGCTCCGTGAATTC TCTGATGGTGGCTTCCCTGACATACAAAGACAAAGTGTA TCTGAATGTGACAACAGATAATACCTCCCTGGATGATTT CCATGTGAATGGGGGGAACTGATTCTGATCCATCAGA ACCCTGGGGAATTTTGTGTGCTGGGCGGAGGGGGAAGT GGCGGCGGAGGCAGTCAGGTGTCCCATCGGTATCCTAG AATCCAGTCTATCAAAGTGCAGTTTACTGAGTACAAAAA AGAGAAAGGATTCATTCTGACCTCTCAGAAAGAGGACG AAATTATGAAGGTGCAGGATAACAGTGTGATTATTAACT GTGATGGGTTCTACCTGATTTCTCTGAAGGGATATTTCA GTCAGGAAGTGGACATCTCACTGCATTACCAGAAGGAT GAAGAACCACTGTTCCAGCTGAAGAAAGTGCGCTCTGT GAATAGCCTGATGGTGGCCTCTCTGACTTATAAGGATAA GGTGTACCTGAATGTGACAACTGACAATACTTCTCTGGA CGACTTTCATGTGAACGGGGGAGAGCTGATTCTGATCCA CCAGAATCCAGGCGAGTTTTGTGTGCTGGGAAGCCCCGG CAGCAGCAGCTCTGGATCCGACAAAACTCACACATGCC CACCGTGCCCAGCACCTGAAGCTGCAGGGGGACCGTCA GTCTTCCTCTTCCCCCCAAAACCCAAGGACACCCTCATG ATCTCCCGGACCCCTGAGGTCACATGCGTGGTGGTGGAC GTGAGCCACGAAGACCCTGAGGTCAAGTTCAACTGGTA CGTGGACGGCGTGGAGGTGCATAATGCCAAGACAAAGC CGCGGGAGGAGCAGTACAACAGCACGTACCGTGTGGTC AGCGTCCTCACCGTCCTGCACCAGGACTGGCTGAATGGC AAGGAGTACAAGTGCAAGGTCTCCAACAAAGCCCTCGG CGCCCCCATCGAGAAAACCATCTCCAAAGCCAAAGGGC AGCCCCGAGAACCACAGGTGTACACCCTGCCCCCATGC CGGGATGAGCTGACCAAGAACCAGGTCAGCCTGTGGTG CCTGGTCAAAGGCTTCTATCCCAGCGACATCGCCGTGGA GTGGGAGAGCAATGGGCAGCCGGAGAACAACTACAAGA CCACGCCTCCCGTGCTGGACTCCGACGGCTCCTTCTTCC TCTACAGCAAGCTCACCGTGGACAAGAGCAGGTGGCAG CAGGGGAACGTCTTCTCATGCTCCGTGATGCATGAGGCT CTGCACAACCACTACACGCAGAAGAGCCTCTCCCTGTCT CCGGGTAAA |

TABLE 27-continued

Sequences of FAP(28H1)-targeted human OX40 ligand trimer-containing Fc (kih) fusion molecule (FAP single chain OX40L trimer) (Compound S10)

| SEQ ID NO: | Description | Sequence |
|---|---|---|
| 67 | nucleotide sequence of anti-FAP(28H1) Fc hole chain | GAAGTGCAGCTGCTGGAATCCGGCGGAGGCCTGGTGCAGCCTGGCGGATCTCTGAGACTGTCCTGCGCCGCCTCCGGCTTCACCTTCTCCTCCCACGCCATGTCCTGGGTCCGACAGGCTCCTGGCAAAGGCCTGGAATGGGTGTCCGCCATCTGGGCCTCCGGCGAGCAGTACTACGCCGACTCTGTGAAGGGCCGGTTCACCATCTCCCGGGACAACTCCAAGAACACCCTGTACCTGCAGATGAACTCCCTGCGGGCCGAGGACACCGCCGTGTACTACTGTGCCAAGGGCTGGCTGGGCAACTTCGACTACTGGGGACAGGGCACCCTGGTCACCGTGTCCAGCGCTAGCACCAAGGGCCCCTCCGTGTTCCCCCTGGCCCCCAGCAGCAAGAGCACCAGCGGCGGCACAGCCGCTCTGGGCTGCCTGGTCAAGGACTACTTCCCCGAGCCCGTGACCGTGTCCTGGAACAGCGGGAGCCCTGACCTCCGGCGTGCACACCTTCCCCGCCGTGCTGCAGAGTTCTGGCCTGTATAGCCTGAGCAGCGTGGTCACCGTGCCTTCTAGCAGCCTGGGCACCCAGACCTACATCTGCAACGTGAACCACAAGCCCAGCAACACCAAGGTGGACAAGAAGGTGGAGCCCAAGAGCTGCGACAAAACTCACACATGCCCACCGTGCCCAGCACCTGAAGCTGCAGGGGACCGTCAGTCTTCCTCTTCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCGGCGCCCCCATCGAGAAAACCATCTCCAAAGCCAAAGGGCAGCCCCGAGAACCACAGGTGTGCACCCTGCCCCCATCCCGGGATGAGCTGACCAAGAACCAGGTCAGCCTCTCGTGCGCAGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCGTGAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA |
| 68 | nucleotide sequence of anti-FAP(28H1) light chain | GAGATCGTGCTGACCCAGTCCCCCGGCACCCTGTCTCTGAGCCCTGGCGAGAGAGCCACCCTGTCCTGCAGAGCCTCCCAGTCCGTGTGTCCCGGTCCTACCTCGCCTGGTATCAGCAGAAGCCCGGCCAGGCCCCTCGGCTGCTGATCATCGGCGCCTCTACCAGAGCCACCGGCATCCCTGACCGGTTCTCCGGCTCTGGCTCCGGCACCGACTTCACCCTGACCATCTCCCGGCTGGAACCCGAGGACTTCGCCGTGTACTACTGCCAGCAGGGCCAGGTCATCCCTCCCACCTTTGGCCAGGGCACCAAGGTGGAAATCAAGCGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |
| 20 | trimeric hu OX40L (51-183)-Fc knob chain | QVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGGGGSGGGGSQVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGGGGSGGGGSQVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGSPGSSSSGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 18 | anti-FAP(28H1) Fc hole chain | EVQLLESGGGLVQPGGSLRLSCAASGFTFSSHAMSWVRQAPGKGLEWVSAIWASGEQYYADSVKGRFTISRDNSKNTLYLQMNSLRAEDTAVYYCAKGWLGNFDYWGQGTLVTVSSAS |

TABLE 27-continued

Sequences of FAP(28H1)-targeted human OX40 ligand trimer-containing Fc (kih) fusion molecule (FAP single chain OX40L trimer) (Compound S10)

| SEQ ID NO: | Description | Sequence |
|---|---|---|
| | | TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKKVEPKSCDKTHTCPPCPAPEAAGGPSVF LFPPKPKDTLMISRTPEVTCVVVDVSHEDPEVKFNWYVDG VEVHNAKTKPREEQYNSTYRVVSVLTVLHQDWLNGKEYK CKVSNKALGAPIEKTISKAKGQPREPQVCTLPPSRDELTKN QVSLSCAVKGFYPSDIAVEWESNGQPENNYKTTPPVLDSD GSFFLVSKLTVDKSRWQQGNVFSCSVMHEALHNHYTQKS LSLSPGK |
| 19 | anti-FAP (28H1) light chain | EIVLTQSPGTLSLSPGERATLSCRASQSVSRSYLAWYQQKP GQAPRLLIIGASTRATGIPDRFSGSGSGTDFTLTISRLEPEDF AVYYCQQGQVIPPTFGQGTKVEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC |

The targeted single chain OX40 ligand trimer-containing Fc (kih) fusion antigen binding molecule encoding sequences were cloned into a plasmid vector driving expression of the insert from an MPSV promoter and containing a synthetic polyA sequence located at the 3' end of the CDS. In addition, the vector contained an EBV OriP sequence for episomal maintenance of the plasmid.

The targeted single chain trimeric OX40 ligand Fc (kih) fusion antigen binding molecule was produced by co-transfecting HEK293-EBNA cells with the mammalian expression vectors using polyethylenimine. The cells were transfected with the corresponding expression vectors in a 1:1:1 ratio ("vector knob chain":"vector hole chain":"vector light chain").

For production in 500 mL shake flasks, 400 million HEK293 EBNA cells were seeded 24 hours before transfection. For transfection cells were centrifuged for 5 minutes at 210×g, and supernatant was replaced by pre-warmed CD CHO medium. Expression vectors were mixed in 20 mL CD CHO medium to a final amount of 200 µg DNA. After addition of 540 µL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% CO2 atmosphere. After the incubation, 160 mL F17 medium was added and cells were cultured for 24 hours. One day after transfection 1 mM valproic acid and 7% Feed with supplements were added. After culturing for 7 days, the supernatant was collected by centrifugation for 15 minutes at 210×g. The solution was sterile filtered (0.22 µm filter), supplemented with sodium azide to a final concentration of 0.01% (w/v), and kept at 4° C.

The targeted single chain OX40 ligand trimer-containing Fc (kih) fusion antigen binding molecule was purified from cell culture supernatants by affinity chromatography using Protein A, followed by size exclusion chromatography. For affinity chromatography, the supernatant was loaded on a HITRAP® ProteinA HP column (CV=5 mL, GE Healthcare) equilibrated with 20 mM sodium phosphate, 20 mM sodium citrate, 0.5 M sodium chloride, 0.01% (v/v) TWEEN® 20 (polysorbate 20) containing buffer (pH 7.5). Unbound protein was removed by washing with at least 10 column volumes of the same buffer. The bound protein was eluted using a linear pH gradient over 20 column volumes to 100% of 20 mM sodium citrate, 0.5 M sodium chloride, 0.01% (v/v) TWEEN® 20 (polysorbate 20) containing buffer (pH 2.5). The column was then washed with 10 column volumes of 20 mM sodium citrate, 0.5 M sodium chloride, 0.01% TWEEN® 20 (polysorbate 20) buffer (pH 2.5).

The pH of collected fractions was adjusted by adding 1/40 (v/v) of 2M Tris, pH8.0. The protein was concentrated prior to loading on a HILOAD® Superdex 200 column (GE Healthcare) equilibrated with 20 mM Histidine, 150 mM sodium chloride, 0.01% (v/v) TWEEN® 20 (polysorbate 20) solution of pH 6.0.

The protein concentration was determined by measuring the optical density (OD) at 280 nm, using the molar extinction coefficient calculated on the basis of the amino acid sequence. Purity and molecular weight of the targeted OX40 ligand trimer-containing Fc (kih) fusion antigen binding molecule was analyzed by SDS-PAGE in the presence and absence of a reducing agent (5 mM 1,4-dithiotreitol) and staining with Coomassie SIMPLYBLUE™ SafeStain (Invitrogen USA). The aggregate content of samples was analyzed using a TSKGEL® G3000 SW XL analytical size-exclusion column (Tosoh) equilibrated in 25 mM $K_2HPO_4$, 125 mM sodium chloride, 200 mM L-arginine monohydrochloride, 0.02% (w/v) $NaN_3$, pH 6.7 running buffer at 25° C.

The targeted single chain OX40 ligand trimer-containing Fc (kih) fusion antigen binding molecule (Compound SC-10) was obtained with a yield of 9.1 mg/ml and a final monomer content of 87% (SEC).

Example 7

Preparation and Purification of "Untargeted" Single Chain OX40 Ligand Trimer-Containing Fc Fusion Antigen Binding Molecules The "untargeted" construct was composed by the-OX40 ligand-Fc knob chain described above, a DP47 germline control-Fc hole chain and a DP47 light chain (FIG. 4B), which were co-transfected in a 1:1:1 ratio ("vector knob chain":"vector hole chain":"vector light chain").

Production and purification were performed as described above for targeted single chain OX40 ligand trimer-containing Fc (kih) fusion antigen binding molecule. The variable region of heavy and light chain DNA sequences of the FAP binder, were replaced with those of a germline control (DP47) and subcloned in frame with either the constant heavy chain of the hole or the constant light chain of human IgG1.

Table 28 shows, respectively, the cDNA and amino acid sequences of the DP47-containing 4-1BB ligand trimer-containing Fc (kih) fusion antigen binding molecule.

TABLE 28

Sequences of DP47-containing single chain OX40 ligand trimer-containing Fc (kih) fusion molecule (DP47 single chain OX40L trimer) (Control 3)

| SEQ ID NO: | Description | Sequence |
|---|---|---|
| 87 | nucleotide sequence of trimeric hu OX40L (51-183)-Fc knob chain | see Table 27 |
| 69 | nucleotide sequence of DP47 Fc hole chain | GAGGTGCAATTGTTGGAGTCTGGGGGAGGCTTGGTAC AGCCTGGGGGGTCCCTGAGACTCTCCTGTGCAGCCTCC GGATTCACCTTTAGCAGTTATGCCATGAGCTGGGTCCG CCAGGCTCCAGGGAAGGGGCTGGAGTGGGTCTCAGCT ATTAGTGGTAGTGGTGGTAGCACATACTACGCAGACTC CGTGAAGGGCCGGTTCACCATCTCCAGAGACAATTCA AGAACACGCTGTATCTGCAGATGAACAGCCTGAGAGC CGAGGACACGGCCGTATATTACTGTGCGAAAGGCAGC GGATTTGACTACTGGGGCCAAGGAACCCTGGTCACCGT CTCGAGTGCTAGCACCAAGGGCCCATCGGTCTTCCCCC TGGCACCCTCCTCCAAGAGCACCTCTGGGGGCACAGCG GCCCTGGGCTGCCTGGTCAAGGACTACTTCCCCGAACC GGTGACGGTGTCGTGGAACTCAGGCGCCCTGACCAGC GGCGTGCACACCTTCCCGGCTGTCCTACAGTCCTCAGG ACTCTACTCCCTCAGCAGCGTGGTGACCGTGCCCTCCA GCAGCTTGGGCACCCAGACCTACATCTGCAACGTGAAT CACAAGCCCAGCAACACCAAGGTGGACAAGAAAGTTG AGCCCAAATCTTGTGACAAAACTCACACATGCCCACCG TGCCCAGCACCTGAAGCTGCAGGGGACCGTCAGTCTT CCTCTTCCCCCCAAAACCCAAGGACACCCTCATGATCT CCCGGACCCCTGAGGTCACATGCGTGGTGGTGGACGTG AGCCACGAAGACCCTGAGGTCAAGTTCAACTGGTACG TGGACGGCGTGGAGGTGCATAATGCCAAGACAAAGCC GCGGGAGGAGCAGTACAACAGCACGTACCGTGTGGTC AGCGTCCTCACCGTCCTGCACCAGGACTGGCTGAATGG CAAGGAGTACAAGTGCAAGGTCTCCAACAAAGCCCTC GGCGCCCCCATCGAGAAAACCATCTCCAAAGCCAAAG GGCAGCCCCGAGAACCACAGGTGTGCACCCTGCCCCC ATCCCGGGATGAGCTGACCAAGAACCAGGTCAGCCTC TCGTGCGCAGTCAAAGGCTTCTATCCCAGCGACATCGC CGTGGAGTGGGAGAGCAATGGGCAGCCGGAGAACAAC TACAAGACCACGCCTCCCGTGCTGGACTCCGACGGCTC CTTCTTCCTCGTGAGCAAGCTCACCGTGGACAAGAGCA GGTGGCAGCAGGGGAACGTCTTCTCATGCTCCGTGATG CATGAGGCTCTGCACAACCACTACACGCAGAAGAGCC TCTCCCTGTCTCCGGGTAAA |
| 70 | nucleotide sequence of DP47 light chain | GAAATCGTGTTAACGCAGTCTCCAGGCACCCTGTCTTT GTCTCCAGGGGAAAGAGCCACCCTCTCTTGCAGGGCCA GTCAGAGTGTTAGCAGCAGCTACTTAGCCTGGTACCAG CAGAAACCTGGCCAGGCTCCCAGGCTCCTCATCTATGG AGCATCCAGCAGGGCCACTGGCATCCCAGACAGGTTC AGTGGCAGTGGATCCGGGACAGACTTCACTCTCACCAT CAGCAGACTGGAGCCTGAAGATTTTGCAGTGTATTACT GTCAGCAGTATGGTAGCTCACCGCTGACGTTCGGCCAG GGGACCAAAGTGGAAATCAAACGTACGGTGGCTGCAC CATCTGTCTTCATCTTCCCGCCATCTGATGAGCAGTTGA AATCTGGAACTGCCTCTGTTGTGTGCCTGCTGAATAAC TTCTATCCCAGAGAGGCCAAAGTACAGTGGAAGGTGG ATAACGCCCTCCAATCGGGTAACTCCCAGGAGAGTGTC ACAGAGCAGGACAGCAAGGACAGCACCTACAGCCTCA GCAGCACCCTGACGCTGAGCAAAGCAGACTACGAGAA ACACAAAGTCTACGCCTGCGAAGTCACCCATCAGGGC CTGAGCTCGCCCGTCACAAAGAGCTTCAACAGGGGAG AGTGT |
| 20 | trimeric hu OX40L (51-183)- Fc knob chain | see Table 27 |
| 71 | DP47 Fc hole chain | EVQLLESGGGLVQPGGSLRLSCAASGFTFSSYAMSWVRQ APGKGLEWVSAISGSGGSTYYADSVKGRFTISRDNSKNTL YLQMNSLRAEDTAVYYCAKGSGFDYWGQGTLVTVSSAS TKGPSVFPLAPSSKSTSGGTAALGCLVKDYFPEPVTVSWN |

TABLE 28-continued

Sequences of DP47-containing single chain OX40 ligand trimer-containing Fc (kih) fusion molecule (DP47 single chain OX40L trimer) (Control 3)

| SEQ ID NO: | Description | Sequence |
|---|---|---|
| | | SGALTSGVHTFPAVLQSSGLYSLSSVVTVPSSSLGTQTYIC NVNHKPSNTKVDKKVEPKSCDKTHTCPPCPAPEAAGGPS VFLFPPKPKDTLMISRTPEVTCVVVDVSHEDPEVKFNWY VDGVEVHNAKTKPREEQYNSTYRVVSVLTVLHQDWLNG KEYKCKVSNKALGAPIEKTISKAKGQPREPQVCTLPPSRD ELTKNQVSLSCAVKGFYPSDIAVEWESNGQPENNYKTTP PVLDSDGSFFLVSKLTVDKSRWQQGNVFSCSVMHEALH NHYTQKSLSLSPGK |
| 72 | DP47 light chain | EIVLTQSPGTLSLSPGERATLSCRASQSVSSSYLAWYQQK PGQAPRLLIYGASSRATGIPDRFSGSGSGTDFTLTISRLEPE DFAVYYCQQYGSSPLTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |

The DP47-containing single chain OX40 ligand trimer-containing Fc (kih) fusion antigen binding molecule (Control 3) was obtained in a yield of 7 mg/ml and a final monomer content of 100% (SEC).

Example 8

Preparation, Purification and Characterization of OX40

DNA sequences encoding the ectodomains of human, mouse or cynomolgus OX40 (Table 11) were subcloned in frame with the human IgG1 heavy chain CH2 and CH3 domains on the knob (Merchant et al., 1998). An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of the OX40 ectodomain containing chain, thus creating a monomeric form of Fc-linked antigen (FIG. 4C). Table 29 shows the amino acid sequences of the various OX40 ectodomains. Table 30 shows the cDNA and amino acid sequences of monomeric antigen Fc(kih) fusion molecules as depicted in FIG. 4C.

TABLE 29

Amino acid numbering of antigen ectodomains (ECD) and their origin

| SEQ ID NO: | Construct | Origin | ECD |
|---|---|---|---|
| 88 | human Ox40 ECD | Synthetized according to P43489 | aa 29-214 |
| 89 | cynomolgusOx40 ECD | isolated from cynomolgus blood | aa 29-214 |
| 90 | murine Ox40 ECD | Synthetized according to P47741 | aa 10-211 |

TABLE 30 cDNA and Amino acid sequences of monomeric antigen Fc(kih) fusion molecules (produced by combination of one Fc hole chain with one antigen Fc knob chain)

| SEQ ID NO: | Antigen | Sequence |
|---|---|---|
| 76 | Nucleotide sequence Fc hole chain | GACAAAACTCACACATGCCCACCGTGCCCAGCACCTGA ACTCCTGGGGGGACCGTCAGTCTTCCTCTTCCCCCCAAA ACCCAAGGACACCCTCATGATCTCCCGGACCCCTGAGGT CACATGCGTGGTGGTGGACGTGAGCCACGAAGACCCTG AGGTCAAGTTCAACTGGTACGTGGACGGCGTGGAGGTG CATAATGCCAAGACAAAGCCGCGGGAGGAGCAGTACAA CAGCACGTACCGTGTGGTCAGCGTCCTCACCGTCCTGCA CCAGGACTGGCTGAATGGCAAGGAGTACAAGTGCAAGG TCTCCAACAAAGCCCTCCCAGCCCCCATCGAGAAAACC ATCTCCAAAGCCAAAGGGCAGCCCCGAGAACCACAGGT GTGCACCCTGCCCCCATCCCGGGATGAGCTGACCAAGA ACCAGGTCAGCCTCTCGTGCGCAGTCAAAGGCTTCTATC CCAGCGACATCGCCGTGGAGTGGGAGAGCAATGGGCAG CCGGAGAACAACTACAAGACCACGCCTCCCGTGCTGGA CTCCGACGGCTCCTTCTTCCTCGTGAGCAAGCTCACCGT GGACAAGAGCAGGTGGCAGCAGGGGAACGTCTTCTCAT GCTCCGTGATGCATGAGGCTCTGCACAACCACTACACGC AGAAGAGCCTCTCCCTGTCTCCGGGTAAA |
| 91 | Nucleotide sequence human OX40 | CTGCACTGCGTGGGCGACACCTACCCCAGCAACGACCG GTGCTGCCACGAGTGCAGACCCGGCAACGGCATGGTGT CCCGGTGCAGCCGGTCCCAGAACACCGTGTGCAGACCTT |

TABLE 30-continued cDNA and Amino acid sequences of monomeric antigen Fc(kih) fusion molecules (produced by combination of one Fc hole chain with one antigen Fc knob chain)

| SEQ ID NO: | Antigen | Sequence |
|---|---|---|
| | antigen Fc knob chain | GCGGCCCTGGCTTCTACAACGACGTGGTGTCCAGCAAGC CCTGCAAGCCTTGTACCTGGTGCAACCTGCGGAGCGGCA GCGAGCGGAAGCAGCTGTGTACCGCCACCCAGGATACC GTGTGCCGGTGTAGAGCCGGCACCCAGCCCCTGGACAG CTACAAACCCGGCGTGGACTGCGCCCCTTGCCCTCCTGG CCACTTCAGCCCTGGCGACAACCAGGCCTGCAAGCCTTG GACCAACTGCACCCTGGCCGGCAAGCACACCCTGCAGC CCGCCAGCAATAGCAGCGACGCCATCTGCGAGGACCGG GATCCTCCTGCCACCCAGCCTCAGGAAACCCAGGGCCCT CCCGCCAGACCCATCACCGTGCAGCCTACAGAGGCCTG GCCCAGAACCAGCCAGGGGCCTAGCACCAGACCCGTGG AAGTGCCTGGCGGCAGAGCCGTCGACGAACAGTTATAT TTTCAGGGCGGCTCACCCAAATCTGCAGACAAAACTCAC ACATGCCCACCGTGCCCAGCACCTGAACTCCTGGGGGG ACCGTCAGTCTTCCTCTTCCCCCCAAAACCCAAGGACAC CCTCATGATCTCCCGGACCCCTGAGGTCACATGCGTGGT GGTGGACGTGAGCCACGAAGACCCTGAGGTCAAGTTCA ACTGGTACGTGGACGGCGTGGAGGTGCATAATGCCAAG ACAAAGCCGCGGGAGGAGCAGTACAACAGCACGTACCG TGTGGTCAGCGTCCTCACCGTCCTGCACCAGGACTGGCT GAATGGCAAGGAGTACAAGTGCAAGGTCTCCAACAAAG CCCTCCCAGCCCCCATCGAGAAAACCATCTCCAAAGCCA AAGGGCAGCCCCGAGAACCACAGGTGTACACCCTGCCC CCATGCCGGGATGAGCTGACCAAGAACCAGGTCAGCCT GTGGTGCCTGGTCAAAGGCTTCTATCCCAGCGACATCGC CGTGGAGTGGGAGAGCAATGGGCAGCCGGAGAACAACT ACAAGACCACGCCTCCCGTGCTGGACTCCGACGGCTCCT TCTTCCTCTACAGCAAGCTCACCGTGGACAAGAGCAGGT GGCAGCAGGGGAACGTCTTCTCATGCTCCGTGATGCATG AGGCTCTGCACAACCACTACACGCAGAAGAGCCTCTCC CTGTCTCCGGGTAAATCCGGAGGCCTGAACGACATCTTC GAGGCCCAGAAGATTGAATGGCACGAG |
| 92 | Nucleotide sequence cynomolgus OX40 antigen Fc knob chain | CTCCACTGTGTCGGGGACACCTACCCCAGCAACGACCG GTGCTGTCAGGAGTGCAGGCCAGGCAACGGGATGGTGA GCCGCTGCAACCGCTCCCAGAACACGGTGTGCCGTCCGT GCGGGCCCGGCTTCTACAACGACGTGGTCAGCGCCAAG CCCTGCAAGGCCTGCACATGGTGCAACCTCAGAAGTGG GAGTGAGCGGAAACAGCCGTGCACGGCCACACAGGACA CAGTCTGCCGCTGCCGGGCGGGCACCCAGCCCCTGGAC AGCTACAAGCCTGGAGTTGACTGTGCCCCCTGCCCTCCA GGGCACTTCTCCCGGGCGACAACCAGGCCTGCAAGCC CTGGACCAACTGCACCTTGGCCGGGAAGCACACCCTGC AGCCAGCCAGCAATAGCTCGGACGCCATCTGTGAGGAC AGGGACCCCCCACCCACACAGCCCCAGGAGACCCAGGG CCCCCCGGCCAGGCCCACCACTGTCCAGCCCACTGAAGC CTGGCCCAGAACCTCACAGAGACCCTCCACCCGGCCCGT GGAGGTCCCCAGGGGCCCTGCGGTCGACGAACAGTTAT ATTTTCAGGGCGGCTCACCCAAATCTGCAGACAAAACTC ACACATGCCCACCGTGCCCAGCACCTGAACTCCTGGGG GGACCGTCAGTCTTCCTCTTCCCCCCAAAACCCAAGGAC ACCCTCATGATCTCCCGGACCCCTGAGGTCACATGCGTG GTGGTGGACGTGAGCCACGAAGACCCTGAGGTCAAGTT CAACTGGTACGTGGACGGCGTGGAGGTGCATAATGCCA AGACAAAGCCGCGGGAGGAGCAGTACAACAGCACGTAC CGTGTGGTCAGCGTCCTCACCGTCCTGCACCAGGACTGG CTGAATGGCAAGGAGTACAAGTGCAAGGTCTCCAACAA AGCCCTCCCAGCCCCCATCGAGAAAACCATCTCCAAAG CCAAAGGGCAGCCCCGAGAACCACAGGTGTACACCCTG CCCCCATGCCGGGATGAGCTGACCAAGAACCAGGTCAG CCTGTGGTGCCTGGTCAAAGGCTTCTATCCCAGCGACAT CGCCGTGGAGTGGGAGAGCAATGGGCAGCCGGAGAACA ACTACAAGACCACGCCTCCCGTGCTGGACTCCGACGGCT CCTTCTTCCTCTACAGCAAGCTCACCGTGGACAAGAGCA GGTGGCAGCAGGGGAACGTCTTCTCATGCTCCGTGATGC ATGAGGCTCTGCACAACCACTACACGCAGAAGAGCCTC TCCCTGTCTCCGGGTAAATCCGGAGGCCTGAACGACATC TTCGAGGCCCAGAAGATTGAATGGCACGAG |
| 93 | murine OX40 antigen Fc knob chain | GTGACCGCCAGACGGCTGAACTGCGTGAAGCACACCTA CCCCAGCGGCCACAAGTGCTGCAGAGAGTGCCAGCCCG GCCACGGCATGGTGTCCAGATGCGACCACACACGGGAC ACCCTGTGCCACCCTTGCGAGACAGGCTTCTACAACGAG GCCGTGAACTACGATACCTGCAAGCAGTGCACCCAGTG |

TABLE 30-continued cDNA and Amino acid sequences of monomeric antigen Fc(kih) fusion molecules (produced by combination of one Fc hole chain with one antigen Fc knob chain)

| SEQ ID NO: | Antigen | Sequence |
|---|---|---|
| | | CAACCACAGAAGCGGCAGCGAGCTGAAGCAGAACTGCA CCCCCACCCAGGATACCGTGTGCAGATGCAGACCCGGC ACCCAGCCCAGACAGGACAGCGGCTACAAGCTGGGCGT GGACTGCGTGCCCTGCCCTCCTGGCCACTTCAGCCCCGG CAACAACCAGGCCTGCAAGCCCTGGACCAACTGCACCC TGAGCGGCAAGCAGACCAGACACCCCGCCAGCGACAGC CTGGATGCCGTGTGCGAGGACAGAAGCCTGCTGGCCAC CCTGCTGTGGGAGACACAGCGGCCCACCTTCAGACCCA CCACCGTGCAGAGCACCACCGTGTGGCCCAGAACCAGC GAGCTGCCCAGTCCTCCTACCCTCGTGACACCTGAGGGC CCCGTCGACGAACAGTTATATTTTCAGGGCGGCTCACCC AAATCTGCAGACAAAACTCACACATGCCCACCGTGCCC AGCACCTGAACTCCTGGGGGACCGTCAGTCTTCCTCTT CCCCCCAAAACCCAAGGACACCCTCATGATCTCCCGGAC CCCTGAGGTCACATGCGTGGTGGTGGACGTGAGCCACG AAGACCCTGAGGTCAAGTTCAACTGGTACGTGGACGGC GTGGAGGTGCATAATGCCAAGACAAAGCCGCGGGAGGA GCAGTACAACAGCACGTACCGTGTGGTCAGCGTCCTCAC CGTCCTGCACCAGGACTGGCTGAATGGCAAGGAGTACA AGTGCAAGGTCTCCAACAAAGCCCTCCCAGCCCCCATCG AGAAAACCATCTCCAAAGCCAAAGGGCAGCCCCGAGAA CCACAGGTGTACACCCTGCCCCCATGCCGGGATGAGCTG ACCAAGAACCAGGTCAGCCTGTGGTGCCTGGTCAAAGG CTTCTATCCCAGCGACATCGCCGTGGAGTGGGAGAGCA ATGGGCAGCCGGAGAACAACTACAAGACCACGCCTCCC GTGCTGGACTCCGACGGCTCCTTCTTCCTCTACAGCAAG CTCACCGTGGACAAGAGCAGGTGGCAGCAGGGGAACGT CTTCTCATGCTCCGTGATGCATGAGGCTCTGCACAACCA CTACACGCAGAAGAGCCTCTCCCTGTCTCCGGGTAAATC CGGAGGCCTGAACGACATCTTCGAGGCCCAGAAGATTG AATGGCACGAG |
| 80 | Fc hole chain | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVCTLPPSRDELTKNQVSLSCAVKGFYPSDIAVEWE SNGQPENNYKTTPPVLDSDGSFFLVSKLTVDKSRWQQGNV FSCSVMHEALHNHYTQKSLSLSPGK |
| 94 | human OX40 antigen Fc knob chain | LHCVGDTYPSNDRCCHECRPGNGMVSRCSRSQNTVCRPC GPGFYNDVVSSKPCKPCTWCNLRSGSERKQLCTATQDTVC RCRAGTQPLDSYKPGVDCAPCPPGHFSPGDNQACKPWTN CTLAGKHTLQPASNSSDAICEDRDPPATQPQETQGPPARPIT VQPTEAWPRTSQGPSTRPVEVPGGRAVDEQLYFQGGSPKS ADKTHTCPPCPAPELLGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALPAPIEKTISKAK GQPREPQVYTLPPCRDELTKNQVSLWCLVKGFYPSDIAVE WESNGQPENNYKTTPPVLDSDGSFFLYSKLTVDKSRWQQ GNVFSCSVMHEALHNHYTQKSLSLSPGKSGGLNDIFEAQKI EWHE |
| 95 | cynomolgus OX40 antigen Fc knob chain | LHCVGDTYPSNDRCCQECRPGNGMVSRCNRSQNTVCRPC GPGFYNDVVSAKPCKACTWCNLRSGSERKQPCTATQDTV CRCRAGTQPLDSYKPGVDCAPCPPGHFSPGDNQACKPWT NCTLAGKHTLQPASNSSDAICEDRDPPPTQPQETQGPPARP TTVQPTEAWPRTSQRPSTRPVEVPRGPAVDEQLYFQGGSP KSADKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTISK AKGQPREPQVYTLPPCRDELTKNQVSLWCLVKGFYPSDIA VEWESNGQPENNYKTTPPVLDSDGSFFLYSKLTVDKSRWQ QGNVFSCSVMHEALHNHYTQKSLSLSPGKSGGLNDIFEAQ KIEWHE |
| 96 | murine OX40 antigen Fc knob chain | VTARRLNCVKHTYPSGHKCCRECQPGHGMVSRCDHTRDT LCHPCETGFYNEAVNYDTCKQCTQCNHRSGSELKQNCTPT QDTVCRCRPGTQPRQDSGYKLGVDCVPCPPGHFSPGNNQA CKPWTNCTLSGKQTRHPASDSLDAVCEDRSLLATLLWETQ RPTFRPTTVQSTTVWPRTSELPSPPTLVTPEGPVDEQLYFQG GSPKSADKTHTCPPCPAPELLGGPSVFLFPPKPKDTLMISRT PEVTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPCRDELTKNQVSLWCLVKGFYP |

TABLE 30-continued cDNA and Amino acid sequences of monomeric antigen
Fc(kih) fusion molecules (produced by combination of
one Fc hole chain with one antigen Fc knob chain)

| SEQ ID NO: Antigen | Sequence |
|---|---|
| | SDIAVEWESNGQPENNYKTTPPVLDSDGSFFLYSKLTVDKS RWQQGNVFSCSVMHEALHNHYTQKSLSLSPGKSGGLNDIF EAQKIEWHE |

All OX40-Fc-fusion encoding sequences were cloned into a plasmid vector driving expression of the insert from an MPSV promoter and containing a synthetic polyA signal sequence located at the 3' end of the CDS. In addition, the vector contained an EBV OriP sequence for episomal maintenance of the plasmid.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob":"Fc hole":"BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 μg of vector DNA. After addition of 540 μL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% CO$_2$ atmosphere. After the incubation, 160 mL of F17 medium was added and cells were cultured for 24 hours. One day after transfection, 1 mM valproic acid and 7% Feed were added to the culture. After 7 days of culturing, the cell supernatant was collected by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HITRAP® ProteinA HP column (CV=5 mL, GE Healthcare) and equilibrated with 20 mM sodium phosphate, 20 mM sodium citrate, 0.5 M sodium chloride, 0.01% (v/v) TWEEN® 20 (polysorbate 20) containing buffer (pH 7.5). Unbound protein was removed by washing with at least 10 column volumes of the same buffer. The bound protein was eluted using a linear pH gradient over 12 column volumes to 100% of 20 mM sodium citrate, 0.5 M sodium chloride, 0.01% (v/v) TWEEN® 20 (polysorbate 20) containing buffer (pH 2.5). The column was then washed with 10 column volumes of 20 mM sodium citrate, 0.5 M sodium chloride, 0.01% TWEEN® 20 (polysorbate 20) buffer (pH 2.5).

The pH of the collected fractions was adjusted by adding 1/40 (v/v) of 2M Tris, pH8.0. The protein was concentrated and filtered prior to loading on a HILOAD® Superdex 200 column (GE Healthcare) equilibrated with 2 mM MOPS, 150 mM sodium chloride, 0.02% (w/v) sodium azide solution of pH 7.4.

For affinity determination to the human receptor, the ectodomain of human OX40 was also subcloned in frame with an avi (GLNDIFEAQKIEWHE, SEQ ID NO:84) and a hexahistidine tag. The sequences are shown in Table 31.

Protein production was performed as described above for the Fc-fusion protein. Secreted proteins were purified from cell culture supernatants by chelating chromatography, followed by size exclusion chromatography. The first chromatographic step was performed on a NiNTA Superflow™ Cartridge (5 ml, Qiagen) equilibrated with a solution of 20 mM sodium phosphate and 500 nM sodium chloride, pH 7.4. Elution was performed by applying a gradient over 12 column volume from 5% to 45% of elution buffer containing 20 mM sodium phosphate, 500 nM sodium chloride and 500 mM Imidazole (pH 7.4). The protein was concentrated and filtered prior to loading on a HILOAD® Superdex 75 column (GE Healthcare) equilibrated with a solution of 2 mM MOPS, 150 mM sodium chloride and 0.02% (w/v) sodium azide (pH 7.4).

TABLE 31

Sequences of monomeric human OX40 His molecule

| SEQ ID NO: | antigen | Sequence |
|---|---|---|
| 97 | nucleotide sequence human OX40 His | CTGCACTGCGTGGGCGACACCTACCCCAGCAACGACCGGT GCTGCCACGAGTGCAGACCCGGCAACGGCATGGTGTCCCG GTGCAGCCGGTCCCAGAACACCGTGTGCAGACCTTGCGGC CCTGGCTTCTACAACGACGTGGTGTCCAGCAAGCCCTGCAA GCCTTGTACCTGGTGCAACCTGCGGAGCGGCAGCGAGCGG AAGCAGCTGTGTACCGCCACCCAGGATACCGTGTGCCGGT GTAGAGCCGGCACCCAGCCCCTGGACAGCTACAAACCCGG CGTGGACTGCGCCCCTTGCCCTCCTGGCCACTTCAGCCCTG GCGACAACCAGGCCTGCAAGCCTTGGACCAACTGCACCCT GGCCGGCAAGCACACCCTGCAGCCCGCCAGCAATAGCAGC GACGCCATCTGCGAGGACCGGGATCCTCCTGCCACCCAGC CTCAGGAAACCCAGGGCCCTCCCGCCAGACCCATCACCGT GCAGCCTACAGAGGCCTGGCCCAGAACCAGCCAGGGGCCT |

TABLE 31-continued

Sequences of monomeric human OX40 His molecule

| SEQ ID NO: | antigen | Sequence |
|---|---|---|
|  |  | AGCACCAGACCCGTGGAAGTGCCTGGCGGCAGAGCCGTCG ACGAACAGTTATATTTTCAGGGCGGCTCAGGCCTGAACGA CATCTTCGAGGCCCAGAAGATCGAGTGGCACGAGGCTCGA GCTCACCACCATCACCATCAC |
| 98 | human OX40 His | LHCVGDTYPSNDRCCHECRPGNGMVSRCSRSQNTVCRPCGP GFYNDVVSSKPCKPCTWCNLRSGSERKQLCTATQDTVCRCR AGTQPLDSYKPGVDCAPCPPGHFSPGDNQACKPWTNCTLAG KHTLQPASNSSDAICEDRDPPATQPQETQGPPARPITVQPTEA WPRTSQGPSTRPVEVPGGRAVDEQLYFQGGSGLNDIFEAQKIE WHEARAHHHHHH |

Example 9

Biochemical Characterization of FAP-Targeted Single Chain OX40 Ligand Trimer-Containing Fc Fusion Antigen Binding Molecule by Surface Plasmon Resonance Binding of FAP-targeted single chain OX40 ligand trimer-containing Fc (kih) fusion antigen binding molecule to recombinant OX40 was assessed by surface plasmon resonance (SPR). All SPR experiments were performed on a BIACORE®T100 instrument at 25° C. with HBS-EP as a running buffer (0.01 M HEPES pH 7.4, 0.15 M NaCl, 3 mM EDTA, 0.005% Surfactant P20, Biacore, Freiburg/Germany).

Figure 8A:
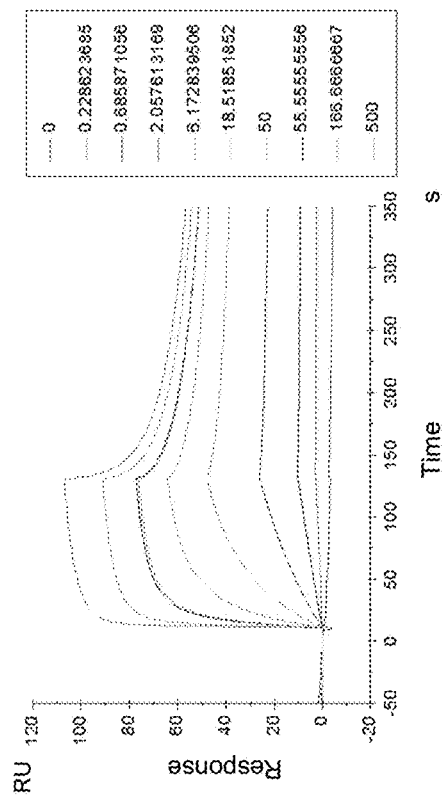
FIGS. 8A-D shows the binding of FAP-targeted OX40 ligand trimer-containing Fc (kih) fusion antigen binding molecule (compound S10) to recombinant OX40 Fc (kih) receptor as assessed by surface plasmon resonance.
Figure 8B:
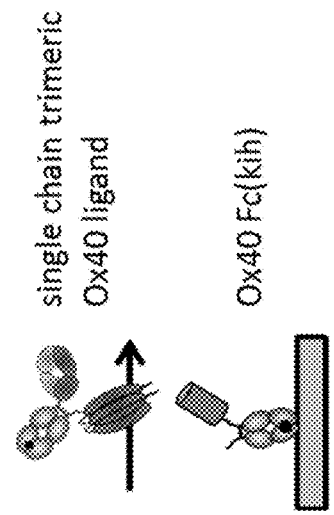
Figure 8C:
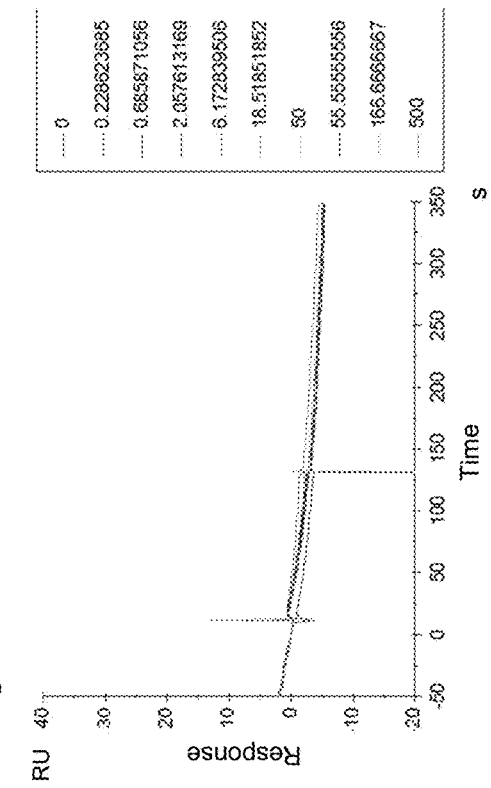
Figure 8D:
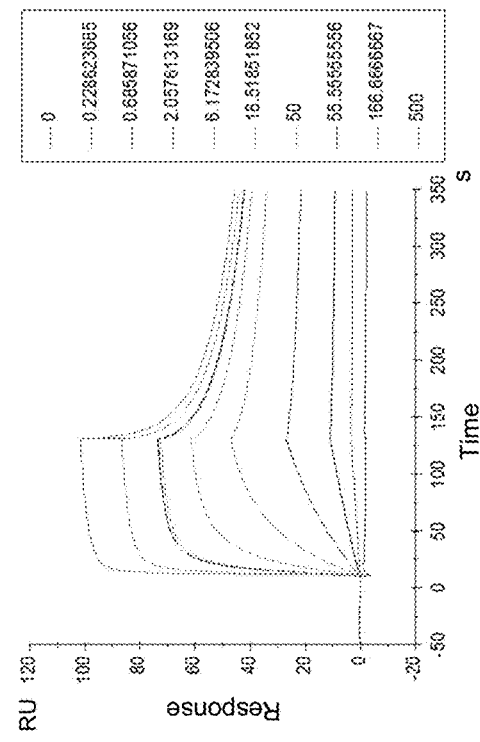
Figure 9A:
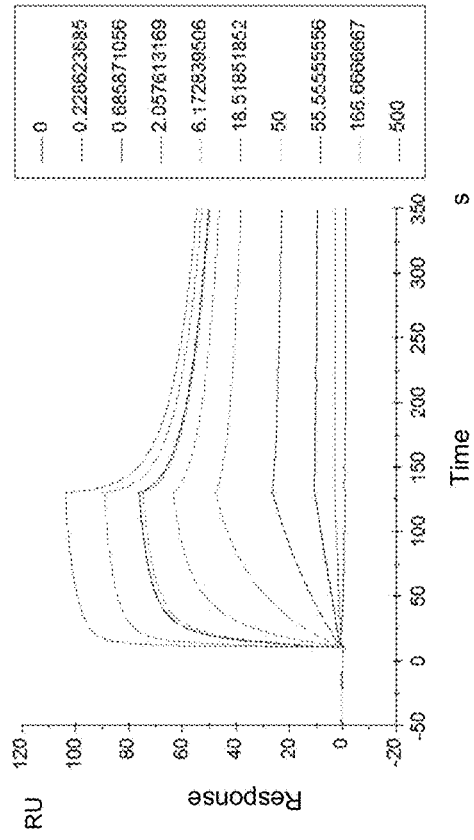
In FIGS. 9A-C, the binding of DP47-containing OX40 ligand trimer-containing Fc (kih) fusion molecule (Control 3) to recombinant OX40 Fc kih receptor is demonstrated. OX40 Fc (kih) is immobilized on a SA chip.
Figure 9C:
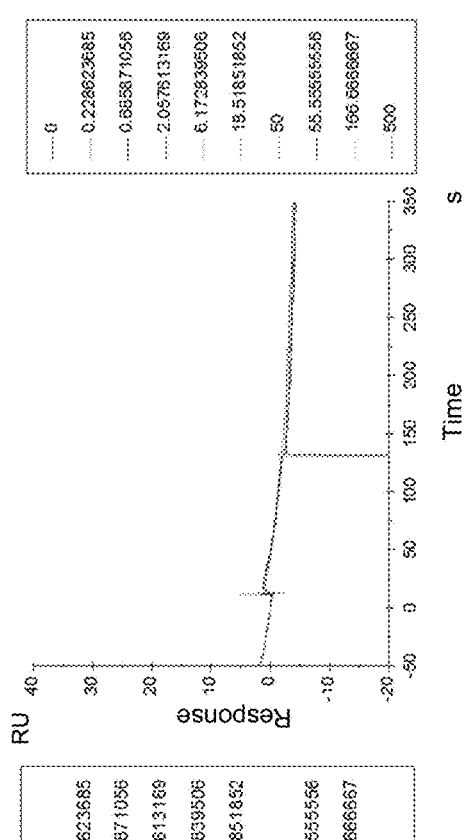
Figure 9B:
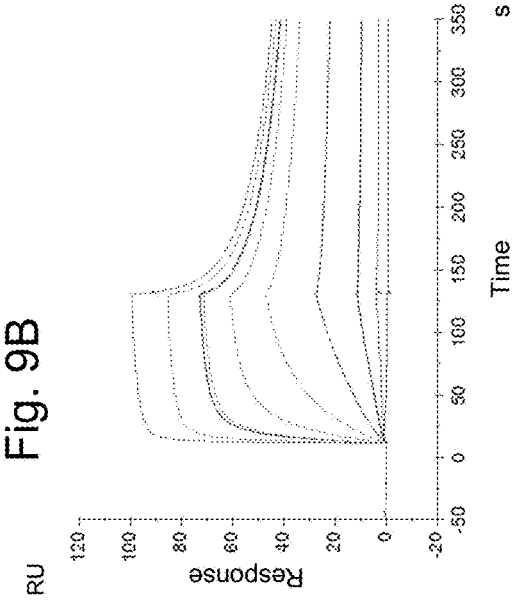

The avidity of the interaction between the FAP-targeted or untargeted OX40 ligand trimer-containing Fc (kih) fusion antigen binding molecules and recombinant OX40 (human, cyno and murine) was determined as illustrated in FIG. 8A. The data demonstrated that both variants of OX40 ligand trimer-containing Fc (kih) fusion antigen binding molecules (FAP single chain OX40 trimer (compound S10 in FIGS. 8A-D, and DP47-containing single chain OX40 trimer (Control 3) in FIGS. 9A-C) bind with comparable avidities to human and cynomolgus OX40 but negligibly to the mouse homolog.

Recombinant biotinylated human, cynomolgus and murine OX40 Fc(kih) fusion molecules were directly coupled on a SA chip using the standard coupling instruction (Biacore, Freiburg/Germany). The immobilization level was about 600 resonance units (RU). FAP-targeted OX40 ligand trimer-containing Fc (kih) fusion antigen binding molecule, or the DP47-containing control, was passed at a concentration range from 0.2 to 500 nM with a flow of 30 μL/minutes through the flow cells over 120 seconds. The dissociation was monitored for 220 seconds. Bulk refractive index differences were corrected by subtracting the response obtained on a reference empty flow cell.

For affinity measurement (FIGS. 10A-C), direct coupling of around 7200 resonance units (RU) of the anti-human Fc specific antibody was performed on a CM5 chip at pH 5.0 using the standard amine coupling kit (GE Healthcare). FAP-targeted or untargeted single chain trimeric OX40 ligand Fc(kih) fusion molecule at 200 nM was captured with a flow rate of 30 μl/min for 60 sec on flow cell 2. A dilution series (31-2000 nM) of huOX40 avi His was passed on both flow cells at 30 μl/min for 120 sec to record the association phase. The dissociation phase was monitored for 180 s and triggered by switching from the sample solution to HBS-EP. The chip surface was regenerated after every cycle using a double injection of 60 sec 3M MgCl$_2$. Bulk refractive index differences were corrected for by subtracting the response obtained on the reference flow cell 1. For the interaction between targeted single chain trimeric OX40 ligand Fc(kih) fusion molecule and huOX40 avi His, the affinity constants were derived from the rate constants by fitting to a 1:1 Langmuir binding using the Biaeval software (GE Healthcare). Dissociation constants can be found in Table 32.

TABLE 32

Fittings to 1:1 Langmuir binding and Affinity constants

| Ligand | Analyte | ka (1/Ms) | kd (1/s) | KD (M) |
|---|---|---|---|---|
| FAP single chain OX40 trimer Compound S10 | Hu OX40 avi His | 1.8E+05 | 1.3E−01 | 7.5E−07 |

Example 10

Functional Characterization of the Targeted 4-1BB Ligand or OX40 Ligand Trimer-Containing Fc Fusion Antigen Binding Molecules 10.1. Binding on Naïve Versus Activated Human PMBCs of the FAP-Targeted 4-1BB Ligand or OX40 Ligand Trimer-Containing Fc (Kih) Fusion Antigen Binding Molecules Buffy coats were obtained from the Zurich blood donation center. To isolate fresh peripheral blood mononuclear cells (PBMCs) the buffy coat was diluted with the same volume of DPBS (Gibco by Life Technologies, Cat. No. 14190 326). 50 mL polypropylene centrifuge tubes (TPP, Cat.-No. 91050) were supplied with 15 mL HISTOPAQUE® 1077 (SIGMA Life Science, Cat.-No. 10771, polysucrose and sodium diatrizoate, adjusted to a density of 1.077 g/mL) and the buffy coat solution were layered above the HISTOPAQUE® 1077. The tubes were centrifuged for 30 min at 450×g. PBMCs were collected from the interface, washed three times with DPBS and resuspended in T cell medium consisting of RPMI 1640 medium (Gibco by Life Technology, Cat. No. 42401-042) supplied with 10% Fetal Bovine Serum (FBS, Gibco by Life Technology, Cat. No. 16000-044, Lot 941273, gamma-irradiated, mycoplasma-free and heat inactivated at 56° C. for 35 min), 1% (v/v) GlutaMAX I (GIBCO by Life Technologies, Cat. No. 35050 038), 1 mM Sodium-Pyruvat (SIGMA, Cat. No. S8636), 1% (v/v) MEM non-essential amino acids (SIGMA, Cat.-No. M7145) and 50 μM β-Mercaptoethanol (SIGMA, M3148).

PBMCs were used directly after isolation (naïve, resting PBMCs) or they were stimulated to induce 4-1BB and OX40 expression on the cell surface of T cells (activated PBMCs) as following: naïve PBMCs were cultured for four days in T cell medium supplemented with 200 U/mL Proleukin and 2 μg/mL PHA-L in a 6-well tissue culture plate. For reactivation cells were further activated for 1 day on 6-well tissue culture plate coated with 10 μg/mL anti-human CD3 (clone OKT3) and 2 μg/mL anti-human CD28 (clone CD28.2) in the T cell medium supplemented with 200 U/mL Proleukin at 37° C. and 5% $CO_2$.

For detection of 4-1BB binding, 0.1×106 naïve or activated PBMCs were added to each well of a round-bottom suspension cell 96-well plates (greiner bio-one, cellstar, Cat. No. 650185). For detection of OX40, naïve human PBMC and activated human PBMC were mixed. To enable discrimination of naïve and activated human PBMC naïve cells were labeled prior to the binding assay using the EFLUOR® 670 cell proliferation dye (eBioscience, Cat.-No. 65-0840-85).

For EFLUOR® 670 cell proliferation dye labelling, cells were harvested, washed with pre-warmed (37° C.) DPBS and adjusted to a cell density of $1\times10^7$ cells/mL in DPBS. EFLUOR® 670 cell proliferation dye (eBioscience, Cat.-No. 65-0840-85) was added to naïve human PBMC at a final concentration of 2.5 mM and a final cell density of $0.5\times10^7$ cells/mL in DPBS. Cells were then incubated for 10 min at room temperature in the dark. To stop labeling reaction, 2 mL FBS were added and cells were washed three times with the T cell medium. A 1 to 1 mixture of $1\times10^5$ naïve, EFLUOR® 670 labeled human PBMC and unlabeled activated human PBMC were then added to each well of a round-bottom suspension cell 96-well plates (greiner bio-one, cellstar, Cat. No. 650185).

Plates were centrifuged 4 minutes at 400×g and at 4° C. and supernatant was flicked off. Cells were washed once with 200 μL 4° C. cold FACS buffer (DPBS supplied with 2% FBS, 5 mM EDTA pH8 (Amresco, Cat. No. E177) and 7.5 mM Sodium azide (Sigma-Aldrich Cat. No. S2002)). Cells were incubated in 50 μL/well of 4° C. cold FACS containing titrated FAP-targeted or DP47 untargeted single chain 4-1BB or OX40 ligand trimer-containing Fc fusion antigen binding molecules for 120 minutes at 4° C. Plates were washed four times with 200 μL/well 4° C. FACS buffer.

For detection of 4-1BB binding, cells were resuspended in 50 μL/well 4° C. cold FACS buffer containing 0.125 μg/mL anti-human CD4-BV421 (clone RPA-T4, mouse IgG1 k, BioLegend, Cat.-No. 300532), 20 μL/mL anti-human CD3-PerCP/Cy5.5 (clone SK7, mouse IgG1k, BD Bioscience, Cat.-No. 332771), 0.25 μg/mL anti-human CD8a-APC (clone RPA-T8, mouse IgG1k, BioLegend, Cat.-No. 301014), 0.25 μg/mL anti-human CD56-AF488 (clone HCD56, mouse IgG1k, BD Pharmingen, Cat.-No. 318310), 2.5 μg/mL anti-human Fcγ-specific goat IgG F(ab)$_2$ fragment-PE (Jackson Immunoresearch, Cat. No. 109 116 098 or 109-116-170) and incubated for 30 minutes at 4° C. in the dark.

For detection of OX40 binding, cells were resuspended in 50 μL/well 4° C. cold FACS buffer containing 0.255 μg/mL anti-human CD4-BV421 (clone RPA-T4, mouse IgG1 k, BioLegend, Cat.-No. 300532), 0.250 μg/mL anti-human CD8-BV711 (clone RPa-T8, mouse IgG1k, BioLegend, Cat.-No. 3010441), 0.250 μg/mL anti-human CD45-PerCP Cy5.5 (clone HI30, mouse IgG1k, BioLegend, Cat.-No. 304028), and 30 μg/mL Fluorescein isothiocyanate (FITC)-conjugated AffiniPure anti-human IgG Fcγ-fragment-specific goat IgG F(ab')$_2$ fragment (Jackson ImmunoResearch, Cat. No. 109 096 098) and incubated for 30 minutes at 4° C. in the dark.

Plates where then washed twice with 200 μL/well 4° C. FACS buffer and cells were finally resuspended in 80 μL/well FACS-buffer containing 0.2 μg/mL DAPI (Santa Cruz Biotec, Cat. No. Sc-3598) and acquired the same day using 5-laser LSR-FORTESSA® (BD Bioscience with DIVA software).

In some cases, cells were fixed and acquired the next day. For this method cells were stained additionally prior to incubation with primary antibody with 100 μL/well DPBS containing 1:1000 diluted LIVE/DEAD® Fixable Blue Dead Cell Stain Kit, for UV excitation (Life Technologies, Molecular Probes, Cat. No. L-23105) for 30 minutes at 4° C. in the dark. After incubation with a secondary antibody cocktail, plates were washed twice with 200 μL/well 4° C. FACS buffer, fixed with 50 DPBS containing 1% Formaldehyde (Sigma, HT501320-9.5L) and incubated overnight at 4° C. For flow cytmtric analysis cells were resuspended in 80 μl/well FACS buffer.

As shown in FIGS. 11A to 11D and FIGS. 12A to 12D, neither FAP-targeted nor DP47-containing single chain 4-1BBL and OX40L trimer-containing Fc (kih) fusion antigen binding molecules did bind to resting human CD4$^+$ T cells or CD8$^+$ T cells. In contrast, all constructs bound strongly to activated CD8$^+$ or CD4$^+$ T cells. The single chain 4-1BBL trimer-containing molecules showed approximately 10 fold lower binding to CD4+ as compared to CD8+ T-cells. In contrast, the single chain OX40L trimer-containing molecules showed approximately 4 fold higher intensity of specific fluorescence upon binding to CD4$^+$ as compared to CD8$^+$ T cells. These differences concur very well with 10-20 fold higher levels of 4-1BB expression on CD8$^+$ human T-cells as compared to CD4$^+$ T-cells while the latter express approximately 4 fold higher levels of OX40 as compared to the CD8$^+$ subset. As shown in FIGS. 11E to 11H, monovalent and bivalent FAP (28H1 or 4B9)-targeted or CEA (sm9b)-targeted or DP47-untargeted single chain trimeric 4-1BB ligand Fc (kih) fusion molecules did not bind to resting human CD4$^+$ or CD8$^+$ T cells but strongly to activated CD8$^+$ T cells and to a less extend to activated CD4$^+$ T cells. As can be seen in FIGS. 11J to 11M, the binding was independent of targeting or bivalency, e.g. independent of the fusion location of the single chain trimeric 4-1BB ligand.

10.2. Binding to FAP-Expressing Tumor Cells

For binding assays on FAP expressing cells, human fibroblast activating protein (huFAP) expressing cells NIH/3T3-huFAP clone 39 or WM266-4 cells (ATCC, Cat. No. CRL-1676) were used. The NIH/3T3-huFAP clone 39 was generated by the transfection of the mouse embryonic fibroblast NIH/3T3 cell line (ATCC, Cat. No. CRL-1658) with the expression vector pETR4921 to express huFAP under 1.5m/mL Puromycin selection.

$0.1\times10^6$ NIH/3T3-huFAP clone 39 (4-1BBL) or $5\times10^4$ WM266-4 cells (OX40L) in DPBS were added to each well of round-bottom suspension cell 96-well plates. Plates were centrifuged 4 minutes, 400×g at 4° C. and supernatants were flicked off. Cells were washed once with 200 μL DPBS and pellets were resuspended by a short and gentle vortex. For binding analysis of the 4-1BBL trimer-containing Fc (kih) fusion antigen binding molecule, 100 μL/well of 4° C. cold DPBS buffer containing 1:5000 diluted Fixable Viability Dye EFLUOR® 450 (eBioscience, Cat. No. 65 0863 18) were added and plates were incubated for 30 minutes at 4° C. Cells were washed once with 200 μL 4° C. cold DPBS buffer. All samples were resuspended in 50 μL/well of 4° C. cold FACS buffer containing the FAP-targeted or DP47-containing single chain 4-1BBL or OX40L trimer-containing molecules at the indicated range of concentrations and incubated for 1 hour at 4° C. Afterwards the cells were washed five times with 200 µL 4° C. FACS buffer and resuspended by a short vortex. Cells were further stained with 50 µL/well of 4° C. cold FACS buffer containing 30 µg/mL Fluorescein isothiocyanate (FITC)-conjugated AffiniPure anti-human IgG Fcγ-fragment-specific goat IgG F(ab')$_2$ fragment (Jackson ImmunoResearch, Cat. No. 109 096 098) for 30 minutes at 4° C. Cells were washed twice with 200 µL 4° C. FACS buffer. Cells stained with OX40L trimer-containing molecule were finally resuspended in 80 µL/well FACS-buffer containing 0.2m/mL DAPI (Santa Cruz Biotec, Cat. No. Sc-3598) and acquired the same day using 5-laser LSR-FORTESSA® (BD Bioscience with DIVA software).

Cells stained with 4-1BBL trimer-containing antigen binding molecules and cells were fixed by resuspension in 50 DPBS containing 1% Formaldehyde. The next day cells were resuspended in 100 µL FACS-buffer and acquired using 5-laser LSR-FORTESSA® (BD Bioscience with DIVA software).

As shown in FIGS. 13A-E, the FAP-targeted molecules containing either the single chain trimeric 4-1BBL (compound 51, FIG. 13A) or OX40L (compound S10, FIG. 13B) efficiently bound to human FAP-expressing cells. In contrast, their counterparts containing the DP47 antibody (Control 1 and 3) showed no such binding (FIGS. 13A and 13B). Therefore, only FAP-targeted single chain trimeric 4-1BBL or OX40L containing molecules showed tumor-targeting properties. As shown, in FIGS. 13C and 13D, monovalent and bivalent FAP (28H1 or 4B9)-targeted, but not DP47-untargeted single chain trimeric 4-1BBL Fc (kih) fusion antigen binding molecules can bind to FAP-expressing human melanoma cell lines MV-3 and WM-266-4. FAP-binding clone 4B9 shows the strongest binding whereas clone 28H1 shows a lower affinity on FAP-expressing tumor cells. Due to the lower affinity, differences between the monovalent FAP (28H1)-targeted single chain trimeric 4-1BBL (kih) fusion molecule and the bivalent binding FAP (28H1)-targeted hu IgG1 P329G LALA control molecule become more obvious. The bivalent binding FAP(28H1)-targeted hu IgG1 P329G LALA control molecule shows a lower MFI (bivalent occupancy of the FAP molecules) and lower $EC_{50}$ value.

10.3. Binding to CEA-Expressing Tumor Cells

For binding assays on CEA-expressing tumor cells, the following human CEA-expressing tumor cell line was used: human gastric cancer (stomach) cell line received from a liver metastasis MKN45 (DMSZ, No. ACC 409). The assays were performed as described for the FAP-expressing MV-3 and WM-266-4 tumor cell lines in Example 10.2.

As shown in FIG. 13E, monovalent and bivalent CEA (sm9b)-targeted but not DP47-untargeted single chain 4-1BB ligand trimer-containing Fc (kih) fusion antigen binding molecules can bind to CEA-expressing human gastric cancer cell line MKN45. Differences between the monovalent CEA (sm9b)-targeted single chain trimeric 4-1BBL Fc (kih) fusion molecule (Compound S5) and the bivalent CEA (sm9b)-targeted single chain trimeric 4-1BBL Fc (kih) fusion molecule (Compound S4) is shown in a lower MFI (bivalent occupancy of the CEA molecules).

10.4. Binding to Activated Mouse Splenocytes Expressing Mouse 4-1BB

Mouse spleens were collected in 3 mL PBS and a single cell suspension was generated using the gentle MACS tubes (Miltenyi Biotec Cat.-No. 130-096-334) and gentle MACS Octo Dissociator (Miltenyi Biotec). Afterwards splenocytes were filtered through a 70 µm pre-separation filters (Miltenyi Biotec Cat.-No. 130-041-407) and centrifuged for 7 min at 350×g and 4° C. Supernatants were aspirated and cells were resuspended in RPMI 1640 medium supplied with 10% (v/v) FBS, 1% (v/v) GlutaMAX I, 1 mM Sodium-Pyruvate, 1% (v/v) MEM non-essential amino acids, 50 u M β-Mercaptoethanol and 10% Penicillin-Streptomycin (SIGMA, Cat.-No. P4333). $10^6$ cells/mL were cultured for 2 days in a 6-well tissue culture plate coated with 10 µg/mL anti-mouse CD3c Armenian hamster IgG (clone 145-2C11, BioLegend, Cat.-No. 100331) and 2 µg/mL anti-mouse CD28 Syrian hamster IgG (clone 37.51, BioLegend, Cat.-No. 102102). Activated mouse splenocytes were harvested, washed in DPBS, counted and $0.1 \times 10^6$ cells were transferred to each well of a 96 U-bottom non-tissue culture treated well plate. Supernatant was removed and cells were stained in 100 uL/well DPBS containing 1:5000 diluted Fixable Viability Dye eF660 (Bioscience, Cat-No. 65-0864-18) for 30 min at 4° C. Cells were washed with DPBS and stained in 50 uL FACS buffer containing different concentration of FAP-targeted or DP47-targeted single chain trimeric 4-1BBL antigen binding molecule or anti-mouse CD137 human IgG1 P329G LALA mAb (clone Lob.12.3). Cells were incubated for 60 min at 4° C. Then cells were washed four times with FACS buffer and stained in 50 µL/well FACS buffer containing 10 µg/mL purified anti-mouse CD16/CD32 rat IgG-Fc-Block (BD Pharmingen, Cat.-No. 553142 clone 2.4G2), 5 µg/mL anti-mouse CD8b rat IgG2bκ-FITC (BioLegend, Cat.-No. 126606, clone YTS156.7.7), 0.67 µg/mL anti-mouse CD3 rat IgG2bκ-APC-Cy7 (BioLegend, Cat.-No. 100222, clone 17A2), 0.67 µg/mL anti-mouse CD4 rat IgG2bκ-PE-Cy7 (BioLegend, Cat.-No. 100422, clone GK1.5), 2 µg/mL anti-mouse NK1.1 Mouse (C3H×BALB/c) IgG2aκ-PerCp-Cy5.5 (BioLegend, Cat.-No. 108728, clone PK136) and 10 µg/mL PE-conjugated AffiniPure polyclonal F(ab')$_2$ Fragment goat anti-human IgG, Fcγ fragment specific, minimal cross-reactive to Bovine mouse and rabbit serum proteins (Jackson ImmunoResearch, Cat.-No. 109-116-170) for 30 min at 4° C. Cells were washed twice with 200 µL/well cold FACS buffer, fixed with 50 µL/well DPBS containing 1% Formaldehyde and stored overnight at 4° C. The next day cells were resuspended in FACS-buffer and acquired using a 3-laser Canto II flow cytometer (BD Bioscience with DIVA software).

As shown in FIGS. 14A-B, the FAP-targeted or DP47-containing single chain trimeric human 4-1BBL molecules (Compound S1 and Control 1) do not bind to mouse 4-1BB. Therefore their activity cannot be tested in immune competent mice. For in vivo mode of action studies either humanized mouse models or surrogates containing single chain trimeric mouse 4-1BBL have to be used.

Example 11

Biological Activity of the Targeted 4-1BB Ligand or OX40 Ligand Trimer-Containing Fc Fusion Antigen Binding Molecules 11.1. NFκB Activation in HeLa Cells Expressing Human 4-1BB or OX40

11.1.1. Generation of HeLa Cells Expressing Human 4-1BB and Luciferase Under Control of an NFκB Enhancer Region The human-papilloma-virus-18-induced cervix carcinoma cell line HeLa (ATCC, Cat. No. CCL-2) was transduced with the expression vector pETR10829, which contains the human sequence of 4-1BB (Uniprot accession Q07011, SEQ ID NO:99) under control of the CMV-promoter and the Puromycin resistance gene. Cells were cultured in DMEM-medium supplied with 10% FBS, 1% GlutaMAX-I and 3 µg/mL Puromycin (InvivoGen, Cat-No. ant-pr). 4-1BB-transduced HeLa cells were tested for 4-1BB expression by flow cytometry: $0.2×10^6$ living cells were resuspended in 100 µL FACS buffer containing 0.1 µs PerCP/Cy5.5 conjugated anti-human 4-1BB mouse IgG1κ clone 4B4-1 (BioLegend Cat. No. 309814) or its isotype control (PerCP/Cy5.5 conjugated mouse IgG1κ isotype control antibody clone MOPC 21, BioLegend Cat. No. 400150) and incubated for 30 minutes at 4° C. Cells were washed twice with FACS buffer, resuspended in 300 µL FACS buffer containing 0.06 µg DAPI and acquired using 5-laser LSR-FORTESSA® the same day. Single clones were generated by limited dilution. To this end, living human-4-1BB transduced HeLa cells were resuspended in medium to a density of 10, 5 and 2.5 cells/mL and 200 µL of these cell suspensions were transferred to round bottom tissue-culture treated 96-well plates (6 plates/cell concentration, TPP Cat. No. 92697). Single clones were harvested, expanded and tested for 4-1BB expression as described above. The clone with the highest expression of 4-1BB (clone 5) was chosen for further transfection with the NF-κB-luciferase expression-vector 5495p Tranlucent HygB, which was generated at Roche. The expression-vector 5495p Tranlucent HygB combines a Hygromycin B resistance into NF-κB(1) Luciferase Reporter Vector (Panomics, Cat. No. LR0051). Human-4-1BB HeLa clone 5 cells were cultured to a confluency of 70 percent. 50 µg (40 µL) of linearized (restriction enzymes AseI and SalI) 5495p Tranlucent HygB expression vector DNA were added to a sterile 0.4 cm Gene Pulser/Micro-Pulser Cuvette (Biorad, Cat.-No. 165-2081). $2.5×10^6$ human-4-1BB HeLa clone 5 cells in 400 µl supplement-free DMEM were added and mixed carefully with the plasmid solution. The cuvette was implemented into the Gene Pulser Xcell total system (Biorad, Cat No. 165 2660) and an electroporation transfection was performed with following settings: Exponential pulse, capacitance 500 µF, voltage 160 V, resistance ∞. Immediately after the pulse transfected cells were transferred to a tissue culture flask 75 cm² (TPP, Cat. No. 90075) with 15 mL 37° C. warm DMEM-Medium supplied with 10% FBS and 1% GlutaMAX I. 24 hours after seeding the selection media was added containing 3 µg/mL Puromycin and 200 µg/mL Hygromycin B (Roche, Cat. No. 10843555001). Afterwards surviving cells were expanded and limited dilution was performed as described above to generate single clones.

Clones were tested for 4-1BB expression as described above and for NF-κB-Luciferase activity as following: Clones were harvested in selection medium and counted using a Cell Counter Vi-cell xr 2.03 (Beckman Coulter, Cat. No. 731050). Cells were set to a cell density of $0.33×10^6$ cells/mL and 150 µL of this cell suspension were transferred to each well of a sterile white 96-well flat bottom tissue culture plate with lid (greiner bio one, Cat. No. 655083) and, as a control, to a conventional 96 well flat bottom tissue culture plate (TPP Cat. No. 92096) to test survival and cell density on the next day. Cells were incubated at 37° C. and 5% $CO_2$ overnight. On the next day 50 µL of medium containing recombinant human tumor necrosis factor alpha (rhTNFα, PeproTech, Cat.-No. 300 01A) at different concentrations were added to each well of the white 96-well plate resulting in final concentrations of 100, 50, 25, 12.5, 6.25 and 0 ng/well rhTNFα. Cells were incubated for 6 hours at 37° C. and 5% $CO_2$ and washed afterwards three times with 200 µL/well DPBS. 30 µl freshly prepared Reporter Lysis Buffer (Promega, Cat-No: E3971) were added to each well and the plates were stored over night at −20° C. The next day frozen cell plates and detection buffer (Luciferase 1000 Assay System, Promega, Cat. No. E4550) were thawed to room temperature. 100 µL of detection buffer were added to each well and the plate was measured immediately using the SpectraMax M5/M5e microplate reader and SoftMax Pro Software (Molecular Devices) with following settings: for luciferase (RLUs), 500 ms integration time, no filter, collecting all wave length and top reading. Measured URLs above control (no rhTNFα added) were taken as luciferase activity. The NF-κB-luc-4-1BB-HeLa clone 26 was chosen for further use exhibiting the highest luciferase activity and a sensible 4-1BB-expression.

11.1.2. NFκB Activation in HeLa Cells Expressing Human 4-1BB Co-Cultured with Crosslinking Anti-Human IgG1 Fcγ-Fragment Specific Goat IgG F(Ab')₂ Fragment NF-κB-luciferase human-4-1BB HeLa cells were harvested and resuspended in DMEM Medium supplied with 10% Fetal Bovine Serum and 1% GlutaMAX I to a concentration of $0.8×10^6$ cells/mL. 100 µL ($8×10^4$ cells) of this cell suspension were transferred to each well of a sterile white 96-well flat bottom tissue culture plate with lid (greiner bio one, Cat. No. 655083) and the plate were incubated at 37° C. and 5% $CO_2$ overnight. The next day 50 µL/well of medium containing titrated FAP- or DP47-targeted single chain trimeric human 4-1BBL antigen binding molecules were added. For crosslinking 50 µL/well of medium containing secondary antibody anti-human IgG Fcγ-fragment-specific goat IgG F(ab')₂ fragment (Jackson ImmunoResearch, Cat. No. 109-006-098) were added in a 1:4 ratio (4 times more secondary antibody than the primary single chain trimeric human 4-1BBL antigen binding molecule).

Plates were incubated for 6 hours at 37° C. and 5% $CO_2$. Luciferase activity was measured as described under Example 11.1.1. The principle of the assay is illustrated in FIG. 15.

As shown in FIG. 16, crosslinking via a secondary polyclonal anti-huIgG1 Fcγ-specific goat IgG F(ab)₂ fragment of FAP-targeted single chain trimeric human 4-1BBL (closed circle) or DP47-containing single chain trimeric human 4-1BBL (open circle, dotted line) leads to similar activation of the NFκB promoter as assessed by the level of luciferase expression in the reporter cell line. Therefore, following their artificially induced non-specific oligomerization, the DP47-containing and FAP-targeted single chain trimeric human 4-1BBL molecules show comparable capacity to agonistically engage 4-1BB at the cell surface.

11.1.3. NFκB Activation in HeLa Cells Expressing Human 4-1BB with FAP-Expressing Tumor Cells NFκB-luciferase human-4-1BB HeLa cells were harvested and resuspended in DMEM Medium supplied with 10% FBS and 1% GlutaMAX I to a concentration of $0.2×10^6$ cells/mL. 100 µL ($2×10^4$ cells) of this cell suspension were transferred to each well of a sterile white 96-well flat bottom tissue culture plate with lid (greiner bio one, Cat. No. 655083) and the plate were incubated at 37° C. and 5% $CO_2$ overnight. On the next day 50 µL of medium containing titrated FAP- or DP47-targeted single chain trimeric human 4-1BBL antigen binding molecule were added.

The following human FAP-expressing tumor cells were resuspended in DMEM supplied with 10% FBS and 1% GlutaMAX-I to a concentration of $2×10^6$ cells/mL:

human melanoma cell line MV3 (first published in van Muijen G N et al. 1991), human female melanoma WM-266-4 cell line (ATCC No. CRL-1676), and mouse embryonic fibroblast NIH/3T3 (ATCC No. CRL-1658) transfected with expression vector pETR4921 to express human FAP and Puromycin resistance: NIH/3T3-huFAP clone 39 as described in Example 10.2.

50 μL of FAP-expressing tumor cell suspension were added to each well. After adding crosslinking FAP-expressing tumor cells or medium (no crosslinking), plates were incubated for 6 hours at 37° C. and 5% $CO_2$. Luciferase activity was measured as described in Example 11.1.1. Incubation time and ratio between NFκB-Luciferase human-CD137 HeLa cells and 3T3-human FAP clone 39 cells were titrated and time and ratio were set to values reaching the luciferase activation plateau. The principle of the assay is shown in FIG. 17.

As shown in FIGS. 18A to 18D, FAP-targeted single chain 4-1BBL trimer-containing Fc (kih) fusion antigen binding molecules (Compound S1) (filled circles) can be crosslinked via FAP-expressing tumor cells that leads to NFκB-mediated luciferase-activation in the reporter cell line in a concentration-dependent manner. In contrast, the DP47-containing single chain trimeric human 4-1BBL (Control 1) is unable to activate the reporter cell line under the same experimental conditions. In the absence of crosslinking (no addition of FAP-expressing tumor cells) both molecules are unable to induce NFκB-mediated luciferase-activation in the reporter cell line.

As shown in FIGS. 19A to 19C, monovalent or bivalent FAP (4B9 or 28H1)-targeted single chain trimeric 4-1BBL Fc (kih) fusion antigen binding molecules can be crosslinked via FAP-expressing tumor cells and therefore can induce NF-κB-mediated luciferase-activation in the reporter cell line HeLa-hu4-1BB-NF-κB-luc in a concentration-dependent manner. In contrast, monovalent or bivalent DP47-untargeted single chain trimeric 4-1BBL Fc (kih) fusion molecules (Controls 1 and 2) are unable to activate the reporter cell line without cross-linking. In the absence of crosslinking (no addition of FAP-expressing tumor cells) all molecules are unable to induce NFκB-mediated luciferase-activation in the reporter cell line. The monovalent FAP-targeted single chain trimeric 4-1BBL Fc(kih) fusion antigen binding molecules induce a stronger activation than the bivalent FAP (4B9)-targeted single chain trimeric 4-1BB ligand (kih) fusion molecule, which reflects also the binding to FAP-expressing tumor cells. The differences between the 4B9 and the 28H1 FAP-binding clones however are not as strong as in the binding assay to FAP-expressing tumor cells. Still the monovalent FAP (4B9)-targeted single chain trimeric 4-1BB ligand (kih) fusion molecule shows a slightly lower $EC_{50}$ value which can be explained by the higher affinity to FAP.

11.1.4. NFκB Activation in HeLa Cells Expressing Human 4-1BB with CEA-Expressing Tumor Cells The NF-κB activation assay using HeLa-human 4-1BB-NF-κB-luc reporter cell together with CEA-expressing tumor cell lines has been performed in the same way as described in 11.1.3., however the FAP-expressing tumor cells were exchanged with CEA-expressing MKN45 tumor cell line described already in Example 10.3 in this application.

As shown in FIGS. 20A and 20B, monovalent and bivalent CEA (sm9b)-targeted single chain trimeric 4-1BBL Fc(kih) fusion antigen binding molecules can be crosslinked via CEA-expressing tumor cells and therefore can induce NF-κB-mediated luciferase-activation in the reporter cell line HeLa-hu4-1BB-NF-κB-luc in a concentration-dependent manner. In contrast monovalent or bivalent DP47-untargeted single chain trimeric 4-1BBL Fc(kih) fusion molecules (Controls 1 and 2) are unable to activate the reporter cell line without cross-linking. In the absence of crosslinking (no addition of CEA-expressing tumor cell line MKN45) all molecules are unable to induce NFκB-mediated luciferase-activation in the reporter cell line. The monovalent CEA (sm9b)-targeted single chain trimeric 4-1BB ligand (kih) fusion molecules (Compound S5) induce a stronger activation than the bivalent CEA (sm9b)-targeted single chain trimeric 4-1BB ligand (kih) fusion molecules (Compound S4), which reflects also the MFI of binding to CEA-expressing human MKN45 tumor cell line shown in FIG. 13E.

11.1.5. HeLa Cells Expressing Human OX40 and Reporter Gene NFκB-Luciferase

Agonstic binding of OX40 to its ligand induces downstream signaling via activation of NFκB (Weinberg et al., 2004). The recombinant reporter cell line HeLa_hOx40_NFκB_Luc1 was generated to express human OX40 on its surface. Additionally, it harbors a reporter plasmid containing the luciferase gene under the control of an NFκB-sensitive enhancer region. OX40 triggering induces dose-dependent activation of NFκB, which translocates in the nucleus, where it binds on the NFκB sensitive enhancer of the reporter plasmid to increase expression of the luciferase protein. Luciferase catalyzes luciferin-oxidation resulting in oxyluciferin which emits light. This can be quantified by a luminometer. The scope of one experiment was to test the capacity of the single chain trimeric human OX40L antigen binding molecule to induce NFκB activation in HeLa_hOx40_NFκB_Luc1 cells.

Morris et al. showed that agonistic co-stimulation with conventional anti-OX40 antibodies relied on surface immobilization (Morris et al., 2007). Thus, to achieve a higher degree of hypercrosslinking of OX40, FAP-targeted single chain trimeric human OX40L antigen binding molecules were hyper-crosslinked with WM-266-4 tumor cells naturally expressing FAP.

11.1.6. NFκB Activation in HeLa Cells Expressing Human OX40 with FAP-Expressing Tumor Cells All centrifugations were done at 350×g for 5 minutes at 4° C. To wash the cells, the tubes or wells were filled up with the indicated buffer. After centrifugation the supernatant was aspirated and the cell pellet resuspended in the indicated buffer.

Adherent HeLa_hOX40_NFκB_Luc1 cells and WM-266-4 cells were harvested using cell dissociation buffer (Invitrogen, Cat.-No. 13151-014) for 10 minutes at 37° C. Cells were washed once with DPBS. HeLa_hOX40_NFκB_Luc1 cells were adjusted to a cell density of $2 \times 10^5$ cells/mL in assay medium containing MEM (Invitrogen, Cat.-No. 22561-021), 10% (v/v) heat-inactivated FBS, 1 mM sodium pyruvate and 1% (v/v) non-essential amino acids. Cells were seeded in a density of $0.3 \times 10^5$ cells per well in a sterile white 96-well flat bottom tissue culture plate with lid (greiner bio one, Cat. No. 655083) and kept over night at 37° C. and 5% $CO_2$ in an incubator (Hera Cell 150). On the next day, HeLa_hOX40_NFκB_Luc1 were stimulated for 6 hours adding assay medium containing titrated FAP-targeted or DP47-containing single chain trimeric human OX40L antigen binding molecules. For hyper-crosslinking human FAP-expressing WM266-4 tumor cells were adjusted to a cell density of $3 \times 106$ cells/mL in assay media and cells were added to a final density of $0.75 \times 10^5$ cells/well.

After 6 hours of incubation at 37° C. and 5% $CO_2$ in an incubator, supernatant was aspirated and plates washed two times with DPBS. Quantification of light emission was done using the luciferase 100 assay system and the reporter lysis buffer (both Promega, Cat. No. E4550 and Cat-No: E3971) according to manufacturer instructions.

Emitted relative light units (URL) were corrected by basal luminescence of HeLa_hOX40_NFκB_Luc1 cells and were blotted against the logarithmic primary antibody concentration using Prism4 (GraphPad Software, USA). Curves were fitted using the inbuilt sigmoidal dose response.

As shown in FIGS. 21A-B, both the FAP-targeted and DP47-containing single chain trimeric human OX40L Fc(kih) fusion molecules (filled and open circles) induced detectable NFκB activation. This is in contrast to what was observed with the single chain trimeric human 4-1BBL molecules which showed no NFkB-inducing activity without hyper-crosslinking through secondary antibodies. Hyper-crosslinking via FAP-expressing tumor cell WM-266-4 strongly increased induction of NFκB-mediated luciferase expression in a concentration-dependent manner by the FAP-targeted single chain trimeric human OX40L Fc(kih) fusion antigen binding molecule (Compounds S10, filled circle). No such effect was seen when the DP47-containing single chain trimeric human OX40L Fc(kih) fusion molecule was used.

11.2 Antigen-Specific $CD8^+$ T Cell-Based Assay 11.2.1. Isolation and Culture of Antigen-Specific CD8 T Cells Fresh blood was obtained from a HLA-A2+ CMV-infected volunteer. PBMCs were isolated as described in Example 10.1 by ficoll density centrifugation. CD8 T cells were purified from PBMCs using a negative selection human CD8 T cell isolation kit according to manufacturer's recommendations (Miltenyi Biotec, Cat. No. 130-094-156). Ten million of isolated CD8 T cells were resuspended in 1 mL sterile DPBS supplemented with 1% (v/v) FBS along with 50 µL of PE-labeled HLA-A2-pentamer containing the CMV-derived NLVPMVATV peptide (ProImmune, Cat. No. F008-2B, SEQ ID NO:183) and incubated for 10 min at room temperature. Cells were washed twice with 3 mL sterile DPBS supplied with 1% (v/v) FBS. Cells were resuspended in 1 mL DPBS supplied with 1% (v/v) FBS containing 1 µg/mL anti-human CD8-FITC (clone LT8, Abcam, Cat. No. Ab28010) and incubated for 30 minutes at 4° C. Then, the cells were washed twice, resuspended to a concentration of $5 \times 10^6$ cells/mL in DPBS supplied with 1% (v/v) FBS, and filtrated through a 30 µm pre-separation nylon-net cell strainer (Miltenyi Biotec, Cat. No. 130-041-407). NLV-peptide-specific $CD8^+$ T cells were isolated by FACS sorting using an ARIA cell sorter (BD Bioscience with DIVA software) with the following settings: 100 µm nozzle and purity sort mask. Sorted cells were collected in a 15 ml polypropylene centrifuge tube (TPP, Cat. No. 91015) containing 5 ml RPMI 1640 medium supplied with 10% (v/v) FBS, 1% (v/v) GlutaMAX-I and 400 U/mL Proleukin. Sorted cells were centrifuged for 7 minutes at 350×g at room temperature and resuspended in same medium to a concentration of $0.53 \times 10^6$ cells/mL. 100 µL/well of this cell suspension were added to each well of a previously prepared plate with PHA-L-activated irradiated allogeneic feeder cells. Feeder cells were prepared from PBMCs as previously described (Levitsky et al., 1998) and distributed to 96-well culture plates using $2 \times 10^5$ feeder cells per well.

After one day of culture, 100 µL medium were removed from each well and replaced by new RPMI 1640 medium supplemented with 10% (v/v) FBS and 1% (v/v) GlutaMAX-I and 400 U/mL Proleukin. This was repeated during culture on a regular basis (every 2-4 days). As soon as NLV-specific $CD8^+$ T cells started to proliferate, they were transferred to 24-well flat-bottom tissue culture plate (TPP, 92024). Cells were expanded/split and reactivated with new feeder cell preparation on a regular basis.

11.2.2. Activation Assay of Antigen-Specific $CD8^+$ T Cells

Cells of the human FAP-expressing melanoma cell line MV3 cell line (described in Example 11.1.3.) were harvested and washed with DPBS and $2 \times 10^7$ cells were resuspended in 250 µL C diluent of the PKH-26 Red Fluorescence Cell linker Kit (Sigma, Cat.-No. PKH26GL). 1 µL PKH26-Red-stain solution was diluted with 250 µL C diluent and added to the suspension of MV3 cells which were then incubated for 5 min at room temperature in the dark. 0.5 mL FBS were added, cells were incubated for 1 minute and washed once with T cell medium consisting of RPMI 1640 medium supplemented with 10% (v/v) FBS, 1% (v/v) GlutaMAX-I, 1 mM sodium pyruvate, 1% (v/v) MEM non-essential amino acids and 50 µM β-Mercaptoethanol. $1 \times 10^6$ MV3 cells/mL were resuspended in T cell medium and separated into three tubes. Synthetic NLVPMVATV peptide (obtained from thinkpeptides, SEQ ID NO: 181) was added to a final concentration of $1 \times 10^{-9}$M or $1 \times 10^{-8}$M and cells were incubated for 90 min under rotation at 37° C. and 5% $CO_2$. MV3 cells were washed once with T cell medium and resuspended to a density of $0.5 \times 10^6$ cells/mL, distributed (100 µL/well) to a 96-well round bottom cell-suspension plate (Greiner bio-one, cellstar, Cat. No. 650185) and incubated over night at 37° C. and 5% $CO_2$.

On the next day, FAP-targeted and DP47-containing single chain trimeric human 4-1BBL molecules were added with 50 µL of T-cell medium to achieve the indicated final concentrations. NLV-specific CD8 T cells were harvested, washed and added in 50 µL medium to each well (final tumor: CD8 T cell ratio 0.125). Cells were incubated for 24 h and 50 µL/well T cell medium containing 2.64 µL/mL Golgi stop (Protein Transport Inhibitor containing Monesin, BD Bioscience, Cat.-No. 554724) were added to each well. Cells were incubated for additional 4 h, washed with 200 µL/well DPBS and stained with 100 µL DPBS containing 1:5000 diluted Fixable Viability Dye-eF450 (eBioscience, Cat. No. 65-0864) for 30 minutes at 4° C. Cells were washed with DPBS and stained in 40 µL/well FACS buffer containing the following fluorescent dye-conjugated antibodies: anti-human CD137-PerCP/Cy5.5 (clone 4B4-1, mouse IgG1κ, BioLegend, Cat. No. 309814), anti-human CD8-BV605 (clone RPA T8, mouse IgG1κ, BioLegend, Cat. No. 301012) and anti-human CD25 PE/Cy7 (clone BC96, mouse IgG1κ, BioLegend, Cat. No. 302612). After incubation for 30 min at 4° C., cells were washed twice with 200 µL/well FACS buffer, resuspended in 50 µL/well freshly prepared FoxP3 Fix/Perm buffer (eBioscience Cat.-No. 00-5123 and 00-5223) and incubated for 30 min at 4° C. Plates were washed twice with 200 µL/well Perm-Buffer (DPBS supplied with 2% (v/v) FBS, 1% (w/v) saponin (Sigma Life Science, 57900) and 1% (w/v) sodium azide (Sigma-Aldrich, 52002) and stained with 50 µL/well Perm-Buffer (eBioscience, Cat.-No. 00-8333-56) containing 0.25 µg/mL anti-human IFNγ-APC (clone B27, mouse IgG1κ, BioLegend, Cat. No. 506510). Plates were incubated for 1 h at 4° C. and washed twice with 200 µL/well Perm-Buffer. For fixation, 50 µL/well DPBS containing 1% formaldehyde were added and cells were stored overnight at 4° C. The next day, cells were resuspended in 100 µL/well FACS buffer and acquired using a 5-laser LSR-FORTESSA® flow cytometer (BD Bioscience with DIVA software). The principle of the assay is shown in FIG. 22.

As shown in FIGS. 23A to 23F, antigen-specific stimulated CD8⁺ T cells, but not unstimulated controls, exhibited increased levels of surface 4-1BB expression in the presence of FAP-targeted single chain trimeric human 4-1BBL Fc(kih) fusion antigen binding molecule (Compound S1, filled circles). This effect of trimeric human 4-1BBL was dose dependent and required FAP-targeting as addition of the untargeted control molecule (Control 1) did not affect the level of 4-1BB expression. Furthermore, T cells activated at a higher peptide concentration ($1\times10^{-8}$ M) showed sustained secretion of INFγ in the presence of FAP-targeted single chain trimeric human 4-1BBL (FIGS. 24A to 24F). Notably, this effect required a stronger primary TCR triggering as compared to the effect of the FAP-targeted single chain trimeric human 4-1BBL on 4-1BB upregulation as the latter was clearly observed also at a low concentration of the peptide. Collectively, these data demonstrate that the FAP-targeted single chain trimeric human 4-1BBL Fc(kih) fusion antigen binding molecule modulates the surface phenotype and responsiveness of antigen specific T-cells in a targeting dependent manner.

As shown in FIGS. 25A-F and 26A-F, antigen-specific CD8+ T cells co-stimulated with NLV-peptide (activation signal 1) and crosslinked monovalent or bivalent FAP (28H1 or 4B9)-targeted single chain trimeric 4-1BBL Fc(kih) fusion antigen binding molecules (activation signal 2), but not unstimulated controls, exhibited increased levels of surface 4-1BB expression and IFNγ-secretion. This effect was dose dependent for the NLV-peptide concentration as well as for the concentration of FAP-targeted single chain trimeric 4-1BBL Fc(kih) fusion antigen binding molecule. Collectively, these data demonstrate that the FAP-targeted single chain trimeric 4-1BBL Fc(kih) fusion antigen binding molecules modulate the surface phenotype and responsiveness of antigen specific T-cells in a targeting dependent manner. The same difference between the monovalent FAP (28H1)-targeted and the FAP (4B9)-targeted single chain trimeric 4-1BB ligand (kih) fusion molecules are seen as in the activation assay using the HeLa-hu4-1BB-NK-κB-luc reporter cell line, e.g. the monovalent FAP (4B9)-targeted single chain trimeric 4-1BBL Fc(kih) fusion antigen binding molecule shows lower $EC_{50}$ values. Different to the HeLa-hu 4-1BB-NK-κB-luc reporter cell line activation assay no big differences are seen between the monovalent and the bivalent FAP (4B9)-targeted single chain trimeric 4-1BB ligand (kih) fusion molecules. At high NLV-peptide concentrations ($10^{-8}$M) it evens seems, that the bivalent FAP (4B9)-targeted single chain trimeric 4-1BBL Fc(kih) fusion antigen binding molecule produces a superior activation than the monovalent FAP (4B9)-targeted single chain trimeric 4-1BBL Fc(kih) fusion antigen binding molecule.

11.3. OX40 Mediated Costimulation of Suboptimally TCR Triggered Resting Human PBMC Human PBMC preparations contain (1) resting OX40 negative CD4⁺ and CD8⁺ T cells and (2) antigen presenting cells with various Fc-γ receptor molecules on their cell surface, e.g. B cells and monocytes. Anti-human CD3 antibody of human IgG1 isotype can bind with its Fc part to Fc-γ receptor molecules and mediate TCR triggering on resting OX40 negative CD4⁺ and CD8⁺ T cells which start to express OX40 within several hours. Functional agonistic compounds against OX40 can signal via the OX40 receptor present on activated CD8⁺ and CD4⁺ T cells and support TCR-mediated stimulation, leading to more prominent phenotypic changes (e.g. higher CD25 expression levels), enhanced proliferation and increased numbers of living CD4⁺ and CD8⁺ T cells.

Experiments with HeLa_hOx40_NFkB_Luc1 reporter cell lines suggested a certain intrinsic capacity of trimeric single chain OX40L molecules to induce NFκB expression (see Example 11.1.5.). The agonistic effect was greatly increased by additional hypercrosslinking of the FAP-targeted compound via FAP expressing tumor cells. Thus, suboptimal TCR stimulation of resting human PBMC was performed in the presence of NIH/3T3-huFAP clone 39 cells and DP47-containing (untargeted) and FAP-targeted trimeric single chain OX40L molecules to test the costimulatory activity with and without further hypercrosslinking.

Mouse embryonic fibroblast NIH/3T3-huFAP clone 39 cells (see Example 9.2.) were harvested using cell dissociation buffer (Invitrogen, Cat.-No. 13151-014) for 10 minutes at 37° C. Cells were washed once with DPBS. NIH/3T3-huFAP clone 39 cells were adjusted to a cell density of $1.6\times10^5$ in T cell media and were seeded at a density of $0.2\times10^5$ cells per well in a sterile 96-well round bottom adhesion tissue culture plate (TPP, Cat. No. 92097). Plates were kept overnight at 37° C. and 5% $CO_2$ in an incubator (Hera Cell 150) before they were irradiated the next day in an xRay irradiator using a dose of 4500 RAD to prevent later overgrowth of human PBMC by the cell line.

Human PBMCs were isolated as described under 9.1. by ficoll density centrifugation and were labeled with CFSE. Cells were stained at a cell density of $1\times10^6$ cells/mL with CFDA-SE (Sigma-Aldrich, Cat.-No. 2188) at a final concentration of [50 nM] for 10 minutes at 37° C. Thereafter, cells were washed twice with excess DPBS containing FBS (10% v/v). Labeled cells were rested in T cell media at 37° C. for 30 minutes. Thereafter, non-converted CFDA-SE was removed by two additional washing steps with DPBS. CFSE-labeled resting human PBMC were adjusted to a cell density of $3\times10^6$ cells/mL in T cell media and were added to each well at a density of $0.75\times10^5$ cells per well. FAP-targeted and DP47-containing single chain trimeric OX40L antigen binding molecules were added at the indicated concentrations and anti-human CD3 antibody (clone V9, human IgG1) at a final concentration of 10 nM. Plates were kept for four days at 37° C. and 5% $CO_2$. After 48 hours a half medium exchange was performed.

After four days cells were washed with DPBS and then stained in 25 μL/well FACS buffer containing following fluorescent dye-conjugated antibodies: 0.250 μg/mL anti-human CD4-BV421 (clone RPA-T4, mouse IgG1 k, BioLegend, Cat.-No. 300532), 0.250 μg/mL CD8-BV711 (clone RPa-T8, mouse IgG1k, BioLegend, Cat.-No. 3010441, 0.250 μg/mL anti-human CD25-PerCP Cy5.5 (clone M-A251, mouse IgG1k, BioLegend, Cat.-No. 356112). After incubation for 30 min at 4° C., cells were washed twice with 200 μL/well FACS buffer, resuspended in 50 μL/well freshly prepared FoxP3 Fix/Perm buffer (eBioscience Cat.-No. 00-5123 and 00-5223) and incubated for 45 min at room temperature in the dark. Plates were washed three times with 200 μL/well Perm-Wash-(eBioscience, Cat.-No. 00-8333-56) and were then stained with 25 μL/well Perm-Buffer (eBioscience, Cat.-No. 00-8333-56) containing 0.25 μg/mL anti-human Granzyme B-PE (clone GB-11, mouse IgG1κ, BD Bioscience, Cat. No. 561142) and 0.60 μg/mL anti-human Eomes EFLUOR® 670 (clone WD2918, mouse IgG1κ, eBioscience, Cat. No. 50-4877-42). Plates were incubated for 1 h at room temperature in the dark and were washed twice with 200 μL/well Perm-Buffer. Cells were resuspended in 85 μL/well FACS buffer and acquired using a 5-laser LSR-FORTESSA® flow cytometer (BD Bioscience with DIVA software).

As shown in FIGS. 27A-F, costimulation with DP47-containing trimeric single chain OX40L binding molecules only slightly promoted proliferation and enhanced the activated cell phenotype (CD25 expression) in human CD4+ (left side) and CD8+ T cells (right side) stimulated suboptimally with anti-human CD3 antibody. Hyper-crosslinking of the FAP-targeted trimeric single chain OX40L by NIH/3T3-huFAP clone 39 cells strongly increased this effect. This is in contrast to findings in the HeLa_hOx40_NFkB_Luc1 cells (FIGS. 21A-B), where the trimeric single chain OX40L molecule per se was already strongly agonistic. This might be due to a non-physiologically high expression of OX40 in the reporter cell line, which most likely results in pre-assembly of low-signaling OX40R oligomer units thereby lowering the threshold for agonistic signaling is the reporter cell line as compared to that Ox40+ T cells. In addition, the cellular context is likely to determine the outcome of OX40 triggering as concomitant signaling through TCR is required in T-cells, but not in the reporter cell line, to observe the effect of OX40 engagement.

CITATIONS

Aggarwal B. B. (2003), Signalling pathways of the TNF superfamily: a double-edged sword. Nat. Rev. Immunol. 3(9),745-56.

Banner D. et al (1993), Crystal structure of the soluble human 55 kd TNF receptor-human TNF beta complex: implications for TNF receptor activation. Cell 73, 431-445.

Baumann R., Shida Y., Simon D., Russmann S., Mueller C. and Simon H.-U. (2004), Functional expression of CD134 by neutrophils. Eur. J. Immunol., 34, 2268-2275.

Bodmer J., Schneider P. and Tschopp, J. (2002), The molecular architecture of the TNF superfamily. Trends in Biochemical Sciences 27(1), 19-26.

Bremer E. (2013), Targeting of the tumor necrosis factor receptor superfamily for cancer immunotherapy. 2013, Article ID 371854, 25 pages. doi:10.1155/2013/371854

Broll K., Richter G., Pauly S., Hofstaedter F. and Schwarz, H. (2001), CD137 expression in tumor vessel walls. High correlation with malignant tumors. Am J Clin Pathol 115, 543-549.

Buechele C., Baessler T., Schmiedel B. J., Schumacher C. E., Grosse-Hovest L., Rittig K. and Salih, H. R. (2012). 4-1BB ligand modulates direct and Rituximab-induced NK-cell reactivity in chronic lymphocytic leukemia. Eur J Immunol 42, 737-748.

Carter P. (2001). Bispecific human IgG by design. J. Immunol. Methods 248, 7-15.

Choi B. K., Kim Y. H., Kwon P. M., Lee S. C., Kang S. W., Kim M. S., Lee M. J., and Kwon B. S. (2009). 4-1BB functions as a survival factor in dendritic cells. J Immunol 182, 4107-4115.

Croft M., Song T., Duan W. and Soroash P. (2009). The significance of OX40 and OX40L to T-cell biology and immune disease. Immunological Reviews 229, 173-191.

Cuadros C., Dominguez A. L., Lollini P. L., Croft M., Mittler R. S., Borgstrom P., and Lustgarten J. (2005). Vaccination with dendritic cells pulsed with apoptotic tumors in combination with anti-OX40 and anti-4-1BB monoclonal antibodies induces T cell-mediated protective immunity in Her-2/neu transgenic mice. Int J Cancer 116, 934-943.

Curran M. A., Kim M., Montalvo W., Al-Shamkhani A., and Allison J. P. (2011). Combination CTLA-4 blockade and 4-1BB activation enhances tumor rejection by increasing T-cell infiltration, proliferation, and cytokine production. PLoS One 6, e19499.

Diehl L., van Mierlo G. J., den Boer A. T., van der Voort E., Fransen M., van Bostelen L., Krimpenfort P., Melief C. J., Mittler R., Toes R. E., and Offringa R. (2002). In vivo triggering through 4-1BB enables Th-independent priming of CTL in the presence of an intact CD28 costimulatory pathway. J Immunol 168, 3755-3762.

Dubrot J., Milheiro F., Alfaro C., Palazon A., Martinez-Forero I., Perez-Gracia J. L., Morales-Kastresana A., Romero-Trevejo J. L., Ochoa M. C., Hervas-Stubbs S., et al. (2010). Treatment with anti-CD137 mAbs causes intense accumulations of liver T cells without selective antitumor immunotherapeutic effects in this organ. Cancer Immunol Immunother 59, 1223-1233.

Futagawa T., Akiba H., Kodama T., Takeda K., Hosoda Y., Yagita H., and Okumura K. (2002). Expression and function of 4-1BB and 4-1BB ligand on murine dendritic cells. Int Immunol 14, 275-286.

Graff, C. P., Chester K., Begent R. and Wittrup K. D. (2004). Directed evolution of an anti-carcinoembryonic antigen scFv with a 4-day monovalent dissociation half-time at 37° C. Protein Engineering, Design & Selection 17, 293-304.

Guo Z., Cheng D., Xia Z., Luan M., Wu L., Wang G., and Zhang S. (2013). Combined TIM-3 blockade and CD137 activation affords the long-term protection in a murine model of ovarian cancer. J Transl Med 11, 215.

Heinisch I. V., Daigle I., Knopfli B., and Simon H. U. (2000). CD137 activation abrogates granulocyte-macrophage colony-stimulating factor-mediated anti-apoptosis in neutrophils. Eur J Immunol 30, 3441-3446.

Hornig, N., Kermer, V., Frey, K., Diebolder, P., Kontermann, R. E., Mueller, D. (2012), Combination of a bispecific antibody and costimulatory antibody-ligand fusion proteins for targeted cancer immunotherapy. J. Immunother. 35, 418-429.

Ju S. A., Cheon S. H., Park S. M., Tam N. Q., Kim Y. M., An W. G., and Kim B. S. (2008). Eradication of established renal cell carcinoma by a combination of 5-fluorouracil and anti-4-1BB monoclonal antibody in mice. Int J Cancer 122, 2784-2790.

Kermer V., Hornig N., Harder M., Bondarieva A., Kontermann R. E., and Müller D. (2014). Combining Antibody-directed presentation of IL-15 and 4-1BBL in a trifunctional fusion protein for Cancer Immunotherapy. Mol. Cancer Ther. 13, 112-121.

Kienzle G., and von Kempis J. (2000). CD137 (ILA/4-1BB), expressed by primary human monocytes, induces monocyte activation and apoptosis of B lymphocytes. Int Immunol 12, 73-82.

Kim D. H., Chang W. S., Lee Y. S., Lee K. A., Kim Y. K., Kwon B. S., and Kang C. Y. (2008). 4-1BB engagement costimulates NKT cell activation and exacerbates NKT cell ligand-induced airway hyperresponsiveness and inflammation. J Immunol 180, 2062-2068.

Kim Y. H., Choi B. K., Oh H. S., Kang W. J., Mittler R. S., and Kwon B. S. (2009). Mechanisms involved in synergistic anticancer effects of anti-4-1BB and cyclophosphamide therapy. Mol Cancer Ther 8, 469-478.

Kwon B. S., and Weissman S. M. (1989). cDNA sequences of two inducible T-cell genes. Proc Natl Acad Sci USA 86, 1963-1967.

Lee H., Park H. J., Sohn H. J., Kim J. M., and Kim S. J. (2011). Combinatorial therapy for liver metastatic colon cancer: dendritic cell vaccine and low-dose agonistic anti-4-1BB antibody co-stimulatory signal. J Surg Res 169, e43-50.

Levitsky V., de Campos-Lima P. O., Frisan T., and Masucci M. G. (1998). The clonal composition of a peptide-specific oligoclonal CTL repertoire selected in response to persistent EBV infection is stable over time. J Immunol 161, 594-601.

Li F., and Ravetch J. V. (2011). Inhibitory Fcgamma receptor engagement drives adjuvant and anti-tumor activities of agonistic CD40 antibodies. Science 333, 1030-1034.

Lin W., Voskens C. J., Zhang X., Schindler D. G., Wood A., Burch E., Wei Y., Chen L., Tian G., Tamada K., et al. (2008). Fc-dependent expression of CD137 on human NK cells: insights into "agonistic" effects of anti-CD137 monoclonal antibodies. Blood 112, 699-707.

Melero I., Johnston J. V., Shufford W. W., Mittler R. S., and Chen L. (1998). NK1.1 cells express 4-1BB (CDw137) costimulatory molecule and are required for tumor immunity elicited by anti-4-1BB monoclonal antibodies. Cell Immunol 190, 167-172.

Melero I., Shuford W. W., Newby S. A., Aruffo A., Ledbetter J. A., Hellstrom K. E., Mittler R. S., and Chen L. (1997). Monoclonal antibodies against the 4-1BB T-cell activation molecule eradicate established tumors. Nat Med 3, 682-685.

Merchant A. M., Zhu Z., Yuan J. Q., Goddard A., Adams C. W., Presta L. G., and Carter P. (1998). An efficient route to human bispecific IgG. Nat Biotechnol 16, 677-681.

Morales-Kastresana A., Sanmamed M. F., Rodriguez I., Palazon A., Martinez-Forero I., Labiano S., Hervas-Stubbs S., Sangro B., Ochoa C., Rouzaut A., et al. (2013). Combined immunostimulatory monoclonal antibodies extend survival in an aggressive transgenic hepatocellular carcinoma mouse model. Clin Cancer Res 19, 6151-6162.

Morris N. P., Peters C., Montler R., Hu H-M, Curti B. D., Urba W. J., and Weinberg A. D. (2007). Development and Characterization of Recombinant Human Fc:OX40L fusion protein linked via a coiled-coil trimerization domain. Mol. Immunol. 44(12), 3112-3121.

Mueller, D., Frey, K., Kontermann, R. E. (2008), A novel antibody-4-1BB1 fusion protein for targeted costimulation in cancer immunotherapy, J. Immunother. 31, 714-722.

Murillo O., Dubrot J., Palazon A., Anna A., Azpilikueta A., Alfaro C., Solano S., Ochoa M. C., Berasain C., Gabari I., et al. (2009). In vivo depletion of DC impairs the antitumor effect of agonistic anti-CD137 mAb. Eur J Immunol 39, 2424-2436.

Narazaki H., Zhu Y., Luo L., Zhu G., and Chen L. (2010). CD137 agonist antibody prevents cancer recurrence: contribution of CD137 on both hematopoietic and nonhematopoietic cells. Blood 115, 1941-1948.

Nishimoto H., Lee S. W., Hong H., Potter K. G., Maeda-Yamamoto M., Kinoshita T., Kawakami Y., Mittler R. S., Kwon B. S., Ware C. F., et al. (2005). Costimulation of mast cells by 4-1BB, a member of the tumor necrosis factor receptor superfamily, with the high-affinity IgE receptor. Blood 106, 4241-4248.

Olofsson P. S., Soderstrom L. A., Wagsater D., Sheikine Y., Ocaya P., Lang F., Rabu C., Chen L., Rudling M., Aukrust P., et al. (2008). CD137 is expressed in human atherosclerosis and promotes development of plaque inflammation in hypercholesterolemic mice. Circulation 117, 1292-1301.

Palazon A., Teijeira A., Martinez-Forero I., Hervas-Stubbs S., Roncal C., Penuelas I., Dubrot J., Morales-Kastresana A., Perez-Gracia J. L., Ochoa M. C., et al. (2011). Agonist anti-CD137 mAb act on tumor endothelial cells to enhance recruitment of activated T lymphocytes. Cancer Res 71, 801-811.

Schwarz H., Valbracht J., Tuckwell J., von Kempis J., and Lotz M. (1995). ILA, the human 4-1BB homologue, is inducible in lymphoid and other cell lineages. Blood 85, 1043-1052.

Shao, Z., and Schwarz, H. (2011). CD137 ligand, a member of the tumor necrosis factor family, regulates immune responses via reverse signal transduction. J Leukoc Biol 89, 21-29.

Shi W., and Siemann D. W. (2006). Augmented antitumor effects of radiation therapy by 4-1BB antibody (BMS-469492) treatment. Anticancer Res 26, 3445-3453.

Simeone E., and Ascierto P. A. (2012). Immunomodulating antibodies in the treatment of metastatic melanoma: the experience with anti-CTLA-4, anti-CD137, and anti-PD1. J Immunotoxicol 9, 241-247.

Snell L. M., Lin G. H., McPherson A. J., Moraes T. J., and Watts T. H. (2011). T-cell intrinsic effects of GITR and 4-1BB during viral infection and cancer immunotherapy. Immunol Rev 244, 197-217.

Song J., So T. and Croft M. (2008). Activation of NF-κB1 by OX40 contributes to antigen-driven T cell expansion and survival. J. Immunology 180(11), 7240-7248.

Stagg J., Loi S., Divisekera U., Ngiow S. F., Duret,H., Yagita H., Teng M. W., and Smyth M. J. (2011). Anti-ErbB-2 mAb therapy requires type I and II interferons and synergizes with anti-PD-1 or anti-CD137 mAb therapy. Proc Natl Acad Sci USA 108, 7142-7147.

Teng M. W., Sharkey J., McLaughlin N. M., Exley M. A., and Smyth M. J. (2009). CD1d-based combination therapy eradicates established tumors in mice. J Immunol 183, 1911-1920.

van Muij en GN, Jansen K F, Cornelissen I M, Smeets D F, Beck J L and Ruiter D J (1991). Establishment and characterization of a human melanoma cell line (MV3) which is highly metastatic in nude mice. Int J Cancer., 48(1), 85-91.

von Kempis J., Schwarz H., and Lotz M. (1997). Differentiation-dependent and stimulus-specific expression of ILA, the human 4-1BB-homologue, in cells of mesenchymal origin. Osteoarthritis Cartilage 5, 394-406.

Watts T. H. (2005). TNF/TNFR family members in costimulation of T cell responses. Annu. Rev. Immunol. 23, 23-68

Wei H., Zhao L., Li W., Fan K., Qian W., Hou S., Wang H., Dai M., Hellstrom I., Hellstrom K. E., and Guo Y. (2013). Combinatorial PD-1 blockade and CD137 activation has therapeutic efficacy in murine cancer models and synergizes with cisplatin. PLoS One 8, e84927.

Weinberg A D, Evans D E, Thalhofer C, Shi T, Prell R A (2004). The generation of T cell memory: a review describing the molecular and cellular events following OX40 (CD134) engagement. J Leukoc Biol. 75(6), 962-972.

Wilcox R. A., Chapoval A. I., Gorski K. S., Otsuji M., Shin T., Flies D. B., Tamada K., Mittler R. S., Tsuchiya H., Pardoll D. M., and Chen L. (2002). Cutting edge: Expression of functional CD137 receptor by dendritic cells. J Immunol 168, 4262-4267.

Wilcox R. A., Tamada K., Flies D. B., Zhu G., Chapoval A. I., Blazar B. R., Kast W. M., and Chen L. (2004). Ligation of CD137 receptor prevents and reverses established anergy of CD8+ cytolytic T lymphocytes in vivo. Blood 103, 177-184.

Zhang, N., Sadun, R. E., Arias, R. S., Flanagan, M. L., Sachsman, S. M., Nien, Y, Khawli, L. A., Hu, P., Epstein, A. L. (2007). Targeted and untargeted CD137L fusion proteins for the immunotherapy of experimental solid tumors. Clin. Cancer Res. 13, 2758-2767.

Zhang X., Voskens C. J., Sallin M., Maniar A., Montes C. L., Zhang Y., Lin W., Li G., Burch E., Tan M., et al. (2010). CD137 promotes proliferation and survival of human B cells. J Immunol 184, 787-795.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A tumor necrosis factor (TNF) family ligand trimer-containing antigen binding molecule comprising
   (a) at least one antigen binding domain comprising an antibody light chain variable region (VL) and an antibody heavy chain variable region (VH) capable of specific binding to a target cell antigen wherein the target cell antigen is Fibroblast Activation Protein (FAP), and
   (b) a polypeptide comprising three ectodomains of a TNF ligand family member or fragments thereof that are connected to each other, wherein the TNF ligand family member is 4-1BBL, and
   (c) an Fc domain composed of a first and a second subunit wherein the first and the second subunit are capable of stable association with each other, and wherein the antigen binding molecule activates the NFκB signaling pathway.

2. The TNF family ligand trimer-containing antigen binding molecule of claim 1, wherein the polypeptide comprising three ectodomains of a TNF ligand family member or fragments thereof are connected to each other by peptide linkers.

3. The TNF family ligand trimer containing antigen binding molecule of claim 2, wherein the polypeptide comprising the three ectodomains of a TNF ligand family member or fragments thereof that are connected to each other by peptide linkers is fused to the N- or C-terminal amino acid of one of the two subunits of the Fc domain, optionally through a peptide linker.

4. The TNF family ligand trimer-containing antigen binding molecule of claim 1, wherein the ectodomain of the TNF ligand family member comprises an amino acid sequence selected from the group consisting of SEQ ID NO:1, SEQ ID NO: 2, SEQ ID NO:3, SEQ ID NO:4, SEQ ID NO:99, SEQ ID NO: 100, SEQ ID NO:101 and SEQ ID NO:102.

5. The TNF family ligand trimer-containing antigen binding molecule of claim 1, wherein the polypeptide comprising three ectodomains of a TNF ligand family member or fragments thereof comprises an amino acid sequence selected from the group consisting of SEQ ID NO:5 and SEQ ID NO:103.

6. The TNF family ligand trimer-containing antigen binding molecule of claim 1, wherein the polypeptide comprising three ectodomains of a TNF ligand family member or fragments thereof is fused at the C-terminal amino acid to an N-terminal amino acid of one of the subunits of the Fc domain.

7. The TNF family ligand trimer-containing antigen binding molecule of claim 1, wherein the polypeptide comprising three ectodomains of a TNF ligand family member or fragments thereof is fused at the N-terminal amino acid to a C-terminal amino acid of one of the subunits of the Fc domain.

8. The TNF family ligand trimer-containing antigen binding molecule of claim 1, wherein the antigen binding domain capable of specific binding to a target cell antigen is selected from the group consisting of an antibody fragment, a Fab molecule, a crossover Fab molecule, a single chain Fab molecule, a Fv molecule, a scFv molecule, a single domain antibody, an aVH and a scaffold antigen binding protein.

9. The TNF family ligand trimer-containing antigen binding molecule of claim 1, wherein the antigen binding domain is a Fab molecule.

10. The TNF family ligand trimer-containing antigen binding molecule of claim 1, wherein the antigen binding domain capable of specific binding to FAP comprises
    (a) a VH domain comprising (i) CDR-H1 comprising the amino acid sequence of SEQ ID NO:9, (ii) CDR-H2 comprising the amino acid sequence of SEQ ID NO:10 and (iii) CDR-H3 comprising the amino acid sequence of SEQ ID NO:11, and a VL domain comprising
    (iv) CDR-L1 comprising the amino acid sequence of SEQ ID NO:12, (v) CDR-L2 comprising the amino acid sequence of SEQ ID NO:13 and (vi) CDR-L3 comprising the amino acid sequence of SEQ ID NO:14, or
    (b) a VH domain comprising (i) CDR-H1 comprising the amino acid sequence of SEQ ID NO:104, (ii) CDR-H2 comprising the amino acid sequence of SEQ ID NO:105 and (iii) CDR-H3 comprising the amino acid sequence of SEQ ID NO:106, and a VL domain comprising (iv) CDR-L1 comprising the amino acid sequence of SEQ ID NO:107, (v) CDR-L2 comprising the amino acid sequence of SEQ ID NO:108 and (vi) CDR-L3 comprising the amino acid sequence of SEQ ID NO:109.

11. The TNF family ligand trimer-containing antigen binding molecule of claim 1, wherein the antigen binding domain capable of specific binding to FAP comprises a variable heavy chain comprising an amino acid sequence of SEQ ID NO:16 and a variable light chain comprising an amino acid sequence of SEQ ID NO:17 or wherein the antigen binding domain capable of specific binding to FAP comprises a variable heavy chain comprising an amino acid sequence of SEQ ID NO:110 and a variable light chain comprising an amino acid sequence of SEQ ID NO:111.

12. The TNF family ligand trimer-containing antigen binding molecule of claim 1, wherein the Fc domain is an IgG domain.

13. The TNF family ligand trimer-containing antigen binding molecule of claim 12, wherein the Fc domain is an IgG1 Fc domain comprising the amino acid substitutions at positions 234 and 235 (EU numbering) and/or 329 (EU numbering) of the IgG heavy chain.

14. The TNF family ligand trimer-containing antigen binding molecule of claim 1, comprising only one antigen binding domain capable of specific binding to a target cell antigen.

15. The TNF family ligand trimer-containing antigen binding molecule of claim 1, wherein the antigen binding molecule comprises
  (i) a first heavy chain comprising the VH domain of a Fab molecule capable of specific binding to a target cell antigen,
  (ii) a light chain comprising the VL domain of a Fab molecule capable of specific binding to a target cell antigen, and
  (iii) a second heavy chain comprising the amino acid sequence of SEQ ID NO:5 or SEQ ID NO:103 or SEQ ID NO:8.

16. The TNF family ligand trimer-containing antigen binding molecule of claim 1, wherein the antigen binding molecule comprises
  (i) a first heavy chain comprising a VH domain comprising an amino acid sequence of SEQ ID NO:16 or a VH domain comprising an amino acid sequence of SEQ ID NO:110,
  (ii) a light chain comprising a VL domain comprising an amino acid sequence of SEQ ID NO:17 or a VL domain comprising an amino acid sequence of SEQ ID NO:111, and
  (iii) a second heavy chain comprising the amino acid sequence of SEQ ID NO:5 or SEQ ID NO:103 or SEQ ID NO:8.

17. The TNF family ligand trimer-containing antigen binding molecule of claim 1, wherein the antigen binding molecule comprises two moieties capable of specific binding to a target cell antigen.

18. The TNF family ligand trimer-containing antigen binding molecule of claim 1, wherein the antigen binding molecule comprises
  (i) a first heavy chain comprising a VH domain of a Fab molecule capable of specific binding to a target cell antigen,
  (ii) two light chains comprising each the VL domain of a Fab molecule capable of specific binding to a target cell antigen, and
  (iii) a second heavy chain comprising a VH domain of a Fab molecule capable of specific binding to a target cell antigen and further comprises the amino acid sequence of SEQ ID NO:5 or SEQ ID NO:103 or SEQ ID NO:8.

19. The TNF family ligand trimer-containing antigen binding molecule of claim 18, wherein the antigen binding molecule comprises
  (i) a first heavy chain comprising a VH domain comprising an amino acid sequence of SEQ ID NO:16 or a VH domain comprising an amino acid sequence of SEQ ID NO:110,
  (ii) two light chains comprising each a VL domain comprising an amino acid sequence of SEQ ID NO:17 or a VL domain comprising an amino acid sequence of SEQ ID NO:111, and
  (iii) a second heavy chain comprising a VH domain comprising an amino acid sequence of SEQ ID NO:16 or a VH domain comprising an amino acid sequence of SEQ ID NO:110 and the amino acid sequence of SEQ ID NO:5 or SEQ ID NO:103 or SEQ ID NO:8.

20. The TNF family ligand trimer-containing antigen binding molecule of claim 12, wherein the Fc domain is an IgG1 Fc domain.

21. The TNF family ligand trimer-containing antigen binding molecule of claim 12, wherein the Fc domain is an IgG4 Fc domain.

22. A pharmaceutical composition comprising the TNF family ligand trimer-containing antigen binding molecule of claim 1 and at least one pharmaceutically acceptable excipient.

* * * * *